(12) United States Patent
Stoloff et al.

(10) Patent No.: US 8,992,934 B2
(45) Date of Patent: Mar. 31, 2015

(54) PEPTIDE SEQUENCES OF HIV POLYPEPTIDES AND COMPOSITIONS THEREOF

(75) Inventors: Gregory Alan Stoloff, London (GB); Wilson Romero Caparros-Wanderlay, Aylesbury (GB)

(73) Assignee: PepTcell Limited (GB)

( * ) Notice: Subject to any disclaimer, the term of this patent is extended or adjusted under 35 U.S.C. 154(b) by 0 days.

(21) Appl. No.: 13/526,467

(22) Filed: Jun. 18, 2012

(65) Prior Publication Data

US 2013/0039937 A1 Feb. 14, 2013

Related U.S. Application Data

(63) Continuation of application No. 12/282,132, filed as application No. PCT/GB2007/000812 on Mar. 9, 2007, now abandoned.

(30) Foreign Application Priority Data

Mar. 10, 2006 (GB) .................................. 0604920.9
Jul. 18, 2006 (GB) .................................. 0614260.8

(51) Int. Cl.
| | | |
|---|---|---|
| A61K 39/21 | (2006.01) | |
| A61K 38/16 | (2006.01) | |
| C07K 14/16 | (2006.01) | |
| C07K 14/005 | (2006.01) | |
| A61K 39/00 | (2006.01) | |

(52) U.S. Cl.
CPC ............... *A61K 39/21* (2013.01); *C07K 14/005* (2013.01); *A61K 2039/55544* (2013.01); *C12N 2740/16322* (2013.01); *C12N 2740/16334* (2013.01)
USPC ........................................ 424/188.1; 530/300

(58) Field of Classification Search
None
See application file for complete search history.

(56) References Cited

U.S. PATENT DOCUMENTS

| | | | |
|---|---|---|---|
| 5,756,666 | A | 5/1998 | Takiguchi et al. |
| 2003/0180314 | A1 | 9/2003 | Degroot |
| 2004/0001845 | A1 | 1/2004 | Altfeld et al. |
| 2005/0226849 | A1 | 10/2005 | Weiner et al. |

FOREIGN PATENT DOCUMENTS

| | | |
|---|---|---|
| DE | 4141970 | 6/1993 |
| EP | 0330359 | 8/1989 |
| RU | 2214274 | 10/2003 |
| WO | 95/10534 A1 | 4/1995 |
| WO | 98/52970 | 11/1998 |
| WO | 99/13896 | 3/1999 |
| WO | 00/26416 | 5/2000 |
| WO | 00/49038 A2 | 8/2000 |
| WO | 00/52040 A1 | 9/2000 |
| WO | 01/24810 | 4/2001 |
| WO | 01/55177 | 8/2001 |
| WO | 02/20555 A2 | 3/2002 |
| WO | 02/069691 | 9/2002 |
| WO | 03/015702 A2 | 2/2003 |
| WO | 03/029285 | 4/2003 |
| WO | 2004/031211 | 4/2004 |
| WO | 2005/012502 | 2/2005 |
| WO | 2007/024941 | 3/2007 |

OTHER PUBLICATIONS

Adachi, Akio et al., "Production of acquired immunodeficiency syndrome-associated retrovirus in human and nonhuman cells transfected with an infectious molecular clone." Journal of Virology, Aug. 1986, vol. 59, Issue 2, pp. 284-291.
Addo et al., "Cytotoxic T-lymphocyte (CTL) responses directed against regulatory and accessory proteins in HIV-1 infection." DNA Cell Biology, 2002, 21(9): 671-8.
Altuvia Y. et al., "A structure-based algorithm to predict potential binding peptides to MHC molecules with hydrophobic binding pockets." Hum. Immunol., 1997, 58: 1-11.
Altuvia Y. et al., "Ranking potential binding peptides to MHC molecules by a computational threading approach." J. Mol. Biol., 1995, 249: 244-250.
Bernardin F. et al., "Human immunodeficiency virus mutations during the first month of infection are preferentially found in known cytotoxic T-lymphocyte epitopes." J. Virol., Sep. 2005, 79(17): 11523-8.
Betts MR et al., "HIV nonprogressors preferentially maintain highly functional HIV-specific CD8+ T-cells." Blood, Feb. 7, 2006.
Brander, Christian et al., "Definition of an optimal cytotoxic T lymphocyte epitope in the latently expressed kaposi's sacroma-associated herpesvirus kaposin protein." The Journal of Infectious Diseases, 2001, vol. 184, pp. 119-126.
Chen, Y et al., "Naturally processed peptides longer than nine amino acid residues bind to the class I MHC molecule HLA-A2.1 with high affinity and in different conformations." J. Immunol., 152, 2874-2881, 1994.
Corbet et al., "Optimization and immune recognition of multiple novel conserved HLA-A2, human immunodeficiency virus type 1-specific CTL epitopes." Journal of General Virology, 2003, 84(Pt 9): 2409-21.
D.F. Hunt et al., "Characterization of peptides bound to the class I MHC molecule HLA-A2.1 by mass spectrometry." Science, vol. 255, 1261-1263, (1992).

(Continued)

*Primary Examiner* — Nicole Kinsey White
(74) *Attorney, Agent, or Firm* — One3 IP Management, P.C.; Dean G. Stathakis; Peter D. Weinstein

(57) ABSTRACT

The present specification discloses an immunogenic composition comprising polypeptide, wherein each of the polypeptides has no more than 100 amino acids, which polypeptides comprises one or more sequences having at least 60% homology with any of SEQ ID 1-4, or comprises two or more epitopes having 7 amino acids or more, each epitope having at least 60% homology with a sub-sequence of any of SEQ ID 1-4 that has the same length as the epitope,
wherein, the polypeptide is immunogenic in a vertebrate expressing a major histocompatibility complex (MHC) allele, and wherein the polypeptide is not a complete HIV virus protein.

25 Claims, 6 Drawing Sheets

(56) References Cited

OTHER PUBLICATIONS

Figure 1:
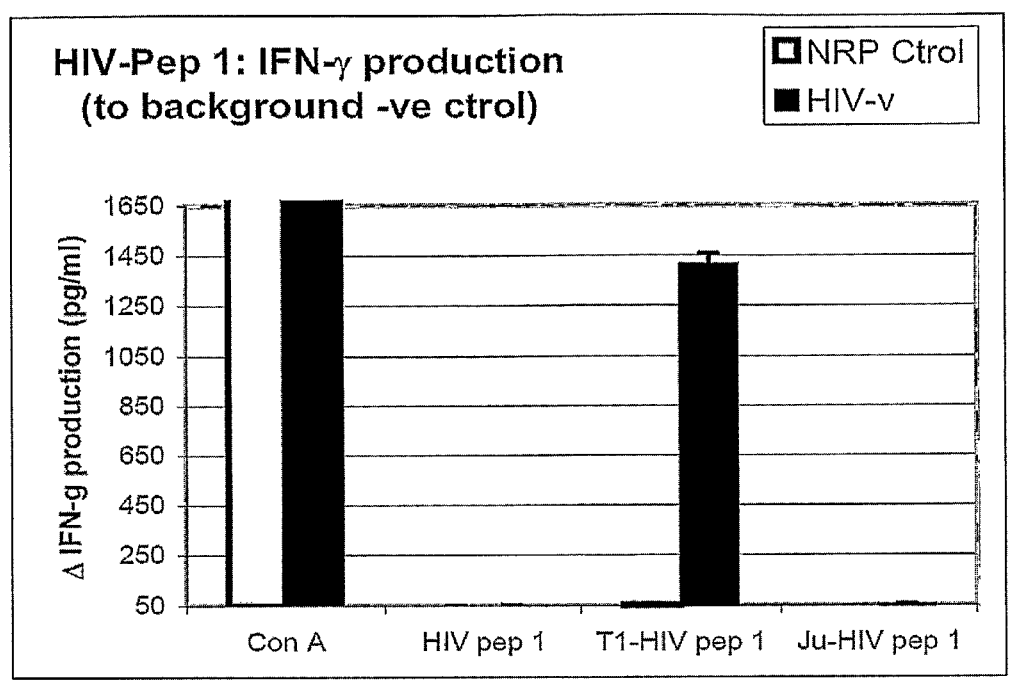

Dakappagari NK et al., "Intracellular delivery of a novel multiepitope peptide vaccine by an amphiphactic peptide carrier enhances cytotoxic T-cell responses on HLA-A 201 mice." Journal of Peptide Research. vol. 65, No. 2 (2005), p. 189-199.
Desrosiers, Nature Medicine, 2004, 10(3): 221-223.
Elliott, T. et al., "Peptide-induced conformational change of the class I heavy chain." Nature, vol. 351, 402-407, (1991).
Ferrantelli et al., Current Opinion in Biotechnology, 2004, 15: 543-556.
Flynn, NM et al., "Placebo-controlled phase 3 trial of a recombinant glycoprotein 120 vaccine to prevent HIV-I infection." J. Infect. Dis. Mar. 2005; 191(5): 654-55. Epub Jan. 27, 2005.
Gilbert, PB et al., "Correlation between immunologic responses to a recombinant glycoprotein 120 vaccine and incidence of HIV-I infection in a phase 3 HIV-I preventive vaccine trial." J. Infect. Dis. Mar. 2005; 191(5): 666-77. Epub Jan. 27, 2005.
Gulukota, K. et al., "Two complementary methods for predicting peptides binding major histocompatibility complex molecules." J. Mol. Biol., 1997, 267: 1258-1267.
Gurgo, C. et al., "Short Communications: Envelope sequences of two new United States HIV-1 isolates." Virology, 1988, vol. 164, pp. 531-536.
Hwai-Chen Guo et al., "Different length peptides bind to HLA-Aw68 similarly at their ends but bulge out in the middle." Nature, vol. 360, 364-367, (1992).
K. Falk, et al., "Allele-specific motifs revealed by sequencing of self-peptides eluted from MHC molecules." Nature, vol. 351, 290-297 (1991).
Lai, RB et al., "Impact of genetic diversity of HIV-I on diagnosis, antiretroviral therapy & vaccine development." Indian J. Med. Res. Apr. 2005, 121(4): 287-314.
Lu et al., Journal of Virology, 1993, 67(11): 6542-6550.
Matano T. et al., "Cytotoxic T lymphocyte-based control of simian immunodeficiency virus replication in a preclinical AIDS vaccine trial." J. Exp. Med. Jun. 21, 2004, 199 (12): 1709-18.
Matthews et al., 1987, AIDS Research and Human Retroviruses, 3(1): 197-206.
McNicholl, JM et al., "Insights into the role of host genetic and T-cell factors in resistance to HIV transmission from studies of highly HIV-exposed Thais." Immunol. Res. 2004; 29(1-3): 161-74.
Meister, G.E. et al., "Two novel T cell epitope prediction algorithms based on MHC-binding motifs; comparison of predicted and published epitopes from *Mycobacterium tuberculosis* and HIV protein sequences." Vaccine, 13: 581-591 (1995).
Pamer, EG et al., "Precise prediction of a dominant class I MHC-restricted epitope of *Listeria monocytogenes*." Nature 1991, 353: 852-855.
Parham, "Deconstructing the MHC." Nature, vol. 360, 300-301, (1992).
Parker KC et al., "Scheme for ranking potential HLA-A2 binding peptides based on independent binding of individual peptide sidechains." J. Immunol., 1994, 152: 163-175.
Peachman, KK et al., "Human dendritic cells and macrophages exhibit different intracellular processing pathways for soluble and liposome-encapsulated antigens." Immunobiology, 2005, 210(5): 321-33.
Rammensee, HG et al., "MHC ligands and peptide motifs: First listing." Immunogenetics 41: 178-228 (1995).
Ruppert J et al., "Prominent role of secondary anchor residues in peptide binding to HLA-A2.1 molecules." Cell, 1993, 74: 929-937.
Schueler-Furman, O et al., "Knowledge-based structure prediction of MHC class I bound peptides: A study of 23 complexes." Fold. Des., 1998, 3: 549-564.
Seaman, MS et al., "Vaccine-elicited memory cytotoxic T lymphocytes contribute to Mamu-A 01-associated control of simian/human immunodeficiency virus 89.6P replication in rhesus monkeys." J. Virol. Apr. 2005, 79(8): 4580-8.
Sette, A. et al., "Peptide binding to the most frequent HLA-A class I alleles measured by quantitative molecular binding assays." Mol. Immunol., 1994, 31: 813-822.
Sette, A. et al., "Prediction of major histocompatibility complex binding regions of protein antigens by sequence pattern analysis." Proc. Natl. Acad. Sci. USA, 1989, 86: 3296-3300.
Sette, A. et al., "The relationship between class I binding affinity and immunogenicity of potential cytotoxic T cell epitopes." J. Immunol., 1994, 153: 5586-5592.
Stevanovic, Stefan, "Structural basis of immunogenicity." Transplant Immunology, 2002, 10: 133-136.
Sturniolo, T. et al., "Generation of tissue-specific and promiscuous HLA ligand databases using DNA microarrays and virtual HLA class II matrices." Nat. Biotechnol., 1999, 17: 555-561.
Sudo, T. et al., "Differences in MHC class I self peptide repertoires among HLA-A2 subtypes." J. Immunol., 155: 4749-4756, 1995.
Tana, T. et al., "A HLA binding motif-aided peptide epitope library: A novel library design for the screening of HLA-DR4-restricted antigenic peptides recognized by CD4+ T cells." J. Human Genet., 43: 14-21 (1998).
Uniport: NEF HV10Y, Jan. 2, 1991, UniRef100_P20886.
Uniprot: Q2NMW1 9HIVI, Jul. 2, 2006, UniRef100_Q2NMW1.
Uniprot: REV HV1C4, Jan. 11, 1988, UnifRef100_P05865.
Uniprot: VPR HV1A2, Jan. 11, 1988, UniRef100_p05952.
Wain-Hobson, Simon et al., "Nucleotide sequence of the AIDS virus." LAV, Cell, Jan. 1985, vol. 40, pp. 9-17.
Woodberry et al., Journal of Virology, 1999, 73(7): 5320-5325.
Yang, OO et al., "Genetic and Stochastic influences on the interaction of human immunodeficiency virus type 1 and cytotoxic T lymphocytes in identical twins." J. Virol., Dec. 2005, 79(24): 15368-75.
Addo, et al., Comprehensive Epitope Analysis of Human Immunodeficiency Virus Type 1 (HIV-1)-Specific T-Cell Responses Directed Against the Entire Expressed HIV-1 Genome Demonstrate Broadly Directed Responses, but no Correlation to Viral Load, J Virol. 77(3): 2081-2092 (2003).
Altfeld, et al. (HIV Study Collaboration), Vpr is Preferentially Targeted by CTL During HIV-1 Infection, J. Immunol. 167 (5): 2743-2752 (2001).
Bråve, et al., Immunization of Mice with the nef Gene from Human Immunodeficiency Virus Type I: Study of Immunological Memory and Long-Term Toxicology, Infect. Agents Cancer 2:14-25 (2007).
Draenert, et al., Persistent Recognition of Autologous Virus by High-Avidity CD8 T Cells in Chronic, Progressive Human Immunodeficiency Virus Type 1 Infection, J. Virol. 78(2): 630-641 (2004).
Giuntini, et al., Combined Roles of Human IgG Subclass, Alternative Complement Pathway Activation, and Epitope Density in the Bactericidal Activity of Antibodies to Meningococcal Factor H Binding Protein, Infect. Immun. 80(1): 187-194 (2012).
Immunologists' Toolbox, In Immunobiology: The Immune System in Health and Disease, Appendix I (5th ed; Janeway CA Jr, Travers P, Walport M, et al. New York: Garland Science; 2001).
Kelley and Sternberg, Protein Structure Prediction on the Web: A Case Study Using the Phyre Server, Nature Protocols 4: 363-371 (2009).
Moureau, et al., Characterization of Humoral and Cellular Immune Responses in Mice Induced by Immunization with HIV-1 Nef Regulatory Protein Encapsulated in Poly(DL-Lactide-Co-Glycolide) Microparticles, Mol. Immunol. 38(8): 607-618 (2002).
Novitsky, et al., Magnitude and Frequency of Cytotoxic T-Lymphocyte Responses: Identification of Immunodominant Regions of Human Immunodeficiency Virus Type 1 Subtype C, J. Virol. 76(20): 10155-10168 (2002).
Pettersen, et al., UCSF Chimera—a visualization system for exploratory research and analysis, J. Comput. Chem. 25 (13): 1605-1612 (2004).
Pleguezuelos, et al., Synthetic Immunotherapy Induces HIV Virus Specific Th1 Cytotoxic Response and Death of an HIV-1 Infected Human Cell Line Through Classic Complement Activation, Virol. J. 10: 107-119 (2013).

PEPTIDE SEQUENCES OF HIV POLYPEPTIDES AND COMPOSITIONS THEREOF

This continuation claims priority pursuant to 35 U.S.C. §120 to patent application U.S. Ser. No. 12/282,132, filed May 29, 2009, now abandoned, a 35 U.S.C. §371 national phase filing of PCT/GB2007/000812, filed Mar. 9, 2007, an international patent application that claims priority to United Kingdom Patent Application GB 0614260.8, filed Jul. 18, 2006, and United Kingdom Patent Application GB 0604920.9, filed Mar. 10, 2006.

The invention concerns peptide sequences, compositions comprising the peptide sequences, and in particular immunodeficiency virus vaccines, such as vaccines against human immunodeficiency virus (HIV) and/or other immunodeficiency viruses which may also be useful against acquired immunodeficiency syndrome (AIDS). The vaccines comprise the sequences and the compositions. The invention also relates to uses of the sequences and compositions. It is especially concerned with vaccines that are protective against a plurality of virus strains, including existing viruses as well as future viruses that have mutated from existing viruses (such as mutated forms of an existing HIV strain).

The defense against disease is critical for the survival of all animals, and the defence mechanism employed for this purpose is the animal immune system. Understanding the immune system is therefore a key to understanding the development of new and more sophisticated treatments for humans and animals alike.

The mechanism of operation of the immune system has been under investigation for many years. The system is composed of a number of cell types and a variety of molecules, making it extremely complex. Even after many years of study, the full extent of the immune system components, and their interaction with each other, is imperfectly understood.

Many years ago it was recognised that a person who recovers from a particular disease may acquire some protection in future against that disease, but not against a disease which that person has not yet contracted. This fundamental aspect of the immune system was interpreted at that time by considering that the immune system acquired a kind of 'memory' against certain pathogens once exposure to such pathogens had taken place, that memory being specific to a certain disease.

Gradually, it became known that exposure to less harmful variants of a pathogen could induce protection against more harmful variants (e.g. exposure to cowpox to protect against smallpox, or exposure to an inactivated anthrax to protect against live anthrax). Thus, the idea of vaccination against a disease arose.

It is now known that the immune system has at least two divisions: innate immunity and adaptive immunity. The innate system is fully functional before a pathogen enters the system, whilst the adaptive system is switched on after the pathogen enters the system. It then develops an attack specific to the pathogen. The innate system comprises a number of components, including phagocytes such as macrophages, which (as the name suggests) 'eat' or engulf foreign bodies such as pathogens.

Typically, but not exclusively, the present invention is concerned with the adaptive immune system, and unless specifically indicated otherwise, 'immune system' in the present context refers to the adaptive immune system.

In order to understand more fully how the immune system functions, the role of its individual components must be carefully considered. In respect of the adaptive immune system, it is well known that immunity against pathogens is provided by the action of lymphocytes, which constitute the most common cell type in the immune system. There are two types of lymphocyte: the B lymphocyte and the T lymphocyte. These are generally termed B cells and T cells respectively.

B cells have the ability to develop into plasma cells, which manufacture antibodies. Antibodies are very important components of the animal immune system. They are produced in response to some signature portion of the invading pathogen (an antigen of the pathogen—antigens here being defined as any foreign substance recognised by the immune system) and are usually specific to that pathogen. However, if two pathogens are very similar, or at least contain the same antigen, then antibodies produced against one can nevertheless be effective against the other (they may 'cross-react'). This explains why inoculation with cowpox may protect against smallpox. It is important to realise that the antibodies 'recognise' only a small portion of the antigenic molecule of the pathogen rather than the pathogen as a whole. These portions are termed epitopes.

T cells do not possess or produce antibodies. Instead, they recognise fragments (i.e. epitopes) of the foreign antigen complexed with major histocompatibility complex (MHC) (or in the case of humans, human leucocyte antigen (HLA)) via a specialised receptor known as TCR (T cell receptor). T cells are themselves divisible into subsets which can have either a regulatory function or an effector function. The effector cells are involved with 'effecting' the removal of foreign substances. For example, cytotoxic T cells (CTL) are effector cells that are able to kill infected cells, as well as other unwanted species such as tumour cells. Regulatory T cells, on the other hand, play a role in helping effector T and B cells to become more effective. Due to this function, these regulatory T cells are often termed 'helper' T cells. Other regulatory T cells, termed 'suppressor' T cells, are thought to inhibit immune responses, but these are less well understood. Regulatory T cells may also interact with components of the innate immune system to boost their activity.

In a normal healthy individual, the lymphocytes in the immune system remain in an inactive 'resting' state until an immune response is triggered. When an immune response is required, the lymphocytes become activated, proliferate and begin to carry out their designated functions. For example, any resting T cell displaying on its surface a TCR that recognises an epitope of the invading pathogen complexed with a MHC molecule is activated, proliferates (this being termed clonal expansion) and the resulting offspring start to actively carry out their predetermined effector functions required to combat the invading organisms.

When the immune response is completed, (i.e. the pathogens and/or infected cells have been eliminated) the lymphocytes revert to a resting state once again. This resting state is not, however, equivalent to the initial inactive resting state. Activated, but resting lymphocytes, can be rapidly recruited and induced to proliferate in response to an infection by the same, or closely related, pathogen at a later time.

This ability of activated resting lymphocytes, to deliver a faster and more powerful response following a second encounter with an invading pathogen, effectively provides the immune system with 'memory'. The exploitation of the immune system's memory is the basis for all long-term immunoprophylactic drugs (e.g. vaccines) and remains the goal of much long-term immunotherapeutic drug development.

In order for cells to perform their functions within the complex systems of an animal, the cells need to have 'receptors' on their surfaces. These receptors are capable of 'recognising' specific substances that control various essential processes such as activation, proliferation and adherence to other cells or substrates. For example, in the case of the immune system, the receptors on T and B cells allow them not only to recognise antigen but also to interact with each other and thus regulate their activities. Without these receptors, the cells would lack an essential means of communication and would be unable to act effectively in the concerted way that is essential for the immune system of a multicellular organism.

In order to be able to specifically recognise and deal with the wide range of pathogens present in the environment, the immune system has developed two types of highly variable antigen receptor on lymphocytes: antibodies in B cells and T cell receptors, or TCRs, in T cells.

There are a great many different possible antigen receptors present in the body, to enable the immune system to recognise a wide variety of invading pathogens. In fact there are approximately $10^{12}$ different B cells and T cell receptors in an individual. Each individual B cell has only one type of receptor, and so to deal with a particular pathogen, a B cell having the 'best fitting' receptor for an antigen of that pathogen must be selected. This process is termed 'clonal selection'. In theory, only a single clone may respond (a monoclonal response) or several (an oligoclonal response) or many (a polyclonal response) depending on the number of antigens/epitopes exhibited by the pathogen, and the specificity of the various selected B cells to these antigen/epitopes.

There is a major difference between the types of antigen that can be recognised by B cells and T cells. As far as it is known, only the receptors on the surface of B lymphocytes (i.e. antibodies) are capable of directly recognising antigens such as proteins on viruses and bacteria, or foreign molecules dissolved in body fluid. Antibodies can also be produced in a soluble form by the B cells when they are activated and develop into plasma cells. The antibodies are also termed immunoglobulins (abbreviated to Ig). T cell receptors, on the other hand, recognise only short peptides, also known as T-cell epitopes, on the surface of cells of the body. These T-cell epitopes are produced by degradation of larger proteins that are either self (i.e. naturally occurring body proteins) or non-self (i.e. derived from foreign organisms infecting the body). Only those derived from foreign proteins, i.e. antigens, are normally capable of inducing an immune response in the body. Once produced, these epitopes are bound to a special type of molecule, the MHC (major histocompatibility complex) and the resulting complex is then presented on the cell surface for binding the T-cell receptor.

It should be clear that due to the destructive nature of the immune response, the response has to act only against foreign pathogens, not against the body's own cells or proteins. Thus, the immune system needs to distinguish between 'self' and 'non-self'. It has been proposed that although clones of lymphocytes reacting against self are produced, they are deleted before any reaction can occur. This process is termed 'clonal deletion'. It has also been proposed that any self-reacting lymphocytes could be retained but only in a 'switched-off' state. This mechanism is termed 'clonal anergy'. Whatever the process considered, it remains unclear what is the exact underlying mechanism allowing lymphoid tissues, such as the thymus, to identify individual T cell clones reacting against self from the pool of T lymphocytes reacting only against non-self. The present inventors have now investigated more fully the mechanism of self/non-self discrimination, which has led to the development of the present invention. The inventors have now established a method of predicting the immunogenicity of a substance such as a peptide, which has enabled quicker identification of immunogenic peptide sequences within large proteins.

It has been known for many years that the major histocompatibility complex (MHC) plays a key role in the immune system of animals. The MHC molecules enable T cells to recognise antigens, as has already been discussed above. There are three general types of MHC molecule, class I, class II and class III. Class I and class II MHC molecules are glycoproteins that are present on the surface of the cell, whilst class III are usually soluble molecules present inside the cell. There are a large number of different types of MHC molecule. For example in humans (where MHC is termed HLA, or Human Leukocyte Antigen) there are several hundred different alleles of the genes coding for MHC molecules, meaning that in the human population there are many different types of HLA. The MHCs of different species are typically named according to different conventions, thus MHC for mouse is termed H-2, for rat RT1 and for rabbit RLA. The different gene regions coding for different MHC molecules in an individual are usually individually named, such as HLA-A, HLA-C etc. in humans.

The MHC molecule is a critical immune system molecule, since it is this molecule that presents the epitopes of the antigens to the immune system. For example, if a T cell is to respond to a particular pathogen, the pathogen must have a least one antigen (such as a protein) that has at least one epitope (such as a peptide portion of the protein) that can bind to an MHC molecule on the surface of a cell and thus interact with a T cell which binds to the MHC-peptide complex. Thus, the immune response is dependent on the ability of the MHC to bind to an epitope. If there is no epitope that the MHC will bind to, or if there is no T cell which will bind to the MHC-peptide complex, then no immune response will occur.

In respect of 'self' proteins, however, one of several epitopes may be able to bind to the MHC molecule and hence potentially induce an immune response. On these occasions a specific "signal" must be provided for the self-reacting lymphocyte clones to be deleted or "switched off".

Since, as indicated above, both self and foreign (i.e. non-self) peptides can bind to MHC molecules, the binding of various peptides to MHC molecules has received particular scrutiny in the immunology field. Many investigations have sought to calculate or predict the strength of binding between certain MHC (particularly HLA and H-2) types and peptide sequences, to try to account for immune responses, or the lack of them (i.e. the "signal" required for discrimination between self and foreign). Examples of these include the following:

Altuvia Y, Schueler O, Margalit H. 1995. "Ranking potential binding peptides to MHC molecules by a computational threading approach". J. Mol. Biol., 249:244-250.

Altuvia Y, Sette A, Sidney J, Southwood S, Margalit H. 1997. "A structure-based algorithm to predict potential binding peptides to MHC molecules with hydrophobic binding pockets". Hum. Immunol. 58: 1-11.

G. E. Meister, C. G. P. Roberts, J. A. Berzofsky, A. S. De Groot, "Two novel T cell epitope prediction algorithms based on MHC-binding motifs; comparison of predicted and published epitopes from *Mycobacterium tuberculosis* and HIV protein sequences" Vaccine, 13:581-591, (1995).

Gulukota K, Sidney J, Sette A, DeLisi C. 1997. "Two complementary methods for predicting peptides binding major histocompatibility complex molecules". J. Mol. Biol. 267: 1258-1267.

Pamer E G, Harty J T, Bevan M J. "Precise prediction of a dominant class I MHC-restricted epitope of *Listeria monocytogenes*". Nature 1991; 353:852-855.

Parker K C, Bednarek M A, Coligan J E. 1994. "Scheme for ranking potential HLA-A2 binding peptides based on independent binding of individual peptide side-chains". J. Immunol. 152:163-175.

Rammensee H G, Friede T, Stevanoviic S. 1995. "MHC ligands and peptide motifs: First listing". Immunogenetics 41:178-228.

Ruppert J, Sidney J, Celis E, Kubo R T, Grey H M, Sette A. 1993. "Prominent role of secondary anchor residues in peptide binding to HLA-A2.1 molecules". Cell 74:929-937.

Schueler-Furman O, Elber R, Margalit H. 1998. "Knowledge-based structure prediction of MHC class I bound peptides: A study of 23 complexes". Fold Des. 3:549-564.

Sette A, Buus S, Appella E, Smith J A, Chesnut R, Miles C, Colon S M, Grey H M. 1989. "Prediction of major histocompatibility complex binding regions of protein antigens by sequence pattern analysis". Proc. Natl. Acad. Sci. USA 86:3296-3300.

Sette A, Sidney J, del Guercio M F, Southwood S, Ruppert J, Dahlberg C, Grey H M, Kubo R T. 1994a. "Peptide binding to the most frequent HLA-A class I alleles measured by quantitative molecular binding assays". Mol. Immunol. 31:813-822.

Sette A, Vitiello A, Reherman B, Fowler P, Nayersina R, Kast W M, Melief C J M, Oseroff C, Yuan L, Ruppert J, et al. 1994b. "The relationship between class I binding affinity and immunogenicity of potential cytotoxic T cell epitopes". J. Immunol. 153:5586-5592.

Stefan Stevanovic (2002): "Structural basis of immunogenicity", Transplant Immunology 10 133-136

Sturniolo T, Bono E, Ding J, Raddrizzani L, Tuereci O, Sahin U, Braxenthaler M, Gallazzi F, Protti M P, Sinigaglia F, Hammer J. 1999. "Generation of tissue-specific and promiscuous HLA ligand databases using DNA microarrays and virtual HLA class II matrices". Nat. Biotechnol. 17:555-561.

T. Sudo, N. Kamikawaji, A. Kimura, Y. Date, C. J. Savoie, H. Nakashima, E. Furuichi, S. Kuhara, and T. Sasazuki, "Differences in MHC Class I self peptide repertoires among HLA-A2 subtypes." J. Immunol.: 155: 4749-4756, (1995).

T. Tana, N. Kamikawaji, C. J. Savoie, T. Sudo, Y. Kinoshita, T. Sasazuki, "A HLA binding motif-aided peptide epitope library: A novel library design for the screening of HLA-DR4-restricted antigenic peptides recognized by CD4+ T cells." J. Human Genet., 43:14-21 (1998).

K. Falk, et al. "Allele-specific motifs revealed by sequencing of self-peptides eluted from MHC molecules", Nature, Vol. 351, 290-297 (1991).

T Elliott et al. "Peptide-induced conformational change of the class I heavy chain", Nature, Vol. 351, 402-407, (1991).

P. Parham, "Deconstructing the MHC", Nature, Vol. 360, 300-301, (1992).

Hwai-Chen Guo et al., "Different length peptides bind to HLA-Aw68 similarly at their ends but bulge out in the middle", Nature, Vol. 360, 364-367, (1992).

Y. Chen et al. "Naturally processed peptides longer than nine amino acid residues bind to the class I MHC molecule HLA-A2.1 with high affinity and in different conformations", J. Immunol., 152, 2874-2881, (1994).

D. F. Hunt et al. "Characterization of peptides bound to the class I MHC molecule HLA-A2.1 by mass spectrometry", Science, Vol. 255, 1261-1263, (1992).

Generally, the prior art attempts to predict the immunogenicity of particular peptides by calculating the strength of binding between that peptide and the known binding environment of a particular MHC molecule. The binding environment involves a 'pocket' in the MHC molecule that is adapted to accept a peptide of a certain length (such as 7-15 amino acids). The structure of the pocket may already be known from previous X-ray crystallographic studies. This strength may be calculated mathematically using appropriate algorithms for atomic and molecular interaction. Alternatively, the prior art may attempt to 'score' the binding strength of a peptide based upon motifs existing in the peptide, such as particular amino acids being present at particular positions in a peptide of a certain length, e.g. a proline present at position 3 in an 8-amino acid peptide binding to a particular known HLA molecule. Generally these approaches have met with limited success.

The present inventors believe that they have improved upon the above theories from a better understanding of how T cells reacting against self-substances such as self-proteins are identified prior to their elimination (clonal deletion) or silencing (clonal anergy). Accordingly, the inventors have been able to identify specific immunogenic peptide sequences that may provide protection against specific pathogens, and have developed vaccines to these pathogens, using the identified sequences. In the case of the present invention, the inventors have developed peptides useful in HIV vaccines eliciting a T cell response.

For many years HIV infection was not a condition susceptible of treatment. When the disease was identified in 1981, existing anti-viral therapies were ineffective in controlling the damage that the virus would cause to a patient's immune system. The virus causes direct and indirect destruction of CD4 positive T cells, which are essential for a fully functioning immune system. As a patient's CD4+ T cell count diminishes, the disease becomes progressively worse. When the CD4+ T cell count falls below a certain level, the patient is considered to have deteriorated to the point of having full-blown AIDS. Definitions of the point at which this occurs vary, but it is generally considered that it is arrived at in healthy HIV positive people with a CD4+ T cell count of less than 200 per ml of blood. More recently, anti-viral therapies have improved, and the progression of the disease has been slowed considerably. Modern combinatorial therapies may (in some patients) delay the onset of full-blown AIDS indefinitely. However, these therapies are expensive, and place a burden on the patient requiring him or her to take a significant number tablets per day (many patients find it difficult to remember to take the required medicine) and in many cases leading to unpleasant side-effects (unsurprising when taking a cocktail containing many different pharmaceuticals, which has to be taken for life). Not only do current therapies suffer from these problems, but they are not curative, merely delaying onset of full-blown AIDS. Moreover, in recent years there has been increased number of reports indicating the appearance and spread of drug-resistant HIV drugs. Accordingly, there is a real and urgent need for a vaccine which could prevent and/or cure immunodeficiency viruses, such as HIV, and also prevent and/or cure AIDS.

Previously, attempts to develop HIV vaccines have been made by identifying an existing HIV strain and then producing a vaccine specific to that virus. Generally, vaccines have been based upon a B cell (antibody) response, the antibody being reactive with the surface antigens of the specific HIV strain against which it has been developed. Typically, the surface proteins comprising the antigens are variable from one HIV strain to the next, since mutation of the virus to produce a new virus tends to occur in the surface proteins. The consequence of this is that conventional HIV vaccines, if they were functional at all, would generally protect only against one specific virus strain, and not against a new strain that results from a mutation. Thus, a new vaccine would be required for protection against an emerging strain. The period of time between emergence of the new virus strain by mutation is very short. Within an infected individual new strains are arising all the time, as a result of the selective pressure imposed by that individual's immune system. As a result, the viral population found in an infected individual changes with time (over a period of weeks, months and years) without any requirement for re-infection due to the high mutation rate. Thus, the only likely way to target immunodeficiency virus infection in an individual, or to target potential new virus strains that might infect or develop in an individual, is to target a conserved region of the proteome. This approach is inherently problematic, since the dominant immune response to HIV is directed to sections that are themselves under a high rate of mutation, due to (a) immunological pressure and (b) low fidelity rates of the replicative machinery of the virus.

A number of studies directed at developing vaccines to immunodeficiency viruses (including vaccines to HIV) have been undertaken in the past. These have for the most part antibody based and concentrated on vaccines based upon HIV glycoprotein 120 and glycoprotein 160 (thought to be the best candidates for an HIV vaccine). Particularly relevant studies are listed in the following:

Blood. 2006 Feb. 7; "HIV nonprogressors preferentially maintain highly functional HIV-specific CD8+ T-cells". Betts M R, Nason M C, West S M, De Rosa S C, Migueles S A, Abraham J, Lederman M M, Benito J M, Goepfert P A, Connors M, Roederer M, Koup R A.

Indian J Med. Res. 2005 April; 121(4):287-314. "Impact of genetic diversity of HIV-1 on diagnosis, antiretroviral therapy & vaccine development". Lal R B, Chakrabarti S, Yang C.

J. Virol. 2005 April; 79(8):4580-8. "Vaccine-elicited memory cytotoxic T lymphocytes contribute to Mamu-A*01-associated control of simian/human immunodeficiency virus 89.6P replication in rhesus monkeys". Seaman M S, Santra S, Newberg M H, Philippon V, Manson K, Xu L, Gelman R S, Panicali D, Mascola J R, Nabel G J, Letvin N L.

Infect Dis. 2005 Mar. 1; 191(5):666-77. Epub 2005 Jan. 27. "Correlation between immunologic responses to a recombinant glycoprotein 120 vaccine and incidence of HIV-1 infection in a phase 3 HIV-1 preventive vaccine trial". Gilbert P B, Peterson M L, Follmann D, Hudgens M G, Francis D P, Gurwith M, Heyward W L, Jobes D V, Popovic V, Self S G, Sinangil F, Burke D, Berman P W.

J Infect Dis. 2005 Mar. 1; 191(5):654-65. Epub 2005 Jan. 27. "Placebo-controlled phase 3 trial of a recombinant glycoprotein 120 vaccine to prevent HIV-1 infection". Flynn N M, Forthal D N, Harro C D, Judson F N, Mayer K H, Para M F.

J Exp Med. 2004 Jun. 21; 199(12):1709-18. "Cytotoxic T lymphocyte-based control of simian immunodeficiency virus replication in a preclinical AIDS vaccine trial". Matano T, Kobayashi M, Igarashi H, Takeda A, Nakamura H, Kano M, Sugimoto C, Mori K, Iida A, Hirata T, Hasegawa M, Yuasa T, Miyazawa M, Takahashi Y, Yasunami M, Kimura A, O'Connor D H, Watkins D I, Nagai Y.

Immunol Res. 2004; 29(1-3):161-74. "Insights into the role of host genetic and T-cell factors in resistance to HIV transmission from studies of highly HIV-exposed Thais". McNicholl J M, Promadej N.

J. Virol. 2005 December; 9(24):15368-75: "Genetic and Stochastic influences on the interaction of human immunodeficiency virus type 1 and cytotoxic T lymphocytes in identical twins". Yang O O, Church J, Kitchen C M, Kilpatrick R, Ali A, Geng Y, Killian M S, Sabado R L, Ng H, Suen J, Bryson Y, Jamieson B D, Krogstad P.

J. Virol. 2005 September 79 (17):11523-8. "Human immunodeficiency virus mutations during the first month of infection are preferentially found in known cytotoxic T-lymphocyte epitopes". Bernardin F, Kong D, Peddada L, Baxter-Lowe L A, Delwart E However, although known epitopes have been studied extensively, none has yet been satisfactory for forming the basis of an HIV vaccine. Moreover, vaccines based upon any single epitope, even if it were to provide some protection, would likely be specific for a particular HLA, making the vaccine ineffective in a large proportion of the human population.

Accordingly, it is an aim of the present invention to solve the problems associated with the known prior art as set out above. It is a further aim of the present invention to provide a polypeptide that is capable of eliciting a CTL immune response in vertebrates against a plurality of immunodeficiency virus strains and/or in a plurality of individuals expressing differing MHCs (HLAs). It is a further aim of the present invention to provide an immunodeficiency virus vaccine (such as an HIV vaccine) using the polypeptide of the invention. Preferably the vaccine is capable of protection against a plurality of virus strains and/or is effective in a plurality of individuals expressing differing MHCs (HLAs).

Accordingly, the present invention provides a polypeptide having no more than 100 amino acids, which polypeptide comprises one or more sequences having at least 60% homology with any of SEQ ID 1-4, or comprises two or more epitopes having 7 amino acids or more, each epitope having at least 60% homology with a sub-sequence of any of SEQ ID 1-4 that has the same length as the epitope:

```
                                                    SEQ ID 1
GDTWAGVEAIIRILQQLLFIHFRIGCQHSR

SEQ ID 2
KVGSLQYLALTALITPKKIKPPLPSVKKLTEDRWNKPQKT

SEQ ID 3
EPVPLQLPPLERLTLDCSEDCGTSGTQ

SEQ ID 4
YKGALDLSHFLKEKGGLEGLIYSQKRQDILDLWVYHTQGYFPD
``` wherein, the polypeptide is immunogenic in a vertebrate expressing a major histocompatibility complex (MHC) allele, and wherein the polypeptide is not a complete HIV virus protein.

Thus, the polypeptide is one that may comprise the whole of (or may comprise at least two 7 or more residue parts of) any of the above sequences, but cannot have more than 100 amino acid residues in total. The polypeptide must also be immunogenic in a vertebrate expressing an MHC (HLA in humans) allele. An immunogenic polypeptide is understood in the present context to mean a polypeptide that elicits an immune response in a vertebrate, such as by binding to a vertebrate MHC and causing it to react with a cytotoxic T cell lymphocyte. One method for determining whether a polypeptide possesses immunogenicity is set out in Experiment 1 below. However, the present invention is not limited to such methods, and the skilled person may select any known method for determining immunogenicity, as desired.

As mentioned above, the polypeptide may be one comprising two 7 or more residue epitopes that react with one or more MHCs and so elicit a broad CTL response. The response may be in a single individual or may be in at least two different individuals (the individuals may be of the same species or different species). Thus, the polypeptide may comprise at least two different 7 or more residue epitopes, each of which individually provides a response to a different subject. An epitope in the context of the present invention is a part of a polypeptide which is capable of binding to an MHC in a vertebrate, preferably eliciting an immune response, such as by causing the MHC-epitope complex to react with a CTL. One method for determining whether a polypeptide is an epitope is set out in Experiment 1 below. However, the present invention is not limited to such methods, and the skilled person may select any known method for determining whether a polypeptide is an epitope, as desired.

The present inventors have found that the above sequences comprise a plurality of CTL epitopes, which may afford protection against immunodeficiency viruses, especially HIV, for a wide variety of vertebrates in a population, and for a wide cross-section of the human population. In addition, the inventors have analysed all known HIV strain sequences, and have found that the specified sequences are remarkably conserved across all known HIV strains. As such, these sequences are very unlikely to be significantly altered in new strains resulting from mutation of existing strains. Accordingly, the epitopes within these sequences that provide protection are highly likely to be present in unchanged form in new strains, since mutation does not normally occur in these regions. Consequently, these epitopes provide excellent opportunity not only for providing protection against existing HIV strains (such as reference strains, e.g. in the case of HIV-1 Clade B, the standard reference HXB-2—more information on reference strains can be found in the http://hiv-web.lanl.gov database), but also protecting against as yet unknown strains, such as mutated forms of the above reference strains.

As discussed above, the sequences have been identified after analysis of all known HIV strain sequences. The sequences are thus consensus sequences developed from the above analysis. Despite being consensus sequences, the sequences in some cases correspond exactly to natural sequences in some of the known HIV strains. Due to the remarkable conservation in the sequences across all viruses, the consensus sequences, even when differing from actual sequences, only differ in a small number of residues, and thus contain many smaller epitopes (8-mers, 9-mers, 10-mers etc.) for which there are no differences from natural sequences. The above consensus sequences as a whole thus contain many effective epitopes that are the same as the natural epitopes, as well as effective epitopes that differ only slightly from natural epitopes. It will be apparent to the skilled person that the invention extends not only to the consensus sequences and their epitopes, but also to the corresponding actual sequences in any immunodeficiency virus (e.g. HIV) strains. Thus, sequences with some homology to the consensus sequences are also within the scope of the invention. Such homology allows substitution of, for example, up to 3 amino acids in an 8-mer epitope (62.5% homology) or in a 9-mer, 10-mer, or 11-mer epitope. It is preferred that no more than 10 such substitutions are identifiable in a sequence of the invention corresponding to the full sequences of SEQ ID 1-4 (66.6% homology for a 30-mer). Such substitutions are preferably conservative substitutions in line with known substitution schemes.

Having in mind that the invention extends from the consensus sequence to the corresponding natural sequences, then the invention also provides a polypeptide having no more than 100 amino acids, which polypeptide comprises one or more sequences defined by the following amino acid residues of an HIV virus protein, or comprises two or more epitopes having 7 amino acids or more from a sequence defined by the following amino acid residues of an HIV virus protein:

residues 51-80 of a VPR protein
residues 142-181 of a VIF protein
residues 69-95 of an REV protein
residues 81-123 of a NEF protein wherein, the polypeptide is immunogenic in a vertebrate expressing a major histocompatibility complex (MHC) allele, and wherein the polypeptide is not a complete HIV protein.

The sequence numbering referred to in the present invention is defined according to well-recognised principles. Thus, the numbering begins at 1 from the recognised translation initiation codon (ATG). This corresponds to a Methionine (M), for the segment of the HIV virus genome coding for the protein of interest. In other words, it begins at 1 in respect of the Methionine shown as the first amino acid in the protein sequence of interest as used and defined by the databases in which the sequences have been set forth (i.e. GenBank, SwissProt, etc.).

The present invention will be described in more detail by way of example only with reference to the following Figures, in which:

FIG. 1 shows IFN-γ production by primary splenocyte cultures of HIV-v and NRP vaccinated mice stimulated with Con A (10 μg/ml), soluble Lysozyme (5 μg/ml), purified soluble polypeptides (P1, P2, P3 and P4; 5 μg/ml) and HLA-matched T1 (T1) and mismatched JURKAT (Ju) human cells transfected with either Lysozyme, P1, P2, P3 or P4 according to the protocol described in the text (splenocyte to transfected cell ratio is 10:1); IFN-γ production is represented as the differential between the level of production in response to the antigen considered minus the IFN-γ produced in response to either soluble Lysozyme or the corresponding cell transfected with Lysozyme. Background levels of Lysozyme mediated production of IFN-γ were for soluble antigen 25±10 pg/ml, for antigen in T1 316±43 pg/ml, and for antigen in Jurkat 19±6 pg/ml;

FIG. 2 shows IFN-γ production by primary splenocyte cultures of HIV-v and NRP vaccinated mice stimulated with Con A (10 μg/ml), soluble Lysozyme (5 μg/ml), purified equimolar solution of recombinant HIV proteins (5 μg/ml) and HLA-matched T1 (T1) and mismatched JURKAT (Ju) human cells transfected with either Lysozyme or purified equimolar solution of recombinant HIV proteins according to the protocol described in the text (splenocyte to transfected cell ratio is 10:1); IFN-γ production is represented as the differential between the level of production in response to the antigen considered minus the IFN-γ produced in response to either soluble Lysozyme or the corresponding cell transfected with Lysozyme; background levels of Lysozyme mediated production of IFN-γ were for soluble antigen 25±10 pg/ml, for antigen in T1 316±43 pg/ml, and for antigen in Jurkat 19±6 pg/ml.

FIG. 3 shows similar IFN-γ production as to FIGS. 1 and 2 in respect of test group 3, confirming reactivity of the peptide of SEQ ID 3;

FIG. 4 shows similar IFN-γ production as to FIGS. 1 and 2 in respect of test group 4, confirming reactivity of the peptide of SEQ ID 4;

FIG. 5 shows similar IFN-γ production as to FIGS. 1 and 2 in respect of test group 5, confirming reactivity of the antigens derived from complete VIF, REV and NEF HIV proteins; and FIG. 6 shows IFN-γ production by primary splenocyte cultures of HIV-v and NRP-v vaccinated mice stimulated with either lonomycin (0.78 μg/ml) and PMA (0.05 μg/ml), Con A (5 μg/ml) or HLA-matched CEM human cells infected with D clade (UG21-R5) or A clade (UG-29-X4) HIV-1 isolates according to the protocol described in the Examples (splenocyte to infected cell ratio is 10:1). IFN-γ production is represented as the number of IFN-γ-producing cells in the HIV-v group minus the number of IFN-γ-producing cells in the NRP-v group. The number of IFN-γ-producing cells values for both HIV-v and NRP-v splenocytes stimulated with Con A or lonomycin and PMA were over 4900 and over 8000 respectively. Statistical significance was established by non-parametric Mann-Whitney analysis of the established IFN-γ values for the HIV-v and NRP-v groups.

The polypeptides of the invention described above typically comprise one or more (preferably two or more) epitopes. These epitopes are preferably T cell epitopes, such as cytotoxic T lymphocyte (CTL) epitopes. Generally the polypeptide is immunogenic to an immunodeficiency virus strain (preferably HIV), and preferably to a plurality of such strains. In the present context, a polypeptide immunogenic to an immunodeficiency virus strain is understood to mean a polypeptide that is part of a virus protein and that elicits an immune response, such as by exhibiting CTL reactivity when bound to an MHC. One method for determining whether a polypeptide possesses such immunogenicity is set out in Experiment 1 below. However, the present invention is not limited to such methods, and the skilled person may select any known method for determining immunogenicity, as desired.

In the present invention, the polypeptide comprises two or more sequences as described above. Typically, two, three, four, five or more such sequences may be present in the polypeptide, if desired. The more such epitopes are present, the greater the breadth of protection afforded within a population of humans and/or animal individuals with differing HLAs or MHCs.

The polypeptide according to the present invention may also comprise one or more further sequences that are not epitopes, if desired. Typically the further sequences are from one or more immunodeficiency virus proteins (preferably HIV proteins). These sequences may be situated between two or more of the sequences (the epitopes) described above, and/or may be situated at one or both ends of the polypeptide. The presence of such further sequences should not affect the function of the polypeptide, provided that the polypeptide as a whole does not become too large, interfering with the presentation of the epitopes in the vertebrate's immune system. In specific embodiments of the invention, when the polypeptide is homologous to SEQ ID 1, the further sequences are preferably one or more from a VPR protein (preferably from an HIV strain), when the polypeptide is homologous to SEQ ID 2, the further sequences are preferably one or more from a VIF protein (preferably from an HIV strain), when the polypeptide is homologous to SEQ ID 3, the further sequences are preferably one or more from a REV protein (preferably from an HIV strain), and when the polypeptide is homologous to SEQ ID 4, the further sequences are preferably one or more from a NEF protein (preferably from an HIV strain).

In the most preferred embodiments, the further sequences from the above-mentioned proteins are ones within the following consensus sequences, or ones having at least 60% homology with a sequence within the following consensus sequences:

```
VPR HIV Consensus -
                                                        SEQ ID 5
MEQAPEDQGPQREPYNEWTLELLEELKNEAVRHFPRPWLHGLGQHIYETYGDTWAGVEAIIRILQQL

LFIHFRIGCQHSRIGIIRQRRARNGASRS

VIF HIV Consensus -
                                                        SEQ ID 6
MENRWQVMIVWQVDRMRIRTWKSLVKHHMYISKKAKGWFYRHHYESTHPRISSEVHIPLGDDAKLVI

TTYWGLHTGERDWHLGQGVSIEWRKKRYSTQVDPDLADQLIHLYYFDCFSESAIRKAILGHIVSPRCE

YQAGHNKVGSLQYL ALTALITPKKIKPPLPSVKKLTEDRWNKPQKTKGHRGSHTMNGH

REV HIV Consensus -
                                                        SEQ ID 7
MAGRSGDSDEELLKAVRIIKILYQSNPYPSPEGTRQARRNRRRRWRARQRQIRSISERILSTCLGRPA

EPVPLQLPPLERLTLDCSEDCGTSGTQQSQGT EEGVGSPQILVESPTVLESGTKE

NEF HIV Consensus -
                                                        SEQ ID 8
MGGKWSKSSVVGWPAVRERMRRAEPAAEGVGAVSRDLEKHGAITSSNTAANNADCAWLEAQEEE

EVGFPVRPQVPLRPMTYKGALDLSHFLKEKGGLEGLIYSQKRQDILDLWVYHTQGYFPDWQNYTPG

PGIRYPLTFGWCFKLVPVEPEKVEEANEGENNCLLHPMSQHGMEDPEREVLVWKFDSRLAFHHMAR

ELHPEYYKDC
```

The homology referred to above in respect of these sequences is preferably 75%, 85%, 95% or substantially 100%.

In the present invention, the immunodeficiency virus strain is not especially limited, and the polypeptides may be immunogenic against, and/or derived from, any known HIV virus strain. Future strains that have mutated from any of these existing strains may also be ones against which the polypeptides are immunogenic, or from which the polypeptides are derived.

The sequences defining the polypeptides of the present invention are situated within the VPR, VIF, REV and NEF proteins from any HIV virus strain (the consensus sequences of which for all analysed sequences, or alternatively the positions of which within the protein, are described above). The following specific sequences were analysed by the inventors, and preferably the HIV sequences referred to in the invention are selected from these specific sequences, or mutations from these sequences. Thus, the specific sequences homologous to SEQ ID 1-4 described above are preferably the ones at the appropriate positions within the following proteins. Similarly, the sequences of the present invention defined by the residue positions within proteins from any virus strain, namely residues 51-80 of VPR protein, residues 142-181 of VIF protein, residues 69-95 of REV protein, and residues 81-123 of NEF protein. The list is in the form |version number (gi number)|database identification (e.g. gb for GenBank) |NCBI accession number|optional further information (e.g. the accession number of the nucleotide sequence from which the protein sequence is derived). The sequences and corresponding virus strains from which they derive can all be found from the public NCBI protein database. The protein database contains sequence data from the translated coding regions from DNA sequences in GenBank, EMBL, and DDBJ as well as protein sequences submitted to Protein Information Resource (PIR), SWISS-PROT, Protein Research Foundation (PRF), and Protein Data Bank (PDB) (sequences from solved structures).

| VPR proteins |
|---|
| \|1469310\|gb\|AAB05046.1\|, \|77167539\|gb\|ABA62729.1\|, \|77168205\|gb\|ABA63062.1\|, \|3218154\|emb\|CAB05081.1\|, \|3218152\|emb\|CAB05080.1\|, \|22596296\|gb\|AAN03081.1\|AF45, \|32351105\|gb\|AAP76513.1\|, \|25166839\|gb\|AAN73627.1\|AF48, \|77168298\|gb\|ABA63108.1\|, \|77167711\|gb\|ABA62815.1\|, \|77167347\|gb\|ABA62633.1\|, \|77167789\|gb\|ABA62854.1\|, \|77167745\|gb\|ABA62832.1\|, \|77167607\|gb\|ABA62763.1\|, \|77167449\|gb\|ABA62684.1\|, \|77167961\|gb\|ABA62940.1\|, \|77167707\|gb\|ABA62813.1\|, \|77167457\|gb\|ABA62688.1\|, \|77167317\|gb\|ABA62618.1\|, \|77167535\|gb\|ABA62727.1\|, \|49472934\|gb\|AAT66278.1\|, \|6910971\|gb\|AAF31322.1\|AF146, \|77167947\|gb\|ABA62933.1\|, \|77167787\|gb\|ABA62853.1\|, \|77167611\|gb\|ABA62765.1\|, \|71726015\|gb\|AAZ39146.1\|, \|82283746\|sp\|Q66MS0\|Q66MS0_9, \|77168227\|gb\|ABA63073.1\|, \|57545334\|gb\|AAW51570.1\|, \|77167367\|gb\|ABA62643.1\|, \|77167381\|gb\|ABA62650.1\|, \|221480\|dbj\|BAA00995.1\|, \|77167689\|gb\|ABA62804.1\|, \|57545338\|gb\|AAW51572.1\|, \|77168272\|gb\|ABA63095.1\|, \|77167513\|gb\|ABA62716.1\|, \|46254407\|gb\|AAS86166.1\|, \|2570312\|gb\|AAC97573.1\|8, \|77167533\|gb\|ABA62726.1\|, \|77168366\|gb\|ABA63142.1\|, \|5001943\|gb\|AAD37222.1\|, \|5001933\|gb\|AAD37217.1\|, \|5001923\|gb\|AAD37212.1\|, \|5001913\|gb\|AAD37207.1\|, \|82307194\|sp\|Q9W9L8\|Q9W9L8_9, \|5001953\|gb\|AAD37227.1\|, \|74273444\|gb\|ABA01428.1\|, \|74273434\|gb\|ABA01419.1\|, \|74273424\|gb\|ABA01410.1\|, \|55735953\|gb\|AAV59686.1\|, \|77168009\|gb\|ABA62964.1\|, \|77167979\|gb\|ABA62949.1\|, \|77167519\|gb\|ABA62719.1\|, \|77167451\|gb\|ABA62685.1\|, \|77168089\|gb\|ABA63004.1\|, \|77167847\|gb\|ABA62883.1\|, \|77168197\|gb\|ABA63058.1\|, \|77167795\|gb\|ABA62857.1\|, \|16118321\|gb\|AAL12694.1\|, \|83026816\|gb\|ABB96451.1\|, \|82284686\|sp\|Q6EFW3\|Q6EFW3_9, \|37677907\|gb\|AAQ97572.1\|, \|37677897\|gb\|AAQ97563.1\|, \|37682582\|gb\|AAQ98264.1\|, \|77167595\|gb\|ABA62757.1\|, \|77167345\|gb\|ABA62632.1\|, \|77167841\|gb\|ABA62880.1\|, \|55735961\|gb\|AAV59693.1\|, \|71725995\|gb\|AAZ39128.1\|, \|57545372\|gb\|AAW51589.1\|, \|57545370\|gb\|AAW51588.1\|, \|77168264\|gb\|ABA63091.1\|, \|77167867\|gb\|ABA62893.1\|, \|77167967\|gb\|ABA62943.1\|, \|3193275\|gb\|AAD03328.1\|, \|77167499\|gb\|ABA62709.1\|, \|5738569\|emb\|CAB53045.1\|, \|46254431\|gb\|AAS86184.1\|, \|77167929\|gb\|ABA62924.1\|, \|77167319\|gb\|ABA62619.1\|, \|77167553\|gb\|ABA62736.1\|, \|77167547\|gb\|ABA62733.1\|, \|77168101\|gb\|ABA63010.1\|, \|77168262\|gb\|ABA63090.1\|, \|77167509\|gb\|ABA62714.1\|, \|77168336\|gb\|ABA63127.1\|, \|77167385\|gb\|ABA62652.1\|, \|77168015\|gb\|ABA62967.1\|, \|77167899\|gb\|ABA62909.1\|, \|77167567\|gb\|ABA62743.1\|, \|2393853\|gb\|AAB70154.1\|, \|71726025\|gb\|AAZ39155.1\|, \|77168378\|gb\|ABA63148.1\|, \|77168294\|gb\|ABA63106.1\|, \|77168035\|gb\|ABA62977.1\|, \|77167721\|gb\|ABA62820.1\|, \|77167565\|gb\|ABA62742.1\|, \|31559665\|dbj\|BAC77489.1\|, \|1688186\|gb\|AAB51055.1\|, \|1688182\|gb\|AAB51053.1\|, \|15407036\|gb\|AAG32142.1\|, \|15407034\|gb\|AAG32141.1\|, \|15407038\|gb\|AAG32143.1\|, \|77168394\|gb\|ABA63156.1\|, \|31559655\|dbj\|BAC77480.1\|, \|77167455\|gb\|ABA62687.1\|, \|77168217\|gb\|ABA63068.1\|, \|77168260\|gb\|ABA63089.1\|, \|77167773\|gb\|ABA62846.1\|, \|77168059\|gb\|ABA62989.1\|, \|77167431\|gb\|ABA62675.1\|, \|77168057\|gb\|ABA62988.1\|, \|77167427\|gb\|ABA62673.1\|, \|2570305\|gb\|AAC63086.1\|, \|77168127\|gb\|ABA63023.1\|, \|77168087\|gb\|ABA63003.1\|, \|77167443\|gb\|ABA62681.1\|, \|77167463\|gb\|ABA62691.1\|, \|77168380\|gb\|ABA63149.1\|, \|77167517\|gb\|ABA62718.1\|, \|77167705\|gb\|ABA62812.1\|, \|55735988\|gb\|AAV59717.1\|, \|77168019\|gb\|ABA62969.1\|, \|77168406\|gb\|ABA63162.1\|, \|77168203\|gb\|ABA63061.1\|, \|77168007\|gb\|ABA62963.1\|, \|77168073\|gb\|ABA62996.1\|, \|77167603\|gb\|ABA62761.1\|, \|77167447\|gb\|ABA62683.1\|, \|77168169\|gb\|ABA63044.1\|, \|77168005\|gb\|ABA62962.1\|, \|77167637\|gb\|ABA62778.1\|, \|77167515\|gb\|ABA62717.1\|, \|77168143\|gb\|ABA63031.1\|, \|77168031\|gb\|ABA62975.1\|, \|77168085\|gb\|ABA63002.1\|, \|77167785\|gb\|ABA62852.1\|, \|77167727\|gb\|ABA62823.1\|, \|2944130\|gb\|AAC05237.1\|, \|3002833\|gb\|AAD03193.1\|, \|5001969\|gb\|AAD37235.1\|, \|57869572\|gb\|AAW57622.1\|, \|1185514\|gb\|AAA87861.1\|, \|1185512\|gb\|AAA87860.1\|, \|62956369\|gb\|AAY23504.1\|, \|25166899\|gb\|AAN73681.1\|AF48, \|18074002\|emb\|CAC86567.1\|, \|38570392\|gb\|AAR24634.1\|, \|57545362\|gb\|AAW51584.1\|, \|3218473\|emb\|CAB05069.1\|, \|57545320\|gb\|AAW51563.1\|, \|77167325\|gb\|ABA62622.1\|, \|6651484\|gb\|AAF22332.1\|AF193, \|6651476\|gb\|AAF22324.1\|AF193, \|18699224\|gb\|AAL78471.1\|AF41, \|83026808\|gb\|ABB96444.1\|, \|18699231\|gb\|AAL78477.1\|AF41, \|18699251\|gb\|AAL78492.1\|AF41, \|29119299\|gb\|AAO63217.1\|, \|829465\|gb\|AAA79594.1\|, \|829458\|gb\|AAA79588.1\|, \|77168402\|gb\|ABA63160.1\|, \|77167963\|gb\|ABA62941.1\|, \|77168179\|gb\|ABA63049.1\|, \|77167551\|gb\|ABA62735.1\|, \|77168117\|gb\|ABA63018.1\|, \|77168213\|gb\|ABA63066.1\|, \|77167919\|gb\|ABA62919.1\|, \|77167635\|gb\|ABA62777.1\|, \|77167793\|gb\|ABA62856.1\|, \|77167371\|gb\|ABA62645.1\|, \|77168039\|gb\|ABA62979.1\|, \|77167557\|gb\|ABA62738.1\|, \|77167369\|gb\|ABA62644.1\|, \|77167699\|gb\|ABA62809.1\|, \|12964721\|gb\|AAK11289.1\|, \|12964719\|gb\|AAK11288.1\|, \|328434\|gb\|AAB04039.1\|, \|77167623\|gb\|ABA62771.1\|, \|7416686\|dbj\|BAA93983.1\|, \|7416688\|dbj\|BAA93984.1\|, \|77168326\|gb\|ABA63122.1\|, \|77167675\|gb\|ABA62797.1\|, \|57545276\|gb\|AAW51541.1\|, \|12964727\|gb\|AAK11292.1\|, \|12964725\|gb\|AAK11291.1\|, \|12964731\|gb\|AAK11294.1\|, \|12964733\|gb\|AAK11295.1\|, \|12964729\|gb\|AAK11293.1\|, \|77167767\|gb\|ABA62843.1\|, \|12964723\|gb\|AAK11290.1\|, \|12964717\|gb\|AAK11287.1\|, \|77168284\|gb\|ABA63101.1\|, \|77167813\|gb\|ABA62866.1\|, \|77167765\|gb\|ABA62842.1\|, \|77167331\|gb\|ABA62625.1\|, \|12964715\|gb\|AAK11286.1\|, |

-continued

| VPR proteins |
|---|
| \|77168362\|gb\|ABA63140.1\|, \|77167949\|gb\|ABA62934.1\|, \|3694864\|gb\|AAC62478.1\|, \|77167679\|gb\|ABA62799.1\|, \|25167049\|gb\|AAN73816.1\|AF48, \|77168316\|gb\|ABA63117.1\|, \|77167391\|gb\|ABA62655.1\|, \|37683040\|gb\|AAQ98596.1\|, \|38491794\|gb\|AAR22172.1\|, \|77167737\|gb\|ABA62828.1\|, \|77168340\|gb\|ABA63129.1\|, \|77168223\|gb\|ABA63071.1\|, \|77168207\|gb\|ABA63063.1\|, \|77167831\|gb\|ABA62875.1\|, \|77167585\|gb\|ABA62752.1\|, \|38570402\|gb\|AAR24639.1\|, \|31559693\|dbj\|BAC77514.1\|, \|77168268\|gb\|ABA63093.1\|, \|78172844\|gb\|ABB29376.1\|, \|77167693\|gb\|ABA62806.1\|, \|77168065\|gb\|ABA62992.1\|, \|77167529\|gb\|ABA62724.1\|, \|77167797\|gb\|ABA62858.1\|, \|77167687\|gb\|ABA62803.1\|, \|77167473\|gb\|ABA62696.1\|, \|77167337\|gb\|ABA62628.1\|, \|77168308\|gb\|ABA63113.1\|, \|77168165\|gb\|ABA63042.1\|, \|77167491\|gb\|ABA62705.1\|, \|77167477\|gb\|ABA62698.1\|, \|77167615\|gb\|ABA62767.1\|, \|77167511\|gb\|ABA62715.1\|, \|77167441\|gb\|ABA62680.1\|, \|77167429\|gb\|ABA62674.1\|, \|77168370\|gb\|ABA63144.1\|, \|77168159\|gb\|ABA63039.1\|, \|77168193\|gb\|ABA63056.1\|, \|77168360\|gb\|ABA63139.1\|, \|77167985\|gb\|ABA62952.1\|, \|77167857\|gb\|ABA62888.1\|, \|77168390\|gb\|ABA63154.1\|, \|77168278\|gb\|ABA63098.1\|, \|77168258\|gb\|ABA63088.1\|, \|77167941\|gb\|ABA62930.1\|, \|77167593\|gb\|ABA62756.1\|, \|77167815\|gb\|ABA62867.1\|, \|77168091\|gb\|ABA63005.1\|, \|77167671\|gb\|ABA62795.1\|, \|77168306\|gb\|ABA63112.1\|, \|77167407\|gb\|ABA62663.1\|, \|77167329\|gb\|ABA62624.1\|, \|77168338\|gb\|ABA63128.1\|, \|77168163\|gb\|ABA63041.1\|, \|77167739\|gb\|ABA62829.1\|, \|77168003\|gb\|ABA62961.1\|, \|77167641\|gb\|ABA62780.1\|, \|77167917\|gb\|ABA62918.1\|, \|77168239\|gb\|ABA63079.1\|, \|77167893\|gb\|ABA62906.1\|, \|77167839\|gb\|ABA62879.1\|, \|77167621\|gb\|ABA62770.1\|, \|77168119\|gb\|ABA63019.1\|, \|77167895\|gb\|ABA62907.1\|, \|2281656\|gb\|AAB64166.1\|, \|77168095\|gb\|ABA63007.1\|, \|24753975\|gb\|AAN64098.1\|, \|77168318\|gb\|ABA63118.1\|, \|25166799\|gb\|AAN73591.1\|AF48, \|77168233\|gb\|ABA63076.1\|, \|77167587\|gb\|ABA62753.1\|, \|51572116\|gb\|AAU06764.1\|, \|37677797\|gb\|AAQ97473.1\|, \|37677787\|gb\|AAQ97464.1\|, \|77168155\|gb\|ABA63037.1\|, \|77167995\|gb\|ABA62957.1\|, \|39777407\|gb\|AAR30986.1\|, \|77167981\|gb\|ABA62950.1\|, \|31559617\|dbj\|BAC77446.1\|, \|77168107\|gb\|ABA63013.1\|, \|66864684\|gb\|AAY57412.1\|, \|55925130\|gb\|AAV67935.1\|, \|55925122\|gb\|AAV67928.1\|, \|55925114\|gb\|AAV67921.1\|, \|55925138\|gb\|AAV67942.1\|, \|77168392\|gb\|ABA63155.1\|, \|77167823\|gb\|ABA62871.1\|, \|77168312\|gb\|ABA63115.1\|, \|77167409\|gb\|ABA62664.1\|, \|77167343\|gb\|ABA62631.1\|, \|77167669\|gb\|ABA62794.1\|, \|77167811\|gb\|ABA62865.1\|, \|77167665\|gb\|ABA62792.1\|, \|77167657\|gb\|ABA62788.1\|, \|1185550\|gb\|AAA87879.1\|, \|32399660\|emb\|CAD58637.1\|, \|11761313\|dbj\|BAB19248.1\|, \|11761306\|dbj\|BAB19242.1\|, \|77168093\|gb\|ABA63006.1\|, \|77167485\|gb\|ABA62702.1\|, \|77167915\|gb\|ABA62917.1\|, \|83026778\|gb\|ABB96417.1\|, \|77167525\|gb\|ABA62722.1\|, \|57545344\|gb\|AAW51575.1\|, \|77168330\|gb\|ABA63124.1\|, \|77167755\|gb\|ABA62837.1\|, \|77168053\|gb\|ABA62986.1\|, \|77167731\|gb\|ABA62825.1\|, \|37725250\|gb\|AAR02312.1\|, \|37725240\|gb\|AAR02303.1\|, \|37725220\|gb\|AAR02285.1\|, \|37725200\|gb\|AAR02267.1\|, \|37725190\|gb\|AAR02258.1\|, \|37725230\|gb\|AAR02294.1\|, \|37725210\|gb\|AAR02276.1\|, \|77168396\|gb\|ABA63157.1\|, \|77167817\|gb\|ABA62868.1\|, \|77167881\|gb\|ABA62900.1\|, \|77167423\|gb\|ABA62671.1\|, \|77167939\|gb\|ABA62929.1\|, \|77167411\|gb\|ABA62665.1\|, \|1160019\|emb\|CAA92863.1\|, \|77167591\|gb\|ABA62755.1\|, \|77167425\|gb\|ABA62672.1\|, \|77167907\|gb\|ABA62913.1\|, \|3218477\|emb\|CAB05071.1\|, \|16118294\|gb\|AAL12670.1\|, \|139395\|sp\|P05954\|VPR_HV1RH, \|328571\|gb\|AAA45055.1\|, \|3114559\|gb\|AAD03178.1\|, \|1160021\|emb\|CAA92864.1\|, \|1477880\|gb\|AAB05523.1\|, \|1477796\|gb\|AAB05481.1\|, \|55735979\|gb\|AAV59709.1\|, \|25166859\|gb\|AAN73645.1\|AF48, \|38570394\|gb\|AAR24635.1\|, \|77168001\|gb\|ABA62960.1\|, \|37677867\|gb\|AAQ97536.1\|, \|37677857\|gb\|AAQ97527.1\|, \|139394\|sp\|P20891\|VPR_HV1OY, \|328446\|gb\|AAA83394.1\|, \|1160107\|emb\|CAA92907.1\|, \|77168081\|gb\|ABA63000.1\|, \|74273383\|gb\|ABA01374.1\|, \|74273375\|gb\|ABA01367.1\|, \|74273358\|gb\|ABA01353.1\|, \|74273349\|gb\|ABA01345.1\|, \|57545296\|gb\|AAW51551.1\|, \|1160039\|emb\|CAA92873.1\|, \|1160091\|emb\|CAA92899.1\|, \|57545312\|gb\|AAW51559.1\|, \|57545282\|gb\|AAW51544.1\|, \|1465784\|gb\|AAB05601.1\|, \|77168372\|gb\|ABA63145.1\|, \|77168037\|gb\|ABA62978.1\|, \|57545330\|gb\|AAW51568.1\|, \|1151163\|gb\|AAA85233.1\|, \|5805265\|gb\|AAD51914.1\|, \|57545354\|gb\|AAW51580.1\|, \|1160035\|emb\|CAA92871.1\|, \|7416664\|dbj\|BAA93972.1\|, \|7416674\|dbj\|BAA93977.1\|, \|7416666\|dbj\|BAA93973.1\|, \|7416670\|dbj\|BAA93975.1\|, \|7416672\|dbj\|BAA93976.1\|, \|7416668\|dbj\|BAA93974.1\|, \|7416708\|dbj\|BAA93994.1\|, \|27446736\|gb\|AAL62481.1\|, \|2286137\|gb\|AAB64283.1\|, \|2286128\|gb\|AAB64275.1\|, \|82279710\|sp\|O42084\|O42084_9, \|4205075\|gb\|AAD10946.1\|, \|4205066\|gb\|AAD10938.1\|, \|4205057\|gb\|AAD10930.1\|, \|4205048\|gb\|AAD10922.1\|, \|4205039\|gb\|AAD10914.1\|, \|4205030\|gb\|AAD10906.1\|, \|4205021\|gb\|AAD10898.1\|, \|4205012\|gb\|AAD10890.1\|, \|4205003\|gb\|AAD10882.1\|, \|4204994\|gb\|AAD10874.1\|, \|38570406\|gb\|AAR24641.1\|, \|38570388\|gb\|AAR24632.1\|, \|139386\|sp\|P05928\|VPR_HV1BR, \|326422\|gb\|AAB59749.1\|, \|28872817\|ref\|NP_057852.2\|, \|551171\|gb\|AAA21763.1\|, \|902802\|gb\|AAB60574.1\|, \|1351413\|sp\|P12520\|VPR_HV1N5, \|328421\|gb\|AAA44990.1\|, \|14269050\|gb\|AAK58007.1\|AF36, \|77168111\|gb\|ABA63015.1\|, \|8218029\|emb\|CAB92789.1\|, \|77167761\|gb\|ABA62840.1\|, \|77167403\|gb\|ABA62661.1\|, \|55740259\|gb\|AAV63830.1\|, \|55740249\|gb\|AAV63821.1\|, \|139384\|sp\|P12519\|VPR_HV1Z2, \|329383\|gb\|AAA45368.1\|, \|61102539\|gb\|AAX37685.1\|, \|61102531\|gb\|AAX37678.1\|, \|2570294\|gb\|AAC32650.1\|, \|77167825\|gb\|ABA62872.1\|, \|77168105\|gb\|ABA63012.1\|, \|38570408\|gb\|AAR24642.1\|, \|77167507\|gb\|ABA62713.1\|, \|37682493\|gb\|AAQ98184.1\|, \|55740239\|gb\|AAV63812.1\|, \|55740229\|gb\|AAV63803.1\|, \|328160\|gb\|AAA44871.1\|, \|25166719\|gb\|AAN73519.1\|AF48, \|38491814\|gb\|AAR22190.1\|, \|24181481\|gb\|AAN47103.1\|, \|139392\|sp\|P05955\|VPR_HV1MA, \|77168025\|gb\|ABA62972.1\|, \|37677887\|gb\|AAQ97554.1\|, \|37677877\|gb\|AAQ97545.1\|, \|139389\|sp\|P05956\|VPR_HV1EL, \|326681\|gb\|AAA44327.1\|, \|57901101\|gb\|AAW57866.1\|, \|32399669\|emb\|CAD58646.1\|, \|38491804\|gb\|AAR22181.1\|, \|77168368\|gb\|ABA63143.1\|, \|3002880\|gb\|AAD03235.1\|, \|77168061\|gb\|ABA62990.1\|, \|77168133\|gb\|ABA63026.1\|, \|77167879\|gb\|ABA62899.1\|, \|16118274\|gb\|AAL12652.1\|, \|37681544\|gb\|AAQ97653.1\|, \|37677847\|gb\|AAQ97518.1\|, \|57545326\|gb\|AAW51566.1\|, \|57545322\|gb\|AAW51564.1\|, |

-continued

| VPR proteins |
|---|
| \|77168071\|gb\|ABA62995.1\|, \|23394922\|gb\|AAN31644.1\|, \|62956358\|gb\|AAY23494.1\|, \|45360202\|gb\|AAS59234.1\|, \|83026788\|gb\|ABB96426.1\|, \|77167749\|gb\|ABA62834.1\|, \|829450\|gb\|AAA79581.1\|, \|829435\|gb\|AAA79568.1\|, \|829443\|gb\|AAA79575.1\|, \|829427\|gb\|AAA79561.1\|, \|829419\|gb\|AAA79554.1\|, \|829411\|gb\|AAA79547.1\|, \|77167571\|gb\|ABA62745.1\|, \|57545304\|gb\|AAW51555.1\|, \|37677767\|gb\|AAQ97446.1\|, \|37677757\|gb\|AAQ97437.1\|, \|7416660\|dbj\|BAA93970.1\|, \|16118325\|gb\|AAL12697.1\|, \|47060058\|gb\|AAT09644.1\|, \|1185518\|gb\|AAA87863.1\|, \|82295315\|sp\|Q89493\|Q89493__9, \|1477852\|gb\|AAB05509.1\|, \|1185546\|gb\|AAA87877.1\|, \|82295327\|sp\|Q89588\|Q89588__9, \|1477854\|gb\|AAB05510.1\|, \|1185538\|gb\|AAA87873.1\|, \|1477860\|gb\|AAB05513.1\|, \|1185526\|gb\|AAA87867.1\|, \|1185522\|gb\|AAA87865.1\|, \|1185544\|gb\|AAA87876.1\|, \|1477848\|gb\|AAB05507.1\|, \|1477846\|gb\|AAB05506.1\|, \|1477858\|gb\|AAB05512.1\|, \|1477856\|gb\|AAB05511.1\|, \|82305555\|sp\|Q9PWZ2\|Q9PWZ2__9, \|1185540\|gb\|AAA87874.1\|, \|1185528\|gb\|AAA87868.1\|, \|1477850\|gb\|AAB05508.1\|, \|1185530\|gb\|AAA87869.1\|, \|57545360\|gb\|AAW51583.1\|, \|57545358\|gb\|AAW51582.1\|, \|3218166\|emb\|CAB05087.1\|, \|3218164\|emb\|CAB05086.1\|, \|3218170\|emb\|CAB05089.1\|, \|1160103\|emb\|CAA92905.1\|, \|77168248\|gb\|ABA63083.1\|, \|77167771\|gb\|ABA62845.1\|, \|77167633\|gb\|ABA62776.1\|, \|77167933\|gb\|ABA62926.1\|, \|77168320\|gb\|ABA63119.1\|, \|3218168\|emb\|CAB05088.1\|, \|1160083\|emb\|CAA92895.1\|, \|57545294\|gb\|AAW51550.1\|, \|11177392\|gb\|AAG32258.1\|, \|11177372\|gb\|AAG32248.1\|, \|11177390\|gb\|AAG32257.1\|, \|11177426\|gb\|AAG32275.1\|, \|11177424\|gb\|AAG32274.1\|, \|11177420\|gb\|AAG32272.1\|, \|11177416\|gb\|AAG32270.1\|, \|11177414\|gb\|AAG32269.1\|, \|11177412\|gb\|AAG32268.1\|, \|11177410\|gb\|AAG32267.1\|, \|11177404\|gb\|AAG32264.1\|, \|11177400\|gb\|AAG32262.1\|, \|11177396\|gb\|AAG32260.1\|, \|11177388\|gb\|AAG32256.1\|, \|11177386\|gb\|AAG32255.1\|, \|11177384\|gb\|AAG32254.1\|, \|11177382\|gb\|AAG32253.1\|, \|11177380\|gb\|AAG32252.1\|, \|11177378\|gb\|AAG32251.1\|, \|11177376\|gb\|AAG32250.1\|, \|11177374\|gb\|AAG32249.1\|, \|11177370\|gb\|AAG32247.1\|, \|11177368\|gb\|AAG32246.1\|, \|11177365\|gb\|AAG32245.1\|, \|11177363\|gb\|AAG32244.1\|, \|11177361\|gb\|AAG32243.1\|, \|11177359\|gb\|AAG32242.1\|, \|11177406\|gb\|AAG32265.1\|, \|11177394\|gb\|AAG32259.1\|, \|11177422\|gb\|AAG32273.1\|, \|11177402\|gb\|AAG32263.1\|, \|11177398\|gb\|AAG32261.1\|, \|11177418\|gb\|AAG32271.1\|, \|11177408\|gb\|AAG32266.1\|, \|1160069\|emb\|CAA92888.1\|, \|1477810\|gb\|AAB05488.1\|, \|57901072\|gb\|AAW57840.1\|, \|77167733\|gb\|ABA62826.1\|, \|82286715\|sp\|Q6SZT1\|Q6SZT1__9, \|38570404\|gb\|AAR24640.1\|, \|38570378\|gb\|AAR24627.1\|, \|54124762\|gb\|AAV30102.1\|, \|77167697\|gb\|ABA62808.1\|, \|3327763\|gb\|AAC41171.1\|, \|3327755\|gb\|AAC41167.1\|, \|3327765\|gb\|AAC41172.1\|, \|3327757\|gb\|AAC41168.1\|, \|3327771\|gb\|AAC41175.1\|, \|3327769\|gb\|AAC41174.1\|, \|3327749\|gb\|AAC41164.1\|, \|3327743\|gb\|AAC41161.1\|, \|3327734\|gb\|AAC41157.1\|, \|3327747\|gb\|AAC41163.1\|, \|3327736\|gb\|AAC41158.1\|, \|3327738\|gb\|AAC41159.1\|, \|3327761\|gb\|AAC41170.1\|, \|3327759\|gb\|AAC41169.1\|, \|3327745\|gb\|AAC41162.1\|, \|3327767\|gb\|AAC41173.1\|, \|3327740\|gb\|AAC41160.1\|, \|3327753\|gb\|AAC41166.1\|, \|22596557\|gb\|AAN03313.1\|AF45, \|1160095\|emb\|CAA92901.1\|, \|77167559\|gb\|ABA62739.1\|, \|3327751\|gb\|AAC41165.1\|, \|3218186\|emb\|CAB05097.1\|, \|3218172\|emb\|CAB05090.1\|, \|1160101\|emb\|CAA92904.1\|, \|1160077\|emb\|CAA92892.1\|, \|1160063\|emb\|CAA92885.1\|, \|23392783\|emb\|CAD26729.1\|, \|23392781\|emb\|CAD26728.1\|, \|23392779\|emb\|CAD26727.1\|, \|1160097\|emb\|CAA92902.1\|, \|1160105\|emb\|CAA92906.1\|, \|3218148\|emb\|CAB05078.1\|, \|1160081\|emb\|CAA92894.1\|, \|1160085\|emb\|CAA92896.1\|, \|57545284\|gb\|AAW51545.1\|, \|1160093\|emb\|CAA92900.1\|, \|1160073\|emb\|CAA92890.1\|, \|57545310\|gb\|AAW51558.1\|, \|77167461\|gb\|ABA62690.1\|, \|22596303\|gb\|AAN03087.1\|AF45, \|3218150\|emb\|CAB05079.1\|, \|77167561\|gb\|ABA62740.1\|, \|1160067\|emb\|CAA92887.1\|, \|1160059\|emb\|CAA92883.1\|, \|1160061\|emb\|CAA92884.1\|, \|1160079\|emb\|CAA92893.1\|, \|36365466\|gb\|AAQ86678.1\|, \|82283750\|sp\|Q66MS8\|Q66MS8__9, \|36365538\|gb\|AAQ86742.1\|, \|36365493\|gb\|AAQ86702.1\|, \|36365484\|gb\|AAQ86694.1\|, \|36365403\|gb\|AAQ86622.1\|, \|36365457\|gb\|AAQ86670.1\|, \|36365448\|gb\|AAQ86662.1\|, \|36365421\|gb\|AAQ86638.1\|, \|36365412\|gb\|AAQ86630.1\|, \|36365394\|gb\|AAQ86614.1\|, \|36365385\|gb\|AAQ86606.1\|, \|36365376\|gb\|AAQ86598.1\|, \|36365439\|gb\|AAQ86654.1\|, \|36365430\|gb\|AAQ86646.1\|, \|36365547\|gb\|AAQ86750.1\|, \|36365529\|gb\|AAQ86734.1\|, \|36365502\|gb\|AAQ86710.1\|, \|36365511\|gb\|AAQ86718.1\|, \|36365475\|gb\|AAQ86686.1\|, \|36365520\|gb\|AAQ86726.1\|, \|82295424\|sp\|Q8AC16\|Q8AC16__9, \|23392753\|emb\|CAD26714.1\|, \|23392751\|emb\|CAD26713.1\|, \|23392749\|emb\|CAD26712.1\|, \|57545350\|gb\|AAW51578.1\|, \|57545318\|gb\|AAW51562.1\|, \|57545292\|gb\|AAW51549.1\|, \|47118233\|gb\|AAT11231.1\|, \|3327730\|gb\|AAC41155.1\|, \|3327728\|gb\|AAC41154.1\|, \|3327682\|gb\|AAC41131.1\|, \|3327680\|gb\|AAC41130.1\|, \|3327732\|gb\|AAC41156.1\|, \|3327714\|gb\|AAC41147.1\|, \|3327726\|gb\|AAC41153.1\|, \|3327722\|gb\|AAC41151.1\|, \|3327716\|gb\|AAC41148.1\|, \|3327702\|gb\|AAC41141.1\|, \|3327700\|gb\|AAC41140.1\|, \|3327698\|gb\|AAC41139.1\|, \|3327696\|gb\|AAC41138.1\|, \|3327694\|gb\|AAC41137.1\|, \|3327692\|gb\|AAC41136.1\|, \|3327686\|gb\|AAC41133.1\|, \|3327684\|gb\|AAC41132.1\|, \|3327678\|gb\|AAC41129.1\|, \|3327712\|gb\|AAC41146.1\|, \|3327690\|gb\|AAC41135.1\|, \|3327720\|gb\|AAC41150.1\|, \|3327710\|gb\|AAC41145.1\|, \|3327706\|gb\|AAC41143.1\|, \|3327688\|gb\|AAC41134.1\|, \|3327704\|gb\|AAC41142.1\|, \|3327718\|gb\|AAC41149.1\|, \|3327708\|gb\|AAC41144.1\|, \|3327724\|gb\|AAC41152.1\|, \|38570400\|gb\|AAR24638.1\|, \|77168075\|gb\|ABA62997.1\|, \|77167969\|gb\|ABA62944.1\|, \|3218162\|emb\|CAB05085.1\|, \|3218160\|emb\|CAB05084.1\|, \|3218481\|emb\|CAB05073.1\|, \|77168123\|gb\|ABA63021.1\|, \|77168067\|gb\|ABA62993.1\|, \|23392777\|emb\|CAD26726.1\|, \|23392775\|emb\|CAD26725.1\|, \|23392773\|emb\|CAD26724.1\|, \|77168131\|gb\|ABA63025.1\|, \|57545342\|gb\|AAW51574.1\|, \|57545272\|gb\|AAW51539.1\|, \|77168342\|gb\|ABA63130.1\|, \|27446734\|gb\|AAL62480.1\|, \|24753986\|gb\|AAN64107.1\|, \|12964709\|gb\|AAK11283.1\|, \|77168215\|gb\|ABA63067.1\|, \|77167989\|gb\|ABA62954.1\|, \|10436172\|gb\|AAG16846.1\|, \|10436115\|gb\|AAG16796.1\|, \|10436105\|gb\|AAG16787.1\|, \|3163933\|emb\|CAA06949.1\|, \|10436143\|gb\|AAG16821.1\|, \|10436162\|gb\|AAG16838.1\|, \|10436153\|gb\|AAG16830.1\|, \|10436134\|gb\|AAG16813.1\|, \|10436124\|gb\|AAG16804.1\|, |

-continued

| VPR proteins |
| --- |
| \|1160089\|emb\|CAA92898.1\|, \|77167465\|gb\|ABA62692.1\|, \|77168079\|gb\|ABA62999.1\|, \|3218182\|emb\|CAB05095.1\|, \|3218180\|emb\|CAB05094.1\|, \|49472952\|gb\|AAT66294.1\|, \|1123016\|gb\|AAC54645.1\|, \|255649\|gb\|AAB23297.1\|, \|1123006\|gb\|AAC54636.1\|, \|3098586\|gb\|AAC68853.1\|,\|549427\|sp\|P35967\|VPR__HV1Y2, \|139385\|sp\|P05952\|VPR__HV1A2, \|328664\|gb\|AAB59878.1\|, \|3098576\|gb\|AAC68844.1\|, \|23392771\|emb\|CAD26723.1\|, \|23392769\|emb\|CAD26722.1\|, \|23392767\|emb\|CAD26721.1\|, \|78172816\|gb\|ABB29351.1\|, \|77168302\|gb\|ABA63110.1\|, \|77167723\|gb\|ABA62821.1\|, \|77167645\|gb\|ABA62782.1\|, \|77167521\|gb\|ABA62720.1\|, \|77168021\|gb\|ABA62970.1\|, \|77167983\|gb\|ABA62951.1\|, \|77167437\|gb\|ABA62678.1\|, \|77167987\|gb\|ABA62953.1\|, \|27446730\|gb\|AAL62478.1\|, \|77168237\|gb\|ABA63078.1\|, \|55275259\|gb\|AAV49471.1\|, \|59710499\|gb\|AAW88729.1\|, \|59710503\|gb\|AAW88731.1\|, \|59710501\|gb\|AAW88730.1\|, \|59710494\|gb\|AAW88727.1\|, \|59710490\|gb\|AAW88725.1\|, \|55275129\|gb\|AAV49354.1\|, \|55275119\|gb\|AAV49345.1\|, \|59710492\|gb\|AAW88726.1\|, \|59710488\|gb\|AAW88724.1\|, \|59710496\|gb\|AAW88728.1\|, \|55275139\|gb\|AAV49363.1\|, \|55275249\|gb\|AAV49462.1\|, \|55275239\|gb\|AAV49453.1\|, \|55275189\|gb\|AAV49408.1\|, \|55275199\|gb\|AAV49417.1\|, \|59710560\|gb\|AAW88757.1\|, \|59710564\|gb\|AAW88759.1\|, \|59710558\|gb\|AAW88756.1\|, \|59710556\|gb\|AAW88755.1\|, \|59710566\|gb\|AAW88760.1\|, \|59710562\|gb\|AAW88758.1\|, \|55275219\|gb\|AAV49435.1\|, \|59710548\|gb\|AAW88752.1\|, \|59710546\|gb\|AAW88751.1\|, \|59710538\|gb\|AAW88748.1\|, \|55275229\|gb\|AAV49444.1\|, \|59710554\|gb\|AAW88754.1\|, \|59710552\|gb\|AAW88753.1\|, \|59710542\|gb\|AAW88749.1\|, \|55275209\|gb\|AAV49426.1\|, \|59710544\|gb\|AAW88750.1\|, \|59710518\|gb\|AAW88738.1\|, \|59710516\|gb\|AAW88737.1\|, \|59710520\|gb\|AAW88739.1\|, \|55275179\|gb\|AAV49399.1\|, \|59710505\|gb\|AAW88732.1\|, \|55275159\|gb\|AAV49381.1\|, \|59710507\|gb\|AAW88733.1\|, \|59710528\|gb\|AAW88743.1\|, \|55275149\|gb\|AAV49372.1\|, \|59710509\|gb\|AAW88734.1\|, \|59710522\|gb\|AAW88740.1\|, \|59710513\|gb\|AAW88736.1\|, \|59710526\|gb\|AAW88742.1\|, \|59710524\|gb\|AAW88741.1\|, \|55275169\|gb\|AAV49390.1\|, \|59710536\|gb\|AAW88747.1\|, \|59710532\|gb\|AAW88745.1\|, \|59710530\|gb\|AAW88744.1\|, \|59710534\|gb\|AAW88746.1\|, \|57545352\|gb\|AAW51579.1\|, \|62548201\|gb\|AAX86752.1\|, \|62548181\|gb\|AAX86734.1\|, \|62548191\|gb\|AAX86743.1\|, \|77167709\|gb\|ABA62814.1\|, \|62548171\|gb\|AAX86725.1\|, \|62548161\|gb\|AAX86716.1\|, \|77168274\|gb\|ABA63096.1\|, \|77167799\|gb\|ABA62859.1\|, \|77167803\|gb\|ABA62861.1\|, \|77167729\|gb\|ABA62824.1\|, \|7416646\|dbj\|BAA93963.1\|, \|7416648\|dbj\|BAA93964.1\|, \|30027257\|gb\|AAP06260.1\|, \|7416678\|dbj\|BAA93979.1\|, \|7416676\|dbj\|BAA93978.1\|, \|7416682\|dbj\|BAA93981.1\|, \|7416680\|dbj\|BAA93980.1\|, \|1160087\|emb\|CAA92897.1\|, \|77167865\|gb\|ABA62892.1\|, \|1185542\|gb\|AAA87875.1\|, \|1477844\|gb\|AAB05505.1\|, \|77167493\|gb\|ABA62706.1\|, \|3327542\|gb\|AAC41064.1\|, \|3327524\|gb\|AAC41056.1\|, \|17046525\|gb\|AAL34565.1\|, \|17902151\|gb\|AAL47814.1\|, \|17864054\|gb\|AAL47047.1\|, \|2570332\|gb\|AAC32659.1\|, \|38491483\|gb\|AAR21895.1\|, \|62361772\|gb\|AAX81420.1\|, \|52421750\|gb\|AAU45386.1\|, \|57545374\|gb\|AAW51590.1\|, \|74315742\|gb\|ABA02468.1\|, \|62467702\|gb\|AAX83957.1\|, \|17902129\|gb\|AAL47796.1\|, \|17902107\|gb\|AAL47778.1\|, \|17902118\|gb\|AAL47787.1\|, \|17864034\|gb\|AAL47029.1\|, \|17902140\|gb\|AAL47805.1\|, \|17902096\|gb\|AAL47769.1\|, \|3403229\|gb\|AAC29062.1\|, \|31980439\|dbj\|BAC77758.1\|, \|31980429\|dbj\|BAC77749.1\|, \|4262340\|gb\|AAD14576.1\|, \|7321147\|emb\|CAB82229.1\|, \|74315752\|gb\|ABA02477.1\|, \|60218867\|gb\|AAX14845.1\|, \|74315782\|gb\|ABA02504.1\|, \|74315735\|gb\|ABA02462.1\|, \|17864044\|gb\|AAL47038.1\|, \|62467712\|gb\|AAX83966.1\|, \|25166949\|gb\|AAN73726.1\|AF48, \|22596351\|gb\|AAN03130.1\|AF45, \|15281443\|gb\|AAK94231.1\|AF36, \|39777387\|gb\|AAR30968.1\|, \|39777377\|gb\|AAR30959.1\|, \|82284358\|sp\|Q69GS5\|Q69GS5__9, \|61102671\|gb\|AAX37799.1\|, \|3808282\|gb\|AAC69308.1\|, \|22596547\|gb\|AAN03304.1\|AF45, \|25166869\|gb\|AAN73654.1\|AF48, \|39777437\|gb\|AAR31013.1\|, \|33331478\|gb\|AAQ10922.1\|, \|33331458\|gb\|AAQ10904.1\|, \|33331468\|gb\|AAQ10913.1\|, \|61102686\|gb\|AAX37812.1\|, \|37682444\|gb\|AAQ98140.1\|, \|25166647\|gb\|AAN73455.1\|AF48, \|22596517\|gb\|AAN03277.1\|AF45, \|22596537\|gb\|AAN03295.1\|AF45, \|29409329\|gb\|AAM67405.1\|, \|71794578\|emb\|CAI28820.1\|, \|29409317\|gb\|AAM67395.1\|, \|29409298\|gb\|AAM67378.1\|, \|71794607\|emb\|CAI28847.1\|, \|71794598\|emb\|CAI28838.1\|, \|29409310\|gb\|AAM67389.1\|, \|71794588\|emb\|CAI28829.1\|, \|25166889\|gb\|AAN73672.1\|AF48, \|22596507\|gb\|AAN03268.1\|AF45, \|14530266\|gb\|AAK65996.1\|AF31, \|22596235\|gb\|AAN03027.1\|AF45, \|5668926\|gb\|AAD46078.1\|AF076, \|62467719\|gb\|AAX83972.1\|, \|5733956\|gb\|AAD49793.1\|AF107, \|5059053\|gb\|AAD38892.1\|AF119, \|3947929\|gb\|AAC82619.1\|, \|5059044\|gb\|AAD38884.1\|AF119, \|1732488\|gb\|AAB38835.1\|, \|6690777\|gb\|AAF24336.1\|AF197, \|37683030\|gb\|AAQ98587.1\|, \|37683020\|gb\|AAQ98578.1\|, \|25166739\|gb\|AAN73537.1\|AF48, \|77167783\|gb\|ABA62851.1\|, \|49472943\|gb\|AAT66286.1\|, \|77167541\|gb\|ABA62730.1\|, \|77167311\|gb\|ABA62615.1\|, \|1185516\|gb\|AAA87862.1\|, \|2801507\|gb\|AAC82595.1\|, \|62291052\|sp\|P69729\|VPR__HV1P, \|62291051\|sp\|P69728\|VPR__HV1I, \|62291050\|sp\|P69727\|VPR__HV1H, \|62291049\|sp\|P69726\|VPR__HV1H, \|62291048\|sp\|P69725\|VPR__HV1B, \|328557\|gb\|AAB59869.1\|, \|326390\|gb\|AAA44203.1\|, \|328455\|gb\|AAA44998.1\|, \|139383\|sp\|P05927\|VPR__HV1B5, \|327463\|gb\|AAA44655.1\|, \|32261273\|gb\|AAP74173.1\|, \|37677817\|gb\|AAQ97491.1\|, \|37677807\|gb\|AAQ97482.1\|, \|32261269\|gb\|AAP74170.1\|, \|5001959\|gb\|AAD37230.1\|, \|5001949\|gb\|AAD37225.1\|, \|5001939\|gb\|AAD37220.1\|, \|5001929\|gb\|AAD37215.1\|, \|5001919\|gb\|AAD37210.1\|, \|77167845\|gb\|ABA62882.1\|, \|77167653\|gb\|ABA62786.1\|, \|59710511\|gb\|AAW88735.1\|, \|77167355\|gb\|ABA62637.1\|, \|77167757\|gb\|ABA62838.1\|, \|3378125\|gb\|AAC28448.1\|, \|77167605\|gb\|ABA62762.1\|, \|59901082\|gb\|AAW57849.1\|, \|77168137\|gb\|ABA63028.1\|, \|57869582\|gb\|AAW57631.1\|, \|74273514\|gb\|ABA01401.1\|, \|74273394\|gb\|ABA01383.1\|, \|74273404\|gb\|ABA01392.1\|, \|77167851\|gb\|ABA62885.1\|, \|77167751\|gb\|ABA62835.1\|, \|4324913\|gb\|AAD17177.1\|, \|4324907\|gb\|AAD17171.1\|, \|4324919\|gb\|AAD17183.1\|, \|17046685\|gb\|AAL34709.1\|, \|22596412\|gb\|AAN03184.1\|AF45, \|25166909\|gb\|AAN73690.1\|AF48, \|25166999\|gb\|AAN73771.1\|AF48, \|38491939\|gb\|AAR22302.1\|, \|11177449\|gb\|AAG32286.1\|, \|11177445\|gb\|AAG32284.1\|, \|11177440\|gb\|AAG32282.1\|, \|11177438\|gb\|AAG32281.1\|, |

VPR proteins

|11177436|gb|AAG32280.1|, |11177434|gb|AAG32279.1|, |11177432|gb|AAG32278.1|,
|11177430|gb|AAG32277.1|, |11177443|gb|AAG32283.1|, |11177447|gb|AAG32285.1|,
|11177428|gb|AAG32276.1|, |11177451|gb|AAG32287.1|, |77168346|gb|ABA63132.1|,
|22596225|gb|AAN03018.1|AF45, |77167597|gb|ABA62758.1|, |2393861|gb|AAB70158.1|,
|2393855|gb|AAB70155.1|, |40021886|gb|AAR37196.1|, |40021716|gb|AAR37077.1|,
|40021876|gb|AAR37189.1|, |40021866|gb|AAR37182.1|, |40021856|gb|AAR37175.1|,
|40021836|gb|AAR37161.1|, |40021826|gb|AAR37154.1|, |40021806|gb|AAR37140.1|,
|40021796|gb|AAR37133.1|, |40021776|gb|AAR37119.1|, |40021766|gb|AAR37112.1|,
|40021736|gb|AAR37091.1|, |40021726|gb|AAR37084.1|, |40021706|gb|AAR37070.1|,
|40021846|gb|AAR37168.1|, |40021746|gb|AAR37098.1|, |40021696|gb|AAR37063.1|,
|40021756|gb|AAR37105.1|, |40021816|gb|AAR37147.1|, |40021786|gb|AAR37126.1|,
|26518640|gb|AAN83914.1|, |77168358|gb|ABA63138.1|, |77167889|gb|ABA62904.1|,
|77167659|gb|ABA62789.1|, |77168129|gb|ABA63024.1|, |77167763|gb|ABA62841.1|,
|77167677|gb|ABA62798.1|, |4324801|gb|AAD17065.1|, |4324785|gb|AAD17049.1|,
|4324794|gb|AAD17058.1|, |4324776|gb|AAD17040.1|, |4324768|gb|AAD17032.1|,
|77168400|gb|ABA63159.1|, |77167701|gb|ABA62810.1|, |77167617|gb|ABA62768.1|,
|77167379|gb|ABA62649.1|, |7416654|dbj|BAA93967.1|, |7416652|dbj|BAA93966.1|,
|25166677|gb|AAN73482.1|AF48, |37677837|gb|AAQ97509.1|, |7416714|dbj|BAA93997.1|,
|7416710|dbj|BAA93995.1|, |7416712|dbj|BAA93996.1|, |62461846|gb|AAX83062.1|,
|67552989|gb|AAY68587.1|, |16118284|gb|AAL12661.1|, |77167833|gb|ABA62876.1|,
|77168145|gb|ABA63032.1|, |77167927|gb|ABA62923.1|, |71725965|gb|AAZ39101.1|,
|77167433|gb|ABA62676.1|, |77167759|gb|ABA62839.1|, |77167753|gb|ABA62836.1|,
|7416706|dbj|BAA93993.1|, |7416704|dbj|BAA93992.1|, |818218|gb|AAB47930.1|,
|77168270|gb|ABA63094.1|, |45361092|gb|AAS59317.1|, |77168374|gb|ABA63146.1|,
|25166749|gb|AAN73546.1|AF48, |16118387|gb|AAL12751.1|, |77167537|gb|ABA62728.1|,
|15788300|gb|AAL07747.1|, |77167991|gb|ABA62955.1|, |57545336|gb|AAW51571.1|,
|57545332|gb|AAW51569.1|, |77168352|gb|ABA63135.1|, |77168115|gb|ABA63017.1|,
|57545328|gb|AAW51567.1|, |1185536|gb|AAA87872.1|, |1477842|gb|AAB05504.1|,
|1477838|gb|AAB05502.1|, |1477834|gb|AAB05500.1|, |1477840|gb|AAB05503.1|,
|1477832|gb|AAB05499.1|, |1477822|gb|AAB05494.1|, |1477828|gb|AAB05497.1|,
|1185534|gb|AAA87871.1|, |82295316|sp|Q89494|Q89494__9, |1477826|gb|AAB05496.1|,
|1477824|gb|AAB05495.1|, |1477906|gb|AAB05536.1|, |1477904|gb|AAB05535.1|,
|1477894|gb|AAB05530.1|, |1477908|gb|AAB05537.1|, |1477900|gb|AAB05533.1|,
|1477898|gb|AAB05532.1|, |1477902|gb|AAB05534.1|, |1477896|gb|AAB05531.1|,
|1477892|gb|AAB05529.1|, |24753956|gb|AAN64083.1|, |1185532|gb|AAA87870.1|,
|1477866|gb|AAB05516.1|, |1477868|gb|AAB05517.1|, |1477816|gb|AAB05491.1|,
|1477814|gb|AAB05490.1|, |1477830|gb|AAB05498.1|, |1477864|gb|AAB05515.1|,
|1477862|gb|AAB05514.1|, |1477818|gb|AAB05492.1|, |1477836|gb|AAB05501.1|,
|1477820|gb|AAB05493.1|, |25166959|gb|AAN73735.1|AF48,
|82286714|sp|Q6SZS8|Q6SZS8__9, |38570410|gb|AAR24643.1|, |38570398|gb|AAR24637.1|,
|1477812|gb|AAB05489.1|, |25167079|gb|AAN73843.1|AF48, |77167955|gb|ABA62937.1|,
|61102652|gb|AAX37783.1|, |61102644|gb|AAX37776.1|, |61102580|gb|AAX37720.1|,
|7021461|gb|AAF35360.1|, |83026798|gb|ABB96435.1|, |1477890|gb|AAB05528.1|,
|1477888|gb|AAB05527.1|, |2393851|gb|AAB70153.1|, |1477886|gb|AAB05526.1|,
|1477878|gb|AAB05522.1|, |13540185|gb|AAK29351.1|, |13569231|gb|AAK30975.1|AF28,
|67633319|gb|AAY78571.1|, |66473533|gb|AAY46413.1|, |67633313|gb|AAY78566.1|,
|54124752|gb|AAV30093.1|, |77168221|gb|ABA63070.1|, |77168199|gb|ABA63059.1|,
|37682464|gb|AAQ98158.1|, |13540175|gb|AAK29342.1|, |34330005|gb|AAO65891.1|,
|26245452|gb|AAN77382.1|, |59003551|gb|AAW83558.1|, |25167069|gb|AAN73834.1|AF48,
|17046555|gb|AAL34592.1|, |67553064|gb|AAY68654.1|, |1185520|gb|AAA87864.1|,
|57869638|gb|AAW57681.1|, |77168364|gb|ABA63141.1|, |17046785|gb|AAL34799.1|,
|15281463|gb|AAK94249.1|AF36, |77168398|gb|ABA63158.1|, |38892719|gb|AAR27716.1|,
|73913924|gb|AAZ91892.1|, |4324891|gb|AAD17155.1|, |4324882|gb|AAD17146.1|,
|4324900|gb|AAD17164.1|, |67553054|gb|AAY68645.1|, |4324759|gb|AAD17023.1|,
|4324750|gb|AAD17014.1|, |4324741|gb|AAD17005.1|, |58220953|gb|AAW68136.1|,
|68522067|gb|AAY98661.1|, |58221030|gb|AAW68205.1|, |82571312|gb|ABB84079.1|,
|38892739|gb|AAR27734.1|, |68522117|gb|AAY98706.1|, |68522077|gb|AAY98670.1|,
|37682413|gb|AAQ98112.1|, |17046815|gb|AAL34826.1|, |82571272|gb|ABB84043.1|,
|73913836|gb|AAZ91813.1|, |59003670|gb|AAW83665.1|, |55139323|gb|AAV41339.1|,
|11761292|dbj|BAB19230.1|, |73913866|gb|AAZ91840.1|, |38892648|gb|AAR27653.1|,
|12957271|gb|AAK09117.1|AF32, |12957265|gb|AAK09112.1|AF32,
|82301933|sp|Q98VM8|Q98VM8__9, |16751252|gb|AAL05328.1|,
|73913826|gb|AAZ91804.1|, |59003640|gb|AAW83638.1|, |16751242|gb|AAL05319.1|,
|16751232|gb|AAL05310.1|, |17046695|gb|AAL34718.1|, |73913816|gb|AAZ91795.1|,
|38892602|gb|AAR27612.1|, |68522156|gb|AAY98741.1|, |17046725|gb|AAL34745.1|,
|59003561|gb|AAW83567.1|, |26245472|gb|AAN77400.1|, |17046535|gb|AAL34574.1|,
|46486649|gb|AAS98754.1|, |15281492|gb|AAK94275.1|AF36, |58220963|gb|AAW68145.1|,
|58221020|gb|AAW68196.1|, |26245462|gb|AAN77391.1|, |67553008|gb|AAY68604.1|,
|58220973|gb|AAW68154.1|, |55139352|gb|AAV41365.1|, |17046645|gb|AAL34673.1|,
|37682513|gb|AAQ98202.1|, |77167647|gb|ABA62783.1|, |57869611|gb|AAW57657.1|,
|67553074|gb|AAY68663.1|, |82571409|gb|ABB84166.1|, |26000267|gb|AAN75301.1|,
|17046891|gb|AAL34894.1|, |24181511|gb|AAN47130.1|, |24181501|gb|AAN47121.1|,
|38892776|gb|AAR27767.1|, |63098403|gb|AAY32444.1|, |17046575|gb|AAL34610.1|,
|56131603|gb|AAV80383.1|, |68521977|gb|AAY98580.1|, |37682424|gb|AAQ98122.1|,
|17046565|gb|AAL34601.1|, |4324849|gb|AAD17113.1|, |58221002|gb|AAW68180.1|,
|4324816|gb|AAD17080.1|, |4324810|gb|AAD17074.1|, |11761299|dbj|BAB19236.1|,
|11761269|dbj|BAB19211.1|, |12957307|gb|AAK09147.1|AF32, |12957301|gb|AAK09142.1|AF32,

| VPR proteins |
| --- |
| \|6016891\|dbj\|BAA85228.1\|, \|3252940\|gb\|AAD12090.1\|, \|23986254\|gb\|AAL12203.1\|, |
| \|23986210\|gb\|AAL12176.1\|, \|23986238\|gb\|AAL12194.1\|, \|23986224\|gb\|AAL12185.1\|, |
| \|11761283\|dbj\|BAB19223.1\|, \|3252950\|gb\|AAD12099.1\|, \|3252970\|gb\|AAD12117.1\|, |
| \|57869620\|gb\|AAW57665.1\|, \|3252922\|gb\|AAD12074.1\|, \|63098355\|gb\|AAY32401.1\|, |
| \|17046901\|gb\|AAL34903.1\|, \|12957295\|gb\|AAK09137.1\|AF32, \|12957283\|gb\|AAK09127.1\|AF32, |
| \|13569291\|gb\|AAK31029.1\|AF28, \|11761276\|dbj\|BAB19217.1\|, \|31559673\|dbj\|BAC77496.1\|, |
| \|11761584\|gb\|AAG38914.1\|, \|11761574\|gb\|AAG38905.1\|, \|27227854\|dbj\|BAC45027.1\|, |
| \|62956389\|gb\|AAY23522.1\|, \|62956379\|gb\|AAY23513.1\|, \|11761594\|gb\|AAG38923.1\|, |
| \|13569271\|gb\|AAK31011.1\|AF28, \|27227844\|dbj\|BAC45018.1\|, \|82571223\|gb\|ABB83999.1\|, |
| \|67553084\|gb\|AAY68672.1\|, \|17046755\|gb\|AAL34772.1\|, \|3252930\|gb\|AAD12081.1\|, |
| \|13569251\|gb\|AAK30993.1\|AF28, \|51572107\|gb\|AAU06756.1\|, \|82571263\|gb\|ABB84035.1\|, |
| \|68522107\|gb\|AAY98697.1\|, \|57338558\|gb\|AAW49353.1\|, \|46486666\|gb\|AAS98769.1\|, |
| \|73913996\|gb\|AAZ91956.1\|, \|59003660\|gb\|AAW83656.1\|, \|58220893\|gb\|AAW68082.1\|, |
| \|17046675\|gb\|AAL34700.1\|, \|15281423\|gb\|AAK94213.1\|AF36, \|63098383\|gb\|AAY32426.1\|, |
| \|12957337\|gb\|AAK09172.1\|AF32, \|12957331\|gb\|AAK09167.1\|AF32, \|55139282\|gb\|AAV41303.1\|, |
| \|73913757\|gb\|AAZ91742.1\|, \|59003630\|gb\|AAW83629.1\|, \|58220873\|gb\|AAW68064.1\|, |
| \|17046861\|gb\|AAL34867.1\|, \|59003521\|gb\|AAW83531.1\|, \|38892692\|gb\|AAR27692.1\|, |
| \|68521967\|gb\|AAY98571.1\|, \|55139302\|gb\|AAV41321.1\|, \|55139274\|gb\|AAV41296.1\|, |
| \|38892673\|gb\|AAR27675.1\|, \|12957373\|gb\|AAK09202.1\|AF32, \|12957367\|gb\|AAK09197.1\|AF32, |
| \|3252960\|gb\|AAD12108.1\|, \|62956398\|gb\|AAY23530.1\|, \|4324873\|gb\|AAD17137.1\|, |
| \|4324864\|gb\|AAD17128.1\|, \|68522057\|gb\|AAY98652.1\|, \|17046841\|gb\|AAL34849.1\|, |
| \|68522147\|gb\|AAY98733.1\|, \|58220883\|gb\|AAW68073.1\|, \|58220863\|gb\|AAW68055.1\|, |
| \|17046911\|gb\|AAL34912.1\|, \|13569321\|gb\|AAK31056.1\|AF28, \|63098423\|gb\|AAY32462.1\|, |
| \|82571352\|gb\|ABB84115.1\|, \|73913846\|gb\|AAZ91822.1\|, \|58220992\|gb\|AAW68171.1\|, |
| \|37682602\|gb\|AAQ98282.1\|, \|37682553\|gb\|AAQ98238.1\|, \|82571214\|gb\|ABB83991.1\|, |
| \|38892629\|gb\|AAR27636.1\|, \|63098316\|gb\|AAY32366.1\|, \|38892612\|gb\|AAR27621.1\|, |
| \|38892657\|gb\|AAR27661.1\|, \|68522027\|gb\|AAY98625.1\|, \|17046705\|gb\|AAL34727.1\|, |
| \|73913968\|gb\|AAZ91931.1\|, \|63098288\|gb\|AAY32341.1\|, \|63098393\|gb\|AAY32435.1\|, |
| \|17046625\|gb\|AAL34655.1\|, \|82571342\|gb\|ABB84106.1\|, \|38892701\|gb\|AAR27700.1\|, |
| \|59003650\|gb\|AAW83647.1\|, \|67553034\|gb\|AAY68627.1\|, \|73913895\|gb\|AAZ91866.1\|, |
| \|63098298\|gb\|AAY32350.1\|, \|16751262\|gb\|AAL05337.1\|, \|82571302\|gb\|ABB84070.1\|, |
| \|55139332\|gb\|AAV41347.1\|, \|68521987\|gb\|AAY98589.1\|, \|59003511\|gb\|AAW83522.1\|, |
| \|63098336\|gb\|AAY32384.1\|, \|37909405\|gb\|AAO65566.1\|, \|59003621\|gb\|AAW83621.1\|, |
| \|73913987\|gb\|AAZ91948.1\|, \|73913885\|gb\|AAZ91857.1\|, \|38892785\|gb\|AAR27775.1\|, |
| \|59003611\|gb\|AAW83612.1\|, \|59003571\|gb\|AAW83576.1\|, \|59003591\|gb\|AAW83594.1\|, |
| \|17046765\|gb\|AAL34781.1\|, \|67552999\|gb\|AAY68596.1\|, \|68521937\|gb\|AAY98544.1\|, |
| \|57338544\|gb\|AAW49341.1\|, \|46486630\|gb\|AAS98737.1\|, \|63098365\|gb\|AAY32410.1\|, |
| \|55139255\|gb\|AAV41279.1\|, \|82571204\|gb\|ABB83982.1\|, \|82571194\|gb\|ABB83973.1\|, |
| \|82571372\|gb\|ABB84133.1\|, \|58220913\|gb\|AAW68100.1\|, \|63098308\|gb\|AAY32359.1\|, |
| \|73913856\|gb\|AAZ91831.1\|, \|82571362\|gb\|ABB84124.1\|, \|68521957\|gb\|AAY98562.1\|, |
| \|68521997\|gb\|AAY98598.1\|, \|13569221\|gb\|AAK30966.1\|AF28, \|73913787\|gb\|AAZ91769.1\|, |
| \|82571243\|gb\|ABB84017.1\|, \|57869628\|gb\|AAW57672.1\|, \|59003581\|gb\|AAW83585.1\|, |
| \|73913905\|gb\|AAZ91875.1\|, \|73913777\|gb\|AAZ91760.1\|, \|68522017\|gb\|AAY98616.1\|, |
| \|67553017\|gb\|AAY68612.1\|, \|38892639\|gb\|AAR27645.1\|, \|73913934\|gb\|AAZ91901.1\|, |
| \|55139311\|gb\|AAV41329.1\|, \|73913797\|gb\|AAZ91778.1\|, \|58220903\|gb\|AAW68091.1\|, |
| \|17046871\|gb\|AAL34876.1\|, \|67553114\|gb\|AAY68699.1\|, \|17046605\|gb\|AAL34637.1\|, |
| \|55139343\|gb\|AAV41357.1\|, \|12957349\|gb\|AAK09182.1\|AF32, \|12957343\|gb\|AAK09177.1\|AF32, |
| \|18643013\|gb\|AAL74048.1\|, \|67553104\|gb\|AAY68690.1\|, \|67552979\|gb\|AAY68578.1\|, |
| \|82571322\|gb\|ABB84088.1\|, \|68522087\|gb\|AAY98679.1\|, \|58220933\|gb\|AAW68118.1\|, |
| \|67553044\|gb\|AAY68636.1\|, \|73913807\|gb\|AAZ91787.1\|, \|38892665\|gb\|AAR27668.1\|, |
| \|38892683\|gb\|AAR27684.1\|, \|17046825\|gb\|AAL34835.1\|, \|82571332\|gb\|ABB84097.1\|, |
| \|68521947\|gb\|AAY98553.1\|, \|17046615\|gb\|AAL34646.1\|, \|59003541\|gb\|AAW83549.1\|, |
| \|32344849\|gb\|AAM82304.1\|, \|17046595\|gb\|AAL34628.1\|, \|58220943\|gb\|AAW68127.1\|, |
| \|37935584\|gb\|AAO65557.1\|, \|38892729\|gb\|AAR27725.1\|, \|12957325\|gb\|AAK09162.1\|AF32, |
| \|22596255\|gb\|AAN03045.1\|AF45, \|68522097\|gb\|AAY98688.1\|, \|78172827\|gb\|ABB29361.1\|, |
| \|58221040\|gb\|AAW68214.1\|, \|58220923\|gb\|AAW68109.1\|, \|82571233\|gb\|ABB84008.1\|, |
| \|12957259\|gb\|AAK09107.1\|AF32, \|12957247\|gb\|AAK09097.1\|AF32, \|26000257\|gb\|AAN75292.1\|, |
| \|63098413\|gb\|AAY32453.1\|, \|17046795\|gb\|AAL34808.1\|, \|13172885\|gb\|AAK14233.1\|, |
| \|11321011\|gb\|AAG34004.1\|, \|82303319\|sp\|Q9DQ13\|Q9DQ13_9, \|11321021\|gb\|AAG34013.1\|, |
| \|11321031\|gb\|AAG34022.1\|, \|11321001\|gb\|AAG33995.1\|, \|32344839\|gb\|AAM82295.1\|, |
| \|38892622\|gb\|AAR27630.1\|, \|37682563\|gb\|AAQ98247.1\|, \|12957277\|gb\|AAK09122.1\|AF32, |
| \|68522007\|gb\|AAY98607.1\|, \|82571399\|gb\|ABB84157.1\|, \|82571253\|gb\|ABB84026.1\|, |
| \|38892757\|gb\|AAR27750.1\|, \|15281502\|gb\|AAK94284.1\|AF36, \|63098374\|gb\|AAY32418.1\|, |
| \|63098326\|gb\|AAY32375.1\|, \|51572097\|gb\|AAU06747.1\|, \|82571282\|gb\|ABB84052.1\|, |
| \|73913876\|gb\|AAZ91849.1\|, \|1353864\|gb\|AAB36503.1\|, \|17046585\|gb\|AAL34619.1\|, |
| \|32261488\|gb\|AAP76550.1\|, \|17046665\|gb\|AAL34691.1\|, \|68522127\|gb\|AAY98715.1\|, |
| \|57338551\|gb\|AAW49347.1\|, \|46486657\|gb\|AAS98761.1\|, \|82571382\|gb\|ABB84142.1\|, |
| \|37682484\|gb\|AAQ98176.1\|, \|11761286\|dbj\|BAB19225.1\|, \|32261468\|gb\|AAP76532.1\|, |
| \|37682503\|gb\|AAQ98193.1\|, \|12957313\|gb\|AAK09152.1\|AF32, \|12957289\|gb\|AAK09132.1\|AF32, |
| \|7321137\|emb\|CAB82220.1\|, \|17046921\|gb\|AAL34921.1\|, \|32261459\|gb\|AAP76524.1\|, |
| \|68522037\|gb\|AAY98634.1\|, \|13569261\|gb\|AAK31002.1\|AF28, \|59003601\|gb\|AAW83603.1\|, |
| \|56193060\|gb\|AAV84139.1\|, \|57901091\|gb\|AAW57857.1\|, \|56193007\|gb\|AAV84112.1\|, |
| \|55139293\|gb\|AAV41313.1\|, \|32261498\|gb\|AAP76559.1\|, \|22596311\|gb\|AAN03094.1\|AF45, |
| \|45738223\|gb\|AAS75881.1\|, \|45738213\|gb\|AAS75872.1\|, \|17046851\|gb\|AAL34858.1\|, |
| \|82571292\|gb\|ABB84061.1\|, \|59003531\|gb\|AAW83540.1\|, \|68522047\|gb\|AAY98643.1\|, |
| \|15281473\|gb\|AAK94258.1\|AF36, \|63098433\|gb\|AAY32471.1\|, \|82571390\|gb\|ABB84149.1\|, |
| \|13569331\|gb\|AAK31065.1\|AF28, \|57338566\|gb\|AAW49360.1\|, \|46486639\|gb\|AAS98745.1\|, |

| VPR proteins |
| --- |
| \|58220982\|gb\|AAW68162.1\|, \|73913767\|gb\|AAZ91751.1\|, \|13569301\|gb\|AAK31038.1\|AF28, \|13569241\|gb\|AAK30984.1\|AF28, \|30269369\|gb\|AAP29647.1\|, \|13569281\|gb\|AAK31020.1\|AF28, \|45361078\|gb\|AAS59308.1\|, \|31559645\|dbj\|BAC77471.1\|, \|17046881\|gb\|AAL34885.1\|, \|17046715\|gb\|AAL34736.1\|, \|56193078\|gb\|AAV84184.1\|, \|31559627\|dbj\|BAC77455.1\|, \|61102604\|gb\|AAX37741.1\|, \|61102596\|gb\|AAX37734.1\|, \|61102588\|gb\|AAX37727.1\|, \|38892766\|gb\|AAR27758.1\|, \|55139264\|gb\|AAV41287.1\|, \|22596527\|gb\|AAN03286.1\|AF45, \|56193043\|gb\|AAV84130.1\|, \|17046735\|gb\|AAL34754.1\|, \|37682592\|gb\|AAQ98273.1\|, \|17046655\|gb\|AAL34682.1\|, \|26000277\|gb\|AAN75310.1\|, \|12957319\|gb\|AAK09157.1\|AF32, \|73913978\|gb\|AAZ91940.1\|, \|14530230\|gb\|AAK65964.1\|AF28, \|17981622\|gb\|AAL51092.1\|, \|12957361\|gb\|AAK09192.1\|AF32, \|12957355\|gb\|AAK09187.1\|AF32, \|12957253\|gb\|AAK09102.1\|AF32, \|67553094\|gb\|AAY68681.1\|, \|77167543\|gb\|ABA62731.1\|, \|77168161\|gb\|ABA63040.1\|, \|77167837\|gb\|ABA62878.1\|, \|77167563\|gb\|ABA62741.1\|, \|68522137\|gb\|AAY98724.1\|, \|56193094\|gb\|AAV84157.1\|, \|63081180\|gb\|AAY30342.1\|, \|48476376\|gb\|AAT44410.1\|, \|1477916\|gb\|AAB05541.1\|, \|1477910\|gb\|AAB05538.1\|, \|5668957\|gb\|AAD46101.1\|AF076, \|1477914\|gb\|AAB05540.1\|, \|1477912\|gb\|AAB05539.1\|, \|1477884\|gb\|AAB05525.1\|, \|1477882\|gb\|AAB05524.1\|, \|2393857\|gb\|AAB70156.1\|, \|82278725\|sp\|O36205\|O36205_9, \|2393865\|gb\|AAB70160.1\|, \|2393863\|gb\|AAB70159.1\|, \|82279702\|sp\|O42054\|O42054_9, \|24753964\|gb\|AAN64089.1\|, \|2393867\|gb\|AAB70161.1\|, \|1477798\|gb\|AAB05482.1\|, \|1477794\|gb\|AAB05480.1\|, \|1477876\|gb\|AAB05521.1\|, \|1477870\|gb\|AAB05518.1\|, \|1477874\|gb\|AAB05520.1\|, \|1477872\|gb\|AAB05519.1\|, \|2393859\|gb\|AAB70157.1\|, \|56193026\|gb\|AAV84121.1\|, \|77167479\|gb\|ABA62699.1\|, \|77168047\|gb\|ABA62983.1\|, \|77168250\|gb\|ABA63084.1\|, \|77168175\|gb\|ABA63047.1\|, \|57545356\|gb\|AAW51581.1\|, \|77167375\|gb\|ABA62647.1\|, \|77167373\|gb\|ABA62646.1\|, \|25166809\|gb\|AAN73600.1\|AF48, \|2194190\|gb\|AAB61128.1\|, \|77167581\|gb\|ABA62750.1\|, \|66864704\|gb\|AAY57430.1\|, \|66864694\|gb\|AAY57421.1\|, \|77168141\|gb\|ABA63030.1\|, \|4324834\|gb\|AAD17098.1\|, \|4324825\|gb\|AAD17089.1\|, \|4324840\|gb\|AAD17104.1\|, \|17046635\|gb\|AAL34664.1\|, \|17046775\|gb\|AAL34790.1\|, \|77168167\|gb\|ABA63043.1\|, \|77167327\|gb\|ABA62623.1\|, \|77167523\|gb\|ABA62721.1\|, \|37682454\|gb\|AAQ98149.1\|, \|77168282\|gb\|ABA63100.1\|, \|77167501\|gb\|ABA62710.1\|, \|77167871\|gb\|ABA62895.1\|, \|77167549\|gb\|ABA62734.1\|, \|77167527\|gb\|ABA62723.1\|, \|77167975\|gb\|ABA62947.1\|, \|77167631\|gb\|ABA62775.1\|, \|17046805\|gb\|AAL34817.1\|, \|17046545\|gb\|AAL34583.1\|, \|77168296\|gb\|ABA63107.1\|, \|25167039\|gb\|AAN73807.1\|AF48, \|61102678\|gb\|AAX37805.1\|, \|25167029\|gb\|AAN73798.1\|AF48, \|55735970\|gb\|AAV59701.1\|, \|45361068\|gb\|AAS59299.1\|, \|57901061\|gb\|AAW57830.1\|, \|15788250\|gb\|AAL07702.1\|, \|25166657\|gb\|AAN73464.1\|AF48, \|25166667\|gb\|AAN73473.1\|AF48, \|22596577\|gb\|AAN03331.1\|AF45, \|77168384\|gb\|ABA63151.1\|, \|77168187\|gb\|ABA63053.1\|, \|77167339\|gb\|ABA62629.1\|, \|61102636\|gb\|AAX37769.1\|, \|61102628\|gb\|AAX37762.1\|, \|57869657\|gb\|AAW57698.1\|, \|57869591\|gb\|AAW57639.1\|, \|25167059\|gb\|AAN73825.1\|AF48, \|25166819\|gb\|AAN73609.1\|AF48, \|82307224\|sp\|Q9WA46\|Q9WA46_9, \|4539050\|emb\|CAB39740.1\|, \|4539037\|emb\|CAB39919.1\|, \|25166697\|gb\|AAN73500.1\|AF48, \|3287165\|emb\|CAA75986.1\|0, \|37935902\|gb\|AAO47148.1\|0, \|3287129\|emb\|CAA75962.1\|0, \|3287124\|emb\|CAA75958.1\|0, \|3287160\|emb\|CAA75982.1\|0, \|3287119\|emb\|CAA75954.1\|0, \|14041639\|emb\|CAC38423.1\|0, \|14041629\|emb\|CAC38432.1\|0, \|3287083\|emb\|CAA75938.1\|0, \|37935843\|gb\|AAO47096.1\|0, \|463061\|gb\|AAA99881.1\|, \|13172678\|gb\|AAK14191.1\|0, \|13172696\|gb\|AAK14206.1\|0, \|13172690\|gb\|AAK14201.1\|0, \|3287114\|emb\|CAA75950.1\|, \|51599142\|gb\|AAU08226.1\|0, \|37935972\|gb\|AAO47210.1\|0, \|45644392\|gb\|AAS72946.1\|0, \|37935913\|gb\|AAO47157.1\|0, \|37935943\|gb\|AAO47184.1\|0, \|13172702\|gb\|AAK14211.1\|0, \|3287149\|emb\|CAA75978.1\|0, \|37935893\|gb\|AAO47140.1\|0, \|3287144\|emb\|CAA75974.1\|0, \|37935873\|gb\|AAO47123.1\|0, \|13172708\|gb\|AAK14216.1\|0, \|3287104\|emb\|CAA75942.1\|0, \|3287109\|emb\|CAA75946.1\|0, \|3287139\|emb\|CAA75970.1\|0, \|37935953\|gb\|AAO47193.1\|0, \|37935923\|gb\|AAO47166.1\|0, \|469243\|gb\|AAA44862.1\|0, \|37935863\|gb\|AAO47114.1\|0, \|3287134\|emb\|CAA75966.1\|0, \|16755647\|gb\|AAL28059.1\|0, \|13172714\|gb\|AAK14221.1\|, \|37935982\|gb\|AAO47219.1\|0, \|3287078\|emb\|CAA75934.1\|0, \|37935962\|gb\|AAO47201.1\|0, \|37935882\|gb\|AAO47131.1\|0, \|37935933\|gb\|AAO47175.1\|0, \|13172684\|gb\|AAK14196.1\|0, \|37935853\|gb\|AAO47105.1\|0, \|77168332\|gb\|ABA63125.1\|, \|77167725\|gb\|ABA62822.1\|, \|77168211\|gb\|ABA63065.1\|, \|51572126\|gb\|AAU06773.1\|, \|15281453\|gb\|AAK94240.1\|AF36, \|77167821\|gb\|ABA62870.1\|, \|5668884\|gb\|AAD46046.1\|AF075, \|38679152\|gb\|AAR26405.1\|, \|22596321\|gb\|AAN03103.1\|AF45, \|1160071\|emb\|CAA92889.1\|, \|77167897\|gb\|ABA62908.1\|, \|25166969\|gb\|AAN73744.1\|AF48, \|37682474\|gb\|AAQ98167.1\|, \|25166989\|gb\|AAN73762.1\|AF48, \|1160099\|emb\|CAA92903.1\|, \|39777397\|gb\|AAR30977.1\|, \|38326773\|gb\|AAR17515.1\|, \|25166632\|gb\|AAN73441.1\|AF48, \|25167019\|gb\|AAN73789.1\|AF48, \|25167009\|gb\|AAN73780.1\|AF48, \|25166829\|gb\|AAN73618.1\|AF48, \|25166779\|gb\|AAN73573.1\|AF48, \|13569311\|gb\|AAK31047.1\|AF28, \|71726035\|gb\|AAZ39164.1\|, \|32261478\|gb\|AAP76541.1\|, \|38892747\|gb\|AAR27741.1\|, \|63098346\|gb\|AAY32393.1\|, \|71725955\|gb\|AAZ39092.1\|, \|77167891\|gb\|ABA62905.1\|, \|78172834\|gb\|ABB29367.1\|, \|1160043\|emb\|CAA92875.1\|, \|29119339\|gb\|AAO63253.1\|, \|77168382\|gb\|ABA63150.1\|, \|77167873\|gb\|ABA62896.1\|, \|77168386\|gb\|ABA63152.1\|, \|77168147\|gb\|ABA63033.1\|, \|3327803\|gb\|AAC41191.1\|, \|3327801\|gb\|AAC41190.1\|, \|3327799\|gb\|AAC41189.1\|, \|3327797\|gb\|AAC41188.1\|, \|3327795\|gb\|AAC41187.1\|, \|3327793\|gb\|AAC41186.1\|, \|3327791\|gb\|AAC41185.1\|, \|3327787\|gb\|AAC41183.1\|, \|3327783\|gb\|AAC41181.1\|, \|3327779\|gb\|AAC41179.1\|, \|3327777\|gb\|AAC41178.1\|, \|3327775\|gb\|AAC41177.1\|, \|3327789\|gb\|AAC41184.1\|, \|3327781\|gb\|AAC41180.1\|, \|3327785\|gb\|AAC41182.1\|, \|3327773\|gb\|AAC41176.1\|, \|3327560\|gb\|AAC41072.1\|, \|3327558\|gb\|AAC41071.1\|, \|3327564\|gb\|AAC41074.1\|, \|3327570\|gb\|AAC41077.1\|, \|3327555\|gb\|AAC41070.1\|, \|3327552\|gb\|AAC41069.1\|, \|3327546\|gb\|AAC41066.1\|, \|3327544\|gb\|AAC41065.1\|, \|3327548\|gb\|AAC41067.1\|, \|3327568\|gb\|AAC41076.1\|, \|3327550\|gb\|AAC41068.1\|, \|3327566\|gb\|AAC41075.1\|, \|3327562\|gb\|AAC41073.1\|, \|25166709\|gb\|AAN73510.1\|AF48, \|38679161\|gb\|AAR26413.1\|, |

-continued

| VPR proteins |
|---|
| |13540165|gb|AAK29333.1|, |5001987|gb|AAD37244.1|, |5001977|gb|AAD37239.1|, |5001967|gb|AAD37234.1|, |5001957|gb|AAD37229.1|, |5001985|gb|AAD37243.1|, |5001975|gb|AAD37238.1|, |5001965|gb|AAD37233.1|, |5001955|gb|AAD37228.1|, |5001947|gb|AAD37224.1|, |5001945|gb|AAD37223.1|, |5001937|gb|AAD37219.1|, |5001935|gb|AAD37218.1|, |5001927|gb|AAD37214.1|, |5001925|gb|AAD37213.1|, |5001917|gb|AAD37209.1|, |5001915|gb|AAD37208.1|, |82307158|sp|Q9W8N4|Q9W8N4__9, |5001973|gb|AAD37237.1|, |5001963|gb|AAD37232.1|, |5001983|gb|AAD37242.1|, |25166879|gb|AAN73663.1|AF48, |1772628|gb|AAC32296.1|, |57545368|gb|AAW51587.1|, |77167953|gb|ABA62936.1|, |77167333|gb|ABA62626.1|, |33438571|gb|AAA45066.2|, |73919591|sp|P19555|VPR_HV1S, |1171168|gb|AAA86249.1|, |38570384|gb|AAR24630.1|, |77167545|gb|ABA62732.1|, |77167393|gb|ABA62656.1|, |57545316|gb|AAW51561.1|, |77167323|gb|ABA62621.1|, |11177344|gb|AAG32241.1|, |11177336|gb|AAG32237.1|, |11177334|gb|AAG32236.1|, |11177332|gb|AAG32235.1|, |11177330|gb|AAG32234.1|, |11177328|gb|AAG32233.1|, |11177326|gb|AAG32232.1|, |11177324|gb|AAG32231.1|, |11177320|gb|AAG32229.1|, |11177317|gb|AAG32228.1|, |11177340|gb|AAG32239.1|, |11177322|gb|AAG32230.1|, |11177342|gb|AAG32240.1|, |11177338|gb|AAG32238.1|, |27446728|gb|AAL62477.1|, |24754007|gb|AAN64125.1|, |77168256|gb|ABA63087.1|, |45360161|gb|AAS59197.1|, |77168286|gb|ABA63102.1|, |77167883|gb|ABA62901.1|, |77167609|gb|ABA62764.1|, |77167743|gb|ABA62831.1|, |77167911|gb|ABA62915.1|, |77167775|gb|ABA62847.1|, |77167713|gb|ABA62816.1|, |77167505|gb|ABA62712.1|, |71726005|gb|AAZ39137.1|, |77167819|gb|ABA62869.1|, |71725985|gb|AAZ39119.1|, |71725975|gb|AAZ39110.1|, |77168183|gb|ABA63051.1|, |71726045|gb|AAZ39173.1|, |77167629|gb|ABA62774.1|, |1185548|gb|AAA87878.1|, |2393816|gb|AAB70135.1|, |2393812|gb|AAB70133.1|, |2393808|gb|AAB70131.1|, |82279708|sp|O42077|O42077__9, |2393810|gb|AAB70132.1|, |2393806|gb|AAB70130.1|, |2393802|gb|AAB70128.1|, |2393798|gb|AAB70126.1|, |2393794|gb|AAB70124.1|, |2393792|gb|AAB70123.1|, |82279700|sp|O42035|O42035__9, |2393800|gb|AAB70127.1|, |2393804|gb|AAB70129.1|, |2393796|gb|AAB70125.1|, |2393790|gb|AAB70122.1|, |2393814|gb|AAB70134.1|, |77167577|gb|ABA62748.1|, |57545288|gb|AAW51547.1|, |57545286|gb|AAW51546.1|, |7416698|dbj|BAA93989.1|, |7416692|dbj|BAA93986.1|, |1160053|emb|CAA92880.1|, |1160051|emb|CAA92879.1|, |5001941|gb|AAD37221.1|, |5001931|gb|AAD37216.1|, |5001921|gb|AAD37211.1|, |5001911|gb|AAD37206.1|, |5001989|gb|AAD37245.1|, |5001979|gb|AAD37240.1|, |77167827|gb|ABA62873.1|, |38570386|gb|AAR24631.1|, |38570380|gb|AAR24628.1|, |7416696|dbj|BAA93988.1|, |77168069|gb|ABA62994.1|, |34811837|gb|AAO40780.1|, |77167843|gb|ABA62881.1|, |38570396|gb|AAR24636.1|, |38570376|gb|AAR24626.1|, |38570382|gb|AAR24629.1|, |7416694|dbj|BAA93987.1|, |7416690|dbj|BAA93985.1|, |38570390|gb|AAR24633.1|, |77167383|gb|ABA62651.1|, |77168292|gb|ABA63105.1|, |3218174|emb|CAB05091.1|, |57545300|gb|AAW51553.1|, |77167747|gb|ABA62833.1|, |1477808|gb|AAB05487.1|, |1477806|gb|AAB05486.1|, |1477804|gb|AAB05485.1|, |1477800|gb|AAB05483.1|, |1477802|gb|AAB05484.1|, |77168322|gb|ABA63120.1|, |77167925|gb|ABA62922.1|, |77167569|gb|ABA62744.1|, |139391|sp|P05950|VPR_HV1MN, |328035|gb|AAA44855.1|, |57545348|gb|AAW51577.1|, |77168027|gb|ABA62973.1|, |77167935|gb|ABA62927.1|, |77168041|gb|ABA62980.1|, |77167453|gb|ABA62686.1|, |22532144|gb|AAM97855.1|AF46, |22532134|gb|AAM97846.1|AF46, |38491784|gb|AAR22163.1|, |17352347|gb|AAL01566.1|, |62467692|gb|AAX83948.1|, |51950723|gb|AAU14915.1|, |14290032|gb|AAK59215.1|, |51950713|gb|AAU14906.1|, |15788241|gb|AAL07694.1|, |9931093|emb|CAC05364.1|, |37682533|gb|AAQ98220.1|, |6651458|gb|AAF22310.1|AF193, |74315725|gb|ABA02453.1|, |38491902|gb|AAR22269.1|, |38679144|gb|AAR26398.1|, |38679135|gb|AAR26390.1|, |22596487|gb|AAN03250.1|AF45, |5668914|gb|AAD46068.1|AF076, |8886635|gb|AAF80534.1|AF179, |15209255|emb|CAC51034.1|, |38491757|gb|AAR22139.1|, |38491737|gb|AAR22121.1|, |18073404|emb|CAC87995.1|, |38491873|gb|AAR22243.1|, |22596467|gb|AAN03232.1|AF45, |15281433|gb|AAK94222.1|AF36, |61102563|gb|AAX37706.1|, |22596371|gb|AAN03148.1|AF45, |57869545|gb|AAW57598.1|, |22596422|gb|AAN03193.1|AF45, |77167931|gb|ABA62925.1|, |22596477|gb|AAN03241.1|AF45, |5305345|gb|AAD41599.1|AF071, |3808274|gb|AAD13361.1|, |3808264|gb|AAC69300.1|, |3808254|gb|AAC69291.1|, |61102663|gb|AAX37792.1|, |61102570|gb|AAX37712.1|, |61102547|gb|AAX37692.1|, |1890687|gb|AAC97544.1|, |25166929|gb|AAN73708.1|AF48, |37682523|gb|AAQ98211.1|, |31980419|dbj|BAC77740.1|, |31980409|dbj|BAC77731.1|, |57869554|gb|AAW57608.1|, |25166769|gb|AAN73564.1|AF48, |38491883|gb|AAR22252.1|, |22596265|gb|AAN03054.1|AF45, |22596401|gb|AAN03175.1|AF45, |22596331|gb|AAN03112.1|AF45, |22596434|gb|AAN03203.1|AF45, |61102620|gb|AAX37755.1|, |61102612|gb|AAX37748.1|, |22596381|gb|AAN03157.1|AF45, |61102555|gb|AAX37699.1|, |61102523|gb|AAX37671.1|, |22596361|gb|AAN03139.1|AF45, |22596286|gb|AAN03072.1|AF45, |22596245|gb|AAN03036.1|AF45, |25166687|gb|AAN73491.1|AF48, |25166789|gb|AAN73582.1|AF48, |22596275|gb|AAN03063.1|AF45, |3808244|gb|AAC69282.1|, |39777417|gb|AAR30995.1|, |22596447|gb|AAN03214.1|AF45, |39777427|gb|AAR31004.1|, |22596567|gb|AAN03322.1|AF45, |5305481|gb|AAD41669.1|AF075, |71148571|gb|AAZ28902.1|, |22596391|gb|AAN03166.1|AF45, |38491774|gb|AAR22154.1|, |38491747|gb|AAR22130.1|, |22532295|gb|AAM97888.1|AF49, |46946847|gb|AAT06637.1|, |18699152|gb|AAL78423.1|AF41, |56609314|gb|AAW03268.1|, |18699129|gb|AAL78403.1|AF41, |18699189|gb|AAL78449.1|AF41, |18699137|gb|AAL78410.1|AF41, |18699144|gb|AAL78416.1|AF41, |56609330|gb|AAW03282.1|, |56609324|gb|AAW03277.1|, |56609274|gb|AAW03232.1|, |56609264|gb|AAW03223.1|, |56609244|gb|AAW03205.1|, |56609304|gb|AAW03259.1|, |41353555|gb|AAS01342.1|, |56609294|gb|AAW03250.1|, |78172854|gb|ABB29385.1|, |22596457|gb|AAN03223.1|AF45, |45361158|gb|AAS59367.1|, |25166979|gb|AAN73753.1|AF48, |38491503|gb|AAR21913.1|, |22596497|gb|AAN03259.1|AF45, |13560262|dbj|BAB40913.1|0, |

| VPR proteins |
| --- |
| \|38491765\|gb\|AAR22146.1\|, \|22532285\|gb\|AAM97879.1\|AF49, \|18073414\|emb\|CAC88004.1\|, \|1899133\|gb\|AAC57013.1\|, \|46946838\|gb\|AAT06629.1\|, \|46946829\|gb\|AAT06621.1\|, \|14530240\|gb\|AAK65973.1\|AF28, \|24181491\|gb\|AAN47112.1\|, \|14530248\|gb\|AAK65980.1\|AF28, \|37682434\|gb\|AAQ98131.1\|, \|74315762\|gb\|ABA02486.1\|, \|5733945\|gb\|AAD49783.1\|AF107, \|7452902\|emb\|CAB86368.1\|, \|45361178\|gb\|AAS59379.1\|, \|1478060\|gb\|AAB51139.1\|, \|45361169\|gb\|AAS59373.1\|, \|38491716\|gb\|AAR22103.1\|, \|5531678\|gb\|AAD44397.1\|AF055, \|5305562\|gb\|AAD41698.1\|AF097, \|5531654\|gb\|AAD44376.1\|AF055, \|5305570\|gb\|AAD41705.1\|AF097, \|3132814\|gb\|AAC29080.1\|, \|3132804\|gb\|AAC29071.1\|, \|46946862\|gb\|AAT06650.1\|, \|33390882\|gb\|AAQ17101.1\|, \|38491569\|gb\|AAR21972.1\|, \|25807940\|gb\|AAN74527.1\|, \|25807930\|gb\|AAN74518.1\|, \|74315772\|gb\|ABA02495.1\|, \|5531670\|gb\|AAD44390.1\|AF055, \|5531662\|gb\|AAD44383.1\|AF055, \|5305578\|gb\|AAD41712.1\|AF097, \|5531646\|gb\|AAD44369.1\|AF055, \|38491599\|gb\|AAR21999.1\|, \|56609341\|gb\|AAW03291.1\|, \|56609284\|gb\|AAW03241.1\|, \|56609254\|gb\|AAW03214.1\|, \|38491641\|gb\|AAR22036.1\|, \|7657892\|emb\|CAB89146.1\|, \|38491726\|gb\|AAR22112.1\|, \|38491493\|gb\|AAR21904.1\|, \|71794616\|emb\|CAI28856.1\|, \|14289986\|gb\|AAK59174.1\|, \|38491671\|gb\|AAR22063.1\|, \|38491651\|gb\|AAR22045.1\|, \|38491513\|gb\|AAR21922.1\|, \|6466843\|gb\|AAF13058.1\|, \|38491631\|gb\|AAR22027.1\|, \|13517086\|dbj\|BAB40424.1\|, \|38491621\|gb\|AAR22018.1\|, \|45361190\|gb\|AAS59384.1\|, \|7452912\|emb\|CAB86377.1\|, \|38491559\|gb\|AAR21963.1\|, \|38491698\|gb\|AAR22087.1\|, \|38491616\|gb\|AAR22014.1\|, \|38491522\|gb\|AAR21930.1\|, \|38491579\|gb\|AAR21981.1\|, \|38491530\|gb\|AAR21937.1\|, \|38491608\|gb\|AAR22007.1\|, \|38491690\|gb\|AAR22080.1\|, \|1732479\|gb\|AAB38827.1\|, \|45361126\|gb\|AAS59344.1\|, \|6690770\|gb\|AAF24329.1\|AF197, \|38491706\|gb\|AAR22094.1\|, \|15982648\|gb\|AAL09936.1\|, \|45644384\|gb\|AAS72939.1\|, \|38491844\|gb\|AAR22217.1\|, \|71794626\|emb\|CAI28865.1\|, \|38491912\|gb\|AAR22278.1\|, \|38491549\|gb\|AAR21954.1\|, \|38491589\|gb\|AAR21990.1\|, \|38491892\|gb\|AAR22260.1\|, \|23194122\|gb\|AAN15030.1\|, \|37683001\|gb\|AAQ98561.1\|, \|37682981\|gb\|AAQ98543.1\|, \|37682892\|gb\|AAQ98464.1\|, \|33328323\|gb\|AAQ09612.1\|2, \|38491863\|gb\|AAR22234.1\|, \|38491854\|gb\|AAR22226.1\|, \|38491681\|gb\|AAR22072.1\|, \|38491539\|gb\|AAR21945.1\|, \|38491661\|gb\|AAR22054.1\|, \|14289996\|gb\|AAK59183.1\|, \|37496501\|emb\|CAD48457.1\|, \|37496485\|emb\|CAD48443.1\|, \|1537054\|gb\|AAC55462.1\|, \|5931495\|dbj\|BAA84672.1\|, \|6690756\|gb\|AAF24315.1\|AF197, \|28933405\|gb\|AAO62619.1\|AF46, \|11066501\|gb\|AAG28616.1\|AF25, \|11066491\|gb\|AAG28607.1\|AF25, \|14209301\|dbj\|BAB55910.1\|, \|6690763\|gb\|AAF24322.1\|AF197, \|11761604\|gb\|AAG38932.1\|, \|11761564\|gb\|AAG38896.1\|, \|37682971\|gb\|AAQ98534.1\|, \|37682824\|gb\|AAQ98405.1\|, \|37682814\|gb\|AAQ98396.1\|, \|37682804\|gb\|AAQ98387.1\|, \|37682734\|gb\|AAQ98324.1\|, \|37682991\|gb\|AAQ98552.1\|, \|18844740\|dbj\|BAB85462.1\|, \|18844730\|dbj\|BAB85453.1\|, \|37682744\|gb\|AAQ98333.1\|, \|37682882\|gb\|AAQ98455.1\|, \|37682864\|gb\|AAQ98441.1\|, \|45361116\|gb\|AAS59335.1\|, \|37682871\|gb\|AAQ98447.1\|, \|45361150\|gb\|AAS59362.1\|, \|19908410\|gb\|AAL96765.1\|, \|33328191\|gb\|AAQ09540.1\|, \|22297043\|gb\|AAM94499.1\|, \|37682931\|gb\|AAQ98498.1\|, \|37682714\|gb\|AAQ98306.1\|, \|37682961\|gb\|AAQ98525.1\|, \|37682774\|gb\|AAQ98360.1\|, \|82284899\|sp\|Q6JNE4\|Q6JNE4_9, \|45361138\|gb\|AAS59353.1\|, \|30720410\|gb\|AAP33678.1\|, \|57869667\|gb\|AAW57707.1\|, \|57869732\|gb\|AAW57765.1\|, \|57869723\|gb\|AAW57757.1\|, \|57869687\|gb\|AAW57725.1\|, \|37682913\|gb\|AAQ98482.1\|, \|37682754\|gb\|AAQ98342.1\|, \|37682764\|gb\|AAQ98351.1\|, \|77167661\|gb\|ABA62790.1\|, \|31559683\|dbj\|BAC77505.1\|, \|31559635\|dbj\|BAC77462.1\|, \|37682724\|gb\|AAQ98315.1\|, \|37682704\|gb\|AAQ98297.1\|, \|37682844\|gb\|AAQ98423.1\|, \|78100203\|gb\|ABB20906.1\|, \|57869714\|gb\|AAW57749.1\|, \|57869696\|gb\|AAW57733.1\|, \|45361202\|gb\|AAS59393.1\|, \|5931486\|dbj\|BAA84664.1\|, \|38491834\|gb\|AAR22208.1\|, \|57869677\|gb\|AAW57716.1\|, \|37682951\|gb\|AAQ98516.1\|, \|45361104\|gb\|AAS59326.1\|, \|57869701\|gb\|AAS59570.1\|, \|37682903\|gb\|AAQ98473.1\|, \|37683011\|gb\|AAQ98570.1\|, \|37682941\|gb\|AAQ98507.1\|, \|37682794\|gb\|AAQ98378.1\|, \|37682784\|gb\|AAQ98369.1\|, \|37682921\|gb\|AAQ98489.1\|, \|37682834\|gb\|AAQ98414.1\|, \|37682854\|gb\|AAQ98432.1\|, \|33328201\|gb\|AAQ09549.1\|, \|57901111\|gb\|AAW57875.1\|, \|3676492\|gb\|AAC61996.1\|, \|46243167\|gb\|AAS83693.1\|, \|46243159\|gb\|AAS83686.1\|, \|38491929\|gb\|AAR22293.1\|, \|3676484\|gb\|AAC61989.1\|, \|14290023\|gb\|AAK59207.1\|, \|14290014\|gb\|AAK59199.1\|, \|52421739\|gb\|AAU45378.1\|, \|37496493\|emb\|CAD48450.1\|, \|57545340\|gb\|AAW51573.1\|, \|3779264\|gb\|AAD03312.1\|, \|9368382\|emb\|CAB98171.1\|, \|4336343\|gb\|AAD17769.1\|, \|4336333\|gb\|AAD17759.1\|, \|46946854\|gb\|AAT06643.1\|, \|22596341\|gb\|AAN03121.1\|AF45, \|6580989\|gb\|AAF18398.1\|AF190, \|3114568\|gb\|AAD03186.1\|, \|37682543\|gb\|AAQ98229.1\|, \|8920155\|emb\|CAB96341.1\|, \|3288392\|emb\|CAA06812.1\|, \|47027391\|gb\|AAT08771.1\|, \|3403219\|gb\|AAC29053.1\|, \|3403211\|gb\|AAC29046.1\|, \|14579615\|gb\|AAK69332.1\|, \|3114551\|gb\|AAD03171.1\|, \|47118223\|gb\|AAT11213.1\|, \|47118253\|gb\|AAT11240.1\|, \|16118377\|gb\|AAL12742.1\|, \|45360171\|gb\|AAS59206.1\|, \|14579595\|gb\|AAK69314.1\|, \|15788280\|gb\|AAL07729.1\|, \|16118353\|gb\|AAL12721.1\|, \|15787962\|gb\|AAL07552.1\|, \|45360141\|gb\|AAS59179.1\|, \|45360151\|gb\|AAS59188.1\|, \|29119327\|gb\|AAO63242.1\|, \|29119318\|gb\|AAO63234.1\|, \|16118367\|gb\|AAL12733.1\|, \|16118314\|gb\|AAL12688.1\|, \|47118213\|gb\|AAT11204.1\|, \|16118331\|gb\|AAL12702.1\|, \|6090968\|gb\|AAF03415.1\|AF075, \|16118343\|gb\|AAL12712.1\|, \|5668942\|gb\|AAD46090.1\|AF077, \|15788290\|gb\|AAL07738.1\|, \|47118263\|gb\|AAT11249.1\|, \|16118264\|gb\|AAL12643.1\|, \|45360212\|gb\|AAS59243.1\|, \|16118397\|gb\|AAL12760.1\|, \|15788260\|gb\|AAL07711.1\|, \|14579605\|gb\|AAK69323.1\|, \|15788270\|gb\|AAL07720.1\|, \|6643029\|gb\|AAF20390.1\|, \|9368372\|emb\|CAB98189.1\|, \|45360192\|gb\|AAS59225.1\|, \|14290005\|gb\|AAK59191.1\|, \|38491824\|gb\|AAR22199.1\|, \|47118243\|gb\|AAT11222.1\|, \|16118304\|gb\|AAL12679.1\|, \|45360181\|gb\|AAS59215.1\|, \|32189802\|gb\|AAP75713.1\|, \|5305357\|gb\|AAD41609.1\|AF071, \|62946404\|gb\|AAY22381.1\|, \|37682572\|gb\|AAQ98255.1\|, \|77168097\|gb\|ABA63008.1\|, \|77168049\|gb\|ABA62984.1\|, \|77167909\|gb\|ABA62914.1\|, \|77168219\|gb\|ABA63069.1\|, \|77167495\|gb\|ABA62707.1\|, \|77167993\|gb\|ABA62956.1\|, \|77167777\|gb\|ABA62848.1\|, \|77168051\|gb\|ABA62985.1\|, \|77167435\|gb\|ABA62677.1\|, \|82295417\|sp\|Q8AC04\|Q8AC04_9, |

-continued

| VPR proteins |
|---|
| \|23392759\|emb\|CAD26717.1\|, \|23392757\|emb\|CAD26716.1\|, \|23392755\|emb\|CAD26715.1\|, \|27446732\|gb\|AAL62479.1\|, \|77168276\|gb\|ABA63097.1\|, \|77167691\|gb\|ABA62805.1\|, \|77167791\|gb\|ABA62855.1\|, \|77167599\|gb\|ABA62759.1\|, \|77167309\|gb\|ABA62614.1\|, \|77168189\|gb\|ABA63054.1\|, \|77167695\|gb\|ABA62807.1\|, \|77167419\|gb\|ABA62669.1\|, \|1072090\|gb\|AAC54546.1\|, \|3002889\|gb\|AAD03243.1\|, \|3002853\|gb\|AAD03211.1\|, \|37681534\|gb\|AAQ97644.1\|, \|37677777\|gb\|AAQ97455.1\|, \|77167807\|gb\|ABA62863.1\|, \|12964713\|gb\|AAK11285.1\|, \|1160049\|emb\|CAA92878.1\|, \|77167481\|gb\|ABA62700.1\|, \|77167467\|gb\|ABA62693.1\|, \|12964711\|gb\|AAK11284.1\|, \|77168125\|gb\|ABA63022.1\|, \|7416700\|dbj\|BAA93990.1\|, \|7416702\|dbj\|BAA93991.1\|, \|3327504\|gb\|AAC41047.1\|, \|3327540\|gb\|AAC41063.1\|, \|3327490\|gb\|AAC41040.1\|, \|3327538\|gb\|AAC41062.1\|, \|3327536\|gb\|AAC41061.1\|, \|3327534\|gb\|AAC41060.1\|, \|3327532\|gb\|AAC41059.1\|, \|3327521\|gb\|AAC41055.1\|, \|3327519\|gb\|AAC41054.1\|, \|3327517\|gb\|AAC41053.1\|, \|3327514\|gb\|AAC41052.1\|, \|3327510\|gb\|AAC41050.1\|, \|3327496\|gb\|AAC41043.1\|, \|3327488\|gb\|AAC41039.1\|, \|3327528\|gb\|AAC41057.1\|, \|3327486\|gb\|AAC41038.1\|, \|3327530\|gb\|AAC41058.1\|, \|3327506\|gb\|AAC41048.1\|, \|3327500\|gb\|AAC41045.1\|, \|3327498\|gb\|AAC41044.1\|, \|3327512\|gb\|AAC41051.1\|, \|3327502\|gb\|AAC41046.1\|, \|3327494\|gb\|AAC41042.1\|, \|3327508\|gb\|AAC41049.1\|, \|3327492\|gb\|AAC41041.1\|, \|55735997\|gb\|AAV59725.1\|, \|50404191\|gb\|AAT76861.1\|, \|77168334\|gb\|ABA63126.1\|, \|25166759\|gb\|AAN73555.1\|AF48, \|77167703\|gb\|ABA62811.1\|, \|77167401\|gb\|ABA62660.1\|, \|38491919\|gb\|AAR22284.1\|, \|23394930\|gb\|AAN31651.1\|, \|1160057\|emb\|CAA92882.1\|, \|16118254\|gb\|AAL12634.1\|, \|7416684\|dbj\|BAA93982.1\|, \|3002871\|gb\|AAD03227.1\|, \|77167717\|gb\|ABA62818.1\|, \|77168149\|gb\|ABA63034.1\|, \|46254439\|gb\|AAS86190.1\|, \|77168083\|gb\|ABA63001.1\|, \|46254417\|gb\|AAS86175.1\|, \|3002843\|gb\|AAD03202.1\|, \|57869601\|gb\|AAW57648.1\|, \|77167583\|gb\|ABA62751.1\|, \|77167413\|gb\|ABA62666.1\|, \|77167395\|gb\|ABA62657.1\|, \|77167861\|gb\|ABA62890.1\|, \|77167405\|gb\|ABA62662.1\|, \|7416722\|dbj\|BAA94001.1\|, \|7416718\|dbj\|BAA93999.1\|, \|7416716\|dbj\|BAA93998.1\|, \|82283749\|sp\|Q66MS6\|Q66MS6_9, \|29119345\|gb\|AAO63258.1\|, \|82283743\|sp\|Q66MR4\|Q66MR4_9, \|7416720\|dbj\|BAA94000.1\|, \|77168225\|gb\|ABA63072.1\|, \|77167903\|gb\|ABA62911.1\|, \|77167651\|gb\|ABA62785.1\|, \|77168310\|gb\|ABA63114.1\|, \|77168288\|gb\|ABA63103.1\|, \|77167869\|gb\|ABA62894.1\|, \|77167489\|gb\|ABA62704.1\|, \|77167335\|gb\|ABA62627.1\|, \|77168201\|gb\|ABA63060.1\|, \|77168195\|gb\|ABA63057.1\|, \|77167357\|gb\|ABA62638.1\|, \|77167905\|gb\|ABA62912.1\|, \|77168304\|gb\|ABA63111.1\|, \|77168181\|gb\|ABA63050.1\|, \|1160045\|emb\|CAA92876.1\|, \|29119279\|gb\|AAO63199.1\|, \|3002862\|gb\|AAD03219.1\|, \|77167779\|gb\|ABA62849.1\|, \|57545324\|gb\|AAW51565.1\|, \|77167863\|gb\|ABA62891.1\|, \|15281483\|gb\|AAK94267.1\|AF36, \|1160109\|emb\|CAA92908.1\|, \|30038317\|gb\|AAP12630.1\|, \|1160111\|emb\|CAA92909.1\|, \|11641109\|gb\|AAG38459.1\|, \|11641105\|gb\|AAG38457.1\|, \|11641099\|gb\|AAG38454.1\|, \|11641107\|gb\|AAG38458.1\|, \|11641103\|gb\|AAG38456.1\|, \|11641101\|gb\|AAG38455.1\|, \|15407144\|gb\|AAG32145.1\|, \|15407142\|gb\|AAG32144.1\|, \|57545302\|gb\|AAW51554.1\|, \|1185524\|gb\|AAA87866.1\|, \|57545298\|gb\|AAW51552.1\|, \|77167613\|gb\|ABA62766.1\|, \|3218146\|emb\|CAB05077.1\|, \|77167781\|gb\|ABA62850.1\|, \|57545290\|gb\|AAW51548.1\|, \|3218184\|emb\|CAB05096.1\|, \|1055033\|gb\|AAA81039.1\|, \|14278628\|pdb\|1ESX\|A, \|3218475\|emb\|CAB05070.1\|, \|77167421\|gb\|ABA62670.1\|, \|77167377\|gb\|ABA62648.1\|, \|77167959\|gb\|ABA62939.1\|, \|2393846\|gb\|AAB70150.1\|, \|2393842\|gb\|AAB70148.1\|, \|2393828\|gb\|AAB70141.1\|, \|77167649\|gb\|ABA62784.1\|, \|77167341\|gb\|ABA62630.1\|, \|57545274\|gb\|AAW51540.1\|, \|77168023\|gb\|ABA62971.1\|, \|3218479\|emb\|CAB05072.1\|, \|3218144\|emb\|CAB05076.1\|, \|77167353\|gb\|ABA62636.1\|, \|77167853\|gb\|ABA62886.1\|, \|77167769\|gb\|ABA62844.1\|, \|77167805\|gb\|ABA62862.1\|, \|77167497\|gb\|ABA62708.1\|, \|77167351\|gb\|ABA62635.1\|, \|1160065\|emb\|CAA92886.1\|, \|25166919\|gb\|AAN73699.1\|AF48, \|3218140\|emb\|CAB05074.1\|, \|25166729\|gb\|AAN73528.1\|AF48, \|77168191\|gb\|ABA63055.1\|, \|77167997\|gb\|ABA62958.1\|, \|49472925\|gb\|AAT66270.1\|, \|77168235\|gb\|ABA63077.1\|, \|77168135\|gb\|ABA63027.1\|, \|77167663\|gb\|ABA62791.1\|, \|77167445\|gb\|ABA62682.1\|, \|77167735\|gb\|ABA62827.1\|, \|77167741\|gb\|ABA62830.1\|, \|2393838\|gb\|AAB70146.1\|, \|2393834\|gb\|AAB70144.1\|, \|2393830\|gb\|AAB70142.1\|, \|82279701\|sp\|O42045\|O42045_9, \|2393871\|gb\|AAB70163.1\|, \|2393840\|gb\|AAB70147.1\|, \|2393832\|gb\|AAB70143.1\|, \|2393869\|gb\|AAB70162.1\|, \|2393836\|gb\|AAB70145.1\|, \|2393824\|gb\|AAB70139.1\|, \|77167627\|gb\|ABA62773.1\|, \|77167573\|gb\|ABA62746.1\|, \|1160027\|emb\|CAA92867.1\|, \|77168314\|gb\|ABA63116.1\|, \|57545314\|gb\|AAW51560.1\|, \|77168328\|gb\|ABA63123.1\|, \|77168356\|gb\|ABA63137.1\|, \|77168029\|gb\|ABA62974.1\|, \|77168324\|gb\|ABA63121.1\|, \|77167715\|gb\|ABA62817.1\|, \|77167875\|gb\|ABA62897.1\|, \|77167829\|gb\|ABA62874.1\|, \|77167809\|gb\|ABA62864.1\|, \|829583\|gb\|AAA79679.1\|, \|829569\|gb\|AAA79667.1\|, \|829562\|gb\|AAA79661.1\|, \|829389\|gb\|AAA79528.1\|, \|829546\|gb\|AAA79647.1\|, \|829538\|gb\|AAA79640.1\|, \|829526\|gb\|AAA79632.1\|, \|829518\|gb\|AAA79625.1\|, \|829510\|gb\|AAA79618.1\|, \|829403\|gb\|AAA79540.1\|, \|829396\|gb\|AAA79534.1\|, \|829381\|gb\|AAA79521.1\|, \|829576\|gb\|AAA79673.1\|, \|327817\|gb\|AAB03747.1\|, \|139388\|sp\|P20883\|VPR_HV1JR, \|829554\|gb\|AAA79654.1\|, \|1160033\|emb\|CAA92870.1\|, \|7416650\|dbj\|BAA93965.1\|, \|3218178\|emb\|CAB05093.1\|, \|3218176\|emb\|CAB05092.1\|, \|328412\|gb\|AAA44983.1\|, \|1160075\|emb\|CAA92891.1\|, \|24753997\|gb\|AAN64116.1\|, \|57545280\|gb\|AAW51543.1\|, \|25166849\|gb\|AAN73636.1\|AF48, \|29893418\|gb\|AAP03071.1\|, \|77168254\|gb\|ABA63086.1\|, \|1160041\|emb\|CAA92874.1\|, \|1160031\|emb\|CAA92869.1\|, \|7416658\|dbj\|BAA93969.1\|, \|7416656\|dbj\|BAA93968.1\|, \|1160055\|emb\|CAA92881.1\|, \|77167363\|gb\|ABA62641.1\|, \|29119308\|gb\|AAO63225.1\|, \|77168300\|gb\|ABA63109.1\|, \|57545278\|gb\|AAW51542.1\|, \|1160023\|emb\|CAA92865.1\|, \|29119259\|gb\|AAC63181.1\|, \|3327628\|gb\|AAC41104.1\|, \|3327626\|gb\|AAC41103.1\|, \|3327622\|gb\|AAC41101.1\|, \|3327618\|gb\|AAC41099.1\|, \|3327612\|gb\|AAC41097.1\|, \|3327610\|gb\|AAC41096.1\|, \|3327608\|gb\|AAC41095.1\|, \|3327606\|gb\|AAC41094.1\|, \|3327604\|gb\|AAC41093.1\|, \|3327602\|gb\|AAC41092.1\|, \|3327600\|gb\|AAC41091.1\|, \|3327598\|gb\|AAC41090.1\|, \|3327596\|gb\|AAC41089.1\|, \|3327594\|gb\|AAC41088.1\|, |

| VPR proteins |
| --- |
| \|3327592\|gb\|AAC41087.1\|, \|3327590\|gb\|AAC41086.1\|, \|3327588\|gb\|AAC41085.1\|, \|3327584\|gb\|AAC41083.1\|, \|3327577\|gb\|AAC41080.1\|, \|3327573\|gb\|AAC41078.1\|, \|3327624\|gb\|AAC41102.1\|, \|3327614\|gb\|AAC41098.1\|, \|3327620\|gb\|AAC41100.1\|, \|3327575\|gb\|AAC41079.1\|, \|3327586\|gb\|AAC41084.1\|, \|3327580\|gb\|AAC41081.1\|, \|3327582\|gb\|AAC41082.1\|, \|77168229\|gb\|ABA63074.1\|, \|77167685\|gb\|ABA62802.1\|, \|5001981\|gb\|AAD37241.1\|, \|5001971\|gb\|AAD37236.1\|, \|5001951\|gb\|AAD37226.1\|, \|5001961\|gb\|AAD37231.1\|, \|3218158\|emb\|CAB05083.1\|, \|3218156\|emb\|CAB05082.1\|, \|77167639\|gb\|ABA62779.1\|, \|1160037\|emb\|CAA92872.1\|, \|77168252\|gb\|ABA63085.1\|, \|77168011\|gb\|ABA62965.1\|, \|77167643\|gb\|ABA62781.1\|, \|77167389\|gb\|ABA62654.1\|, \|77167361\|gb\|ABA62640.1\|, \|3327676\|gb\|AAC41128.1\|, \|3327674\|gb\|AAC41127.1\|, \|3327672\|gb\|AAC41126.1\|, \|3327668\|gb\|AAC41124.1\|, \|3327664\|gb\|AAC41122.1\|, \|3327662\|gb\|AAC41121.1\|, \|3327656\|gb\|AAC41118.1\|, \|3327652\|gb\|AAC41116.1\|, \|3327646\|gb\|AAC41113.1\|, \|3327642\|gb\|AAC41111.1\|, \|3327638\|gb\|AAC41109.1\|, \|3327636\|gb\|AAC41108.1\|, \|3327634\|gb\|AAC41107.1\|, \|3327632\|gb\|AAC41106.1\|, \|3327666\|gb\|AAC41123.1\|, \|3327630\|gb\|AAC41105.1\|, \|3327660\|gb\|AAC41120.1\|, \|3327654\|gb\|AAC41117.1\|, \|3327658\|gb\|AAC41119.1\|, \|3327648\|gb\|AAC41114.1\|, \|3327644\|gb\|AAC41112.1\|, \|3327670\|gb\|AAC41125.1\|, \|3327640\|gb\|AAC41110.1\|, \|3327650\|gb\|AAC41115.1\|, \|77167913\|gb\|ABA62916.1\|, \|77167923\|gb\|ABA62921.1\|, \|77167801\|gb\|ABA62860.1\|, \|77167469\|gb\|ABA62694.1\|, \|77167601\|gb\|ABA62760.1\|, \|77167487\|gb\|ABA62703.1\|, \|77167315\|gb\|ABA62617.1\|, \|77168348\|gb\|ABA63133.1\|, \|77167625\|gb\|ABA62772.1\|, \|77167877\|gb\|ABA62898.1\|, \|77167399\|gb\|ABA62659.1\|, \|77168157\|gb\|ABA63038.1\|, \|77167619\|gb\|ABA62769.1\|, \|77167321\|gb\|ABA62620.1\|, \|77167415\|gb\|ABA62667.1\|, \|139396\|sp\|P05951\|VPR__HV1SC, \|328637\|gb\|AAA45062.1\|, \|77167937\|gb\|ABA62928.1\|, \|77167483\|gb\|ABA62701.1\|, \|2393844\|gb\|AAB70149.1\|, \|2393826\|gb\|AAB70140.1\|, \|2393822\|gb\|AAB70138.1\|, \|2393820\|gb\|AAB70137.1\|, \|82279707\|sp\|O42071\|O42071__9, \|77168033\|gb\|ABA62976.1\|, \|29119269\|gb\|AAC63190.1\|, \|77168246\|gb\|ABA63082.1\|, \|77167973\|gb\|ABA62946.1\|, \|77168404\|gb\|ABA63161.1\|, \|77167475\|gb\|ABA62697.1\|, \|77167901\|gb\|ABA62910.1\|, \|77168121\|gb\|ABA63020.1\|, \|77168103\|gb\|ABA63011.1\|, \|77167849\|gb\|ABA62884.1\|, \|77167971\|gb\|ABA62945.1\|, \|57545308\|gb\|AAW51557.1\|, \|77167921\|gb\|ABA62920.1\|, \|77167313\|gb\|ABA62616.1\|, \|77167681\|gb\|ABA62800.1\|, \|1160047\|emb\|CAA92877.1\|, \|77168388\|gb\|ABA63153.1\|, \|77168244\|gb\|ABA63081.1\|, \|77168185\|gb\|ABA63052.1\|, \|1160029\|emb\|CAA92868.1\|, \|77167503\|gb\|ABA62711.1\|, \|7416662\|dbj\|BAA93971.1\|, \|77168045\|gb\|ABA62982.1\|, \|82295423\|sp\|Q8AC14\|Q8AC14__9, \|23392765\|emb\|CAD26720.1\|, \|23392763\|emb\|CAD26719.1\|, \|23392761\|emb\|CAD26718.1\|, \|77167965\|gb\|ABA62942.1\|, \|77167999\|gb\|ABA62959.1\|, \|77167957\|gb\|ABA62938.1\|, \|77167439\|gb\|ABA62679.1\|, \|77167719\|gb\|ABA62819.1\|, \|57545346\|gb\|AAW51576.1\|, \|57545364\|gb\|AAW51585.1\|, \|1160025\|emb\|CAA92866.1\|, \|77168231\|gb\|ABA63075.1\|, \|77167885\|gb\|ABA62902.1\|, \|77168055\|gb\|ABA62987.1\|0, \|77167555\|gb\|ABA62737.1\|0, \|77167589\|gb\|ABA62754.1\|, \|77167365\|gb\|ABA62642.1\|, \|77167859\|gb\|ABA62889.1\|, \|77168173\|gb\|ABA63046.1\|, \|77168376\|gb\|ABA63147.1\|, \|77167575\|gb\|ABA62747.1\|, \|77168171\|gb\|ABA63045.1\|, \|77167945\|gb\|ABA62932.1\|, \|77167579\|gb\|ABA62749.1\|, \|77167977\|gb\|ABA62948.1\|, \|77167307\|gb\|ABA62613.1\|, \|77167855\|gb\|ABA62887.1\|, \|77167683\|gb\|ABA62801.1\|, \|3218142\|emb\|CAB05075.1\|, \|77167349\|gb\|ABA62634.1\|, \|77168113\|gb\|ABA63016.1\|, \|29119289\|gb\|AAC63208.1\|, \|57545306\|gb\|AAW51556.1\|, \|11095914\|gb\|AAG30118.1\|AF28, \|1176378\|gb\|AAA86733.1\|, \|77167417\|gb\|ABA62668.1\|, \|77168266\|gb\|ABA63092.1\|, \|77168344\|gb\|ABA63131.1\|, \|77168241\|gb\|ABA63080.1\|, \|77168109\|gb\|ABA63014.1\|, \|77167951\|gb\|ABA62935.1\|, \|77168354\|gb\|ABA63136.1\|, \|77167835\|gb\|ABA62877.1\|, \|77168017\|gb\|ABA62968.1\|, \|77167471\|gb\|ABA62695.1\|, \|77168290\|gb\|ABA63104.1\|, \|77168209\|gb\|ABA63064.1\|, \|77167655\|gb\|ABA62787.1\|, \|77168043\|gb\|ABA62981.1\|, \|77167397\|gb\|ABA62658.1\|, \|77168063\|gb\|ABA62991.1\|, \|77168077\|gb\|ABA62998.1\|, \|77167887\|gb\|ABA62903.1\|, \|77167359\|gb\|ABA62639.1\|, \|77167943\|gb\|ABA62931.1\|, \|77167459\|gb\|ABA62689.1\|, \|77168177\|gb\|ABA63048.1\|, \|77168013\|gb\|ABA62966.1\|, \|77167673\|gb\|ABA62796.1\|, \|77167387\|gb\|ABA62653.1\|, \|77167531\|gb\|ABA62725.1\|, \|74273483\|gb\|ABA01463.1\|, \|74273454\|gb\|ABA01437.1\|, \|74273473\|gb\|ABA01454.1\|, \|74273463\|gb\|ABA01445.1\|, \|77168151\|gb\|ABA63035.1\|, \|77168153\|gb\|ABA63036.1\|, \|57869647\|gb\|AAW57689.1\|, \|82283742\|sp\|Q66MR2\|Q66MR2__9, \|77168350\|gb\|ABA63134.1\|, \|82283738\|sp\|Q66MQ4\|Q66MQ4__9, \|82283739\|sp\|Q66MQ6\|Q66MQ6__9, \|82283736\|sp\|Q66MQ0\|Q66MQ0__9, \|82283741\|sp\|Q66MR0\|Q66MR0__9, \|82283735\|sp\|Q66MP5\|Q66MP5__9 |
| VIF proteins |
| \|1857262\|gb\|AAB54105.1\|, \|38491783\|gb\|AAR22162.1\|, \|29409328\|gb\|AAM67404.1\|, \|29409297\|gb\|AAM67377.1\|, \|38491862\|gb\|AAR22233.1\|, \|38491853\|gb\|AAR22225.1\|, \|17352346\|gb\|AAL01565.1\|, \|14290031\|gb\|AAK59214.1\|, \|38491928\|gb\|AAR22292.1\|, \|38491938\|gb\|AAR22301.1\|, \|38491793\|gb\|AAR22171.1\|, \|70633594\|gb\|AAZ06076.1\|, \|70633592\|gb\|AAZ06075.1\|, \|70633590\|gb\|AAZ06074.1\|, \|38491813\|gb\|AAR22189.1\|, \|38491803\|gb\|AAR22180.1\|, \|2570293\|gb\|AAC32649.1\|, \|1568312\|emb\|CAA02186.1\|, \|38491918\|gb\|AAR22283.1\|, \|57901100\|gb\|AAW57865.1\|, \|38326772\|gb\|AAR17514.1\|, \|57901060\|gb\|AAW57829.1\|, \|5668883\|gb\|AAD46045.1\|AF075, \|2570311\|gb\|AAC97572.1\|, \|7021458\|gb\|AAF35357.1\|, \|83026797\|gb\|ABB96434.1\|, \|70633584\|gb\|AAZ06071.1\|, \|83026787\|gb\|ABB96425.1\|, \|70633670\|gb\|AAZ06114.1\|, \|70633668\|gb\|AAZ06113.1\|, \|70633660\|gb\|AAZ06109.1\|, \|70633658\|gb\|AAZ06108.1\|, \|62461845\|gb\|AAX83061.1\|, \|70633656\|gb\|AAZ06107.1\|, \|70633662\|gb\|AAZ06110.1\|, \|70633666\|gb\|AAZ06112.1\|, \|70633664\|gb\|AAZ06111.1\|, \|70633588\|gb\|AAZ06073.1\|, \|70633586\|gb\|AAZ06072.1\|, \|70633466\|gb\|AAZ06013.1\|, \|70633464\|gb\|AAZ06012.1\|, \|70633468\|gb\|AAZ06014.1\|, \|70633558\|gb\|AAZ06058.1\|, \|70633556\|gb\|AAZ06057.1\|, \|70633582\|gb\|AAZ06070.1\|, |

| VPR proteins |
| --- |
| \|70633580\|gb\|AAZ06069.1\|, \|70633578\|gb\|AAZ06068.1\|, \|70633576\|gb\|AAZ06067.1\|, \|70633572\|gb\|AAZ06065.1\|, \|70633574\|gb\|AAZ06066.1\|, \|70633504\|gb\|AAZ06031.1\|, \|70633498\|gb\|AAZ06028.1\|, \|70633502\|gb\|AAZ06030.1\|, \|70633500\|gb\|AAZ06029.1\|, \|70633552\|gb\|AAZ06055.1\|, \|70633550\|gb\|AAZ06054.1\|, \|70633554\|gb\|AAZ06056.1\|, \|70633528\|gb\|AAZ06043.1\|, \|70633526\|gb\|AAZ06042.1\|, \|70633540\|gb\|AAZ06049.1\|, \|70633538\|gb\|AAZ06048.1\|, \|70633602\|gb\|AAZ06080.1\|, \|83026807\|gb\|ABB96443.1\|, \|70633642\|gb\|AAZ06100.1\|, \|70633604\|gb\|AAZ06081.1\|, \|70633620\|gb\|AAZ06089.1\|, \|70633616\|gb\|AAZ06087.1\|, \|70633618\|gb\|AAZ06088.1\|, \|70633614\|gb\|AAZ06086.1\|, \|70633514\|gb\|AAZ06036.1\|, \|70633512\|gb\|AAZ06035.1\|, \|70633516\|gb\|AAZ06037.1\|, \|70633476\|gb\|AAZ06017.1\|, \|70633474\|gb\|AAZ06016.1\|, \|83026777\|gb\|ABB96416.1\|, \|70633494\|gb\|AAZ06026.1\|, \|70633492\|gb\|AAZ06025.1\|, \|70633496\|gb\|AAZ06027.1\|, \|70633634\|gb\|AAZ06096.1\|, \|70633632\|gb\|AAZ06095.1\|, \|70633630\|gb\|AAZ06094.1\|, \|70633636\|gb\|AAZ06097.1\|, \|83026815\|gb\|ABB96450.1\|, \|70633640\|gb\|AAZ06099.1\|, \|70633638\|gb\|AAZ06098.1\|, \|70633564\|gb\|AAZ06061.1\|, \|70633562\|gb\|AAZ06060.1\|, \|70633560\|gb\|AAZ06059.1\|, \|70633644\|gb\|AAZ06101.1\|, \|70633674\|gb\|AAZ06116.1\|, \|70633672\|gb\|AAZ06115.1\|, \|70633610\|gb\|AAZ06084.1\|, \|70633608\|gb\|AAZ06083.1\|, \|70633606\|gb\|AAZ06082.1\|, \|70633622\|gb\|AAZ06090.1\|, \|70633524\|gb\|AAZ06041.1\|, \|70633522\|gb\|AAZ06040.1\|, \|70633520\|gb\|AAZ06039.1\|, \|70633518\|gb\|AAZ06038.1\|, \|70633462\|gb\|AAZ06011.1\|, \|70633460\|gb\|AAZ06010.1\|, \|70633488\|gb\|AAZ06023.1\|, \|70633486\|gb\|AAZ06022.1\|, \|70633490\|gb\|AAZ06024.1\|, \|45361201\|gb\|AAS59392.1\|, \|70633472\|gb\|AAZ06015.1\|, \|6580987\|gb\|AAF18396.1\|AF190, \|46254430\|gb\|AAS86183.1\|, \|70633544\|gb\|AAZ06051.1\|, \|70633542\|gb\|AAZ06050.1\|, \|70633546\|gb\|AAZ06052.1\|, \|70633548\|gb\|AAZ06053.1\|, \|70633508\|gb\|AAZ06033.1\|, \|70633506\|gb\|AAZ06032.1\|, \|70633510\|gb\|AAZ06034.1\|, \|328433\|gb\|AAB04038.1\|, \|902801\|gb\|AAB60573.1\|, \|2154663\|dbj\|BAA20319.1\|, \|2154653\|dbj\|BAA20315.1\|, \|2154659\|dbj\|BAA20318.1\|, \|2154657\|dbj\|BAA20317.1\|, \|2154655\|dbj\|BAA20316.1\|, \|2154665\|dbj\|BAA20320.1\|, \|78172843\|gb\|ABB29375.1\|, \|18699230\|gb\|AAL78476.1\|AF41, \|1151162\|gb\|AAA85232.1\|, \|2154671\|dbj\|BAA20323.1\|, \|2154667\|dbj\|BAA20321.1\|, \|2154673\|dbj\|BAA20324.1\|, \|74273413\|gb\|ABA01400.1\|, \|74273403\|gb\|ABA01391.1\|, \|74273393\|gb\|ABA01382.1\|, \|78172815\|gb\|ABB29350.1\|, \|70905447\|gb\|AAZ14782.1\|, \|70905445\|gb\|AAZ14781.1\|, \|70633568\|gb\|AAZ06063.1\|, \|70633566\|gb\|AAZ06062.1\|, \|70633570\|gb\|AAZ06064.1\|, \|70905433\|gb\|AAZ14775.1\|, \|70905431\|gb\|AAZ14774.1\|, \|70905429\|gb\|AAZ14773.1\|, \|74416538\|dbj\|BAA93914.1\|, \|57648405\|gb\|AAW55906.1\|, \|7416548\|dbj\|BAA93919.1\|, \|8218028\|emb\|CAB92788.1\|, \|1072089\|gb\|AAC54545.1\|, \|46254406\|gb\|AAS86165.1\|, \|70633628\|gb\|AAZ06093.1\|, \|70633626\|gb\|AAZ06092.1\|, \|70633624\|gb\|AAZ06091.1\|, \|829449\|gb\|AAA79580.1\|, \|829410\|gb\|AAA79546.1\|, \|829418\|gb\|AAA79553.1\|, \|829442\|gb\|AAA79574.1\|, \|829426\|gb\|AAA79560.1\|, \|829434\|gb\|AAA79567.1\|, \|2944132\|gb\|AAC05239.1\|, \|62956363\|gb\|AAY23499.1\|, \|62956368\|gb\|AAY23503.1\|, \|73625136\|gb\|AAZ79333.1\|, \|73625126\|gb\|AAZ79328.1\|, \|73625098\|gb\|AAZ79314.1\|, \|73625108\|gb\|AAZ79319.1\|, \|73625082\|gb\|AAZ79306.1\|, \|73625096\|gb\|AAZ79313.1\|, \|73625100\|gb\|AAZ79315.1\|, \|73625084\|gb\|AAZ79307.1\|, \|73625130\|gb\|AAZ79330.1\|, \|73625102\|gb\|AAZ79316.1\|, \|73625090\|gb\|AAZ79310.1\|, \|73625094\|gb\|AAZ79312.1\|, \|73625092\|gb\|AAZ79311.1\|, \|73625118\|gb\|AAZ79324.1\|, \|73625134\|gb\|AAZ79332.1\|, \|73625110\|gb\|AAZ79320.1\|, \|73625086\|gb\|AAZ79308.1\|, \|73625120\|gb\|AAZ79325.1\|, \|73625128\|gb\|AAZ79329.1\|, \|73625088\|gb\|AAZ79309.1\|, \|73625112\|gb\|AAZ79321.1\|, \|73625106\|gb\|AAZ79318.1\|, \|73625122\|gb\|AAZ79326.1\|, \|73625116\|gb\|AAZ79323.1\|, \|73625124\|gb\|AAZ79327.1\|, \|73625132\|gb\|AAZ79331.1\|, \|73625114\|gb\|AAZ79322.1\|, \|73625104\|gb\|AAZ79317.1\|, \|60195\|emb\|CAA77623.1\|, \|7416592\|dbj\|BAA93941.1\|, \|7416584\|dbj\|BAA93937.1\|, \|74273482\|gb\|ABA01462.1\|, \|74273472\|gb\|ABA01453.1\|, \|74273462\|gb\|ABA01444.1\|, \|74273453\|gb\|ABA01436.1\|, \|74273382\|gb\|ABA01373.1\|, \|74273374\|gb\|ABA01366.1\|, \|74273357\|gb\|ABA01352.1\|, \|74273348\|gb\|ABA01344.1\|, \|70905451\|gb\|AAZ14784.1\|, \|70905449\|gb\|AAZ14783.1\|, \|57901110\|gb\|AAW57874.1\|, \|70633650\|gb\|AAZ06104.1\|, \|70633646\|gb\|AAZ06102.1\|, \|70633648\|gb\|AAZ06103.1\|, \|70633446\|gb\|AAZ06003.1\|, \|70633454\|gb\|AAZ06007.1\|, \|70633452\|gb\|AAZ06006.1\|, \|70633456\|gb\|AAZ06008.1\|, \|55275138\|gb\|AAV49362.1\|, \|55275128\|gb\|AAV49353.1\|, \|55275258\|gb\|AAV49470.1\|, \|55275118\|gb\|AAV49344.1\|, \|55275178\|gb\|AAV49398.1\|, \|55275158\|gb\|AAV49380.1\|, \|55275148\|gb\|AAV49371.1\|, \|55275168\|gb\|AAV49389.1\|, \|55275238\|gb\|AAV49452.1\|, \|55275188\|gb\|AAV49407.1\|, \|55275198\|gb\|AAV49416.1\|, \|55275248\|gb\|AAV49461.1\|, \|55275228\|gb\|AAV49443.1\|, \|55275218\|gb\|AAV49434.1\|, \|55275208\|gb\|AAV49425.1\|, \|2154633\|dbj\|BAA20305.1\|, \|2154631\|dbj\|BAA20304.1\|, \|2154628\|dbj\|BAA20303.1\|, \|2154626\|dbj\|BAA20302.1\|, \|2154635\|dbj\|BAA20306.1\|, \|2154624\|dbj\|BAA20301.1\|, \|57901081\|gb\|AAW57848.1\|, \|57901071\|gb\|AAW57839.1\|, \|2154651\|dbj\|BAA20314.1\|, \|2154639\|dbj\|BAA20308.1\|, \|2154645\|dbj\|BAA20311.1\|, \|2154643\|dbj\|BAA20310.1\|, \|2154647\|dbj\|BAA20312.1\|, \|2154641\|dbj\|BAA20309.1\|, \|2154637\|dbj\|BAA20307.1\|, \|2154649\|dbj\|BAA20313.1\|, \|70633482\|gb\|AAZ06020.1\|, \|70633478\|gb\|AAZ06018.1\|, \|70633480\|gb\|AAZ06019.1\|, \|70633484\|gb\|AAZ06021.1\|, \|1123015\|gb\|AAC54644.1\|, \|255648\|gb\|AAB23296.1\|, \|1123005\|gb\|AAC54635.1\|, \|70633442\|gb\|AAZ06001.1\|, \|70633440\|gb\|AAZ06000.1\|, \|70633438\|gb\|AAZ05999.1\|, \|70633444\|gb\|AAZ06002.1\|, \|46254438\|gb\|AAS86189.1\|, \|46254416\|gb\|AAS86174.1\|, \|665535\|gb\|AAA76687.1\|, \|1398967\|dbj\|BAA12998.1\|, \|9629361\|ref\|NP_057851.1\|, \|1398976\|dbj\|BAA12990.1\|, \|2801506\|gb\|AAC82594.1\|, \|3098585\|gb\|AAC68852.1\|, \|3098575\|gb\|AAC68843.1\|, \|70633536\|gb\|AAZ06047.1\|, \|70633534\|gb\|AAZ06046.1\|, \|70633532\|gb\|AAZ06045.1\|, \|70633530\|gb\|AAZ06044.1\|, \|829464\|gb\|AAA79593.1\|, \|829457\|gb\|AAA79587.1\|, \|2154685\|dbj\|BAA20329.1\|, \|2154681\|dbj\|BAA20327.1\|, \|2154683\|dbj\|BAA20328.1\|, \|2154677\|dbj\|BAA20326.1\|, \|2154688\|dbj\|BAA20330.1\|, \|829582\|gb\|AAA79678.1\|, \|829568\|gb\|AAA79666.1\|, \|829561\|gb\|AAA79660.1\|, \|829395\|gb\|AAA79533.1\|, \|829380\|gb\|AAA79520.1\|, \|829402\|gb\|AAA79539.1\|, |

VPR proteins

|829517|gb|AAA79624.1|, |829388|gb|AAA79527.1|, |829525|gb|AAA79631.1|,
|829575|gb|AAA79672.1|, |829553|gb|AAA79653.1|, |829545|gb|AAA79646.1|,
|74273443|gb|ABA01427.1|, |74273433|gb|ABA01418.1|, |74273423|gb|ABA01409.1|,
|70905427|gb|AAZ14772.1|, |70905423|gb|AAZ14770.1|, |70905425|gb|AAZ14771.1|,
|70905421|gb|AAZ14769.1|, |70905419|gb|AAZ14768.1|, |18307192|gb|AAL65581.1|,
|70633450|gb|AAZ06005.1|, |70633448|gb|AAZ06004.1|, |1176377|gb|AAA86732.1|,
|70905439|gb|AAZ14778.1|, |70905435|gb|AAZ14776.1|, |70905437|gb|AAZ14777.1|,
|45686211|gb|AAS75787.1|, |2154621|dbj|BAA20300.1|, |2154619|dbj|BAA20299.1|,
|70905443|gb|AAZ14780.1|, |70905441|gb|AAZ14779.1|, |78172833|gb|ABB29366.1|,
|6580997|gb|AAF18405.1|AF190, |3114567|gb|AAD03185.1|, |3114558|gb|AAD03177.1|,
|6090967|gb|AAF03414.1|AF075, |3114550|gb|AAD03170.1|, |14579621|gb|AAK69338.1|,
|16118263|gb|AAL12642.1|, |5668941|gb|AAD46089.1|AF077, |14579601|gb|AAK69320.1|,
|14579611|gb|AAK69329.1|, |16118253|gb|AAL12633.1|, |6636488|gb|AAF20195.1|AF200,
|5668956|gb|AAD46100.1|AF076, |6651457|gb|AAF22309.1|AF193, |38491756|gb|AAR22138.1|,
|38491736|gb|AAR22120.1|, |8886634|gb|AAF80533.1|AF179, |38491773|gb|AAR22153.1|,
|38491746|gb|AAR22129.1|, |14290004|gb|AAK59190.1|, |38491823|gb|AAR22198.1|,
|14290022|gb|AAK59206.1|, |6466842|gb|AAF13057.1|, |70633458|gb|AAZ06009.1|,
|45361168|gb|AAS59372.1|, |1478059|gb|AAB51138.1|, |38491670|gb|AAR22062.1|,
|38491650|gb|AAR22044.1|, |45644383|gb|AAS72938.1|, |14289985|gb|AAK59173.1|,
|5733944|gb|AAD49782.1|AF107, |2570322|gb|AAC97582.1|, |70633654|gb|AAZ06106.1|,
|70633652|gb|AAZ06105.1|, |38491660|gb|AAR22053.1|, |38491492|gb|AAR21903.1|,
|45361189|gb|AAS59383.1|, |14289995|gb|AAK59182.1|, |38491725|gb|AAR22111.1|,
|38491689|gb|AAR22079.1|, |38491715|gb|AAR22102.1|, |38491620|gb|AAR22017.1|,
|38491558|gb|AAR21962.1|, |38491697|gb|AAR22088.1|, |38491615|gb|AAR22013.1|,
|38491502|gb|AAR21912.1|, |38491640|gb|AAR22035.1|, |38491630|gb|AAR22028.1|,
|38491607|gb|AAR22008.1|, |38491578|gb|AAR21980.1|, |38491568|gb|AAR21971.1|,
|38491548|gb|AAR21983.1|, |38491705|gb|AAR22093.1|, |38491588|gb|AAR21989.1|,
|38491538|gb|AAR21944.1|, |38491680|gb|AAR22071.1|, |38491512|gb|AAR21921.1|,
|38491764|gb|AAR22145.1|, |38491529|gb|AAR21938.1|, |38491521|gb|AAR21929.1|,
|3808281|gb|AAC69307.1|, |3808243|gb|AAC69281.1|, |6836492|gb|AAF20197.1|AF200,
|5305344|gb|AAD41598.1|AF071,
|3808273|gb|AAD13360.1|, |70633612|gb|AAZ06085.1|, |3808263|gb|AAC69299.1|,
|3808253|gb|AAC69290.1|, |38491882|gb|AAR22251.1|, |5733953|gb|AAD49790.1|AF107,
|45361067|gb|AAS59298.1|, |6636490|gb|AAF20196.1|AF200, |74315771|gb|ABA02494.1|,
|74315761|gb|ABA02485.1|, |13560261|dbj|BAB40912.1|, |11993204|gb|AAG42636.1|,
|45361149|gb|AAS59361.1|, |37683029|gb|AAQ98586.1|, |37683019|gb|AAQ98577.1|,
|37682960|gb|AAQ98524.1|, |37682773|gb|AAQ98359.1|, |37682853|gb|AAQ98431.1|,
|37682833|gb|AAQ98413.1|, |37682920|gb|AAQ98488.1|, |45361137|gb|AAS59352.1|,
|45361115|gb|AAS59334.1|, |37682881|gb|AAQ98454.1|, |45361103|gb|AAS59325.1|,
|37682980|gb|AAQ98542.1|, |37682891|gb|AAQ98463.1|, |37682843|gb|AAQ98422.1|,
|37682753|gb|AAQ98341.1|, |14209300|dbj|BAB55909.1|, |37682940|gb|AAQ98506.1|,
|37682743|gb|AAQ98332.1|, |1537053|gb|AAC55461.1|, |37682990|gb|AAQ98551.1|,
|37682723|gb|AAQ98314.1|, |37682703|gb|AAQ98296.1|, |37682930|gb|AAQ98497.1|,
|37682713|gb|AAQ98305.1|, |37682793|gb|AAQ98377.1|, |37682783|gb|AAQ98368.1|,
|37682763|gb|AAQ98350.1|, |37682863|gb|AAQ98440.1|, |37682970|gb|AAQ98533.1|,
|37682823|gb|AAQ98404.1|, |37682813|gb|AAQ98395.1|, |37682733|gb|AAQ98323.1|,
|37682803|gb|AAQ98386.1|, |37682912|gb|AAQ98481.1|, |37683000|gb|AAQ98560.1|,
|37683010|gb|AAQ98569.1|, |37682950|gb|AAQ98515.1|, |37682902|gb|AAQ98472.1|,
|37683039|gb|AAQ98595.1|, |45361125|gb|AAS59343.1|, |2570331|gb|AAC32658.1|,
|38491482|gb|AAR21894.1|, |3403218|gb|AAC29052.1|, |74315781|gb|ABA02503.1|,
|74315751|gb|ABA02476.1|, |74315741|gb|ABA02467.1|, |74315734|gb|ABA02461.1|,
|14290013|gb|AAK59198.1|, |38491901|gb|AAR22268.1|, |74315724|gb|ABA02452.1|,
|18699151|gb|AAL78422.1|AF41, |18699143|gb|AAL78415.1|AF41, |18699136|gb|AAL78409.1|AF41,
|18699133|gb|AAL78407.1|AF41, |78172853|gb|ABB29384.1|, |38491872|gb|AAR22242.1|,
|70633600|gb|AAZ06079.1|, |70633596|gb|AAZ06077.1|, |70633598|gb|AAZ06078.1|,
|38491843|gb|AAR22216.1|, |38491833|gb|AAR22207.1|, |38491911|gb|AAR22277.1|,
|6016890|dbj|BAA85227.1|, |62956397|gb|AAY23529.1|, |62956388|gb|AAY23521.1|,
|62956378|gb|AAY23512.1|, |1353863|gb|AAB36502.1|, |2570300|gb|AAC63081.1|,
|4324899|gb|AAD17163.1|, |4324881|gb|AAD17145.1|, |4324890|gb|AAD17154.1|,
|4324872|gb|AAD17136.1|, |4324863|gb|AAD17127.1|, |4324848|gb|AAD17112.1|,
|4324749|gb|AAD17013.1|, |4324740|gb|AAD17004.1|, |4324758|gb|AAD17022.1|,
|78172826|gb|ABB29360.1|, |4324809|gb|AAD17073.1|, |45361077|gb|AAS59307.1|,
|4324833|gb|AAD17097.1|, |57901090|gb|AAW57856.1|, |45361091|gb|AAS59316.1|,
|4324800|gb|AAD17064.1|, |4324784|gb|AAD17048.1|, |4324793|gb|AAD17057.1|,
|4324775|gb|AAD17039.1|, |4324767|gb|AAD17031.1|, |5305356|gb|AAD41608.1|AF071,
|4324918|gb|AAD17182.1|, |4324912|gb|AAD17176.1|, |4324906|gb|AAD17170.1|,
|62946403|gb|AAY22380.1|, |8920154|emb|CAB96340.1|, |14041624|emb|CAC38390.1|,
|3287123|emb|CAA75957.1|, |3287082|emb|CAA75937.1|, |3287164|emb|CAA75985.1|,
|3287128|emb|CAA75961.1|, |3287159|emb|CAA75981.1|, |3287143|emb|CAA75973.1|,
|3287148|emb|CAA75977.1|, |3287103|emb|CAA75941.1|, |3287108|emb|CAA75945.1|,
|45644391|gb|AAS72945.1|, |3287118|emb|CAA75953.1|, |3287113|emb|CAA75949.1|,
|3287138|emb|CAA75969.1|, |51599132|gb|AAU08217.1|, |51599141|gb|AAU08225.1|,
|3287077|emb|CAA75933.1|, |3287133|emb|CAA75965.1|, |52421748|gb|AAU45384.1|,
|52421743|gb|AAU45382.1|, |22596340|gb|AAN03120.1|AF45, |22596320|gb|AAN03102.1|AF45,
|41353554|gb|AAS01341.1|, |22596295|gb|AAN03080.1|AF45, |22596556|gb|AAN03312.1|AF45,
|328907|gb|AAA75020.1|,
|22596411|gb|AAN03183.1|AF45, |22596224|gb|AAN03017.1|AF45, |7452911|emb|CAB86376.1|,

| VPR proteins |
| --- |
| |13517085|dbj|BAB40423.1|, |25807939|gb|AAN74526.1|, |25807929|gb|AAN74517.1|, |7452901|emb|CAB86367.1|, |7331129|gb|AAF60287.1|AF233, |46405261|gb|AAS93489.1|, |46405259|gb|AAS93488.1|, |459517|emb|CAA83114.1|, |4539049|emb|CAB39739.1|, |4539036|emb|CAB39918.1|, |19908409|gb|AAL96764.1|, |23394929|gb|AAN31650.1|, |22297042|gb|AAM94498.1|, |82318409|sp|Q6JNH2|Q6JNH2_9, |7188636|gb|AAF37823.1|AF215, |28933404|gb|AAO62618.1|AF46, |23394921|gb|AAN31643.1|, |37682542|gb|AAQ98228.1|, |37682433|gb|AAQ98130.1|, |39777416|gb|AAR30994.1|, |22596433|gb|AAN03202.1|AF45, |22596466|gb|AAN03231.1|AF45, |22596566|gb|AAN03321.1|AF45, |22596456|gb|AAN03222.1|AF45, |22596380|gb|AAN03156.1|AF45, |22596330|gb|AAN03111.1|AF45, |22596264|gb|AAN03053.1|AF45, |22596486|gb|AAN03249.1|AF45, |22596536|gb|AAN03294.1|AF45, |22596506|gb|AAN03267.1|AF45, |39777436|gb|AAR31012.1|, |22596496|gb|AAN03258.1|AF45, |37682443|gb|AAQ98139.1|, |22596350|gb|AAN03129.1|AF45, |39777386|gb|AAR30967.1|, |39777376|gb|AAR30958.1|, |22596516|gb|AAN03276.1|AF45, |22596546|gb|AAN03303.1|AF45, |39777426|gb|AAR31003.1|, |71148570|gb|AAZ28901.1|, |22596274|gb|AAN03062.1|AF45, |22596390|gb|AAN03165.1|AF45, |22596370|gb|AAN03147.1|AF45, |37682522|gb|AAQ98210.1|, |22596421|gb|AAN03192.1|AF45, |22596285|gb|AAN03071.1|AF45, |22596476|gb|AAN03240.1|AF45, |22596400|gb|AAN03174.1|AF45, |22596244|gb|AAN03035.1|AF45, |22596446|gb|AAN03213.1|AF45, |22596360|gb|AAN03138.1|AF45, |37682532|gb|AAQ98219.1|, |22596234|gb|AAN03026.1|AF45, |66473532|gb|AAY46412.1|, |46405339|gb|AAS93528.1|, |46405341|gb|AAS93529.1|, |7331131|gb|AAF60288.1|AF233, |29119326|gb|AAO63241.1|, |29119317|gb|AAO63233.1|, |16118376|gb|AAL12741.1|, |45360180|gb|AAS59214.1|, |16118396|gb|AAL12759.1|, |16118342|gb|AAL12711.1|, |16118330|gb|AAL12701.1|, |16118303|gb|AAL12678.1|, |45360170|gb|AAS59205.1|, |16118313|gb|AAL12687.1|, |45360150|gb|AAS59187.1|, |45360140|gb|AAS59178.1|, |16118366|gb|AAL12732.1|, |16118352|gb|AAL12720.1|, |45360211|gb|AAS59242.1|, |45360191|gb|AAS59224.1|, |71726044|gb|AAZ39172.1|, |16118338|gb|AAL12708.1|, |57648397|gb|AAW55902.1|, |57648395|gb|AAW55901.1|, |57648393|gb|AAW55900.1|, |57648403|gb|AAW55905.1|, |57648391|gb|AAW55899.1|, |57648389|gb|AAW55898.1|, |57648387|gb|AAW55897.1|, |57648399|gb|AAW55903.1|, |459626|emb|CAA83174.1|, |459455|emb|CAA83082.1|, |7416542|dbj|BAA93916.1|, |7416540|dbj|BAA93915.1|, |7416536|dbj|BAA93913.1|, |82308945|sp|O42061|O42061_9, |7416578|dbj|BAA93934.1|, |7416572|dbj|BAA93931.1|, |7416576|dbj|BAA93933.1|, |7416574|dbj|BAA93932.1|, |7416580|dbj|BAA93935.1|, |82309077|sp|O57303|O57303_9, |56417608|gb|AAV90746.1|, |459624|emb|CAA83173.1|, |459620|emb|CAA83171.1|, |6118386|gb|AAL12750.1|, |49472924|gb|AAT66269.1|, |16118293|gb|AAL12669.1|, |29119258|gb|AAO63180.1|, |46405301|gb|AAS93509.1|, |46405299|gb|AAS93508.1|, |24753963|gb|AAN64088.1|, |24753955|gb|AAN64082.1|, |46405255|gb|AAS93486.1|, |46405253|gb|AAS93485.1|, |459449|emb|CAA83079.1|, |459527|emb|CAA83119.1|, |6118273|gb|AAL12651.1|, |459507|emb|CAA83109.1|, |459459|emb|CAA83084.1|, |459493|emb|CAA83102.1|, |459485|emb|CAA83098.1|, |459513|emb|CAA83112.1|, |29119344|gb|AAO63257.1|, |459481|emb|CAA83096.1|, |3002842|gb|AAD03201.1|, |459473|emb|CAA83092.1|, |29119268|gb|AAO63189.1|, |459465|emb|CAA83088.1|, |171167|gb|AAA86248.1|, |459483|emb|CAA83097.1|, |459632|emb|CAA83133.1|, |459539|emb|CAA83085.1|, |459463|emb|CAA83086.1|, |459479|emb|CAA83095.1|, |459489|emb|CAA83100.1|, |459487|emb|CAA83099.1|, |459525|emb|CAA83118.1|, |459622|emb|CAA83172.1|, |49472942|gb|AAT66285.1|, |459447|emb|CAA83078.1|, |23392825|emb|CAD26952.1|, |23392823|emb|CAD26951.1|, |459497|emb|CAA83104.1|, |29119288|gb|AAO63207.1|, |23392835|emb|CAD26957.1|, |23392833|emb|CAD26956.1|, |23392837|emb|CAD26958.1|, |459596|emb|CAA83159.1|, |459521|emb|CAA83116.1|, |3378124|gb|AAC28447.1|, |459469|emb|CAA83090.1|, |29119298|gb|AAO63216.1|, |23392849|emb|CAD26964.1|, |23392847|emb|CAD26963.1|, |23392845|emb|CAD26962.1|, |82312473|sp|Q8AC00|Q8AC00_9, |11177289|gb|AAG32214.1|, |11177263|gb|AAG32201.1|, |11177269|gb|AAG32204.1|, |11177277|gb|AAG32208.1|, |11177228|gb|AAG32185.1|, |11177275|gb|AAG32207.1|, |11177273|gb|AAG32206.1|, |11177255|gb|AAG32197.1|, |11177251|gb|AAG32195.1|, |11177249|gb|AAG32194.1|, |11177240|gb|AAG32190.1|, |11177232|gb|AAG32186.1|, |11177247|gb|AAG32193.1|, |11177236|gb|AAG32188.1|, |11177234|gb|AAG32187.1|, |11177253|gb|AAG32196.1|, |11177242|gb|AAG32191.1|, |11177238|gb|AAG32189.1|, |11177245|gb|AAG32192.1|, |11177265|gb|AAG32202.1|, |11177224|gb|AAG32183.1|, |11177257|gb|AAG32198.1|, |11177283|gb|AAG32211.1|, |11177261|gb|AAG32200.1|, |11177226|gb|AAG32184.1|, |11177267|gb|AAG32203.1|, |11177285|gb|AAG32212.1|, |11177281|gb|AAG32210.1|, |11177279|gb|AAG32209.1|, |11177259|gb|AAG32199.1|, |11177271|gb|AAG32205.1|, |11177287|gb|AAG32213.1|, |7416634|dbj|BAA93962.1|, |7416632|dbj|BAA93961.1|, |7416630|dbj|BAA93960.1|, |7416546|dbj|BAA93918.1|, |7416544|dbj|BAA93917.1|, |3002832|gb|AAD03192.1|, |459495|emb|CAA83103.1|, |11177315|gb|AAG32227.1|, |11177311|gb|AAG32225.1|, |11177307|gb|AAG32223.1|, |11177299|gb|AAG32219.1|, |11177295|gb|AAG32217.1|, |11177291|gb|AAG32215.1|, |11177301|gb|AAG32220.1|, |11177309|gb|AAG32224.1|, |11177305|gb|AAG32222.1|, |11177303|gb|AAG32221.1|, |11177297|gb|AAG32218.1|, |11177293|gb|AAG32216.1|, |11177313|gb|AAG32226.1|, |48762715|gb|AAS93515.2|, |48686726|gb|AAS93520.2|, |46405325|gb|AAS93521.1|, |46405365|gb|AAS93541.1|, |46405305|gb|AAS93511.1|, |46405303|gb|AAS93510.1|, |46405265|gb|AAS93491.1|, |46405263|gb|AAS93490.1|, |46405311|gb|AAS93514.1|, |46405317|gb|AAS93517.1|, |46405315|gb|AAS93516.1|, |46405269|gb|AAS93493.1|, |46405267|gb|AAS93492.1|, |46405355|gb|AAS93536.1|, |46405351|gb|AAS93534.1|, |46405353|gb|AAS93535.1|, |46405275|gb|AAS93496.1|, |46405273|gb|AAS93495.1|, |46405321|gb|AAS93519.1|, |

-continued

| VPR proteins |
|---|
| \|46405319\|gb\|AAS93518.1\|, \|46405309\|gb\|AAS93513.1\|, \|46405307\|gb\|AAS93512.1\|, \|46405247\|gb\|AAS93482.1\|, \|46405175\|gb\|AAS93447.1\|, \|46405171\|gb\|AAS93445.1\|, \|46405173\|gb\|AAS93446.1\|, \|46405243\|gb\|AAS93480.1\|, \|46405241\|gb\|AAS93479.1\|, \|46405245\|gb\|AAS93481.1\|, \|46405209\|gb\|AAS93464.1\|, \|46405207\|gb\|AAS93463.1\|, \|46405165\|gb\|AAS93442.1\|, \|46405195\|gb\|AAS93457.1\|, \|46405193\|gb\|AAS93456.1\|, \|46405205\|gb\|AAS93462.1\|, \|46405203\|gb\|AAS93461.1\|, \|46405163\|gb\|AAS93441.1\|, \|46405161\|gb\|AAS93440.1\|, \|46405217\|gb\|AAS93468.1\|, \|46405215\|gb\|AAS93467.1\|, \|46405169\|gb\|AAS93444.1\|, \|46405167\|gb\|AAS93443.1\|, \|48686723\|gb\|AAS93483.2\|, \|46405251\|gb\|AAS93484.1\|, \|46405232\|gb\|AAS93475.1\|, \|46405183\|gb\|AAS93451.1\|, \|46405199\|gb\|AAS93459.1\|, \|46405197\|gb\|AAS93458.1\|, \|46405201\|gb\|AAS93460.1\|, \|46405237\|gb\|AAS93477.1\|, \|46405225\|gb\|AAS93472.1\|, \|46405223\|gb\|AAS93471.1\|, \|46405229\|gb\|AAS93474.1\|, \|46405227\|gb\|AAS93473.1\|, \|46405239\|gb\|AAS93478.1\|, \|46405221\|gb\|AAS93470.1\|, \|46405219\|gb\|AAS93469.1\|, \|46405281\|gb\|AAS93499.1\|, \|46405279\|gb\|AAS93498.1\|, \|46405277\|gb\|AAS93497.1\|, \|46405213\|gb\|AAS93466.1\|, \|46405211\|gb\|AAS93465.1\|, \|46405329\|gb\|AAS93523.1\|, \|46405327\|gb\|AAS93522.1\|, \|46405235\|gb\|AAS93476.1\|, \|46405349\|gb\|AAS93533.1\|, \|46405347\|gb\|AAS93532.1\|, \|46405343\|gb\|AAS93530.1\|, \|46405345\|gb\|AAS93531.1\|, \|46405191\|gb\|AAS93455.1\|, \|46405187\|gb\|AAS93453.1\|, \|46405189\|gb\|AAS93454.1\|, \|46405185\|gb\|AAS93452.1\|, \|46405271\|gb\|AAS93494.1\|, \|46405359\|gb\|AAS93538.1\|, \|46405357\|gb\|AAS93537.1\|, \|46405337\|gb\|AAS93527.1\|, \|46405335\|gb\|AAS93526.1\|, \|46405333\|gb\|AAS93525.1\|, \|46405331\|gb\|AAS93524.1\|, \|46405297\|gb\|AAS93507.1\|, \|46405293\|gb\|AAS93505.1\|, \|46405295\|gb\|AAS93506.1\|, \|46405291\|gb\|AAS93504.1\|, \|46405289\|gb\|AAS93503.1\|, \|46405287\|gb\|AAS93502.1\|, \|46405285\|gb\|AAS93501.1\|, \|46405283\|gb\|AAS93500.1\|, \|46405181\|gb\|AAS93450.1\|, \|46405179\|gb\|AAS93449.1\|, \|46405177\|gb\|AAS93448.1\|, \|71725984\|gb\|AAZ39118.1\|, \|71725974\|gb\|AAZ39109.1\|, \|71726024\|gb\|AAZ39154.1\|, \|71726014\|gb\|AAZ39145.1\|, \|71726004\|gb\|AAZ39136.1\|, \|17981621\|gb\|AAL51091.1\|, \|459602\|emb\|CAA83162.1\|, \|459600\|emb\|CAA83161.1\|, \|459604\|emb\|CAA83163.1\|, \|23392829\|emb\|CAD26954.1\|, \|23392827\|emb\|CAD26953.1\|, \|23392831\|emb\|CAD26955.1\|, \|23396014\|emb\|CAD27178.1\|, \|23392853\|emb\|CAD26966.1\|, \|23392851\|emb\|CAD26965.1\|, \|23392855\|emb\|CAD26967.1\|, \|29119340\|gb\|AAO63254.1\|, \|459519\|emb\|CAA83115.1\|, \|459610\|emb\|CAA83166.1\|, \|7416620\|dbj\|BAA93955.1\|, \|7416618\|dbj\|BAA93954.1\|, \|7416616\|dbj\|BAA93953.1\|, \|7416614\|dbj\|BAA93952.1\|, \|7416612\|dbj\|BAA93951.1\|, \|7416560\|dbj\|BAA93925.1\|, \|7416558\|dbj\|BAA93924.1\|, \|459509\|emb\|CAA83110.1\|, \|1465780\|gb\|AAB05600.1\|, \|459501\|emb\|CAA83106.1\|, \|459499\|emb\|CAA83105.1\|, \|46405257\|gb\|AAS93487.1\|, \|459505\|emb\|CAA83108.1\|, \|459616\|emb\|CAA83169.1\|, \|459614\|emb\|CAA83168.1\|, \|459471\|emb\|CAA83091.1\|, \|7416588\|dbj\|BAA93939.1\|, \|7416586\|dbj\|BAA93938.1\|, \|7416582\|dbj\|BAA93936.1\|, \|459491\|emb\|CAA83101.1\|, \|459606\|emb\|CAA83164.1\|, \|459475\|emb\|CAA83093.1\|, \|71726034\|gb\|AAZ39163.1\|, \|16118283\|gb\|AAL12660.1\|, \|71725994\|gb\|AAZ39127.1\|, \|71725964\|gb\|AAZ39100.1\|, \|71725954\|gb\|AAZ39091.1\|, \|45360201\|gb\|AAS59233.1\|, \|45360160\|gb\|AAS59196.1\|, \|49472951\|gb\|AAT66293.1\|, \|459467\|emb\|CAA83089.1\|, \|7416626\|dbj\|BAA93958.1\|, \|7416622\|dbj\|BAA93956.1\|, \|7416624\|dbj\|BAA93957.1\|, \|7416628\|dbj\|BAA93959.1\|, \|7416594\|dbj\|BAA93942.1\|, \|7416590\|dbj\|BAA93940.1\|, \|7416570\|dbj\|BAA93930.1\|, \|7416564\|dbj\|BAA93927.1\|, \|7416568\|dbj\|BAA93929.1\|, \|7416566\|dbj\|BAA93928.1\|, \|7416562\|dbj\|BAA93926.1\|, \|7416554\|dbj\|BAA93922.1\|, \|7416552\|dbj\|BAA93921.1\|, \|7416556\|dbj\|BAA93923.1\|, \|7416550\|dbj\|BAA93920.1\|, \|459618\|emb\|CAA83170.1\|, \|459457\|emb\|CAA83083.1\|, \|459511\|emb\|CAA83111.1\|, \|459451\|emb\|CAA83080.1\|, \|459630\|emb\|CAA83176.1\|, \|818217\|gb\|AAB47929.1\|, \|459612\|emb\|CAA83167.1\|, \|46405363\|gb\|AAS93540.1\|, \|46405361\|gb\|AAS93539.1\|, \|459598\|emb\|CAA83160.1\|, \|11177209\|gb\|AAG32182.1\|, \|11177184\|gb\|AAG32170.1\|, \|11177204\|gb\|AAG32180.1\|, \|11177188\|gb\|AAG32172.1\|, \|11177206\|gb\|AAG32181.1\|, \|11177202\|gb\|AAG32179.1\|, \|11177190\|gb\|AAG32173.1\|, \|11177198\|gb\|AAG32177.1\|, \|11177186\|gb\|AAG32171.1\|, \|11177182\|gb\|AAG32169.1\|, \|11177200\|gb\|AAG32178.1\|, \|11177194\|gb\|AAG32175.1\|, \|11177196\|gb\|AAG32176.1\|, \|11177192\|gb\|AAG32174.1\|, \|82309078\|sp\|O57309\|O57309_9, \|29119307\|gb\|AAO63224.1\|, \|24753985\|gb\|AAN64106.1\|, \|24753974\|gb\|AAN64097.1\|, \|24753996\|gb\|AAN64115.1\|, \|24754006\|gb\|AAN64124.1\|, \|29119278\|gb\|AAO63198.1\|, \|7416598\|dbj\|BAA93944.1\|, \|7416596\|dbj\|BAA93943.1\|, \|7416600\|dbj\|BAA93945.1\|, \|459608\|emb\|CAA83165.1\|, \|459523\|emb\|CAA83117.1\|, \|459515\|emb\|CAA83113.1\|, \|459503\|emb\|CAA83107.1\|, \|459628\|emb\|CAA83175.1\|, \|459461\|emb\|CAA83087.1\|, \|459477\|emb\|CAA83094.1\|, \|459453\|emb\|CAA83081.1\|, \|23392843\|emb\|CAD26961.1\|, \|23392839\|emb\|CAD26959.1\|, \|23392841\|emb\|CAD26960.1\|, \|7416610\|dbj\|BAA93950.1\|, \|7416608\|dbj\|BAA93949.1\|, \|7416604\|dbj\|BAA93947.1\|, \|7416602\|dbj\|BAA93946.1\|, \|7416606\|dbj\|BAA93948.1\|, \|25166993\|gb\|AAN73765.1\|AF48, \|37682492\|gb\|AAQ98183.1\|, \|25166743\|gb\|AAN73540.1\|AF48, \|22596576\|gb\|AAN03330.1\|AF45, \|39777396\|gb\|AAR30976.1\|, \|39777406\|gb\|AAR30985.1\|, \|82571311\|gb\|ABB84078.1\|, \|73913776\|gb\|AAZ91759.1\|, \|37682601\|gb\|AAQ98281.1\|, \|82571232\|gb\|ABB84007.1\|, \|73913894\|gb\|AAZ91865.1\|, \|82571381\|gb\|ABB84141.1\|, \|82571398\|gb\|ABB84156.1\|, \|73913933\|gb\|AAZ91900.1\|, \|82571242\|gb\|ABB84016.1\|, \|73913967\|gb\|AAZ91930.1\|, \|82571252\|gb\|ABB84025.1\|, \|73913796\|gb\|AAZ91777.1\|, \|82571331\|gb\|ABB84096.1\|, \|73913786\|gb\|AAZ91768.1\|, \|32261506\|gb\|AAP76566.1\|, \|82571213\|gb\|ABB83990.1\|, \|82571301\|gb\|ABB84069.1\|, \|73913806\|gb\|AAZ91786.1\|, \|3252969\|gb\|AAD12116.1\|, \|3252929\|gb\|AAD12080.1\|, \|3252939\|gb\|AAD12089.1\|, \|82571321\|gb\|ABB84087.1\|, \|82571222\|gb\|ABB83998.1\|, \|73913875\|gb\|AAZ91848.1\|, \|73913825\|gb\|AAZ91803.1\|, \|73913855\|gb\|AAZ91830.1\|, \|73913815\|gb\|AAZ91794.1\|, \|82571203\|gb\|ABB83981.1\|, \|82571193\|gb\|ABB83972.1\|, \|82571291\|gb\|ABB84060.1\|, \|73913923\|gb\|AAZ91891.1\|, \|82571408\|gb\|ABB84165.1\|, \|82318458\|sp\|Q98VH0\|Q98VH0_9, \|32261467\|gb\|AAP76531.1\|, \|37682591\|gb\|AAQ98272.1\|, \|37682552\|gb\|AAQ98237.1\|, \|82571361\|gb\|ABB84123.1\|, \|82571351\|gb\|ABB84114.1\|, |

| VPR proteins |
| --- |
| |82571281|gb|ABB84051.1|, |82571341|gb|ABB84105.1|, |73913865|gb|AAZ91839.1|, |22596254|gb|AAN03044.1|AF45, |73913904|gb|AAZ91874.1|, |82571371|gb|ABB84132.1|, |73913995|gb|AAZ91955.1|, |37682483|gb|AAQ98175.1|, |32261497|gb|AAP76558.1|, |22596526|gb|AAN03285.1|AF45, |2194189|gb|AAB61127.1|, |63081179|gb|AAY30341.1|, |37682473|gb|AAQ98166.1|, |37682512|gb|AAQ98201.1|, |37682463|gb|AAQ98157.1|, |32261487|gb|AAP76549.1|, |32261458|gb|AAP76523.1|, |22596310|gb|AAN03093.1|AF45, |37682412|gb|AAQ98111.1|, |82571271|gb|ABB84042.1|, |82571262|gb|ABB84034.1|, |73913835|gb|AAZ91812.1|, |37682502|gb|AAQ98192.1|, |32261477|gb|AAP76540.1|, |73913845|gb|AAZ91821.1|, |73913914|gb|AAZ91883.1|, |37682453|gb|AAQ98148.1|, |37682423|gb|AAQ98121.1|, |73913977|gb|AAZ91939.1|, |37682581|gb|AAQ98263.1|, |37682571|gb|AAQ98254.1|, |37682562|gb|AAQ98246.1|, |5305569|gb|AAD41704.1|AF097, |5305561|gb|AAD41697.1|AF097, |5305577|gb|AAD41711.1|AF097, |14041638|emb|CAC38422.1|, |14041628|emb|CAC38431.1|, |37935971|gb|AAO47209.1|, |37935901|gb|AAO47147.1|, |37935892|gb|AAO47139.1|, |37935872|gb|AAO47122.1|, |37935852|gb|AAO47104.1|, |37935842|gb|AAO47095.1|, |37935912|gb|AAO47156.1|, |37935932|gb|AAO47174.1|, |37935952|gb|AAO47192.1|, |37935922|gb|AAO47165.1|, |37935961|gb|AAO47200.1|, |37935981|gb|AAO47218.1|, |37935881|gb|AAO47130.1|, |37935942|gb|AAO47183.1|, |37935862|gb|AAO47113.1|, |41223201|emb|CAD92650.1|, |47027390|gb|AAT08770.1|, |46243166|gb|AAS83692.1|, |46243156|gb|AAS83683.1|, |936837|emb|CAB98188.1|, |6643028|gb|AAF20389.1|, |37496492|emb|CAD48449.1|, |5738568|emb|CAB53044.1|, |9368381|emb|CAB98170.1|, |3779263|gb|AAD03311.1|, |29409316|gb|AAM67394.1|, |29409309|gb|AAM67388.1|, |71794577|emb|CAI28819.1|, |22532133|gb|AAM97845.1|AF46, |38679143|gb|AAR26397.1|, |38679134|gb|AAR26389.1|, |24181480|gb|AAN47102.1|, |4336341|gb|AAD17767.1|, |4336332|gb|AAD17758.1|, |5019906|gb|AAD37900.1|, |5019878|gb|AAD37872.1|, |57869600|gb|AAW57647.1|, |5019905|gb|AAD37899.1|, |5019898|gb|AAD37892.1|, |30027256|gb|AAP06259.1|, |11095913|gb|AAG30117.1|AF28, |3694863|gb|AAC62477.1|, |3002879|gb|AAD03234.1|, |57869571|gb|AAW57621.1|, |5019890|gb|AAD37884.1|, |5019875|gb|AAD37869.1|, |5019871|gb|AAD37865.1|, |5019870|gb|AAD37864.1|, |2286136|gb|AAB64282.1|, |2286127|gb|AAB64274.1|, |15407026|gb|AAG41567.1|, |15407024|gb|AAG41566.1|, |15407021|gb|AAG41565.1|, |32261283|gb|AAP74182.1|, |32261272|gb|AAP74172.1|, |32261262|gb|AAP74163.1|, |5019919|gb|AAD37913.1|, |5019915|gb|AAD37909.1|, |5019877|gb|AAD37871.1|, |5019910|gb|AAD37904.1|, |6910970|gb|AAF31321.1|AF146, |5019916|gb|AAD37910.1|, |5019904|gb|AAD37898.1|, |5019912|gb|AAD37906.1|, |5019883|gb|AAD37877.1|, |5019914|gb|AAD37908.1|, |5019900|gb|AAD37894.1|, |5019897|gb|AAD37891.1|, |5019888|gb|AAD37882.1|, |5019891|gb|AAD37885.1|, |5019917|gb|AAD37911.1|, |5019913|gb|AAD37907.1|, |5019894|gb|AAD37888.1|, |5019892|gb|AAD37886.1|, |5019907|gb|AAD37901.1|, |5019903|gb|AAD37897.1|, |40021885|gb|AAR37195.1|, |40021825|gb|AAR37153.1|, |40021805|gb|AAR37139.1|, |40021775|gb|AAR37118.1|, |40021765|gb|AAR37111.1|, |40021735|gb|AAR37090.1|, |40021715|gb|AAR37076.1|, |40021865|gb|AAR37181.1|, |40021725|gb|AAR37083.1|, |40021795|gb|AAR37132.1|, |40021695|gb|AAR37062.1|, |40021845|gb|AAR37167.1|, |40021755|gb|AAR37104.1|, |40021855|gb|AAR37174.1|, |40021705|gb|AAR37069.1|, |40021745|gb|AAR37097.1|, |40021835|gb|AAR37160.1|, |40021815|gb|AAR37146.1|, |40021875|gb|AAR37188.1|, |5019889|gb|AAD37883.1|, |5019882|gb|AAD37876.1|, |5019895|gb|AAD37889.1|, |5019873|gb|AAD37867.1|, |5019887|gb|AAD37881.1|, |5019886|gb|AAD37880.1|, |5019901|gb|AAD37895.1|, |5019902|gb|AAD37896.1|, |5019880|gb|AAD37874.1|, |5019918|gb|AAD37912.1|, |5019879|gb|AAD37873.1|, |5019911|gb|AAD37905.1|, |5019876|gb|AAD37870.1|, |6651482|gb|AAF22330.1|AF193, |6651475|gb|AAF22323.1|AF193, |5019872|gb|AAD37866.1|, |3002870|gb|AAD03226.1|, |5019909|gb|AAD37903.1|, |5019899|gb|AAD37893.1|, |5019893|gb|AAD37887.1|, |5019896|gb|AAD37890.1|, |5019881|gb|AAD37875.1|, |5019874|gb|AAD37868.1|, |5019884|gb|AAD37878.1|, |57869581|gb|AAW57630.1|, |3002888|gb|AAD03242.1|, |3002852|gb|AAD03210.1|, |3002861|gb|AAD03218.1|, |57869562|gb|AAW57613.1|, |14269049|gb|AAK58006.1|AF36, |31559692|dbj|BAC77513.1|, |11761312|dbj|BAB19247.1|, |11761305|dbj|BAB19241.1|, |26518639|gb|AAN83913.1|, |31559616|dbj|BAC77445.1|, |31559664|dbj|BAC77488.1|, |34811836|gb|AAO40779.1|, |5019908|gb|AAD37902.1|, |55925129|gb|AAV67934.1|, |55925121|gb|AAV67927.1|, |55925113|gb|AAV67920.1|, |55925137|gb|AAV67941.1|, |15407136|gb|AAG41570.1|, |15407132|gb|AAG41568.1|, |15407134|gb|AAG41569.1|, |32189801|gb|AAP75712.1|, |30038316|gb|AAP12629.1|, |19072106|dbj|BAB85753.1|, |55740248|gb|AAV63820.1|, |55740228|gb|AAV63802.1|, |55740238|gb|AAV63811.1|, |18074001|emb|CAC86566.1|, |25166893|gb|AAN73675.1|AF48, |5668913|gb|AAD46067.1|AF076, |17902150|gb|AAL47813.1|, |17864053|gb|AAL47046.1|, |17902128|gb|AAL47795.1|, |17902117|gb|AAL47786.1|, |17902106|gb|AAL47777.1|, |17864033|gb|AAL47028.1|, |17902139|gb|AAL47804.1|, |17902095|gb|AAL47768.1|, |17864043|gb|AAL47037.1|, |62361771|gb|AAX81419.1|, |71794625|emb|CAI28864.1|, |71794615|emb|CAI28855.1|, |71794606|emb|CAI28846.1|, |71794597|emb|CAI28837.1|, |37496484|emb|CAD48442.1|, |7321146|emb|CAB82228.1|, |7321136|emb|CAB82219.1|, |25166641|gb|AAN73449.1|AF48, |38679151|gb|AAR26404.1|, |25166943|gb|AAN73720.1|AF48, |15281442|gb|AAK94230.1|AF36, |57869544|gb|AAW57597.1|, |15281432|gb|AAK94221.1|AF36, |31980438|dbj|BAC77757.1|, |31980428|dbj|BAC77748.1|, |25166923|gb|AAN73702.1|AF48, |25166973|gb|AAN73747.1|AF48, |25166681|gb|AAN73485.1|AF48, |31980418|dbj|BAC77739.1|, |31980408|dbj|BAC77730.1|, |25166783|gb|AAN73576.1|AF48, |25166763|gb|AAN73558.1|AF48, |7657891|emb|CAB89145.1|, |33390881|gb|AAQ17100.1|, |1732477|gb|AAB38825.1|, |3676491|gb|AAC61995.1|, |62467713|gb|AAX83967.1|, |62467704|gb|AAX83959.1|, |15982650|gb|AAL09938.1|, |56609329|gb|AAW03281.1|, |56609263|gb|AAW03222.1|, |56609243|gb|AAW03204.1|, |

| VPR proteins |
|---|
| \|56609303\|gb\|AAW03258.1\|, \|56609323\|gb\|AAW03276.1\|, \|56609293\|gb\|AAW03249.1\|, \|56609273\|gb\|AAW03231.1\|, \|56609313\|gb\|AAW03267.1\|, \|25166883\|gb\|AAN73666.1\|AF48, \|33331477\|gb\|AAQ10921.1\|, \|33331457\|gb\|AAQ10903.1\|, \|33331467\|gb\|AAQ10912.1\|, \|37496500\|emb\|CAD48456.1\|, \|25166863\|gb\|AAN73648.1\|AF48, \|57869722\|gb\|AAW57756.1\|, \|1732487\|gb\|AAB38834.1\|, \|11066500\|gb\|AAG28615.1\|AF25, \|11066490\|gb\|AAG28606.1\|AF25, \|7715904\|gb\|AAF68194.1\|, \|7715899\|gb\|AAF68190.1\|, \|7715894\|gb\|AAF68186.1\|, \|7715887\|gb\|AAF68181.1\|, \|7715891\|gb\|AAF68184.1\|, \|33328322\|gb\|AAQ09611.1\|, \|57869686\|gb\|AAW57724.1\|, \|18844739\|dbj\|BAB85461.1\|, \|18844729\|dbj\|BAB85452.1\|, \|33328200\|gb\|AAQ09548.1\|, \|57869676\|gb\|AAW57715.1\|, \|57869695\|gb\|AAW57732.1\|, \|57869713\|gb\|AAW57748.1\|, \|23194121\|gb\|AAN15029.1\|, \|57869704\|gb\|AAW57740.1\|, \|31559682\|dbj\|BAC77504.1\|, \|33328190\|gb\|AAQ09539.1\|, \|31559634\|dbj\|BAC77461.1\|, \|57869666\|gb\|AAW57706.1\|, \|57869731\|gb\|AAW57764.1\|, \|14530265\|gb\|AAK65995.1\|AF31, \|56609340\|gb\|AAW03290.1\|, \|56609253\|gb\|AAW03213.1\|, \|56609283\|gb\|AAW03240.1\|, \|14530247\|gb\|AAK65979.1\|AF28, \|14530239\|gb\|AAK65972.1\|AF28, \|14530256\|gb\|AAK65987.1\|AF28, \|14530229\|gb\|AAK65963.1\|AF28, \|51950722\|gb\|AAU14914.1\|, \|51950712\|gb\|AAU14905.1\|, \|71794587\|emb\|CAI28828.1\|, \|18073403\|emb\|CAC87994.1\|, \|15209254\|emb\|CAC51033.1\|, \|18073413\|emb\|CAC88003.1\|, \|22532294\|gb\|AAM97887.1\|AF49, \|22532284\|gb\|AAM97878.1\|AF49, \|59003610\|gb\|AAW83611.1\|, \|12957276\|gb\|AAK09121.1\|AF32, \|38892700\|gb\|AAR27699.1\|, \|73913756\|gb\|AAZ91741.1\|, \|55139310\|gb\|AAV41328.1\|, \|67553053\|gb\|AAY68644.1\|, \|58220991\|gb\|AAW68170.1\|, \|63098335\|gb\|AAY32383.1\|, \|12957270\|gb\|AAK09116.1\|AF32, \|12957264\|gb\|AAK09111.1\|AF32, \|63098432\|gb\|AAY32470.1\|, \|37935583\|gb\|AAO65556.1\|, \|37909404\|gb\|AAO65565.1\|, \|58220962\|gb\|AAW68144.1\|, \|12957324\|gb\|AAK09161.1\|AF32, \|63098307\|gb\|AAY32358.1\|, \|11321030\|gb\|AAG34021.1\|, \|11321010\|gb\|AAG34003.1\|, \|11321020\|gb\|AAG34012.1\|, \|11321000\|gb\|AAG33994.1\|, \|13569290\|gb\|AAK31028.1\|AF28, \|58220942\|gb\|AAW68126.1\|, \|67552978\|gb\|AAY68577.1\|, \|67552988\|gb\|AAY68586.1\|, \|38892647\|gb\|AAR27652.1\|, \|51572106\|gb\|AAU06755.1\|, \|58220922\|gb\|AAW68108.1\|, \|18643012\|gb\|AAL74047.1\|, \|38892738\|gb\|AAR27733.1\|, \|68522036\|gb\|AAY98633.1\|, \|46486629\|gb\|AAS98736.1\|, \|12957294\|gb\|AAK09136.1\|AF32, \|12957282\|gb\|AAK09126.1\|AF32, \|55139273\|gb\|AAV41295.1\|, \|73913766\|gb\|AAZ91750.1\|, \|67553016\|gb\|AAY68611.1\|, \|63098325\|gb\|AAY32374.1\|, \|51572096\|gb\|AAU06746.1\|, \|58220892\|gb\|AAW68081.1\|, \|59003649\|gb\|AAW83646.1\|, \|59003510\|gb\|AAW83521.1\|, \|58221029\|gb\|AAW68204.1\|, \|63098392\|gb\|AAY32434.1\|, \|38892691\|gb\|AAR27691.1\|, \|38892756\|gb\|AAR27749.1\|, \|67553024\|gb\|AAY68618.1\|, \|63098422\|gb\|AAY32461.1\|, \|58220872\|gb\|AAW68063.1\|, \|57869627\|gb\|AAW57671.1\|, \|68522146\|gb\|AAY98732.1\|, \|59003620\|gb\|AAW83620.1\|, \|38892682\|gb\|AAR27683.1\|, \|38892656\|gb\|AAR27660.1\|, \|68522086\|gb\|AAY98678.1\|, \|67552998\|gb\|AAY68595.1\|, \|38892601\|gb\|AAR27611.1\|, \|68521996\|gb\|AAY98597.1\|, \|67553103\|gb\|AAY68689.1\|, \|58220912\|gb\|AAW68099.1\|, \|63098412\|gb\|AAY32452.1\|, \|55139331\|gb\|AAV41346.1\|, \|55139263\|gb\|AAV41286.1\|, \|38892718\|gb\|AAR27715.1\|, \|58220882\|gb\|AAW68072.1\|, \|59003570\|gb\|AAW83575.1\|, \|12957336\|gb\|AAK09171.1\|AF32, \|12957330\|gb\|AAK09166.1\|AF32, \|55139351\|gb\|AAV41364.1\|, \|59003560\|gb\|AAW83566.1\|, \|58220932\|gb\|AAW68117.1\|, \|13569320\|gb\|AAK31055.1\|AF28, \|38892728\|gb\|AAR27724.1\|, \|68521956\|gb\|AAY98561.1\|, \|58220862\|gb\|AAW68054.1\|, \|68522006\|gb\|AAY98606.1\|, \|24181490\|gb\|AAN47111.1\|, \|13569220\|gb\|AAK30965.1\|AF28, \|38892664\|gb\|AAR27667.1\|, \|55139254\|gb\|AAV41278.1\|, \|12957288\|gb\|AAK09131.1\|AF32, \|68521986\|gb\|AAY98588.1\|, \|67553083\|gb\|AAY68671.1\|, \|58220972\|gb\|AAW68153.1\|, \|15281501\|gb\|AAK94283.1\|AF36, \|59003590\|gb\|AAW83593.1\|, \|59003530\|gb\|AAW83539.1\|, \|68522016\|gb\|AAY98615.1\|, \|68521966\|gb\|AAY98570.1\|, \|15281472\|gb\|AAK94257.1\|AF36, \|13569210\|gb\|AAK30956.1\|AF28, \|57869619\|gb\|AAW57664.1\|, \|13569270\|gb\|AAK31010.1\|AF28, \|13569280\|gb\|AAK31019.1\|AF28, \|13569240\|gb\|AAK30983.1\|AF28, \|30269368\|gb\|AAP29646.1\|, \|31559644\|dbj\|BAC77470.1\|, \|11761285\|dbj\|BAB19224.1\|, \|11761282\|dbj\|BAB19222.1\|, \|11761298\|dbj\|BAB19235.1\|, \|11761275\|dbj\|BAB19216.1\|, \|31559672\|dbj\|BAC77495.1\|, \|31559654\|dbj\|BAC77479.1\|, \|31559626\|dbj\|BAC77454.1\|, \|11761268\|dbj\|BAB19210.1\|, \|307204409\|gb\|AAP33677.1\|, \|13569300\|gb\|AAK31037.1\|AF28, \|23986253\|gb\|AAL12202.1\|, \|23986209\|gb\|AAL12175.1\|, \|23986237\|gb\|AAL12193.1\|, \|23986223\|gb\|AAL12184.1\|, \|58220902\|gb\|AAW68090.1\|, \|63098364\|gb\|AAY32409.1\|, \|68522096\|gb\|AAY98687.1\|, \|15281491\|gb\|AAK94274.1\|AF36, \|63098297\|gb\|AAY32349.1\|, \|13569250\|gb\|AAK30992.1\|AF28, \|58221019\|gb\|AAW68195.1\|, \|59003629\|gb\|AAW83628.1\|, \|32344838\|gb\|AAM82294.1\|, \|16751251\|gb\|AAL05327.1\|, \|55139281\|gb\|AAV41302.1\|, \|38892621\|gb\|AAR27629.1\|, \|38892611\|gb\|AAR27620.1\|, \|63098373\|gb\|AAY32417.1\|, \|59003540\|gb\|AAW83548.1\|, \|12957372\|gb\|AAK09201.1\|AF32, \|12957366\|gb\|AAK09196.1\|AF32, \|46486648\|gb\|AAS98753.1\|, \|24181500\|gb\|AAN47120.1\|, \|58221039\|gb\|AAW68213.1\|, \|16751261\|gb\|AAL05336.1\|, \|38892784\|gb\|AAR27774.1\|, \|38892638\|gb\|AAR27644.1\|, \|38892628\|gb\|AAR27635.1\|, \|38892765\|gb\|AAR27757.1\|, \|63098354\|gb\|AAY32400.1\|, \|68522066\|gb\|AAY98660.1\|, \|58220952\|gb\|AAW68135.1\|, \|68521936\|gb\|AAY98543.1\|, \|46486656\|gb\|AAS98760.1\|, \|16751241\|gb\|AAL05318.1\|, \|38892775\|gb\|AAR27766.1\|, \|55139342\|gb\|AAV41356.1\|, \|59003600\|gb\|AAW83602.1\|, \|26000256\|gb\|AAN75291.1\|, \|12957246\|gb\|AAK09096.1\|AF32, \|51572115\|gb\|AAU06763.1\|, \|68522126\|gb\|AAY98714.1\|, \|63098345\|gb\|AAY32392.1\|, \|51572125\|gb\|AAU06772.1\|, \|57869637\|gb\|AAW57680.1\|, \|68522116\|gb\|AAY98705.1\|, \|13569330\|gb\|AAK31064.1\|AF28, \|68522076\|gb\|AAY98669.1\|, \|59003550\|gb\|AAW83557.1\|, \|67553093\|gb\|AAY68680.1\|, \|15281452\|gb\|AAK94239.1\|AF36, \|26000276\|gb\|AAN75309.1\|, \|12957318\|gb\|AAK09156.1\|AF32, \|12957360\|gb\|AAK09191.1\|AF32, \|12957354\|gb\|AAK09186.1\|AF32, \|12957252\|gb\|AAK09101.1\|AF32, \|68522046\|gb\|AAY98642.1\|, \|12957312\|gb\|AAK09151.1\|AF32, \|48476375\|gb\|AAT44409.1\|, \|13569260\|gb\|AAK31001.1\|AF28, \|45738212\|gb\|AAS75871.1\|, \|13569230\|gb\|AAK30974.1\|AF28, \|38892672\|gb\|AAR27674.1\|, \|59003639\|gb\|AAW83637.1\|, |

| VPR proteins |
| --- |
| \|68522136\|gb\|AAY98723.1\|, \|13569310\|gb\|AAK31046.1\|AF28, \|57869646\|gb\|AAW57688.1\|, \|67553063\|gb\|AAY68653.1\|, \|67553073\|gb\|AAY68662.1\|, \|57869610\|gb\|AAW57656.1\|, \|26000266\|gb\|AAN75300.1\|, \|63098402\|gb\|AAY32443.1\|, \|68522056\|gb\|AAY98651.1\|, \|59003580\|gb\|AAW83584.1\|, \|67553113\|gb\|AAY68698.1\|, \|12957306\|gb\|AAK09146.1\|AF32, \|12957300\|gb\|AAK09141.1\|AF32, \|59003520\|gb\|AAW83530.1\|, \|58221001\|gb\|AAW68179.1\|, \|38892709\|gb\|AAR27707.1\|, \|68522026\|gb\|AAY98624.1\|, \|57338565\|gb\|AAW49359.1\|, \|46486638\|gb\|AAS98744.1\|, \|63098382\|gb\|AAY32425.1\|, \|59003659\|gb\|AAW83655.1\|, \|55139292\|gb\|AAV41312.1\|, \|68521946\|gb\|AAY98552.1\|, \|67553007\|gb\|AAY68603.1\|, \|12957348\|gb\|AAK09181.1\|AF32, \|12957342\|gb\|AAK09176.1\|AF32, \|67553033\|gb\|AAY68626.1\|, \|59003669\|gb\|AAW83664.1\|, \|32344848\|gb\|AAM82303.1\|, \|12957258\|gb\|AAK09106.1\|AF32, \|57338557\|gb\|AAW49352.1\|, \|46486665\|gb\|AAS98768.1\|, \|55139322\|gb\|AAV41338.1\|, \|24181510\|gb\|AAN47129.1\|, \|68522106\|gb\|AAY98696.1\|, \|45738222\|gb\|AAS75880.1\|, \|68522155\|gb\|AAY98740.1\|, \|68521976\|gb\|AAY98579.1\|, \|15281462\|gb\|AAK94248.1\|AF36, \|67553043\|gb\|AAY68635.1\|, \|63098287\|gb\|AAY32340.1\|, \|57869656\|gb\|AAW57697.1\|, \|25166983\|gb\|AAN73756.1\|AF48, \|25166913\|gb\|AAN73693.1\|AF48, \|25167003\|gb\|AAN73774.1\|AF48, \|25166873\|gb\|AAN73657.1\|AF48, \|25166853\|gb\|AAN73639.1\|AF48, \|25166823\|gb\|AAN73612.1\|AF48, \|25166723\|gb\|AAN73522.1\|AF48, \|25166631\|gb\|AAN73440.1\|AF48, \|25166963\|gb\|AAN73738.1\|AF48, \|25166773\|gb\|AAN73567.1\|AF48, \|25166671\|gb\|AAN73476.1\|AF48, \|32351104\|gb\|AAP76512.1\|, \|25167013\|gb\|AAN73783.1\|AF48, \|25166793\|gb\|AAN73585.1\|AF48, \|25166843\|gb\|AAN73630.1\|AF48, \|25166803\|gb\|AAN73594.1\|AF48, \|25166833\|gb\|AAN73621.1\|AF48, \|25167063\|gb\|AAN73828.1\|AF48, \|25166903\|gb\|AAN73684.1\|AF48, \|25166703\|gb\|AAN73504.1\|AF48, \|25167023\|gb\|AAN73792.1\|AF48, \|25166691\|gb\|AAN73494.1\|AF48, \|25166753\|gb\|AAN73549.1\|AF48, \|25167043\|gb\|AAN73810.1\|AF48, \|25166713\|gb\|AAN73513.1\|AF48, \|25166661\|gb\|AAN73467.1\|AF48, \|25167073\|gb\|AAN73837.1\|AF48, \|25167033\|gb\|AAN73801.1\|AF48, \|38679160\|gb\|AAR26412.1\|, \|25167053\|gb\|AAN73819.1\|AF48, \|25166813\|gb\|AAN73603.1\|AF48, \|25166953\|gb\|AAN73729.1\|AF48, \|25166733\|gb\|AAN73531.1\|AF48, \|25166651\|gb\|AAN73458.1\|AF48, \|15281482\|gb\|AAK94266.1\|AF36, \|15281422\|gb\|AAK94212.1\|AF36, \|5059052\|gb\|AAD38891.1\|AF119, \|5059043\|gb\|AAD38883.1\|AF119, \|1899135\|gb\|AAC57015.1\|, \|18699186\|gb\|AAL78446.1\|AF41, \|3403228\|gb\|AAC29061.1\|, \|62467718\|gb\|AAX83971.1\|, \|6690761\|gb\|AAF24320.1\|AF197, \|5931485\|dbj\|BAA84663.1\|, \|11761603\|gb\|AAG38931.1\|, \|11761563\|gb\|AAG38895.1\|, \|6690755\|gb\|AAF24314.1\|AF197, \|5931494\|dbj\|BAA84671.1\|, \|78100202\|gb\|ABB20905.1\|, \|6690776\|gb\|AAF24335.1\|AF197, \|6690769\|gb\|AAF24328.1\|AF197, \|4262339\|gb\|AAD14575.1\|, \|138506\|sp\|P24737\|VIF_HV1U4, \|3132813\|gb\|AAC29079.1\|, \|3132803\|gb\|AAC29070.1\|, \|82309894\|sp\|Q6PT01\|Q6PT01_9, \|46946861\|gb\|AAT06649.1\|, \|46946853\|gb\|AAT06642.1\|, \|46946846\|gb\|AAT06636.1\|, \|46946837\|gb\|AAT06628.1\|, \|46946828\|gb\|AAT06620.1\|, \|61102685\|gb\|AAX37811.1\|, \|1107648\|emb\|CAA62718.1\|, \|1107656\|emb\|CAA62725.1\|, \|1107654\|emb\|CAA62724.1\|, \|61102670\|gb\|AAX37798.1\|, \|1107612\|emb\|CAA62723.1\|, \|1107608\|emb\|CAA62720.1\|, \|61102662\|gb\|AAX37791.1\|, \|61102546\|gb\|AAX37691.1\|, \|1107620\|emb\|CAA62699.1\|, \|1107604\|emb\|CAA62713.1\|, \|1107602\|emb\|CAA62712.1\|, \|1107600\|emb\|CAA62711.1\|, \|1107598\|emb\|CAA62710.1\|, \|1890686\|gb\|AAC97543.1\|, \|61102619\|gb\|AAX37754.1\|, \|61102611\|gb\|AAX37747.1\|, \|61102562\|gb\|AAX37705.1\|, \|61102554\|gb\|AAX37698.1\|, \|61102522\|gb\|AAX37670.1\|, \|1107652\|emb\|CAA62721.1\|, \|1107610\|emb\|CAA62722.1\|, \|1107632\|emb\|CAA62697.1\|, \|1107630\|emb\|CAA62704.1\|, \|61102538\|gb\|AAX37684.1\|, \|61102530\|gb\|AAX37677.1\|, \|60218866\|gb\|AAX14844.1\|, \|61102603\|gb\|AAX37740.1\|, \|61102595\|gb\|AAX37733.1\|, \|61102587\|gb\|AAX37726.1\|, \|17046744\|gb\|AAL34762.1\|, \|56193006\|gb\|AAV84111.1\|, \|17046574\|gb\|AAL34609.1\|, \|56193042\|gb\|AAV84129.1\|, \|56193093\|gb\|AAV84156.1\|, \|56193077\|gb\|AAV84147.1\|, \|56193059\|gb\|AAV84138.1\|, \|56193025\|gb\|AAV84120.1\|, \|17046764\|gb\|AAL34780.1\|, \|17046564\|gb\|AAL34600.1\|, \|17046910\|gb\|AAL34911.1\|, \|17046694\|gb\|AAL34717.1\|, \|17046774\|gb\|AAL34789.1\|, \|17046664\|gb\|AAL34690.1\|, \|17046644\|gb\|AAL34672.1\|, \|17046920\|gb\|AAL34920.1\|, \|17046654\|gb\|AAL34681.1\|, \|17046544\|gb\|AAL34582.1\|, \|17046514\|gb\|AAL34555.1\|, \|17046900\|gb\|AAL34902.1\|, \|17046594\|gb\|AAL34627.1\|, \|17046754\|gb\|AAL34771.1\|, \|17046674\|gb\|AAL34699.1\|, \|17046734\|gb\|AAL34753.1\|, \|17046584\|gb\|AAL34618.1\|, \|26245471\|gb\|AAN77399.1\|, \|26245461\|gb\|AAN77390.1\|, \|17046794\|gb\|AAL34807.1\|, \|17046614\|gb\|AAL34645.1\|, \|17046724\|gb\|AAL34744.1\|, \|3252959\|gb\|AAD12107.1\|, \|3252949\|gb\|AAD12098.1\|, \|17046850\|gb\|AAL34857.1\|, \|17046834\|gb\|AAL34843.1\|, \|3252921\|gb\|AAD12073.1\|, \|17046890\|gb\|AAL34893.1\|, \|17046840\|gb\|AAL34848.1\|, \|13172884\|gb\|AAK14232.1\|, \|17046870\|gb\|AAL34875.1\|, \|17046860\|gb\|AAL34866.1\|, \|17046704\|gb\|AAL34726.1\|, \|17046784\|gb\|AAL34798.1\|, \|17046554\|gb\|AAL34591.1\|, \|17046824\|gb\|AAL34834.1\|, \|17046604\|gb\|AAL34636.1\|, \|56131602\|gb\|AAV80382.1\|, \|17046814\|gb\|AAL34825.1\|, \|17046804\|gb\|AAL34816.1\|, \|17046534\|gb\|AAL34573.1\|, \|17046624\|gb\|AAL34654.1\|, \|17046880\|gb\|AAL34884.1\|, \|17046714\|gb\|AAL34735.1\|, \|17046634\|gb\|AAL34663.1\|, \|17046684\|gb\|AAL34708.1\|, \|26245451\|gb\|AAN77381.1\|, \|17046524\|gb\|AAL34564.1\|, \|3676483\|gb\|AAC61988.1\|, \|5668925\|gb\|AAD46077.1\|AF076, \|1127913\|gb\|AAA83802.1\|, \|1127911\|gb\|AAA83801.1\|, \|1127909\|gb\|AAA83800.1\|, \|1127905\|gb\|AAA83798.1\|, \|1127903\|gb\|AAA83797.1\|, \|1127907\|gb\|AAA83799.1\|, \|3193274\|gb\|AAD03327.1\|, \|1127954\|gb\|AAA83822.1\|, \|2843169\|gb\|AAC02322.1\|, \|2843157\|gb\|AAC02316.1\|, \|2843159\|gb\|AAC02317.1\|, \|2843143\|gb\|AAC02309.1\|, \|2843167\|gb\|AAC02321.1\|, \|2843165\|gb\|AAC02320.1\|, \|2843127\|gb\|AAC02301.1\|, \|2843137\|gb\|AAC02306.1\|, \|2843135\|gb\|AAC02305.1\|, \|2843141\|gb\|AAC02308.1\|, \|2843129\|gb\|AAC02302.1\|, \|2843139\|gb\|AAC02307.1\|, \|2843131\|gb\|AAC02303.1\|, \|2843133\|gb\|AAC02304.1\|, \|2843149\|gb\|AAC02312.1\|, |

-continued

| VPR proteins |
|---|
| \|2843163\|gb\|AAC02319.1\|, \|2843161\|gb\|AAC02318.1\|, \|2843153\|gb\|AAC02314.1\|, \|2843147\|gb\|AAC02311.1\|, \|2843155\|gb\|AAC02315.1\|, \|2843151\|gb\|AAC02313.1\|, \|2843145\|gb\|AAC02310.1\|, \|62291047\|sp\|P69724\|VIF_HV1P, \|62291045\|sp\|P69722\|VIF_HV11, \|62291043\|sp\|P69720\|VIF_HV1B, \|328556\|gb\|AAB59868.1\|, \|62291046\|sp\|P69723\|VIF_HV1H, \|62291044\|sp\|P69721\|VIF_HV1B, \|401363\|sp\|P31820\|VIF_HV1NA, \|138494\|sp\|P04598\|VIF_HV1B5, \|1127952\|gb\|AAA83821.1\|, \|1127873\|gb\|AAA83782.1\|, \|1127865\|gb\|AAA83778.1\|, \|1127871\|gb\|AAA83781.1\|, \|1127867\|gb\|AAA83779.1\|, \|1055032\|gb\|AAA81038.1\|, \|1127968\|gb\|AAA83829.1\|, \|82317065\|sp\|Q5U8A2\|Q5U8A2_9, \|62548190\|gb\|AAX86742.1\|, \|62548180\|gb\|AAX86733.1\|, \|62548200\|gb\|AAX86751.1\|, \|62548170\|gb\|AAX86724.1\|, \|62548160\|gb\|AAX86715.1\|, \|1772627\|gb\|AAC32295.1\|, \|82317952\|sp\|Q6EG63\|Q6EG63_9, \|37677796\|gb\|AAQ97472.1\|, \|37677786\|gb\|AAQ97463.1\|, \|549324\|sp\|P35964\|VIF_HV1Y2, \|138496\|sp\|P03402\|VIF_HV1A2, \|327816\|gb\|AAB03746.1\|, \|138497\|sp\|P20877\|VIF_HV1JR, \|1127956\|gb\|AAA83823.1\|, \|37725229\|gb\|AAR02293.1\|, \|37725219\|gb\|AAR02284.1\|, \|37725199\|gb\|AAR02266.1\|, \|37725189\|gb\|AAR02257.1\|, \|82310551\|sp\|Q6TEA8\|Q6TEA8_9, \|37725209\|gb\|AAR02275.1\|, \|37725239\|gb\|AAR02302.1\|, \|37725249\|gb\|AAR02311.1\|, \|221479\|dbj\|BAA00994.1\|, \|687903\|gb\|AAB31804.1\|, \|687902\|gb\|AAB31803.1\|, \|138502\|sp\|P12504\|VIF_HV1N5, \|1127944\|gb\|AAA83817.1\|, \|1127937\|gb\|AAA83814.1\|, \|1127939\|gb\|AAA83815.1\|, \|1127931\|gb\|AAA83811.1\|, \|1127933\|gb\|AAA83812.1\|, \|1127917\|gb\|AAA83804.1\|, \|1127915\|gb\|AAA83803.1\|, \|1127929\|gb\|AAA83810.1\|, \|1127921\|gb\|AAA83806.1\|, \|1127919\|gb\|AAA83805.1\|, \|1127925\|gb\|AAA83808.1\|, \|138504\|sp\|P05900\|VIF_HV1RH, \|2853529\|gb\|AAC02398.1\|, \|2853520\|gb\|AAC02394.1\|, \|2853525\|gb\|AAC02396.1\|, \|2853522\|gb\|AAC02395.1\|, \|2853513\|gb\|AAC02391.1\|, \|2853500\|gb\|AAC02385.1\|, \|2853490\|gb\|AAC02380.1\|, \|2853506\|gb\|AAC02388.1\|, \|2853516\|gb\|AAC02392.1\|, \|2853502\|gb\|AAC02386.1\|, \|2853496\|gb\|AAC02383.1\|, \|2853504\|gb\|AAC02387.1\|, \|2853527\|gb\|AAC02397.1\|, \|2853498\|gb\|AAC02384.1\|, \|2853492\|gb\|AAC02381.1\|, \|2853508\|gb\|AAC02389.1\|, \|2853494\|gb\|AAC02382.1\|, \|2853518\|gb\|AAC02393.1\|, \|2853510\|gb\|AAC02390.1\|, \|138503\|sp\|P20890\|VIF_HV1OY, \|1127948\|gb\|AAA83819.1\|, \|54124751\|gb\|AAV30092.1\|, \|18699250\|gb\|AAL78491.1\|AF41, \|2281655\|gb\|AAB64165.1\|, \|1127942\|gb\|AAA83816.1\|, \|37677766\|gb\|AAQ97445.1\|, \|37677756\|gb\|AAQ97436.1\|, \|1127897\|gb\|AAA83794.1\|, \|1127893\|gb\|AAA83792.1\|, \|1127891\|gb\|AAA83791.1\|, \|1127881\|gb\|AAA83786.1\|, \|1127889\|gb\|AAA83790.1\|, \|1127885\|gb\|AAA83788.1\|, \|1127895\|gb\|AAA83793.1\|, \|1127879\|gb\|AAA83785.1\|, \|1127877\|gb\|AAA83784.1\|, \|1127887\|gb\|AAA83789.1\|, \|1127883\|gb\|AAA83787.1\|, \|2853482\|gb\|AAC02376.1\|, \|2853462\|gb\|AAC02366.1\|, \|2853466\|gb\|AAC02368.1\|, \|2853464\|gb\|AAC02367.1\|, \|2853447\|gb\|AAC02359.1\|, \|2853455\|gb\|AAC02363.1\|, \|2853488\|gb\|AAC02379.1\|, \|2853468\|gb\|AAC02369.1\|, \|2853478\|gb\|AAC02374.1\|, \|2853476\|gb\|AAC02373.1\|, \|2853486\|gb\|AAC02378.1\|, \|2853443\|gb\|AAC02357.1\|, \|2853439\|gb\|AAC02355.1\|, \|2853457\|gb\|AAC02364.1\|, \|2853451\|gb\|AAC02361.1\|, \|2853474\|gb\|AAC02372.1\|, \|2853484\|gb\|AAC02377.1\|, \|2853472\|gb\|AAC02371.1\|, \|2853445\|gb\|AAC02358.1\|, \|2853453\|gb\|AAC02362.1\|, \|2853449\|gb\|AAC02360.1\|, \|2853480\|gb\|AAC02375.1\|, \|2853437\|gb\|AAC02354.1\|, \|2853441\|gb\|AAC02356.1\|, \|2853470\|gb\|AAC02370.1\|, \|2853459\|gb\|AAC02365.1\|, \|82317942\|sp\|Q6EFW4\|Q6EFW4_9, \|37677906\|gb\|AAQ97571.1\|, \|37677896\|gb\|AAQ97562.1\|, \|37681533\|gb\|AAQ97643.1\|, \|37677776\|gb\|AAQ97454.1\|, \|36365546\|gb\|AAQ86749.1\|, \|36365510\|gb\|AAQ86717.1\|, \|36365438\|gb\|AAQ86653.1\|, \|36365411\|gb\|AAQ86629.1\|, \|36365456\|gb\|AAQ86669.1\|, \|36365429\|gb\|AAQ86645.1\|, \|36365420\|gb\|AAQ86637.1\|, \|36365402\|gb\|AAQ86621.1\|, \|36365393\|gb\|AAQ86613.1\|, \|36365375\|gb\|AAQ86597.1\|, \|36365384\|gb\|AAQ86605.1\|, \|36365537\|gb\|AAQ86741.1\|, \|36365447\|gb\|AAQ86661.1\|, \|36365483\|gb\|AAQ86693.1\|, \|36365465\|gb\|AAQ86677.1\|, \|36365501\|gb\|AAQ86709.1\|, \|36365492\|gb\|AAQ86701.1\|, \|36365474\|gb\|AAQ86685.1\|, \|36365528\|gb\|AAQ86733.1\|, \|36365519\|gb\|AAQ86725.1\|, \|47118232\|gb\|AAT11230.1\|, \|4205074\|gb\|AAD10945.1\|, \|4205047\|gb\|AAD10921.1\|, \|4205065\|gb\|AAD10937.1\|, \|4205056\|gb\|AAD10929.1\|, \|4204993\|gb\|AAD10873.1\|, \|4205020\|gb\|AAD10897.1\|, \|4205002\|gb\|AAD10881.1\|, \|4205011\|gb\|AAD10889.1\|, \|4205029\|gb\|AAD10905.1\|, \|4205038\|gb\|AAD10913.1\|, \|2853583\|gb\|AAC02424.1\|, \|2853535\|gb\|AAC02401.1\|, \|2853563\|gb\|AAC02414.1\|, \|2853546\|gb\|AAC02406.1\|, \|2853577\|gb\|AAC02421.1\|, \|2853581\|gb\|AAC02423.1\|, \|2853573\|gb\|AAC02419.1\|, \|2853556\|gb\|AAC02411.1\|, \|2853559\|gb\|AAC02412.1\|, \|2853554\|gb\|AAC02410.1\|, \|2853569\|gb\|AAC02417.1\|, \|2853544\|gb\|AAC02405.1\|, \|2853539\|gb\|AAC02403.1\|, \|2853537\|gb\|AAC02402.1\|, \|2853575\|gb\|AAC02420.1\|, \|2853565\|gb\|AAC02415.1\|, \|2853548\|gb\|AAC02407.1\|, \|2853579\|gb\|AAC02422.1\|, \|2853567\|gb\|AAC02416.1\|, \|2853542\|gb\|AAC02404.1\|, \|2853561\|gb\|AAC02413.1\|, \|2853552\|gb\|AAC02409.1\|, \|2853533\|gb\|AAC02400.1\|, \|2853531\|gb\|AAC02399.1\|, \|2853571\|gb\|AAC02418.1\|, \|2853550\|gb\|AAC02408.1\|, \|1127901\|gb\|AAA83796.1\|, \|1127899\|gb\|AAA83795.1\|, \|50404190\|gb\|AAT76860.1\|, \|1127830\|gb\|AAA83768.1\|, \|1127828\|gb\|AAA83767.1\|, \|37677866\|gb\|AAQ97535.1\|, \|37677856\|gb\|AAQ97526.1\|, \|1127970\|gb\|AAA83830.1\|, \|2853434\|gb\|AAC02353.1\|, \|2853407\|gb\|AAC02341.1\|, \|2853409\|gb\|AAC02342.1\|, \|2853423\|gb\|AAC02349.1\|, \|2853431\|gb\|AAC02352.1\|, \|2853429\|gb\|AAC02351.1\|, \|2853371\|gb\|AAC02324.1\|, \|2853369\|gb\|AAC02323.1\|, \|2853382\|gb\|AAC02329.1\|, \|2853427\|gb\|AAC02350.1\|, \|2853392\|gb\|AAC02334.1\|, \|2853388\|gb\|AAC02332.1\|, \|2853375\|gb\|AAC02326.1\|, \|2853384\|gb\|AAC02330.1\|, \|2853378\|gb\|AAC02327.1\|, \|2853405\|gb\|AAC02340.1\|, \|2853403\|gb\|AAC02339.1\|, \|2853380\|gb\|AAC02328.1\|, \|2853394\|gb\|AAC02335.1\|, \|2853415\|gb\|AAC02345.1\|, \|2853411\|gb\|AAC02343.1\|, \|2853400\|gb\|AAC02338.1\|, \|2853390\|gb\|AAC02333.1\|, \|2853386\|gb\|AAC02331.1\|, \|2853417\|gb\|AAC02346.1\|, \|2853373\|gb\|AAC02325.1\|, \|2853419\|gb\|AAC02347.1\|, \|2853413\|gb\|AAC02344.1\|, \|2853421\|gb\|AAC02348.1\|, \|2853398\|gb\|AAC02337.1\|, \|2853396\|gb\|AAC02336.1\|, |

| VPR proteins |
| --- |
| \|1127960\|gb\|AAA83825.1\|, \|33359203\|gb\|AAQ17028.1\|, \|37681543\|gb\|AAQ97652.1\|, \|37677846\|gb\|AAQ97517.1\|, \|1127966\|gb\|AAA83828.1\|, \|1127964\|gb\|AAA83827.1\|, \|82317948\|sp\|Q6EG27\|Q6EG27__9, \|37677836\|gb\|AAQ97508.1\|, \|37677826\|gb\|AAQ97499.1\|, \|66864703\|gb\|AAY57429.1\|, \|66864693\|gb\|AAY57420.1\|, \|66864683\|gb\|AAY57411.1\|, \|37677816\|gb\|AAQ97490.1\|, \|37677806\|gb\|AAQ97481.1\|, \|54124761\|gb\|AAV30101.1\|, \|82309893\|sp\|Q6PSX3\|Q6PSX3__9, \|82309892\|sp\|Q6PSV4\|Q6PSV4__9, \|82309895\|sp\|Q6PT24\|Q6PT24__9, \|1127857\|gb\|AAA83774.1\|, \|1127855\|gb\|AAA83773.1\|, \|1127853\|gb\|AAA83772.1\|, \|127851\|gb\|AAA83771.1\|, \|3511262\|gb\|AAC33784.1\|, \|138500\|sp\|P05898\|VIF__HV1MN, \|1127950\|gb\|AAA83820.1\|, \|37677886\|gb\|AAQ97553.1\|, \|37677876\|gb\|AAQ97544.1\|, \|1127946\|gb\|AAA83818.1\|, \|1127958\|gb\|AAA83824.1\|, \|61102651\|gb\|AAX37782.1\|, \|61102643\|gb\|AAX37775.1\|, \|61102579\|gb\|AAX37719.1\|, \|61102635\|gb\|AAX37768.1\|, \|61102627\|gb\|AAX37761.1\|, \|1107636\|emb\|CAA62707.1\|, \|1107634\|emb\|CAA62706.1\|, \|5805264\|gb\|AAD51913.1\|, \|61102677\|gb\|AAX37804.1\|, \|1107670\|emb\|CAA62732.1\|, \|1107668\|emb\|CAA62731.1\|, \|1107664\|emb\|CAA62729.1\|, \|1107666\|emb\|CAA62730.1\|, \|1107662\|emb\|CAA62728.1\|, \|1107658\|emb\|CAA62726.1\|, \|1107660\|emb\|CAA62727.1\|, \|1107646\|emb\|CAA62717.1\|, \|1107644\|emb\|CAA62716.1\|, \|1107642\|emb\|CAA62714.1\|, \|1107606\|emb\|CAA62715.1\|, \|1107638\|emb\|CAA62708.1\|, \|3540184\|gb\|AAK29350.1\|, \|3540164\|gb\|AAK29332.1\|, \|3540174\|gb\|AAK29341.1\|, \|34330004\|gb\|AAO65890.1\|, \|34330000\|gb\|AAO65887.1\|, \|1107626\|emb\|CAA62702.1\|, \|1107622\|emb\|CAA62700.1\|, \|1107624\|emb\|CAA62701.1\|, \|1107628\|emb\|CAA62703.1\|, \|1107616\|emb\|CAA62705.1\|, \|1107614\|emb\|CAA62696.1\|, \|1107618\|emb\|CAA62698.1\|, \|138507\|sp\|P04596\|VIF__HV1Z6, \|138495\|sp\|P12503\|VIF__HV1Z2, \|138498\|sp\|P04597\|VIF__HV1EL, \|138499\|sp\|P18805\|VIF__HV1ND, \|32399668\|emb\|CAD58645.1\|, \|32399659\|emb\|CAD58636.1\|, \|47118252\|gb\|AAT11239.1\|, \|15788299\|gb\|AAL07746.1\|, \|15787961\|gb\|AAL07551.1\|, \|15788279\|gb\|AAL07728.1\|, \|15788249\|gb\|AAL07701.1\|, \|15788289\|gb\|AAL07737.1\|, \|15788269\|gb\|AAL07719.1\|, \|55735996\|gb\|AAV59724.1\|, \|47118262\|gb\|AAT11248.1\|, \|15788240\|gb\|AAL07693.1\|, \|47118242\|gb\|AAT11221.1\|, \|47118222\|gb\|AAT11212.1\|, \|47118212\|gb\|AAT11203.1\|, \|55735987\|gb\|AAV59716.1\|, \|55735952\|gb\|AAV59685.1\|, \|55735960\|gb\|AAV59692.1\|, \|15788259\|gb\|AAL07710.1\|, \|55735969\|gb\|AAV59700.1\|, \|55735978\|gb\|AAV59708.1\|, \|12407075\|emb\|CAC24836.1\|, \|12407065\|emb\|CAC24830.1\|, \|62467691\|gb\|AAX83947.1\|, \|138501\|sp\|P04599\|VIF__HV1MA, \|1107650\|emb\|CAA62719.1\|, \|1107640\|emb\|CAA62709.1\|, \|3288391\|emb\|CAA06811.1\|, \|138521\|sp\|P17284\|VIF__SIVCZ, \|463060\|gb\|AAA99880.1\|, \|3172677\|gb\|AAK14190.1\|, \|3172707\|gb\|AAK14215.1\|, \|3172695\|gb\|AAK14205.1\|, \|3172689\|gb\|AAK14200.1\|, \|3172683\|gb\|AAK14195.1\|, \|16755646\|gb\|AAL28058.1\|, \|3172701\|gb\|AAK14210.1\|, \|469242\|gb\|AAA44861.1\|, \|5531677\|gb\|AAD44396.1\|AF055, \|5531653\|gb\|AAD44375.1\|AF055, \|5531669\|gb\|AAD44389.1\|AF055, \|5531645\|gb\|AAD44368.1\|AF055, \|5531661\|gb\|AAD44382.1\|AF055 |
| REV proteins |
| \|60141\|emb\|CAA41586.1\|, \|32261463\|gb\|AAP76528.1\|truncated, \|17352349\|gb\|AAL01568.1\|, \|2944135\|gb\|AAC05242.1\|, \|4324921\|gb\|AAD17185.1\|, \|4324915\|gb\|AAD17179.1\|, \|4324909\|gb\|AAD17173.1\|, \|4324902\|gb\|AAD17166.1\|, \|4324893\|gb\|AAD17157.1\|, \|4324884\|gb\|AAD17148.1\|, \|4324875\|gb\|AAD17139.1\|, \|4324866\|gb\|AAD17130.1\|, \|4324857\|gb\|AAD17121.1\|, \|4324851\|gb\|AAD17115.1\|, \|4324842\|gb\|AAD17106.1\|, \|4324836\|gb\|AAD17100.1\|, \|4324827\|gb\|AAD17091.1\|, \|4324818\|gb\|AAD17082.1\|, \|4324812\|gb\|AAD17076.1\|, \|4324803\|gb\|AAD17067.1\|, \|4324796\|gb\|AAD17060.1\|, \|4324787\|gb\|AAD17051.1\|, \|4324778\|gb\|AAD17042.1\|, \|4324770\|gb\|AAD17034.1\|, \|4324761\|gb\|AAD17025.1\|, \|4324752\|gb\|AAD17016.1\|, \|4324743\|gb\|AAD17007.1\|, \|8886637\|gb\|AAF80536.1\|AF179368__6, \|3114565\|gb\|AAD03183.1\|, \|3114557\|gb\|AAD03176.1\|, \|3114548\|gb\|AAD03168.1\|, \|2570319\|gb\|AAC97579.1\|, \|2570310\|gb\|AAC97571.1\|, \|2570304\|gb\|AAC63085.1\|, \|1537056\|gb\|AAC55464.1\|, \|2570329\|gb\|AAC32657.1\|, \|2570291\|gb\|AAC32648.1\|, \|16555093\|gb\|AAL06141.1\|, \|16555085\|gb\|AAL06140.1\|, \|16555077\|gb\|AAL06139.1\|, \|16555069\|gb\|AAL06138.1\|, \|16555061\|gb\|AAL06137.1\|, \|16555053\|gb\|AAL06136.1\|, \|16555045\|gb\|AAL06135.1\|, \|16555037\|gb\|AAL06134.1\|, \|16555029\|gb\|AAL06133.1\|, \|16555013\|gb\|AAL06131.1\|, \|16555005\|gb\|AAL06130.1\|, \|16554997\|gb\|AAL06129.1\|, \|16554989\|gb\|AAL06128.1\|, \|13560264\|dbj\|BAB40915.1\|, \|6581000\|gb\|AAF18408.1\|AF190128__8, \|6580991\|gb\|AAF18400.1\|AF190127__8, \|14530267\|gb\|AAK65997.1\|AF316544__6, \|11993202\|gb\|AAG42634.1\|, \|11066503\|gb\|AAG28618.1\|AF259955__6, \|15733959\|gb\|AAD49796.1\|AF107771__9, \|15733949\|gb\|AAD49787.1\|AF107770__9, \|1209817\|gb\|AAB40974.1\|, \|1209815\|gb\|AAB40973.1\|, \|1209813\|gb\|AAB40972.1\|, \|1209811\|gb\|AAB40971.1\|, \|1209809\|gb\|AAB40970.1\|, \|1209807\|gb\|AAB40969.1\|, \|1209805\|gb\|AAB40968.1\|, \|1209803\|gb\|AAB40967.1\|, \|1209801\|gb\|AAB40966.1\|, \|1209799\|gb\|AAB40965.1\|, \|1209797\|gb\|AAB40964.1\|, \|1209795\|gb\|AAB40963.1\|, \|1209793\|gb\|AAB40962.1\|, \|1209791\|gb\|AAB40961.1\|, \|1209789\|gb\|AAB40960.1\|, \|1209787\|gb\|AAB40959.1\|, \|1209785\|gb\|AAB40958.1\|, \|1209783\|gb\|AAB40957.1\|, \|1209781\|gb\|AAB40956.1\|, \|1353866\|gb\|AAB36505.1\|, \|1575477\|gb\|AAB09539.1\|, \|82321217\|sp\|Q97255\|Q97255__9HIV1, \|82321193\|sp\|Q9YKM6\|Q9YKM6__9HIV1, \|82320058\|sp\|Q9YKX5\|Q9YKX5__9HIV1, \|82320057\|sp\|Q9YKX2\|Q9YKX2__9HIV1, \|82320056\|sp\|Q9YKW8\|Q9YKW8__9HIV1, \|82320055\|sp\|Q9YKW2\|Q9YKW2__9HIV1, \|82320054\|sp\|Q9YKV8\|Q9YKV8__9HIV1, \|82320053\|sp\|Q9YKV3\|Q9YKV3__9HIV1, \|82320052\|sp\|Q9YKU8\|Q9YKU8__9HIV1, \|82320051\|sp\|Q9YKU3\|Q9YKU3__9HIV1, \|82320050\|sp\|Q9YKS9\|Q9YKS9__9HIV1, \|82320049\|sp\|Q9YKS3\|Q9YKS3__9HIV1, \|82320048\|sp\|Q9YKR9\|Q9YKR9__9HIV1, \|82320047\|sp\|Q9YKR2\|Q9YKR2__9HIV1, \|82320046\|sp\|Q9YKP6\|Q9YKP6__9HIV1, \|82320045\|sp\|Q9YKN9\|Q9YKN9__9HIV1, \|82320044\|sp\|Q9YKN2\|Q9YKN2__9HIV1, \|82320040\|sp\|Q9YJK5\|Q9YJK5__9HIV1, \|82320039\|sp\|Q9YJH5\|Q9YJH5__9HIV1, \|82320034\|sp\|Q9YJJ7\|Q9YIJ7__9HIV1, \|82314776\|sp\|Q97063\|Q97063__9HIV1, \|82313586\|sp\|Q8UMQ0\|Q8UMQ0__9HIV1, |

| VPR proteins |
| --- |
| \|82311083\|sp\|Q75006\|Q75006__9HIV1, \|82309089\|sp\|O70900\|O70900__9HIV1, \|82309088\|sp\|O70894\|O70894__9HIV1, \|82309087\|sp\|O70890\|O70890__9HIV1, \|82308941\|sp\|O41802\|O41802__9HIV1, \|82308940\|sp\|O41796\|O41796__9HIV1, \|82308939\|sp\|O41787\|O41787__9HIV1, \|82308938\|sp\|O41778\|O41778__9HIV1, \|82308937\|sp\|O41770\|O41770__9HIV1, \|6466840\|gb\|AAF13055.1\|, \|7021459\|gb\|AAF35358.1\|, \|2801503\|gb\|AAC82592.1\|, \|1123018\|gb\|AAC54647.1\|, \|1123008\|gb\|AAC54638.1\|, \|1072092\|gb\|AAC54548.1\|, \|1151165\|gb\|AAA85235.1\|, \|665536\|gb\|AAA76688.1\|, \|9629359\|ref\|NP_057854.1\|, \|82319769\|sp\|Q9QRX3\|Q9QRX3__9HIV1, \|82319768\|sp\|Q9QRW4\|Q9QRW4__9HIV1, \|82319641\|sp\|Q9QEF5\|Q9QEF5__9HIV1, \|82319631\|sp\|Q9Q716\|Q9Q716__9HIV1, \|82319630\|sp\|Q9Q707\|Q9Q707__9HIV1, \|82319531\|sp\|Q9J0G7\|Q9J0G7__9HIV1, \|82319301\|sp\|Q9JMJ3\|Q9JMJ3__9HIV1, \|82318851\|sp\|Q9DSM0\|Q9DSM0__9HIV1, \|82318817\|sp\|Q9DHB3\|Q9DHB3__9HIV1, \|82318650\|sp\|Q998E7\|Q998E7__9HIV1, \|82314713\|sp\|Q90QJ8\|Q90QJ8__9HIV1, \|82313889\|sp\|Q900M7\|Q900M7__9HIV1, \|82313888\|sp\|Q900M6\|Q900M6__9HIV1, \|82313887\|sp\|Q900M5\|Q900M5__9HIV1, \|82313886\|sp\|Q900M4\|Q900M4__9HIV1, \|82313885\|sp\|Q900M3\|Q900M3__9HIV1, \|82313884\|sp\|Q900M2\|Q900M2__9HIV1, \|82313883\|sp\|Q900M1\|Q900M1__9HIV1, \|82313882\|sp\|Q900M0\|Q900M0__9HIV1, \|82313881\|sp\|Q900L9\|Q900L9__9HIV1, \|82313880\|sp\|Q900L8\|Q900L8__9HIV1, \|82313879\|sp\|Q900L7\|Q900L7__9HIV1, \|82313878\|sp\|Q900K2\|Q900K2__9HIV1, \|82313877\|sp\|Q900K1\|Q900K1__9HIV1, \|82313876\|sp\|Q900K0\|Q900K0__9HIV1, \|82311301\|sp\|Q77YF8\|Q77YF8__9HIV1, \|82311056\|sp\|Q74597\|Q74597__9HIV1, \|82311053\|sp\|Q74088\|Q74088__9HIV1, \|82311051\|sp\|Q73334\|Q73334__9HIV1, \|82309086\|sp\|O70677\|O70677__9HIV1, \|1568314\|emb\|CAA02188.1\|, \|1398979\|dbj\|BAA12993.1\|, \|1398970\|dbj\|BAA13001.1\|, \|255651\|gb\|AAB23299.1\|, \|16555021\|gb\|AAL06132.1\|, \|6016893\|dbj\|BAA85230.1\|, \|82311300\|sp\|Q77Y21\|Q77Y219PLVG, \|9629921\|ref\|NP_046128.1\|, \|2828043\|gb\|AAB99964.1\|, \|82319609\|sp\|Q9PXZ1\|Q9PXZ1__9HIV1, \|82319757\|sp\|Q9QN93\|Q9QN93__9HIV1, \|8218031\|emb\|CAB92791.1\|, \|3002873\|gb\|AAD03229.1\|, \|912750\|gb\|AAA82867.1\|, \|912747\|gb\|AAA82865.1\|, \|912744\|gb\|AAA82863.1\|, \|912739\|gb\|AAA82860.1\|, \|912736\|gb\|AAA82858.1\|, \|912733\|gb\|AAA82856.1\|, \|912730\|gb\|AAA82854.1\|, \|912727\|gb\|AAA82852.1\|, \|912724\|gb\|AAA82850.1\|, \|912721\|gb\|AAA82848.1\|, \|912718\|gb\|AAA82846.1\|, \|912715\|gb\|AAA82844.1\|, \|912710\|gb\|AAA82841.1\|, \|912707\|gb\|AAA82839.1\|, \|912704\|gb\|AAA82837.1\|, \|912701\|gb\|AAA82835.1\|, \|912698\|gb\|AAA82833.1\|, \|912695\|gb\|AAA82831.1\|, \|912692\|gb\|AAA82829.1\|, \|912689\|gb\|AAA82827.1\|, \|912686\|gb\|AAA82825.1\|, \|912683\|gb\|AAA82823.1\|, \|912680\|gb\|AAA82821.1\|, \|912677\|gb\|AAA82819.1\|, \|912674\|gb\|AAA82817.1\|, \|912671\|gb\|AAA82815.1\|, \|912668\|gb\|AAA82813.1\|, \|912665\|gb\|AAA82811.1\|, \|912662\|gb\|AAA82809.1\|, \|912659\|gb\|AAA82807.1\|, \|912656\|gb\|AAA82805.1\|, \|912653\|gb\|AAA82803.1\|, \|912650\|gb\|AAA82801.1\|, \|912647\|gb\|AAA82799.1\|, \|912644\|gb\|AAA82797.1\|, \|912641\|gb\|AAA82795.1\|, \|912638\|gb\|AAA82793.1\|, \|912635\|gb\|AAA82791.1\|, \|912632\|gb\|AAA82789.1\|, \|912629\|gb\|AAA82787.1\|, \|912626\|gb\|AAA82785.1\|, \|912623\|gb\|AAA82783.1\|, \|912620\|gb\|AAA82781.1\|, \|912617\|gb\|AAA82779.1\|, \|912614\|gb\|AAA82777.1\|, \|912611\|gb\|AAA82775.1\|, \|912608\|gb\|AAA82773.1\|, \|912605\|gb\|AAA82771.1\|, \|912602\|gb\|AAA82769.1\|, \|912599\|gb\|AAA82767.1\|, \|912596\|gb\|AAA82765.1\|, \|912593\|gb\|AAA82763.1\|, \|912590\|gb\|AAA82761.1\|, \|912587\|gb\|AAA82759.1\|, \|912584\|gb\|AAA82757.1\|, \|7416431\|dbj\|BAA93863.1\|, \|7416425\|dbj\|BAA93860.1\|, \|7416419\|dbj\|BAA93857.1\|, \|7416396\|dbj\|BAA93846.1\|, \|7416394\|dbj\|BAA93845.1\|, \|7416421\|dbj\|BAA93858.1\|, \|7416401\|dbj\|BAA93848.1\|, \|7416398\|dbj\|BAA93847.1\|, \|7416429\|dbj\|BAA93862.1\|, \|7416413\|dbj\|BAA93854.1\|, \|7416407\|dbj\|BAA93851.1\|, \|7416427\|dbj\|BAA93861.1\|, \|7416423\|dbj\|BAA93859.1\|, \|7416417\|dbj\|BAA93856.1\|, \|7416415\|dbj\|BAA93855.1\|, \|7416411\|dbj\|BAA93853.1\|, \|7416409\|dbj\|BAA93852.1\|, \|7416405\|dbj\|BAA93850.1\|, \|7416403\|dbj\|BAA93849.1\|, \|18844742\|dbj\|BAB85464.1\|, \|1055035\|gb\|AAA81041.1\|, \|2745746\|gb\|AAC97530.1\|, \|3252972\|gb\|AAD12119.1\|truncated, \|3252962\|gb\|AAD12110.1\|truncated, \|3252952\|gb\|AAD12101.1\|truncated, \|3252932\|gb\|AAD12083.1\|truncated, \|3252924\|gb\|AAD12076.1\|truncated, \|3193277\|gb\|AAD03330.1\|, \|3193269\|gb\|AAD03323.1\|, \|1890689\|gb\|AAC97546.1\|, \|3378127\|gb\|AAC28450.1\|, \|20271245\|gb\|AAM18556.1\|AF493673__1mutant, \|20271243\|gb\|AAM18555.1\|AF493672__1mutant, \|17046923\|gb\|AAL34923.1\|, \|17046913\|gb\|AAL34914.1\|, \|17046903\|gb\|AAL34905.1\|, \|17046893\|gb\|AAL34896.1\|, \|17046873\|gb\|AAL34878.1\|, \|17046863\|gb\|AAL34869.1\|, \|17046853\|gb\|AAL34860.1\|, \|17046843\|gb\|AAL34851.1\|, \|17046827\|gb\|AAL34837.1\|, \|17046817\|gb\|AAL34828.1\|, \|17046807\|gb\|AAL34819.1\|, \|17046797\|gb\|AAL34810.1\|, \|17046787\|gb\|AAL34801.1\|, \|17046777\|gb\|AAL34792.1\|, \|17046767\|gb\|AAL34783.1\|, \|17046757\|gb\|AAL34774.1\|, \|17046747\|gb\|AAL34765.1\|, \|17046737\|gb\|AAL34756.1\|, \|17046727\|gb\|AAL34747.1\|, \|17046717\|gb\|AAL34738.1\|, \|17046707\|gb\|AAL34729.1\|, \|17046697\|gb\|AAL34720.1\|, \|17046687\|gb\|AAL34711.1\|, \|17046677\|gb\|AAL34702.1\|, \|17046667\|gb\|AAL34693.1\|, \|17046657\|gb\|AAL34684.1\|, \|17046647\|gb\|AAL34675.1\|, \|17046637\|gb\|AAL34666.1\|, \|17046627\|gb\|AAL34657.1\|, \|17046617\|gb\|AAL34648.1\|, \|17046607\|gb\|AAL34639.1\|, \|17046597\|gb\|AAL34630.1\|, \|17046587\|gb\|AAL34621.1\|, \|17046577\|gb\|AAL34612.1\|, \|17046567\|gb\|AAL34603.1\|, \|17046557\|gb\|AAL34594.1\|, \|17046547\|gb\|AAL34585.1\|, \|17046537\|gb\|AAL34576.1\|, \|17046527\|gb\|AAL34567.1\|, \|17046517\|gb\|AAL34558.1\|, \|1463017\|gb\|AAB05176.1\|, \|14209303\|dbj\|BAB55912.1\|, \|15788305\|gb\|AAL07752.1\|, \|15788295\|gb\|AAL07743.1\|, \|15788284\|gb\|AAL07733.1\|, \|15788275\|gb\|AAL07725.1\|, \|15788265\|gb\|AAL07716.1\|, \|15788255\|gb\|AAL07707.1\|, \|15788246\|gb\|AAL07699.1\|, \|15787963\|gb\|AAL07553.1\|, \|5805262\|gb\|AAD51911.1\|, \|13172886\|gb\|AAK14234.1\|, \|13540189\|gb\|AAK29355.1\|, \|13540179\|gb\|AAK29346.1\|, \|13540169\|gb\|AAK29337.1\|, \|11761601\|gb\|AAG38929.1\|, \|11761591\|gb\|AAG38920.1\|truncated, |

-continued

| VPR proteins |
|---|
| |11761581|gb|AAG38911.1|truncated, |11761571|gb|AAG38902.1|truncated, |11761561|gb|AAG38893.1|, |3252942|gb|AAD12092.1|, |3947931|gb|AAC82621.1|, |3098588|gb|AAC68855.1|, |3098578|gb|AAC68846.1|, |1899132|gb|AAC57012.1|, |1899117|gb|AAC56999.1|, |1899111|gb|AAC56994.1|, |1899106|gb|AAC56990.1|, |1899101|gb|AAC56986.1|, |3511264|gb|AAC33786.1|, |1772630|gb|AAC32298.1|, |3403224|gb|AAC29058.1|, |3403215|gb|AAC29050.1|, |3132816|gb|AAC29082.1|, |3132806|gb|AAC29073.1|, |2351239|gb|AAB68449.1|, |2351233|gb|AAB68444.1|, |2351228|gb|AAB68438.1|, |2194192|gb|AAB61130.1|, |23986256|gb|AAL12205.1|truncated, |23986240|gb|AAL12196.1|truncated, |23986226|gb|AAL12187.1|truncated, |23986212|gb|AAL12178.1|truncated, |21616429|gb|AAM66251.1|, |21616425|gb|AAM66248.1|, |21616420|gb|AAM66244.1|, |21616415|gb|AAM66240.1|, |21616410|gb|AAM66236.1|, |21616405|gb|AAM66232.1|, |21616400|gb|AAM66228.1|, |21616395|gb|AAM66224.1|, |21616390|gb|AAM66220.1|, |21616385|gb|AAM66216.1|, |21616380|gb|AAM66212.1|, |21616375|gb|AAM66208.1|, |21616370|gb|AAM66204.1|, |21616366|gb|AAM66201.1|, |21616361|gb|AAM66197.1|, |18844732|dbj|BAB85455.1|, |18643015|gb|AAL74050.1|, |3462804|gb|AAC33102.1|, |3462800|gb|AAC33099.1|, |16751267|gb|AAL05342.1|, |16751257|gb|AAL05333.1|, |16751244|gb|AAL05321.1|, |16751234|gb|AAL05312.1|, |15281504|gb|AAK94286.1|AF361879__6, |15281494|gb|AAK94277.1|AF361878__6, |15281485|gb|AAK94269.1|AF361877__6, |15281475|gb|AAK94260.1|AF361876__6, |15281465|gb|AAK94251.1|AF361875__6, |15281455|gb|AAK94242.1|AF361874__6truncated, |15281445|gb|AAK94233.1|AF361873__6, |15281435|gb|AAK94224.1|AF361872__6, |15281425|gb|AAK94215.1|AF361871__6, |14530232|gb|AAK65966.1|AF286236__6, |15982649|gb|AAL09937.1|, |3002845|gb|AAD03204.1|, |3002835|gb|AAD03195.1|, |5931497|dbj|BAA84674.1|, |5931488|dbj|BAA84666.1|, |13517088|dbj|BAB40426.1|, |3779270|gb|AAD03318.1|, |14530258|gb|AAK65989.1|AF286239__6, |14530250|gb|AAK65982.1|AF286238__6, |13569333|gb|AAK31067.1|AF286235__6, |13569323|gb|AAK31058.1|AF286234__6, |13569313|gb|AAK31049.1|AF286233__6, |13569303|gb|AAK31040.1|AF286232__6, |13569293|gb|AAK31031.1|AF286231__6, |13569283|gb|AAK31022.1|AF286230__6, |13569273|gb|AAK31013.1|AF286229__6, |13569263|gb|AAK31004.1|AF286228__6, |13569253|gb|AAK30995.1|AF286227__6, |13569243|gb|AAK30986.1|AF286226__6, |13569233|gb|AAK30977.1|AF286225__6, |13569223|gb|AAK30968.1|AF286224__6, |13569213|gb|AAK30959.1|AF286223__6, |13194604|gb|AAK15483.1|, |13194602|gb|AAK15482.1|, |13194600|gb|AAK15481.1|, |13194598|gb|AAK15480.1|, |13194596|gb|AAK15479.1|, |13194594|gb|AAK15478.1|, |13194592|gb|AAK15477.1|, |11321033|gb|AAG34024.1|, |11321023|gb|AAG34015.1|, |11321013|gb|AAG34006.1|, |11321003|gb|AAG33997.1|, |11095916|gb|AAG30120.1|AF286365__6, |11066493|gb|AAG28609.1|AF259954__6, |3808284|gb|AAC69310.1|, |5305359|gb|AAD41611.1|AF071474__6, |5305347|gb|AAD41601.1|AF071473__6, |3808276|gb|AAD13363.1|, |3808266|gb|AAC69302.1|, |3808256|gb|AAC69293.1|, |3808246|gb|AAC69284.1|, |6651488|gb|AAF22336.1|AF193277__9, |6651477|gb|AAF22325.1|AF193276__7, |6643034|gb|AAF20395.1|, |6651463|gb|AAF22315.1|AF193253__9, |6090970|gb|AAF03417.1|AF075703__5, |5668959|gb|AAD46103.1|AF076998__5, |5668944|gb|AAD46092.1|AF077336__6, |6910973|gb|AAF31324.1|AF146728__6, |5668928|gb|AAD46080.1|AF076475__6, |5668915|gb|AAD46069.1|AF076474__5, |5668885|gb|AAD46047.1|AF075701__5, |5305482|gb|AAD41670.1|AF075702__5, |5059055|gb|AAD38894.1|AF119820__6, |5059046|gb|AAD38886.1|AF119819__6, |3002891|gb|AAD03245.1|, |3002882|gb|AAD03237.1|, |3002864|gb|AAD03221.1|, |3002855|gb|AAD03213.1|, |3694866|gb|AAC62480.1|, |2281658|gb|AAB64168.1|, |1857266|gb|AAB54109.1|, |14290025|gb|AAK59209.1|, |14290016|gb|AAK59201.1|, |14290007|gb|AAK59193.1|, |14289998|gb|AAK59185.1|, |14289988|gb|AAK59176.1|, |912742|gb|AAA82862.1|, |62362596|gb|AAX81604.1|, |62362588|gb|AAX81600.1|, |82321178|sp|Q72819|Q72819__9HIV1, |82320172|sp|Q9YV23|Q9YV23__9HIV1, |82311052|sp|Q73371|Q73371__9HIV1, |82311047|sp|Q72857|Q72857__9HIV1, |82311045|sp|Q72855|Q72855__9HIV1, |82311043|sp|Q72853|Q72853__9HIV1, |82311041|sp|Q72851|Q72851__9HIV1, |82311040|sp|Q72850|Q72850__9HIV1, |82311038|sp|Q72848|Q72848__9HIV1, |82311036|sp|Q72846|Q72846__9HIV1, |82311034|sp|Q72844|Q72844__9HIV1, |82311032|sp|Q72842|Q72842__9HIV1, |82311030|sp|Q72840|Q72840__9HIV1, |82311028|sp|Q72838|Q72838__9HIV1, |82311026|sp|Q72836|Q72836__9HIV1, |82311024|sp|Q72834|Q72834__9HIV1, |82311021|sp|Q72831|Q72831__9HIV1, |82311019|sp|Q72829|Q72829__9HIV1, |82311017|sp|Q72827|Q72827__9HIV1, |82311015|sp|Q72825|Q72825__9HIV1, |82311013|sp|Q72823|Q72823__9HIV1, |82311011|sp|Q72821|Q72821__9HIV1, |82311009|sp|Q72817|Q72817__9HIV1, |82311007|sp|Q72815|Q72815__9HIV1, |82311005|sp|Q72813|Q72813__9HIV1, |82311003|sp|Q72811|Q72811__9HIV1, |82311001|sp|Q72809|Q72809__9HIV1, |82310999|sp|Q72807|Q72807__9HIV1, |82310997|sp|Q72805|Q72805__9HIV1, |82310995|sp|Q72803|Q72803__9HIV1, |82310993|sp|Q72801|Q72801__9HIV1, |82310991|sp|Q72799|Q72799__9HIV1, |82310989|sp|Q72797|Q72797__9HIV1, |82310987|sp|Q72795|Q72795__9HIV1, |82310985|sp|Q72793|Q72793__9HIV1, |82310983|sp|Q72791|Q72791__9HIV1, |82310981|sp|Q72789|Q72789__9HIV1, |82310979|sp|Q72787|Q72787__9HIV1, |82310977|sp|Q72785|Q72785__9HIV1, |82310975|sp|Q72783|Q72783__9HIV1, |82310973|sp|Q72781|Q72781__9HIV1, |82310971|sp|Q72779|Q72779__9HIV1, |82310969|sp|Q72777|Q72777__9HIV1, |82310967|sp|Q72775|Q72775__9HIV1, |82310965|sp|Q72773|Q72773__9HIV1, |82310963|sp|Q72771|Q72771__9HIV1, |82310961|sp|Q72769|Q72769__9HIV1, |82310959|sp|Q72767|Q72767__9HIV1, |82310957|sp|Q72765|Q72765__9HIV1, |82310955|sp|Q72763|Q72763__9HIV1, |82310953|sp|Q72761|Q72761__9HIV1, |

-continued

| VPR proteins |
|---|
| \|82310951\|sp\|Q72759\|Q72759__9HIV1, \|82310949\|sp\|Q72757\|Q72757__9HIV1, |
| \|82310947\|sp\|Q72755\|Q72755__9HIV1, \|82310945\|sp\|Q72753\|Q72753__9HIV1, |
| \|82310943\|sp\|Q72751\|Q72751__9HIV1, \|82310941\|sp\|Q72749\|Q72749__9HIV1, |
| \|82310939\|sp\|Q72747\|Q72747__9HIV1, \|82309226\|sp\|P89696\|P89696__9HIV1, |
| \|82309172\|sp\|O92653\|O92653__9HIV1, \|82309121\|sp\|O90154\|O90154__9HIV1, |
| \|66864706\|gb\|AAY57432.1\|, \|66864696\|gb\|AAY57423.1\|, \|66864686\|gb\|AAY57414.1\|, |
| \|27526993\|emb\|CAD43152.1\|, \|27526991\|emb\|CAD43151.1\|, |
| \|25166815\|gb\|AAN73605.1\|AF484496__5, \|25166765\|gb\|AAN73560.1\|AF484491__5, |
| \|25166705\|gb\|AAN73506.1\|AF484485__5truncated, \|56417610\|gb\|AAV90748.1\|, |
| \|56193096\|gb\|AAV84159.1\|, \|56193080\|gb\|AAV84150.1\|, \|56193062\|gb\|AAV84141.1\|, |
| \|56193045\|gb\|AAV84132.1\|, \|56193009\|gb\|AAV84114.1\|, \|54124764\|gb\|AAV30104.1\|, |
| \|54124754\|gb\|AAV30095.1\|, \|50404188\|gb\|AAT76858.1\|, \|47118265\|gb\|AAT11251.1\|, |
| \|47118255\|gb\|AAT11242.1\|, \|47118245\|gb\|AAT11224.1\|, \|47118235\|gb\|AAT11233.1\|, |
| \|47118225\|gb\|AAT11215.1\|, \|47118215\|gb\|AAT11206.1\|, \|1732490\|gb\|AAB38837.1\|, |
| \|1732480\|gb\|AAB38828.1\|, \|16755648\|gb\|AAL28060.1\|, \|32261500\|gb\|AAP76561.1\|truncated, |
| \|32261490\|gb\|AAP76552.1\|truncated, \|32261480\|gb\|AAP76543.1\|truncated, |
| \|32261470\|gb\|AAP76534.1\|truncated, \|33359207\|gb\|AAQ17030.1\|, \|26245474\|gb\|AAN77402.1\|, |
| \|26245464\|gb\|AAN77393.1\|, \|26245454\|gb\|AAN77384.1\|, \|1478062\|gb\|AAB51141.1\|, |
| \|22596257\|gb\|AAN03047.1\|AF457054__6, \|6690779\|gb\|AAF24338.1\|AF197341__5, |
| \|6690772\|gb\|AAF24331.1\|AF197340__5, \|6690765\|gb\|AAF24324.1\|AF197339__3, |
| \|6690758\|gb\|AAF24317.1\|AF197338__5, \|17981624\|gb\|AAL51094.1\|, |
| \|1469312\|gb\|AAB05048.1\|, \|328654\|gb\|AAA80322.1\|, \|14579617\|gb\|AAK69334.1\|, |
| \|14579607\|gb\|AAK69325.1\|, \|16118399\|gb\|AAL12762.1\|, \|16118389\|gb\|AAL12753.1\|, |
| \|16118379\|gb\|AAL12744.1\|, \|16118369\|gb\|AAL12735.1\|, \|16118361\|gb\|AAL12728.1\|, |
| \|16118355\|gb\|AAL12723.1\|, \|16118345\|gb\|AAL12714.1\|, \|16118333\|gb\|AAL12704.1\|, |
| \|16118316\|gb\|AAL12690.1\|, \|16118306\|gb\|AAL12681.1\|, \|16118296\|gb\|AAL12672.1\|, |
| \|16118286\|gb\|AAL12663.1\|, \|16118276\|gb\|AAL12654.1\|, \|16118266\|gb\|AAL12645.1\|, |
| \|16118256\|gb\|AAL12636.1\|, \|45360214\|gb\|AAS59245.1\|, \|45360204\|gb\|AAS59236.1\|, |
| \|45360194\|gb\|AAS59227.1\|, \|45360183\|gb\|AAS59217.1\|, \|45360173\|gb\|AAS59208.1\|, |
| \|45360163\|gb\|AAS59199.1\|, \|45360153\|gb\|AAS59190.1\|, \|45360143\|gb\|AAS59181.1\|, |
| \|82320179\|sp\|Q9YX51\|Q9YX5__9HIV1, \|82320178\|sp\|Q9YW94\|Q9YW94__9HIV1, |
| \|82320176\|sp\|Q9YV64\|Q9YV64__9HIV1 truncated, \|82319767\|sp\|Q9QRB3\|Q9QRB3__9HIV1, |
| \|82319624\|sp\|Q9Q6I5\|Q9Q6I5__9HIV1, \|82319623\|sp\|Q9Q6H9\|Q9Q6H9__9HIV1, |
| \|82319622\|sp\|Q9Q6H2\|Q9Q6H2__9HIV1, \|82319621\|sp\|Q9Q6G5\|Q9Q6G5__9HIV1, |
| \|82319339\|sp\|Q9IQP6\|Q9IQP6__9HIV1, \|82319338\|sp\|Q9IQP5\|Q9IQP5__9HIV1, |
| \|82319337\|sp\|Q9IQP4\|Q9IQP4__9HIV1, \|82319336\|sp\|Q9IQP3\|Q9IQP3__9HIV1, |
| \|82319335\|sp\|Q9IQP2\|Q9IQP2__9HIV1, \|82319334\|sp\|Q9IQP1\|Q9IQP1__9HIV1, |
| \|82319333\|sp\|Q9IQP0\|Q9IQP0__9HIV1, \|82319332\|sp\|Q9IQN9\|Q9IQN9__9HIV1, |
| \|82319331\|sp\|Q9IQN8\|Q9IQN8__9HIV1, \|82319330\|sp\|Q9IQN7\|Q9IQN7__9HIV1, |
| \|82319329\|sp\|Q9IQN6\|Q9IQN6__9HIV1, \|82319328\|sp\|Q9IQN5\|Q9IQN5__9HIV1, |
| \|82319327\|sp\|Q9IQN4\|Q9IQN4__9HIV1, \|82319326\|sp\|Q9IQN3\|Q9IQN3__9HIV1, |
| \|82319325\|sp\|Q9IQN2\|Q9IQN2__9HIV1, \|82319324\|sp\|Q9IQN1\|Q9IQN1__9HIV1, |
| \|82319323\|sp\|Q9IQN0\|Q9IQN0__9HIV1, \|82319322\|sp\|Q9IQM9\|Q9IQM9__9HIV1, |
| \|82319321\|sp\|Q9IQM8\|Q9IQM8__9HIV1, \|82319068\|sp\|Q9IBN5\|Q9IBN5__9HIV1, |
| \|82318824\|sp\|Q9DKG8\|Q9DKG8__9HIV1, \|82318823\|sp\|Q9DKG0\|Q9DKG0__9HIV1 truncated, |
| \|82318822\|sp\|Q9DKF2\|Q9DKF2__9HIV1 truncated, |
| \|82318821\|sp\|Q9DKE4\|Q9DKE4__9HIV1 truncated, |
| \|82318820\|sp\|Q9DKD5\|Q9DKD5__9HIV1, \|82318682\|sp\|Q99BZ8\|Q99BZ8__9HIV1, |
| \|82318620\|sp\|Q994C7\|Q994C7__9HIV1, \|82318619\|sp\|Q994B8\|Q994B8__9HIV1, |
| \|82318618\|sp\|Q994A9\|Q994A9__9HIV1, \|82317959\|sp\|Q6EK38\|Q6EK38__9HIV1, |
| \|82317958\|sp\|Q6EK22\|Q6EK22__9HIV1, \|82317957\|sp\|Q6EJW6\|Q6EJW6__9HIV1, |
| \|82317956\|sp\|Q6EJV0\|Q6EJV0__9HIV1, \|82317955\|sp\|Q6EJR8\|Q6EJR8__9HIV1, |
| \|82317954\|sp\|Q6EJQ2\|Q6EJQ2__9HIV1, \|82317880\|sp\|Q6E6X6\|Q6E6X6__9HIV1, |
| \|82317879\|sp\|Q6E6X0\|Q6E6X0__9HIV1, \|82317878\|sp\|Q6E6W3\|Q6E6W3__9HIV1, |
| \|82317877\|sp\|Q6E6V6\|Q6E6V6__9HIV1, \|82317876\|sp\|Q6E6U8\|Q6E6U8__9HIV1, |
| \|82317875\|sp\|Q6E6U1\|Q6E6U1__9HIV1, \|82317307\|sp\|Q5VCT6\|Q5VCT6__9HIV1, |
| \|82317054\|sp\|Q5S5D0\|Q5S5D0__9HIV1, \|82317053\|sp\|Q5S5C2\|Q5S5C2__9HIV1, |
| \|82317052\|sp\|Q5S5B4\|Q5S5B4__9HIV1, \|82317051\|sp\|Q5S5A2\|Q5S5A2__9HIV1, |
| \|82317050\|sp\|Q5S594\|Q5S594__9HIV1, \|82314773\|sp\|Q90VT0\|Q90VT0__9HIV1, |
| \|82314204\|sp\|Q90DD7\|Q90DD7__9HIV1, \|82314155\|sp\|Q909R5\|Q909R5__9HIV1, |
| \|82314069\|sp\|Q908N3\|Q908N3__9HIV1, \|82314068\|sp\|Q908M4\|Q908M4__9HIV1, |
| \|82314067\|sp\|Q908L5\|Q908L5__9HIV1, \|82314066\|sp\|Q908K6\|Q908K6__9HIV1, |
| \|82314065\|sp\|Q908J7\|Q908J7__9HIV1, \|82314064\|sp\|Q908I8\|Q908I8__9HIV1, |
| \|82314063\|sp\|Q908H9\|Q908H9__9HIV1, \|82313862\|sp\|Q8UTU1\|Q8UTU1__9HIV1, |
| \|82313861\|sp\|Q8UTT2\|Q8UTT2__9HIV1, \|82313860\|sp\|Q8UTS3\|Q8UTS3__9HIV1, |
| \|82313859\|sp\|Q8UTR4\|Q8UTR4__9HIV1, \|82313858\|sp\|Q8UTQ5\|Q8UTQ5__9HIV1, |
| \|82313857\|sp\|Q8UTP6\|Q8UTP6__9HIV1, \|82313856\|sp\|Q8UTN7\|Q8UTN7__9HIV1, |
| \|82313855\|sp\|Q8UTM8\|Q8UTM8__9HIV1, \|82313854\|sp\|Q8UTL9\|Q8UTL9__9HIV1, |
| \|82313853\|sp\|Q8UTL0\|Q8UTL0__9HIV1, \|82313852\|sp\|Q8UTK1\|Q8UTK1__9HIV1, |
| \|82313850\|sp\|Q8UTJ2\|Q8UTJ2__9HIV1, \|82313849\|sp\|Q8UTI3\|Q8UTI3__9HIV1, |
| \|82313848\|sp\|Q8UTH4\|Q8UTH4__9HIV1, \|82313847\|sp\|Q8UTG5\|Q8UTG5__9HIV1, |
| \|82313846\|sp\|Q8UTF6\|Q8UTF6__9HIV1, \|82313845\|sp\|Q8UTE7\|Q8UTE7__9HIV1, |
| \|82313844\|sp\|Q8UTD8\|Q8UTD8__9HIV1, \|82313843\|sp\|Q8UTC9\|Q8UTC9__9HIV1, |
| \|82313842\|sp\|Q8UTC0\|Q8UTC0__9HIV1, \|82313841\|sp\|Q8UTB1\|Q8UTB1__9HIV1, |
| \|82313840\|sp\|Q8UTA2\|Q8UTA2__9HIV1, \|82313839\|sp\|Q8UT93\|Q8UT93__9HIV1, |
| \|82313838\|sp\|Q8UT84\|Q8UT84__9HIV1, \|82313837\|sp\|Q8UT75\|Q8UT75__9HIV1, |
| \|82313836\|sp\|Q8UT66\|Q8UT66__9HIV1, \|82313835\|sp\|Q8UT57\|Q8UT57__9HIV1, |

-continued

| VPR proteins |
|---|
| |82313834|sp|Q8UT48|Q8UT48__9HIV1, |82313833|sp|Q8UT39|Q8UT39__9HIV1, |82313832|sp|Q8UT30|Q8UT30__9HIV1, |82313831|sp|Q8UT21|Q8UT21__9HIV1, |82313830|sp|Q8UT12|Q8UT12__9HIV1, |82313828|sp|Q8USZ8|Q8USZ8__9HIV1, |82313827|sp|Q8USY9|Q8USY9__9HIV1, |82313826|sp|Q8USY0|Q8USY0__9HIV1, |82313825|sp|Q8USX1|Q8USX1__9HIV1, |82313823|sp|Q8USV3|Q8USV3__9HIV1, |82313822|sp|Q8USU4|Q8USU4__9HIV1, |82313821|sp|Q8UST5|Q8UST5__9HIV1, |82313820|sp|Q8USS6|Q8USS6__9HIV1, |82313632|sp|Q8UNF7|Q8UNF7__9HIV1, |82313386|sp|Q8Q2T1|Q8Q2T1__9HIV1mutant, |82313385|sp|Q8Q2T0|Q8Q2T0__9HIV1mutant, |82312603|sp|Q8AFF5|Q8AFF5__9HIV1, |82312602|sp|Q8AFE6|Q8AFE6__9HIV1, |82312601|sp|Q8AFD7|Q8AFD7__9HIV1, |82312212|sp|Q80159|Q80159__9HIV1, |82311079|sp|Q74904|Q74904__9HIV1, |82311078|sp|Q74903|Q74903__9HIV1, |82311077|sp|Q74902|Q74902__9HIV1, |82311076|sp|Q74901|Q74901__9HIV1, |82311075|sp|Q74900|Q74900__9HIV1, |82311074|sp|Q74899|Q74899__9HIV1, |82311073|sp|Q74898|Q74898__9HIV1, |82311072|sp|Q74897|Q74897__9HIV1, |82311071|sp|Q74896|Q74896__9HIV1, |82311070|sp|Q74895|Q74895__9HIV1, |82311069|sp|Q74894|Q74894__9HIV1, |82311068|sp|Q74893|Q74893__9HIV1, |82311067|sp|Q74892|Q74892__9HIV1, |82311066|sp|Q74891|Q74891__9HIV1, |82311065|sp|Q74890|Q74890__9HIV1, |82311064|sp|Q74889|Q74889__9HIV1, |82311063|sp|Q74888|Q74888__9HIV1, |82311062|sp|Q74887|Q74887__9HIV1, |82311061|sp|Q74886|Q74886__9HIV1, |82311058|sp|Q74748|Q74748__9HIV1, |82311055|sp|Q74457|Q74457__9HIV1, |82310819|sp|Q70141|Q70141__9HIV1, |82310552|sp|Q6TEB4|Q6TEB4__9HIV1, |82310550|sp|Q6TEA5|Q6TEA5__9HIV1, |82310549|sp|Q6TE96|Q6TE96__9HIV1, |82310548|sp|Q6TE87|Q6TE87__9HIV1, |82310547|sp|Q6TE78|Q6TE78__9HIV1, |82310546|sp|Q6TE69|Q6TE69__9HIV1, |82310545|sp|Q6TE60|Q6TE60__9HIV1, |82309402|sp|Q5DID6|Q5DID6__9HIV1, |82309247|sp|P90444|P90444__9HIV1, |82309232|sp|P89834|P89834__9HIV1, |82309231|sp|P89831|P89831__9HIV1, |82309230|sp|P89828|P89828__9HIV1, |82309229|sp|P89825|P89825__9HIV1, |82309228|sp|P89822|P89822__9HIV1, |82309227|sp|P89818|P89818__9HIV1, |82309220|sp|P88160|P88160__9HIV1, |82309219|sp|P88154|P88154__9HIV1, |82309194|sp|O92940|O92940__9HIV1, |82309132|sp|O91084|O91084__9HIV1, |82309124|sp|O90292|O90292__9HIV1, |82309122|sp|O90176|O90176__9HIV1, |82309120|sp|O90094|O90094__9HIV1 truncated, |82309119|sp|O90086|O90086__9HIV1truncated, |82309118|sp|O90077|O90077__9HIV1, |82309117|sp|O90068|O90068__9HIV1truncated, |82309116|sp|O90061|O90061__9HIV1 truncated, |82309115|sp|O89930|O89930__9HIV1, |82309104|sp|O72617|O72617__9HIV1, |82309103|sp|O72612|O72612__9HIV1, |82309102|sp|O71969|O71969__9HIV1, |82308885|sp|O12162|O12162__9HIV1, |74099687|gb|AAZ28904.1|, |78100205|gb|ABB20908.1|, |74273484|gb|ABA01464.1|, |74273475|gb|ABA01456.1|, |74273465|gb|ABA01447.1|, |74273455|gb|ABA01438.1|, |74273446|gb|ABA01430.1|, |74273436|gb|ABA01421.1|, |74273426|gb|ABA01412.1|, |74273416|gb|ABA01403.1|, |74273406|gb|ABA01394.1|, |74273396|gb|ABA01385.1|, |74273368|gb|ABA01361.1|, |74273364|gb|ABA01358.1|, |74273342|gb|ABA01339.1|, |74315784|gb|ABA02506.1|, |74315774|gb|ABA02497.1 truncated, |74315764|gb|ABA02488.1|, |74315754|gb|ABA02479.1|, |74315744|gb|ABA02470.1|, |74315727|gb|ABA02455.1|, |64310622|gb|AAY41252.1|, |64310551|gb|AAY41246.1|, |64310508|gb|AAY41243.1|, |62946406|gb|AAY22383.1|, |57869734|gb|AAW57767.1|, |57869725|gb|AAW57759.1|, |57869716|gb|AAW57751.1|, |57869706|gb|AAW57742.1|, |57869698|gb|AAW57735.1|, |57869689|gb|AAW57727.1|, |57869679|gb|AAW57718.1|, |57869669|gb|AAW57709.1|, |57869659|gb|AAW57700.1|, |57869649|gb|AAW57691.1|, |57869630|gb|AAW57674.1|, |57869622|gb|AAW57667.1|, |57869613|gb|AAW57659.1|, |57869603|gb|AAW57650.1|, |57869593|gb|AAW57641.1|, |57869584|gb|AAW57633.1|, |57869574|gb|AAW57624.1|, |57869564|gb|AAW57615.1|, |57869556|gb|AAW57608.1|, |57869547|gb|AAW57600.1|, |18699245|gb|AAL78487.1|AF414005__3, |18699174|gb|AAL78439.1|AF413982__2, |18699171|gb|AAL78437.1|AF413981__4, |18699165|gb|AAL78432.1|AF413980__3, |60218869|gb|AAX14847.1|, |55740250|gb|AAV63822.1|, |55740241|gb|AAV63814.1|, |55740231|gb|AAV63805.1|, |45361204|gb|AAS59395.1|, |45361192|gb|AAS59386.1|, |45361179|gb|AAS59380.1|, |45361171|gb|AAS59375.1|, |45361159|gb|AAS59368.1|, |45361152|gb|AAS59364.1|, |45361140|gb|AAS59355.1|, |45361128|gb|AAS59346.1|, |45361118|gb|AAS59337.1|, |45361106|gb|AAS59328.1|, |45361094|gb|AAS59319.1|, |45361080|gb|AAS59310.1|, |45361070|gb|AAS59301.1|, |62467721|gb|AAX83974.1|, |62467716|gb|AAX83970.1|, |62467706|gb|AAX83961.1|, |52421753|gb|AAU45389.1|, |52421742|gb|AAU45381.1|, |62467696|gb|AAX83952.1|, |51950725|gb|AAU14917.1|, |51950715|gb|AAU14908.1|, |3288394|emb|CAA06814.1|, |26000279|gb|AAN75312.1|, |26000269|gb|AAN75303.1|truncated, |26000259|gb|AAN75294.1|, |25167075|gb|AAN73839.1|AF484522__5, |25167065|gb|AAN73830.1|AF484521__5, |25167055|gb|AAN73821.1|AF484520__5, |25167045|gb|AAN73812.1|AF484519__5, |25167035|gb|AAN73803.1|AF484518__5, |25167025|gb|AAN73794.1|AF484517__5, |25167015|gb|AAN73785.1|AF484516__5, |25167005|gb|AAN73776.1|AF484515__5, |25166995|gb|AAN73767.1|AF484514__5, |25166985|gb|AAN73758.1|AF484513__5, |25166975|gb|AAN73749.1|AF484512__5, |25166965|gb|AAN73740.1|AF484511__5, |25166955|gb|AAN73731.1|AF484510__5, |25166945|gb|AAN73722.1|AF484509__5, |25166935|gb|AAN73713.1|AF484508__5, |25166925|gb|AAN73704.1|AF484507__5, |25166915|gb|AAN73695.1|AF484506__5, |25166905|gb|AAN73686.1|AF484505__5, |25166895|gb|AAN73677.1|AF484504__5, |25166885|gb|AAN73668.1|AF484503__5, |25166875|gb|AAN73659.1|AF484502__5, |25166865|gb|AAN73650.1|AF484501__5, |25166855|gb|AAN73641.1|AF484500__5, |25166845|gb|AAN73632.1|AF484499__5, |

| VPR proteins |
| --- |
| |25166835|gb|AAN73623.1|AF484498__5, |25166825|gb|AAN73614.1|AF484497__5, |
| |25166805|gb|AAN73596.1|AF484495__5, |25166795|gb|AAN73587.1|AF484494__5, |
| |25166785|gb|AAN73578.1|AF484493__5, |25166775|gb|AAN73569.1|AF484492__5, |
| |25166755|gb|AAN73551.1|AF484490__5, |25166745|gb|AAN73542.1|AF484489__5, |
| |25166735|gb|AAN73533.1|AF484488__5, |25166725|gb|AAN73524.1|AF484487__5, |
| |25166715|gb|AAN73515.1|AF484486__5, |25166699|gb|AAN73501.1|AF484484__1, |
| |25166693|gb|AAN73496.1|AF484483__5, |25166683|gb|AAN73487.1|AF484482__5, |
| |25166673|gb|AAN73478.1|AF484481__5, |25166663|gb|AAN73469.1|AF484480__5, |
| |25166653|gb|AAN73460.1|AF484479__5, |25166643|gb|AAN73451.1|AF484478__5, |
| |25166634|gb|AAN73443.1|AF484477__6, |23194117|gb|AAN15025.1|, |41400298|gb|AAS01344.1|, |
| |55735999|gb|AAV59727.1|, |55735990|gb|AAV59719.1|, |55735981|gb|AAV59711.1|, |
| |55735972|gb|AAV59703.1|, |55735963|gb|AAV59695.1|, |55735954|gb|AAV59687.1|, |
| |45644394|gb|AAS72948.1|, |45644386|gb|AAS72941.1|, |36365549|gb|AAQ86752.1|, |
| |36365540|gb|AAQ86744.1|, |36365531|gb|AAQ86736.1|, |36365522|gb|AAQ86728.1|, |
| |36365513|gb|AAQ86720.1|, |36365504|gb|AAQ86712.1|, |36365495|gb|AAQ86704.1|, |
| |36365486|gb|AAQ86696.1|, |36365477|gb|AAQ86688.1|, |36365468|gb|AAQ86680.1|, |
| |36365459|gb|AAQ86672.1|, |36365450|gb|AAQ86664.1|, |36365441|gb|AAQ86656.1|, |
| |36365432|gb|AAQ86648.1|, |36365423|gb|AAQ86640.1|, |36365414|gb|AAQ86632.1|, |
| |36365405|gb|AAQ86624.1|, |36365396|gb|AAQ86616.1|, |36365387|gb|AAQ86608.1|, |
| |36365378|gb|AAQ86600.1|, |56193028|gb|AAV84123.1|, |56131605|gb|AAV80385.1|, |
| |46946856|gb|AAT06645.1|, |51599144|gb|AAU08228.1|, |51599134|gb|AAU08219.1|, |
| |47027393|gb|AAT08773.1|, |29409331|gb|AAM67407.1|, |29409319|gb|AAM67397.1|, |
| |29409311|gb|AAM67390.1|, |29409300|gb|AAM67380.1|, |39777439|gb|AAR31015.1|, |
| |39777429|gb|AAR31006.1|, |39777419|gb|AAR30997.1|, |39777409|gb|AAR30988.1|, |
| |39777399|gb|AAR30979.1|, |39777389|gb|AAR30970.1|, |39777379|gb|AAR30961.1|, |
| |38491941|gb|AAR22304.1|, |38491931|gb|AAR22295.1|, |38491920|gb|AAR22285.1|, |
| |38491904|gb|AAR22271.1|, |38491894|gb|AAR22262.1|, |38491885|gb|AAR22254.1|, |
| |38491875|gb|AAR22245.1|, |38491865|gb|AAR22236.1|, |38491856|gb|AAR22228.1|, |
| |38491846|gb|AAR22219.1|, |38491836|gb|AAR22210.1|, |38491826|gb|AAR22201.1|, |
| |38491816|gb|AAR22192.1|, |38491806|gb|AAR22183.1|, |38491796|gb|AAR22174.1|, |
| |38491786|gb|AAR22165.1|, |38491776|gb|AAR22156.1|, |38491767|gb|AAR22148.1|, |
| |38491759|gb|AAR22141.1|, |38491749|gb|AAR22132.1|, |38491739|gb|AAR22123.1|, |
| |38491728|gb|AAR22114.1|, |38491718|gb|AAR22105.1|, |38491708|gb|AAR22096.1|, |
| |38491700|gb|AAR22089.1|, |38491692|gb|AAR22082.1|, |38491683|gb|AAR22074.1|, |
| |38491673|gb|AAR22065.1|, |38491663|gb|AAR22056.1|, |38491653|gb|AAR22047.1|, |
| |38491643|gb|AAR22038.1|, |38491633|gb|AAR22029.1|, |38491623|gb|AAR22020.1|, |
| |38491617|gb|AAR22015.1|, |38491610|gb|AAR22009.1|, |38491601|gb|AAR22001.1|, |
| |38491591|gb|AAR21992.1|, |38491581|gb|AAR21983.1|, |38491571|gb|AAR21974.1|, |
| |38491561|gb|AAR21965.1|, |38491551|gb|AAR21956.1|, |38491541|gb|AAR21947.1|, |
| |38491532|gb|AAR21939.1|, |38491524|gb|AAR21932.1|, |38491515|gb|AAR21924.1|, |
| |38491505|gb|AAR21915.1|, |38491495|gb|AAR21906.1|, |38491485|gb|AAR21897.1|, |
| |37683042|gb|AAQ98598.1|, |37683032|gb|AAQ98589.1|, |37683022|gb|AAQ98580.1|, |
| |37683013|gb|AAQ98572.1|, |37683003|gb|AAQ98563.1|, |37682993|gb|AAQ98554.1|, |
| |37682983|gb|AAQ98545.1|, |37682973|gb|AAQ98536.1|, |37682963|gb|AAQ98527.1|, |
| |37682953|gb|AAQ98518.1|, |37682943|gb|AAQ98509.1|, |37682933|gb|AAQ98500.1|, |
| |37682923|gb|AAQ98491.1|, |37682915|gb|AAQ98484.1|, |37682905|gb|AAQ98475.1|, |
| |37682894|gb|AAQ98466.1|, |37682884|gb|AAQ98457.1|, |37682877|gb|AAQ98451.1|, |
| |37682875|gb|AAQ98450.1|, |37682873|gb|AAQ98449.1|, |37682866|gb|AAQ98443.1|, |
| |37682856|gb|AAQ98434.1|, |37682846|gb|AAQ98425.1|, |37682836|gb|AAQ98416.1|, |
| |37682826|gb|AAQ98407.1|, |37682816|gb|AAQ98398.1|, |37682806|gb|AAQ98389.1|, |
| |37682796|gb|AAQ98380.1|, |37682786|gb|AAQ98371.1|, |37682776|gb|AAQ98362.1|, |
| |37682766|gb|AAQ98353.1|, |37682756|gb|AAQ98344.1|, |37682746|gb|AAQ98335.1|, |
| |37682736|gb|AAQ98326.1|, |37682726|gb|AAQ98317.1|, |37682716|gb|AAQ98308.1|, |
| |37682706|gb|AAQ98299.1|, |33331480|gb|AAQ10924.1|, |33331470|gb|AAQ10915.1|, |
| |33331460|gb|AAQ10906.1|, |4336347|gb|AAD17773.1|, |4336338|gb|AAD17764.1|, |
| |37935589|gb|AAO65562.1|, |37909410|gb|AAO65571.1|, |37935984|gb|AAO47221.1|, |
| |37935974|gb|AAO47212.1|, |37935964|gb|AAO47203.1|, |37935955|gb|AAO47195.1|, |
| |37935945|gb|AAO47186.1|, |37935935|gb|AAO47177.1|, |37935925|gb|AAO47168.1|, |
| |37935915|gb|AAO47159.1|, |37935904|gb|AAO47150.1|, |37935895|gb|AAO47142.1|, |
| |37935884|gb|AAO47133.1|, |37935875|gb|AAO47125.1|, |37935865|gb|AAO47116.1|, |
| |37935855|gb|AAO47107.1|, |37935845|gb|AAO47098.1|, |30269371|gb|AAP29649.1|, |
| |19908412|gb|AAL96767.1|, |34811838|gb|AAO40781.1|, |32189804|gb|AAP75715.1|, |
| |28933407|gb|AAO62621.1|AF468970__6, |23394931|gb|AAN31652.1|, |23394924|gb|AAN31646.1|, |
| |33390885|gb|AAQ17104.1|, |32344851|gb|AAM82306.1|, |32344841|gb|AAM82297.1|, |
| |33328325|gb|AAQ09614.1|, |33328203|gb|AAQ09551.1|, |33328193|gb|AAQ09542.1|, |
| |30720411|gb|AAP33679.1|, |25807942|gb|AAN74529.1|, |25807932|gb|AAN74520.1|, |
| |30038319|gb|AAP12632.1|, |30027261|gb|AAP06264.1|, |29119347|gb|AAO63260.1|, |
| |29119335|gb|AAO63249.1|, |29119329|gb|AAO63244.1|, |29119320|gb|AAO63236.1|, |
| |29119310|gb|AAO63227.1|, |29119301|gb|AAO63219.1|, |29119291|gb|AAO63210.1|, |
| |29119281|gb|AAO63201.1|, |29119271|gb|AAO63192.1|, |29119264|gb|AAO63186.1|, |
| |26518642|gb|AAN83916.1|, |24754009|gb|AAN64127.1|, |24753999|gb|AAN64118.1|, |
| |24753988|gb|AAN64109.1|, |24753977|gb|AAN64100.1|, |24753966|gb|AAN64091.1|, |
| |24753954|gb|AAN64081.1|, |24181513|gb|AAN47132.1|, |24181503|gb|AAN47123.1|, |
| |24181493|gb|AAN47114.1|, |24181483|gb|AAN47105.1|, |22596584|gb|AAN03337.1|AF457091__1, |
| |22596579|gb|AAN03333.1|AF457090__6, |22596569|gb|AAN03324.1|AF457089__6, |
| |22596559|gb|AAN03315.1|AF457088__6, |22596549|gb|AAN03306.1|AF457087__6, |
| |22596539|gb|AAN03297.1|AF457086__6, |22596529|gb|AAN03288.1|AF457085__6, |

| VPR proteins |
| --- |
| \|22596519\|gb\|AAN03279.1\|AF457084__6, \|22596509\|gb\|AAN03270.1\|AF457083__6, \|22596499\|gb\|AAN03261.1\|AF457082__6, \|22596489\|gb\|AAN03252.1\|AF457081__6, \|22596479\|gb\|AAN03243.1\|AF457080__6, \|22596469\|gb\|AAN03234.1\|AF457079__6, \|22596459\|gb\|AAN03225.1\|AF457078__6, \|22596449\|gb\|AAN03216.1\|AF457077__6, \|22596436\|gb\|AAN03205.1\|AF457075__6, \|22596424\|gb\|AAN03195.1\|AF457073__6, \|22596414\|gb\|AAN03186.1\|AF457072__6, \|22596403\|gb\|AAN03177.1\|AF457070__6, \|22596393\|gb\|AAN03168.1\|AF457069__6, \|22596383\|gb\|AAN03159.1\|AF457068__6, \|22596373\|gb\|AAN03150.1\|AF457067__6, \|22596363\|gb\|AAN03141.1\|AF457066__6, \|22596353\|gb\|AAN03132.1\|AF457065__6, \|22596343\|gb\|AAN03123.1\|AF457064__6, \|22596333\|gb\|AAN03114.1\|AF457063__6, \|22596323\|gb\|AAN03105.1\|AF457062__6, \|22596313\|gb\|AAN03096.1\|AF457061__6, \|22596298\|gb\|AAN03083.1\|AF457059__6, \|22596288\|gb\|AAN03074.1\|AF457058__6, \|22596277\|gb\|AAN03065.1\|AF457056__6, \|22596267\|gb\|AAN03056.1\|AF457055__6, \|22596247\|gb\|AAN03038.1\|AF457053__6, \|22596237\|gb\|AAN03029.1\|AF457052__6, \|22596227\|gb\|AAN03020.1\|AF457051__6, \|2286139\|gb\|AAB64285.1\|, \|2286130\|gb\|AAB64277.1\|, \|17902153\|gb\|AAL47816.1\|, \|17902142\|gb\|AAL47807.1\|, \|17902131\|gb\|AAL47798.1\|, \|17902120\|gb\|AAL47789.1\|, \|17902109\|gb\|AAL47780.1\|, \|17902098\|gb\|AAL47771.1\|, \|17864056\|gb\|AAL47049.1\|, \|17864046\|gb\|AAL47040.1\|, \|17864036\|gb\|AAL47031.1\|, \|22532297\|gb\|AAM97890.1\|AF492624__6, \|22532287\|gb\|AAM97881.1\|AF492623__6, \|22532145\|gb\|AAM97856.1\|AF460974__6, \|22532136\|gb\|AAM97848.1\|AF460972__6, \|22297045\|gb\|AAM94501.1\|, \|902804\|gb\|AAB60576.1\|, \|818220\|gb\|AAB47932.1\|, \|1465782\|gb\|AAB05603.1\|, \|1171170\|gb\|AAA86251.1\|, \|326428\|gb\|AAA44219.1\|, \|60652141\|gb\|AAX33205.1\|, \|60652128\|gb\|AAX33193.1\|, \|60652118\|gb\|AAX33184.1\|, \|60652108\|gb\|AAX33175.1\|, \|60652098\|gb\|AAX33166.1\|, \|60652088\|gb\|AAX33157.1\|, \|60652078\|gb\|AAX33148.1\|, \|60652071\|gb\|AAX33142.1\|, \|60652060\|gb\|AAX33132.1\|, \|60652050\|gb\|AAX33123.1\|, \|60652040\|gb\|AAX33114.1\|, \|60652030\|gb\|AAX33105.1\|, \|60652020\|gb\|AAX33096.1\|, \|60652011\|gb\|AAX33088.1\|, \|60652001\|gb\|AAX33079.1\|, \|60651991\|gb\|AAX33070.1\|, \|60651981\|gb\|AAX33061.1\|, \|60651971\|gb\|AAX33052.1\|, \|60651961\|gb\|AAX33043.1\|, \|60651951\|gb\|AAX33034.1\|, \|60651941\|gb\|AAX33025.1\|, \|60651931\|gb\|AAX33016.1\|, \|60651921\|gb\|AAX33007.1\|, \|60651911\|gb\|AAX32998.1\|, \|60651902\|gb\|AAX32990.1\|, \|60651892\|gb\|AAX32981.1\|, \|60651882\|gb\|AAX32972.1\|, \|60651872\|gb\|AAX32963.1\|, \|60651862\|gb\|AAX32954.1\|, \|60651852\|gb\|AAX32945.1\|, \|60651843\|gb\|AAX32937.1\|, \|60651833\|gb\|AAX32928.1\|, \|60544792\|gb\|AAX22737.1\|, \|60544782\|gb\|AAX22728.1\|, \|71726047\|gb\|AAZ39175.1\|, \|71726037\|gb\|AAZ39166.1\|, \|71726027\|gb\|AAZ39157.1\|, \|71726017\|gb\|AAZ39148.1\|, \|71726007\|gb\|AAZ39139.1\|, \|71725997\|gb\|AAZ39130.1\|, \|71725987\|gb\|AAZ39121.1\|, \|71725977\|gb\|AAZ39112.1\|, \|71725967\|gb\|AAZ39103.1\|, \|71725957\|gb\|AAZ39094.1\|, \|62956404\|gb\|AAY23536.1\|, \|62956392\|gb\|AAY23525.1\|, \|62956381\|gb\|AAY23515.1\|, \|62956371\|gb\|AAY23506.1\|, \|62956360\|gb\|AAY23496.1\|, \|83026818\|gb\|ABB96453.1\|, \|83026810\|gb\|ABB96446.1\|, \|83026800\|gb\|ABB96437.1\|, \|83026790\|gb\|ABB96428.1\|, \|83026780\|gb\|ABB96419.1\|, \|14579597\|gb\|AAK69316.1\|, \|82571411\|gb\|ABB84168.1\|, \|82571401\|gb\|ABB84159.1\|, \|82571391\|gb\|ABB84150.1\|, \|82571384\|gb\|ABB84144.1\|, \|82571374\|gb\|ABB84135.1\|, \|82571364\|gb\|ABB84126.1\|, \|82571354\|gb\|ABB84117.1\|, \|82571344\|gb\|ABB84108.1\|, \|82571334\|gb\|ABB84099.1\|, \|82571324\|gb\|ABB84090.1\|, \|82571314\|gb\|ABB84081.1\|, \|82571304\|gb\|ABB84072.1\|, \|82571294\|gb\|ABB84063.1\|, \|82571284\|gb\|ABB84054.1\|, \|82571274\|gb\|ABB84045.1\|, \|82571265\|gb\|ABB84037.1\|, \|82571255\|gb\|ABB84028.1\|, \|82571245\|gb\|ABB84019.1\|, \|82571235\|gb\|ABB84010.1\|, \|82571225\|gb\|ABB84001.1\|, \|82571206\|gb\|ABB83984.1\|, \|82571196\|gb\|ABB83975.1\|, \|82322076\|sp\|Q50D72\|Q50D72__9HIV1, \|82322073\|sp\|Q50D63\|Q50D63__9HIV1, \|82322070\|sp\|Q50D56\|Q50D56__9HIV1, \|82321311\|sp\|Q507F0\|Q507F0__9HIV1, \|82321307\|sp\|Q507E4\|Q507E4__9HIV1, \|82321303\|sp\|Q507C9\|Q507C9__9HIV1, \|82321301\|sp\|Q507C1\|Q507C1__9HIV1, \|82321298\|sp\|Q507B5\|Q507B5__9HIV1, \|82321027\|sp\|Q52VK9\|Q52VK9__9HIV1, \|82320177\|sp\|Q9YVF0\|Q9YVF0__9HIV1, \|82320171\|sp\|Q9YV16\|Q9YV16__9HIV1, \|82320170\|sp\|Q9YV02\|Q9YV02__9HIV1, \|82320169\|sp\|Q9YUZ5\|Q9YUZ5__9HIV1, \|82320029\|sp\|Q9WSF5\|Q9WSF5__9HIV1, \|82320028\|sp\|Q9WSE6\|Q9WSE6__9HIV1, \|82320027\|sp\|Q9WS47\|Q9WS47__9HIV1, \|82319988\|sp\|Q9WQI4\|Q9WQI4__9HIV1, \|82319987\|sp\|Q9WQH6\|Q9WQH6__9HIV1, \|82319978\|sp\|Q9WLH7\|Q9WLH7__9HIV1, \|82319977\|sp\|Q9WLH0\|Q9WLH0__9HIV1, \|82319893\|sp\|Q9WIR9\|Q9WIR9__9HIV1, \|82319794\|sp\|Q9WC67\|Q9WC67__9HIV1, \|82319793\|sp\|Q9WC58\|Q9WC58__9HIV1, \|82319774\|sp\|Q9QSU4\|Q9QSU4__9HIV1, \|82319773\|sp\|Q9QST5\|Q9QST5__9HIV1, \|82319772\|sp\|Q9QSS6\|Q9QSS6__9HIV1, \|82319771\|sp\|Q9QSR8\|Q9QSR8__9HIV1, \|82319770\|sp\|Q9QSQ9\|Q9QSQ9__9HIV1, \|82319756\|sp\|Q9QML7\|Q9QML7__9HIV1, \|82319755\|sp\|Q9QMK9\|Q9QMK9__9HIV1, \|82319754\|sp\|Q9QM85\|Q9QM85__9HIV1, \|82319629\|sp\|Q9Q6Y8\|Q9Q6Y8__9HIV1, \|82319628\|sp\|Q9Q6X1\|Q9Q6X1__9HIV1, \|82319627\|sp\|Q9Q6W0\|Q9Q6W0__9HIV1, \|82319626\|sp\|Q9Q6V2\|Q9Q6V2__9HIV1, \|82319545\|sp\|Q9JAC3\|Q9JAC3__9HIV1, \|82319476\|sp\|Q9IW65\|Q9IW65__9HIV1, \|82319475\|sp\|Q9IW48\|Q9IW48__9HIV1, \|82319473\|sp\|Q9IW39\|Q9IW39__9HIV1, \|82319470\|sp\|Q9IV99\|Q9IV99__9HIV1, \|82319469\|sp\|Q9IV90\|Q9IV90__9HIV1, \|82319468\|sp\|Q9IV14\|Q9IV14__9HIV1, \|82319102\|sp\|Q9IDV4\|Q9IDV4__9HIV1, \|82319101\|sp\|Q9IDA0\|Q9IDA0__9HIV1, \|82319100\|sp\|Q9ID91\|Q9ID91__9HIV1, \|82318835\|sp\|Q9DQ28\|Q9DQ28__9HIV1, \|82318834\|sp\|Q9DQ11\|Q9DQ11__9HIV1, \|82318833\|sp\|Q9DQ04\|Q9DQ04__9HIV1, \|82318812\|sp\|Q9DGV0\|Q9DGV0__9HIV1, \|82318651\|sp\|Q998H3\|Q998H3__9HIV1, \|82318634\|sp\|Q994R7\|Q994R7__9HIV1, \|82318633\|sp\|Q994Q8\|Q994Q8__9HIV1, \|82318632\|sp\|Q994P9\|Q994P9__9HIV1, \|82318631\|sp\|Q994P0\|Q994P0__9HIV1, \|82318630\|sp\|Q994N1\|Q994N1__9HIV1, \|82318629\|sp\|Q994M2\|Q994M2__9HIV1, \|82318627\|sp\|Q994L3\|Q994L3__9HIV1, \|82318626\|sp\|Q994K4\|Q994K4__9HIV1, \|82318625\|sp\|Q994J5\|Q994J5__9HIV1, |

| VPR proteins |
| --- |
| \|82318624\|sp\|Q994I6\|Q994I6_9HIV1, \|82318623\|sp\|Q994H7\|Q994H7_9HIV1, \|82318622\|sp\|Q994G8\|Q994G8_9HIV1, \|82318621\|sp\|Q994F9\|Q994F9_9HIV1, \|82318611\|sp\|Q993N4\|Q993N4_9HIV1, \|82318610\|sp\|Q993N3\|Q993N3_9HIV1, \|82318609\|sp\|Q993N2\|Q993N2_9HIV1, \|82318608\|sp\|Q993N1\|Q993N1_9HIV1, \|82318607\|sp\|Q993N0\|Q993N0_9HIV1, \|82318606\|sp\|Q993M9\|Q993M9_9HIV1, \|82318605\|sp\|Q993M7\|Q993M7_9HIV1, \|82318433\|sp\|Q6JP20\|Q6JP20_9HIV1, \|82318432\|sp\|Q6JP11\|Q6JP11_9HIV1, \|82318431\|sp\|Q6JP02\|Q6JP02_9HIV1, \|82318430\|sp\|Q6JNY4\|Q6JNY4_9HIV1, \|82318429\|sp\|Q6JNX5\|Q6JNX5_9HIV1, \|82318428\|sp\|Q6JNW6\|Q6JNW6_9HIV1, \|82318427\|sp\|Q6JNV7\|Q6JNV7_9HIV1, \|82318426\|sp\|Q6JNU8\|Q6JNU8_9HIV1, \|82318425\|sp\|Q6JNT9\|Q6JNT9_9HIV1, \|82318424\|sp\|Q6JNT0\|Q6JNT0_9HIV1, \|82318423\|sp\|Q6JNS1\|Q6JNS1_9HIV1, \|82318422\|sp\|Q6JNR2\|Q6JNR2_9HIV1, \|82318421\|sp\|Q6JNQ3\|Q6JNQ3_9HIV1, \|82318420\|sp\|Q6JNP4\|Q6JNP4_9HIV1, \|82318419\|sp\|Q6JNN5\|Q6JNN5_9HIV1, \|82318418\|sp\|Q6JNM6\|Q6JNM6_9HIV1, \|82318417\|sp\|Q6JNM0\|Q6JNM0_9HIV1, \|82318416\|sp\|Q6JNL9\|Q6JNL9_9HIV1, \|82318415\|sp\|Q6JNL8\|Q6JNL8_9HIV1, \|82318414\|sp\|Q6JNL2\|Q6JNL2_9HIV1, \|82318413\|sp\|Q6JNK3\|Q6JNK3_9HIV1, \|82318412\|sp\|Q6JNJ4\|Q6JNJ4_9HIV1, \|82318411\|sp\|Q6JNI5\|Q6JNI5_9HIV1, \|82318410\|sp\|Q6JNH8\|Q6JNH8_9HIV1, \|82318408\|sp\|Q6JNG9\|Q6JNG9_9HIV1, \|82318407\|sp\|Q6JNG0\|Q6JNG0_9HIV1, \|82318406\|sp\|Q6JNF1\|Q6JNF1_9HIV1, \|82318405\|sp\|Q6JNE2\|Q6JNE2_9HIV1, \|82318404\|sp\|Q6JNC4\|Q6JNC4_9HIV1, \|82318403\|sp\|Q6JNB5\|Q6JNB5_9HIV1, \|82318402\|sp\|Q6JNA6\|Q6JNA6_9HIV1, \|82318401\|sp\|Q6JN97\|Q6JN97_9HIV1, \|82318400\|sp\|Q6JN89\|Q6JN89_9HIV1, \|82318399\|sp\|Q6JN80\|Q6JN80_9HIV1, \|82318398\|sp\|Q6JN71\|Q6JN71_9HIV1, \|82317976\|sp\|Q6H1T8\|Q6H1T8_9HIV1, \|82317975\|sp\|Q6H1S9\|Q6H1S9_9HIV1, \|82317974\|sp\|Q6H1S0\|Q6H1S0_9HIV1, \|82317973\|sp\|Q6H1R1\|Q6H1R1_9HIV1, \|82317972\|sp\|Q6H1Q2\|Q6H1Q2_9HIV1, \|82317971\|sp\|Q6H1P3\|Q6H1P3_9HIV1, \|82317970\|sp\|Q6H1N4\|Q6H1N4_9HIV1, \|82317969\|sp\|Q6H1M5\|Q6H1M5_9HIV1, \|82317953\|sp\|Q6EG87\|Q6EG87_9HIV1, \|82317950\|sp\|Q6EG60\|Q6EG60_9HIV1, \|82317949\|sp\|Q6EG42\|Q6EG42_9HIV1, \|82317947\|sp\|Q6EG24\|Q6EG24_9HIV1, \|82317945\|sp\|Q6EFZ7\|Q6EFZ7_9HIV1, \|82317944\|sp\|Q6EFY8\|Q6EFY8_9HIV1, \|82317943\|sp\|Q6EFX9\|Q6EFX9_9HIV1, \|82317941\|sp\|Q6EFW1\|Q6EFW1_9HIV1, \|82317938\|sp\|Q6EFN2\|Q6EFN2_9HIV1, \|82317937\|sp\|Q6EFM3\|Q6EFM3_9HIV1, \|82317782\|sp\|Q6B4P3\|Q6B4P3_9HIV1, \|82317781\|sp\|Q69GT2\|Q69GT2_9HIV1, \|82317780\|sp\|Q69GS3\|Q69GS3_9HIV1, \|82317779\|sp\|Q69GR4\|Q69GR4_9HIV1, \|82317778\|sp\|Q69GQ5\|Q69GQ5_9HIV1, \|82317777\|sp\|Q69GP6\|Q69GP6_9HIV1, \|82317776\|sp\|Q69GN7\|Q69GN7_9HIV1, \|82317775\|sp\|Q69GM8\|Q69GM8_9HIV1, \|82317644\|sp\|Q673V8\|Q673V8_9HIV1, \|82317643\|sp\|Q673U6\|Q673U6_9HIV1, \|82317642\|sp\|Q672U5\|Q672U5_9HIV1, \|82317641\|sp\|Q672T7\|Q672T7_9HIV1, \|82317640\|sp\|Q672S9\|Q672S9_9HIV1, \|82317639\|sp\|Q672S1\|Q672S1_9HIV1, \|82317633\|sp\|Q66TT6\|Q66TT6_9HIV1, \|82317632\|sp\|Q66TS6\|Q66TS6_9HIV1, \|82317631\|sp\|Q66TR8\|Q66TR8_9HIV1, \|82317630\|sp\|Q66TQ7\|Q66TQ7_9HIV1, \|82317628\|sp\|Q66Q72\|Q66Q72_9HIV1, \|82317484\|sp\|Q5VGP8\|Q5VGP8_9HIV1, \|82317198\|sp\|Q5UEH6\|Q5UEH6_9HIV1, \|82317197\|sp\|Q5UEG7\|Q5UEG7_9HIV1, \|82317086\|sp\|Q5U9C1\|Q5U9C1_9HIV1, \|82317085\|sp\|Q5U9B2\|Q5U9B2_9HIV1, \|82317084\|sp\|Q5U9A4\|Q5U9A4_9HIV1, \|82317083\|sp\|Q5U995\|Q5U995_9HIV1, \|82317082\|sp\|Q5U987\|Q5U987_9HIV1, \|82317081\|sp\|Q5U980\|Q5U980_9HIV1, \|82317080\|sp\|Q5U971\|Q5U971_9HIV1, \|82317079\|sp\|Q5U962\|Q5U962_9HIV1, \|82317078\|sp\|Q5U947\|Q5U947_9HIV1, \|82317077\|sp\|Q5U940\|Q5U940_9HIV1, \|82317076\|sp\|Q5U8K7\|Q5U8K7_9HIV1, \|82317075\|sp\|Q5U8J8\|Q5U8J8_9HIV1, \|82317074\|sp\|Q5U8I9\|Q5U8I9_9HIV1, \|82317073\|sp\|Q5U8I0\|Q5U8I0_9HIV1, \|82317072\|sp\|Q5U8H1\|Q5U8H1_9HIV1, \|82317071\|sp\|Q5U8G2\|Q5U8G2_9HIV1, \|82317070\|sp\|Q5U8F3\|Q5U8F3_9HIV1, \|82317069\|sp\|Q5U8D5\|Q5U8D5_9HIV1, \|82317068\|sp\|Q5U8C6\|Q5U8C6_9HIV1, \|82317067\|sp\|Q5U8B7\|Q5U8B7_9HIV1, \|82317066\|sp\|Q5U8A8\|Q5U8A8_9HIV1, \|82317063\|sp\|Q5U890\|Q5U890_9HIV1, \|82317062\|sp\|Q5U881\|Q5U881_9HIV1, \|82317055\|sp\|Q5SFQ3\|Q5SFQ3_9HIV1, \|82315003\|sp\|Q5QCV9\|Q5QCV9_9HIV1, \|82315002\|sp\|Q5QCV0\|Q5QCV0_9HIV1, \|82315001\|sp\|Q5QCU1\|Q5QCU1_9HIV1, \|82315000\|sp\|Q5QCT2\|Q5QCT2_9HIV1, \|82314999\|sp\|Q5QCS3\|Q5QCS3_9HIV1, \|82314998\|sp\|Q5QCR4\|Q5QCR4_9HIV1, \|82314916\|sp\|Q5PZV6\|Q5PZV6_9HIV1, \|82314915\|sp\|Q5PYN9\|Q5PYN9_9HIV1, \|82314914\|sp\|Q5PYM6\|Q5PYM6_9HIV1, \|82314715\|sp\|Q90QP9\|Q90QP9_9HIV1, \|82314714\|sp\|Q90QP2\|Q90QP2_9HIV1, \|82314596\|sp\|Q90MM5\|Q90MM5_9HIV1, \|82314595\|sp\|Q90ML6\|Q90ML6_9HIV1, \|82314594\|sp\|Q90MK7\|Q90MK7_9HIV1, \|82314307\|sp\|Q90DZ4\|Q90DZ4_9HIV1, \|82314306\|sp\|Q90DU3\|Q90DU3_9HIV1, \|82314189\|sp\|Q90D26\|Q90D26_9HIV1, \|82314188\|sp\|Q90D17\|Q90D17_9HIV1, \|82314187\|sp\|Q90D08\|Q90D08_9HIV1, \|82314186\|sp\|Q90CZ9\|Q90CZ9_9HIV1truncated, \|82314185\|sp\|Q90CZ0\|Q90CZ0_9HIV1, \|82314184\|sp\|Q90CY1\|Q90CY1_9HIV1, \|82314183\|sp\|Q90CX2\|Q90CX2_9HIV1, \|82314182\|sp\|Q90CW4\|Q90CW4_9HIV1, \|82314181\|sp\|Q90CV5\|Q90CV5_9HIV1, \|82314166\|sp\|Q90CK8\|Q90CK8_9HIV1, \|82314165\|sp\|Q90CJ9\|Q90CJ9_9HIV1, \|82314164\|sp\|Q90CJ1\|Q90CJ1_9HIV1, \|82314163\|sp\|Q90CI3\|Q90CI3_9HIV1, \|82314162\|sp\|Q90CH5\|Q90CH5_9HIV1, \|82313943\|sp\|Q902U4\|Q902U4_9HIV1, \|82313942\|sp\|Q902T5\|Q902T5_9HIV1, \|82313941\|sp\|Q902S6\|Q902S6_9HIV1, \|82313940\|sp\|Q902R7\|Q902R7_9HIV1, \|82313939\|sp\|Q902Q8\|Q902Q8_9HIV1, \|82313938\|sp\|Q902P9\|Q902P9_9HIV1, \|82313937\|sp\|Q902P0\|Q902P0_9HIV1, \|82313936\|sp\|Q902N4\|Q902N4_9HIV1, \|82313935\|sp\|Q902M6\|Q902M6_9HIV1, \|82313934\|sp\|Q902L6\|Q902L6_9HIV1, \|82313933\|sp\|Q902K7\|Q902K7_9HIV1, \|82313932\|sp\|Q902K2\|Q902K2_9HIV1, \|82313931\|sp\|Q902J5\|Q902J5_9HIV1, \|82313930\|sp\|Q902I6\|Q902I6_9HIV1, |

-continued

| VPR proteins |
|---|
| \|82313929\|sp\|Q902H7\|Q902H7__9HIV1, \|82313928\|sp\|Q902G8\|Q902G8__9HIV1, |
| \|82313927\|sp\|Q902G1\|Q902G1__9HIV1, \|82313925\|sp\|Q901Z2\|Q901Z2__9HIV1, |
| \|82313924\|sp\|Q901Y3\|Q901Y3__9HIV1, \|82313923\|sp\|Q901X4\|Q901X4__9HIV1, |
| \|82313922\|sp\|Q901W5\|Q901W5__9HIV1, \|82313920\|sp\|Q900Z6\|Q900Z6__9HIV1, |
| \|82313919\|sp\|Q900Y7\|Q900Y7__9HIV1, \|82313641\|sp\|Q8UPQ7\|Q8UPQ7__9HIV1, |
| \|82313640\|sp\|Q8UPP9\|Q8UPP9__9HIV1, \|82313639\|sp\|Q8UPP0\|Q8UPP0__9HIV1, |
| \|82313638\|sp\|Q8UPN2\|Q8UPN2__9HIV1, \|82313637\|sp\|Q8UPM3\|Q8UPM3__9HIV1, |
| \|82313636\|sp\|Q8UPL4\|Q8UPL4__9HIV1, \|82313635\|sp\|Q8UNM1\|Q8UNM1__9HIV1, |
| \|82313634\|sp\|Q8UNL2\|Q8UNL2__9HIV1, \|82313633\|sp\|Q8UNK3\|Q8UNK3__9HIV1, |
| \|82313585\|sp\|Q8UMG7\|Q8UMG7__9HIV1, \|82313584\|sp\|Q8UMF8\|Q8UMF8__9HIV1, |
| \|82313581\|sp\|Q8UMD6\|Q8UMD6__9HIV1, \|82313472\|sp\|Q8QDF7\|Q8QDF7__9HIV1, |
| \|82313467\|sp\|Q8Q7Z2\|Q8Q7Z2__9HIV1, \|82313383\|sp\|Q8Q2F4\|Q8Q2F4__9HIV1, |
| \|82313382\|sp\|Q8Q0Y4\|Q8Q0Y4__9HIV1, \|82313374\|sp\|Q8JDM8\|Q8JDM8__9HIV1, |
| \|82313373\|sp\|Q8JDM4\|Q8JDM4__9HIV1, \|82313372\|sp\|Q8JDM1\|Q8JDM1__9HIV1, |
| \|82313371\|sp\|Q8JDL7\|Q8JDL7__9HIV1, \|82313370\|sp\|Q8JDL3\|Q8JDL3__9HIV1, |
| \|82313369\|sp\|Q8JDK9\|Q8JDK9__9HIV1, \|82313368\|sp\|Q8JDK5\|Q8JDK5__9HIV1, |
| \|82313367\|sp\|Q8JDK1\|Q8JDK1__9HIV1, \|82313366\|sp\|Q8JDJ7\|Q8JDJ7__9HIV1, |
| \|82313365\|sp\|Q8JDJ3\|Q8JDJ3__9HIV1, \|82313364\|sp\|Q8JDI9\|Q8JDI9__9HIV1, |
| \|82313363\|sp\|Q8JDI5\|Q8JDI5__9HIV1, \|82313362\|sp\|Q8JDI1\|Q8JDI1__9HIV1, |
| \|82313361\|sp\|Q8JDH7\|Q8JDH7__9HIV1, \|82313360\|sp\|Q8JDH3\|Q8JDH3__9HIV1, |
| \|82313338\|sp\|Q8JC73\|Q8JC73__9HIV1, \|82313337\|sp\|Q8JC64\|Q8JC64__9HIV1, |
| \|82313336\|sp\|Q8JC55\|Q8JC55__9HIV1, \|82313335\|sp\|Q8JC46\|Q8JC46__9HIV1, |
| \|82313334\|sp\|Q8JC37\|Q8JC37__9HIV1, \|82313333\|sp\|Q8JC28\|Q8JC28__9HIV1, |
| \|82313332\|sp\|Q8JC19\|Q8JC19__9HIV1, \|82313331\|sp\|Q8JC10\|Q8JC10__9HIV1, |
| \|82313330\|sp\|Q8BZ7\|Q8BZ7__9HIV1, \|82313329\|sp\|Q8JBY8\|Q8JBY8__9HIV1, |
| \|82313328\|sp\|Q8JBX9\|Q8JBX9__9HIV1, \|82313327\|sp\|Q8JBX0\|Q8JBX0__9HIV1, |
| \|82313326\|sp\|Q8JBW1\|Q8JBW1__9HIV1, \|82313325\|sp\|Q8JBV2\|Q8JBV2__9HIV1, |
| \|82313324\|sp\|Q8JBU3\|Q8JBU3__9HIV1, \|82313323\|sp\|Q8JBT4\|Q8JBT4__9HIV1, |
| \|82313322\|sp\|Q8JBS5\|Q8JBS5__9HIV1, \|82313321\|sp\|Q8JBR6\|Q8JBR6__9HIV1, |
| \|82313320\|sp\|Q8JBQ7\|Q8JBQ7__9HIV1, \|82313319\|sp\|Q8JBP8\|Q8JBP8__9HIV1, |
| \|82313318\|sp\|Q8JBN8\|Q8JBN8__9HIV1, \|82313317\|sp\|Q8JBM7\|Q8JBM7__9HIV1, |
| \|82313316\|sp\|Q8JBL8\|Q8JBL8__9HIV1, \|82313315\|sp\|Q8JBK9\|Q8JBK9__9HIV1, |
| \|82313314\|sp\|Q8JBK0\|Q8JBK0__9HIV1, \|82313313\|sp\|Q8JBJ1\|Q8JBJ1__9HIV1, |
| \|82313312\|sp\|Q8JBI2\|Q8JBI2__9HIV1, \|82313311\|sp\|Q8JBH3\|Q8JBH3__9HIV1, |
| \|82313310\|sp\|Q8JBG4\|Q8JBG4__9HIV1, \|82313309\|sp\|Q8JBF5\|Q8JBF5__9HIV1, |
| \|82313308\|sp\|Q8JBE6\|Q8JBE6__9HIV1, \|82313307\|sp\|Q8JBD7\|Q8JBD7__9HIV1, |
| \|82313306\|sp\|Q8JBC8\|Q8JBC8__9HIV1, \|82313305\|sp\|Q8JBB9\|Q8JBB9__9HIV1, |
| \|82313304\|sp\|Q8JBB0\|Q8JBB0__9HIV1, \|82313303\|sp\|Q8JBA6\|Q8JBA6__9HIV1, |
| \|82313302\|sp\|Q8JAX8\|Q8JAX8__9HIV1, \|82313301\|sp\|Q8JAX0\|Q8JAX0__9HIV1, |
| \|82313290\|sp\|Q8J9C0\|Q8J9C0__9HIV1, \|82313289\|sp\|Q8J9B1\|Q8J9B1__9HIV1, |
| \|82312946\|sp\|Q8J3U5\|Q8J3U5__9HIV1, \|82312899\|sp\|Q8AUI0\|Q8AUI0__9HIV1, |
| \|82312898\|sp\|Q8AU88\|Q8AU88__9HIV1, \|82312897\|sp\|Q8AU79\|Q8AU79__9HIV1, |
| \|82312896\|sp\|Q8AU70\|Q8AU70__9HIV1, \|82312895\|sp\|Q8AU61\|Q8AU61__9HIV1, |
| \|82312859\|sp\|Q8ATN9\|Q8ATN9__9HIV1, \|82312858\|sp\|Q8ATN3\|Q8ATN3__9HIV1, |
| \|82312853\|sp\|Q8AQV9\|Q8AQV9__9HIV1, \|82312852\|sp\|Q8AQV0\|Q8AQV0__9HIV1, |
| \|82312851\|sp\|Q8AQU1\|Q8AQU1__9HIV1, \|82312850\|sp\|Q8AQT2\|Q8AQT2__9HIV1, |
| \|82312849\|sp\|Q8AQS3\|Q8AQS3__9HIV1, \|82312746\|sp\|Q8AMN0\|Q8AMN0__9HIV1, truncated, |
| \|82312732\|sp\|Q8AK11\|Q8AK11__9HIV1, \|82312731\|sp\|Q8AK02\|Q8AK02__9HIV1, |
| \|82312587\|sp\|Q8AF23\|Q8AF23__9HIV1, \|82312579\|sp\|Q8AEW6\|Q8AEW6__9HIV1, |
| \|82312541\|sp\|Q8AE76\|Q8AE76__9HIV1, \|82312540\|sp\|Q8AE68\|Q8AE68__9HIV1, |
| \|82312539\|sp\|Q8AE60\|Q8AE60__9HIV1, \|82312538\|sp\|Q8AE52\|Q8AE52__9HIV1, |
| \|82312537\|sp\|Q8AE44\|Q8AE44__9HIV1, \|82312536\|sp\|Q8AE36\|Q8AE36__9HIV1, |
| \|82312535\|sp\|Q8AE28\|Q8AE28__9HIV1, \|82312534\|sp\|Q8AE24\|Q8AE24__9HIV1, |
| \|82312533\|sp\|Q8AE19\|Q8AE19__9HIV1truncated, \|82312532\|sp\|Q8AE11\|Q8AE11__9HIV1, |
| \|82312531\|sp\|Q8AE03\|Q8AE03__9HIV1, \|82312530\|sp\|Q8ADZ5\|Q8ADZ5__9HIV1, |
| \|82312529\|sp\|Q8ADY7\|Q8ADY7__9HIV1, \|82312528\|sp\|Q8ADX9\|Q8ADX9__9HIV1, |
| \|82312527\|sp\|Q8ADX1\|Q8ADX1__9HIV1, \|82312526\|sp\|Q8ADW3\|Q8ADW3__9HIV1, |
| \|82312525\|sp\|Q8ADV5\|Q8ADV5__9HIV1, \|82312524\|sp\|Q8ADU7\|Q8ADU7__9HIV1, |
| \|82312523\|sp\|Q8ADT9\|Q8ADT9__9HIV1, \|82312522\|sp\|Q8ADT1\|Q8ADT1__9HIV1, |
| \|82312521\|sp\|Q8ADS3\|Q8ADS3__9HIV1, \|82312520\|sp\|Q8ADR5\|Q8ADR5__9HIV1, |
| \|82312519\|sp\|Q8ADQ7\|Q8ADQ7__9HIV1, \|82312518\|sp\|Q8ADP9\|Q8ADP9__9HIV1, |
| \|82312517\|sp\|Q8ADP1\|Q8ADP1__9HIV1, \|82312516\|sp\|Q8ADN3\|Q8ADN3__9HIV1, |
| \|82312515\|sp\|Q8ADM5\|Q8ADM5__9HIV1, \|82312514\|sp\|Q8ADL7\|Q8ADL7__9HIV1, |
| \|82312513\|sp\|Q8ADK9\|Q8ADK9__9HIV1, \|82312511\|sp\|Q8ADK1\|Q8ADK1__9HIV1, |
| \|82312510\|sp\|Q8ADJ3\|Q8ADJ3__9HIV1, \|82312509\|sp\|Q8ADI5\|Q8ADI5__9HIV1, |
| \|82312508\|sp\|Q8ADH7\|Q8ADH7__9HIV1, \|82312507\|sp\|Q8ADG9\|Q8ADG9__9HIV1, |
| \|82312506\|sp\|Q8ADG1\|Q8ADG1__9HIV1, \|82312505\|sp\|Q8ADF3\|Q8ADF3__9HIV1, |
| \|82312504\|sp\|Q8ADE5\|Q8ADE5__9HIV1, \|82312503\|sp\|Q8ADD7\|Q8ADD7__9HIV1, |
| \|82312502\|sp\|Q8ADC9\|Q8ADC9__9HIV1, \|82312501\|sp\|Q8ADC1\|Q8ADC1__9HIV1, |
| \|82312500\|sp\|Q8ADB3\|Q8ADB3__9HIV1, \|82312499\|sp\|Q8ADA5\|Q8ADA5__9HIV1, |
| \|82312498\|sp\|Q8AD97\|Q8AD97__9HIV1, \|82312497\|sp\|Q8AD89\|Q8AD89__9HIV1, |
| \|82312496\|sp\|Q8AD81\|Q8AD81__9HIV1, \|82312495\|sp\|Q8AD73\|Q8AD73__9HIV1, |
| \|82312480\|sp\|Q8ACA9\|Q8ACA9__9HIV1, \|82312477\|sp\|Q8AC83\|Q8AC83__9HIV1, |
| \|82312476\|sp\|Q8AC75\|Q8AC75__9HIV1truncated, \|82312475\|sp\|Q8AC67\|Q8AC67__9HIV1, |
| \|82312474\|sp\|Q8AC18\|Q8AC18__9HIV1truncated, \|82312179\|sp\|Q7ZMI6\|Q7ZMI6__9HIV1, |
| \|82312178\|sp\|Q7ZMH7\|Q7ZMH7__9HIV1, \|82312177\|sp\|Q7ZMG9\|Q7ZMG9__9HIV1, |
| \|82312176\|sp\|Q7ZMF9\|Q7ZMF9__9HIV1, \|82311990\|sp\|Q7ZJJ3\|Q7ZJJ3__9HIV1, |

-continued

| VPR proteins |
|---|
| \|82311989\|sp\|Q7ZJG3\|Q7ZJG3__9HIV1, \|82311988\|sp\|Q7ZJF7\|Q7ZJF7__9HIV1,
\|82311987\|sp\|Q7ZJE8\|Q7ZJE8__9HIV1, \|82311986\|sp\|Q7ZJD9\|Q7ZJD9__9HIV1,
\|82311985\|sp\|Q7ZJD0\|Q7ZJD0__9HIV1, \|82311984\|sp\|Q7ZJC2\|Q7ZJC2__9HIV1,
\|82311983\|sp\|Q7ZJB3\|Q7ZJB3__9HIV1, \|82311982\|sp\|Q7ZJA5\|Q7ZJA5__9HIV1,
\|82311981\|sp\|Q7ZJA0\|Q7ZJA0__9HIV1, \|82311980\|sp\|Q7ZJ89\|Q7ZJ89__9HIV1,
\|82311975\|sp\|Q7ZGR6\|Q7ZGR6__9HIV1, \|82311700\|sp\|Q7ZC22\|Q7ZC22__9HIV1,
\|82311695\|sp\|Q7ZBG3\|Q7ZBG3__9HIV1, \|82311619\|sp\|Q7SV40\|Q7SV40__9HIV1,
\|82311618\|sp\|Q7SV24\|Q7SV24__9HIV1, \|82311617\|sp\|Q7SV15\|Q7SV15__9HIV1,
\|82311616\|sp\|Q7SV06\|Q7SV06__9HIV1, \|82311615\|sp\|Q7SUZ7\|Q7SUZ7__9HIV1,
\|82311614\|sp\|Q7SUZ0\|Q7SUZ0__9HIV1, \|82311613\|sp\|Q7SUY1\|Q7SUY1__9HIV1,
\|82311612\|sp\|Q7SUX2\|Q7SUX2__9HIV1, \|82311606\|sp\|Q7SQN0\|Q7SQN0__9HIV1,
\|82311542\|sp\|Q7SQA9\|Q7SQA9__9HIV1, \|82311541\|sp\|Q7SQA4\|Q7SQA4__9HIV1,
\|82311539\|sp\|Q7SQ50\|Q7SQ50__9HIV1, \|82311538\|sp\|Q7SQ41\|Q7SQ41__9HIV1,
\|82311534\|sp\|Q7SPU4\|Q7SPU4__9HIV1, \|82311533\|sp\|Q7SPT4\|Q7SPT4__9HIV1,
\|82311518\|sp\|Q7SPQ5\|Q7SPQ5__9HIV1, \|82311515\|sp\|Q7SPP9\|Q7SPP9__9HIV1,
\|82311422\|sp\|Q7SKH5\|Q7SKH5__9HIV1, \|82311421\|sp\|Q7SKG6\|Q7SKG6__9HIV1,
\|82311420\|sp\|Q7SKF7\|Q7SKF7__9HIV1, \|82311419\|sp\|Q7SIJ3\|Q7SIJ3__9HIV1,
\|82311418\|sp\|Q7SII3\|Q7SII3__9HIV1, \|82311201\|sp\|Q76PP8\|Q76PP8__9HIV1,
\|82311089\|sp\|Q7S759\|Q7S759__9HIV1, \|82311060\|sp\|Q74839\|Q74839__9HIV1,
\|82311059\|sp\|Q74811\|Q74811__9HIV1, \|82311050\|sp\|Q72991\|Q72991__9HIV1,
\|82311049\|sp\|Q72982\|Q72982__9HIV1, \|82310929\|sp\|Q72501\|Q72501__9HIV1,
\|82310923\|sp\|Q71AY7\|Q71AY7__9HIV1, \|82310922\|sp\|Q71AX8\|Q71AX8__9HIV1,
\|82310921\|sp\|Q71AW9\|Q71AW9__9HIV1, \|82310902\|sp\|Q71817\|Q71817__9HIV1,
\|82310818\|sp\|Q6YA59\|Q6YA59__9HIV1, \|82310815\|sp\|Q6Y943\|Q6Y943__9HIV1,
\|82310814\|sp\|Q6Y934\|Q6Y934__9HIV1, \|82310813\|sp\|Q6Y925\|Q6Y925__9HIV1,
\|82310812\|sp\|Q6Y916\|Q6Y916__9HIV1, \|82310811\|sp\|Q6Y907\|Q6Y907__9HIV1,
\|82310810\|sp\|Q6Y8Z8\|Q6Y8Z8__9HIV1, \|82310808\|sp\|Q6Y8Y9\|Q6Y8Y9__9HIV1,
\|82310807\|sp\|Q6Y8Y0\|Q6Y8Y0__9HIV1, \|82310806\|sp\|Q6Y8X1\|Q6Y8X1__9HIV1,
\|82310805\|sp\|Q6Y8W2\|Q6Y8W2__9HIV1, \|82310804\|sp\|Q6Y8V3\|Q6Y8V3__9HIV1,
\|82310803\|sp\|Q6Y8U4\|Q6Y8U4__9HIV1, \|82310802\|sp\|Q6Y8T6\|Q6Y8T6__9HIV1,
\|82310801\|sp\|Q6Y8S7\|Q6Y8S7__9HIV1, \|82310800\|sp\|Q6Y8R8\|Q6Y8R8__9HIV1,
\|82310798\|sp\|Q6XKC7\|Q6XKC7__9HIV1, \|82310797\|sp\|Q6XKB8\|Q6XKB8__9HIV1,
\|82310791\|sp\|Q6X6X3\|Q6X6X3__9HIV1, \|82310790\|sp\|Q6X6W4\|Q6X6W4__9HIV1,
\|82310789\|sp\|Q6X6V5\|Q6X6V5__9HIV1, \|82310787\|sp\|Q6X6U7\|Q6X6U7__9HIV1,
\|82310786\|sp\|Q6X6T8\|Q6X6T8__9HIV1, \|82310785\|sp\|Q6X6S9\|Q6X6S9__9HIV1,
\|82310784\|sp\|Q6X6S0\|Q6X6S0__9HIV1, \|82310783\|sp\|Q6X6R3\|Q6X6R3__9HIV1,
\|82310780\|sp\|Q6X6Q4\|Q6X6Q4__9HIV1, \|82310779\|sp\|Q6X6P5\|Q6X6P5__9HIV1,
\|82310778\|sp\|Q6X6N6\|Q6X6N6__9HIV1, \|82310777\|sp\|Q6X6M8\|Q6X6M8__9HIV1,
\|82310774\|sp\|Q6X6L9\|Q6X6L9__9HIV1, \|82310773\|sp\|Q6X6L0\|Q6X6L0__9HIV1,
\|82310772\|sp\|Q6X6K1\|Q6X6K1__9HIV1, \|82310771\|sp\|Q6X6J4\|Q6X6J4__9HIV1,
\|82310768\|sp\|Q6X6I6\|Q6X6I6__9HIV1, \|82310767\|sp\|Q6X6H7\|Q6X6H7__9HIV1,
\|82310764\|sp\|Q6X6G9\|Q6X6G9__9HIV1, \|82310747\|sp\|Q6WS71\|Q6WS71__9HIV1,
\|82310656\|sp\|Q6V3T5\|Q6V3T5__9HIV1, \|82310655\|sp\|Q6V3S7\|Q6V3S7__9HIV1,
\|82310617\|sp\|Q6UFQ7\|Q6UFQ7__9HIV1, \|82310616\|sp\|Q6UFP8\|Q6UFP8__9HIV1,
\|82310615\|sp\|Q6UFN9\|Q6UFN9__9HIV1, \|82310614\|sp\|Q6UFN0\|Q6UFN0__9HIV1,
\|82310613\|sp\|Q6UFM2\|Q6UFM2__9HIV1, \|82310612\|sp\|Q6UFL5\|Q6UFL5__9HIV1,
\|82310611\|sp\|Q6UFK7\|Q6UFK7__9HIV1, \|82310610\|sp\|Q6UFJ8\|Q6UFJ8__9HIV1,
\|82310609\|sp\|Q6UFI9\|Q6UFI9__9HIV1, \|82310608\|sp\|Q6UFI0\|Q6UFI0__9HIV1,
\|82310607\|sp\|Q6UFH1\|Q6UFH1__9HIV1, \|82310606\|sp\|Q6UFG2\|Q6UFG2__9HIV1,
\|82310605\|sp\|Q6UFF3\|Q6UFF3__9HIV1, \|82310604\|sp\|Q6UFE5\|Q6UFE5__9HIV1,
\|82310603\|sp\|Q6UFD9\|Q6UFD9__9HIV1, \|82310602\|sp\|Q6UFD4\|Q6UFD4__9HIV1,
\|82310601\|sp\|Q6UFC5\|Q6UFC5__9HIV1, \|82310600\|sp\|Q6UFB6\|Q6UFB6__9HIV1,
\|82310599\|sp\|Q6UFA7\|Q6UFA7__9HIV1, \|82310598\|sp\|Q6UF98\|Q6UF98__9HIV1,
\|82310597\|sp\|Q6UF89\|Q6UF89__9HIV1, \|82310596\|sp\|Q6UF80\|Q6UF80__9HIV1,
\|82310595\|sp\|Q6UF72\|Q6UF72__9HIV1, \|82310594\|sp\|Q6UF65\|Q6UF65__9HIV1,
\|82310593\|sp\|Q6UF58\|Q6UF58__9HIV1, \|82310592\|sp\|Q6UF49\|Q6UF49__9HIV1,
\|82310591\|sp\|Q6UF40\|Q6UF40__9HIV1, \|82310590\|sp\|Q6UF31\|Q6UF31__9HIV1,
\|82310589\|sp\|Q6UF22\|Q6UF22__9HIV1, \|82310588\|sp\|Q6UF13\|Q6UF13__9HIV1,
\|82310587\|sp\|Q6UF06\|Q6UF06__9HIV1, \|82310586\|sp\|Q6UEZ8\|Q6UEZ8__9HIV1,
\|82310585\|sp\|Q6UEY9\|Q6UEY9__9HIV1, \|82310584\|sp\|Q6UEY0\|Q6UEY0__9HIV1,
\|82310583\|sp\|Q6UEX1\|Q6UEX1__9HIV1, \|82310582\|sp\|Q6UEW2\|Q6UEW2__9HIV1,
\|82310581\|sp\|Q6UEV3\|Q6UEV3__9HIV1, \|82310580\|sp\|Q6UEU4\|Q6UEU4__9HIV1,
\|82310579\|sp\|Q6UET5\|Q6UET5__9HIV1, \|82310578\|sp\|Q6UE56\|Q6UE56__9HIV1,
\|82310577\|sp\|Q6UER8\|Q6UER8__9HIV1, \|82310578\|sp\|Q6UEQ9\|Q6UEQ9__9HIV1,
\|82310575\|sp\|Q6UEQ0\|Q6UEQ0__9HIV1, \|82310574\|sp\|Q6UEP2\|Q6UEP2__9HIV1,
\|82310573\|sp\|Q6UEN3\|Q6UEN3__9HIV1, \|82310572\|sp\|Q6UEL8\|Q6UEL8__9HIV1,
\|82310571\|sp\|Q6UEK9\|Q6UEK9__9HIV1, \|82310570\|sp\|Q6UEK0\|Q6UEK0__9HIV1,
\|82310468\|sp\|Q6S887\|Q6S887__9HIV1, \|82310467\|sp\|Q6S878\|Q6S878__9HIV1,
\|82310466\|sp\|Q6S863\|Q6S863__9HIV1, \|82310465\|sp\|Q6S854\|Q6S854__9HIV1,
\|82310464\|sp\|Q6S846\|Q6S846__9HIV1, \|82310463\|sp\|Q6S838\|Q6S838__9HIV1,
\|82310462\|sp\|Q6S831\|Q6S831__9HIV1, \|82310461\|sp\|Q6S824\|Q6S824__9HIV1,
\|82310460\|sp\|Q6S815\|Q6S815__9HIV1, \|82310459\|sp\|Q6S807\|Q6S807__9HIV1,
\|82310458\|sp\|Q6S7Z9\|Q6S7Z9__9HIV1, \|82310457\|sp\|Q6S7Z2\|Q6S7Z2__9HIV1,
\|82310456\|sp\|Q6S7Y3\|Q6S7Y3__9HIV1, \|82310455\|sp\|Q6S7X4\|Q6S7X4__9HIV1,
\|82310454\|sp\|Q6S7W5\|Q6S7W5__9HIV1, \|82310453\|sp\|Q6S7V8\|Q6S7V8__9HIV1,
\|82310452\|sp\|Q6S7U9\|Q6S7U9__9HIV1, \|82310451\|sp\|Q6S7U1\|Q6S7U1__9HIV1,
\|82310450\|sp\|Q6S7T2\|Q6S7T2__9HIV1, \|82310449\|sp\|Q6S7S4\|Q6S7S4__9HIV1, |

| VPR proteins |
| --- |
| \|82310411\|sp\|Q6RJG0\|Q6RJG0__9HIV1, \|82310408\|sp\|Q6RJE6\|Q6RJE6__9HIV1, \|82310404\|sp\|Q6RJD2\|Q6RJD2__9HIV1, \|82310402\|sp\|Q6RJC5\|Q6RJC5__9HIV1, \|82310399\|sp\|Q6RJB1\|Q6RJB1__9HIV1, \|82310394\|sp\|Q6RJ83\|Q6RJ83__9HIV1, \|82310392\|sp\|Q6RJ76\|Q6RJ76__9HIV1, \|82310389\|sp\|Q6RJ69\|Q6RJ69__9HIV1, \|82310387\|sp\|Q6RJ62\|Q6RJ62__9HIV1, \|82310382\|sp\|Q6RFP3\|Q6RFP3__9HIV1, \|82310039\|sp\|Q6QKY1\|Q6QKY1__9HIV1, \|82310038\|sp\|Q6QKX2\|Q6QKX2__9HIV1, \|82309906\|sp\|Q6Q462\|Q6Q462__9HIV1, \|82309905\|sp\|Q6Q453\|Q6Q453__9HIV1, \|82309904\|sp\|Q6Q436\|Q6Q436__9HIV1, \|82309903\|sp\|Q6Q2V9\|Q6Q2V9__9HIV1, \|82309902\|sp\|Q6Q2V0\|Q6Q2V0__9HIV1, \|82309891\|sp\|Q6PR27\|Q6PR27__9HIV1, \|82309890\|sp\|Q6PR19\|Q6PR19__9HIV1, \|82309889\|sp\|Q6PR11\|Q6PR11__9HIV1mutant, \|82309887\|sp\|Q6PR04\|Q6PR04__9HIV1mutant, \|82309886\|sp\|Q6PQZ6\|Q6PQZ6__9HIV1, \|82309884\|sp\|Q5MJ74\|Q5MJ74__9HIV1, \|82309835\|sp\|Q5MH14\|Q5MH14__9HIV1, \|82309832\|sp\|Q5MH05\|Q5MH05__9HIV1, \|82309829\|sp\|Q5MGZ6\|Q5MGZ6__9HIV1, \|82309826\|sp\|Q5MGY7\|Q5MGY7__9HIV1, \|82309823\|sp\|Q5MGX8\|Q5MGX8__9HIV1, \|82309820\|sp\|Q5MGW9\|Q5MGW9__9HIV1, \|82309817\|sp\|Q5MGW1\|Q5MGW1__9HIV1, \|82309812\|sp\|Q5MGT8\|Q5MGT8__9HIV1, \|82309773\|sp\|Q5G7F3\|Q5G7F3__9HIV1, \|82309772\|sp\|Q5G7E4\|Q5G7E4__9HIV1, \|82309770\|sp\|Q5G7C7\|Q5G7C7__9HIV1, \|82309769\|sp\|Q5G7B8\|Q5G7B8__9HIV1, \|82309768\|sp\|Q5G7A9\|Q5G7A9__9HIV1, \|82309754\|sp\|Q5FY40\|Q5FY40__9HIV1, \|82309753\|sp\|Q5FY31\|Q5FY31__9HIV1, \|82309752\|sp\|Q5FY22\|Q5FY22__9HIV1, \|82309751\|sp\|Q5FY13\|Q5FY13__9HIV1, \|82309750\|sp\|Q5FY04\|Q5FY04__9HIV1, \|82309749\|sp\|Q5FXZ5\|Q5FXZ5__9HIV1, \|82309748\|sp\|Q5FXY6\|Q5FXY6__9HIV1, \|82309747\|sp\|Q5FXX7\|Q5FXX7__9HIV1, \|82309746\|sp\|Q5FXW8\|Q5FXW8__9HIV1, \|82309745\|sp\|Q5FXV9\|Q5FXV9__9HIV1, \|82309744\|sp\|Q5FXV0\|Q5FXV0__9HIV1, \|82309743\|sp\|Q5FXT3\|Q5FXT3__9HIV1, \|82309742\|sp\|Q5FXS4\|Q5FXS4__9HIV1, \|82309741\|sp\|Q5FXR5\|Q5FXR5__9HIV1, \|82309740\|sp\|Q5FXQ8\|Q5FXQ8__9HIV1, \|82309739\|sp\|Q5FXP9\|Q5FXP9__9HIV1, \|82309738\|sp\|Q5FXP0\|Q5FXP0__9HIV1, \|82309737\|sp\|Q5FXN1\|Q5FXN1__9HIV1, \|82309556\|sp\|Q5EEJ2\|Q5EEJ2__9HIV1, \|82309555\|sp\|Q5EEI3\|Q5EEI3__9HIV1, \|82309554\|sp\|Q5EEH4\|Q5EEH4__9HIV1, \|82309553\|sp\|Q5EEG6\|Q5EEG6__9HIV1, \|82309552\|sp\|Q5EEF7\|Q5EEF7__9HIV1, \|82309551\|sp\|Q5EEE8\|Q5EEE8__9HIV1, \|82309550\|sp\|Q5EED9\|Q5EED9__9HIV1, \|82309549\|sp\|Q5EED1\|Q5EED1__9HIV1, \|82309548\|sp\|Q5EEC2\|Q5EEC2__9HIV1, \|82309547\|sp\|Q5EEB3\|Q5EEB3__9HIV1, \|82309546\|sp\|Q5EEA4\|Q5EEA4__9HIV1, \|82309545\|sp\|Q5EE96\|Q5EE96__9HIV1, \|82309544\|sp\|Q5EE88\|Q5EE88__9HIV1, \|82309543\|sp\|Q5EE79\|Q5EE79__9HIV1, \|82309542\|sp\|Q5EE72\|Q5EE72__9HIV1, \|82309541\|sp\|Q5EE64\|Q5EE64__9HIV1, \|82309540\|sp\|Q5EE56\|Q5EE56__9HIV1, \|82309383\|sp\|Q5C9Y5\|Q5C9Y5__9HIV1, \|82309380\|sp\|Q5C9X6\|Q5C9X6__9HIV1, \|82309244\|sp\|P90241\|P90241__9HIV1, \|82309217\|sp\|P87922\|P87922__9HIV1, \|82309198\|sp\|O93023\|O93023__9HIV1, \|82309193\|sp\|O92896\|O92896__9HIV1, \|82309192\|sp\|O92889\|O92889__9HIV1, \|82309191\|sp\|O92886\|O92886__9HIV1, \|82309190\|sp\|O92881\|O92881__9HIV1, \|82309171\|sp\|O92298\|O92298__9HIV1, \|82309128\|sp\|O90597\|O90597__9HIV1, \|82309126\|sp\|O90594\|O90594__9HIV1, \|82309097\|sp\|O71278\|O71278__9HIV1, \|82309096\|sp\|O71268\|O71268__9HIV1, \|82308946\|sp\|O42063\|O42063__9HIV1, \|82308901\|sp\|O40220\|O40220__9HIV1, \|82308772\|sp\|Q56CX7\|Q56CX7__9HIV1, \|82308768\|sp\|Q56CX3\|Q56CX3__9HIV1, \|82282692\|sp\|Q5FXU1\|Q5FXU1__9HIV1, \|78172859\|gb\|ABB29390.1\|, \|78172849\|gb\|ABB29381.1\|, \|78172839\|gb\|ABB29372.1\|, \|78172829\|gb\|ABB29363.1\|, \|78172821\|gb\|ABB29356.1\|, \|63081182\|gb\|AAY30344.1\|truncated, \|55275261\|gb\|AAV49473.1\|, \|55275251\|gb\|AAV49464.1\|, \|55275241\|gb\|AAV49455.1\|, \|55275231\|gb\|AAV49446.1\|, \|55275221\|gb\|AAV49437.1\|, \|55275211\|gb\|AAV49428.1\|, \|55275201\|gb\|AAV49419.1\|, \|55275191\|gb\|AAV49410.1\|, \|55275181\|gb\|AAV49401.1\|, \|55275171\|gb\|AAV49392.1\|, \|55275161\|gb\|AAV49383.1\|, \|55275151\|gb\|AAV49374.1\|, \|55275141\|gb\|AAV49365.1\|, \|55275131\|gb\|AAV49356.1\|, \|55275121\|gb\|AAV49347.1\|, \|73913998\|gb\|AAZ91958.1\|, \|73913980\|gb\|AAZ91942.1\|, \|73913970\|gb\|AAZ91933.1\|, \|73913945\|gb\|AAZ91911.1\|, \|73913936\|gb\|AAZ91903.1\|, \|73913926\|gb\|AAZ91894.1\|, \|73913916\|gb\|AAZ91885.1\|, \|73913907\|gb\|AAZ91877.1\|, \|73913897\|gb\|AAZ91868.1\|, \|73913887\|gb\|AAZ91859.1\|, \|73913878\|gb\|AAZ91851.1\|, \|73913868\|gb\|AAZ91842.1\|, \|73913858\|gb\|AAZ91833.1\|, \|73913848\|gb\|AAZ91824.1\|, \|73913838\|gb\|AAZ91815.1\|, \|73913828\|gb\|AAZ91806.1\|, \|73913818\|gb\|AAZ91797.1\|, \|73913808\|gb\|AAZ91788.1\|, \|73913799\|gb\|AAZ91780.1\|, \|73913789\|gb\|AAZ91771.1\|, \|73913779\|gb\|AAZ91762.1\|, \|73913769\|gb\|AAZ91753.1\|, \|73913759\|gb\|AAZ91744.1\|, \|46243169\|gb\|AAS83695.1\|, \|46243161\|gb\|AAS83688.1\|, \|37681536\|gb\|AAQ97646.1\|, \|37681546\|gb\|AAQ97655.1\|, \|37677909\|gb\|AAQ97574.1\|, \|37677899\|gb\|AAQ97565.1\|, \|37677889\|gb\|AAQ97556.1\|, \|37677879\|gb\|AAQ97547.1\|, \|37677869\|gb\|AAQ97538.1\|, \|37677859\|gb\|AAQ97529.1\|, \|37677849\|gb\|AAQ97520.1\|, \|37677839\|gb\|AAQ97511.1\|, \|37677829\|gb\|AAQ97502.1\|, \|37677819\|gb\|AAQ97493.1\|, \|37677809\|gb\|AAQ97484.1\|, \|37677799\|gb\|AAQ97475.1\|, \|37677789\|gb\|AAQ97466.1\|, \|37677779\|gb\|AAQ97457.1\|, \|37677769\|gb\|AAQ97448.1\|, \|37677759\|gb\|AAQ97439.1\|, \|62361777\|gb\|AAX81425.1\|, \|71794628\|emb\|CAI28867.1\|, \|71794618\|emb\|CAI28858.1\|, \|71794608\|emb\|CAI28849.1\|, \|71794599\|emb\|CAI28840.1\|, \|71794590\|emb\|CAI28831.1\|, \|71794580\|emb\|CAI28822.1\|, \|57901114\|gb\|AAW57878.1\|, \|57901102\|gb\|AAW57867.1\|, \|57901095\|gb\|AAW57861.1\|, \|57901086\|gb\|AAW57853.1\|, \|57901073\|gb\|AAW57841.1\|, \|57901063\|gb\|AAW57832.1\|, \|58221042\|gb\|AAW68216.1\|, \|58221032\|gb\|AAW68207.1\|, \|58221022\|gb\|AAW68198.1\|, \|58221012\|gb\|AAW68189.1\|, \|58221004\|gb\|AAW68182.1\|, \|58220994\|gb\|AAW68173.1\|, \|58220984\|gb\|AAW68164.1\|, \|58220975\|gb\|AAW68156.1\|, \|58220965\|gb\|AAW68147.1\|, \|58220955\|gb\|AAW68138.1\|, \|58220945\|gb\|AAW68129.1\|, \|58220935\|gb\|AAW68120.1\|, \|58220925\|gb\|AAW68111.1\|, \|58220915\|gb\|AAW68102.1\|, \|58220905\|gb\|AAW68093.1\|, \|58220895\|gb\|AAW68084.1\|, \|58220885\|gb\|AAW68075.1\|, |

| VPR proteins |
| --- |
| \|58220875\|gb\|AAW68066.1\|, \|58220865\|gb\|AAW68057.1\|, \|38892787\|gb\|AAR27777.1\|, \|38892778\|gb\|AAR27769.1\|, \|38892768\|gb\|AAR27760.1\|, \|38892759\|gb\|AAR27752.1\|, \|38892749\|gb\|AAR27743.1\|, \|38892741\|gb\|AAR27736.1\|, \|38892731\|gb\|AAR27727.1\|, \|38892721\|gb\|AAR27718.1\|, \|38892711\|gb\|AAR27709.1\|, \|38892703\|gb\|AAR27702.1\|, \|38892694\|gb\|AAR27694.1\|, \|38892685\|gb\|AAR27686.1\|, \|38892675\|gb\|AAR27677.1\|, \|38892667\|gb\|AAR27670.1\|, \|38892659\|gb\|AAR27663.1\|, \|38892650\|gb\|AAR27655.1\|, \|38892641\|gb\|AAR27647.1\|, \|38892631\|gb\|AAR27638.1\|, \|38892614\|gb\|AAR27623.1\|, \|38892604\|gb\|AAR27614.1\|, \|55139354\|gb\|AAV41367.1\|, \|55139345\|gb\|AAV41359.1\|, \|55139334\|gb\|AAV41349.1\|, \|55139325\|gb\|AAV41341.1\|, \|55139313\|gb\|AAV41331.1\|, \|55139304\|gb\|AAV41323.1\|, \|55139295\|gb\|AAV41315.1\|, \|55139284\|gb\|AAV41305.1\|, \|55139275\|gb\|AAV41297.1\|, \|55139266\|gb\|AAV41289.1\|, \|55139257\|gb\|AAV41281.1\|, \|68522158\|gb\|AAY98743.1\|, \|68522149\|gb\|AAY98735.1\|, \|68522139\|gb\|AAY98726.1\|, \|68522129\|gb\|AAY98717.1\|, \|68522119\|gb\|AAY98708.1\|, \|68522109\|gb\|AAY98699.1\|, \|68522099\|gb\|AAY98690.1\|, \|68522089\|gb\|AAY98681.1\|, \|68522079\|gb\|AAY98672.1\|, \|68522069\|gb\|AAY98663.1\|, \|68522059\|gb\|AAY98654.1\|, \|68522049\|gb\|AAY98645.1\|, \|68522039\|gb\|AAY98636.1\|, \|68522029\|gb\|AAY98627.1\|, \|68522019\|gb\|AAY98618.1\|, \|68522009\|gb\|AAY98609.1\|, \|68521999\|gb\|AAY98600.1\|, \|68521989\|gb\|AAY98591.1\|, \|68521979\|gb\|AAY98582.1\|, \|68521969\|gb\|AAY98573.1\|, \|68521959\|gb\|AAY98564.1\|, \|68521949\|gb\|AAY98555.1\|, \|68521939\|gb\|AAY98546.1\|, \|67553116\|gb\|AAY68701.1\|, \|67553106\|gb\|AAY68692.1\|, \|67553096\|gb\|AAY68683.1\|, \|67553086\|gb\|AAY68674.1\|, \|67553076\|gb\|AAY68665.1\|, \|67553066\|gb\|AAY68656.1\|, \|67553056\|gb\|AAY68647.1\|, \|67553046\|gb\|AAY68638.1\|, \|67553036\|gb\|AAY68629.1\|, \|67553026\|gb\|AAY68620.1\|, \|67553019\|gb\|AAY68614.1\|, \|67553010\|gb\|AAY68606.1\|, \|67553001\|gb\|AAY68598.1\|, \|67552991\|gb\|AAY68589.1\|, \|67552981\|gb\|AAY68580.1\|, \|63098435\|gb\|AAY32473.1\|, \|63098425\|gb\|AAY32464.1\|, \|63098415\|gb\|AAY32455.1\|, \|63098405\|gb\|AAY32446.1\|, \|63098395\|gb\|AAY32437.1\|, \|63098385\|gb\|AAY32428.1\|, \|63098376\|gb\|AAY32420.1\|, \|63098367\|gb\|AAY32412.1\|, \|63098357\|gb\|AAY32403.1\|, \|63098348\|gb\|AAY32395.1\|, \|63098338\|gb\|AAY32386.1\|, \|63098328\|gb\|AAY32377.1\|, \|63098318\|gb\|AAY32368.1\|, \|63098309\|gb\|AAY32360.1\|, \|63098300\|gb\|AAY32352.1\|, \|63098290\|gb\|AAY32343.1\|, \|56609346\|gb\|AAW03296.1\|, \|56609335\|gb\|AAW03287.1\|, \|56609319\|gb\|AAW03273.1\|, \|56609309\|gb\|AAW03264.1\|, \|56609299\|gb\|AAW03255.1\|, \|56609289\|gb\|AAW03246.1\|, \|56609279\|gb\|AAW03237.1\|, \|56609269\|gb\|AAW03228.1\|, \|56609259\|gb\|AAW03219.1\|, \|56609249\|gb\|AAW03210.1\|, \|60197\|emb\|CAA77626.1\|, \|3163935\|emb\|CAA06951.1\|, \|32399670\|emb\|CAD58648.1\|, \|32399661\|emb\|CAD58639.1\|, \|18074004\|emb\|CAC86569.1\|, \|18073419\|emb\|CAC88009.1\|, \|18073409\|emb\|CAC88000.1\|, \|15209260\|emb\|CAC51039.1\|, \|14041641\|emb\|CAC38425.1\|, \|14041631\|emb\|CAC38434.1\|, \|9368384\|emb\|CAB98173.1\|, \|9368374\|emb\|CAB98191.1\|, \|8920157\|emb\|CAB96343.1\|, \|7657894\|emb\|CAB89148.1\|, \|7630101\|emb\|CAB53047.2\|, \|7452914\|emb\|CAB86379.1\|, \|7452904\|emb\|CAB86370.1\|, \|7321149\|emb\|CAB82231.1\|, \|7321139\|emb\|CAB82222.1\|, \|4539039\|emb\|CAB39921.1\|, \|59003672\|gb\|AAW83667.1\|, \|59003662\|gb\|AAW83658.1\|, \|59003652\|gb\|AAW83649.1\|, \|59003642\|gb\|AAW83640.1\|, \|59003632\|gb\|AAW83631.1\|, \|59003623\|gb\|AAW83623.1\|, \|59003613\|gb\|AAW83614.1\|, \|59003603\|gb\|AAW83605.1\|, \|59003593\|gb\|AAW83596.1\|, \|59003583\|gb\|AAW83587.1\|, \|59003573\|gb\|AAW83578.1\|, \|59003563\|gb\|AAW83569.1\|, \|59003553\|gb\|AAW83560.1\|, \|59003543\|gb\|AAW83551.1\|, \|59003533\|gb\|AAW83542.1\|, \|59003523\|gb\|AAW83533.1\|, \|59003513\|gb\|AAW83524.1\|, \|45738227\|gb\|AAS75885.1\|, \|45738217\|gb\|AAS75876.1\|, \|38326777\|gb\|AAR17519.1\|, \|55925140\|gb\|AAV67944.1\|, \|55925132\|gb\|AAV67937.1\|, \|55925124\|gb\|AAV67930.1\|, \|55925116\|gb\|AAV67923.1\|, \|51572131\|gb\|AAU06778.1\|, \|51572121\|gb\|AAU06769.1\|, \|51572112\|gb\|AAU06761.1\|, \|51572099\|gb\|AAU06749.1\|, \|47060061\|gb\|AAT09647.1\|, \|49472954\|gb\|AAT66296.1\|, \|49472945\|gb\|AAT66288.1\|, \|49472936\|gb\|AAT66280.1\|, \|49472927\|gb\|AAT66272.1\|, \|37682604\|gb\|AAQ98284.1\|, \|37682594\|gb\|AAQ98275.1\|, \|37682584\|gb\|AAQ98266.1\|, \|37682574\|gb\|AAQ98257.1\|, \|37682565\|gb\|AAQ98249.1\|, \|37682555\|gb\|AAQ98240.1\|, \|37682545\|gb\|AAQ98231.1\|, \|37682535\|gb\|AAQ98222.1\|, \|37682525\|gb\|AAQ98213.1\|, \|37682515\|gb\|AAQ98204.1\|, \|37682505\|gb\|AAQ98195.1\|, \|37682495\|gb\|AAQ98186.1\|, \|37682486\|gb\|AAQ98178.1\|, \|37682476\|gb\|AAQ98169.1\|, \|37682466\|gb\|AAQ98160.1\|, \|37682456\|gb\|AAQ98151.1\|, \|37682446\|gb\|AAQ98142.1\|, \|37682436\|gb\|AAQ98133.1\|, \|37682426\|gb\|AAQ98124.1\|, \|37682415\|gb\|AAQ98114.1 truncated, \|46486668\|gb\|AAS98771.1\|, \|46486659\|gb\|AAS98763.1\|mutant, \|46486651\|gb\|AAS98756.1\|mutant, \|46486641\|gb\|AAS98747.1\|, \|46486631\|gb\|AAS98738.1\|, \|46254445\|gb\|AAS86195.1\|, \|46254421\|gb\|AAS86179.1\|, \|46254411\|gb\|AAS86170.1\|, \|38679163\|gb\|AAR26415.1\|, \|38679154\|gb\|AAR26407.1\|, \|19072109\|dbj\|BAB85756.1\|, \|32261286\|gb\|AAP74185.1\|, \|32261275\|gb\|AAP74175.1\|, \|32261264\|gb\|AAP74165.1\|, \|32351108\|gb\|AAP76516.1\|, \|31980441\|dbj\|BAC77760.1\|, \|31980431\|dbj\|BAC77751.1\|, \|31980421\|dbj\|BAC77742.1\|, \|31980411\|dbj\|BAC77733.1\|, \|31559695\|dbj\|BAC77516.1\|, \|31559685\|dbj\|BAC77507.1\|, \|31559675\|dbj\|BAC77498.1\|, \|31559667\|dbj\|BAC77491.1\|, \|31559657\|dbj\|BAC77482.1\|, \|31559647\|dbj\|BAC77473.1\|, \|31559637\|dbj\|BAC77464.1\|, \|31559619\|dbj\|BAC77448.1\|, \|132438\|sp\|P04618\|REV__HV1H2, \|548725\|sp\|P35960\|REV__HV1Y2, \|132425\|sp\|P19548\|REV__HV1S1, \|132424\|sp\|P19547\|REV__HV1S3, \|132437\|sp\|P05866\|REV__HV1W2, \|132418\|sp\|P05864\|REV__HV1B8, \|132420\|sp\|P04620\|REV__HV1BR, \|132414\|sp\|P04325\|REV__HV112, \|62288905\|sp\|P69719\|REV__HV1PV, \|62288904\|sp\|P69718\|REV__HV1H3, \|3024538\|sp\|Q70624\|REV__HV1LW, \|1350575\|sp\|P18803\|REV__HV1ND, \|132439\|sp\|P04619\|REV__HV1Z6, \|132435\|sp\|P05872\|REV__HV1SC, \|132432\|sp\|P20887\|REV__HV1OY, \|132431\|sp\|P04622\|REV__HV1MA, \|132428\|sp\|P12484\|REV__HV1J3, \|132427\|sp\|P12485\|REV__HV1BN, \|132423\|sp\|P04621\|REV__HV1EL, \|132422\|sp\|P20869\|REV__HV1JR, \|132421\|sp\|P05865\|REV__HV1C4, \|132419\|sp\|P04623\|REV__HV1A2, |

| VPR proteins |
| --- |
| \|132417\|sp\|P12483\|REV__HV1Z2, \|132416\|sp\|P05869\|REV__HV1Z8, \|132413\|sp\|P04616\|REV__HV1B1, \|132434\|sp\|P05870\|REV__HV1RH, \|132430\|sp\|P05871\|REV__HV1MN, \|132426\|sp\|P05868\|REV__HV1ZH, \|132415\|sp\|P05867\|REV__HV1Z3, \|10436176\|gb\|AAG16850.1\|, \|10436164\|gb\|AAG16840.1\|, \|10436155\|gb\|AAG16832.1\|, \|10436145\|gb\|AAG16823.1\|, \|10436136\|gb\|AAG16815.1\|, \|10436126\|gb\|AAG16806.1\|, \|10436117\|gb\|AAG16798.1\|, \|10436107\|gb\|AAG16789.1\|, \|221476\|dbj\|BAA00997.1\|, \|326677\|gb\|AAA44323.1\|, \|329364\|gb\|AAB12992.1\|, \|326466\|gb\|AAA44310.1\|, \|328553\|gb\|AAB59871.1\|, \|327468\|gb\|AAA44659.1\|, \|4262344\|gb\|AAD14580.1\|, \|82313506\|sp\|Q8QDN6\|Q8QDN6__9PLVG, \|82311278\|sp\|Q77MH4\|Q77MH4__9PLVG, \|82308871\|sp\|O11406\|O11406__9PLVG, \|18766388\|gb\|AAL78994.1\|AF465242__6, \|10180809\|gb\|AAG14294.1\|AF251194__2, \|2895571\|gb\|AAD12140.1\|, \|62362853\|gb\|AAX81731.1\|, \|62362851\|gb\|AAX81730.1\|, \|62362849\|gb\|AAX81729.1\|, \|62362847\|gb\|AAX81728.1\|, \|62362845\|gb\|AAX81727.1\|, \|62362843\|gb\|AAX81726.1\|, \|62362841\|gb\|AAX81725.1\|, \|62362839\|gb\|AAX81724.1\|, \|62362837\|gb\|AAX81723.1\|, \|62362835\|gb\|AAX81722.1\|, \|62362833\|gb\|AAX81721.1\|, \|62362831\|gb\|AAX81720.1\|, \|62362829\|gb\|AAX81719.1\|, \|62362827\|gb\|AAX81718.1\|, \|62362825\|gb\|AAX81717.1\|, \|62362823\|gb\|AAX81716.1\|, \|62362821\|gb\|AAX81715.1\|, \|62362819\|gb\|AAX81714.1\|, \|62362817\|gb\|AAX81713.1\|, \|62362815\|gb\|AAX81712.1\|, \|62362813\|gb\|AAX81711.1\|, \|62362811\|gb\|AAX81710.1\|, \|62362809\|gb\|AAX81709.1\|, \|62362807\|gb\|AAX81708.1\|, \|62362805\|gb\|AAX81707.1\|, \|62362803\|gb\|AAX81706.1\|, \|62362801\|gb\|AAX81705.1\|, \|62362799\|gb\|AAX81704.1\|, \|62362797\|gb\|AAX81703.1\|, \|62362795\|gb\|AAX81702.1\|, \|62362793\|gb\|AAX81701.1\|, \|62362791\|gb\|AAX81700.1\|, \|62362789\|gb\|AAX81699.1\|, \|62362787\|gb\|AAX81698.1\|, \|62362785\|gb\|AAX81697.1\|, \|62362783\|gb\|AAX81696.1\|, \|62362781\|gb\|AAX81695.1\|, \|62362779\|gb\|AAX81694.1\|, \|62362777\|gb\|AAX81693.1\|, \|62362775\|gb\|AAX81692.1\|, \|62362773\|gb\|AAX81691.1\|, \|62362771\|gb\|AAX81690.1\|, \|62362769\|gb\|AAX81689.1\|, \|62362767\|gb\|AAX81688.1\|, \|62362765\|gb\|AAX81687.1\|, \|62362763\|gb\|AAX81686.1\|, \|62362761\|gb\|AAX81685.1\|, \|62362759\|gb\|AAX81684.1\|, \|62362757\|gb\|AAX81683.1\|, \|62362755\|gb\|AAX81682.1\|, \|62362753\|gb\|AAX81681.1\|, \|62362751\|gb\|AAX81680.1\|, \|62362749\|gb\|AAX81679.1\|, \|62362747\|gb\|AAX81678.1\|, \|62362745\|gb\|AAX81677.1\|, \|62362743\|gb\|AAX81676.1\|, \|62362741\|gb\|AAX81675.1\|, \|62362739\|gb\|AAX81674.1\|, \|62362737\|gb\|AAX81673.1\|, \|62362735\|gb\|AAX81672.1\|, \|62362733\|gb\|AAX81671.1\|, \|62362731\|gb\|AAX81670.1\|, \|62362729\|gb\|AAX81669.1\|, \|62362727\|gb\|AAX81668.1\|, \|62362725\|gb\|AAX81667.1\|, \|62362723\|gb\|AAX81666.1\|, \|62362721\|gb\|AAX81665.1\|, \|62362719\|gb\|AAX81664.1\|, \|62362717\|gb\|AAX81663.1\|, \|62362715\|gb\|AAX81662.1\|, \|62362713\|gb\|AAX81661.1\|, \|62362711\|gb\|AAX81660.1\|, \|62362709\|gb\|AAX81659.1\|, \|62362707\|gb\|AAX81658.1\|, \|62362705\|gb\|AAX81657.1\|, \|62362703\|gb\|AAX81656.1\|, \|62362701\|gb\|AAX81655.1\|, \|62362699\|gb\|AAX81654.1\|, \|62362697\|gb\|AAX81653.1\|, \|62362695\|gb\|AAX81652.1\|, \|62362693\|gb\|AAX81651.1\|, \|62362691\|gb\|AAX81650.1\|, \|62362689\|gb\|AAX81649.1\|, \|62362687\|gb\|AAX81648.1\|, \|62362685\|gb\|AAX81647.1\|, \|62362683\|gb\|AAX81646.1\|, \|62362681\|gb\|AAX81645.1\|, \|62362679\|gb\|AAX81644.1\|, \|62362677\|gb\|AAX81643.1\|, \|62362675\|gb\|AAX81642.1\|, \|62362673\|gb\|AAX81641.1\|, \|62362671\|gb\|AAX81640.1\|, \|62362669\|gb\|AAX81639.1\|, \|62362667\|gb\|AAX81638.1\|, \|62362665\|gb\|AAX81637.1\|, \|62362663\|gb\|AAX81636.1\|, \|62362661\|gb\|AAX81635.1\|, \|62362659\|gb\|AAX81634.1\|, \|62362657\|gb\|AAX81633.1\|, \|62362655\|gb\|AAX81632.1\|, \|62362653\|gb\|AAX81631.1\|, \|62362651\|gb\|AAX81630.1\|, \|62362649\|gb\|AAX81629.1\|, \|62362647\|gb\|AAX81628.1\|, \|62362645\|gb\|AAX81627.1\|, \|62362643\|gb\|AAX81626.1\|, \|62362641\|gb\|AAX81625.1\|, \|62362639\|gb\|AAX81624.1\|, \|62362637\|gb\|AAX81623.1\|, \|62362635\|gb\|AAX81622.1\|, \|62362633\|gb\|AAX81621.1\|, \|62362631\|gb\|AAX81620.1\|, \|62362629\|gb\|AAX81619.1\|, \|62362626\|gb\|AAX81618.1\|, \|62362624\|gb\|AAX81617.1\|, \|62362622\|gb\|AAX81616.1\|, \|62362620\|gb\|AAX81615.1\|, \|62362616\|gb\|AAX81614.1\|, \|62362614\|gb\|AAX81613.1\|, \|62362612\|gb\|AAX81612.1\|, \|62362610\|gb\|AAX81611.1\|, \|62362608\|gb\|AAX81610.1\|, \|62362606\|gb\|AAX81609.1\|, \|62362604\|gb\|AAX81608.1\|, \|62362602\|gb\|AAX81607.1\|, \|62362600\|gb\|AAX81606.1\|, \|62362598\|gb\|AAX81605.1\|, \|62362594\|gb\|AAX81603.1\|, \|62362592\|gb\|AAX81602.1\|, \|62362590\|gb\|AAX81601.1\|, \|18699254\|gb\|AAL78495.1\|AF414006__7, \|18699192\|gb\|AAL78452.1\|AF413987__7, \|37725252\|gb\|AAR02314.1\|, \|37725242\|gb\|AAR02305.1\|, \|37725232\|gb\|AAR02296.1\|, \|37725222\|gb\|AAR02287.1\|, \|37725212\|gb\|AAR02278.1\|, \|37725202\|gb\|AAR02269.1\|, \|37725196\|gb\|AAR02264.1\|, \|27227856\|dbj\|BAC45029.1\|, \|27227846\|dbj\|BAC45020.1\|, \|328417\|gb\|AAA44986.1\|, \|326387\|gb\|AAA44200.1\|, \|16118323\|gb\|AAL12696.1\|, \|82318816\|sp\|Q9DH39\|Q9DH39__9HIV1, \|82318815\|sp\|Q9DH16\|Q9DH16__9HIV1, \|82318814\|sp\|Q9DGZ4\|Q9DGZ4__9HIV1, \|82318813\|sp\|Q9DGW4\|Q9DGW4__9HIV1, \|82312479\|sp\|Q8ACA0\|Q8ACA0__9HIV1, \|82312478\|sp\|Q8AC91\|Q8AC91__9HIV1, \|82311318\|sp\|Q78232\|Q78232__9HIV1, \|74273388\|gb\|ABA01378.1\|, \|40021891\|gb\|AAR37201.1\|, \|40021881\|gb\|AAR37194.1\|, \|40021871\|gb\|AAR37187.1\|, \|40021861\|gb\|AAR37180.1\|, \|40021851\|gb\|AAR37173.1\|, \|40021841\|gb\|AAR37166.1\|, \|40021831\|gb\|AAR37159.1\|, \|40021821\|gb\|AAR37152.1\|, \|40021811\|gb\|AAR37145.1\|, \|40021801\|gb\|AAR37138.1\|, \|40021791\|gb\|AAR37131.1\|, \|40021781\|gb\|AAR37124.1\|, \|40021771\|gb\|AAR37117.1\|, \|40021761\|gb\|AAR37110.1\|, \|40021751\|gb\|AAR37103.1\|, \|40021741\|gb\|AAR37096.1\|, \|40021730\|gb\|AAR37088.1\|, \|40021721\|gb\|AAR37082.1\|, \|40021711\|gb\|AAR37075.1\|, \|40021701\|gb\|AAR37068.1\|, \|4205071\|gb\|AAD10942.1\|, \|4205062\|gb\|AAD10934.1\|, \|4205053\|gb\|AAD10926.1\|, \|4205044\|gb\|AAD10918.1\|, \|4205035\|gb\|AAD10910.1\|, \|4205026\|gb\|AAD10902.1\|, \|4205017\|gb\|AAD10894.1\|, \|4205008\|gb\|AAD10886.1\|, \|4204999\|gb\|AAD10878.1\|, \|4204990\|gb\|AAD10870.1\|, \|328660\|gb\|AAB59880.1\|, \|326419\|gb\|AAB59746.1\|, \|329396\|gb\|AAB53950.1\|, \|327781\|gb\|AAB03525.1\|, \|328442\|gb\|AAA83396.1\|, \|329401\|gb\|AAA45378.1\|, \|329391\|gb\|AAA45375.1\|, \|329379\|gb\|AAA45364.1\|, \|328636\|gb\|AAA45061.1\|, |

| VPR proteins |
| --- |
| \|328567\|gb\|AAA45051.1\|, \|328457\|gb\|AAA45000.1\|, \|328156\|gb\|AAA44867.1\|, \|328032\|gb\|AAA44852.1\|, \|327825\|gb\|AAA44686.1\|, \|327754\|gb\|AAA44677.1\|, \|82320737\|sp\|Q52S67\|Q52S67__9HIV1, \|82320736\|sp\|Q52S60\|Q52S60__9HIV1, \|82320733\|sp\|Q52S51\|Q52S51__9HIV1, \|82320730\|sp\|Q52S41\|Q52S41__9HIV1, \|82320727\|sp\|Q52S30\|Q52S30__9HIV1, \|82320166\|sp\|Q9YTC6\|Q9YTC6__9HIV1, \|82320064\|sp\|Q9YP36\|Q9YP36__9HIV1, \|82320063\|sp\|Q9YP32\|Q9YP32__9HIV1, \|82319934\|sp\|Q9WJW6\|Q9WJW6__9HIV1, \|82319933\|sp\|Q9WJW2\|Q9WJW2__9HIV1, \|82319932\|sp\|Q9WJV8\|Q9WJV8__9HIV1, \|82319931\|sp\|Q9WJV6\|Q9WJV6__9HIV1, \|82319930\|sp\|Q9WJV1\|Q9WJV1__9HIV1, \|82319929\|sp\|Q9WJU9\|Q9WJU9__9HIV1, \|82319928\|sp\|Q9WJU5\|Q9WJU5__9HIV1, \|82319927\|sp\|Q9WJU2\|Q9WJU2__9HIV1, \|82311259\|sp\|Q77689\|Q77689__9HIV1, \|82308771\|sp\|Q56CX6\|Q56CX6__9HIV1, \|82308770\|sp\|Q56CX5\|Q56CX5__9HIV1, \|82308769\|sp\|Q56CX4\|Q56CX4__9HIV1, \|82308767\|sp\|Q56CX2\|Q56CX2__9HIV1, \|82308766\|sp\|Q56CX1\|Q56CX1__9HIV1, \|82308765\|sp\|Q56CX0\|Q56CX0__9HIV1, \|82308764\|sp\|Q56CW9\|Q56CW9__9HIV1, \|82308763\|sp\|Q56CW8\|Q56CW8__9HIV1, \|82308762\|sp\|Q56CW7\|Q56CW7__9HIV1, \|82308761\|sp\|Q56CW6\|Q56CW6__9HIV1, \|82308760\|sp\|Q56CW5\|Q56CW5__9HIV1, \|82308759\|sp\|Q56CW4\|Q56CW4__9HIV1, \|82308758\|sp\|Q56CW3\|Q56CW3__9HIV1, \|82308757\|sp\|Q56CW2\|Q56CW2__9HIV1, \|82308756\|sp\|Q56CW1\|Q56CW1__9HIV1, \|82308755\|sp\|Q56CW0\|Q56CW0__9HIV1, \|82308754\|sp\|Q56CV9\|Q56CV9__9HIV1, \|82308753\|sp\|Q56CV8\|Q56CV8__9HIV1, \|82308752\|sp\|Q56CV7\|Q56CV7__9HIV1, \|82308751\|sp\|Q56CV6\|Q56CV6__9HIV1, \|82308750\|sp\|Q56CV5\|Q56CV5__9HIV1, \|82308749\|sp\|Q56CV4\|Q56CV4__9HIV1, \|82308748\|sp\|Q56CV3\|Q56CV3__9HIV1, \|82308747\|sp\|Q56CV2\|Q56CV2__9HIV1, \|82308746\|sp\|Q56CV1\|Q56CV1__9HIV1, \|82308745\|sp\|Q56CV0\|Q56CV0__9HIV1, \|82308744\|sp\|Q56CU9\|Q56CU9__9HIV1, \|82308743\|sp\|Q56CU8\|Q56CU8__9HIV1, \|82308742\|sp\|Q56CU7\|Q56CU7__9HIV1, \|82308741\|sp\|Q56CU6\|Q56CU6__9HIV1, \|82308740\|sp\|Q56CU5\|Q56CU5__9HIV1, \|82308739\|sp\|Q56CU4\|Q56CU4__9HIV1, \|82308738\|sp\|Q56CU3\|Q56CU3__9HIV1, \|82308737\|sp\|Q56CU2\|Q56CU2__9HIV1, \|82308736\|sp\|Q56CU1\|Q56CU1__9HIV1, \|82308735\|sp\|Q56CU0\|Q56CU0__9HIV1, \|82308734\|sp\|Q56CT9\|Q56CT9__9HIV1, \|82308733\|sp\|Q56CT8\|Q56CT8__9HIV1, \|82308732\|sp\|Q56CT7\|Q56CT7__9HIV1, \|82308731\|sp\|Q56CT6\|Q56CT6__9HIV1, \|82308730\|sp\|Q56CT5\|Q56CT5__9HIV1, \|82308729\|sp\|Q56CT4\|Q56CT4__9HIV1, \|82308728\|sp\|Q56CT3\|Q56CT3__9HIV1, \|82308727\|sp\|Q56CT2\|Q56CT2__9HIV1, \|82308726\|sp\|Q56CT1\|Q56CT1__9HIV1, \|82308725\|sp\|Q56CT0\|Q56CT0__9HIV1, \|82308724\|sp\|Q56CS9\|Q56CS9__9HIV1, \|82308723\|sp\|Q56CS8\|Q56CS8__9HIV1, \|82308722\|sp\|Q56CS7\|Q56CS7__9HIV1, \|82308721\|sp\|Q56CS6\|Q56CS6__9HIV1, \|82308720\|sp\|Q56CS5\|Q56CS5__9HIV1, \|82308719\|sp\|Q56CS4\|Q56CS4__9HIV1, \|82308718\|sp\|Q56CS3\|Q56CS3__9HIV1, \|82308717\|sp\|Q56CS2\|Q56CS2__9HIV1, \|82308716\|sp\|Q56CS1\|Q56CS1__9HIV1, \|82308715\|sp\|Q56CS0\|Q56CS0__9HIV1, \|82308714\|sp\|Q56CR9\|Q56CR9__9HIV1, \|82308713\|sp\|Q56CR8\|Q56CR8__9HIV1, \|82308712\|sp\|Q56CR7\|Q56CR7__9HIV1, \|82308711\|sp\|Q56CR6\|Q56CR6__9HIV1, \|82308710\|sp\|Q56CR5\|Q56CR5__9HIV1, \|82308709\|sp\|Q56CR4\|Q56CR4__9HIV1, \|82308708\|sp\|Q56CR3\|Q56CR3__9HIV1, \|82308707\|sp\|Q56CR2\|Q56CR2__9HIV1, \|82308706\|sp\|Q56CR1\|Q56CR1__9HIV1, \|82308705\|sp\|Q56CR0\|Q56CR0__9HIV1, \|82308704\|sp\|Q56CQ9\|Q56CQ9__9HIV1, \|82308703\|sp\|Q56CQ8\|Q56CQ8__9HIV1, \|82308702\|sp\|Q56CQ7\|Q56CQ7__9HIV1, \|82308701\|sp\|Q56CQ6\|Q56CQ6__9HIV1, \|82308700\|sp\|Q56CQ5\|Q56CQ5__9HIV1, \|82308699\|sp\|Q56CQ4\|Q56CQ4__9HIV1, \|82308698\|sp\|Q56CQ3\|Q56CQ3__9HIV1, \|82308697\|sp\|Q56CQ2\|Q56CQ2__9HIV1, \|82308696\|sp\|Q56CQ1\|Q56CQ1__9HIV1, \|82308695\|sp\|Q56CQ0\|Q56CQ0__9HIV1, \|82308694\|sp\|Q56CP9\|Q56CP9__9HIV1, \|82308693\|sp\|Q56CP8\|Q56CP8__9HIV1, \|82308692\|sp\|Q56CP7\|Q56CP7__9HIV1, \|82308691\|sp\|Q56CP6\|Q56CP6__9HIV1, \|82308690\|sp\|Q56CP5\|Q56CP5__9HIV1, \|82308689\|sp\|Q56CP4\|Q56CP4__9HIV1, \|82308688\|sp\|Q56CP3\|Q56CP3__9HIV1, \|82308687\|sp\|Q56CP2\|Q56CP2__9HIV1, \|82308686\|sp\|Q56CP1\|Q56CP1__9HIV1, \|82308685\|sp\|Q56CP0\|Q56CP0__9HIV1, \|82308684\|sp\|Q56CN9\|Q56CN9__9HIV1, \|82308683\|sp\|Q56CN8\|Q56CN8__9HIV1, \|82308682\|sp\|Q56CN7\|Q56CN7__9HIV1, \|82308681\|sp\|Q56CN6\|Q56CN6__9HIV1, \|82308680\|sp\|Q56CN5\|Q56CN5__9HIV1, \|82308679\|sp\|Q56CN4\|Q56CN4__9HIV1, \|82308678\|sp\|Q56CN3\|Q56CN3__9HIV1, \|82308677\|sp\|Q56CN2\|Q56CN2__9HIV1, \|82308676\|sp\|Q56CN1\|Q56CN1__9HIV1, \|82308675\|sp\|Q56CN0\|Q56CN0__9HIV1, \|82308674\|sp\|Q56CM9\|Q56CM9__9HIV1, \|82308673\|sp\|Q56CM8\|Q56CM8__9HIV1, \|82308672\|sp\|Q56CM7\|Q56CM7__9HIV1, \|82308671\|sp\|Q56CM6\|Q56CM6__9HIV1, \|82308670\|sp\|Q56CM5\|Q56CM5__9HIV1, \|82308669\|sp\|Q56CM4\|Q56CM4__9HIV1, \|82308668\|sp\|Q56CM3\|Q56CM3__9HIV1, \|82308667\|sp\|Q56CM2\|Q56CM2__9HIV1, \|82308666\|sp\|Q56CM1\|Q56CM1__9HIV1, \|82308665\|sp\|Q56CM0\|Q56CM0__9HIV1, \|82308664\|sp\|Q56CL9\|Q56CL9__9HIV1, \|82308663\|sp\|Q56CL8\|Q56CL8__9HIV1, \|82308662\|sp\|Q56CL7\|Q56CL7__9HIV1, \|82308661\|sp\|Q56CL6\|Q56CL6__9HIV1, \|82308660\|sp\|Q56CL5\|Q56CL5__9HIV1, \|82308659\|sp\|Q56CL4\|Q56CL4__9HIV1, \|82308658\|sp\|Q56CL3\|Q56CL3__9HIV1, \|82308657\|sp\|Q56CL2\|Q56CL2__9HIV1, \|82308656\|sp\|Q56CL1\|Q56CL1__9HIV1, \|82308655\|sp\|Q56CL0\|Q56CL0__9HIV1, \|82308654\|sp\|Q56CK9\|Q56CK9__9HIV1, \|82308653\|sp\|Q56CK8\|Q56CK8__9HIV1, \|82308652\|sp\|Q56CK7\|Q56CK7__9HIV1, \|82308651\|sp\|Q56CK6\|Q56CK6__9HIV1, \|82308650\|sp\|Q56CK5\|Q56CK5__9HIV1, \|82308649\|sp\|Q56CK4\|Q56CK4__9HIV1, \|82308648\|sp\|Q56CK3\|Q56CK3__9HIV1, \|82308647\|sp\|Q56CK2\|Q56CK2__9HIV1, \|82308646\|sp\|Q56CK1\|Q56CK1__9HIV1, \|82308645\|sp\|Q56CK0\|Q56CK0__9HIV1, \|82308644\|sp\|Q56CJ9\|Q56CJ9__9HIV1, \|82308643\|sp\|Q56CJ8\|Q56CJ8__9HIV1, \|82308642\|sp\|Q56CJ7\|Q56CJ7__9HIV1, \|82308641\|sp\|Q56CJ6\|Q56CJ6__9HIV1, \|62548203\|gb\|AAX86754.1\|, \|62548193\|gb\|AAX86745.1\|, \|62548183\|gb\|AAX86736.1\|, \|62548173\|gb\|AAX86727.1\|, |

| VPR proteins |
| --- |
| |62548163|gb|AAX86718.1|, |132436|sp|P24739|REV_HV1U4, |82319606|sp|Q9PXH4|Q9PXH4_9HIV1 REV-TH |

NEF proteins
|60114|emb|CAA41585.1|, |17352352|gb|AAL01571.1|, |6382040|dbj|BAA86702.1|,
|6382038|dbj|BAA86701.1|, |6382036|dbj|BAA86695.1|, |6362237|dbj|BAA86715.1|,
|6362230|dbj|BAA86714.1|, |6362226|dbj|BAA86713.1|, |6362224|dbj|BAA86712.1|,
|6362222|dbj|BAA86711.1|, |6362220|dbj|BAA86710.1|, |6362218|dbj|BAA86709.1|,
|6362216|dbj|BAA86708.1|, |6362214|dbj|BAA86707.1|, |6362209|dbj|BAA86706.1|,
|6362203|dbj|BAA86705.1|, |6362197|dbj|BAA86704.1|, |6362192|dbj|BAA86703.1|,
|6362111|dbj|BAA86700.1|, |6362105|dbj|BAA86699.1|, |6362099|dbj|BAA86698.1|,
|6362058|dbj|BAA86697.1|, |6362052|dbj|BAA86696.1|, |6362035|dbj|BAA86694.1|,
|6362029|dbj|BAA86693.1|, |6362024|dbj|BAA86692.1|, |6362018|dbj|BAA86691.1|,
|606603|gb|AAA58320.1|, |606601|gb|AAA58319.1|, |606599|gb|AAA58318.1|,
|606597|gb|AAA58317.1|, |606595|gb|AAA58316.1|, |606593|gb|AAA58315.1|,
|606591|gb|AAA58314.1|, |606589|gb|AAA58313.1|, |606587|gb|AAA58312.1|,
|606585|gb|AAA58311.1|, |606583|gb|AAA58310.1|, |606581|gb|AAA58309.1|,
|606579|gb|AAA58308.1|, |606577|gb|AAA58307.1|, |606575|gb|AAA58306.1|,
|606573|gb|AAA58305.1|, |606571|gb|AAA58304.1|, |606569|gb|AAA58303.1|,
|606567|gb|AAA58302.1|, |606565|gb|AAA58301.1|, |606563|gb|AAA58300.1|,
|606561|gb|AAA58299.1|, |606559|gb|AAA58298.1|, |606557|gb|AAA58297.1|,
|606555|gb|AAA58296.1|, |606553|gb|AAA58295.1|, |606551|gb|AAA58294.1|,
|606549|gb|AAA58293.1|, |606547|gb|AAA58292.1|, |606545|gb|AAA58291.1|,
|606543|gb|AAA58290.1|, |606541|gb|AAA58289.1|, |606537|gb|AAA58288.1|,
|606535|gb|AAA58287.1|, |606533|gb|AAA58286.1|, |606522|gb|AAA58285.1|,
|606518|gb|AAA58284.1|, |606516|gb|AAA58283.1|, |606514|gb|AAA58282.1|,
|606512|gb|AAA58281.1|, |606510|gb|AAA58280.1|, |606508|gb|AAA58279.1|,
|606506|gb|AAA58278.1|, |606504|gb|AAA58277.1|, |606502|gb|AAA58276.1|,
|606500|gb|AAA58275.1|, |606495|gb|AAA58274.1|, |606493|gb|AAA58273.1|,
|606491|gb|AAA58272.1|, |606489|gb|AAA58271.1|, |606487|gb|AAA58270.1|,
|606484|gb|AAA58269.1|, |606482|gb|AAA58268.1|, |606480|gb|AAA58267.1|,
|606478|gb|AAA58266.1|, |606476|gb|AAA58265.1|, |606474|gb|AAA58264.1|,
|606472|gb|AAA58263.1|, |606470|gb|AAA58262.1|, |606468|gb|AAA58261.1|,
|606466|gb|AAA58260.1|, |606464|gb|AAA58259.1|, |606462|gb|AAA58258.1|,
|2108041|gb|AAC57215.1|, |2108039|gb|AAC57214.1|, |2108037|gb|AAC57213.1|,
|2108035|gb|AAC57212.1|, |2108031|gb|AAC57210.1|, |2108029|gb|AAC57209.1|,
|2108027|gb|AAC57208.1|, |2108025|gb|AAC57207.1|, |2108023|gb|AAC57206.1|,
|2108021|gb|AAC57205.1|, |2108019|gb|AAC57204.1|, |2108017|gb|AAC57203.1|,
|2108015|gb|AAC57202.1|, |2108013|gb|AAC57201.1|, |2108011|gb|AAC57200.1|,
|2108009|gb|AAC57199.1|, |2108007|gb|AAC57198.1|, |2108005|gb|AAC57197.1|,
|2108000|gb|AAC57195.1|, |2107997|gb|AAC57194.1|, |2107995|gb|AAC57193.1|,
|2107993|gb|AAC57192.1|, |2107989|gb|AAC57190.1|, |2107987|gb|AAC57189.1|,
|2107985|gb|AAC57188.1|, |2107983|gb|AAC57187.1|, |2107981|gb|AAC57186.1|,
|2107979|gb|AAC57185.1|, |2107977|gb|AAC57184.1|, |2107975|gb|AAC57183.1|,
|2107973|gb|AAC57182.1|, |2107971|gb|AAC57181.1|, |2107967|gb|AAC57179.1|,
|2107965|gb|AAC57178.1|, |2107963|gb|AAC57177.1|, |2107961|gb|AAC57176.1|,
|2107959|gb|AAC57175.1|, |2107957|gb|AAC57174.1|, |2107955|gb|AAC57173.1|,
|2107953|gb|AAC57172.1|, |2107951|gb|AAC57171.1|, |2107949|gb|AAC57170.1|,
|16541334|gb|AAL06127.1|, |16541332|gb|AAL06126.1|, |16541330|gb|AAL06125.1|,
|16541328|gb|AAL06124.1|, |16541326|gb|AAL06123.1|, |16541324|gb|AAL06122.1|,
|16541322|gb|AAL06121.1|, |16541320|gb|AAL06120.1|, |16541318|gb|AAL06119.1|,
|16541316|gb|AAL06118.1|, |16541314|gb|AAL06117.1|, |16541312|gb|AAL06116.1|,
|16541310|gb|AAL06115.1|, |15430226|gb|AAK98514.1|AF397575_1,
|15430224|gb|AAK98513.1|AF397574_1, |15430222|gb|AAK98512.1|AF397573_1,
|15430220|gb|AAK98511.1|AF397572_1, |15430218|gb|AAK98510.1|AF397571_1,
|15430216|gb|AAK98509.1|AF397570_1, |15430214|gb|AAK98508.1|AF397569_1,
|15430212|gb|AAK98507.1|AF397568_1, |15430210|gb|AAK98506.1|AF397567_1,
|15430208|gb|AAK98505.1|AF397566_1, |15430206|gb|AAK98504.1|AF397565_1,
|15430204|gb|AAK98503.1|AF397564_1, |15430202|gb|AAK98502.1|AF397563_1,
|15430200|gb|AAK98501.1|AF397562_1, |15430198|gb|AAK98500.1|AF397561_1,
|15430196|gb|AAK98499.1|AF397560_1, |15430194|gb|AAK98498.1|AF397559_1,
|15430192|gb|AAK98497.1|AF397558_1, |15430190|gb|AAK98496.1|AF397557_1,
|15430188|gb|AAK98495.1|AF397556_1, |15430186|gb|AAK98494.1|AF397555_1,
|15430184|gb|AAK98493.1|AF397554_1, |15430182|gb|AAK98492.1|AF397553_1,
|15430180|gb|AAK98491.1|AF397552_1, |15430178|gb|AAK98490.1|AF397551_1,
|15430176|gb|AAK98489.1|AF397550_1, |15430174|gb|AAK98488.1|AF397549_1,
|15430172|gb|AAK98487.1|AF397548_1, |15430170|gb|AAK98486.1|AF397547_1,
|15430168|gb|AAK98485.1|AF397546_1, |15430166|gb|AAK98484.1|AF397545_1,
|15430164|gb|AAK98483.1|AF397544_1, |15430162|gb|AAK98482.1|AF397543_1,
|15430160|gb|AAK98481.1|AF397542_1, |15430158|gb|AAK98480.1|AF397541_1,
|15430156|gb|AAK98479.1|AF397540_1, |15430154|gb|AAK98478.1|AF397539_1,
|15430152|gb|AAK98477.1|AF397538_1, |15430150|gb|AAK98476.1|AF397537_1,
|15430148|gb|AAK98475.1|AF397536_1, |15430146|gb|AAK98474.1|AF397535_1,
|15430144|gb|AAK98473.1|AF397534_1, |15430142|gb|AAK98472.1|AF397533_1,
|4324905|gb|AAD17169.1|, |4324896|gb|AAD17160.1|, |4324887|gb|AAD17151.1|,
|4324878|gb|AAD17142.1|, |4324869|gb|AAD17133.1|, |4324860|gb|AAD17124.1|,
|4324853|gb|AAD17117.1|, |4324845|gb|AAD17109.1|, |4324839|gb|AAD17103.1|,
|4324830|gb|AAD17094.1|, |4324821|gb|AAD17085.1|, |4324815|gb|AAD17079.1|,

VPR proteins

|4324806|gb|AAD17070.1|, |4324799|gb|AAD17063.1|, |4324790|gb|AAD17054.1|,
|4324781|gb|AAD17045.1|, |4324772|gb|AAD17036.1|, |4324764|gb|AAD17028.1|,
|4324755|gb|AAD17019.1|, |4324746|gb|AAD17010.1|,
|8886639|gb|AAF80538.1|AF179368_8, |3114569|gb|AAD03187.1|,
|3114561|gb|AAD03180.1|, |3114546|gb|AAD03166.1|, |2570313|gb|AAC97574.1|,
|2570302|gb|AAC63083.1|, |1537059|gb|AAC55467.1|, |2570333|gb|AAC32660.1|,
|2570296|gb|AAC32652.1|, |13560267|dbj|BAB40918.1|, |6580996|gb|AAF18404.1|AF190128_3,
|6580986|gb|AAF18395.1|AF190127_3, |11993206|gb|AAG42638.1|,
|5733954|gb|AAD49791.1|AF107771_4, |5733947|gb|AAD49785.1|AF107770_7,
|3618020|emb|CAA13474.1|, |3617984|emb|CAA13462.1|, |3617934|emb|CAA13441.1|,
|3617930|emb|CAA13439.1|, |3617964|emb|CAA13455.1|, |722234|emb|AAA63883.1|,
|722232|gb|AAA63882.1|, |722230|gb|AAA63881.1|, |722228|gb|AAA63880.1|,
|722226|gb|AAA63879.1|, |722224|gb|AAA63878.1|, |722222|gb|AAA63877.1|,
|722220|gb|AAA63876.1|, |722218|gb|AAA63875.1|, |722216|gb|AAA63874.1|,
|722214|gb|AAA63873.1|, |722212|gb|AAA63872.1|, |722210|gb|AAA63871.1|,
|722208|gb|AAA63870.1|, |722205|gb|AAA63869.1|, |722203|gb|AAA63868.1|,
|722201|gb|AAA63867.1|, |722199|gb|AAA63866.1|, |722197|gb|AAA63865.1|,
|722195|gb|AAA63864.1|, |722193|gb|AAA63863.1|, |722191|gb|AAA63862.1|,
|722188|gb|AAA63861.1|, |722186|gb|AAA63860.1|, |722184|gb|AAA63859.1|,
|722182|gb|AAA63858.1|, |722180|gb|AAA63857.1|, |722178|gb|AAA63856.1|,
|722176|gb|AAA63855.1|, |722174|gb|AAA63854.1|, |722172|gb|AAA63853.1|,
|722170|gb|AAA63852.1|, |722167|gb|AAA63851.1|, |722165|gb|AAA63850.1|,
|722163|gb|AAA63849.1|, |722161|gb|AAA63848.1|, |722159|gb|AAA63847.1|,
|722157|gb|AAA63846.1|, |722155|gb|AAA63845.1|, |722153|gb|AAA63844.1|,
|722151|gb|AAA63843.1|, |722149|gb|AAA63842.1|, |722147|gb|AAA63841.1|,
|722145|gb|AAA63840.1|, |722142|gb|AAA63839.1|, |722140|gb|AAA63838.1|,
|722138|gb|AAA63837.1|, |722136|gb|AAA63836.1|, |722134|gb|AAA63835.1|,
|722132|gb|AAA63834.1|, |722130|gb|AAA63833.1|, |722128|gb|AAA63832.1|,
|722126|gb|AAA63831.1|, |722124|gb|AAA63830.1|, |722122|gb|AAA63829.1|,
|722120|gb|AAA63828.1|, |722117|gb|AAA63827.1|, |722115|gb|AAA63826.1|,
|722113|gb|AAA63825.1|, |722111|gb|AAA63824.1|, |722109|gb|AAA63823.1|,
|722107|gb|AAA63822.1|, |722105|gb|AAA63821.1|, |722103|gb|AAA63820.1|,
|722101|gb|AAA63819.1|, |722099|gb|AAA63818.1|, |722097|gb|AAA63817.1|,
|722095|gb|AAA63816.1|, |722093|gb|AAA63815.1|, |722091|gb|AAA63814.1|,
|722089|gb|AAA63813.1|, |722086|gb|AAA63812.1|, |722084|gb|AAA63811.1|,
|722082|gb|AAA63810.1|, |722080|gb|AAA63809.1|, |722077|gb|AAA63808.1|,
|722074|gb|AAA63807.1|, |722070|gb|AAA63806.1|, |722068|gb|AAA63805.1|,
|722066|gb|AAA63804.1|, |349694|gb|AAA02668.1|, |306071|gb|AAA02672.1|,
|306069|gb|AAA02671.1|, |306067|gb|AAA02670.1|, |306058|gb|AAA02665.1|,
|306056|gb|AAA02664.1|, |306054|gb|AAA02663.1|, |306052|gb|AAA02662.1|,
|306041|gb|AAA02657.1|, |306039|gb|AAA02656.1|, |306037|gb|AAA02655.1|,
|306028|gb|AAA02651.1|, |306026|gb|AAA02650.1|, |306023|gb|AAA02649.1|,
|306021|gb|AAA02648.1|, |306019|gb|AAA02647.1|, |306017|gb|AAA02646.1|,
|306013|gb|AAA02644.1|, |306011|gb|AAA02643.1|, |306009|gb|AAA02642.1|,
|306007|gb|AAA02641.1|, |306005|gb|AAA02640.1|, |306003|gb|AAA02639.1|,
|306001|gb|AAA02638.1|, |305999|gb|AAA02637.1|, |305997|gb|AAA02636.1|,
|305995|gb|AAA02635.1|, |305993|gb|AAA02633.1|, |305991|gb|AAA02634.1|,
|6448459|dbj|BAA86906.1|, |6448457|dbj|BAA86905.1|, |6448455|dbj|BAA86904.1|,
|6448453|dbj|BAA86903.1|, |6448451|dbj|BAA86902.1|, |82307533|sp|Q9WIR5|Q9WIR5_9HIV1,
|82307532|sp|Q9WIR4|Q9WIR4_9HIV1, |82307531|sp|Q9WIR3|Q9WIR3_9HIV1,
|82307530|sp|Q9WIR2|Q9WIR2_9HIV1, |82307529|sp|Q9WIR1|Q9WIR1_9HIV1,
|82307528|sp|Q9WIR0|Q9WIR0_9HIV1, |82307527|sp|Q9WIQ9|Q9WIQ9_9HIV1,
|82307526|sp|Q9WIQ8|Q9WIQ8_9HIV1, |82307525|sp|Q9WIQ7|Q9WIQ7_9HIV1,
|82307524|sp|Q9WIQ6|Q9WIQ6_9HIV1, |82307523|sp|Q9WIQ5|Q9WIQ5_9HIV1,
|82307522|sp|Q9WIQ4|Q9WIQ4_9HIV1, |82307521|sp|Q9WIQ3|Q9WIQ3_9HIV1,
|82307520|sp|Q9WIQ2|Q9WIQ2_9HIV1, |82307519|sp|Q9WIQ1|Q9WIQ1_9HIV1,
|82307518|sp|Q9WIQ0|Q9WIQ0_9HIV1, |82307517|sp|Q9WIP9|Q9WIP9_9HIV1,
|82307516|sp|Q9WIP8|Q9WIP8_9HIV1, |82307515|sp|Q9WIP7|Q9WIP7_9HIV1,
|82307514|sp|Q9WIP6|Q9WIP6_9HIV1, |82307513|sp|Q9WIP5|Q9WIP5_9HIV1,
|82307512|sp|Q9WIP4|Q9WIP4_9HIV1, |82307511|sp|Q9WIP3|Q9WIP3_9HIV1,
|82307510|sp|Q9WIP2|Q9WIP2_9HIV1, |82307509|sp|Q9WIP1|Q9WIP1_9HIV1,
|82307508|sp|Q9WIP0|Q9WIP0_9HIV1, |82307507|sp|Q9WIN9|Q9WIN9_9HIV1,
|82307506|sp|Q9WIN8|Q9WIN8_9HIV1, |82307505|sp|Q9WIN7|Q9WIN7_9HIV1,
|82307504|sp|Q9WIN6|Q9WIN6_9HIV1, |82307503|sp|Q9WIN5|Q9WIN5_9HIV1,
|82307502|sp|Q9WIN4|Q9WIN4_9HIV1, |82307501|sp|Q9WIN3|Q9WIN3_9HIV1,
|82307500|sp|Q9WIN2|Q9WIN2_9HIV1, |82307499|sp|Q9WIN1|Q9WIN1_9HIV1,
|82307498|sp|Q9WIN0|Q9WIN0_9HIV1, |82307497|sp|Q9WIM9|Q9WIM9_9HIV1,
|82307496|sp|Q9WIM8|Q9WIM8_9HIV1, |82307495|sp|Q9WIM7|Q9WIM7_9HIV1,
|82307494|sp|Q9WIM6|Q9WIM6_9HIV1, |82307493|sp|Q9WIM5|Q9WIM5_9HIV1,
|82307492|sp|Q9WIM4|Q9WIM4_9HIV1, |82307491|sp|Q9WIM3|Q9WIM3_9HIV1,
|82307490|sp|Q9WIM2|Q9WIM2_9HIV1, |82307489|sp|Q9WIM1|Q9WIM1_9HIV1,
|82307488|sp|Q9WIM0|Q9WIM0_9HIV1, |82307487|sp|Q9WIL9|Q9WIL9_9HIV1,
|82307486|sp|Q9WIL8|Q9WIL8_9HIV1, |82307485|sp|Q9WIL7|Q9WIL7_9HIV1,
|82307212|sp|Q9W9W3|Q9W9W3_9HIV1, |82307199|sp|Q9W9N5|Q9W9N5_9HIV1,
|82307197|sp|Q9W9N0|Q9W9N0_9HIV1, |82307171|sp|Q9W908|Q9W908_9HIV1,
|82307166|sp|Q9W8U5|Q9W8U5_9HIV1, |82307156|sp|Q9W8M8|Q9W8M8_9HIV1,
|82306521|sp|Q9QMF6|Q9QMF6_9HIV1, |82306520|sp|Q9QMF5|Q9QMF5_9HIV1, -continued

| VPR proteins |
|---|
| |82306519|sp|Q9QMF4|Q9QMF4__9HIV1, |82305566|sp|Q9PX37|Q9PX37__9HIV1, |82305554|sp|Q9PWX9|Q9PWX9__9HIV1, |82301533|sp|Q97066|Q97066__9HIV1, |82295336|sp|Q89665|Q89665__9HIV1, |82289663|sp|Q75752|Q75752__9HIV1, |82289631|sp|Q75718|Q75718__9HIV1, |82289626|sp|Q75713|Q75713__9HIV1, |3618026|emb|CAA13477.1|, |3618018|emb|CAA13473.1|, |3618014|emb|CAA13471.1|, |3618010|emb|CAA13469.1|, |3618008|emb|CAA13468.1|, |3618006|emb|CAA13467.1|, |3618004|emb|CAA13466.1|, |3617996|emb|CAA13464.1|, |3617978|emb|CAA13461.1|, |3617972|emb|CAA13459.1|, |3617970|emb|CAA13458.1|, |3617966|emb|CAA13456.1|, |3617962|emb|CAA13454.1|, |3617958|emb|CAA13452.1|, |3617956|emb|CAA13451.1|, |3617948|emb|CAA13448.1|, |3617946|emb|CAA13447.1|, |3617944|emb|CAA13446.1|, |3617942|emb|CAA13445.1|, |3617940|emb|CAA13444.1|, |3617938|emb|CAA13443.1|, |3617936|emb|CAA13442.1|, |3617928|emb|CAA13438.1|, |3617926|emb|CAA13437.1|, |475669|gb|AAB04094.1|, |475666|gb|AAB04092.1|, |475663|gb|AAB04090.1|, |475660|gb|AAB04088.1|, |475657|gb|AAB04086.1|, |475654|gb|AAB04084.1|, |475651|gb|AAB04082.1|, |475648|gb|AAB04080.1|, |475645|gb|AAB04078.1|, |475643|gb|AAB17018.1|, |475640|gb|AAB04077.1|, |475638|gb|AAB04076.1|, |475635|gb|AAB04074.1|, |475632|gb|AAB04072.1|, |475629|gb|AAB04070.1|, |475626|gb|AAB04068.1|, |475623|gb|AAB04066.1|, |475620|gb|AAB04064.1|, |3618024|emb|CAA13476.1|, |3618022|emb|CAA13475.1|, |3618016|emb|CAA13472.1|, |3618012|emb|CAA13470.1|, |3618000|emb|CAA13465.1|, |3617990|emb|CAA13463.1|, |3617974|emb|CAA13460.1|, |3617968|emb|CAA13457.1|, |3617960|emb|CAA13453.1|, |3617952|emb|CAA13450.1|, |3617950|emb|CAA13449.1|, |3617932|emb|CAA13440.1|, |1177210|gb|AAB38220.1|, |1177208|gb|AAB38219.1|, |1177206|gb|AAB38218.1|, |1177204|gb|AAB38217.1|, |1177202|gb|AAB38216.1|, |1177200|gb|AAB38215.1|, |1177198|gb|AAB38214.1|, |1177196|gb|AAB38213.1|, |1177194|gb|AAB38212.1|, |1177192|gb|AAB38211.1|, |1177190|gb|AAB38210.1|, |1177188|gb|AAB38209.1|, |1177183|gb|AAB38207.1|, |1177181|gb|AAB38206.1|, |1177179|gb|AAB38205.1|, |1177177|gb|AAB38204.1|, |1177175|gb|AAB38203.1|, |1177173|gb|AAB38202.1|, |1177171|gb|AAB38201.1|, |1177169|gb|AAB38200.1|, |1177167|gb|AAB38199.1|, |1177165|gb|AAB38198.1|, |1177163|gb|AAB38197.1|, |1177161|gb|AAB38196.1|, |1177159|gb|AAB38195.1|, |1353869|gb|AAB36508.1|, |487258|gb|AAB05028.1|, |487255|gb|AAB05026.1|, |1458084|gb|AAB04753.1|, |1458082|gb|AAB04752.1|, |1458080|gb|AAB04751.1|, |1458078|gb|AAB04750.1|, |1458076|gb|AAB04749.1|, |1458074|gb|AAB04748.1|, |1458072|gb|AAB04747.1|, |1458070|gb|AAB04746.1|, |1458068|gb|AAB04745.1|, |1458066|gb|AAB04744.1|, |1458064|gb|AAB04743.1|, |1458062|gb|AAB04742.1|, |1458060|gb|AAB04741.1|, |1458058|gb|AAB04740.1|, |1458056|gb|AAB04739.1|, |1458054|gb|AAB04738.1|, |1458052|gb|AAB04737.1|, |1458050|gb|AAB04736.1|, |1458048|gb|AAB04735.1|, |1458046|gb|AAB04734.1|, |1458044|gb|AAB04733.1|, |1458042|gb|AAB04732.1|, |1458040|gb|AAB04731.1|, |1458038|gb|AAB04730.1|, |1458036|gb|AAB04729.1|, |1458034|gb|AAB04728.1|, |1458032|gb|AAB04727.1|, |1458030|gb|AAB04726.1|, |1458028|gb|AAB04725.1|, |1458026|gb|AAB04724.1|, |1458024|gb|AAB04723.1|, |1458015|gb|AAB04719.1|, |1458013|gb|AAB04718.1|, |1458009|gb|AAB04717.1|, |1458007|gb|AAB04716.1|, |1458005|gb|AAB04715.1|, |1458003|gb|AAB04714.1|, |1458001|gb|AAB04713.1|, |1457999|gb|AAB04712.1|, |1457997|gb|AAB04711.1|, |1457995|gb|AAB04710.1|, |1457989|gb|AAB04707.1|, |1457987|gb|AAB04706.1|, |1457985|gb|AAB04705.1|, |1457983|gb|AAB04704.1|, |1457981|gb|AAB04703.1|, |1457979|gb|AAB04702.1|, |1457977|gb|AAB04701.1|, |1457975|gb|AAB04700.1|, |1457973|gb|AAB04699.1|, |1457971|gb|AAB04698.1|, |1457969|gb|AAB04697.1|, |1457967|gb|AAB04696.1|, |1457965|gb|AAB04695.1|, |327820|gb|AAB03750.1|, |829488|gb|AAA79607.1|, |829486|gb|AAA79606.1|, |829484|gb|AAA79605.1|, |829482|gb|AAA79604.1|, |829480|gb|AAA79603.1|, |829478|gb|AAA79602.1|, |829475|gb|AAA79601.1|, |829473|gb|AAA79600.1|, |829471|gb|AAA79599.1|, |328677|gb|AAA45073.1|, |28872818|ref|NP_057857.2|, |14579620|gb|AAK69337.1|, |14579610|gb|AAK69328.1|, |82311082|sp|Q75000|Q75000__9HIV1, |82308082|sp|Q9YKU0|Q9YKU0__9HIV1, |82308080|sp|Q9YKT6|Q9YKT6__9HIV1, |82308078|sp|Q9YKT3|Q9YKT3__9HIV1, |82308077|sp|Q9YKS7|Q9YKS7__9HIV1, |82308075|sp|Q9YKR6|Q9YKR6__9HIV1, |82308073|sp|Q9YKR0|Q9YKR0__9HIV1, |82308068|sp|Q9YKP3|Q9YKP3__9HIV1, |82308066|sp|Q9YKN6|Q9YKN6__9HIV1, |82308064|sp|Q9YKM9|Q9YKM9__9HIV1, |82307351|sp|Q9WF95|Q9WF95__9HIV1, |82307349|sp|Q9WF91|Q9WF91__9HIV1, |82307347|sp|Q9WF88|Q9WF88__9HIV1, |82307344|sp|Q9WF83|Q9WF83__9HIV1, |82307341|sp|Q9WF76|Q9WF76__9HIV1, |82307339|sp|Q9WF73|Q9WF73__9HIV1, |82307337|sp|Q9WF70|Q9WF70__9HIV1, |82307335|sp|Q9WF67|Q9WF67__9HIV1, |82307333|sp|Q9WF64|Q9WF64__9HIV1, |82307331|sp|Q9WF61|Q9WF61__9HIV1, |82307330|sp|Q9WF58|Q9WF58__9HIV1, |82300238|sp|Q90B86|Q90B86__9HIV1, |82300237|sp|Q90B85|Q90B85__9HIV1, |82300236|sp|Q90B84|Q90B84__9HIV1, |82300235|sp|Q90B83|Q90B83__9HIV1, |82300234|sp|Q90B82|Q90B82__9HIV1, |82300233|sp|Q90B81|Q90B81__9HIV1, |82300232|sp|Q90B80|Q90B80__9HIV1, |82300231|sp|Q90B79|Q90B79__9HIV1, |82300230|sp|Q90B78|Q90B78__9HIV1, |82300229|sp|Q90B77|Q90B77__9HIV1, |82300228|sp|Q90B76|Q90B76__9HIV1, |82300227|sp|Q90B75|Q90B75__9HIV1, |82300226|sp|Q90B74|Q90B74__9HIV1, |82300225|sp|Q90B73|Q90B73__9HIV1, |82300224|sp|Q90B72|Q90B72__9HIV1, |82300223|sp|Q90B71|Q90B71__9HIV1, |82300222|sp|Q90B70|Q90B70__9HIV1, |82300221|sp|Q90B69|Q90B69__9HIV1, |82300220|sp|Q90B68|Q90B68__9HIV1, |82300219|sp|Q90B67|Q90B67__9HIV1, |82300218|sp|Q90B66|Q90B66__9HIV1, |82300217|sp|Q90B65|Q90B65__9HIV1, |82300216|sp|Q90B64|Q90B64__9HIV1, |82300215|sp|Q90B63|Q90B63__9HIV1, |82300214|sp|Q90B62|Q90B62__9HIV1, |

| VPR proteins |
| --- |
| \|82300213\|sp\|Q90B61\|Q90B61__9HIV1, \|82300212\|sp\|Q90B60\|Q90B60__9HIV1, \|82300211\|sp\|Q90B59\|Q90B59__9HIV1, \|82300210\|sp\|Q90B58\|Q90B58__9HIV1, \|82300209\|sp\|Q90B57\|Q90B57__9HIV1, \|82300208\|sp\|Q90B56\|Q90B56__9HIV1, \|82300207\|sp\|Q90B55\|Q90B55__9HIV1, \|82300206\|sp\|Q90B54\|Q90B54__9HIV1, \|82300205\|sp\|Q90B53\|Q90B53__9HIV1, \|82300204\|sp\|Q90B52\|Q90B52__9HIV1, \|82300203\|sp\|Q90B51\|Q90B51__9HIV1, \|82300202\|sp\|Q90B50\|Q90B50__9HIV1, \|82300201\|sp\|Q90B49\|Q90B49__9HIV1, \|82300200\|sp\|Q90B48\|Q90B48__9HIV1, \|82300199\|sp\|Q90B47\|Q90B47__9HIV1, \|82300198\|sp\|Q90B46\|Q90B46__9HIV1, \|82300197\|sp\|Q90B45\|Q90B45__9HIV1, \|82300196\|sp\|Q90B44\|Q90B44__9HIV1, \|82299526\|sp\|Q901V1\|Q901V1__9HIV1, \|82299525\|sp\|Q901V0\|Q901V0__9HIV1, \|82299524\|sp\|Q901U9\|Q901U9__9HIV1, \|82299523\|sp\|Q901U8\|Q901U8__9HIV1, \|82299522\|sp\|Q901U7\|Q901U7__9HIV1, \|82299521\|sp\|Q901U6\|Q901U6__9HIV1, \|82299520\|sp\|Q901U5\|Q901U5__9HIV1, \|82299519\|sp\|Q901U4\|Q901U4__9HIV1, \|82299518\|sp\|Q901U3\|Q901U3__9HIV1, \|82299517\|sp\|Q901U2\|Q901U2__9HIV1, \|82299516\|sp\|Q901U1\|Q901U1__9HIV1, \|82299515\|sp\|Q901U0\|Q901U0__9HIV1, \|82299514\|sp\|Q901T9\|Q901T9__9HIV1, \|82298954\|sp\|Q8UMP7\|Q8UMP7__9HIV1, \|82295323\|sp\|Q89561\|Q89561__9HIV1, \|82289533\|sp\|Q75009\|Q75009__9HIV1, \|82289530\|sp\|Q74927\|Q74927__9HIV1, \|82289529\|sp\|Q74926\|Q74926__9HIV1, \|82289528\|sp\|Q74925\|Q74925__9HIV1, \|82289527\|sp\|Q74924\|Q74924__9HIV1, \|82289526\|sp\|Q74923\|Q74923__9HIV1, \|82289525\|sp\|Q74922\|Q74922__9HIV1, \|82289524\|sp\|Q74921\|Q74921__9HIV1, \|82289523\|sp\|Q74920\|Q74920__9HIV1, \|82289522\|sp\|Q74919\|Q74919__9HIV1, \|82289521\|sp\|Q74918\|Q74918__9HIV1, \|82289520\|sp\|Q74917\|Q74917__9HIV1, \|82289519\|sp\|Q74916\|Q74916__9HIV1, \|82289518\|sp\|Q74915\|Q74915__9HIV1, \|82289517\|sp\|Q74914\|Q74914__9HIV1, \|82289516\|sp\|Q74913\|Q74913__9HIV1, \|82289515\|sp\|Q74912\|Q74912__9HIV1, \|82289514\|sp\|Q74911\|Q74911__9HIV1, \|82289513\|sp\|Q74910\|Q74910__9HIV1, \|82289512\|sp\|Q74909\|Q74909__9HIV1, \|82289511\|sp\|Q74908\|Q74908__9HIV1, \|82289510\|sp\|Q74907\|Q74907__9HIV1, \|82289509\|sp\|Q74906\|Q74906__9HIV1, \|82289508\|sp\|Q74905\|Q74905__9HIV1, \|82288075\|sp\|Q70201\|Q70201__9HIV1, \|82288074\|sp\|Q70199\|Q70199__9HIV1, \|82288046\|sp\|Q70021\|Q70021__9HIV1, \|82288045\|sp\|Q70019\|Q70019__9HIV1, \|82288044\|sp\|Q70017\|Q70017__9HIV1, \|82288043\|sp\|Q70015\|Q70015__9HIV1, \|82288042\|sp\|Q70013\|Q70013__9HIV1, \|82288041\|sp\|Q70011\|Q70011__9HIV1, \|82288040\|sp\|Q70009\|Q70009__9HIV1, \|82288039\|sp\|Q70007\|Q70007__9HIV1, \|82288038\|sp\|Q70005\|Q70005__9HIV1, \|82288037\|sp\|Q70004\|Q70004__9HIV1, \|82288036\|sp\|Q70002\|Q70002__9HIV1, \|82288035\|sp\|Q70001\|Q70001__9HIV1, \|82284332\|sp\|Q69999\|Q69999__9HIV1, \|82284331\|sp\|Q69997\|Q69997__9HIV1, \|82284330\|sp\|Q69995\|Q69995__9HIV1, \|82284329\|sp\|Q69993\|Q69993__9HIV1, \|82284328\|sp\|Q69991\|Q69991__9HIV1, \|82284327\|sp\|Q69989\|Q69989__9HIV1, \|82280443\|sp\|O89293\|O89293__9HIV1, \|82279844\|sp\|O70903\|O70903__9HIV1, \|82279842\|sp\|O70896\|O70896__9HIV1, \|82279692\|sp\|O41804\|O41804__9HIV1, \|82279690\|sp\|O41790\|O41790__9HIV1, \|82279687\|sp\|O41781\|O41781__9HIV1, \|82279685\|sp\|O41773\|O41773__9HIV1, \|2276306\|emb\|CAB10831.1\|, \|2276304\|emb\|CAB10830.1\|, \|2276302\|emb\|CAB10829.1\|, \|2276300\|emb\|CAB10828.1\|, \|2276298\|emb\|CAB10827.1\|, \|2276296\|emb\|CAB10826.1\|, \|2276294\|emb\|CAB10825.1\|, \|2276292\|emb\|CAB10824.1\|, \|2276290\|emb\|CAB10823.1\|, \|2276288\|emb\|CAB10822.1\|, \|2276286\|emb\|CAB10821.1\|, \|2276284\|emb\|CAB10820.1\|, \|2276282\|emb\|CAB10819.1\|, \|2276280\|emb\|CAB10818.1\|, \|2276278\|emb\|CAB10817.1\|, \|2276276\|emb\|CAB10816.1\|, \|2276274\|emb\|CAB10815.1\|, \|60116\|emb\|CAA44766.1\|, \|6466845\|gb\|AAF13060.1\|, \|7021462\|gb\|AAF35361.1\|, \|2801509\|gb\|AAC82597.1\|, \|1123021\|gb\|AAC54650.1\|, \|1123011\|gb\|AAC54641.1\|, \|1171192\|gb\|AAB47920.1\|, \|554990\|gb\|AAB04042.1\|, \|60237\|emb\|CAA44771.1\|, \|1176382\|gb\|AAA86737.1\|, \|1171196\|gb\|AAA86259.1\|, \|1171194\|gb\|AAA86258.1\|, \|1171172\|gb\|AAA86253.1\|, \|1151168\|gb\|AAA85238.1\|, \|665534\|gb\|AAA76691.1\|, \|326372\|gb\|AAA44192.1\|, \|4579600\|gb\|AAK69319.1\|, \|82318849\|sp\|Q9DSL7\|Q9DSL7__9HIV1, \|82306993\|sp\|Q9QRX0\|Q9QRX0__9HIV1, \|82306991\|sp\|Q9QRW1\|Q9QRW1__9HIV1, \|82306102\|sp\|Q9QEF2\|Q9QEF2__9HIV1, \|82305934\|sp\|Q9Q713\|Q9Q713__9HIV1, \|82305932\|sp\|Q9Q704\|Q9Q704__9HIV1, \|82305168\|sp\|Q9J0G4\|Q9J0G4__9HIV1, \|82304876\|sp\|Q9IMJ1\|Q9IMJ1__9HIV1, \|82302367\|sp\|Q998E4\|Q998E4__9HIV1, \|82300665\|sp\|Q90MM2\|Q90MM2__9HIV1, \|82300663\|sp\|Q90ML3\|Q90ML3__9HIV1, \|82300661\|sp\|Q90MK4\|Q90MK4__9HIV1, \|82295355\|sp\|Q89896\|Q89896__9HIV1, \|82295352\|sp\|Q89880\|Q89880__9HIV1, \|82295344\|sp\|Q89766\|Q89766__9HIV1, \|82295322\|sp\|Q89553\|Q89553__9HIV1, \|82289664\|sp\|Q75753\|Q75753__9HIV1, \|82289662\|sp\|Q75751\|Q75751__9HIV1, \|82289661\|sp\|Q75750\|Q75750__9HIV1, \|82289660\|sp\|Q75749\|Q75749__9HIV1, \|82289659\|sp\|Q75748\|Q75748__9HIV1, \|82289658\|sp\|Q75747\|Q75747__9HIV1, \|82289657\|sp\|Q75746\|Q75746__9HIV1, \|82289656\|sp\|Q75745\|Q75745__9HIV1, \|82289655\|sp\|Q75744\|Q75744__9HIV1, \|82289654\|sp\|Q75743\|Q75743__9HIV1, \|82289653\|sp\|Q75742\|Q75742__9HIV1, \|82289652\|sp\|Q75741\|Q75741__9HIV1, \|82289651\|sp\|Q75740\|Q75740__9HIV1, \|82289650\|sp\|Q75739\|Q75739__9HIV1, \|82289649\|sp\|Q75738\|Q75738__9HIV1, \|82289648\|sp\|Q75737\|Q75737__9HIV1, \|82289647\|sp\|Q75736\|Q75736__9HIV1, \|82289646\|sp\|Q75735\|Q75735__9HIV1, \|82289645\|sp\|Q75734\|Q75734__9HIV1, \|82289644\|sp\|Q75733\|Q75733__9HIV1, \|82289643\|sp\|Q75732\|Q75732__9HIV1, \|82289639\|sp\|Q75728\|Q75728__9HIV1, \|82289638\|sp\|Q75727\|Q75727__9HIV1, \|82289637\|sp\|Q75726\|Q75726__9HIV1, \|82289636\|sp\|Q75725\|Q75725__9HIV1, \|82289635\|sp\|Q75724\|Q75724__9HIV1, \|82289634\|sp\|Q75723\|Q75723__9HIV1, \|82289633\|sp\|Q75722\|Q75722__9HIV1, \|82289632\|sp\|Q75719\|Q75719__9HIV1, \|82289630\|sp\|Q75717\|Q75717__9HIV1, \|82289629\|sp\|Q75716\|Q75716__9HIV1, |

VPR proteins

|82289628|sp|Q75715|Q75715__9HIV1, |82289627|sp|Q75714|Q75714__9HIV1,
|82289497|sp|Q74842|Q74842__9HIV1, |82288908|sp|Q73328|Q73328__9HIV1,
|82288768|sp|Q72496|Q72496__9HIV1, |3850011|emb|CAA76050.1|, |3618131|emb|CAA13528.1|,
|3618129|emb|CAA13527.1|, |3618127|emb|CAA13526.1|, |3618125|emb|CAA13525.1|,
|3618123|emb|CAA13524.1|, |3618121|emb|CAA13523.1|, |3618118|emb|CAA13522.1|,
|3618116|emb|CAA13521.1|, |3618114|emb|CAA13520.1|, |3618112|emb|CAA13519.1|,
|3618108|emb|CAA13518.1|, |3618106|emb|CAA13517.1|, |3618104|emb|CAA13516.1|,
|3618102|emb|CAA13515.1|, |3618100|emb|CAA13514.1|, |3618098|emb|CAA13513.1|,
|3618096|emb|CAA13512.1|, |3618094|emb|CAA13511.1|, |3618090|emb|CAA13509.1|,
|3618088|emb|CAA13508.1|, |3618086|emb|CAA13507.1|, |3618084|emb|CAA13506.1|,
|3618082|emb|CAA13505.1|, |3618080|emb|CAA13504.1|, |3618078|emb|CAA13503.1|,
|3618076|emb|CAA13502.1|, |3618074|emb|CAA13501.1|, |3618072|emb|CAA13500.1|,
|3618070|emb|CAA13499.1|, |3618068|emb|CAA13498.1|, |3618066|emb|CAA13497.1|,
|3618064|emb|CAA13496.1|, |3618062|emb|CAA13495.1|, |3618060|emb|CAA13494.1|,
|3618058|emb|CAA13493.1|, |3618056|emb|CAA13492.1|, |3618054|emb|CAA13491.1|,
|3618052|emb|CAA13490.1|, |3618050|emb|CAA13489.1|, |3618048|emb|CAA13488.1|,
|3618046|emb|CAA13487.1|, |3618044|emb|CAA13486.1|, |3618042|emb|CAA13485.1|,
|3618040|emb|CAA13484.1|, |3618036|emb|CAA13482.1|, |3618034|emb|CAA13481.1|,
|3618032|emb|CAA13480.1|, |3618030|emb|CAA13479.1|, |3618028|emb|CAA13478.1|,
|1568317|emb|CAA02191.1|, |3850017|emb|CAA76053.1|, |3850015|emb|CAA76052.1|,
|3850013|emb|CAA76051.1|, |3618092|emb|CAA13510.1|, |3618038|emb|CAA13483.1|,
|1299712|gb|AAB26291.1|, |255653|gb|AAB23301.1|, |5070579|gb|AAD39193.1|,
|5070578|gb|AAD39192.1|, |5070577|gb|AAD39191.1|, |5070576|gb|AAD39190.1|,
|5070575|gb|AAD39189.1|, |5070574|gb|AAD39188.1|, |5070573|gb|AAD39187.1|,
|5070572|gb|AAD39186.1|, |5070571|gb|AAD39185.1|, |5070570|gb|AAD39184.1|,
|5730861|gb|AAD48750.1|AF120923__1, |5730860|gb|AAD48749.1|AF120922__1,
|5730859|gb|AAD48748.1|AF120920__1, |5730858|gb|AAD48747.1|AF120919__1,
|5730857|gb|AAD48746.1|AF120918__1, |5730856|gb|AAD48745.1|AF120917__1,
|5730855|gb|AAD48744.1|AF120916__1, |5730854|gb|AAD48743.1|AF120915__1,
|5730853|gb|AAD48742.1|AF120914__1, |5730852|gb|AAD48741.1|AF120913__1,
|5730851|gb|AAD48740.1|AF120912__1, |5730850|gb|AAD48739.1|AF120911__1,
|5730849|gb|AAD48738.1|AF120909__1, |5730848|gb|AAD48737.1|AF120908__1,
|5730847|gb|AAD48736.1|AF120907__1, |5730846|gb|AAD48735.1|AF120906__1,
|5730845|gb|AAD48734.1|AF120905__1, |5730844|gb|AAD48733.1|AF120904__1,
|5730843|gb|AAD48732.1|AF120897__1, |5730842|gb|AAD48731.1|AF120896__1,
|5730841|gb|AAD48730.1|AF120895__1, |5730840|gb|AAD48729.1|AF120894__1,
|5730839|gb|AAD48728.1|AF120893__1, |5730838|gb|AAD48727.1|AF120892__1,
|5730837|gb|AAD48726.1|AF120891__1, |5730836|gb|AAD48725.1|AF120890__1,
|5730835|gb|AAD48724.1|AF120889__1, |5730834|gb|AAD48723.1|AF120888__1,
|5730833|gb|AAD48722.1|AF120887__1, |5730832|gb|AAD48721.1|AF120886__1,
|5730831|gb|AAD48720.1|AF120885__1, |5730830|gb|AAD48719.1|AF120884__1,
|5730829|gb|AAD48718.1|AF120883__1, |5730828|gb|AAD48717.1|AF120882__1,
|5730827|gb|AAD48716.1|AF120881__1, |5730826|gb|AAD48715.1|AF120880__1,
|5730825|gb|AAD48714.1|AF120879__1, |5730824|gb|AAD48713.1|AF120878__1,
|5730823|gb|AAD48712.1|AF120877__1, |5730822|gb|AAD48711.1|AF120876__1,
|5730821|gb|AAD48710.1|AF120875__1, |5730820|gb|AAD48709.1|AF120874__1,
|5730819|gb|AAD48708.1|AF120873__1, |5730818|gb|AAD48707.1|AF120872__1,
|5730817|gb|AAD48706.1|AF120871__1, |5730816|gb|AAD48705.1|AF120870__1,
|5730815|gb|AAD48704.1|AF120869__1, |5730814|gb|AAD48703.1|AF120868__1,
|5730813|gb|AAD48702.1|AF120867__1, |5730812|gb|AAD48701.1|AF120865__1,
|5730811|gb|AAD48700.1|AF120864__1, |5730810|gb|AAD48699.1|AF120863__1,
|5730809|gb|AAD48698.1|AF120862__1, |5730808|gb|AAD48697.1|AF120861__1,
|5730807|gb|AAD48696.1|AF120860__1, |5730806|gb|AAD48695.1|AF120859__1,
|5730805|gb|AAD48694.1|AF120858__1, |5730804|gb|AAD48693.1|AF120857__1,
|5730803|gb|AAD48692.1|AF120856__1, |5730802|gb|AAD48691.1|AF120855__1,
|5730801|gb|AAD48690.1|AF120854__1, |5730800|gb|AAD48689.1|AF120853__1,
|5730799|gb|AAD48688.1|AF120852__1, |5730798|gb|AAD48687.1|AF120851__1,
|5730797|gb|AAD48686.1|AF120850__1, |5730796|gb|AAD48685.1|AF120847__1,
|5730795|gb|AAD48684.1|AF120846__1, |5730794|gb|AAD48683.1|AF120839__1,
|5730793|gb|AAD48682.1|AF120838__1, |5730792|gb|AAD48681.1|AF120837__1,
|5730791|gb|AAD48680.1|AF120836__1, |5730790|gb|AAD48679.1|AF120835__1,
|5730789|gb|AAD48678.1|AF120834__1, |5730788|gb|AAD48677.1|AF120833__1,
|5730787|gb|AAD48676.1|AF120832__1, |5730786|gb|AAD48675.1|AF120831__1,
|5730785|gb|AAD48674.1|AF120830__1, |5730784|gb|AAD48673.1|AF120829__1,
|5730783|gb|AAD48672.1|AF120828__1, |5730782|gb|AAD48671.1|AF120827__1,
|5730781|gb|AAD48670.1|AF120826__1, |5730780|gb|AAD48669.1|AF120825__1,
|5730779|gb|AAD48668.1|AF120822__1, |5730778|gb|AAD48667.1|AF120821__1,
|5730777|gb|AAD48666.1|AF120818__1, |5730776|gb|AAD48665.1|AF120817__1,
|5730775|gb|AAD48664.1|AF120815__1, |5730774|gb|AAD48663.1|AF120814__1,
|5730773|gb|AAD48662.1|AF120811__1, |5730772|gb|AAD48661.1|AF120810__1,
|5730771|gb|AAD48660.1|AF120809__1, |5730770|gb|AAD48659.1|AF120808__1,
|5730769|gb|AAD48658.1|AF120806__1, |5730768|gb|AAD48657.1|AF120805__1,
|5730767|gb|AAD48656.1|AF120804__1, |5730766|gb|AAD48655.1|AF120803__1,
|5730765|gb|AAD48654.1|AF120802__1, |5730764|gb|AAD48653.1|AF120801__1,
|5730763|gb|AAD48652.1|AF120800__1, |5730762|gb|AAD48651.1|AF120799__1,
|5730761|gb|AAD48650.1|AF120798__1, |5730760|gb|AAD48649.1|AF120797__1,
|5730759|gb|AAD48648.1|AF120796__1, |5730758|gb|AAD48647.1|AF120795__1,

| VPR proteins |
|---|
| |5730757|gb|AAD48646.1|AF120794_1, |5730756|gb|AAD48645.1|AF120793_1, |5730755|gb|AAD48644.1|AF120792_1, |5730754|gb|AAD48643.1|AF120790_1, |5730753|gb|AAD48642.1|AF120789_1, |5730752|gb|AAD48641.1|AF120787_1, |5730751|gb|AAD48640.1|AF120786_1, |5730750|gb|AAD48639.1|AF120785_1, |5730749|gb|AAD48638.1|AF120778_1, |5730748|gb|AAD48637.1|AF120777_1, |5730747|gb|AAD48636.1|AF120776_1, |5730746|gb|AAD48635.1|AF120774_1, |5730745|gb|AAD48634.1|AF120773_1, |5730744|gb|AAD48633.1|AF120772_1, |5730743|gb|AAD48632.1|AF120771_1, |5730742|gb|AAD48631.1|AF120770_1, |5730741|gb|AAD48630.1|AF120769_1, |5730740|gb|AAD48629.1|AF120768_1, |5730739|gb|AAD48628.1|AF120767_1, |5730738|gb|AAD48627.1|AF120766_1, |5730737|gb|AAD48626.1|AF120761_1, |5730736|gb|AAD48625.1|AF120752_1, |5730735|gb|AAD48624.1|AF120751_1, |5730734|gb|AAD48623.1|AF120749_1, |5730733|gb|AAD48622.1|AF120747_1, |5730732|gb|AAD48621.1|AF120746_1, |5730731|gb|AAD48620.1|AF120745_1, |6016896|dbj|BAA85233.1|, |82307835|sp|Q9WP20|Q9WP20_9HIV1, |82307834|sp|Q9WP19|Q9WP19_9HIV1, |82307833|sp|Q9WP18|Q9WP18_9HIV1, |82307832|sp|Q9WP17|Q9WP17_9HIV1, |82307831|sp|Q9WP16|Q9WP16_9HIV1, |82307830|sp|Q9WP15|Q9WP15_9HIV1, |82307829|sp|Q9WP14|Q9WP14_9HIV1, |82307828|sp|Q9WP13|Q9WP13_9HIV1, |82307827|sp|Q9WP12|Q9WP12_9HIV1, |82307826|sp|Q9WP11|Q9WP11_9HIV1, |82306990|sp|Q9QRL7|Q9QRL7_9HIV1, |82306989|sp|Q9QRL6|Q9QRL6_9HIV1, |82306988|sp|Q9QRL5|Q9QRL5_9HIV1, |82306987|sp|Q9QRL4|Q9QRL4_9HIV1, |82306986|sp|Q9QRL3|Q9QRL3_9HIV1, |82306985|sp|Q9QRL2|Q9QRL2_9HIV1, |82306984|sp|Q9QRL1|Q9QRL1_9HIV1, |82306983|sp|Q9QRL0|Q9QRL0_9HIV1, |82306982|sp|Q9QRK9|Q9QRK9_9HIV1, |82306981|sp|Q9QRK8|Q9QRK8_9HIV1, |82306980|sp|Q9QRK7|Q9QRK7_9HIV1, |82306979|sp|Q9QRK6|Q9QRK6_9HIV1, |82306978|sp|Q9QRK5|Q9QRK5_9HIV1, |82306977|sp|Q9QRK4|Q9QRK4_9HIV1, |82306976|sp|Q9QRK3|Q9QRK3_9HIV1, |82306975|sp|Q9QRK2|Q9QRK2_9HIV1, |82306974|sp|Q9QRK1|Q9QRK1_9HIV1, |82306973|sp|Q9QRK0|Q9QRK0_9HIV1, |82306972|sp|Q9QRJ9|Q9QRJ9_9HIV1, |82306971|sp|Q9QRJ8|Q9QRJ8_9HIV1, |82306970|sp|Q9QRJ7|Q9QRJ7_9HIV1, |82306969|sp|Q9QRJ6|Q9QRJ6_9HIV1, |82306968|sp|Q9QRJ5|Q9QRJ5_9HIV1, |82306967|sp|Q9QRJ4|Q9QRJ4_9HIV1, |82306966|sp|Q9QRJ3|Q9QRJ3_9HIV1, |82306965|sp|Q9QRJ2|Q9QRJ2_9HIV1, |82306964|sp|Q9QRJ1|Q9QRJ1_9HIV1, |82306963|sp|Q9QRJ0|Q9QRJ0_9HIV1, |82306962|sp|Q9QRI9|Q9QRI9_9HIV1, |82306961|sp|Q9QRI8|Q9QRI8_9HIV1, |82306960|sp|Q9QRI7|Q9QRI7_9HIV1, |82306959|sp|Q9QRI6|Q9QRI6_9HIV1, |82306958|sp|Q9QRI5|Q9QRI5_9HIV1, |82306957|sp|Q9QRI4|Q9QRI4_9HIV1, |82306956|sp|Q9QRI3|Q9QRI3_9HIV1, |82306955|sp|Q9QRI2|Q9QRI2_9HIV1, |82306954|sp|Q9QRI1|Q9QRI1_9HIV1, |82306953|sp|Q9QRI0|Q9QRI0_9HIV1, |82306952|sp|Q9QRH9|Q9QRH9_9HIV1, |82306951|sp|Q9QRH8|Q9QRH8_9HIV1, |82306950|sp|Q9QRH7|Q9QRH7_9HIV1, |82306949|sp|Q9QRH6|Q9QRH6_9HIV1, |82306948|sp|Q9QRH5|Q9QRH5_9HIV1, |82306947|sp|Q9QRH4|Q9QRH4_9HIV1, |82306946|sp|Q9QRH3|Q9QRH3_9HIV1, |82306945|sp|Q9QRH2|Q9QRH2_9HIV1, |82306944|sp|Q9QRH1|Q9QRH1_9HIV1, |82306943|sp|Q9QRH0|Q9QRH0_9HIV1, |82306942|sp|Q9QRG9|Q9QRG9_9HIV1, |82306941|sp|Q9QRG8|Q9QRG8_9HIV1, |82306940|sp|Q9QRG7|Q9QRG7_9HIV1, |82306939|sp|Q9QRG6|Q9QRG6_9HIV1, |82306938|sp|Q9QRG5|Q9QRG5_9HIV1, |82306937|sp|Q9QRG4|Q9QRG4_9HIV1, |82306936|sp|Q9QRG3|Q9QRG3_9HIV1, |82306935|sp|Q9QRG2|Q9QRG2_9HIV1, |82306934|sp|Q9QRG1|Q9QRG1_9HIV1, |82306933|sp|Q9QRG0|Q9QRG0_9HIV1, |82306932|sp|Q9QRF9|Q9QRF9_9HIV1, |82306931|sp|Q9QRF8|Q9QRF8_9HIV1, |82306930|sp|Q9QRF7|Q9QRF7_9HIV1, |82306929|sp|Q9QRF6|Q9QRF6_9HIV1, |82306928|sp|Q9QRF5|Q9QRF5_9HIV1, |82306927|sp|Q9QRF4|Q9QRF4_9HIV1, |82306926|sp|Q9QRF3|Q9QRF3_9HIV1, |82306925|sp|Q9QRF2|Q9QRF2_9HIV1, |82306924|sp|Q9QRF1|Q9QRF1_9HIV1, |82306923|sp|Q9QRF0|Q9QRF0_9HIV1, |82306922|sp|Q9QRE9|Q9QRE9_9HIV1, |82306921|sp|Q9QRE8|Q9QRE8_9HIV1, |82306920|sp|Q9QRE7|Q9QRE7_9HIV1, |82306919|sp|Q9QRE6|Q9QRE6_9HIV1, |82306918|sp|Q9QRE5|Q9QRE5_9HIV1, |82306917|sp|Q9QRE4|Q9QRE4_9HIV1, |82306916|sp|Q9QRE3|Q9QRE3_9HIV1, |82306915|sp|Q9QRE2|Q9QRE2_9HIV1, |82306914|sp|Q9QRE1|Q9QRE1_9HIV1, |82306913|sp|Q9QRE0|Q9QRE0_9HIV1, |82306912|sp|Q9QRD9|Q9QRD9_9HIV1, |82306911|sp|Q9QRD8|Q9QRD8_9HIV1, |82306910|sp|Q9QRD7|Q9QRD7_9HIV1, |82306909|sp|Q9QRD6|Q9QRD6_9HIV1, |82306908|sp|Q9QRD5|Q9QRD5_9HIV1, |82306907|sp|Q9QRD4|Q9QRD4_9HIV1, |82306906|sp|Q9QRD3|Q9QRD3_9HIV1, |82306905|sp|Q9QRD2|Q9QRD2_9HIV1, |82306904|sp|Q9QRD1|Q9QRD1_9HIV1, |82306903|sp|Q9QRD0|Q9QRD0_9HIV1, |82306902|sp|Q9QRC9|Q9QRC9_9HIV1, |82306901|sp|Q9QRC8|Q9QRC8_9HIV1, |82306900|sp|Q9QRC7|Q9QRC7_9HIV1, |82305574|sp|Q9PXA5|Q9PXA5_9HIV1, |82305573|sp|Q9PX97|Q9PX97_9HIV1, |82305572|sp|Q9PX78|Q9PX78_9HIV1, |82305570|sp|Q9PX56|Q9PX56_9HIV1, |82305569|sp|Q9PX55|Q9PX55_9HIV1, |82305568|sp|Q9PX48|Q9PX48_9HIV1, |82305562|sp|Q9PX09|Q9PX09_9HIV1, |82305561|sp|Q9PX04|Q9PX04_9HIV1, |82305557|sp|Q9PWZ7|Q9PWZ7_9HIV1, |82305556|sp|Q9PWZ6|Q9PWZ6_9HIV1, |82305552|sp|Q9PWW5|Q9PWW5_9HIV1, |82305551|sp|Q9PWW2|Q9PWW2_9HIV1, |82305550|sp|Q9PWW0|Q9PWW0_9HIV1, |82305549|sp|Q9PWV8|Q9PWV8_9HIV1, |82305548|sp|Q9PWV2|Q9PWV2_9HIV1, |82305547|sp|Q9PWT7|Q9PWT7_9HIV1, |82306540|sp|Q9QN90|Q9QN90_9HIV1, |8218034|emb|CAB92794.1|, |3252975|gb|AAD12122.1| elongated, |7416196|dbj|BAA93749.1|, |7416180|dbj|BAA93741.1|, |7416170|dbj|BAA93736.1|, |7416150|dbj|BAA93726.1|, |1688184|gb|AAB51054.1|, |1688180|gb|AAB51052.1|, |7416242|dbj|BAA93772.1|, |

| VPR proteins |
| --- |
| |7416240|dbj|BAA93771.1|, |7416238|dbj|BAA93770.1|, |7416236|dbj|BAA93769.1|, |7416234|dbj|BAA93768.1|, |7416232|dbj|BAA93767.1|, |7416230|dbj|BAA93766.1|, |7416228|dbj|BAA93765.1|, |7416226|dbj|BAA93764.1|, |7416224|dbj|BAA93763.1|, |7416222|dbj|BAA93762.1|, |7416220|dbj|BAA93761.1|, |7416218|dbj|BAA93760.1|, |7416216|dbj|BAA93759.1|, |7416214|dbj|BAA93758.1|, |7416212|dbj|BAA93757.1|, |7416210|dbj|BAA93756.1|, |7416208|dbj|BAA93755.1|, |7416206|dbj|BAA93754.1|, |7416204|dbj|BAA93753.1|, |7416202|dbj|BAA93752.1|, |7416200|dbj|BAA93751.1|, |7416198|dbj|BAA93750.1|, |7416194|dbj|BAA93748.1|, |7416192|dbj|BAA93747.1|, |7416190|dbj|BAA93746.1|, |7416188|dbj|BAA93745.1|, |7416186|dbj|BAA93744.1|, |7416184|dbj|BAA93743.1|, |7416182|dbj|BAA93742.1|, |7416178|dbj|BAA93740.1|, |7416176|dbj|BAA93739.1|, |7416174|dbj|BAA93738.1|, |7416172|dbj|BAA93737.1|, |7416168|dbj|BAA93735.1|, |7416166|dbj|BAA93734.1|, |7416164|dbj|BAA93733.1|, |7416162|dbj|BAA93732.1|, |7416160|dbj|BAA93731.1|, |7416158|dbj|BAA93730.1|, |7416156|dbj|BAA93729.1|, |7416154|dbj|BAA93728.1|, |7416152|dbj|BAA93727.1|, |7416148|dbj|BAA93725.1|, |7416146|dbj|BAA93724.1|, |7416144|dbj|BAA93723.1|, |7416142|dbj|BAA93722.1|, |7416140|dbj|BAA93721.1|, |1055038|gb|AAA81044.1|, |6382034|dbj|BAA86687.1|, |6382032|dbj|BAA86661.1|, |6362012|dbj|BAA86690.1|, |6362006|dbj|BAA86689.1|, |6362000|dbj|BAA86688.1|, |6361979|dbj|BAA86686.1|, |6361973|dbj|BAA86685.1|, |6361967|dbj|BAA86684.1|, |6361962|dbj|BAA86683.1|, |6361957|dbj|BAA86682.1|, |6361951|dbj|BAA86681.1|, |6361945|dbj|BAA86680.1|, |6361940|dbj|BAA86679.1|, |6361934|dbj|BAA86678.1|, |6361928|dbj|BAA86677.1|, |6361922|dbj|BAA86676.1|, |6361916|dbj|BAA86675.1|, |6361910|dbj|BAA86674.1|, |6361904|dbj|BAA86673.1|, |6361898|dbj|BAA86672.1|, |6361892|dbj|BAA86671.1|, |6361886|dbj|BAA86670.1|, |6361880|dbj|BAA86669.1|, |6361871|dbj|BAA86668.1|, |6361865|dbj|BAA86667.1|, |6361859|dbj|BAA86666.1|, |6361853|dbj|BAA86665.1|, |6361848|dbj|BAA86664.1|, |6361842|dbj|BAA86663.1|, |6361837|dbj|BAA86662.1|, |6361801|dbj|BAA86660.1|, |6361795|dbj|BAA86659.1|, |4868331|gb|AAD31265.1|, |4868329|gb|AAD31264.1|, |4868327|gb|AAD31263.1|, |4868325|gb|AAD31262.1|, |4868323|gb|AAD31261.1|, |4868321|gb|AAD31260.1|, |4868319|gb|AAD31259.1|, |4868317|gb|AAD31258.1|, |4868315|gb|AAD31257.1|, |4868313|gb|AAD31256.1|, |4868311|gb|AAD31255.1|, |4868309|gb|AAD31254.1|, |4868307|gb|AAD31253.1|, |4868305|gb|AAD31252.1|, |4868303|gb|AAD31251.1|, |4868301|gb|AAD31250.1|, |4868299|gb|AAD31249.1|, |4868297|gb|AAD31248.1|, |4868295|gb|AAD31247.1|, |4868293|gb|AAD31246.1|, |4868291|gb|AAD31245.1|, |4868289|gb|AAD31244.1|, |4868287|gb|AAD31243.1|, |4868285|gb|AAD31242.1|, |4868283|gb|AAD31241.1|, |4868281|gb|AAD31240.1|, |4868279|gb|AAD31239.1|, |4868277|gb|AAD31238.1|, |4868275|gb|AAD31237.1|, |4868273|gb|AAD31236.1|, |4868271|gb|AAD31235.1|, |4868269|gb|AAD31234.1|, |4868267|gb|AAD31233.1|, |4868265|gb|AAD31232.1|, |4868263|gb|AAD31231.1|, |4868261|gb|AAD31230.1|, |4868259|gb|AAD31229.1|, |4868257|gb|AAD31228.1|, |4868255|gb|AAD31227.1|, |4868253|gb|AAD31226.1|, |4868251|gb|AAD31225.1|, |4868249|gb|AAD31224.1|, |4868247|gb|AAD31223.1|, |4868245|gb|AAD31222.1|, |4868243|gb|AAD31221.1|, |4868241|gb|AAD31220.1|, |4868239|gb|AAD31219.1|, |4868237|gb|AAD31218.1|, |4868235|gb|AAD31217.1|, |4868233|gb|AAD31216.1|, |4868231|gb|AAD31215.1|, |4868229|gb|AAD31214.1|, |4868227|gb|AAD31213.1|, |4868225|gb|AAD31212.1|, |4868223|gb|AAD31211.1|, |4868221|gb|AAD31210.1|, |4868219|gb|AAD31209.1|, |4868217|gb|AAD31208.1|, |4868215|gb|AAD31207.1|, |4868213|gb|AAD31206.1|, |4868211|gb|AAD31205.1|, |4868209|gb|AAD31204.1|, |4868207|gb|AAD31203.1|, |2745747|gb|AAC97531.1|, |3193280|gb|AAD03333.1|, |3193271|gb|AAD03325.1|, |1890692|gb|AAC97549.1|, |2351785|gb|AAC59272.1|, |3378130|gb|AAC28453.1|, |23394686|gb|AAN31556.1|, |23394684|gb|AAN31555.1|, |23394682|gb|AAN31554.1|, |23394680|gb|AAN31553.1|, |23394678|gb|AAN31552.1|, |23394676|gb|AAN31551.1|, |23394674|gb|AAN31550.1|, |23394672|gb|AAN31549.1|, |23394669|gb|AAN31548.1|, |23394667|gb|AAN31547.1|, |23394665|gb|AAN31546.1|, |23394663|gb|AAN31545.1|, |23394661|gb|AAN31544.1|, |23394659|gb|AAN31543.1|, |23394657|gb|AAN31542.1|, |23394655|gb|AAN31541.1|, |23394652|gb|AAN31540.1|, |23394650|gb|AAN31539.1|, |23394648|gb|AAN31538.1|, |23394646|gb|AAN31537.1|, |23394644|gb|AAN31536.1|, |23394642|gb|AAN31535.1|, |23394640|gb|AAN31534.1|, |23394638|gb|AAN31533.1|, |23394635|gb|AAN31532.1|, |23394633|gb|AAN31531.1|, |23394631|gb|AAN31530.1|, |23394629|gb|AAN31529.1|, |23394627|gb|AAN31528.1|, |23394625|gb|AAN31527.1|, |23394623|gb|AAN31526.1|, |17046926|gb|AAL34926.1|, |17046916|gb|AAL34917.1|, |17046906|gb|AAL34908.1|, |17046896|gb|AAL34899.1|, |17046886|gb|AAL34890.1|, |17046876|gb|AAL34881.1|, |17046866|gb|AAL34872.1|, |17046856|gb|AAL34863.1|, |17046846|gb|AAL34854.1|, |17046836|gb|AAL34845.1|, |17046830|gb|AAL34840.1|, |17046820|gb|AAL34831.1|, |17046810|gb|AAL34822.1|, |17046800|gb|AAL34813.1|, |17046790|gb|AAL34804.1|, |17046780|gb|AAL34795.1|, |17046770|gb|AAL34786.1|, |17046760|gb|AAL34777.1|, |17046750|gb|AAL34768.1|, |17046739|gb|AAL34758.1|, |17046730|gb|AAL34750.1|, |17046720|gb|AAL34741.1|, |17046710|gb|AAL34732.1|, |17046700|gb|AAL34723.1|, |17046690|gb|AAL34714.1|, |17046680|gb|AAL34705.1|, |17046670|gb|AAL34696.1|, |17046660|gb|AAL34687.1|, |17046650|gb|AAL34678.1|, |17046640|gb|AAL34669.1|, |17046630|gb|AAL34660.1|, |17046620|gb|AAL34651.1|, |17046610|gb|AAL34642.1|, |17046600|gb|AAL34633.1|, |17046590|gb|AAL34624.1|, |17046580|gb|AAL34615.1|, |17046570|gb|AAL34606.1|, |17046560|gb|AAL34597.1|, |17046550|gb|AAL34588.1|, |17046540|gb|AAL34579.1|, |17046530|gb|AAL34570.1|, |17046520|gb|AAL34561.1|, |14209306|dbj|BAB55915.1|, |15788303|gb|AAL07750.1|, |15788293|gb|AAL07741.1|, |15788283|gb|AAL07732.1|, |15788273|gb|AAL07723.1|, |15788263|gb|AAL07714.1|, |15788253|gb|AAL07705.1|, |15788244|gb|AAL07697.1|, |15787966|gb|AAL07556.1|, |

| VPR proteins |
| --- |
| \|18201637\|gb\|AAL65389.1\|, \|18201635\|gb\|AAL65388.1\|, \|18201633\|gb\|AAL65387.1\|, \|18201631\|gb\|AAL65386.1\|, \|18201629\|gb\|AAL65385.1\|, \|18201627\|gb\|AAL65384.1\|, \|18201625\|gb\|AAL65383.1\|, \|18201623\|gb\|AAL65382.1\|, \|18201621\|gb\|AAL65381.1\|, \|18201619\|gb\|AAL65380.1\|, \|18201617\|gb\|AAL65379.1\|, \|18201615\|gb\|AAL65378.1\|, \|18201613\|gb\|AAL65377.1\|, \|18201611\|gb\|AAL65376.1\|, \|18201609\|gb\|AAL65375.1\|, \|18201607\|gb\|AAL65374.1\|, \|18201605\|gb\|AAL65373.1\|, \|18201601\|gb\|AAL65371.1\|, \|18201599\|gb\|AAL65370.1\|, \|18201597\|gb\|AAL65369.1\|, \|18201589\|gb\|AAL65365.1\|, \|18201587\|gb\|AAL65364.1\|, \|18201585\|gb\|AAL65363.1\|, \|18201573\|gb\|AAL65357.1\|, \|18201571\|gb\|AAL65356.1\|truncated, \|18201569\|gb\|AAL65355.1\|, \|18201567\|gb\|AAL65354.1\|truncated, \|18201565\|gb\|AAL65353.1\|, \|18201563\|gb\|AAL65352.1\|, \|18201561\|gb\|AAL65351.1\|, \|18201547\|gb\|AAL65344.1\|, \|18201545\|gb\|AAL65343.1\|, \|18201541\|gb\|AAL65341.1\|, \|18201539\|gb\|AAL65340.1\|, \|18201537\|gb\|AAL65339.1\|, \|18201535\|gb\|AAL65338.1\|, \|18201533\|gb\|AAL65337.1\|, \|18201531\|gb\|AAL65336.1\|truncated, \|18201529\|gb\|AAL65335.1\|, \|18201527\|gb\|AAL65334.1\|, \|18201525\|gb\|AAL65333.1\|, \|18201523\|gb\|AAL65332.1\|, \|18201515\|gb\|AAL65328.1\|, \|18201511\|gb\|AAL65326.1\|, \|18201509\|gb\|AAL65325.1\|truncated, \|18201507\|gb\|AAL65324.1\|, \|18201501\|gb\|AAL65321.1\|, \|18201495\|gb\|AAL65318.1\|, \|18201493\|gb\|AAL65317.1\|, \|18201491\|gb\|AAL65316.1\|, \|18201489\|gb\|AAL65315.1\|, \|18201487\|gb\|AAL65314.1\|, \|18201485\|gb\|AAL65313.1\|, \|18201483\|gb\|AAL65312.1\|, \|18201481\|gb\|AAL65311.1\|, \|18201479\|gb\|AAL65310.1\|, \|18201477\|gb\|AAL65309.1\|, \|18201475\|gb\|AAL65308.1\|, \|18201473\|gb\|AAL65307.1\|, \|18201471\|gb\|AAL65306.1\|, \|18201469\|gb\|AAL65305.1\|, \|18201467\|gb\|AAL65304.1\|, \|18201465\|gb\|AAL65303.1\|, \|18201463\|gb\|AAL65302.1\|, \|18201461\|gb\|AAL65301.1\|, \|18201459\|gb\|AAL65300.1\|, \|18201457\|gb\|AAL65299.1\|, \|18201455\|gb\|AAL65298.1\|, \|18201453\|gb\|AAL65297.1\|, \|18201451\|gb\|AAL65296.1\|, \|18201449\|gb\|AAL65295.1\|, \|18201447\|gb\|AAL65294.1\|, \|18201445\|gb\|AAL65293.1\|, \|3549113\|gb\|AAC34564.1\|, \|3549109\|gb\|AAC34562.1\|, \|3549107\|gb\|AAC34561.1\|, \|3549055\|gb\|AAC34535.1\|, \|3549049\|gb\|AAC34532.1\|, \|3549043\|gb\|AAC34529.1\|, \|3549037\|gb\|AAC34526.1\|, \|3549033\|gb\|AAC34524.1\|, \|3549031\|gb\|AAC34523.1\|, \|3549029\|gb\|AAC34522.1\|, \|3549027\|gb\|AAC34521.1\|, \|6063087\|gb\|AAF03127.1\|, \|6063086\|gb\|AAF03126.1\|, \|6063085\|gb\|AAF03125.1\|, \|6063084\|gb\|AAF03124.1\|, \|6063083\|gb\|AAF03123.1\|, \|6063082\|gb\|AAF03122.1\|, \|6063081\|gb\|AAF03121.1\|, \|6063080\|gb\|AAF03120.1\|, \|6063079\|gb\|AAF03119.1\|, \|6063078\|gb\|AAF03118.1\|, \|6063077\|gb\|AAF03117.1\|, \|6063076\|gb\|AAF03116.1\|, \|6063075\|gb\|AAF03115.1\|, \|6063074\|gb\|AAF03114.1\|, \|6063073\|gb\|AAF03113.1\|, \|6063072\|gb\|AAF03112.1\|, \|6063071\|gb\|AAF03111.1\|, \|6063070\|gb\|AAF03110.1\|, \|6063069\|gb\|AAF03109.1\|, \|6063068\|gb\|AAF03108.1\|, \|6063067\|gb\|AAF03107.1\|, \|6063066\|gb\|AAF03106.1\|, \|6063065\|gb\|AAF03105.1\|, \|6063064\|gb\|AAF03104.1\|, \|6063063\|gb\|AAF03103.1\|, \|6063062\|gb\|AAF03102.1\|, \|3549017\|gb\|AAC34516.1\|, \|3549013\|gb\|AAC34514.1\|, \|3549009\|gb\|AAC34512.1\|, \|3549007\|gb\|AAC34511.1\|, \|3549005\|gb\|AAC34510.1\|, \|3549003\|gb\|AAC34509.1\|, \|3548995\|gb\|AAC34505.1\|, \|3548992\|gb\|AAC34504.1\|, \|3548988\|gb\|AAC34502.1\|, \|3548982\|gb\|AAC34499.1\|, \|3548980\|gb\|AAC34498.1\|, \|5805267\|gb\|AAD51916.1\|, \|15407118\|gb\|AAG15585.1\|truncated, \|15407116\|gb\|AAG15584.1\|truncated, \|15407114\|gb\|AAG15583.1\|truncated, \|15128166\|gb\|AAK84407.1\|AF397201__1, \|15128164\|gb\|AAK84406.1\|AF397200__1, \|1688178\|gb\|AAB51051.1\|, \|1688176\|gb\|AAB51050.1\|, \|1688174\|gb\|AAB51049.1\|, \|1688172\|gb\|AAB51048.1\|, \|1688170\|gb\|AAB51047.1\|, \|1688168\|gb\|AAB51046.1\|, \|1688166\|gb\|AAB51045.1\|, \|1688164\|gb\|AAB51044.1\|, \|1688162\|gb\|AAB51043.1\|, \|13172882\|gb\|AAK14230.1\|, \|13540188\|gb\|AAK29354.1\|, \|13540178\|gb\|AAK29345.1\|, \|13540168\|gb\|AAK29336.1\|, \|12004923\|gb\|AAG44234.1\|, \|12004919\|gb\|AAG44233.1\|, \|12004917\|gb\|AAG44232.1\|, \|12004915\|gb\|AAG44231.1\|, \|12004913\|gb\|AAG44230.1\|truncated, \|12004911\|gb\|AAG44229.1\|, \|12004909\|gb\|AAG44228.1\|truncated, \|12004907\|gb\|AAG44227.1\|truncated, \|12004905\|gb\|AAG44226.1\|, \|12004903\|gb\|AAG44225.1\|, \|12004901\|gb\|AAG44224.1\|, \|12004899\|gb\|AAG44223.1\|, \|12004897\|gb\|AAG44222.1\|, \|12004895\|gb\|AAG44221.1\|, \|12004893\|gb\|AAG44220.1\|, \|12004889\|gb\|AAG44218.1\|, \|12004887\|gb\|AAG44217.1\|, \|12004885\|gb\|AAG44216.1\|, \|12004883\|gb\|AAG44215.1\|, \|12004881\|gb\|AAG44214.1\|, \|12004879\|gb\|AAG44213.1\|, \|12004877\|gb\|AAG44212.1\|, \|12004875\|gb\|AAG44211.1\|, \|12004873\|gb\|AAG44210.1\|, \|12004871\|gb\|AAG44209.1\|, \|12004869\|gb\|AAG44208.1\|, \|12004867\|gb\|AAG44207.1\|, \|12004859\|gb\|AAG44206.1\|, \|12004857\|gb\|AAG44205.1\|, \|12004855\|gb\|AAG44204.1\|, \|12004853\|gb\|AAG44203.1\|, \|12004851\|gb\|AAG44202.1\|truncated, \|12004849\|gb\|AAG44201.1\|truncated, \|12004847\|gb\|AAG44200.1\|truncated, \|12004845\|gb\|AAG44199.1\|truncated, \|12004841\|gb\|AAG44197.1\|truncated, \|12004835\|gb\|AAG44194.1\|truncated, \|12004829\|gb\|AAG44191.1\|, \|12004825\|gb\|AAG44189.1\|, \|12004823\|gb\|AAG44188.1\|, \|12004821\|gb\|AAG44187.1\|, \|12004819\|gb\|AAG44186.1\|, \|12004815\|gb\|AAG44184.1\|truncated, \|12004813\|gb\|AAG44183.1\|truncated, \|12004811\|gb\|AAG44182.1\|truncated, \|12004809\|gb\|AAG44181.1\|, \|12004807\|gb\|AAG44180.1\|, \|12004805\|gb\|AAG44179.1\|, \|12004803\|gb\|AAG44178.1\|truncated, \|12004801\|gb\|AAG44177.1\|, \|12004799\|gb\|AAG44176.1\|truncated, \|12004797\|gb\|AAG44175.1\|, \|12004795\|gb\|AAG44174.1\|, \|12004793\|gb\|AAG44173.1\|, \|12004791\|gb\|AAG44172.1\|, \|12004789\|gb\|AAG44171.1\|, \|12004787\|gb\|AAG44170.1\|, \|12004785\|gb\|AAG44169.1\|, \|12004783\|gb\|AAG44168.1\|, \|12004781\|gb\|AAG44167.1\|truncated, \|12004779\|gb\|AAG44166.1\|, \|12004773\|gb\|AAG44163.1\|, \|12004771\|gb\|AAG44162.1\|, \|12004769\|gb\|AAG44161.1\|, \|12004767\|gb\|AAG44160.1\|, \|12004765\|gb\|AAG44159.1\|, \|12004762\|gb\|AAG44158.1\|, \|12004760\|gb\|AAG44157.1\|, \|12004758\|gb\|AAG44156.1\|, |

| VPR proteins |
| --- |
| |12004751|gb|AAG44155.1|, |12004749|gb|AAG44154.1|, |12004747|gb|AAG44153.1|, |12004745|gb|AAG44152.1|, |12004743|gb|AAG44151.1|, |12004741|gb|AAG44150.1|, |12004739|gb|AAG44149.1|, |12004737|gb|AAG44148.1|, |12004735|gb|AAG44147.1|, |12004733|gb|AAG44146.1|, |12004731|gb|AAG44145.1|, |12004729|gb|AAG44144.1|, |12004726|gb|AAG44143.1|, |12004724|gb|AAG44142.1|, |12004722|gb|AAG44141.1|, |12004720|gb|AAG44140.1|, |12004718|gb|AAG44139.1|, |12004716|gb|AAG44138.1|, |12004708|gb|AAG44137.1|, |11761606|gb|AAG38934.1|, |11761596|gb|AAG38925.1|, |11761586|gb|AAG38916.1|, |11761576|gb|AAG38907.1|, |11761566|gb|AAG38898.1|, |11345187|gb|AAG34634.1|, |11345185|gb|AAG34633.1|, |11345183|gb|AAG34632.1|, |11345181|gb|AAG34631.1|, |11345179|gb|AAG34630.1|, |11345177|gb|AAG34629.1|, |11345175|gb|AAG34628.1|, |11345173|gb|AAG34627.1|, |11345171|gb|AAG34626.1|, |11345169|gb|AAG34625.1|, |11345167|gb|AAG34624.1|, |11345165|gb|AAG34623.1|, |11345163|gb|AAG34622.1|, |11345161|gb|AAG34621.1|, |11345159|gb|AAG34620.1|, |11345157|gb|AAG34619.1|, |11345155|gb|AAG34618.1|, |11345153|gb|AAG34617.1|, |11345151|gb|AAG34616.1|, |11345149|gb|AAG34615.1|, |11345147|gb|AAG34614.1|, |11345145|gb|AAG34613.1|, |11345143|gb|AAG34612.1|, |11345141|gb|AAG34611.1|, |11345139|gb|AAG34610.1|, |11345137|gb|AAG34609.1|, |11345135|gb|AAG34608.1|, |11345133|gb|AAG34607.1|, |11345131|gb|AAG34606.1|, |11345129|gb|AAG34605.1|, |11345127|gb|AAG34604.1|, |11345125|gb|AAG34603.1|, |11345123|gb|AAG34602.1|, |11345121|gb|AAG34601.1|, |11345119|gb|AAG34600.1|, |11345117|gb|AAG34599.1|, |11345115|gb|AAG34598.1|, |11345113|gb|AAG34597.1|, |11345111|gb|AAG34596.1|, |11345109|gb|AAG34595.1|, |11345107|gb|AAG34594.1|, |11345105|gb|AAG34593.1|, |11345103|gb|AAG34592.1|, |11345101|gb|AAG34591.1|, |11345099|gb|AAG34590.1|, |11345097|gb|AAG34589.1|, |11345095|gb|AAG34588.1|, |11345093|gb|AAG34587.1|, |11345091|gb|AAG34586.1|, |11345089|gb|AAG34585.1|, |11345087|gb|AAG34584.1|, |11345085|gb|AAG34583.1|, |11345083|gb|AAG34582.1|, |11345081|gb|AAG34581.1|, |11345079|gb|AAG34580.1|, |11345077|gb|AAG34579.1|, |11345072|gb|AAG34578.1|, |11345070|gb|AAG34577.1|, |11345068|gb|AAG34576.1|, |11345066|gb|AAG34575.1|, |11345064|gb|AAG34574.1|, |11345062|gb|AAG34573.1|, |11345060|gb|AAG34572.1|, |11345058|gb|AAG34571.1|, |11345056|gb|AAG34570.1|, |11345054|gb|AAG34569.1|, |7188381|gb|AAF37747.1|, |7188379|gb|AAF37746.1|, |7188377|gb|AAF37745.1|, |7188375|gb|AAF37744.1|, |7188373|gb|AAF37743.1|, |7188371|gb|AAF37742.1|, |7188369|gb|AAF37741.1|, |7188367|gb|AAF37740.1|, |5713170|gb|AAD47831.1|AF166101_1, |3252965|gb|AAD12113.1|, |3252955|gb|AAD12104.1|, |3252945|gb|AAD12095.1|, |3252935|gb|AAD12086.1|, |3252926|gb|AAD12078.1|, |4105547|gb|AAD02461.1|, |4105545|gb|AAD02460.1|, |4105543|gb|AAD02459.1|, |4105541|gb|AAD02458.1|, |4105539|gb|AAD02457.1|, |4105537|gb|AAD02456.1|, |4105535|gb|AAD02455.1|, |4105533|gb|AAD02454.1|, |4102306|gb|AAD01472.1|, |4102304|gb|AAD01471.1|, |4102302|gb|AAD01470.1|, |4102300|gb|AAD01469.1|, |4102298|gb|AAD01468.1|, |4102296|gb|AAD01467.1|, |4102294|gb|AAD01466.1|, |4102292|gb|AAD01465.1|, |4102290|gb|AAD01464.1|, |4102288|gb|AAD01463.1|, |4102286|gb|AAD01462.1|, |4102284|gb|AAD01461.1|, |4102282|gb|AAD01460.1|, |4102280|gb|AAD01459.1|, |4102278|gb|AAD01458.1|, |4102276|gb|AAD01457.1|, |4102274|gb|AAD01456.1|, |4102272|gb|AAD01455.1|, |4102270|gb|AAD01454.1|, |4102268|gb|AAD01453.1|, |4102266|gb|AAD01452.1|, |4102264|gb|AAD01451.1|, |4102262|gb|AAD01450.1|, |4102260|gb|AAD01449.1|, |4102258|gb|AAD01448.1|, |4102256|gb|AAD01447.1|, |3947934|gb|AAC82624.1|, |3098591|gb|AAC68858.1|, |3098581|gb|AAC68849.1|, |2290188|gb|AAC58933.1|, |2290183|gb|AAC58930.1|, |2290122|gb|AAC58899.1|, |2290113|gb|AAC58894.1|, |2290108|gb|AAC58891.1|, |2290101|gb|AAC58887.1|, |2290092|gb|AAC58882.1|, |2290089|gb|AAC58880.1|, |2290074|gb|AAC58872.1|, |2290069|gb|AAC58869.1|, |2290060|gb|AAC58864.1|, |2290051|gb|AAC58859.1|, |2290046|gb|AAC58856.1|, |2290040|gb|AAC58852.1|, |2290035|gb|AAC58849.1|, |2290028|gb|AAC58845.1|, |2290021|gb|AAC58841.1|, |2290010|gb|AAC58835.1|, |2289997|gb|AAC58828.1|, |2289994|gb|AAC58826.1|, |2289985|gb|AAC58821.1|, |2289982|gb|AAC58819.1|, |1905983|gb|AAC57005.1|, |1899110|gb|AAC56993.1|, |1899104|gb|AAC56988.1|, |1899099|gb|AAC56984.1|, |3025691|gb|AAC40692.1|, |3025689|gb|AAC40691.1|, |3025687|gb|AAC40690.1|, |3025685|gb|AAC40689.1|, |3025683|gb|AAC40688.1|, |3025681|gb|AAC40687.1|, |3025679|gb|AAC40686.1|, |2992625|gb|AAC40649.1|, |2992623|gb|AAC40648.1|, |2992621|gb|AAC40647.1|, |2992619|gb|AAC40646.1|, |2992617|gb|AAC40645.1|, |2992615|gb|AAC40644.1|, |2992613|gb|AAC40643.1|, |2992611|gb|AAC40642.1|, |2992609|gb|AAC40641.1|, |2992606|gb|AAC40640.1|, |2992604|gb|AAC40639.1|, |2992602|gb|AAC40638.1|, |2992600|gb|AAC40637.1|, |2992598|gb|AAC40636.1|, |2992596|gb|AAC40635.1|, |2992594|gb|AAC40634.1|, |2992592|gb|AAC40633.1|, |2992590|gb|AAC40632.1|, |1469161|gb|AAC37975.1|, |1772633|gb|AAC32301.1|, |3403231|gb|AAC29064.1|, |3403222|gb|AAC29056.1|, |3403213|gb|AAC29048.1|, |3132819|gb|AAC29085.1|, |3132809|gb|AAC29076.1|, |3171209|gb|AAC18382.1|, |3171207|gb|AAC18381.1|, |3171205|gb|AAC18380.1|, |3171203|gb|AAC18379.1|, |3171201|gb|AAC18378.1|, |3171199|gb|AAC18377.1|, |3171197|gb|AAC18376.1|, |3171195|gb|AAC18375.1|, |3171193|gb|AAC18374.1|, |3171191|gb|AAC18373.1|, |3171189|gb|AAC18372.1|, |3171187|gb|AAC18371.1|, |3171185|gb|AAC18370.1|, |3171183|gb|AAC18369.1|, |3171181|gb|AAC18368.1|, |3171179|gb|AAC18367.1|, |3171177|gb|AAC18366.1|, |3171175|gb|AAC18365.1|, |3171173|gb|AAC18364.1|, |3171171|gb|AAC18363.1|, |3171169|gb|AAC18362.1|, |3171167|gb|AAC18361.1|, |3169624|gb|AAC17904.1|, |3169622|gb|AAC17903.1|, |3169620|gb|AAC17902.1|, |3169618|gb|AAC17901.1|, |3169616|gb|AAC17900.1|, |3169614|gb|AAC17899.1|, |3169612|gb|AAC17898.1|, |3169610|gb|AAC17897.1|, |

-continued

| VPR proteins |
|---|
| |3169608|gb|AAC17896.1|, |3169606|gb|AAC17895.1|, |3169604|gb|AAC17894.1|, |3169602|gb|AAC17893.1|, |3169599|gb|AAC17892.1|, |3169597|gb|AAC17891.1|, |3169595|gb|AAC17890.1|, |3169592|gb|AAC17889.1|, |3169590|gb|AAC17888.1|, |3169587|gb|AAC17887.1|, |3169585|gb|AAC17886.1|, |3169583|gb|AAC17885.1|, |3169581|gb|AAC17884.1|, |3169579|gb|AAC17883.1|, |3169577|gb|AAC17882.1|, |2351790|gb|AAB71220.1|, |2351779|gb|AAB71215.1|, |2351236|gb|AAB68447.1|, |1899080|gb|AAB68441.1|, |2194187|gb|AAB61125.1|, |1749847|gb|AAB42064.1|, |1749845|gb|AAB42063.1|, |23986259|gb|AAL12208.1|, |23986243|gb|AAL12199.1|, |23986229|gb|AAL12190.1|, |23986215|gb|AAL12181.1|, |1469864|gb|AAB05189.1|, |1469862|gb|AAB05178.1|, |18844745|dbj|BAB85467.1|, |18844735|dbj|BAB85458.1|, |18643018|gb|AAL74053.1|, |6694608|gb|AAF25321.1|, |6694606|gb|AAF25320.1|, |6694604|gb|AAF25319.1|, |6694602|gb|AAF25318.1|, |6694600|gb|AAF25317.1|, |6694598|gb|AAF25316.1|, |6694596|gb|AAF25315.1|, |6694594|gb|AAF25314.1|, |6694592|gb|AAF25313.1|, |6694590|gb|AAF25312.1|, |6694588|gb|AAF25311.1|, |6694586|gb|AAF25310.1|, |6694584|gb|AAF25309.1|, |6694582|gb|AAF25308.1|, |6694580|gb|AAF25307.1|, |6694578|gb|AAF25306.1|, |6694576|gb|AAF25305.1|, |6694574|gb|AAF25304.1|, |6694572|gb|AAF25303.1|, |6694570|gb|AAF25302.1|, |6694564|gb|AAF25299.1|, |6694560|gb|AAF25297.1|, |6694558|gb|AAF25296.1|, |6694556|gb|AAF25295.1|, |6694554|gb|AAF25294.1|, |6694552|gb|AAF25293.1|, |6694550|gb|AAF25292.1|, |6694548|gb|AAF25291.1|, |6694546|gb|AAF25290.1|, |6694544|gb|AAF25289.1|, |6694542|gb|AAF25288.1|, |6694540|gb|AAF25287.1|, |6694538|gb|AAF25286.1|, |6694536|gb|AAF25285.1|, |6694534|gb|AAF25284.1|, |6694532|gb|AAF25283.1|, |6694530|gb|AAF25282.1|, |6694528|gb|AAF25281.1|, |6694526|gb|AAF25280.1|, |6694524|gb|AAF25279.1|truncated, |6694522|gb|AAF25278.1|, |6694520|gb|AAF25277.1|, |6694518|gb|AAF25276.1|, |6694516|gb|AAF25275.1|, |6694514|gb|AAF25274.1|, |6694512|gb|AAF25273.1|, |6694510|gb|AAF25272.1|, |6694508|gb|AAF25271.1|, |6694506|gb|AAF25270.1|, |6694504|gb|AAF25269.1|, |6694502|gb|AAF25268.1|, |6694500|gb|AAF25267.1|, |6694498|gb|AAF25266.1|, |6694496|gb|AAF25265.1|, |6694494|gb|AAF25264.1|, |6694492|gb|AAF25263.1|, |6694490|gb|AAF25262.1|, |6694488|gb|AAF25261.1|, |6694486|gb|AAF25260.1|, |6694484|gb|AAF25259.1|, |6694482|gb|AAF25258.1|truncated, |6694480|gb|AAF25257.1|truncated, |6694478|gb|AAF25256.1|truncated, |6694476|gb|AAF25255.1|truncated, |6694474|gb|AAF25254.1|truncated, |6694472|gb|AAF25253.1|truncated, |6694470|gb|AAF25252.1|truncated, |6694468|gb|AAF25251.1|truncated, |6694466|gb|AAF25250.1|truncated, |6694464|gb|AAF25249.1|, |6694462|gb|AAF25248.1|, |6694460|gb|AAF25247.1|, |6694458|gb|AAF25246.1|, |6694456|gb|AAF25245.1|, |6694454|gb|AAF25244.1|, |6694452|gb|AAF25243.1|, |6694450|gb|AAF25242.1|, |6694448|gb|AAF25241.1|, |6694446|gb|AAF25240.1|, |6694444|gb|AAF25239.1|, |6694442|gb|AAF25238.1|, |6694440|gb|AAF25237.1|truncated, |6694438|gb|AAF25236.1|truncated, |6694436|gb|AAF25235.1|, |6694434|gb|AAF25234.1|, |6694432|gb|AAF25233.1|, |6694430|gb|AAF25232.1|, |6694428|gb|AAF25231.1|, |6694426|gb|AAF25230.1|, |10880736|gb|AAG24369.1|, |16751265|gb|AAL05340.1|, |16751255|gb|AAL05331.1|, |16751247|gb|AAL05324.1|, |16751236|gb|AAL05314.1|, |15281507|gb|AAK94289.1|AF361879_9, |15281497|gb|AAK94280.1|AF361878_9, |15281487|gb|AAK94271.1|AF361877_9, |15281478|gb|AAK94263.1|AF361876_9, |15281468|gb|AAK94254.1|AF361875_9, |15281458|gb|AAK94245.1|AF361874_9, |15281448|gb|AAK94236.1|AF361873_9, |15281438|gb|AAK94227.1|AF361872_9, |15281428|gb|AAK94218.1|AF361871_9, |14530235|gb|AAK65969.1|AF286236_9, |3002848|gb|AAD03207.1|, |3002838|gb|AAD03198.1|, |5931499|dbj|BAA84676.1|, |5931490|dbj|BAA84668.1|, |13517091|dbj|BAB40429.1|, |3779267|gb|AAD03315.1|, |14530270|gb|AAK66000.1|AF316544_9, |14530261|gb|AAK65992.1|AF286239_9, |14530253|gb|AAK65985.1|AF286238_9, |14530244|gb|AAK65977.1|AF286237_10, |13569336|gb|AAK31070.1|AF286235_9, |13569326|gb|AAK31061.1|AF286234_9, |13569316|gb|AAK31052.1|AF286233_9, |13569306|gb|AAK31043.1|AF286232_9, |13569296|gb|AAK31034.1|AF286231_9, |13569286|gb|AAK31025.1|AF286230_9, |13569276|gb|AAK31016.1|AF286229_9, |13569256|gb|AAK30998.1|AF286227_9, |13569246|gb|AAK30989.1|AF286226_9, |13569236|gb|AAK30980.1|AF286225_9, |13569226|gb|AAK30971.1|AF286224_9, |13569216|gb|AAK30962.1|AF286223_9, |11321029|gb|AAG34020.1|, |11321019|gb|AAG34011.1|, |11321009|gb|AAG34002.1|, |11320999|gb|AAG33993.1|, |11095919|gb|AAG30123.1|AF286365_9, |11066506|gb|AAG28621.1|AF259955_9, |11066496|gb|AAG28612.1|AF259954_9, |3808286|gb|AAC69312.1|, |5305362|gb|AAD41614.1|AF071474_9, |5305350|gb|AAD41604.1|AF071473_9, |3808278|gb|AAD13365.1|, |3808269|gb|AAC69305.1|, |3808259|gb|AAC69296.1|, |3808249|gb|AAC69287.1|, |6651483|gb|AAF22331.1|AF193277_4, |6651474|gb|AAF22322.1|AF193276_4, |6643032|gb|AAF20393.1|, |6651460|gb|AAF22312.1|AF193253_6, |6090973|gb|AAF03420.1|AF075703_8, |5668962|gb|AAD46106.1|AF076998_8, |5668947|gb|AAD46095.1|AF077336_9, |6910976|gb|AAF31327.1|AF146728_1|, |2944131|gb|AAC05238.1|, |5668931|gb|AAD46083.1|AF076475_9, |5668918|gb|AAD46072.1|AF076474_8, |5668888|gb|AAD46050.1|AF075701_8, |5305485|gb|AAD41673.1|AF075702_8, |5059058|gb|AAD38897.1|AF119820_9, |5059049|gb|AAD38889.1|AF119819_9, |4097723|gb|AAD00166.1|, |4097720|gb|AAD00165.1|, |2231611|gb|AAC59358.1|, |2231607|gb|AAC59356.1|, |2231604|gb|AAC59354.1|, |2231602|gb|AAC59353.1|, |2231600|gb|AAC59352.1|, |2231597|gb|AAC59350.1|, |2231595|gb|AAC59349.1|, |328651|gb|AAC32231.1|, |2281661|gb|AAB64171.1|, |14289991|gb|AAK59179.1|, |21633166|gb|AAL65476.1|, |21633164|gb|AAL65475.1|, |21633162|gb|AAL65474.1|, |21633160|gb|AAL65473.1|, |21633158|gb|AAL65472.1|, |21633156|gb|AAL65471.1|, |21633154|gb|AAL65470.1|, |

| VPR proteins |
| --- |
| |21633152|gb|AAL65469.1|, |21633150|gb|AAL65468.1|, |21633148|gb|AAL65467.1|, |21633146|gb|AAL65466.1|, |21633144|gb|AAL65465.1|, |21633142|gb|AAL65464.1|, |21633140|gb|AAL65463.1|, |21633138|gb|AAL65462.1|, |21633136|gb|AAL65461.1|, |21633134|gb|AAL65460.1|, |21633132|gb|AAL65459.1|, |21633130|gb|AAL65458.1|, |21633128|gb|AAL65457.1|, |21633126|gb|AAL65456.1|, |21633124|gb|AAL65455.1|, |21633122|gb|AAL65454.1|, |21633120|gb|AAL65453.1|, |21633118|gb|AAL65452.1|, |21633116|gb|AAL65451.1|, |21633112|gb|AAL65450.1|, |21633110|gb|AAL65580.1|, |21633108|gb|AAL65579.1|, |21633106|gb|AAL65578.1|, |21633104|gb|AAL65577.1|, |21633102|gb|AAL65576.1|, |21633100|gb|AAL65575.1|, |21633097|gb|AAL65574.1|, |21633095|gb|AAL65573.1|, |21633093|gb|AAL65572.1|, |21633091|gb|AAL65571.1|, |21633089|gb|AAL65570.1|, |21633087|gb|AAL65569.1|, |21633085|gb|AAL65568.1|, |21633083|gb|AAL65567.1|, |21633081|gb|AAL65566.1|, |21633079|gb|AAL65565.1|, |21633077|gb|AAL65564.1|, |21633074|gb|AAL65563.1|, |21633072|gb|AAL65562.1|, |21633070|gb|AAL65561.1|, |21633068|gb|AAL65560.1|, |21633065|gb|AAL65559.1|, |21633060|gb|AAL65558.1|, |21633058|gb|AAL65557.1|, |21633056|gb|AAL65556.1|, |21633054|gb|AAL65555.1|, |21633052|gb|AAL65554.1|, |21633050|gb|AAL65553.1|, |21633048|gb|AAL65552.1|, |21633046|gb|AAL65551.1|, |21633044|gb|AAL65550.1|, |21633042|gb|AAL65549.1|, |21633040|gb|AAL65548.1|, |21633038|gb|AAL65547.1|, |21633036|gb|AAL65546.1|, |21633033|gb|AAL65545.1|, |21633031|gb|AAL65544.1|, |21633029|gb|AAL65543.1|, |21633027|gb|AAL65542.1|, |21633025|gb|AAL65541.1|, |21633023|gb|AAL65540.1|, |21633021|gb|AAL65539.1|, |21633019|gb|AAL65538.1|, |21633017|gb|AAL65537.1|, |21633015|gb|AAL65536.1|, |21633013|gb|AAL65535.1|, |21633011|gb|AAL65534.1|, |21633009|gb|AAL65533.1|, |21633007|gb|AAL65532.1|, |21633005|gb|AAL65531.1|, |21633002|gb|AAL65530.1|, |21633000|gb|AAL65529.1|, |21632998|gb|AAL65528.1|, |21632996|gb|AAL65527.1|, |21632994|gb|AAL65526.1|, |21632992|gb|AAL65525.1|, |21632990|gb|AAL65524.1|, |21632988|gb|AAL65523.1|, |21632986|gb|AAL65522.1|, |21632984|gb|AAL65521.1|, |21632982|gb|AAL65520.1|, |21632980|gb|AAL65519.1|, |21632978|gb|AAL65518.1|, |21632976|gb|AAL65517.1|, |21632973|gb|AAL65516.1|, |21632971|gb|AAL65515.1|, |21632968|gb|AAL65514.1|, |21632966|gb|AAL65513.1|, |21632964|gb|AAL65512.1|, |21632961|gb|AAL65511.1|, |21632959|gb|AAL65510.1|, |21632957|gb|AAL65509.1|, |21632955|gb|AAL65508.1|, |21632953|gb|AAL65507.1|, |21632951|gb|AAL65506.1|, |21632949|gb|AAL65505.1|, |21632947|gb|AAL65504.1|, |21632945|gb|AAL65503.1|, |21632943|gb|AAL65502.1|, |21632941|gb|AAL65501.1|, |21632939|gb|AAL65500.1|, |21632937|gb|AAL65499.1|, |21632935|gb|AAL65498.1|, |21632933|gb|AAL65497.1|, |21632931|gb|AAL65496.1|, |21632929|gb|AAL65495.1|, |21632926|gb|AAL65494.1|, |21632924|gb|AAL65493.1|, |21632922|gb|AAL65492.1|, |21632920|gb|AAL65491.1|, |21632918|gb|AAL65490.1|, |21632916|gb|AAL65489.1|, |21632914|gb|AAL65488.1|, |21632912|gb|AAL65487.1|, |21632910|gb|AAL65486.1|, |21632908|gb|AAL65485.1|, |21632906|gb|AAL65484.1|, |21632904|gb|AAL65483.1|, |21632902|gb|AAL65482.1|, |21632900|gb|AAL65481.1|, |21632898|gb|AAL65480.1|, |21632896|gb|AAL65479.1|, |21632894|gb|AAL65478.1|, |21632892|gb|AAL65477.1|, |21632890|gb|AAL65449.1|, |21632888|gb|AAL65448.1|, |21632886|gb|AAL65447.1|, |21632882|gb|AAL65446.1|, |21632879|gb|AAL65445.1|, |21632877|gb|AAL65444.1|, |21632875|gb|AAL65443.1|, |21632873|gb|AAL65442.1|, |21632871|gb|AAL65441.1|, |21632869|gb|AAL65440.1|, |21632861|gb|AAL65439.1|, |21632858|gb|AAL65438.1|, |21632856|gb|AAL65437.1|, |21632854|gb|AAL65436.1|, |21632852|gb|AAL65435.1|, |21632850|gb|AAL65434.1|, |21632848|gb|AAL65433.1|, |21632846|gb|AAL65432.1|, |21632844|gb|AAL65431.1|, |21632842|gb|AAL65430.1|, |21632840|gb|AAL65429.1|, |21632838|gb|AAL65428.1|, |21632836|gb|AAL65427.1|, |21632834|gb|AAL65426.1|, |21632832|gb|AAL65425.1|, |21632830|gb|AAL65424.1|, |21632827|gb|AAL65423.1|, |21632825|gb|AAL65422.1|, |21632823|gb|AAL65421.1|, |21632821|gb|AAL65420.1|, |21632819|gb|AAL65419.1|, |21632817|gb|AAL65418.1|, |21632815|gb|AAL65417.1|, |21632813|gb|AAL65416.1|, |21632811|gb|AAL65415.1|, |21632809|gb|AAL65414.1|, |21632807|gb|AAL65413.1|, |21632805|gb|AAL65412.1|, |21632803|gb|AAL65411.1|, |21632801|gb|AAL65410.1|, |59805183|gb|AAX08137.1|, |59805181|gb|AAX08136.1|, |59805179|gb|AAX08135.1|, |59805177|gb|AAX08134.1|, |59805175|gb|AAX08133.1|, |59805173|gb|AAX08132.1|, |59805171|gb|AAX08131.1|, |59805169|gb|AAX08130.1|, |59805167|gb|AAX08129.1|, |59805165|gb|AAX08128.1|, |59805163|gb|AAX08127.1|, |59805161|gb|AAX08126.1|, |59805159|gb|AAX08125.1|, |59805157|gb|AAX08124.1|, |1401124|gb|AAC54990.1|, |1401122|gb|AAC54989.1|, |1401120|gb|AAC54988.1|, |1401118|gb|AAC54987.1|, |1401116|gb|AAC54986.1|, |1401114|gb|AAC54985.1|, |1401112|gb|AAC54984.1|, |1401110|gb|AAC54983.1|, |1401108|gb|AAC54982.1|, |1401106|gb|AAC54981.1|, |1401104|gb|AAC54980.1|, |1401102|gb|AAC54979.1|, |1401100|gb|AAC54978.1|, |1401098|gb|AAC54977.1|, |1401096|gb|AAC54976.1|, |1401094|gb|AAC54975.1|, |1401092|gb|AAC54974.1|, |1401090|gb|AAC54973.1|, |1401088|gb|AAC54972.1|, |1401086|gb|AAC54971.1|, |53690223|gb|AAU90015.1|, |53690221|gb|AAU90014.1|, |53690219|gb|AAU90013.1|, |53690217|gb|AAU90012.1|, |53690215|gb|AAU90011.1|, |53690213|gb|AAU90010.1|, |53690211|gb|AAU90009.1|, |53690209|gb|AAU90008.1|, |53690207|gb|AAU90007.1|, |53690205|gb|AAU90006.1|, |53690203|gb|AAU90005.1|, |53690201|gb|AAU90004.1|, |53690199|gb|AAU90003.1|, |53690197|gb|AAU90002.1|, |53690195|gb|AAU90001.1|, |53690193|gb|AAU90000.1|, |53690191|gb|AAU89999.1|, |53690189|gb|AAU89998.1|, |53690187|gb|AAU89997.1|, |53690185|gb|AAU89996.1|, |53690183|gb|AAU89995.1|, |53690180|gb|AAU89994.1|, |53690178|gb|AAU89993.1|, |53690176|gb|AAU89992.1|, |53690174|gb|AAU89991.1|, |53690172|gb|AAU89990.1|, |53690170|gb|AAU89989.1|, |53690168|gb|AAU89988.1|, |53690166|gb|AAU89987.1|, |53690164|gb|AAU89986.1|, |53690162|gb|AAU89985.1|, |53690160|gb|AAU89984.1|, |53690158|gb|AAU89983.1|, |

| VPR proteins |
|---|
| |78714208|gb|ABB51086.1|, |18699184|gb|AAL78445.1|AF413986_1,
|18699182|gb|AAL78444.1|AF413985_1, |18699180|gb|AAL78443.1|AF413984_1,
|18699178|gb|AAL78442.1|AF413983_1, |56783229|gb|AAW28927.1|, |56783227|gb|AAW28926.1|,
|56783225|gb|AAW28925.1|, |56783223|gb|AAW28924.1|, |56783221|gb|AAW28923.1|,
|56783219|gb|AAW28922.1|, |56783217|gb|AAW28921.1|, |56783215|gb|AAW28920.1|,
|56783213|gb|AAW28919.1|, |56783211|gb|AAW28918.1|, |56783209|gb|AAW28917.1|,
|56783207|gb|AAW28916.1|, |56783205|gb|AAW28915.1|, |56783203|gb|AAW28914.1|,
|56783201|gb|AAW28913.1|, |56783199|gb|AAW28912.1|, |56783197|gb|AAW28911.1|,
|56783195|gb|AAW28910.1|, |56783193|gb|AAW28909.1|, |56783191|gb|AAW28908.1|,
|56783189|gb|AAW28907.1|, |56783187|gb|AAW28906.1|, |56783185|gb|AAW28905.1|,
|56783183|gb|AAW28904.1|, |47779138|gb|AAT38453.1|, |47779136|gb|AAT38452.1|,
|47779134|gb|AAT38451.1|, |47779132|gb|AAT38450.1|, |47779130|gb|AAT38449.1|,
|47779128|gb|AAT38448.1|, |47779126|gb|AAT38447.1|, |47779124|gb|AAT38446.1|,
|47779122|gb|AAT38445.1|, |47779120|gb|AAT38444.1|, |47779118|gb|AAT38443.1|,
|47779116|gb|AAT38442.1|, |47779114|gb|AAT38441.1|, |47779112|gb|AAT38440.1|,
|47779110|gb|AAT38439.1|, |47779108|gb|AAT38438.1|, |47779106|gb|AAT38437.1|,
|47779104|gb|AAT38436.1|, |47779102|gb|AAT38435.1|, |47779100|gb|AAT38434.1|,
|47779098|gb|AAT38433.1|, |47779096|gb|AAT38432.1|, |47779094|gb|AAT38431.1|,
|47779092|gb|AAT38430.1|, |47779090|gb|AAT38429.1|, |47779088|gb|AAT38428.1|,
|47779086|gb|AAT38427.1|, |47779084|gb|AAT38426.1|, |47779082|gb|AAT38425.1|,
|47779080|gb|AAT38424.1|, |47779078|gb|AAT38423.1|, |47779076|gb|AAT38422.1|,
|47779074|gb|AAT38421.1|, |47779072|gb|AAT38420.1|, |47779070|gb|AAT38419.1|,
|47779068|gb|AAT38418.1|, |47779066|gb|AAT38417.1|, |47779064|gb|AAT38416.1|,
|47779062|gb|AAT38415.1|, |47779060|gb|AAT38414.1|, |47779058|gb|AAT38413.1|,
|47779056|gb|AAT38412.1|, |47779054|gb|AAT38411.1|, |22759338|gb|AAN05793.1|truncated,
|1277021|gb|AAC55008.1|, |1277019|gb|AAC55007.1|, |1277017|gb|AAC55006.1|,
|1277015|gb|AAC55005.1|, |1277013|gb|AAC55004.1|, |1277011|gb|AAC55003.1|,
|1277009|gb|AAC55002.1|, |1277007|gb|AAC55001.1|, |1277005|gb|AAC55000.1|,
|1277003|gb|AAC54999.1|, |1277001|gb|AAC54998.1|, |1276999|gb|AAC54997.1|,
|1276997|gb|AAC54996.1|, |1276995|gb|AAC54995.1|, |1276993|gb|AAC54994.1|,
|1276991|gb|AAC54993.1|, |1276989|gb|AAC54992.1|, |1276987|gb|AAC54991.1|,
|862879|gb|AAA87550.1|, |862877|gb|AAA87549.1|, |862875|gb|AAA87548.1|,
|862873|gb|AAA87547.1|, |862871|gb|AAA87546.1|, |862869|gb|AAA87545.1|,
|862867|gb|AAA87544.1|, |862865|gb|AAA87543.1|, |862863|gb|AAA87542.1|,
|862861|gb|AAA87541.1|, |862859|gb|AAA87540.1|, |862857|gb|AAA87539.1|,
|862855|gb|AAA87538.1|, |862853|gb|AAA87537.1|, |862851|gb|AAA87536.1|,
|862849|gb|AAA87535.1|, |862847|gb|AAA87534.1|, |862845|gb|AAA87533.1|,
|862843|gb|AAA87532.1|, |862841|gb|AAA87531.1|, |862839|gb|AAA87530.1|,
|862837|gb|AAA87529.1|, |862835|gb|AAA87528.1|, |862833|gb|AAA87527.1|,
|862831|gb|AAA87526.1|, |862829|gb|AAA87525.1|, |862827|gb|AAA87524.1|,
|862825|gb|AAA87523.1|, |862823|gb|AAA87522.1|, |862821|gb|AAA87521.1|,
|862819|gb|AAA87520.1|, |862817|gb|AAA87519.1|, |862815|gb|AAA87518.1|,
|862813|gb|AAA87517.1|, |862811|gb|AAA87516.1|, |862809|gb|AAA87515.1|,
|862807|gb|AAA87514.1|, |862805|gb|AAA87513.1|, |862803|gb|AAA87512.1|,
|862801|gb|AAA87511.1|, |862799|gb|AAA87510.1|, |862797|gb|AAA87509.1|,
|862795|gb|AAA87508.1|, |862793|gb|AAA87507.1|, |862791|gb|AAA87506.1|,
|862789|gb|AAA87505.1|, |862787|gb|AAA87504.1|, |862785|gb|AAA87503.1|,
|862783|gb|AAA87502.1|, |862781|gb|AAA87501.1|, |862779|gb|AAA87500.1|,
|862777|gb|AAA87499.1|, |862775|gb|AAA87498.1|, |862773|gb|AAA87497.1|,
|862771|gb|AAA87496.1|, |862769|gb|AAA87495.1|, |862767|gb|AAA87494.1|,
|862765|gb|AAA87493.1|, |862763|gb|AAA87492.1|, |862761|gb|AAA87491.1|,
|862759|gb|AAA87490.1|, |862757|gb|AAA87489.1|, |862755|gb|AAA87488.1|,
|862753|gb|AAA87487.1|, |862751|gb|AAA87486.1|, |862749|gb|AAA87485.1|,
|862747|gb|AAA87484.1|, |862745|gb|AAA87483.1|, |862743|gb|AAA87482.1|,
|862741|gb|AAA87481.1|, |862739|gb|AAA87480.1|, |862737|gb|AAA87479.1|,
|862735|gb|AAA87478.1|, |862733|gb|AAA87477.1|, |862731|gb|AAA87476.1|,
|862729|gb|AAA87475.1|, |862727|gb|AAA87474.1|, |862725|gb|AAA87473.1|,
|862723|gb|AAA87472.1|, |862721|gb|AAA87471.1|, |862719|gb|AAA87470.1|,
|862717|gb|AAA87469.1|, |862715|gb|AAA87468.1|, |862713|gb|AAA87467.1|,
|862711|gb|AAA87466.1|, |862709|gb|AAA87465.1|, |862707|gb|AAA87464.1|,
|862705|gb|AAA87463.1|, |474897|gb|AAA44918.1|, |328380|gb|AAA44981.1|,
|328378|gb|AAA44980.1|, |328376|gb|AAA44979.1|, |328374|gb|AAA44978.1|,
|328372|gb|AAA44977.1|, |328370|gb|AAA44976.1|, |328368|gb|AAA44975.1|,
|328366|gb|AAA44974.1|, |328364|gb|AAA44973.1|, |328362|gb|AAA44972.1|,
|328360|gb|AAA44971.1|, |328358|gb|AAA44970.1|, |328356|gb|AAA44969.1|,
|328354|gb|AAA44968.1|, |328352|gb|AAA44967.1|, |328350|gb|AAA44966.1|,
|328348|gb|AAA44965.1|, |328346|gb|AAA44964.1|, |328344|gb|AAA44963.1|,
|328342|gb|AAA44962.1|, |328340|gb|AAA44961.1|, |328338|gb|AAA44960.1|,
|328336|gb|AAA44959.1|, |328334|gb|AAA44958.1|, |328332|gb|AAA44957.1|,
|328330|gb|AAA44956.1|, |328328|gb|AAA44955.1|, |328326|gb|AAA44954.1|,
|328324|gb|AAA44953.1|, |328322|gb|AAA44952.1|, |328320|gb|AAA44951.1|,
|328318|gb|AAA44950.1|, |328316|gb|AAA44949.1|, |328314|gb|AAA44948.1|,
|328312|gb|AAA44947.1|, |328310|gb|AAA44946.1|, |328308|gb|AAA44945.1|,
|328306|gb|AAA44944.1|, |328304|gb|AAA44943.1|, |328302|gb|AAA44942.1|,
|328300|gb|AAA44941.1|, |328298|gb|AAA44940.1|, |328296|gb|AAA44939.1|,
|328294|gb|AAA44938.1|, |328292|gb|AAA44937.1|, |328290|gb|AAA44936.1|,
|328288|gb|AAA44935.1|, |328286|gb|AAA44934.1|, |328284|gb|AAA44933.1|, |

| VPR proteins |
|---|
| \|328282\|gb\|AAA44932.1\|, \|328280\|gb\|AAA44931.1\|, \|328278\|gb\|AAA44930.1\|,
\|328276\|gb\|AAA44929.1\|, \|328274\|gb\|AAA44928.1\|, \|328271\|gb\|AAA44927.1\|,
\|328269\|gb\|AAA44926.1\|, \|328267\|gb\|AAA44925.1\|, \|328265\|gb\|AAA44924.1\|,
\|328263\|gb\|AAA44923.1\|, \|328261\|gb\|AAA44922.1\|, \|328259\|gb\|AAA44921.1\|,
\|328257\|gb\|AAA44920.1\|, \|328255\|gb\|AAA44919.1\|, \|328252\|gb\|AAA44917.1\|,
\|328250\|gb\|AAA44916.1\|, \|328246\|gb\|AAA44915.1\|, \|328244\|gb\|AAA44914.1\|,
\|328242\|gb\|AAA44913.1\|, \|328238\|gb\|AAA44911.1\|, \|328236\|gb\|AAA44910.1\|,
\|328234\|gb\|AAA44909.1\|, \|328232\|gb\|AAA44908.1\|, \|328230\|gb\|AAA44907.1\|,
\|328228\|gb\|AAA44906.1\|, \|328226\|gb\|AAA44905.1\|, \|328224\|gb\|AAA44904.1\|,
\|328222\|gb\|AAA44903.1\|, \|328220\|gb\|AAA44902.1\|, \|328218\|gb\|AAA44901.1\|,
\|328216\|gb\|AAA44900.1\|, \|328214\|gb\|AAA44899.1\|, \|328212\|gb\|AAA44898.1\|,
\|328210\|gb\|AAA44897.1\|, \|328208\|gb\|AAA44896.1\|, \|328206\|gb\|AAA44895.1\|,
\|328204\|gb\|AAA44894.1\|, \|328200\|gb\|AAA44892.1\|, \|328198\|gb\|AAA44891.1\|,
\|328196\|gb\|AAA44890.1\|, \|328194\|gb\|AAA44889.1\|, \|328192\|gb\|AAA44888.1\|,
\|328190\|gb\|AAA44887.1\|, \|328185\|gb\|AAA44885.1\|, \|328183\|gb\|AAA44884.1\|,
\|328179\|gb\|AAA44882.1\|, \|328177\|gb\|AAA44881.1\|, \|328175\|gb\|AAA44880.1\|,
\|328173\|gb\|AAA44879.1\|, \|328171\|gb\|AAA44878.1\|, \|328169\|gb\|AAA44877.1\|,
\|328167\|gb\|AAA44876.1\|, \|328165\|gb\|AAA44875.1\|, \|82319758\|sp\|Q9QND4\|Q9QND4__9HIV1,
\|82312470\|sp\|Q89842\|Q89842__9HIV1, \|82308357\|sp\|Q9YV21\|Q9YV21__9HIV1,
\|82307898\|sp\|Q9WPY3\|Q9WPY3__9HIV1, \|82307897\|sp\|Q9WPY2\|Q9WPY2__9HIV1,
\|82307896\|sp\|Q9WPY1\|Q9WPY1__9HIV1, \|82307895\|sp\|Q9WPY0\|Q9WPY0__9HIV1,
\|82307894\|sp\|Q9WPX9\|Q9WPX9__9HIV1, \|82307893\|sp\|Q9WPX8\|Q9WPX8__9HIV1,
\|82307892\|sp\|Q9WPX7\|Q9WPX7__9HIV1, \|82307891\|sp\|Q9WPX6\|Q9WPX6__9HIV1,
\|82307890\|sp\|Q9WPX5\|Q9WPX5__9HIV1, \|82307889\|sp\|Q9WPX4\|Q9WPX4__9HIV1,
\|82307888\|sp\|Q9WPX3\|Q9WPX3__9HIV1, \|82307887\|sp\|Q9WPX2\|Q9WPX2__9HIV1,
\|82307886\|sp\|Q9WPX1\|Q9WPX1__9HIV1, \|82307885\|sp\|Q9WPX0\|Q9WPX0__9HIV1,
\|82307884\|sp\|Q9WPW9\|Q9WPW9__9HIV1, \|82307883\|sp\|Q9WPW8\|Q9WPW8__9HIV1,
\|82307882\|sp\|Q9WPW7\|Q9WPW7__9HIV1, \|82307881\|sp\|Q9WPW6\|Q9WPW6__9HIV1,
\|82307880\|sp\|Q9WPW5\|Q9WPW5__9HIV1, \|82307879\|sp\|Q9WPW4\|Q9WPW4__9HIV1,
\|82307878\|sp\|Q9WPW3\|Q9WPW3__9HIV1, \|82307877\|sp\|Q9WPW2\|Q9WPW2__9HIV1,
\|82307876\|sp\|Q9WPW1\|Q9WPW1__9HIV1, \|82307875\|sp\|Q9WPW0\|Q9WPW0__9HIV1,
\|82307874\|sp\|Q9WPV9\|Q9WPV9__9HIV1, \|82307873\|sp\|Q9WPV8\|Q9WPV8__9HIV1,
\|82307872\|sp\|Q9WPV7\|Q9WPV7__9HIV1, \|82307871\|sp\|Q9WPV6\|Q9WPV6__9HIV1,
\|82307870\|sp\|Q9WPV5\|Q9WPV5__9HIV1, \|82307869\|sp\|Q9WPV4\|Q9WPV4__9HIV1,
\|82307868\|sp\|Q9WPV3\|Q9WPV3__9HIV1, \|82307867\|sp\|Q9WPV2\|Q9WPV2__9HIV1,
\|82307866\|sp\|Q9WPV1\|Q9WPV1__9HIV1, \|82307865\|sp\|Q9WPV0\|Q9WPV0__9HIV1,
\|82307864\|sp\|Q9WPU9\|Q9WPU9__9HIV1, \|82307863\|sp\|Q9WPU8\|Q9WPU8__9HIV1,
\|82307862\|sp\|Q9WPU7\|Q9WPU7__9HIV1, \|82307861\|sp\|Q9WPU6\|Q9WPU6__9HIV1,
\|82307860\|sp\|Q9WPU5\|Q9WPU5__9HIV1, \|82307859\|sp\|Q9WPU4\|Q9WPU4__9HIV1,
\|82307858\|sp\|Q9WPU3\|Q9WPU3__9HIV1, \|82307857\|sp\|Q9WPU2\|Q9WPU2__9HIV1,
\|82307856\|sp\|Q9WPU1\|Q9WPU1__9HIV1, \|82307855\|sp\|Q9WPU0\|Q9WPU0__9HIV1,
\|82307854\|sp\|Q9WPT9\|Q9WPT9__9HIV1, \|82307853\|sp\|Q9WPT8\|Q9WPT8__9HIV1,
\|82307852\|sp\|Q9WPT7\|Q9WPT7__9HIV1, \|82307851\|sp\|Q9WPT6\|Q9WPT6__9HIV1,
\|82307850\|sp\|Q9WPT5\|Q9WPT5__9HIV1, \|82307849\|sp\|Q9WPT4\|Q9WPT4__9HIV1,
\|82307848\|sp\|Q9WPT3\|Q9WPT3__9HIV1, \|82307847\|sp\|Q9WPT2\|Q9WPT2__9HIV1,
\|82307846\|sp\|Q9WPT1\|Q9WPT1__9HIV1, \|82307845\|sp\|Q9WPT0\|Q9WPT0__9HIV1,
\|82307844\|sp\|Q9WPS9\|Q9WPS9__9HIV1, \|82307843\|sp\|Q9WPS8\|Q9WPS8__9HIV1,
\|82307842\|sp\|Q9WPS7\|Q9WPS7__9HIV1, \|82307841\|sp\|Q9WPS6\|Q9WPS6__9HIV1,
\|82307840\|sp\|Q9WPS5\|Q9WPS5__9HIV1, \|82306563\|sp\|Q9QNF1\|Q9QNF1__9HIV1,
\|82306562\|sp\|Q9QNF0\|Q9QNF0__9HIV1, \|82306561\|sp\|Q9QNE9\|Q9QNE9__9HIV1,
\|82306560\|sp\|Q9QNE8\|Q9QNE8__9HIV1, \|82306559\|sp\|Q9QNE7\|Q9QNE7__9HIV1,
\|82306558\|sp\|Q9QNE6\|Q9QNE6__9HIV1, \|82306557\|sp\|Q9QNE5\|Q9QNE5__9HIV1,
\|82306556\|sp\|Q9QNE3\|Q9QNE3__9HIV1, \|82306555\|sp\|Q9QNE2\|Q9QNE2__9HIV1,
\|82306554\|sp\|Q9QNE1\|Q9QNE1__9HIV1, \|82306553\|sp\|Q9QNE0\|Q9QNE0__9HIV1,
\|82306552\|sp\|Q9QND9\|Q9QND9__9HIV1, \|82306551\|sp\|Q9QND8\|Q9QND8__9HIV1,
\|82306550\|sp\|Q9QND7\|Q9QND7__9HIV1, \|82306549\|sp\|Q9QND6\|Q9QND6__9HIV1,
\|82306548\|sp\|Q9QND5\|Q9QND5__9HIV1, \|82306547\|sp\|Q9QND3\|Q9QND3__9HIV1,
\|82306546\|sp\|Q9QND2\|Q9QND2__9HIV1, \|82306545\|sp\|Q9QND1\|Q9QND1__9HIV1,
\|82306544\|sp\|Q9QND0\|Q9QND0__9HIV1, \|82306543\|sp\|Q9QNC9\|Q9QNC9__9HIV1,
\|82306542\|sp\|Q9QNC8\|Q9QNC8__9HIV1, \|82306539\|sp\|Q9QN68\|Q9QN68__9HIV1,
\|82306538\|sp\|Q9QN67\|Q9QN67__9HIV1, \|82306537\|sp\|Q9QN66\|Q9QN66__9HIV1,
\|82306536\|sp\|Q9QN65\|Q9QN65__9HIV1, \|82306535\|sp\|Q9QN64\|Q9QN64__9HIV1,
\|82306534\|sp\|Q9QN63\|Q9QN63__9HIV1, \|82306533\|sp\|Q9QN62\|Q9QN62__9HIV1,
\|82306532\|sp\|Q9QN61\|Q9QN61__9HIV1, \|82306531\|sp\|Q9QN60\|Q9QN60__9HIV1,
\|82306530\|sp\|Q9QN59\|Q9QN59__9HIV1, \|82306529\|sp\|Q9QN58\|Q9QN58__9HIV1,
\|82306528\|sp\|Q9QN57\|Q9QN57__9HIV1, \|82306527\|sp\|Q9QN56\|Q9QN56__9HIV1,
\|82306526\|sp\|Q9QN55\|Q9QN55__9HIV1, \|82305567\|sp\|Q9PX46\|Q9PX46__9HIV1,
\|82305565\|sp\|Q9PX21\|Q9PX21__9HIV1, \|82305560\|sp\|Q9PX02\|Q9PX02__9HIV1,
\|82305559\|sp\|Q9PX00\|Q9PX00__9HIV1, \|82305558\|sp\|Q9PWZ8\|Q9PWZ8__9HIV1,
\|82297265\|sp\|Q8J5P2\|Q8J5P2__9HIV1, \|82297264\|sp\|Q8J5P1\|Q8J5P1__9HIV1,
\|82297263\|sp\|Q8J5P0\|Q8J5P0__9HIV1, \|82297262\|sp\|Q8J5N9\|Q8J5N9__9HIV1,
\|82297261\|sp\|Q8J5N8\|Q8J5N8__9HIV1, \|82297260\|sp\|Q8J5N7\|Q8J5N7__9HIV1,
\|82297259\|sp\|Q8J5N6\|Q8J5N6__9HIV1, \|82297258\|sp\|Q8J5N5\|Q8J5N5__9HIV1,
\|82297257\|sp\|Q8J5N4\|Q8J5N4__9HIV1, \|82297256\|sp\|Q8J5N3\|Q8J5N3__9HIV1,
\|82297255\|sp\|Q8J5N2\|Q8J5N2__9HIV1, \|82297254\|sp\|Q8J5N1\|Q8J5N1__9HIV1,
\|82297253\|sp\|Q8J5N0\|Q8J5N0__9HIV1, \|82297252\|sp\|Q8J5M9\|Q8J5M9__9HIV1,
\|82297251\|sp\|Q8J5M8\|Q8J5M8__9HIV1, \|82297250\|sp\|Q8J5M7\|Q8J5M7__9HIV1, |

VPR proteins

|82297249|sp|Q8J5M6|Q8J5M6__9HIV1, |82297248|sp|Q8J5M5|Q8J5M5__9HIV1,
|82297247|sp|Q8J5M4|Q8J5M4__9HIV1, |82297246|sp|Q8J5M3|Q8J5M3__9HIV1,
|82297245|sp|Q8J5M2|Q8J5M2__9HIV1, |82297244|sp|Q8J5M1|Q8J5M1__9HIV1,
|82297243|sp|Q8J5M0|Q8J5M0__9HIV1, |82297242|sp|Q8J5L9|Q8J5L9__9HIV1,
|82297241|sp|Q8J5L8|Q8J5L8__9HIV1, |82297240|sp|Q8J5L7|Q8J5L7__9HIV1,
|82297239|sp|Q8J5L6|Q8J5L6__9HIV1, |82297238|sp|Q8J5L5|Q8J5L5__9HIV1,
|82297237|sp|Q8J5L4|Q8J5L4__9HIV1, |82297236|sp|Q8J5L3|Q8J5L3__9HIV1,
|82297235|sp|Q8J5L2|Q8J5L2__9HIV1, |82297234|sp|Q8J5L1|Q8J5L1__9HIV1,
|82297233|sp|Q8J5L0|Q8J5L0__9HIV1, |82297232|sp|Q8J5K9|Q8J5K9__9HIV1,
|82297231|sp|Q8J5K8|Q8J5K8__9HIV1, |82297230|sp|Q8J5K7|Q8J5K7__9HIV1,
|82297229|sp|Q8J5K6|Q8J5K6__9HIV1, |82297228|sp|Q8J5K5|Q8J5K5__9HIV1,
|82297227|sp|Q8J5K4|Q8J5K4__9HIV1, |82297226|sp|Q8J5K3|Q8J5K3__9HIV1,
|82297225|sp|Q8J5K2|Q8J5K2__9HIV1, |82297224|sp|Q8J5K1|Q8J5K1__9HIV1,
|82297223|sp|Q8J5K0|Q8J5K0__9HIV1, |82297222|sp|Q8J5J9|Q8J5J9__9HIV1,
|82297221|sp|Q8J5J8|Q8J5J8__9HIV1, |82297220|sp|Q8J5J7|Q8J5J7__9HIV1,
|82297219|sp|Q8J5J6|Q8J5J6__9HIV1, |82297218|sp|Q8J5J5|Q8J5J5__9HIV1,
|82297217|sp|Q8J5J4|Q8J5J4__9HIV1, |82297216|sp|Q8J5J3|Q8J5J3__9HIV1,
|82297215|sp|Q8J5J2|Q8J5J2__9HIV1, |82297214|sp|Q8J5J1|Q8J5J1__9HIV1,
|82297213|sp|Q8J5J0|Q8J5J0__9HIV1, |82297212|sp|Q8J5I9|Q8J5I9__9HIV1,
|82297211|sp|Q8J5I8|Q8J5I8__9HIV1, |82297210|sp|Q8J5I7|Q8J5I7__9HIV1,
|82297209|sp|Q8J5I6|Q8J5I6__9HIV1, |82297208|sp|Q8J5I5|Q8J5I5__9HIV1,
|82297207|sp|Q8J5I4|Q8J5I4__9HIV1, |82297206|sp|Q8J5I3|Q8J5I3__9HIV1,
|82297205|sp|Q8J5I2|Q8J5I2__9HIV1, |82297204|sp|Q8J5I1|Q8J5I1__9HIV1,
|82297203|sp|Q8J5I0|Q8J5I0__9HIV1, |82297202|sp|Q8J5H9|Q8J5H9__9HIV1,
|82297201|sp|Q8J5H8|Q8J5H8__9HIV1, |82297200|sp|Q8J5H7|Q8J5H7__9HIV1,
|82297199|sp|Q8J5H6|Q8J5H6__9HIV1, |82297198|sp|Q8J5H5|Q8J5H5__9HIV1,
|82297197|sp|Q8J5H4|Q8J5H4__9HIV1, |82297196|sp|Q8J5H3|Q8J5H3__9HIV1,
|82297195|sp|Q8J5H2|Q8J5H2__9HIV1, |82297194|sp|Q8J5H1|Q8J5H1__9HIV1,
|82297193|sp|Q8J5H0|Q8J5H0__9HIV1, |82297192|sp|Q8J5G9|Q8J5G9__9HIV1,
|82297191|sp|Q8J5G8|Q8J5G8__9HIV1, |82297190|sp|Q8J5G7|Q8J5G7__9HIV1,
|82297189|sp|Q8J5G6|Q8J5G6__9HIV1, |82297188|sp|Q8J5G5|Q8J5G5__9HIV1,
|82297187|sp|Q8J5G4|Q8J5G4__9HIV1, |82297186|sp|Q8J5G3|Q8J5G3__9HIV1,
|82297185|sp|Q8J5G2|Q8J5G2__9HIV1, |82297184|sp|Q8J5G1|Q8J5G1__9HIV1,
|82297183|sp|Q8J5G0|Q8J5G0__9HIV1,
|82297182|sp|Q8J5F9|Q8J5F9__9HIV1, |82297181|sp|Q8J5F8|Q8J5F8__9HIV1,
|82297180|sp|Q8J5F7|Q8J5F7__9HIV1, |82297179|sp|Q8J5F6|Q8J5F6__9HIV1,
|82297178|sp|Q8J5F5|Q8J5F5__9HIV1, |82297177|sp|Q8J5F4|Q8J5F4__9HIV1,
|82297176|sp|Q8J5F3|Q8J5F3__9HIV1, |82297175|sp|Q8J5F2|Q8J5F2__9HIV1,
|82297174|sp|Q8J5F1|Q8J5F1__9HIV1, |82297173|sp|Q8J5F0|Q8J5F0__9HIV1,
|82297172|sp|Q8J5E9|Q8J5E9__9HIV1, |82297171|sp|Q8J5E8|Q8J5E8__9HIV1,
|82297170|sp|Q8J5E7|Q8J5E7__9HIV1, |82297169|sp|Q8J5E6|Q8J5E6__9HIV1,
|82297168|sp|Q8J5E5|Q8J5E5__9HIV1, |82297167|sp|Q8J5E4|Q8J5E4__9HIV1,
|82297166|sp|Q8J5E3|Q8J5E3__9HIV1, |82297165|sp|Q8J5E2|Q8J5E2__9HIV1,
|82297164|sp|Q8J5E1|Q8J5E1__9HIV1, |82297163|sp|Q8J5E0|Q8J5E0__9HIV1,
|82297162|sp|Q8J5D9|Q8J5D9__9HIV1, |82297161|sp|Q8J5D8|Q8J5D8__9HIV1,
|82297160|sp|Q8J5D7|Q8J5D7__9HIV1, |82297159|sp|Q8J5D6|Q8J5D6__9HIV1,
|82297158|sp|Q8J5D5|Q8J5D5__9HIV1, |82297157|sp|Q8J5D4|Q8J5D4__9HIV1,
|82297156|sp|Q8J5D3|Q8J5D3__9HIV1, |82297155|sp|Q8J5D2|Q8J5D2__9HIV1,
|82297154|sp|Q8J5D1|Q8J5D1__9HIV1, |82297153|sp|Q8J5D0|Q8J5D0__9HIV1,
|82297152|sp|Q8J5C9|Q8J5C9__9HIV1, |82297151|sp|Q8J5C8|Q8J5C8__9HIV1,
|82297150|sp|Q8J5C7|Q8J5C7__9HIV1, |82297149|sp|Q8J5C6|Q8J5C6__9HIV1,
|82297148|sp|Q8J5C5|Q8J5C5__9HIV1, |82297147|sp|Q8J5C4|Q8J5C4__9HIV1,
|82297146|sp|Q8J5C3|Q8J5C3__9HIV1, |82297145|sp|Q8J5C2|Q8J5C2__9HIV1,
|82297144|sp|Q8J5C1|Q8J5C1__9HIV1, |82297143|sp|Q8J5C0|Q8J5C0__9HIV1,
|82297142|sp|Q8J5B9|Q8J5B9__9HIV1, |82297141|sp|Q8J5B8|Q8J5B8__9HIV1,
|82297140|sp|Q8J5B7|Q8J5B7__9HIV1, |82297139|sp|Q8J5B6|Q8J5B6__9HIV1,
|82297138|sp|Q8J5B5|Q8J5B5__9HIV1, |82297137|sp|Q8J5B4|Q8J5B4__9HIV1,
|82297136|sp|Q8J5B3|Q8J5B3__9HIV1, |82297135|sp|Q8J5B2|Q8J5B2__9HIV1,
|82297134|sp|Q8J5B1|Q8J5B1__9HIV1, |82297133|sp|Q8J5B0|Q8J5B0__9HIV1,
|82297132|sp|Q8J5A9|Q8J5A9__9HIV1, |82297131|sp|Q8J5A8|Q8J5A8__9HIV1,
|82297130|sp|Q8J5A7|Q8J5A7__9HIV1, |82297129|sp|Q8J5A6|Q8J5A6__9HIV1,
|82297128|sp|Q8J5A5|Q8J5A5__9HIV1, |82297127|sp|Q8J5A4|Q8J5A4__9HIV1,
|82297126|sp|Q8J5A3|Q8J5A3__9HIV1, |82297125|sp|Q8J5A2|Q8J5A2__9HIV1,
|82297124|sp|Q8J5A1|Q8J5A1__9HIV1, |82297123|sp|Q8J5A0|Q8J5A0__9HIV1,
|82297122|sp|Q8J599|Q8J599__9HIV1, |82297121|sp|Q8J598|Q8J598__9HIV1,
|82297120|sp|Q8J597|Q8J597__9HIV1, |82297119|sp|Q8J596|Q8J596__9HIV1,
|82297118|sp|Q8J595|Q8J595__9HIV1, |82297117|sp|Q8J594|Q8J594__9HIV1,
|82297116|sp|Q8J593|Q8J593__9HIV1, |82297115|sp|Q8J592|Q8J592__9HIV1,
|82297114|sp|Q8J591|Q8J591__9HIV1, |82297113|sp|Q8J590|Q8J590__9HIV1,
|82297112|sp|Q8J589|Q8J589__9HIV1, |82297111|sp|Q8J588|Q8J588__9HIV1,
|82297110|sp|Q8J587|Q8J587__9HIV1, |82297109|sp|Q8J586|Q8J586__9HIV1,
|82297108|sp|Q8J585|Q8J585__9HIV1, |82297107|sp|Q8J584|Q8J584__9HIV1,
|82296833|sp|Q8J318|Q8J318__9HIV1, |82296832|sp|Q8J315|Q8J315__9HIV1,
|82296831|sp|Q8J314|Q8J314__9HIV1, |82296830|sp|Q8J313|Q8J313__9HIV1,
|82295871|sp|Q8AIJ8|Q8AIJ8__9HIV1truncated, |82295354|sp|Q89889|Q89889__9HIV1,
|82295353|sp|Q89888|Q89888__9HIV1, |82295350|sp|Q89866|Q89866__9HIV1,
|82295349|sp|Q89851|Q89851__9HIV1, |82295348|sp|Q89844|Q89844__9HIV1, -continued

| VPR proteins |
|---|
| |82295346|sp|Q89821|Q89821__9HIV1, |82295345|sp|Q89778|Q89778__9HIV1, |
| |82295343|sp|Q89758|Q89758__9HIV1, |82295341|sp|Q89734|Q89734__9HIV1, |
| |82295340|sp|Q89706|Q89706__9HIV1, |82295339|sp|Q89688|Q89688__9HIV1, |
| |82295338|sp|Q89672|Q89672__9HIV1, |82295337|sp|Q89668|Q89668__9HIV1, |
| |82295335|sp|Q89646|Q89646__9HIV1, |82295334|sp|Q89630|Q89630__9HIV1, |
| |82295333|sp|Q89629|Q89629__9HIV1, |82295332|sp|Q89623|Q89623__9HIV1, |
| |82295326|sp|Q89587|Q89587__9HIV1, |82295325|sp|Q89586|Q89586__9HIV1, |
| |82295324|sp|Q89575|Q89575__9HIV1, |82295320|sp|Q89537|Q89537__9HIV1, |
| |82295318|sp|Q89515|Q89515__9HIV1, |82295317|sp|Q89511|Q89511__9HIV1, |
| |82295314|sp|Q89463|Q89463__9HIV1, |82295313|sp|Q89438|Q89438__9HIV1, |
| |82295312|sp|Q89436|Q89436__9HIV1, |82295311|sp|Q89430|Q89430__9HIV1, |
| |82291329|sp|Q79785|Q79785__9HIV1, |82291328|sp|Q79784|Q79784__9HIV1, |
| |82291327|sp|Q79783|Q79783__9HIV1, |82291326|sp|Q79782|Q79782__9HIV1, |
| |82291325|sp|Q79781|Q79781__9HIV1, |82291324|sp|Q79780|Q79780__9HIV1, |
| |82291323|sp|Q79779|Q79779__9HIV1, |82291322|sp|Q79778|Q79778__9HIV1, |
| |82291321|sp|Q79777|Q79777__9HIV1, |82291320|sp|Q79776|Q79776__9HIV1, |
| |82291319|sp|Q79775|Q79775__9HIV1, |82291318|sp|Q79774|Q79774__9HIV1, |
| |82291317|sp|Q79773|Q79773__9HIV1, |82291316|sp|Q79772|Q79772__9HIV1, |
| |82291315|sp|Q79771|Q79771__9HIV1, |82291314|sp|Q79770|Q79770__9HIV1, |
| |82291313|sp|Q79769|Q79769__9HIV1, |82291312|sp|Q79768|Q79768__9HIV1, |
| |82291311|sp|Q79767|Q79767__9HIV1, |82291310|sp|Q79766|Q79766__9HIV1, |
| |82291309|sp|Q79765|Q79765__9HIV1, |82291308|sp|Q79764|Q79764__9HIV1, |
| |82291307|sp|Q79763|Q79763__9HIV1, |82291306|sp|Q79762|Q79762__9HIV1, |
| |82291305|sp|Q79761|Q79761__9HIV1, |82291304|sp|Q79760|Q79760__9HIV1, |
| |82291303|sp|Q79759|Q79759__9HIV1, |82291302|sp|Q79758|Q79758__9HIV1, |
| |82291301|sp|Q79757|Q79757__9HIV1, |82291300|sp|Q79756|Q79756__9HIV1, |
| |82291299|sp|Q79755|Q79755__9HIV1, |82291298|sp|Q79754|Q79754__9HIV1, |
| |82291297|sp|Q79753|Q79753__9HIV1, |82291296|sp|Q79752|Q79752__9HIV1, |
| |82291295|sp|Q79751|Q79751__9HIV1, |82291294|sp|Q79750|Q79750__9HIV1, |
| |82291293|sp|Q79749|Q79749__9HIV1, |82291292|sp|Q79748|Q79748__9HIV1, |
| |82291291|sp|Q79747|Q79747__9HIV1, |82291290|sp|Q79746|Q79746__9HIV1, |
| |82291289|sp|Q79745|Q79745__9HIV1, |82291288|sp|Q79744|Q79744__9HIV1, |
| |82291287|sp|Q79743|Q79743__9HIV1, |82291286|sp|Q79742|Q79742__9HIV1, |
| |82291285|sp|Q79741|Q79741__9HIV1, |82291284|sp|Q79740|Q79740__9HIV1, |
| |82291283|sp|Q79739|Q79739__9HIV1, |82291282|sp|Q79738|Q79738__9HIV1, |
| |82291281|sp|Q79737|Q79737__9HIV1, |82291280|sp|Q79736|Q79736__9HIV1, |
| |82291279|sp|Q79735|Q79735__9HIV1, |82291278|sp|Q79734|Q79734__9HIV1, |
| |82291277|sp|Q79733|Q79733__9HIV1, |82291276|sp|Q79732|Q79732__9HIV1, |
| |82291275|sp|Q79731|Q79731__9HIV1, |82291274|sp|Q79730|Q79730__9HIV1, |
| |82291273|sp|Q79727|Q79727__9HIV1, |82291272|sp|Q79726|Q79726__9HIV1, |
| |82291271|sp|Q79725|Q79725__9HIV1, |82291270|sp|Q79724|Q79724__9HIV1, |
| |82291269|sp|Q79722|Q79722__9HIV1, |82291268|sp|Q79721|Q79721__9HIV1, |
| |82291267|sp|Q79720|Q79720__9HIV1, |82291266|sp|Q79719|Q79719__9HIV1, |
| |82291265|sp|Q79718|Q79718__9HIV1, |82291264|sp|Q79717|Q79717__9HIV1, |
| |82291263|sp|Q79716|Q79716__9HIV1, |82291262|sp|Q79715|Q79715__9HIV1, |
| |82291261|sp|Q79714|Q79714__9HIV1, |82291260|sp|Q79713|Q79713__9HIV1, |
| |82291259|sp|Q79712|Q79712__9HIV1, |82291258|sp|Q79711|Q79711__9HIV1, |
| |82291257|sp|Q79710|Q79710__9HIV1, |82291256|sp|Q79709|Q79709__9HIV1, |
| |82291255|sp|Q79708|Q79708__9HIV1, |82291254|sp|Q79707|Q79707__9HIV1, |
| |82291253|sp|Q79706|Q79706__9HIV1, |82291252|sp|Q79705|Q79705__9HIV1, |
| |82291251|sp|Q79704|Q79704__9HIV1, |82291250|sp|Q79703|Q79703__9HIV1, |
| |82291249|sp|Q79702|Q79702__9HIV1, |82291248|sp|Q79701|Q79701__9HIV1, |
| |82291246|sp|Q79699|Q79699__9HIV1, |82291245|sp|Q79698|Q79698__9HIV1, |
| |82291244|sp|Q79697|Q79697__9HIV1, |82291243|sp|Q79696|Q79696__9HIV1, |
| |82291242|sp|Q79695|Q79695__9HIV1, |82291241|sp|Q79694|Q79694__9HIV1, |
| |82291240|sp|Q79693|Q79693__9HIV1, |82291239|sp|Q79692|Q79692__9HIV1, |
| |82291238|sp|Q79691|Q79691__9HIV1, |82291237|sp|Q79690|Q79690__9HIV1, |
| |82291236|sp|Q79689|Q79689__9HIV1, |82291235|sp|Q79688|Q79688__9HIV1, |
| |82291234|sp|Q79687|Q79687__9HIV1, |82291232|sp|Q79685|Q79685__9HIV1, |
| |82291231|sp|Q79684|Q79684__9HIV1, |82291230|sp|Q79683|Q79683__9HIV1, |
| |82291228|sp|Q79681|Q79681__9HIV1, |82291227|sp|Q79680|Q79680__9HIV1, |
| |82291226|sp|Q79678|Q79678__9HIV1, |82291225|sp|Q79677|Q79677__9HIV1, |
| |82291224|sp|Q79676|Q79676__9HIV1, |82291223|sp|Q79675|Q79675__9HIV1, |
| |82291222|sp|Q79674|Q79674__9HIV1, |82291221|sp|Q79673|Q79673__9HIV1, |
| |82289471|sp|Q74688|Q74688__9HIV1, |82289470|sp|Q74687|Q74687__9HIV1, |
| |82289469|sp|Q74686|Q74686__9HIV1, |82289468|sp|Q74685|Q74685__9HIV1, |
| |82289467|sp|Q74684|Q74684__9HIV1, |82289466|sp|Q74683|Q74683__9HIV1, |
| |82289465|sp|Q74682|Q74682__9HIV1, |82289464|sp|Q74681|Q74681__9HIV1, |
| |82289463|sp|Q74680|Q74680__9HIV1, |82289462|sp|Q74679|Q74679__9HIV1, |
| |82289461|sp|Q74678|Q74678__9HIV1, |82289460|sp|Q74677|Q74677__9HIV1, |
| |82289459|sp|Q74676|Q74676__9HIV1, |82289458|sp|Q74675|Q74675__9HIV1, |
| |82288766|sp|Q72481|Q72481__9HIV1, |82288765|sp|Q72480|Q72480__9HIV1, |
| |82288764|sp|Q72479|Q72479__9HIV1, |82288763|sp|Q72478|Q72478__9HIV1, |
| |82288762|sp|Q72477|Q72477__9HIV1, |82288761|sp|Q72476|Q72476__9HIV1, |
| |82288760|sp|Q72475|Q72475__9HIV1, |82288759|sp|Q72474|Q72474__9HIV1, |
| |82288758|sp|Q72473|Q72473__9HIV1, |82288757|sp|Q72472|Q72472__9HIV1, |
| |82288756|sp|Q72471|Q72471__9HIV1, |82288755|sp|Q72470|Q72470__9HIV1, |

-continued

| VPR proteins |
|---|
| 82288754\|sp\|Q72469\|Q72469_9HIV1, 82288753\|sp\|Q72468\|Q72468_9HIV1, |
| 82288752\|sp\|Q72467\|Q72467_9HIV1, 82288751\|sp\|Q72466\|Q72466_9HIV1, |
| 82288750\|sp\|Q72465\|Q72465_9HIV1, 82288749\|sp\|Q72464\|Q72464_9HIV1, |
| 82288748\|sp\|Q72463\|Q72463_9HIV1, 82288747\|sp\|Q72462\|Q72462_9HIV1, |
| 82288746\|sp\|Q72461\|Q72461_9HIV1, 82288745\|sp\|Q72460\|Q72460_9HIV1, |
| 82288744\|sp\|Q72459\|Q72459_9HIV1, 82288743\|sp\|Q72458\|Q72458_9HIV1, |
| 82288742\|sp\|Q72457\|Q72457_9HIV1, 82288741\|sp\|Q72456\|Q72456_9HIV1, |
| 82288740\|sp\|Q72455\|Q72455_9HIV1, 82288739\|sp\|Q72454\|Q72454_9HIV1, |
| 82288738\|sp\|Q72453\|Q72453_9HIV1, 82288737\|sp\|Q72452\|Q72452_9HIV1, |
| 82288736\|sp\|Q72451\|Q72451_9HIV1, 82288735\|sp\|Q72450\|Q72450_9HIV1, |
| 82288734\|sp\|Q72449\|Q72449_9HIV1, 82288733\|sp\|Q72448\|Q72448_9HIV1, |
| 82288732\|sp\|Q72447\|Q72447_9HIV1, 82288731\|sp\|Q72446\|Q72446_9HIV1, |
| 82288730\|sp\|Q72445\|Q72445_9HIV1, 82288729\|sp\|Q72444\|Q72444_9HIV1, |
| 82288728\|sp\|Q72443\|Q72443_9HIV1, 82288727\|sp\|Q72442\|Q72442_9HIV1, |
| 82288726\|sp\|Q72441\|Q72441_9HIV1, 82288725\|sp\|Q72440\|Q72440_9HIV1, |
| 82288724\|sp\|Q72439\|Q72439_9HIV1, 82288723\|sp\|Q72438\|Q72438_9HIV1, |
| 82288722\|sp\|Q72437\|Q72437_9HIV1, 82288721\|sp\|Q72436\|Q72436_9HIV1, |
| 82288720\|sp\|Q72435\|Q72435_9HIV1, 82288719\|sp\|Q72433\|Q72433_9HIV1, |
| 82288718\|sp\|Q72432\|Q72432_9HIV1, 82288717\|sp\|Q72431\|Q72431_9HIV1, |
| 82288716\|sp\|Q72430\|Q72430_9HIV1, 82288715\|sp\|Q72429\|Q72429_9HIV1, |
| 82288714\|sp\|Q72427\|Q72427_9HIV1, 82288713\|sp\|Q72426\|Q72426_9HIV1, |
| 82288712\|sp\|Q72425\|Q72425_9HIV1, 82288711\|sp\|Q72424\|Q72424_9HIV1, |
| 82288710\|sp\|Q72423\|Q72423_9HIV1, 82288709\|sp\|Q72422\|Q72422_9HIV1, |
| 82288708\|sp\|Q72421\|Q72421_9HIV1, 82288707\|sp\|Q72420\|Q72420_9HIV1, |
| 82288706\|sp\|Q72419\|Q72419_9HIV1, 82288495\|sp\|Q71185\|Q71185_9HIV1, |
| 82288494\|sp\|Q71184\|Q71184_9HIV1, 82288493\|sp\|Q71183\|Q71183_9HIV1, |
| 82288492\|sp\|Q71182\|Q71182_9HIV1, 82288491\|sp\|Q71181\|Q71181_9HIV1, |
| 82288490\|sp\|Q71180\|Q71180_9HIV1, 82288489\|sp\|Q71179\|Q71179_9HIV1, |
| 82288488\|sp\|Q71178\|Q71178_9HIV1, 82288487\|sp\|Q71177\|Q71177_9HIV1, |
| 82288486\|sp\|Q71176\|Q71176_9HIV1, 82288485\|sp\|Q71175\|Q71175_9HIV1, |
| 82288484\|sp\|Q71174\|Q71174_9HIV1, 82288483\|sp\|Q71173\|Q71173_9HIV1, |
| 82288482\|sp\|Q71172\|Q71172_9HIV1, 82288481\|sp\|Q71171\|Q71171_9HIV1, |
| 82288480\|sp\|Q71170\|Q71170_9HIV1, 82288479\|sp\|Q71169\|Q71169_9HIV1, |
| 82288478\|sp\|Q71168\|Q71168_9HIV1, 82288477\|sp\|Q71167\|Q71167_9HIV1, |
| 82288476\|sp\|Q71166\|Q71166_9HIV1, 82288475\|sp\|Q71165\|Q71165_9HIV1, |
| 82288474\|sp\|Q71164\|Q71164_9HIV1, 82288473\|sp\|Q71163\|Q71163_9HIV1, |
| 82288472\|sp\|Q71162\|Q71162_9HIV1, 82288471\|sp\|Q71161\|Q71161_9HIV1, |
| 82288470\|sp\|Q71160\|Q71160_9HIV1, 82283483\|sp\|Q5Y3C5\|Q5Y3C5_9HIV1, |
| 82283482\|sp\|Q5Y3C4\|Q5Y3C4_9HIV1, 82283481\|sp\|Q5Y3C3\|Q5Y3C3_9HIV1, |
| 82283480\|sp\|Q5Y3C2\|Q5Y3C2_9HIV1, 82283479\|sp\|Q5Y3C1\|Q5Y3C1_9HIV1, |
| 82283478\|sp\|Q5Y3C0\|Q5Y3C0_9HIV1, 82283477\|sp\|Q5Y3B9\|Q5Y3B9_9HIV1, |
| 82283476\|sp\|Q5Y3B8\|Q5Y3B8_9HIV1, 82283475\|sp\|Q5Y3B7\|Q5Y3B7_9HIV1, |
| 82283474\|sp\|Q5Y3B6\|Q5Y3B6_9HIV1, 82283473\|sp\|Q5Y3B5\|Q5Y3B5_9HIV1, |
| 82283472\|sp\|Q5Y3B4\|Q5Y3B4_9HIV1, 82283471\|sp\|Q5Y3B3\|Q5Y3B3_9HIV1, |
| 82283470\|sp\|Q5Y3B2\|Q5Y3B2_9HIV1, 82283469\|sp\|Q5Y3B1\|Q5Y3B1_9HIV1, |
| 82283468\|sp\|Q5Y3B0\|Q5Y3B0_9HIV1, 82283467\|sp\|Q5Y3A9\|Q5Y3A9_9HIV1, |
| 82283466\|sp\|Q5Y3A8\|Q5Y3A8_9HIV1, 82283465\|sp\|Q5Y3A7\|Q5Y3A7_9HIV1, |
| 82283464\|sp\|Q5Y3A6\|Q5Y3A6_9HIV1, 82283463\|sp\|Q5Y3A5\|Q5Y3A5_9HIV1, |
| 82283462\|sp\|Q5Y3A4\|Q5Y3A4_9HIV1, 82283461\|sp\|Q5Y3A3\|Q5Y3A3_9HIV1, |
| 82283460\|sp\|Q5Y3A2\|Q5Y3A2_9HIV1, 82283459\|sp\|Q5Y3A1\|Q5Y3A1_9HIV1, |
| 82283458\|sp\|Q5Y3A0\|Q5Y3A0_9HIV1, 82283457\|sp\|Q5Y398\|Q5Y398_9HIV1, |
| 82283456\|sp\|Q5Y397\|Q5Y397_9HIV1, 82283455\|sp\|Q5Y396\|Q5Y396_9HIV1, |
| 82283454\|sp\|Q5Y395\|Q5Y395_9HIV1, 82283453\|sp\|Q5Y394\|Q5Y394_9HIV1, |
| 82283452\|sp\|Q5Y393\|Q5Y393_9HIV1, 82281567\|sp\|P89698\|P89698_9HIV1, |
| 82281075\|sp\|O92654\|O92654_9HIV1, 82280743\|sp\|O91087\|O91087_9HIV1, |
| 82280705\|sp\|O91043\|O91043_9HIV1, 82280704\|sp\|O91042\|O91042_9HIV1, |
| 82280703\|sp\|O91041\|O91041_9HIV1, 82280702\|sp\|O91040\|O91040_9HIV1, |
| 82280701\|sp\|O91039\|O91039_9HIV1, 82280700\|sp\|O91038\|O91038_9HIV1, |
| 82280699\|sp\|O91037\|O91037_9HIV1, 82280698\|sp\|O91036\|O91036_9HIV1, |
| 82280697\|sp\|O91035\|O91035_9HIV1, 82280696\|sp\|O91034\|O91034_9HIV1, |
| 82280695\|sp\|O91033\|O91033_9HIV1, 82280694\|sp\|O91032\|O91032_9HIV1, |
| 82280693\|sp\|O91031\|O91031_9HIV1, 82280692\|sp\|O91030\|O91030_9HIV1, |
| 82280691\|sp\|O91029\|O91029_9HIV1, 82280690\|sp\|O91028\|O91028_9HIV1, |
| 82280689\|sp\|O91027\|O91027_9HIV1, 82280688\|sp\|O91026\|O91026_9HIV1, |
| 82280687\|sp\|O91025\|O91025_9HIV1, 82280686\|sp\|O91024\|O91024_9HIV1, |
| 82280685\|sp\|O91023\|O91023_9HIV1, 82280684\|sp\|O91022\|O91022_9HIV1, |
| 82280683\|sp\|O91021\|O91021_9HIV1, 82280682\|sp\|O91020\|O91020_9HIV1, |
| 82280681\|sp\|O91019\|O91019_9HIV1, 82280680\|sp\|O91018\|O91018_9HIV1, |
| 82280679\|sp\|O91017\|O91017_9HIV1, 82280678\|sp\|O91016\|O91016_9HIV1, |
| 82280677\|sp\|O91015\|O91015_9HIV1, 82280676\|sp\|O91014\|O91014_9HIV1, |
| 82280675\|sp\|O91013\|O91013_9HIV1, 82280674\|sp\|O91012\|O91012_9HIV1, |
| 82280673\|sp\|O91011\|O91011_9HIV1, 82280672\|sp\|O91010\|O91010_9HIV1, |
| 82280671\|sp\|O91009\|O91009_9HIV1, 82280670\|sp\|O91008\|O91008_9HIV1, |
| 82280669\|sp\|O91007\|O91007_9HIV1, 82280668\|sp\|O91006\|O91006_9HIV1, |
| 82280667\|sp\|O91005\|O91005_9HIV1, 82280666\|sp\|O91004\|O91004_9HIV1, |
| 82280665\|sp\|O91003\|O91003_9HIV1, 82280509\|sp\|O90156\|O90156_9HIV1, |
| 82278699\|sp\|O12404\|O12404_9HIV1, 82278698\|sp\|O12390\|O12390_9HIV1, |

| VPR proteins |
|---|
| \|82278098\|sp\|O10843\|O10843__9HIV1, \|82278097\|sp\|O10842\|O10842__9HIV1, \|82278096\|sp\|O10841\|O10841__9HIV1, \|82278095\|sp\|O10840\|O10840__9HIV1, \|82278094\|sp\|O10839\|O10839__9HIV1, \|82278093\|sp\|O10838\|O10838__9HIV1, \|82278092\|sp\|O10837\|O10837__9HIV1, \|82278091\|sp\|O10836\|O10836__9HIV1, \|82278090\|sp\|O10835\|O10835__9HIV1, \|82278089\|sp\|O10834\|O10834__9HIV1, \|82278088\|sp\|O10833\|O10833__9HIV1, \|82278087\|sp\|O10832\|O10832__9HIV1, \|82278086\|sp\|O10831\|O10831__9HIV1, \|82278085\|sp\|O10830\|O10830__9HIV1, \|82278084\|sp\|O10829\|O10829__9HIV1, \|82278083\|sp\|O10828\|O10828__9HIV1, \|82278082\|sp\|O10827\|O10827__9HIV1, \|82278081\|sp\|O10826\|O10826__9HIV1, \|82278080\|sp\|O10825\|O10825__9HIV1, \|82278079\|sp\|O10824\|O10824__9HIV1, \|82278078\|sp\|O10823\|O10823__9HIV1, \|82278077\|sp\|O10822\|O10822__9HIV1, \|82278076\|sp\|O10820\|O10820__9HIV1, \|82278075\|sp\|O10819\|O10819__9HIV1, \|82278074\|sp\|O10818\|O10818__9HIV1, \|82278073\|sp\|O10817\|O10817__9HIV1, \|82278072\|sp\|O10816\|O10816__9HIV1, \|82278071\|sp\|O10815\|O10815__9HIV1, \|82278070\|sp\|O10814\|O10814__9HIV1, \|82278069\|sp\|O10813\|O10813__9HIV1, \|82278068\|sp\|O10812\|O10812__9HIV1, \|82278067\|sp\|O10811\|O10811__9HIV1, \|82278066\|sp\|O10810\|O10810__9HIV1, \|82278065\|sp\|O10809\|O10809__9HIV1, \|82278064\|sp\|O10808\|O10808__9HIV1, \|82278063\|sp\|O10807\|O10807__9HIV1, \|82278062\|sp\|O10806\|O10806__9HIV1, \|82278061\|sp\|O10805\|O10805__9HIV1, \|66864707\|gb\|AAY57433.1\|, \|66864699\|gb\|AAY57426.1\|, \|66864689\|gb\|AAY57417.1\|, \|25167078\|gb\|AAN73842.1\|AF484522__8, \|25167068\|gb\|AAN73833.1\|AF484521__8, \|25166878\|gb\|AAN73662.1\|AF484502__8truncated, \|58200359\|gb\|AAW66382.1\|, \|58200357\|gb\|AAW66381.1\|, \|58200355\|gb\|AAW66380.1\|, \|58200353\|gb\|AAW66379.1\|, \|58200351\|gb\|AAW66378.1\|, \|58200349\|gb\|AAW66377.1\|, \|58200347\|gb\|AAW66376.1\|, \|58200345\|gb\|AAW66375.1\|, \|58200343\|gb\|AAW66374.1\|, \|58200341\|gb\|AAW66373.1\|, \|58200339\|gb\|AAW66372.1\|, \|58200337\|gb\|AAW66371.1\|, \|58200335\|gb\|AAW66370.1\|, \|58200333\|gb\|AAW66369.1\|, \|58200331\|gb\|AAW66368.1\|, \|58200329\|gb\|AAW66367.1\|, \|58200327\|gb\|AAW66366.1\|, \|58200325\|gb\|AAW66365.1\|, \|58200323\|gb\|AAW66364.1\|, \|58200321\|gb\|AAW66363.1\|, \|58200319\|gb\|AAW66362.1\|, \|58200317\|gb\|AAW66361.1\|, \|58200315\|gb\|AAW66360.1\|, \|58200313\|gb\|AAW66359.1\|, \|58200311\|gb\|AAW66358.1\|, \|58200309\|gb\|AAW66357.1\|, \|38326776\|gb\|AAR17518.1\|, \|32724983\|gb\|AAM93785.2\|, \|32724981\|gb\|AAM93782.2\|, \|31087572\|gb\|AAM93788.1\|, \|31087570\|gb\|AAM93787.1\|, \|31087567\|gb\|AAM93786.1\|, \|31087563\|gb\|AAM93784.1\|, \|31087561\|gb\|AAM93783.1\|, \|31087557\|gb\|AAM93781.1\|, \|31087555\|gb\|AAM93780.1\|, \|31087549\|gb\|AAM93779.1\|, \|31087547\|gb\|AAM93778.1\|, \|31087545\|gb\|AAM93777.1\|, \|31087543\|gb\|AAM93776.1\|, \|31087541\|gb\|AAM93775.1\|, \|31087539\|gb\|AAM93774.1\|, \|56417612\|gb\|AAV90750.1\|, \|56193099\|gb\|AAV84162.1\|, \|56193083\|gb\|AAV84153.1\|, \|56193065\|gb\|AAV84144.1\|, \|56193048\|gb\|AAV84135.1\|, \|56193012\|gb\|AAV84117.1\|, \|54124767\|gb\|AAV30107.1\|, \|54124757\|gb\|AAV30098.1\|, \|51599147\|gb\|AAU08231.1\|, \|51599137\|gb\|AAU08222.1\|, \|50404193\|gb\|AAT76863.1\|, \|47118268\|gb\|AAT11254.1\|truncated, \|47118258\|gb\|AAT11245.1\|truncated, \|47118248\|gb\|AAT11227.1\|truncated, \|47118238\|gb\|AAT11236.1\|, \|47118228\|gb\|AAT11218.1\|truncated, \|47118218\|gb\|AAT11209.1\|truncated, \|46849854\|gb\|AAS97976.2\|, \|46451810\|gb\|AAS98022.1\|, \|46451808\|gb\|AAS98021.1\|, \|46451806\|gb\|AAS98020.1\|, \|46451803\|gb\|AAS98019.1\|, \|46451801\|gb\|AAS98018.1\|, \|46451799\|gb\|AAS98017.1\|, \|46451796\|gb\|AAS98016.1\|, \|46451794\|gb\|AAS98015.1\|, \|46451792\|gb\|AAS98014.1\|, \|46451790\|gb\|AAS98013.1\|, \|46451788\|gb\|AAS98012.1\|, \|46451786\|gb\|AAS98011.1\|, \|46451784\|gb\|AAS98010.1\|, \|46451782\|gb\|AAS98009.1\|, \|46451780\|gb\|AAS98008.1\|, \|46451778\|gb\|AAS98007.1\|, \|46451776\|gb\|AAS98006.1\|, \|46451774\|gb\|AAS98005.1\|, \|46451772\|gb\|AAS98004.1\|, \|46451770\|gb\|AAS98003.1\|, \|46451768\|gb\|AAS98002.1\|, \|46451766\|gb\|AAS98001.1\|, \|46451764\|gb\|AAS98000.1\|, \|46451762\|gb\|AAS97999.1\|, \|46451760\|gb\|AAS97998.1\|, \|46451758\|gb\|AAS97997.1\|, \|46451756\|gb\|AAS97996.1\|, \|46451754\|gb\|AAS97995.1\|, \|46451752\|gb\|AAS97994.1\|, \|46451751\|gb\|AAS97993.1\|, \|46451748\|gb\|AAS97992.1\|, \|46451745\|gb\|AAS97991.1\|, \|46451743\|gb\|AAS97990.1\|, \|46451741\|gb\|AAS97989.1\|, \|46451739\|gb\|AAS97988.1\|, \|46451737\|gb\|AAS97987.1\|, \|46451735\|gb\|AAS97986.1\|, \|46451733\|gb\|AAS97985.1\|, \|46451731\|gb\|AAS97984.1\|, \|46451729\|gb\|AAS97983.1\|, \|46451726\|gb\|AAS97982.1\|, \|46451723\|gb\|AAS97981.1\|, \|46451720\|gb\|AAS97980.1\|, \|46451718\|gb\|AAS97979.1\|, \|46451716\|gb\|AAS97978.1\|, \|46451714\|gb\|AAS97977.1\|, \|46451710\|gb\|AAS97975.1\|, \|46451708\|gb\|AAS97974.1\|, \|37956596\|gb\|AAO92596.1\|, \|33641499\|gb\|AAQ24311.1\|, \|33641497\|gb\|AAQ24310.1\|, \|33641493\|gb\|AAQ24309.1\|, \|33641491\|gb\|AAQ24308.1\|, \|33641489\|gb\|AAQ24307.1\|, \|33641487\|gb\|AAQ24306.1\|, \|33641485\|gb\|AAQ24305.1\|, \|33641483\|gb\|AAQ24304.1\|, \|33641481\|gb\|AAQ24303.1\|, \|33641479\|gb\|AAQ24302.1\|, \|33641477\|gb\|AAQ24301.1\|, \|33641475\|gb\|AAQ24300.1\|, \|33641473\|gb\|AAQ24299.1\|, \|33641471\|gb\|AAQ24298.1\|, \|33641467\|gb\|AAQ24297.1\|, \|33641465\|gb\|AAQ24296.1\|, \|33641463\|gb\|AAQ24295.1\|, \|33641461\|gb\|AAQ24294.1\|, \|33641459\|gb\|AAQ24293.1\|, \|33641457\|gb\|AAQ24292.1\|, \|33641455\|gb\|AAQ24291.1\|, \|33641452\|gb\|AAQ24290.1\|, \|16755651\|gb\|AAL28063.1\|, \|30575565\|gb\|AAP32904.1\|, \|30575563\|gb\|AAP32903.1\|, \|30575561\|gb\|AAP32902.1\|, \|30575559\|gb\|AAP32901.1\|, \|30575557\|gb\|AAP32900.1\|, \|30575555\|gb\|AAP32899.1\|, \|30575553\|gb\|AAP32898.1\|, \|30575551\|gb\|AAP32897.1\|, \|30575548\|gb\|AAP32895.1\|, \|30575542\|gb\|AAP32894.1\|, \|30575540\|gb\|AAP32893.1\|, \|30575538\|gb\|AAP32892.1\|, \|30575536\|gb\|AAP32891.1\|, \|30575534\|gb\|AAP32890.1\|, \|30575531\|gb\|AAP32889.1\|, \|30575529\|gb\|AAP32888.1\|, \|30575527\|gb\|AAP32887.1\|, \|30575525\|gb\|AAP32886.1\|, \|30575523\|gb\|AAP32885.1\|, \|30575521\|gb\|AAP32884.1\|, \|30575519\|gb\|AAP32883.1\|, \|30575517\|gb\|AAP32882.1\|, \|30575515\|gb\|AAP32881.1\|, \|30575513\|gb\|AAP32880.1\|, \|30575511\|gb\|AAP32879.1\|, \|30575508\|gb\|AAP32878.1\|, \|30575504\|gb\|AAP32877.1\|, \|30575502\|gb\|AAP32876.1\|, \|30575500\|gb\|AAP32875.1\|, \|30575498\|gb\|AAP32874.1\|, |

-continued

| VPR proteins |
|---|
| |30575496|gb|AAP32873.1|, |30575494|gb|AAP32872.1|, |30575492|gb|AAP32871.1|, |30575490|gb|AAP32870.1|, |32261510|gb|AAP76570.1| truncated, |32261503|gb|AAP76564.1|, |32261493|gb|AAP76555.1|, |32261483|gb|AAP76546.1|, |32261473|gb|AAP76537.1|, |32261457|gb|AAP76522.1|, |34500810|gb|AAQ73893.1|, |34500808|gb|AAQ73892.1|, |34500806|gb|AAQ73891.1|, |34500803|gb|AAQ73890.1|, |34500800|gb|AAQ73889.1|, |34500796|gb|AAQ73888.1|, |34500794|gb|AAQ73887.1|, |34500792|gb|AAQ73886.1|, |34500790|gb|AAQ73885.1|, |34500788|gb|AAQ73884.1|, |34500786|gb|AAQ73883.1|, |34500784|gb|AAQ73882.1|, |34500782|gb|AAQ73881.1|, |34500780|gb|AAQ73880.1|, |34500778|gb|AAQ73879.1|, |34500776|gb|AAQ73878.1|, |34500774|gb|AAQ73877.1|, |34500772|gb|AAQ73876.1|, |34500770|gb|AAQ73875.1|, |34500768|gb|AAQ73874.1|, |34500766|gb|AAQ73873.1|, |34500763|gb|AAQ73872.1|, |34500760|gb|AAQ73871.1|, |34500758|gb|AAQ73870.1|, |34500755|gb|AAQ73869.1|, |34500753|gb|AAQ73868.1|, |34500751|gb|AAQ73867.1|, |34500747|gb|AAQ73865.1|, |34500745|gb|AAQ73864.1|, |34500740|gb|AAQ73862.1|, |34500738|gb|AAQ73861.1|, |34500736|gb|AAQ73860.1|, |34500734|gb|AAQ73859.1|, |34500732|gb|AAQ73858.1|, |34500730|gb|AAQ73857.1|, |34500724|gb|AAQ73856.1|, |34500721|gb|AAQ73855.1|, |34500719|gb|AAQ73854.1|, |34500717|gb|AAQ73853.1|, |34500715|gb|AAQ73852.1|, |34500713|gb|AAQ73851.1|, |34500710|gb|AAQ73850.1|, |34500708|gb|AAQ73849.1|, |34500706|gb|AAQ73848.1|, |34500704|gb|AAQ73847.1|, |33359205|gb|AAQ17032.1|, |32724999|gb|AAM93867.2|, |32724997|gb|AAM93864.2|, |32724995|gb|AAM93825.2|, |32724993|gb|AAM93816.2|, |32724991|gb|AAM93805.2|, |32724989|gb|AAM93801.2|, |32724987|gb|AAM93795.2|, |32724985|gb|AAM93794.2|, |31087655|gb|AAM93800.1|, |31087653|gb|AAM93799.1|, |31087651|gb|AAM93798.1|, |31087649|gb|AAM93797.1|, |31087646|gb|AAM93796.1|, |31087640|gb|AAM93793.1|, |31087638|gb|AAM93792.1|, |31087636|gb|AAM93791.1|, |31087634|gb|AAM93790.1|, |31087632|gb|AAM93789.1|, |31087630|gb|AAM93870.1|, |31087628|gb|AAM93869.1|, |31087626|gb|AAM93868.1|, |31087622|gb|AAM93866.1|, |31087620|gb|AAM93865.1|, |31087615|gb|AAM93863.1|, |31087613|gb|AAM93862.1|, |31087611|gb|AAM93861.1|, |31087609|gb|AAM93860.1|, |31087490|gb|AAM93836.1|, |31087488|gb|AAM93835.1|, |31087486|gb|AAM93834.1|, |31087484|gb|AAM93833.1|, |31087482|gb|AAM93832.1|, |31087480|gb|AAM93831.1|, |31087478|gb|AAM93830.1|, |31087476|gb|AAM93829.1|, |31087474|gb|AAM93828.1|, |31087472|gb|AAM93827.1|, |31087469|gb|AAM93826.1|, |31087465|gb|AAM93824.1|, |31087463|gb|AAM93823.1|, |31087460|gb|AAM93822.1|, |31087458|gb|AAM93821.1|, |31087456|gb|AAM93820.1|, |31087451|gb|AAM93819.1|, |31087449|gb|AAM93818.1|, |31087447|gb|AAM93817.1|, |31087441|gb|AAM93806.1|, |31087437|gb|AAM93804.1|, |31087435|gb|AAM93803.1|, |31087433|gb|AAM93802.1|, |31087728|gb|AAM93905.1|, |31087726|gb|AAM93904.1|, |31087724|gb|AAM93903.1|, |31087722|gb|AAM93902.1|, |31087720|gb|AAM93901.1|, |31087718|gb|AAM93900.1|, |31087716|gb|AAM93899.1|, |31087714|gb|AAM93898.1|, |31087712|gb|AAM93897.1|, |31087710|gb|AAM93896.1|, |31087708|gb|AAM93895.1|, |31087706|gb|AAM93894.1|, |31087704|gb|AAM93893.1|, |31087702|gb|AAM93892.1|, |31087700|gb|AAM93891.1|, |31087698|gb|AAM93890.1|, |31087696|gb|AAM93889.1|, |31087694|gb|AAM93888.1|, |31087692|gb|AAM93887.1|, |31087690|gb|AAM93886.1|, |31087687|gb|AAM93885.1|, |31087685|gb|AAM93884.1|, |31087683|gb|AAM93883.1|, |31087681|gb|AAM93882.1|, |31087679|gb|AAM93881.1|, |31087677|gb|AAM93880.1|, |31087675|gb|AAM93879.1|, |31087673|gb|AAM93878.1|, |31087671|gb|AAM93877.1|, |31087669|gb|AAM93876.1|, |31087667|gb|AAM93875.1|, |31087665|gb|AAM93874.1|, |31087663|gb|AAM93873.1|, |31087661|gb|AAM93872.1|, |31087659|gb|AAM93871.1|, |31087607|gb|AAM93773.1|, |31087605|gb|AAM93772.1|, |31087603|gb|AAM93771.1|, |31087601|gb|AAM93770.1|, |31087599|gb|AAM93769.1|, |31087596|gb|AAM93768.1|, |31087594|gb|AAM93767.1|, |31087592|gb|AAM93766.1|, |31087590|gb|AAM93765.1|, |31087588|gb|AAM93764.1|, |31087586|gb|AAM93763.1|, |31087584|gb|AAM93762.1|, |31087582|gb|AAM93761.1|, |31087580|gb|AAM93760.1|, |31087578|gb|AAM93759.1|, |31087576|gb|AAM93758.1|, |31087574|gb|AAM93757.1|, |31087537|gb|AAM93859.1|, |31087535|gb|AAM93858.1|, |31087533|gb|AAM93857.1|, |31087531|gb|AAM93856.1|, |31087529|gb|AAM93855.1|, |31087527|gb|AAM93854.1|, |31087525|gb|AAM93853.1|, |31087523|gb|AAM93852.1|, |31087521|gb|AAM93851.1|, |31087519|gb|AAM93850.1|, |31087517|gb|AAM93849.1|, |31087514|gb|AAM93848.1|, |31087512|gb|AAM93847.1|, |31087510|gb|AAM93846.1|, |31087508|gb|AAM93845.1|, |31087506|gb|AAM93844.1|, |31087504|gb|AAM93843.1|, |31087502|gb|AAM93842.1|, |31087500|gb|AAM93841.1|, |31087498|gb|AAM93840.1|, |31087496|gb|AAM93839.1|, |31087494|gb|AAM93838.1|, |31087492|gb|AAM93837.1|, |31087430|gb|AAM93814.1|, |31087428|gb|AAM93813.1|, |31087426|gb|AAM93812.1|, |31087424|gb|AAM93811.1|, |31087422|gb|AAM93810.1|, |31087420|gb|AAM93809.1|, |31087418|gb|AAM93808.1|, |31087416|gb|AAM93807.1|, |31087409|gb|AAM93815.1|, |30351032|gb|AAP22706.1|, |30351030|gb|AAP22705.1|, |30351028|gb|AAP22704.1|, |30351026|gb|AAP22703.1|, |30351024|gb|AAP22702.1|, |30351022|gb|AAP22701.1|, |30351020|gb|AAP22700.1|, |30351018|gb|AAP22699.1|, |30351016|gb|AAP22698.1|, |30351014|gb|AAP22697.1|, |30351012|gb|AAP22696.1|, |30351010|gb|AAP22695.1|, |30351008|gb|AAP22694.1|, |30351006|gb|AAP22693.1|, |30351004|gb|AAP22692.1|, |30351002|gb|AAP22691.1|, |30351000|gb|AAP22690.1|, |30350998|gb|AAP22689.1|, |30350996|gb|AAP22688.1|, |30350994|gb|AAP22687.1|, |30350992|gb|AAP22686.1|, |30350990|gb|AAP22685.1|, |30350988|gb|AAP22684.1|, |30350986|gb|AAP22683.1|, |30350984|gb|AAP22682.1|, |30350982|gb|AAP22681.1|, |30350980|gb|AAP22680.1|, |30350978|gb|AAP22679.1|, |30350976|gb|AAP22678.1|, |30350974|gb|AAP22677.1|, |30350972|gb|AAP22676.1|, |30350970|gb|AAP22675.1|, |30350968|gb|AAP22674.1|, |30350966|gb|AAP22673.1|, |30350964|gb|AAP22672.1|, |30350962|gb|AAP22671.1|, |30350960|gb|AAP22670.1|, |30350958|gb|AAP22669.1|, |30350956|gb|AAP22668.1|, |30350954|gb|AAP22667.1|, |

| VPR proteins |
| --- |
| \|30350952\|gb\|AAP22666.1\|, \|30350950\|gb\|AAP22665.1\|, \|30350948\|gb\|AAP22664.1\|, \|30350946\|gb\|AAP22663.1\|, \|30350944\|gb\|AAP22662.1\|, \|30350942\|gb\|AAP22661.1\|, \|30350940\|gb\|AAP22660.1\|, \|30350938\|gb\|AAP22659.1\|, \|30350936\|gb\|AAP22658.1\|, \|30350934\|gb\|AAP22657.1\|, \|30350932\|gb\|AAP22656.1\|, \|30350930\|gb\|AAP22655.1\|, \|30350928\|gb\|AAP22654.1\|, \|26245477\|gb\|AAN77405.1\|, \|26245467\|gb\|AAN77396.1\|, \|26245457\|gb\|AAN77387.1\|, \|1478065\|gb\|AAB51144.1\|, \|27885102\|gb\|AAF97045.4\|, \|27885100\|gb\|AAF97041.1\|, \|22141040\|gb\|AAF97037.2\|, \|9664258\|gb\|AAF97044.1\|, \|9664256\|gb\|AAF97043.1\|, \|9664254\|gb\|AAF97042.1\|, \|9664250\|gb\|AAF97040.1\|, \|9664246\|gb\|AAF97038.1\|mutant, \|9664242\|gb\|AAF97036.1\|, \|9664240\|gb\|AAF97035.1\|mutant, \|23954674\|gb\|AAN40128.1\|, \|23954672\|gb\|AAN40127.1\|, \|23954670\|gb\|AAN40126.1\|, \|23954668\|gb\|AAN40125.1\|, \|23954666\|gb\|AAN40124.1\|, \|23954664\|gb\|AAN40123.1\|, \|23954662\|gb\|AAN40122.1\|, \|23954660\|gb\|AAN40121.1\|, \|23954658\|gb\|AAN40120.1\|, \|23954656\|gb\|AAN40119.1\|, \|23954654\|gb\|AAN40118.1\|, \|23954652\|gb\|AAN40117.1\|, \|23954650\|gb\|AAN40116.1\|, \|23954648\|gb\|AAN40115.1\|, \|23954646\|gb\|AAN40114.1\|, \|23954642\|gb\|AAN40112.1\|, \|23954640\|gb\|AAN40111.1\|, \|23954638\|gb\|AAN40110.1\|, \|23954636\|gb\|AAN40109.1\|, \|23954634\|gb\|AAN40108.1\|, \|23954632\|gb\|AAN40107.1\|, \|23954630\|gb\|AAN40106.1\|, \|23954628\|gb\|AAN40105.1\|, \|23954626\|gb\|AAN40104.1\|, \|23954622\|gb\|AAN40102.1\|, \|23954620\|gb\|AAN40101.1\|, \|23954618\|gb\|AAN40100.1\|, \|23954616\|gb\|AAN40099.1\|, \|23954614\|gb\|AAN40098.1\|, \|23954612\|gb\|AAN40097.1\|, \|23954610\|gb\|AAN40096.1\|, \|23954608\|gb\|AAN40095.1\|, \|23954606\|gb\|AAN40094.1\|, \|23954604\|gb\|AAN40093.1\|, \|23954602\|gb\|AAN40092.1\|, \|23954600\|gb\|AAN40091.1\|, \|23954598\|gb\|AAN40090.1\|, \|23954596\|gb\|AAN40089.1\|, \|23954594\|gb\|AAN40088.1\|, \|23954592\|gb\|AAN40087.1\|, \|23954590\|gb\|AAN40086.1\|, \|23954588\|gb\|AAN40085.1\|, \|23954586\|gb\|AAN40084.1\|, \|23954584\|gb\|AAN40083.1\|, \|23954582\|gb\|AAN40082.1\|, \|23954580\|gb\|AAN40081.1\|, \|6690780\|gb\|AAF24339.1\|AF197341_6, \|6690774\|gb\|AAF24333.1\|AF197340_7, \|6690767\|gb\|AAF24326.1\|AF197339_5, \|6690760\|gb\|AAF24319.1\|AF197338_7, \|17981627\|gb\|AAL51097.1\|, \|1495983\|gb\|AAB06260.1\|, \|1495978\|gb\|AAB06257.1\|, \|1495975\|gb\|AAB06255.1\|, \|1495972\|gb\|AAB06253.1\|, \|1495969\|gb\|AAB06251.1\|, \|1495966\|gb\|AAB06249.1\|, \|1495963\|gb\|AAB06247.1\|, \|1495960\|gb\|AAB06245.1\|, \|1495957\|gb\|AAB06243.1\|, \|1495954\|gb\|AAB06241.1\|, \|1469314\|gb\|AAB05050.1\|, \|1263019\|gb\|AAB05098.1\|, \|328657\|gb\|AAA80325.1\|, \|469246\|gb\|AAA44865.1\|, \|56200052\|gb\|AAM10883.2\|, \|30410842\|gb\|AAM10902.2\|, \|29029458\|gb\|AAM10899.2\|, \|27885082\|gb\|AAM10877.2\|, \|27885080\|gb\|AAM10853.2\|, \|27777706\|gb\|AAM10913.2\|, \|24967273\|gb\|AAM10856.2\|, \|22858662\|gb\|AAN05831.1\|, \|22858660\|gb\|AAN05830.1\|, \|22858658\|gb\|AAN05829.1\|, \|22858656\|gb\|AAN05828.1\|, \|22858654\|gb\|AAN05827.1\|, \|22858652\|gb\|AAN05826.1\|, \|22858650\|gb\|AAN05825.1\|, \|22858648\|gb\|AAN05824.1\|, \|22858646\|gb\|AAN05823.1\|, \|22858644\|gb\|AAN05822.1\|, \|22858642\|gb\|AAN05821.1\|, \|22858640\|gb\|AAN05820.1\|, \|22858638\|gb\|AAN05819.1\|, \|22858636\|gb\|AAN05818.1\|, \|22858633\|gb\|AAN05817.1\|, \|22858630\|gb\|AAN05816.1\|, \|22858628\|gb\|AAN05815.1\|, \|22858626\|gb\|AAN05814.1\|, \|22858624\|gb\|AAN05813.1\|, \|22858622\|gb\|AAN05812.1\|, \|22858620\|gb\|AAN05811.1\|, \|22858618\|gb\|AAN05810.1\|, \|22858615\|gb\|AAN05809.1\|, \|22858613\|gb\|AAN05808.1\|, \|22858611\|gb\|AAN05807.1\|, \|22858609\|gb\|AAN05806.1\|, \|22858607\|gb\|AAN05805.1\|, \|22858605\|gb\|AAN05804.1\|, \|22858603\|gb\|AAN05803.1\|, \|22858601\|gb\|AAN05802.1\|, \|22858599\|gb\|AAN05801.1\|, \|22858597\|gb\|AAN05800.1\|, \|22858595\|gb\|AAN05799.1\|, \|22858593\|gb\|AAN05798.1\|, \|22858591\|gb\|AAN05797.1\|, \|22858589\|gb\|AAN05796.1\|, \|22858587\|gb\|AAN05795.1\|, \|22858585\|gb\|AAN05794.1\|, \|22143038\|gb\|AAM10917.2\|, \|20142335\|gb\|AAM10842.2\|, \|20126988\|gb\|AAM10929.1\|, \|20126986\|gb\|AAM10928.1\|, \|20126984\|gb\|AAM10927.1\|, \|20126982\|gb\|AAM10926.1\|, \|20126980\|gb\|AAM10925.1\|, \|20126978\|gb\|AAM10924.1\|, \|20126975\|gb\|AAM10923.1\|, \|20126973\|gb\|AAM10922.1\|, \|20126970\|gb\|AAM10921.1\|, \|20126968\|gb\|AAM10920.1\|, \|20126965\|gb\|AAM10919.1\|, \|20126963\|gb\|AAM10918.1\|, \|20126959\|gb\|AAM10916.1\|, \|20126957\|gb\|AAM10915.1\|, \|20126954\|gb\|AAM10914.1\|, \|20126949\|gb\|AAM10912.1\|, \|20126947\|gb\|AAM10911.1\|, \|20126945\|gb\|AAM10910.1\|, \|20126943\|gb\|AAM10909.1\|, \|20126941\|gb\|AAM10908.1\|, \|20126939\|gb\|AAM10907.1\|, \|20126937\|gb\|AAM10906.1\|, \|20126935\|gb\|AAM10905.1\|, \|20126933\|gb\|AAM10904.1\|, \|20126931\|gb\|AAM10903.1\|, \|20126927\|gb\|AAM10901.1\|, \|20126925\|gb\|AAM10900.1\|, \|20126921\|gb\|AAM10898.1\|, \|20126919\|gb\|AAM10897.1\|, \|20126917\|gb\|AAM10896.1\|, \|20126915\|gb\|AAM10895.1\|, \|20126913\|gb\|AAM10894.1\|, \|20126909\|gb\|AAM10892.1\|, \|20126907\|gb\|AAM10891.1\|, \|20126905\|gb\|AAM10890.1\|, \|20126903\|gb\|AAM10889.1\|, \|20126899\|gb\|AAM10887.1\|, \|20126897\|gb\|AAM10886.1\|, \|20126895\|gb\|AAM10885.1\|, \|20126893\|gb\|AAM10884.1\|, \|20126889\|gb\|AAM10882.1\|, \|20126887\|gb\|AAM10881.1\|, \|20126885\|gb\|AAM10880.1\|, \|20126883\|gb\|AAM10879.1\|, \|20126881\|gb\|AAM10878.1\|, \|20126875\|gb\|AAM10875.1\|, \|20126873\|gb\|AAM10874.1\|, \|20126871\|gb\|AAM10873.1\|, \|20126869\|gb\|AAM10872.1\|, \|20126867\|gb\|AAM10871.1\|, \|20126865\|gb\|AAM10870.1\|, \|20126863\|gb\|AAM10869.1\|, \|20126861\|gb\|AAM10868.1\|, \|20126859\|gb\|AAM10867.1\|, \|20126857\|gb\|AAM10866.1\|, \|20126855\|gb\|AAM10865.1\|, \|20126853\|gb\|AAM10864.1\|, \|20126851\|gb\|AAM10863.1\|, \|20126849\|gb\|AAM10862.1\|, \|20126847\|gb\|AAM10861.1\|, \|20126845\|gb\|AAM10860.1\|, \|20126843\|gb\|AAM10859.1\|, \|20126841\|gb\|AAM10858.1\|, \|20126839\|gb\|AAM10857.1\|, \|20126835\|gb\|AAM10855.1\|, \|20126833\|gb\|AAM10854.1\|, \|20126828\|gb\|AAM10852.1\|, \|20126826\|gb\|AAM10851.1\|, \|20126824\|gb\|AAM10850.1\|, \|20126822\|gb\|AAM10849.1\|, \|20126820\|gb\|AAM10848.1\|, \|20126818\|gb\|AAM10847.1\|, \|20126816\|gb\|AAM10846.1\|, \|20126814\|gb\|AAM10845.1\|, \|20126812\|gb\|AAM10844.1\|, \|20126810\|gb\|AAM10843.1\|, \|20126806\|gb\|AAM10841.1\|, \|20126804\|gb\|AAM10840.1\|, \|20126802\|gb\|AAM10839.1\|, \|20126800\|gb\|AAM10838.1\|, \|20126798\|gb\|AAM10837.1\|, \|16118401\|gb\|AAL12764.1\|, \|16118391\|gb\|AAL12755.1\|, \|16118381\|gb\|AAL12746.1\|, \|16118371\|gb\|AAL12737.1\|, \|16118357\|gb\|AAL12725.1\|, \|16118347\|gb\|AAL12716.1\|, \|16118335\|gb\|AAL12706.1\|, \|16118318\|gb\|AAL12692.1\|, \|16118308\|gb\|AAL12683.1\|, |

-continued

| VPR proteins |
|---|
| \|16118298\|gb\|AAL12674.1\|, \|16118288\|gb\|AAL12665.1\|, \|16118278\|gb\|AAL12656.1\|, \|16118268\|gb\|AAL12647.1\|, \|16118258\|gb\|AAL12638.1\|, \|45360217\|gb\|AAS59248.1\|, \|45360207\|gb\|AAS59239.1\|, \|45360197\|gb\|AAS59230.1\|, \|45360186\|gb\|AAS59220.1\|, \|45360176\|gb\|AAS59211.1\|, \|45360166\|gb\|AAS59202.1\|, \|45360156\|gb\|AAS59193.1\|, \|45360146\|gb\|AAS59184.1\|, \|82319636\|sp\|Q9QBZ7\|Q9QBZ7__9HIV1, \|82319635\|sp\|Q9QBZ3\|Q9QBZ3__9HIV1, \|82319634\|sp\|Q9QBY9\|Q9QBY9__9HIV1, \|82319633\|sp\|Q9QBY5\|Q9QBY5__9HIV1, \|82319632\|sp\|Q9QBY1\|Q9QBY1__9HIV1, \|82319066\|sp\|Q9IBN2\|Q9IBN2__9HIV1, \|82314771\|sp\|Q90VS7\|Q90VS7__9HIV1, \|82313851\|sp\|Q8UTJ8\|Q8UTJ8__9HIV1, \|82313829\|sp\|Q8UT04\|Q8UT04__9HIV1, \|82309401\|sp\|Q5DID4\|Q5DID4__9HIV1, \|82309245\|sp\|P90297\|P90297__9HIV1, \|82309222\|sp\|P88432\|P88432__9HIV1, \|82308943\|sp\|O41884\|O41884__9HIV1, \|82308858\|sp\|O09529\|O09529__9HIV1, \|82308857\|sp\|O09527\|O09527__9HIV1, \|82308265\|sp\|Q9YPG6\|Q9YPG6__9HIV1, \|82307713\|sp\|Q9WLX9\|Q9WLX9__9HIV1, \|82307712\|sp\|Q9WLX8\|Q9WLX8__9HIV1, \|82307711\|sp\|Q9WLX7\|Q9WLX7__9HIV1, \|82307710\|sp\|Q9WLX6\|Q9WLX6__9HIV1, \|82307709\|sp\|Q9WLX5\|Q9WLX5__9HIV1, \|82307708\|sp\|Q9WLX4\|Q9WLX4__9HIV1, \|82307707\|sp\|Q9WLX3\|Q9WLX3__9HIV1, \|82307706\|sp\|Q9WLX2\|Q9WLX2__9HIV1, \|82307705\|sp\|Q9WLX1\|Q9WLX1__9HIV1, \|82307704\|sp\|Q9WLXO\|Q9WLXO__9HIV1, \|82307703\|sp\|Q9WLW9\|Q9WLW9__9HIV1, \|82307692\|sp\|Q9WLL7\|Q9WLL7__9HIV1, \|82307691\|sp\|Q9WLL6\|Q9WLL6__9HIV1, \|82307223\|sp\|Q9WA35\|Q9WA35__9HIV1, \|82307127\|sp\|Q9W7X3\|Q9W7X3__9HIV1, \|82307126\|sp\|Q9W7X2\|Q9W7X2__9HIV1, \|82307125\|sp\|Q9W7X1\|Q9W7X1__9HIV1, \|82307124\|sp\|Q9W7X0\|Q9W7X0__9HIV1, \|82307121\|sp\|Q9W7U0\|Q9W7U0__9HIV1, \|82306895\|sp\|Q9QRB0\|Q9QRB0__9HIV1, \|82306571\|sp\|Q9QNZ7\|Q9QNZ7__9HIV1, \|82306241\|sp\|Q9QGW1\|Q9QGW1__9HIV1, \|82306240\|sp\|Q9QGW0\|Q9QGW0__9HIV1, \|82306239\|sp\|Q9QGV9\|Q9QGV9__9HIV1, \|82306238\|sp\|Q9QGV8\|Q9QGV8__9HIV1, \|82306237\|sp\|Q9QGV7\|Q9QGV7__9HIV1, \|82306236\|sp\|Q9QGV6\|Q9QGV6__9HIV1, \|82306235\|sp\|Q9QGV5\|Q9QGV5__9HIV1, \|82306234\|sp\|Q9QGV4\|Q9QGV4__9HIV1, \|82306233\|sp\|Q9QGV3\|Q9QGV3__9HIV1, \|82306232\|sp\|Q9QGV2\|Q9QGV2__9HIV1, \|82306231\|sp\|Q9QGV1\|Q9QGV1__9HIV1, \|82306230\|sp\|Q9QGV0\|Q9QGV0__9HIV1, \|82306229\|sp\|Q9QGU9\|Q9QGU9__9HIV1, \|82306228\|sp\|Q9QGU8\|Q9QGU8__9HIV1, \|82306227\|sp\|Q9QGU7\|Q9QGU7__9HIV1, \|82306226\|sp\|Q9QGU6\|Q9QGU6__9HIV1, \|82306225\|sp\|Q9QGU5\|Q9QGU5__9HIV1, \|82306224\|sp\|Q9QGU4\|Q9QGU4__9HIV1, \|82306223\|sp\|Q9QGU3\|Q9QGU3__9HIV1, \|82306222\|sp\|Q9QGU2\|Q9QGU2__9HIV1, \|82306221\|sp\|Q9QGU1\|Q9QGU1__9HIV1, \|82306220\|sp\|Q9QGU0\|Q9QGU0__9HIV1, \|82306219\|sp\|Q9QGT9\|Q9QGT9__9HIV1, \|82306218\|sp\|Q9QGT8\|Q9QGT8__9HIV1, \|82306217\|sp\|Q9QGT7\|Q9QGT7__9HIV1, \|82306216\|sp\|Q9QGT6\|Q9QGT6__9HIV1, \|82305876\|sp\|Q9Q6I3\|Q9Q6I3__9HIV1, \|82305874\|sp\|Q9Q6H7\|Q9Q6H7__9HIV1, \|82305873\|sp\|Q9Q6H0\|Q9Q6H0__9HIV1, \|82305872\|sp\|Q9Q6G4\|Q9Q6G4__9HIV1, \|82305416\|sp\|Q9JE93\|Q9JE93__9HIV1, \|82305415\|sp\|Q9JE92\|Q9JE92__9HIV1, \|82305414\|sp\|Q9JE91\|Q9JE91__9HIV1, \|82305413\|sp\|Q9JE90\|Q9JE90__9HIV1, \|82305412\|sp\|Q9JE89\|Q9JE89__9HIV1, \|82305411\|sp\|Q9JE88\|Q9JE88__9HIV1, \|82305410\|sp\|Q9JE87\|Q9JE87__9HIV1, \|82305409\|sp\|Q9JE86\|Q9JE86__9HIV1, \|82305047\|sp\|Q9IR18\|Q9IR18__9HIV1, \|82305046\|sp\|Q9IR17\|Q9IR17__9HIV1, \|82305045\|sp\|Q9IR16\|Q9IR16__9HIV1, \|82305044\|sp\|Q9IR15\|Q9IR15__9HIV1, \|82305043\|sp\|Q9IR14\|Q9IR14__9HIV1, \|82305042\|sp\|Q9IR13\|Q9IR13__9HIV1, \|82305041\|sp\|Q9IR12\|Q9IR12__9HIV1, \|82305040\|sp\|Q9IR11\|Q9IR11__9HIV1, \|82305039\|sp\|Q9IR10\|Q9IR10__9HIV1, \|82305038\|sp\|Q9IR09\|Q9IR09__9HIV1, \|82305037\|sp\|Q9IR08\|Q9IR08__9HIV1, \|82305036\|sp\|Q9IR07\|Q9IR07__9HIV1, \|82305035\|sp\|Q9IR06\|Q9IR06__9HIV1, \|82305034\|sp\|Q9IR05\|Q9IR05__9HIV1, \|82305033\|sp\|Q9IR04\|Q9IR04__9HIV1, \|82305032\|sp\|Q9IR03\|Q9IR03__9HIV1, \|82305031\|sp\|Q9IR02\|Q9IR02__9HIV1, \|82305030\|sp\|Q9IR01\|Q9IR01__9HIV1, \|82305029\|sp\|Q9IR00\|Q9IR00__9HIV1, \|82305028\|sp\|Q9IQZ9\|Q9IQZ9__9HIV1, \|82305027\|sp\|Q9IQZ8\|Q9IQZ8__9HIV1, \|82305026\|sp\|Q9IQZ7\|Q9IQZ7__9HIV1, \|82305025\|sp\|Q9IQZ6\|Q9IQZ6__9HIV1, \|82305024\|sp\|Q9IQZ5\|Q9IQZ5__9HIV1, \|82305023\|sp\|Q9IQZ4\|Q9IQZ4__9HIV1, \|82305022\|sp\|Q9IQZ3\|Q9IQZ3__9HIV1, \|82305021\|sp\|Q9IQZ2\|Q9IQZ2__9HIV1, \|82305020\|sp\|Q9IQZ1\|Q9IQZ1__9HIV1, \|82305019\|sp\|Q9IQZ0\|Q9IQZ0__9HIV1, \|82305018\|sp\|Q9IQY9\|Q9IQY9__9HIV1, \|82305017\|sp\|Q9IQY8\|Q9IQY8__9HIV1, \|82305016\|sp\|Q9IQY7\|Q9IQY7__9HIV1, \|82305015\|sp\|Q9IQY6\|Q9IQY6__9HIV1, \|82305014\|sp\|Q9IQY5\|Q9IQY5__9HIV1, \|82305013\|sp\|Q9IQY4\|Q9IQY4__9HIV1, \|82305012\|sp\|Q9IQY3\|Q9IQY3__9HIV1, \|82305011\|sp\|Q9IQY2\|Q9IQY2__9HIV1, \|82305010\|sp\|Q9IQY1\|Q9IQY1__9HIV1, \|82305009\|sp\|Q9IQY0\|Q9IQY0__9HIV1, \|82305008\|sp\|Q9IQX9\|Q9IQX9__9HIV1, \|82305007\|sp\|Q9IQX8\|Q9IQX8__9HIV1, \|82305006\|sp\|Q9IQX7\|Q9IQX7__9HIV1, \|82305005\|sp\|Q9IQX6\|Q9IQX6__9HIV1, \|82305004\|sp\|Q9IQX5\|Q9IQX5__9HIV1, \|82305003\|sp\|Q9IQX4\|Q9IQX4__9HIV1, \|82305002\|sp\|Q9IQX3\|Q9IQX3__9HIV1, \|82305001\|sp\|Q9IQX2\|Q9IQX2__9HIV1, \|82305000\|sp\|Q9IQX1\|Q9IQX1__9HIV1, \|82304999\|sp\|Q9IQX0\|Q9IQX0__9HIV1, \|82304998\|sp\|Q9IQW9\|Q9IQW9__9HIV1, \|82304669\|sp\|Q9ICH2\|Q9ICH2__9HIV1, \|82303504\|sp\|Q9DQV2\|Q9DQV2__9HIV1, \|82303503\|sp\|Q9DQV1\|Q9DQV1__9HIV1, \|82303502\|sp\|Q9DQV0\|Q9DQV0__9HIV1, \|82303501\|sp\|Q9DQU9\|Q9DQU9__9HIV1, \|82303500\|sp\|Q9DQU8\|Q9DQU8__9HIV1, \|82303499\|sp\|Q9DQU7\|Q9DQU7__9HIV1, \|82303498\|sp\|Q9DQU6\|Q9DQU6__9HIV1, \|82303497\|sp\|Q9DQU5\|Q9DQU5__9HIV1, \|82303496\|sp\|Q9DQU4\|Q9DQU4__9HIV1, \|82303495\|sp\|Q9DQU3\|Q9DQU3__9HIV1, \|82303494\|sp\|Q9DQU2\|Q9DQU2__9HIV1, \|82303493\|sp\|Q9DQU1\|Q9DQU1__9HIV1, \|82303492\|sp\|Q9DQU0\|Q9DQU0__9HIV1, \|82303491\|sp\|Q9DQT9\|Q9DQT9__9HIV1, \|82303490\|sp\|Q9DQT8\|Q9DQT8__9HIV1, \|82303489\|sp\|Q9DQT7\|Q9DQT7__9HIV1, \|82303488\|sp\|Q9DQT6\|Q9DQT6__9HIV1, \|82303487\|sp\|Q9DQT5\|Q9DQT5__9HIV1, \|82303486\|sp\|Q9DQT4\|Q9DQT4__9HIV1, |

| VPR proteins |
|---|
| \|82303485\|sp\|Q9DQT3\|Q9DQT3__9HIV1, \|82303484\|sp\|Q9DQT2\|Q9DQT2__9HIV1, |
| \|82303483\|sp\|Q9DQT1\|Q9DQT1__9HIV1, \|82303482\|sp\|Q9DQT0\|Q9DQT0__9HIV1, |
| \|82303481\|sp\|Q9DQS9\|Q9DQS9__9HIV1, \|82303480\|sp\|Q9DQS8\|Q9DQS8__9HIV1, |
| \|82303479\|sp\|Q9DQS7\|Q9DQS7__9HIV1, \|82303478\|sp\|Q9DQS6\|Q9DQS6__9HIV1, |
| \|82303477\|sp\|Q9DQS5\|Q9DQS5__9HIV1, \|82303476\|sp\|Q9DQS4\|Q9DQS4__9HIV1, |
| \|82303475\|sp\|Q9DQS3\|Q9DQS3__9HIV1, \|82303474\|sp\|Q9DQS2\|Q9DQS2__9HIV1, |
| \|82303473\|sp\|Q9DQS1\|Q9DQS1__9HIV1, \|82303472\|sp\|Q9DQS0\|Q9DQS0__9HIV1, |
| \|82303471\|sp\|Q9DQR9\|Q9DQR9__9HIV1, \|82303470\|sp\|Q9DQR8\|Q9DQR8__9HIV1, |
| \|82303469\|sp\|Q9DQR7\|Q9DQR7__9HIV1, \|82303468\|sp\|Q9DQR6\|Q9DQR6__9HIV1, |
| \|82303467\|sp\|Q9DQR5\|Q9DQR5__9HIV1, \|82303466\|sp\|Q9DQR4\|Q9DQR4__9HIV1, |
| \|82303465\|sp\|Q9DQR3\|Q9DQR3__9HIV1, \|82303464\|sp\|Q9DQR2\|Q9DQR2__9HIV1, |
| \|82303463\|sp\|Q9DQR1\|Q9DQR1__9HIV1, \|82303462\|sp\|Q9DQR0\|Q9DQR0__9HIV1, |
| \|82303461\|sp\|Q9DQQ9\|Q9DQQ9__9HIV1, \|82303460\|sp\|Q9DQQ8\|Q9DQQ8__9HIV1, |
| \|82303459\|sp\|Q9DQQ7\|Q9DQQ7__9HIV1, \|82303458\|sp\|Q9DQQ6\|Q9DQQ6__9HIV1, |
| \|82303457\|sp\|Q9DQQ5\|Q9DQQ5__9HIV1, \|82303456\|sp\|Q9DQQ4\|Q9DQQ4__9HIV1, |
| \|82303455\|sp\|Q9DQQ3\|Q9DQQ3__9HIV1, \|82303454\|sp\|Q9DQQ2\|Q9DQQ2__9HIV1, |
| \|82303453\|sp\|Q9DQQ1\|Q9DQQ1__9HIV1, \|82303452\|sp\|Q9DQQ0\|Q9DQQ0__9HIV1, |
| \|82303451\|sp\|Q9DQP9\|Q9DQP9__9HIV1, \|82303450\|sp\|Q9DQP8\|Q9DQP8__9HIV1, |
| \|82303449\|sp\|Q9DQP7\|Q9DQP7__9HIV1, \|82303448\|sp\|Q9DQP6\|Q9DQP6__9HIV1, |
| \|82303447\|sp\|Q9DQP5\|Q9DQP5__9HIV1, \|82303446\|sp\|Q9DQP4\|Q9DQP4__9HIV1, |
| \|82303445\|sp\|Q9DQP3\|Q9DQP3__9HIV1, \|82303444\|sp\|Q9DQP2\|Q9DQP2__9HIV1, |
| \|82303443\|sp\|Q9DQP1\|Q9DQP1__9HIV1, \|82303442\|sp\|Q9DQP0\|Q9DQP0__9HIV1, |
| \|82303441\|sp\|Q9DQN9\|Q9DQN9__9HIV1, \|82303440\|sp\|Q9DQN8\|Q9DQN8__9HIV1, |
| \|82303439\|sp\|Q9DQN7\|Q9DQN7__9HIV1, \|82303228\|sp\|Q9DKG5\|Q9DKG5__9HIV1, |
| \|82303226\|sp\|Q9DKF7\|Q9DKF7__9HIV1, \|82303224\|sp\|Q9DKE9\|Q9DKE9__9HIV1, |
| \|82303222\|sp\|Q9DKE1\|Q9DKE1__9HIV1, \|82303220\|sp\|Q9DKD2\|Q9DKD2__9HIV1, |
| \|82302500\|sp\|Q99BZ6\|Q99BZ6__9HIV1, \|82302338\|sp\|Q994C4\|Q994C4__9HIV1, |
| \|82302336\|sp\|Q994B5\|Q994B5__9HIV1, \|82302334\|sp\|Q994A6\|Q994A6__9HIV1, |
| \|82301507\|sp\|Q97014\|Q97014__9HIV1, \|82301506\|sp\|Q97012\|Q97012__9HIV1, |
| \|82301505\|sp\|Q97010\|Q97010__9HIV1, \|82301504\|sp\|Q97007\|Q97007__9HIV1, |
| \|82301503\|sp\|Q97005\|Q97005__9HIV1, \|82300512\|sp\|Q90DD4\|Q90DD4__9HIV1, |
| \|82300079\|sp\|Q909R2\|Q909R2__9HIV1, \|82299983\|sp\|Q908N0\|Q908N0__9HIV1, |
| \|82299981\|sp\|Q908M1\|Q908M1__9HIV1, \|82299979\|sp\|Q908L2\|Q908L2__9HIV1, |
| \|82299977\|sp\|Q908K3\|Q908K3__9HIV1, \|82299975\|sp\|Q908J4\|Q908J4__9HIV1, |
| \|82299973\|sp\|Q908I5\|Q908I5__9HIV1, \|82299971\|sp\|Q908H6\|Q908H6__9HIV1, |
| \|82299269\|sp\|Q8UTT8\|Q8UTT8__9HIV1, \|82299267\|sp\|Q8UTS9\|Q8UTS9__9HIV1, |
| \|82299265\|sp\|Q8UTS0\|Q8UTS0__9HIV1, \|82299263\|sp\|Q8UTR1\|Q8UTR1__9HIV1, |
| \|82299261\|sp\|Q8UTQ2\|Q8UTQ2__9HIV1, \|82299259\|sp\|Q8UTP3\|Q8UTP3__9HIV1, |
| \|82299257\|sp\|Q8UTN4\|Q8UTN4__9HIV1, \|82299255\|sp\|Q8UTM5\|Q8UTM5__9HIV1, |
| \|82299253\|sp\|Q8UTL6\|Q8UTL6__9HIV1, \|82299251\|sp\|Q8UTK7\|Q8UTK7__9HIV1, |
| \|82299248\|sp\|Q8UTI9\|Q8UTI9__9HIV1, \|82299246\|sp\|Q8UTI0\|Q8UTI0__9HIV1, |
| \|82299244\|sp\|Q8UTH1\|Q8UTH1__9HIV1, |
| \|82299242\|sp\|Q8UTG2\|Q8UTG2__9HIV1, \|82299240\|sp\|Q8UTF3\|Q8UTF3__9HIV1, |
| \|82299237\|sp\|Q8UTE4\|Q8UTE4__9HIV1, \|82299235\|sp\|Q8UTD5\|Q8UTD5__9HIV1, |
| \|82299233\|sp\|Q8UTC6\|Q8UTC6__9HIV1, \|82299231\|sp\|Q8UTB7\|Q8UTB7__9HIV1, |
| \|82299229\|sp\|Q8UTA8\|Q8UTA8__9HIV1, \|82299227\|sp\|Q8UT99\|Q8UT99__9HIV1, |
| \|82299224\|sp\|Q8UT90\|Q8UT90__9HIV1, \|82299222\|sp\|Q8UT81\|Q8UT81__9HIV1, |
| \|82299220\|sp\|Q8UT72\|Q8UT72__9HIV1, \|82299218\|sp\|Q8UT63\|Q8UT63__9HIV1, |
| \|82299216\|sp\|Q8UT54\|Q8UT54__9HIV1, \|82299214\|sp\|Q8UT45\|Q8UT45__9HIV1, |
| \|82299212\|sp\|Q8UT36\|Q8UT36__9HIV1, \|82299210\|sp\|Q8UT27\|Q8UT27__9HIV1, |
| \|82299208\|sp\|Q8UT18\|Q8UT18__9HIV1, \|82299206\|sp\|Q8UT09\|Q8UT09__9HIV1, |
| \|82299204\|sp\|Q8USZ5\|Q8USZ5__9HIV1, \|82299202\|sp\|Q8USY6\|Q8USY6__9HIV1, |
| \|82299200\|sp\|Q8USX7\|Q8USX7__9HIV1, \|82299198\|sp\|Q8USW8\|Q8USW8__9HIV1, |
| \|82299196\|sp\|Q8USV9\|Q8USV9__9HIV1, \|82299194\|sp\|Q8USV0\|Q8USV0__9HIV1, |
| \|82299192\|sp\|Q8USU1\|Q8USU1__9HIV1, \|82299190\|sp\|Q8UST2\|Q8UST2__9HIV1, |
| \|82299188\|sp\|Q8USS3\|Q8USS3__9HIV1, \|82299014\|sp\|Q8UNF4\|Q8UNF4__9HIV1, |
| \|82295688\|sp\|Q8AFF2\|Q8AFF2__9HIV1, \|82295686\|sp\|Q8AFE3\|Q8AFE3__9HIV1, |
| \|82295684\|sp\|Q8AFD4\|Q8AFD4__9HIV1, \|82293903\|sp\|Q80I62\|Q80I62__9HIV1, |
| \|82292064\|sp\|Q7SP79\|Q7SP79__9HIV1, \|82292063\|sp\|Q7SP78\|Q7SP78__9HIV1, |
| \|82292062\|sp\|Q7SP77\|Q7SP77__9HIV1, \|82292061\|sp\|Q7SP76\|Q7SP76__9HIV1, |
| \|82292060\|sp\|Q7SP75\|Q7SP75__9HIV1, \|82292059\|sp\|Q7SP74\|Q7SP74__9HIV1, |
| \|82292058\|sp\|Q7SP73\|Q7SP73__9HIV1, \|82292057\|sp\|Q7SP72\|Q7SP72__9HIV1, |
| \|82292056\|sp\|Q7SP71\|Q7SP71__9HIV1, \|82292055\|sp\|Q7SP70\|Q7SP70__9HIV1, |
| \|82292054\|sp\|Q7SP69\|Q7SP69__9HIV1, \|82292053\|sp\|Q7SP68\|Q7SP68__9HIV1, |
| \|82292052\|sp\|Q7SP67\|Q7SP67__9HIV1, \|82292051\|sp\|Q7SP66\|Q7SP66__9HIV1, |
| \|82292050\|sp\|Q7SP65\|Q7SP65__9HIV1, \|82292049\|sp\|Q7SP64\|Q7SP64__9HIV1, |
| \|82292048\|sp\|Q7SP63\|Q7SP63__9HIV1, \|82292047\|sp\|Q7SP62\|Q7SP62__9HIV1, |
| \|82292046\|sp\|Q7SP61\|Q7SP61__9HIV1, \|82292045\|sp\|Q7SP60\|Q7SP60__9HIV1, |
| \|82292044\|sp\|Q7SP59\|Q7SP59__9HIV1, \|82292043\|sp\|Q7SP58\|Q7SP58__9HIV1, |
| \|82292042\|sp\|Q7SP57\|Q7SP57__9HIV1, \|82292041\|sp\|Q7SP56\|Q7SP56__9HIV1, |
| \|82292040\|sp\|Q7SP55\|Q7SP55__9HIV1, \|82292039\|sp\|Q7SP54\|Q7SP54__9HIV1, |
| \|82292038\|sp\|Q7SP53\|Q7SP53__9HIV1, \|82292037\|sp\|Q7SP52\|Q7SP52__9HIV1, |
| \|82292036\|sp\|Q7SP51\|Q7SP51__9HIV1, \|82292035\|sp\|Q7SP50\|Q7SP50__9HIV1, |
| \|82292034\|sp\|Q7SP49\|Q7SP49__9HIV1, \|82292033\|sp\|Q7SP48\|Q7SP48__9HIV1, |
| \|82292032\|sp\|Q7SP47\|Q7SP47__9HIV1, \|82292031\|sp\|Q7SP46\|Q7SP46__9HIV1, |
| \|82292030\|sp\|Q7SP45\|Q7SP45__9HIV1, \|82292029\|sp\|Q7SP44\|Q7SP44__9HIV1, |
| \|82292028\|sp\|Q7SP43\|Q7SP43__9HIV1, \|82292027\|sp\|Q7SP42\|Q7SP42__9HIV1, |

| VPR proteins |
| --- |
| \|82292026\|sp\|Q7SP41\|Q7SP41__9HIV1, \|82292025\|sp\|Q7SP40\|Q7SP40__9HIV1, \|82292024\|sp\|Q7SP39\|Q7SP39__9HIV1, \|82292023\|sp\|Q7SP38\|Q7SP38__9HIV1, \|82292022\|sp\|Q7SP37\|Q7SP37__9HIV1, \|82292021\|sp\|Q7SP36\|Q7SP36__9HIV1, \|82292020\|sp\|Q7SP35\|Q7SP35__9HIV1, \|82292019\|sp\|Q7SP34\|Q7SP34__9HIV1, \|82292018\|sp\|Q7SP33\|Q7SP33__9HIV1, \|82292017\|sp\|Q7SP32\|Q7SP32__9HIV1, \|82292016\|sp\|Q7SP31\|Q7SP31__9HIV1, \|82292015\|sp\|Q7SP30\|Q7SP30__9HIV1, \|82292014\|sp\|Q7SP29\|Q7SP29__9HIV1, \|82292013\|sp\|Q7SP28\|Q7SP28__9HIV1, \|82292012\|sp\|Q7SP27\|Q7SP27__9HIV1, \|82292011\|sp\|Q7SP26\|Q7SP26__9HIV1, \|82292010\|sp\|Q7SP25\|Q7SP25__9HIV1, \|82292009\|sp\|Q7SP24\|Q7SP24__9HIV1, \|82292008\|sp\|Q7SP23\|Q7SP23__9HIV1, \|82292007\|sp\|Q7SP22\|Q7SP22__9HIV1, \|82292006\|sp\|Q7SP21\|Q7SP21__9HIV1, \|82292005\|sp\|Q7SP20\|Q7SP20__9HIV1, \|82292004\|sp\|Q7SP19\|Q7SP19__9HIV1, \|82292003\|sp\|Q7SP18\|Q7SP18__9HIV1, \|82292002\|sp\|Q7SP17\|Q7SP17__9HIV1, \|82292001\|sp\|Q7SP16\|Q7SP16__9HIV1, \|82292000\|sp\|Q7SP15\|Q7SP15__9HIV1, \|82291999\|sp\|Q7SP14\|Q7SP14__9HIV1, \|82291998\|sp\|Q7SP13\|Q7SP13__9HIV1, \|82291997\|sp\|Q7SP12\|Q7SP12__9HIV1, \|82291996\|sp\|Q7SP11\|Q7SP11__9HIV1, \|82291995\|sp\|Q7SP10\|Q7SP10__9HIV1, \|82291994\|sp\|Q7SP09\|Q7SP09__9HIV1, \|82291993\|sp\|Q7SP08\|Q7SP08__9HIV1, \|82291992\|sp\|Q7SP07\|Q7SP07__9HIV1, \|82291991\|sp\|Q7SP06\|Q7SP06__9HIV1, \|82291990\|sp\|Q7SP05\|Q7SP05__9HIV1, \|82291989\|sp\|Q7SP04\|Q7SP04__9HIV1, \|82291988\|sp\|Q7SP03\|Q7SP03__9HIV1, \|82291987\|sp\|Q7SP02\|Q7SP02__9HIV1, \|82291986\|sp\|Q7SP01\|Q7SP01__9HIV1, \|82291985\|sp\|Q7SP00\|Q7SP00__9HIV1, \|82291984\|sp\|Q7SNZ9\|Q7SNZ9__9HIV1, \|82291983\|sp\|Q7SNZ8\|Q7SNZ8__9HIV1, \|82291982\|sp\|Q7SNZ7\|Q7SNZ7__9HIV1, \|82291981\|sp\|Q7SNZ6\|Q7SNZ6__9HIV1, \|82291980\|sp\|Q7SNZ5\|Q7SNZ5__9HIV1, \|82291979\|sp\|Q7SNZ4\|Q7SNZ4__9HIV1, \|82291978\|sp\|Q7SNZ3\|Q7SNZ3__9HIV1, \|82291977\|sp\|Q7SNZ2\|Q7SNZ2__9HIV1, \|82291976\|sp\|Q7SNZ1\|Q7SNZ1__9HIV1, \|82291975\|sp\|Q7SNZ0\|Q7SNZ0__9HIV1, \|82291974\|sp\|Q7SNY9\|Q7SNY9__9HIV1, \|82291973\|sp\|Q7SNY8\|Q7SNY8__9HIV1, \|82291972\|sp\|Q7SNY7\|Q7SNY7__9HIV1, \|82291971\|sp\|Q7SNY6\|Q7SNY6__9HIV1, \|82291970\|sp\|Q7SNY5\|Q7SNY5__9HIV1, \|82291969\|sp\|Q7SNY4\|Q7SNY4__9HIV1, \|82291968\|sp\|Q7SNY3\|Q7SNY3__9HIV1, \|82291967\|sp\|Q7SNY2\|Q7SNY2__9HIV1, \|82291966\|sp\|Q7SNY1\|Q7SNY1__9HIV1, \|82291965\|sp\|Q7SNY0\|Q7SNY0__9HIV1, \|82291964\|sp\|Q7SNX9\|Q7SNX9__9HIV1, \|82291963\|sp\|Q7SNX8\|Q7SNX8__9HIV1, \|82291962\|sp\|Q7SNX7\|Q7SNX7__9HIV1, \|82291961\|sp\|Q7SNX6\|Q7SNX6__9HIV1, \|82291960\|sp\|Q7SNX5\|Q7SNX5__9HIV1, \|82291959\|sp\|Q7SNX4\|Q7SNX4__9HIV1, \|82291958\|sp\|Q7SNX3\|Q7SNX3__9HIV1, \|82291957\|sp\|Q7SNX2\|Q7SNX2__9HIV1, \|82291956\|sp\|Q7SNX1\|Q7SNX1__9HIV1, \|82291955\|sp\|Q7SNX0\|Q7SNX0__9HIV1, \|82291954\|sp\|Q7SNW9\|Q7SNW9__9HIV1, \|82291953\|sp\|Q7SNW8\|Q7SNW8__9HIV1, \|82291952\|sp\|Q7SNW7\|Q7SNW7__9HIV1, \|82291951\|sp\|Q7SNW6\|Q7SNW6__9HIV1, \|82291950\|sp\|Q7SNW5\|Q7SNW5__9HIV1, \|82291949\|sp\|Q7SNW4\|Q7SNW4__9HIV1, \|82291948\|sp\|Q7SNW3\|Q7SNW3__9HIV1, \|82291947\|sp\|Q7SNW2\|Q7SNW2__9HIV1, \|82291946\|sp\|Q7SNW1\|Q7SNW1__9HIV1, \|82291409\|sp\|Q7SIK4\|Q7SIK4__9HIV1, \|82291408\|sp\|Q7SIK3\|Q7SIK3__9HIV1, \|82291407\|sp\|Q7SIJ9\|Q7SIJ9__9HIV1, \|82291406\|sp\|Q7SIJ7\|Q7SIJ7__9HIV1, \|82291405\|sp\|Q7SIJ6\|Q7SIJ6__9HIV1, \|82291404\|sp\|Q7SIJ4\|Q7SIJ4__9HIV1, \|82291402\|sp\|Q7SIJ9\|Q7SIJ9__9HIV1, \|82291400\|sp\|Q7SII5\|Q7SII5__9HIV1, \|82291399\|sp\|Q7SII0\|Q7SII0__9HIV1, \|82291398\|sp\|Q7SIH9\|Q7SIH9__9HIV1, \|82291395\|sp\|Q7SIH4\|Q7SIH4__9HIV1, \|82291330\|sp\|Q79786\|Q79786__9HIV1, \|82291220\|sp\|Q79671\|Q79671__9HIV1, \|82290630\|sp\|Q77YS9\|Q77YS9__9HIV1, \|82289769\|sp\|Q76352\|Q76352__9HIV1, \|82289768\|sp\|Q76351\|Q76351__9HIV1, \|82289767\|sp\|Q76350\|Q76350__9HIV1, \|82289766\|sp\|Q76349\|Q76349__9HIV1, \|82289765\|sp\|Q76348\|Q76348__9HIV1, \|82289618\|sp\|Q75640\|Q75640__9HIV1, \|82289617\|sp\|Q75639\|Q75639__9HIV1, \|82289616\|sp\|Q75638\|Q75638__9HIV1, \|82289615\|sp\|Q75637\|Q75637__9HIV1, \|82289614\|sp\|Q75635\|Q75635__9HIV1, \|82289613\|sp\|Q75634\|Q75634__9HIV1, \|82289612\|sp\|Q75633\|Q75633__9HIV1, \|82289611\|sp\|Q75632\|Q75632__9HIV1, \|82289610\|sp\|Q75631\|Q75631__9HIV1, \|82289609\|sp\|Q75630\|Q75630__9HIV1, \|82289608\|sp\|Q75629\|Q75629__9HIV1, \|82289607\|sp\|Q75628\|Q75628__9HIV1, \|82289606\|sp\|Q75627\|Q75627__9HIV1, \|82289605\|sp\|Q75626\|Q75626__9HIV1, \|82289604\|sp\|Q75625\|Q75625__9HIV1, \|82289603\|sp\|Q75624\|Q75624__9HIV1, \|82289602\|sp\|Q75623\|Q75623__9HIV1, \|82289601\|sp\|Q75622\|Q75622__9HIV1, \|82289600\|sp\|Q75621\|Q75621__9HIV1, \|82289551\|sp\|Q75148\|Q75148__9HIV1, \|82289550\|sp\|Q75147\|Q75147__9HIV1, \|82289549\|sp\|Q75146\|Q75146__9HIV1, \|82289548\|sp\|Q75145\|Q75145__9HIV1, \|82289547\|sp\|Q75144\|Q75144__9HIV1, \|82289546\|sp\|Q75143\|Q75143__9HIV1, \|82289545\|sp\|Q75142\|Q75142__9HIV1, \|82289544\|sp\|Q75141\|Q75141__9HIV1, \|82289543\|sp\|Q75140\|Q75140__9HIV1, \|82289542\|sp\|Q75139\|Q75139__9HIV1, \|82289541\|sp\|Q75138\|Q75138__9HIV1, \|82289540\|sp\|Q75137\|Q75137__9HIV1, \|82289539\|sp\|Q75136\|Q75136__9HIV1, \|82289538\|sp\|Q75135\|Q75135__9HIV1, \|82289537\|sp\|Q75134\|Q75134__9HIV1, \|82289536\|sp\|Q75133\|Q75133__9HIV1, \|82289535\|sp\|Q75132\|Q75132__9HIV1, \|82289534\|sp\|Q75131\|Q75131__9HIV1, \|82289472\|sp\|Q74750\|Q74750__9HIV1, \|82289396\|sp\|Q74460\|Q74460__9HIV1, \|82288892\|sp\|Q72745\|Q72745__9HIV1, \|82288578\|sp\|Q71957\|Q71957__9HIV1, \|82288577\|sp\|Q71956\|Q71956__9HIV1, \|82288576\|sp\|Q71955\|Q71955__9HIV1, \|82288575\|sp\|Q71954\|Q71954__9HIV1, \|82288574\|sp\|Q71953\|Q71953__9HIV1, \|82288573\|sp\|Q71952\|Q71952__9HIV1, \|82288572\|sp\|Q71951\|Q71951__9HIV1, \|82288571\|sp\|Q71950\|Q71950__9HIV1, \|82288570\|sp\|Q71949\|Q71949__9HIV1, \|82288076\|sp\|Q70203\|Q70203__9HIV1, \|82288061\|sp\|Q70151\|Q70151__9HIV1, \|82288060\|sp\|Q70146\|Q70146__9HIV1, \|82287862\|sp\|Q6X0I1\|Q6X0I1__9HIV1, \|82287861\|sp\|Q6X0I0\|Q6X0I0__9HIV1, |

| VPR proteins |
|---|
| |82287860|sp|Q6X0H9|Q6X0H9__9HIV1, |82287859|sp|Q6X0H8|Q6X0H8__9HIV1, |82287858|sp|Q6X0H7|Q6X0H7__9HIV1, |82287857|sp|Q6X0H6|Q6X0H6__9HIV1, |82287856|sp|Q6X0H5|Q6X0H5__9HIV1, |82287855|sp|Q6X0H4|Q6X0H4__9HIV1, |82287854|sp|Q6X0H2|Q6X0H2__9HIV1, |82287853|sp|Q6X0H1|Q6X0H1__9HIV1, |82287852|sp|Q6X0G9|Q6X0G9__9HIV1, |82287851|sp|Q6X0G7|Q6X0G7__9HIV1, |82287850|sp|Q6X0G6|Q6X0G6__9HIV1, |82287849|sp|Q6X0G5|Q6X0G5__9HIV1, |82287848|sp|Q6X0G4|Q6X0G4__9HIV1, |82287847|sp|Q6X0G3|Q6X0G3__9HIV1, |82287846|sp|Q6X0G2|Q6X0G2__9HIV1, |82287845|sp|Q6X0G1|Q6X0G1__9HIV1, |82287844|sp|Q6X0G0|Q6X0G0__9HIV1, |82287843|sp|Q6X0F9|Q6X0F9__9HIV1, |82286786|sp|Q6TEB1|Q6TEB1__9HIV1, |82286784|sp|Q6TEA2|Q6TEA2__9HIV1, |82286782|sp|Q6TE93|Q6TE93__9HIV1, |82286780|sp|Q6TE84|Q6TE84__9HIV1, |82286778|sp|Q6TE75|Q6TE75__9HIV1, |82286776|sp|Q6TE66|Q6TE66__9HIV1, |82286774|sp|Q6TE57|Q6TE57__9HIV1, |82285546|sp|Q6QJ03|Q6QJ03__9HIV1, |82285545|sp|Q6QJ02|Q6QJ02__9HIV1, |82285544|sp|Q6QJ01|Q6QJ01__9HIV1, |82285543|sp|Q6QJ00|Q6QJ00__9HIV1, |82285542|sp|Q6QIZ9|Q6QIZ9__9HIV1, |82285541|sp|Q6QIZ8|Q6QIZ8__9HIV1, |82284710|sp|Q6EK52|Q6EK52__9HIV1, |82284709|sp|Q6EK36|Q6EK36__9HIV1, |82284708|sp|Q6EJZ6|Q6EJZ6__9HIV1, |82284707|sp|Q6EJW4|Q6EJW4__9HIV1, |82284706|sp|Q6EJU0|Q6EJU0__9HIV1, |82284705|sp|Q6EJT2|Q6EJT2__9HIV1, |82284704|sp|Q6EJQ8|Q6EJQ8__9HIV1, |82284674|sp|Q6E6V3|Q6E6V3__9HIV1, |82283785|sp|Q66Q69|Q66Q69__9HIV1, |82283343|sp|Q5VCV6|Q5VCV6__9HIV1, |82283341|sp|Q5VCU8|Q5VCU8__9HIV1, |82283339|sp|Q5VCU1|Q5VCU1__9HIV1, |82283336|sp|Q5VCS7|Q5VCS7__9HIV1, |82283211|sp|Q5S5C8|Q5S5C8__9HIV1, |82283210|sp|Q5S5C0|Q5S5C0__9HIV1, |82283209|sp|Q5S5B2|Q5S5B2__9HIV1, |82283208|sp|Q5S5A0|Q5S5A0__9HIV1, |82283207|sp|Q5S592|Q5S592__9HIV1, |82281650|sp|P90286|P90286__9HIV1, |82281649|sp|P90285|P90285__9HIV1, |82281648|sp|P90284|P90284__9HIV1, |82281647|sp|P90281|P90281__9HIV1, |82281646|sp|P90280|P90280__9HIV1, |82281645|sp|P90279|P90279__9HIV1, |82281592|sp|P89824|P89824__9HIV1, |82281591|sp|P89820|P89820__9HIV1, |82281275|sp|P88435|P88435__9HIV1, |82281274|sp|P88433|P88433__9HIV1, |82281273|sp|P88431|P88431__9HIV1, |82281272|sp|P88430|P88430__9HIV1, |82281271|sp|P88429|P88429__9HIV1, |82281270|sp|P88428|P88428__9HIV1, |82281269|sp|P88427|P88427__9HIV1, |82281179|sp|O93014|O93014__9HIV1, |82281178|sp|O93013|O93013__9HIV1, |82281177|sp|O93012|O93012__9HIV1, |82281176|sp|O93011|O93011__9HIV1, |82281175|sp|O93010|O93010__9HIV1, |82281174|sp|O93009|O93009__9HIV1, |82281161|sp|O92938|O92938__9HIV1, |82281145|sp|O92803|O92803__9HIV1, |82281133|sp|O92772|O92772__9HIV1, |82281132|sp|O92771|O92771__9HIV1, |82280572|sp|O90647|O90647__9HIV1, |82280570|sp|O90645|O90645__9HIV1, |82280569|sp|O90644|O90644__9HIV1, |82280563|sp|O90534|O90534__9HIV1, |82280560|sp|O90531|O90531__9HIV1, |82280558|sp|O90528|O90528__9HIV1, |82280556|sp|O90526|O90526__9HIV1, |82280554|sp|O90524|O90524__9HIV1, |82280553|sp|O90523|O90523__9HIV1, |82280552|sp|O90522|O90522__9HIV1, |82280551|sp|O90521|O90521__9HIV1, |82280546|sp|O90516|O90516__9HIV1, |82280544|sp|O90514|O90514__9HIV1, |82280542|sp|O90512|O90512__9HIV1, |82280541|sp|O90511|O90511__9HIV1, |82280540|sp|O90510|O90510__9HIV1, |82280539|sp|O90509|O90509__9HIV1, |82280535|sp|O90505|O90505__9HIV1, |82280534|sp|O90504|O90504__9HIV1, |82280532|sp|O90502|O90502__9HIV1, |82280530|sp|O90500|O90500__9HIV1, |82280529|sp|O90499|O90499__9HIV1, |82280513|sp|O90179|O90179__9HIV1, |82280484|sp|O90104|O90104__9HIV1 Elongated, |82280482|sp|O90097|O90097__9HIV1, |82280480|sp|O90089|O90089__9HIV1, |82280478|sp|O90080|O90080__9HIV1, |82280476|sp|O90071|O90071__9HIV1, |82280474|sp|O90063|O90063__9HIV1, |82280473|sp|O89964|O89964__9HIV1, |82280472|sp|O89961|O89961__9HIV1, |82280471|sp|O89945|O89945__9HIV1, |82280469|sp|O89938|O89938__9HIV1, |82280467|sp|O89932|O89932__9HIV1, |82280427|sp|O73573|O73573__9HIV1, |82280426|sp|O73570|O73570__9HIV1, |82280314|sp|O72652|O72652__9HIV1, |82280313|sp|O72651|O72651__9HIV1, |82280312|sp|O72650|O72650__9HIV1, |82280311|sp|O72649|O72649__9HIV1, |82280310|sp|O72648|O72648__9HIV1, |82280309|sp|O72647|O72647__9HIV1, |82280308|sp|O72646|O72646__9HIV1, |82280307|sp|O72645|O72645__9HIV1, |82280306|sp|O72644|O72644__9HIV1, |82280305|sp|O72643|O72643__9HIV1, |82280304|sp|O72642|O72642__9HIV1, |82280303|sp|O72640|O72640__9HIV1, |82280302|sp|O72639|O72639__9HIV1, |82280301|sp|O72638|O72638__9HIV1, |82280300|sp|O72637|O72637__9HIV1, |82280299|sp|O72636|O72636__9HIV1, |82280298|sp|O72635|O72635__9HIV1, |82280297|sp|O72634|O72634__9HIV1, |82280296|sp|O72633|O72633__9HIV1, |82280295|sp|O72632|O72632__9HIV1, |82280294|sp|O72631|O72631__9HIV1, |82280293|sp|O72630|O72630__9HIV1, |82280292|sp|O72629|O72629__9HIV1, |82280291|sp|O72628|O72628__9HIV1, |82280290|sp|O72627|O72627__9HIV1, |82280289|sp|O72626|O72626__9HIV1, |82280288|sp|O72625|O72625__9HIV1, |82280287|sp|O72624|O72624__9HIV1, |82280286|sp|O72623|O72623__9HIV1, |82280285|sp|O72622|O72622__9HIV1, |82280284|sp|O72621|O72621__9HIV1, |82279875|sp|O71127|O71127__9HIV1, |82279874|sp|O71126|O71126__9HIV1, |82279873|sp|O71125|O71125__9HIV1, |82279872|sp|O71124|O71124__9HIV1, |82279868|sp|O71087|O71087__9HIV1, |82279867|sp|O71086|O71086__9HIV1, |82279866|sp|O71085|O71085__9HIV1, |82279706|sp|O42068|O42068__9HIV1, |82279630|sp|O40603|O40603__9HIV1, |82279629|sp|O40602|O40602__9HIV1, |82279628|sp|O40601|O40601__9HIV1, |82279627|sp|O40600|O40600__9HIV1, |82279626|sp|O40599|O40599__9HIV1, |

| VPR proteins |
|---|
| \|82279625\|sp\|O40598\|O40598_9HIV1, \|82279624\|sp\|O40597\|O40597_9HIV1, \|82279623\|sp\|O40596\|O40596_9HIV1, \|82279622\|sp\|O40595\|O40595_9HIV1, \|82279621\|sp\|O40594\|O40594_9HIV1, \|82279620\|sp\|O40593\|O40593_9HIV1, \|82279619\|sp\|O40592\|O40592_9HIV1, \|82279618\|sp\|O40591\|O40591_9HIV1, \|82279617\|sp\|O40590\|O40590_9HIV1, \|82279616\|sp\|O40589\|O40589_9HIV1, \|82278692\|sp\|O12165\|O12165_9HIV1, \|74099689\|gb\|AAZ28907.1\|, \|78100208\|gb\|ABB20911.1\|, \|74273487\|gb\|ABA01467.1\|, \|74273478\|gb\|ABA01459.1\|, \|74273468\|gb\|ABA01450.1\|, \|74273457\|gb\|ABA01440.1\|, \|74273449\|gb\|ABA01433.1\|, \|74273439\|gb\|ABA01424.1\|, \|74273429\|gb\|ABA01415.1\|, \|74273419\|gb\|ABA01406.1\|, \|74273409\|gb\|ABA01397.1\|, \|74273399\|gb\|ABA01388.1\|, \|74273389\|gb\|ABA01379.1\|, \|74273370\|gb\|ABA01363.1\|, \|74273366\|gb\|ABA01360.1\|, \|74273344\|gb\|ABA01341.1\|, \|74315787\|gb\|ABA02509.1\|, \|74315777\|gb\|ABA02500.1\|, \|74315767\|gb\|ABA02491.1\|, \|74315757\|gb\|ABA02482.1\|, \|74315747\|gb\|ABA02473.1\|, \|74315730\|gb\|ABA02458.1\|, \|64310552\|gb\|AAY41247.1\|, \|62946408\|gb\|AAY22385.1\|, \|71801570\|gb\|AAZ41740.1\|, \|71801566\|gb\|AAZ41739.1\|, \|71801564\|gb\|AAZ41738.1\|, \|71801562\|gb\|AAZ41737.1\|, \|71801559\|gb\|AAZ41736.1\|, \|71801557\|gb\|AAZ41735.1\|, \|71801555\|gb\|AAZ41734.1\|, \|71801553\|gb\|AAZ41733.1\|, \|71801551\|gb\|AAZ41732.1\|, \|71801549\|gb\|AAZ41731.1\|, \|71801544\|gb\|AAZ41730.1\|, \|71801542\|gb\|AAZ41729.1\|, \|71801540\|gb\|AAZ41728.1\|, \|71801538\|gb\|AAZ41727.1\|, \|71801536\|gb\|AAZ41726.1\|, \|71801534\|gb\|AAZ41725.1\|, \|71801532\|gb\|AAZ41724.1\|, \|71801530\|gb\|AAZ41723.1\|, \|71801528\|gb\|AAZ41722.1\|, \|71801526\|gb\|AAZ41721.1\|, \|71801524\|gb\|AAZ41720.1\|, \|71801522\|gb\|AAZ41719.1\|, \|71801520\|gb\|AAZ41718.1\|, \|71801518\|gb\|AAZ41717.1\|, \|71801516\|gb\|AAZ41716.1\|, \|71801514\|gb\|AAZ41715.1\|, \|71801512\|gb\|AAZ41714.1\|, \|71801510\|gb\|AAZ41713.1\|, \|71801508\|gb\|AAZ41712.1\|, \|71801506\|gb\|AAZ41711.1\|, \|71801504\|gb\|AAZ41710.1\|, \|71801502\|gb\|AAZ41709.1\|, \|71801500\|gb\|AAZ41708.1\|, \|71801497\|gb\|AAZ41707.1\|, \|71801495\|gb\|AAZ41706.1\|, \|71801492\|gb\|AAZ41705.1\|, \|71801490\|gb\|AAZ41704.1\|, \|71801488\|gb\|AAZ41703.1\|, \|71801486\|gb\|AAZ41702.1\|, \|71801484\|gb\|AAZ41701.1\|, \|71801482\|gb\|AAZ41700.1\|, \|71801480\|gb\|AAZ41699.1\|, \|71801478\|gb\|AAZ41698.1\|, \|71801476\|gb\|AAZ41697.1\|, \|71801474\|gb\|AAZ41696.1\|, \|71801472\|gb\|AAZ41695.1\|, \|71801470\|gb\|AAZ41694.1\|, \|71801468\|gb\|AAZ41693.1\|, \|71801466\|gb\|AAZ41692.1\|, \|71801464\|gb\|AAZ41691.1\|, \|71801462\|gb\|AAZ41690.1\|, \|71801460\|gb\|AAZ41689.1\|, \|71801458\|gb\|AAZ41688.1\|, \|71801456\|gb\|AAZ41687.1\|, \|71801454\|gb\|AAZ41686.1\|, \|71801452\|gb\|AAZ41685.1\|, \|71801450\|gb\|AAZ41684.1\|, \|71801448\|gb\|AAZ41683.1\|, \|71801445\|gb\|AAZ41682.1\|, \|71801443\|gb\|AAZ41681.1\|, \|71801441\|gb\|AAZ41680.1\|, \|71801439\|gb\|AAZ41679.1\|, \|71801437\|gb\|AAZ41678.1\|, \|71801434\|gb\|AAZ41677.1\|, \|71801432\|gb\|AAZ41676.1\|, \|71801430\|gb\|AAZ41675.1\|, \|71801428\|gb\|AAZ41674.1\|, \|71801426\|gb\|AAZ41673.1\|, \|71801424\|gb\|AAZ41672.1\|, \|71801420\|gb\|AAZ41671.1\|, \|71801417\|gb\|AAZ41670.1\|, \|71801409\|gb\|AAZ41669.1\|, \|71801407\|gb\|AAZ41668.1\|, \|71801405\|gb\|AAZ41667.1\|, \|71801403\|gb\|AAZ41666.1\|, \|71801401\|gb\|AAZ41665.1\|, \|71801399\|gb\|AAZ41664.1\|, \|71801397\|gb\|AAZ41663.1\|, \|71801395\|gb\|AAZ41662.1\|, \|71801393\|gb\|AAZ41661.1\|, \|71801391\|gb\|AAZ41660.1\|, \|71801389\|gb\|AAZ41659.1\|, \|71801387\|gb\|AAZ41658.1\|, \|71801385\|gb\|AAZ41657.1\|, \|71801383\|gb\|AAZ41656.1\|, \|71801381\|gb\|AAZ41655.1\|, \|71801379\|gb\|AAZ41654.1\|, \|71801377\|gb\|AAZ41653.1\|, \|71801375\|gb\|AAZ41652.1\|, \|71801373\|gb\|AAZ41651.1\|, \|71801371\|gb\|AAZ41650.1\|, \|71801369\|gb\|AAZ41649.1\|, \|71801367\|gb\|AAZ41648.1\|, \|71801365\|gb\|AAZ41647.1\|, \|71801362\|gb\|AAZ41646.1\|, \|71801360\|gb\|AAZ41645.1\|, \|71801357\|gb\|AAZ41644.1\|, \|71801354\|gb\|AAZ41643.1\|, \|71801352\|gb\|AAZ41642.1\|, \|71801350\|gb\|AAZ41641.1\|, \|71801348\|gb\|AAZ41640.1\|, \|71801346\|gb\|AAZ41639.1\|, \|71801343\|gb\|AAZ41638.1\|, \|71801341\|gb\|AAZ41637.1\|, \|71801338\|gb\|AAZ41636.1\|, \|71801334\|gb\|AAZ41635.1\|, \|71801332\|gb\|AAZ41634.1\|, \|71801330\|gb\|AAZ41633.1\|, \|71801328\|gb\|AAZ41632.1\|, \|71801326\|gb\|AAZ41631.1\|, \|71801324\|gb\|AAZ41630.1\|, \|71801322\|gb\|AAZ41629.1\|, \|71801320\|gb\|AAZ41628.1\|, \|71801318\|gb\|AAZ41627.1\|, \|71801316\|gb\|AAZ41626.1\|, \|71801314\|gb\|AAZ41625.1\|, \|71801312\|gb\|AAZ41624.1\|, \|71801310\|gb\|AAZ41623.1\|, \|71801308\|gb\|AAZ41622.1\|, \|71801306\|gb\|AAZ41621.1\|, \|71801304\|gb\|AAZ41620.1\|, \|71801301\|gb\|AAZ41619.1\|, \|71801298\|gb\|AAZ41618.1\|, \|71801296\|gb\|AAZ41617.1\|, \|71801292\|gb\|AAZ41616.1\|, \|71801289\|gb\|AAZ41615.1\|, \|71801287\|gb\|AAZ41614.1\|, \|71801285\|gb\|AAZ41613.1\|, \|71801283\|gb\|AAZ41612.1\|, \|71801281\|gb\|AAZ41611.1\|, \|71801278\|gb\|AAZ41610.1\|, \|71801276\|gb\|AAZ41609.1\|, \|71801273\|gb\|AAZ41608.1\|, \|71801271\|gb\|AAZ41607.1\|, \|71801269\|gb\|AAZ41606.1\|, \|71801267\|gb\|AAZ41605.1\|, \|71801265\|gb\|AAZ41604.1\|, \|71801263\|gb\|AAZ41603.1\|, \|71801260\|gb\|AAZ41602.1\|, \|71801258\|gb\|AAZ41601.1\|, \|71801255\|gb\|AAZ41600.1\|, \|71801252\|gb\|AAZ41599.1\|, \|71801250\|gb\|AAZ41598.1\|, \|71801247\|gb\|AAZ41597.1\|, \|71801245\|gb\|AAZ41596.1\|, \|71801243\|gb\|AAZ41595.1\|, \|71801241\|gb\|AAZ41594.1\|, \|71801239\|gb\|AAZ41593.1\|, \|71801237\|gb\|AAZ41592.1\|, \|71801235\|gb\|AAZ41591.1\|, \|71801233\|gb\|AAZ41590.1\|, \|71801231\|gb\|AAZ41589.1\|, \|71801229\|gb\|AAZ41588.1\|, \|71801226\|gb\|AAZ41587.1\|, \|71801224\|gb\|AAZ41586.1\|, \|71801222\|gb\|AAZ41585.1\|, \|71801219\|gb\|AAZ41584.1\|, \|71801214\|gb\|AAZ41583.1\|, \|71801212\|gb\|AAZ41582.1\|, \|71801210\|gb\|AAZ41581.1\|, \|71801208\|gb\|AAZ41580.1\|, \|71801206\|gb\|AAZ41579.1\|, \|71801204\|gb\|AAZ41578.1\|, \|71801202\|gb\|AAZ41577.1\|, \|71801199\|gb\|AAZ41576.1\|, \|71801197\|gb\|AAZ41575.1\|, \|71801195\|gb\|AAZ41574.1\|, \|71801193\|gb\|AAZ41573.1\|, \|71801191\|gb\|AAZ41572.1\|, \|71801189\|gb\|AAZ41571.1\|, \|71801187\|gb\|AAZ41570.1\|, \|71801185\|gb\|AAZ41569.1\|, \|71801183\|gb\|AAZ41568.1\|, \|71801181\|gb\|AAZ41567.1\|, \|71801179\|gb\|AAZ41566.1\|, \|71801175\|gb\|AAZ41565.1\|, \|71801173\|gb\|AAZ41564.1\|, \|71801171\|gb\|AAZ41563.1\|, \|71801169\|gb\|AAZ41562.1\|, \|71801167\|gb\|AAZ41561.1\|, \|71801165\|gb\|AAZ41560.1\|, \|71801163\|gb\|AAZ41559.1\|, \|71801161\|gb\|AAZ41558.1\|, \|71801159\|gb\|AAZ41557.1\|, \|71801157\|gb\|AAZ41556.1\|, \|71801155\|gb\|AAZ41555.1\|, \|71801153\|gb\|AAZ41554.1\|, \|71801151\|gb\|AAZ41553.1\|, \|71801149\|gb\|AAZ41552.1\|, \|71801147\|gb\|AAZ41551.1\|, |

| VPR proteins |
| --- |
| |71801144|gb|AAZ41550.1|, |71801142|gb|AAZ41549.1|, |71801140|gb|AAZ41548.1|, |71801138|gb|AAZ41547.1|, |71801136|gb|AAZ41546.1|, |71801134|gb|AAZ41545.1|, |71801132|gb|AAZ41544.1|, |71801130|gb|AAZ41543.1|, |71801126|gb|AAZ41542.1|, |71801123|gb|AAZ41541.1|, |71801121|gb|AAZ41540.1|, |71801119|gb|AAZ41539.1|, |71801117|gb|AAZ41538.1|, |71801115|gb|AAZ41537.1|, |71801113|gb|AAZ41536.1|, |71801111|gb|AAZ41535.1|, |71801107|gb|AAZ41534.1|, |71801105|gb|AAZ41533.1|, |71801102|gb|AAZ41532.1|, |71801100|gb|AAZ41531.1|, |71801097|gb|AAZ41530.1|, |71801095|gb|AAZ41529.1|, |71801093|gb|AAZ41528.1|, |71801091|gb|AAZ41527.1|, |71801089|gb|AAZ41526.1|, |71801087|gb|AAZ41525.1|, |71801085|gb|AAZ41524.1|, |71801083|gb|AAZ41523.1|, |71801078|gb|AAZ41522.1|, |71801076|gb|AAZ41521.1|, |71801074|gb|AAZ41520.1|, |71801072|gb|AAZ41519.1|, |71801070|gb|AAZ41518.1|, |71801068|gb|AAZ41517.1|, |71801066|gb|AAZ41516.1|, |71801064|gb|AAZ41515.1|, |71801061|gb|AAZ41514.1|, |71801059|gb|AAZ41513.1|, |71801057|gb|AAZ41512.1|, |71801055|gb|AAZ41511.1|, |71801053|gb|AAZ41510.1|, |71801051|gb|AAZ41509.1|, |71801049|gb|AAZ41508.1|, |71801045|gb|AAZ41507.1|, |71801043|gb|AAZ41506.1|, |71801040|gb|AAZ41505.1|, |71801038|gb|AAZ41504.1|, |71801036|gb|AAZ41503.1|, |71801034|gb|AAZ41502.1|, |71801032|gb|AAZ41501.1|, |71801030|gb|AAZ41500.1|, |71801028|gb|AAZ41499.1|, |71801026|gb|AAZ41498.1|, |71801024|gb|AAZ41497.1|, |71801022|gb|AAZ41496.1|, |71801020|gb|AAZ41495.1|, |71801018|gb|AAZ41494.1|, |71801016|gb|AAZ41493.1|, |71801014|gb|AAZ41492.1|, |71801012|gb|AAZ41491.1|, |71801008|gb|AAZ41490.1|, |71801004|gb|AAZ41489.1|, |71801001|gb|AAZ41488.1|, |71800999|gb|AAZ41487.1|, |71800997|gb|AAZ41486.1|, |71800995|gb|AAZ41485.1|, |71800993|gb|AAZ41484.1|, |71800990|gb|AAZ41483.1|, |71800988|gb|AAZ41482.1|, |71800986|gb|AAZ41481.1|, |71800982|gb|AAZ41480.1|, |71800980|gb|AAZ41479.1|, |71800978|gb|AAZ41478.1|, |71800976|gb|AAZ41477.1|, |71800974|gb|AAZ41476.1|, |71800972|gb|AAZ41475.1|, |71800969|gb|AAZ41474.1|, |71800966|gb|AAZ41473.1|, |71800964|gb|AAZ41472.1|, |71800962|gb|AAZ41471.1|, |71800957|gb|AAZ41470.1|, |71800954|gb|AAZ41469.1|, |71800952|gb|AAZ41468.1|, |71800950|gb|AAZ41467.1|, |71800948|gb|AAZ41466.1|, |71800946|gb|AAZ41465.1|, |71800944|gb|AAZ41464.1|, |71800942|gb|AAZ41463.1|, |71800940|gb|AAZ41462.1|, |71800938|gb|AAZ41461.1|, |71800936|gb|AAZ41460.1|, |71800932|gb|AAZ41459.1|, |71800930|gb|AAZ41458.1|, |71800928|gb|AAZ41457.1|, |71800926|gb|AAZ41456.1|, |71800924|gb|AAZ41455.1|, |71800922|gb|AAZ41454.1|, |71800920|gb|AAZ41453.1|, |71800918|gb|AAZ41452.1|, |71800916|gb|AAZ41451.1|, |71800914|gb|AAZ41450.1|, |71800912|gb|AAZ41449.1|, |71800910|gb|AAZ41448.1|, |71800908|gb|AAZ41447.1|, |71800905|gb|AAZ41446.1|, |71800902|gb|AAZ41445.1|, |71800899|gb|AAZ41444.1|, |71800897|gb|AAZ41443.1|, |71800895|gb|AAZ41442.1|, |71800892|gb|AAZ41441.1|, |71800888|gb|AAZ41440.1|, |71800886|gb|AAZ41439.1|, |71800881|gb|AAZ41438.1|, |71800879|gb|AAZ41437.1|, |71800876|gb|AAZ41436.1|, |71800874|gb|AAZ41435.1|, |71800872|gb|AAZ41434.1|, |71800870|gb|AAZ41433.1|, |71800868|gb|AAZ41432.1|, |71800866|gb|AAZ41431.1|, |71800864|gb|AAZ41430.1|, |71800862|gb|AAZ41429.1|, |71800858|gb|AAZ41428.1|, |71800856|gb|AAZ41427.1|, |71800854|gb|AAZ41426.1|, |71800852|gb|AAZ41425.1|, |71800849|gb|AAZ41424.1|, |71800847|gb|AAZ41423.1|, |71800845|gb|AAZ41422.1|, |71800843|gb|AAZ41421.1|, |71800841|gb|AAZ41420.1|, |71800839|gb|AAZ41419.1|, |71800837|gb|AAZ41418.1|, |71800834|gb|AAZ41417.1|, |71800832|gb|AAZ41416.1|, |71800830|gb|AAZ41415.1|, |71800827|gb|AAZ41414.1|, |71800825|gb|AAZ41413.1|, |71800822|gb|AAZ41412.1|, |71800820|gb|AAZ41411.1|, |71800818|gb|AAZ41410.1|, |71800815|gb|AAZ41409.1|, |71800813|gb|AAZ41408.1|, |71800811|gb|AAZ41407.1|, |71800809|gb|AAZ41406.1|, |71800804|gb|AAZ41405.1|, |71800802|gb|AAZ41404.1|, |71800800|gb|AAZ41403.1|, |71800798|gb|AAZ41402.1|, |71800796|gb|AAZ41401.1|, |71800792|gb|AAZ41400.1|, |71800788|gb|AAZ41399.1|, |71800785|gb|AAZ41398.1|, |71800783|gb|AAZ41397.1|, |71800780|gb|AAZ41396.1|, |71800776|gb|AAZ41395.1|, |71800774|gb|AAZ41394.1|, |71800772|gb|AAZ41393.1|, |71800770|gb|AAZ41392.1|, |71800768|gb|AAZ41391.1|, |71800766|gb|AAZ41390.1|, |71800764|gb|AAZ41389.1|, |71800762|gb|AAZ41388.1|, |71800760|gb|AAZ41387.1|, |71800758|gb|AAZ41386.1|, |71800756|gb|AAZ41385.1|, |57869736|gb|AAW57769.1|, |57869727|gb|AAW57761.1|, |57869718|gb|AAW57753.1|, |57869709|gb|AAW57745.1|, |57869701|gb|AAW57738.1|, |57869691|gb|AAW57729.1|, |57869682|gb|AAW57721.1|, |57869672|gb|AAW57712.1|, |57869662|gb|AAW57703.1|, |57869652|gb|AAW57694.1|, |57869642|gb|AAW57685.1|, |57869633|gb|AAW57677.1|, |57869625|gb|AAW57670.1|, |57869615|gb|AAW57661.1|, |57869606|gb|AAW57653.1|, |57869596|gb|AAW57644.1|, |57869587|gb|AAW57636.1|, |57869577|gb|AAW57627.1|, |57869567|gb|AAW57618.1|, |57869559|gb|AAW57611.1|, |57869550|gb|AAW57603.1|, |18699244|gb|AAL78486.1|AF414005_2, |18699176|gb|AAL78441.1|AF413982_4, |18699168|gb|AAL78434.1|AF413981_1, |18699164|gb|AAL78431.1|AF413980_2, |60218872|gb|AAX14850.1|, |55740262|gb|AAV63833.1|, |55740253|gb|AAV63825.1|, |55740244|gb|AAV63817.1|, |55740234|gb|AAV63808.1|, |45361207|gb|AAS59398.1|, |45361195|gb|AAS59389.1|, |45361174|gb|AAS59378.1|, |45361154|gb|AAS59366.1|, |45361143|gb|AAS59358.1|, |45361131|gb|AAS59349.1|, |45361121|gb|AAS59340.1|, |45361109|gb|AAS59331.1|, |45361097|gb|AAS59322.1|, |45361083|gb|AAS59313.1|, |45361073|gb|AAS59304.1|, |62467722|gb|AAX83975.1|, |62467711|gb|AAX83965.1|, |62467701|gb|AAX83956.1|, |52421751|gb|AAU45387.1|, |52421740|gb|AAU45379.1|, |62467694|gb|AAX83950.1|, |51950728|gb|AAU14920.1|, |51950718|gb|AAU14911.1|, |3724197|emb|CAA77077.1|, |2570005|emb|CAA75393.1|, |2570003|emb|CAA75392.1|, |2570001|emb|CAA75391.1|, |2569999|emb|CAA75390.1|, |2569997|emb|CAA75389.1|, |2569995|emb|CAA75388.1|, |2569993|emb|CAA75387.1|, |60124|emb|CAA44770.1|, |60122|emb|CAA44769.1|, |60120|emb|CAA44768.1|, |60118|emb|CAA44767.1|, |21425747|emb|CAD23405.1|, |21425745|emb|CAD23404.1|, |

| VPR proteins |
| --- |
| \|21425743\|emb\|CAD23403.1\|, \|21425741\|emb\|CAD23402.1\|, \|21425739\|emb\|CAD23401.1\|, \|21425737\|emb\|CAD23400.1\|, \|21425735\|emb\|CAD23399.1\|, \|21425733\|emb\|CAD23398.1\|, \|21425731\|emb\|CAD23397.1\|, \|21425729\|emb\|CAD23396.1\|, \|21425727\|emb\|CAD23395.1\|, \|21425725\|emb\|CAD23394.1\|, \|21425723\|emb\|CAD23393.1\|, \|21425721\|emb\|CAD23392.1\|, \|21425719\|emb\|CAD23391.1\|, \|21425717\|emb\|CAD23390.1\|, \|21425715\|emb\|CAD23389.1\|, \|21425713\|emb\|CAD23388.1\|, \|21425711\|emb\|CAD23387.1\|, \|21425709\|emb\|CAD23386.1\|, \|21425707\|emb\|CAD23385.1\|, \|21425705\|emb\|CAD23384.1\|, \|21425703\|emb\|CAD23383.1\|, \|21425701\|emb\|CAD23382.1\|, \|21425699\|emb\|CAD23381.1\|, \|21425697\|emb\|CAD23380.1\|, \|21425695\|emb\|CAD23379.1\|, \|6093160\|emb\|CAB58991.1\|, \|6093155\|emb\|CAB58987.1\|, \|6093150\|emb\|CAB58983.1\|, \|6093145\|emb\|CAB58979.1\|, \|6093140\|emb\|CAB59010.1\|, \|5763680\|emb\|CAB53243.1\|, \|3288397\|emb\|CAA06817.1\|, \|26000282\|gb\|AAN75315.1\|, \|26000272\|gb\|AAN75306.1\|, \|26000262\|gb\|AAN75297.1\|, \|25167058\|gb\|AAN73824.1\|AF484520__8, \|25167048\|gb\|AAN73815.1\|AF484519__8, \|25167038\|gb\|AAN73806.1\|AF484518__8, \|25167028\|gb\|AAN73797.1\|AF484517__8, \|25167018\|gb\|AAN73788.1\|AF484516__8, \|25167008\|gb\|AAN73779.1\|AF484515__8, \|25166998\|gb\|AAN73770.1\|AF484514__8, \|25166988\|gb\|AAN73761.1\|AF484513__8, \|25166978\|gb\|AAN73752.1\|AF484512__8, \|25166968\|gb\|AAN73743.1\|AF484511__8, \|25166958\|gb\|AAN73734.1\|AF484510__8, \|25166948\|gb\|AAN73725.1\|AF484509__8, \|25166938\|gb\|AAN73716.1\|AF484508__8, \|25166928\|gb\|AAN73707.1\|AF484507__8, \|25166918\|gb\|AAN73698.1\|AF484506__8, \|25166898\|gb\|AAN73680.1\|AF484504__8, \|25166888\|gb\|AAN73671.1\|AF484503__8, \|25166868\|gb\|AAN73653.1\|AF484501__8, \|25166858\|gb\|AAN73644.1\|AF484500__8, \|25166848\|gb\|AAN73635.1\|AF484499__8, \|25166838\|gb\|AAN73626.1\|AF484498__8, \|25166828\|gb\|AAN73617.1\|AF484497__8, \|25166818\|gb\|AAN73608.1\|AF484496__8, \|25166808\|gb\|AAN73599.1\|AF484495__8, \|25166798\|gb\|AAN73590.1\|AF484494__8, \|25166788\|gb\|AAN73581.1\|AF484493__8, \|25166778\|gb\|AAN73572.1\|AF484492__8, \|25166768\|gb\|AAN73563.1\|AF484491__8, \|25166758\|gb\|AAN73554.1\|AF484490__8, \|25166748\|gb\|AAN73545.1\|AF484489__8, \|25166738\|gb\|AAN73536.1\|AF484488__8, \|25166728\|gb\|AAN73527.1\|AF484487__8, \|25166718\|gb\|AAN73518.1\|AF484486__8, \|25166708\|gb\|AAN73509.1\|AF484485__8, \|25166696\|gb\|AAN73499.1\|AF484483__8, \|25166686\|gb\|AAN73490.1\|AF484482__8, \|25166676\|gb\|AAN73481.1\|AF484481__8, \|25166666\|gb\|AAN73472.1\|AF484480__8, \|25166656\|gb\|AAN73463.1\|AF484479__8, \|25166646\|gb\|AAN73454.1\|AF484478__8, \|25166637\|gb\|AAN73446.1\|AF484477__9, \|23194115\|gb\|AAN15023.1\|, \|41353560\|gb\|AAS01347.1\|, \|55736001\|gb\|AAV59729.1\|, \|55735992\|gb\|AAV59721.1\|, \|55735983\|gb\|AAV59713.1\|, \|55735974\|gb\|AAV59705.1\|, \|55735965\|gb\|AAV59697.1\|, \|55735956\|gb\|AAV59689.1\|, \|45644397\|gb\|AAS72951.1\|, \|36365551\|gb\|AAQ86754.1\|, \|36365542\|gb\|AAQ86746.1\|, \|36365533\|gb\|AAQ86738.1\|, \|36365524\|gb\|AAQ86730.1\|, \|36365515\|gb\|AAQ86722.1\|, \|36365506\|gb\|AAQ86714.1\|, \|36365497\|gb\|AAQ86706.1\|, \|36365488\|gb\|AAQ86698.1\|, \|36365479\|gb\|AAQ86690.1\|, \|36365470\|gb\|AAQ86682.1\|, \|36365461\|gb\|AAQ86674.1\|, \|36365452\|gb\|AAQ86666.1\|, \|36365443\|gb\|AAQ86658.1\|, \|36365434\|gb\|AAQ86650.1\|, \|36365425\|gb\|AAQ86642.1\|, \|36365416\|gb\|AAQ86634.1\|, \|36365407\|gb\|AAQ86626.1\|, \|36365398\|gb\|AAQ86618.1\|, \|36365389\|gb\|AAQ86610.1\|, \|36365380\|gb\|AAQ86602.1\|, \|56193031\|gb\|AAV84126.1\|, \|56131608\|gb\|AAV80388.1\|, \|46946866\|gb\|AAT06654.1\|, \|46946850\|gb\|AAT06640.1\|, \|46946842\|gb\|AAT06633.1\|, \|46946833\|gb\|AAT06625.1\|, \|40021889\|gb\|AAR37199.1\|, \|40021879\|gb\|AAR37192.1\|, \|40021869\|gb\|AAR37185.1\|, \|40021859\|gb\|AAR37178.1\|, \|40021849\|gb\|AAR37171.1\|, \|40021839\|gb\|AAR37164.1\|, \|40021829\|gb\|AAR37157.1\|, \|40021819\|gb\|AAR37150.1\|, \|40021809\|gb\|AAR37143.1\|, \|40021799\|gb\|AAR37136.1\|, \|40021789\|gb\|AAR37129.1\|, \|40021779\|gb\|AAR37122.1\|, \|40021769\|gb\|AAR37115.1\|, \|40021759\|gb\|AAR37108.1\|, \|40021749\|gb\|AAR37101.1\|, \|40021739\|gb\|AAR37094.1\|, \|40021729\|gb\|AAR37087.1\|, \|40021719\|gb\|AAR37080.1\|, \|40021709\|gb\|AAR37073.1\|, \|40021699\|gb\|AAR37066.1\|, \|47027396\|gb\|AAT08776.1\|, \|29409334\|gb\|AAM67410.1\|, \|29409322\|gb\|AAM67400.1\|, \|29409307\|gb\|AAM67386.1\|, \|29409303\|gb\|AAM67383.1\|, \|39777442\|gb\|AAR31018.1\|, \|39777432\|gb\|AAR31009.1\|, \|39777422\|gb\|AAR31000.1\|, \|39777412\|gb\|AAR30991.1\|, \|39777402\|gb\|AAR30982.1\|, \|39777392\|gb\|AAR30973.1\|, \|39777382\|gb\|AAR30964.1\|, \|38426984\|gb\|AAR20515.1\|, \|38426982\|gb\|AAR20514.1\|, \|38426980\|gb\|AAR20513.1\|, \|38426978\|gb\|AAR20512.1\|, \|38426976\|gb\|AAR20511.1\|, \|38426974\|gb\|AAR20510.1\|, \|38426972\|gb\|AAR20509.1\|, \|38426970\|gb\|AAR20508.1\|, \|38426968\|gb\|AAR20507.1\|, \|38426966\|gb\|AAR20506.1\|truncated, \|38426964\|gb\|AAR20505.1\|, \|38426962\|gb\|AAR20504.1\|, \|38426960\|gb\|AAR20503.1\|, \|38426958\|gb\|AAR20502.1\|, \|38426956\|gb\|AAR20501.1\|, \|38491944\|gb\|AAR22307.1\|, \|38491934\|gb\|AAR22298.1\|, \|38491923\|gb\|AAR22288.1\|, \|38491914\|gb\|AAR22280.1\|, \|38491907\|gb\|AAR22274.1\|, \|38491897\|gb\|AAR22265.1\|, \|38491888\|gb\|AAR22257.1\|, \|38491878\|gb\|AAR22248.1\|, \|38491868\|gb\|AAR22239.1\|, \|38491858\|gb\|AAR22230.1\|, \|38491849\|gb\|AAR22222.1\|, \|38491839\|gb\|AAR22213.1\|, \|38491829\|gb\|AAR22204.1\|, \|38491819\|gb\|AAR22195.1\|, \|38491809\|gb\|AAR22186.1\|, \|38491799\|gb\|AAR22177.1\|, \|38491789\|gb\|AAR22168.1\|, \|38491779\|gb\|AAR22159.1\|, \|38491769\|gb\|AAR22150.1\|, \|38491762\|gb\|AAR22144.1\|, \|38491752\|gb\|AAR22135.1\|, \|38491742\|gb\|AAR22126.1\|, \|38491731\|gb\|AAR22117.1\|, \|38491721\|gb\|AAR22108.1\|, \|38491711\|gb\|AAR22099.1\|, \|38491695\|gb\|AAR22085.1\|, \|38491676\|gb\|AAR22068.1\|, \|38491666\|gb\|AAR22059.1\|, \|38491656\|gb\|AAR22050.1\|, \|38491646\|gb\|AAR22041.1\|, \|38491636\|gb\|AAR22032.1\|, \|38491626\|gb\|AAR22023.1\|, \|38491613\|gb\|AAR22012.1\|, \|38491603\|gb\|AAR22003.1\|, \|38491594\|gb\|AAR21995.1\|, \|38491584\|gb\|AAR21986.1\|, \|38491574\|gb\|AAR21977.1\|, \|38491564\|gb\|AAR21968.1\|, \|38491554\|gb\|AAR21959.1\|, \|38491544\|gb\|AAR21950.1\|, \|38491534\|gb\|AAR21941.1\|, \|38491527\|gb\|AAR21935.1\|, \|38491508\|gb\|AAR21918.1\|, \|38491498\|gb\|AAR21909.1\|, \|38491488\|gb\|AAR21900.1\|, \|37683045\|gb\|AAQ98601.1\|, \|37683035\|gb\|AAQ98592.1\|, \|37683025\|gb\|AAQ98583.1\|, \|37683015\|gb\|AAQ98574.1\|, \|37683006\|gb\|AAQ98566.1\|, |

| VPR proteins |
|---|
| \|37682996\|gb\|AAQ98557.1\|, \|37682986\|gb\|AAQ98548.1\|, \|37682976\|gb\|AAQ98539.1\|, \|37682966\|gb\|AAQ98530.1\|, \|37682956\|gb\|AAQ98521.1\|, \|37682946\|gb\|AAQ98512.1\|, \|37682936\|gb\|AAQ98503.1\|, \|37682926\|gb\|AAQ98494.1\|, \|37682918\|gb\|AAQ98487.1\|, \|37682908\|gb\|AAQ98478.1\|, \|37682897\|gb\|AAQ98469.1\|, \|37682887\|gb\|AAQ98460.1\|, \|37682869\|gb\|AAQ98446.1\|, \|37682859\|gb\|AAQ98437.1\|, \|37682849\|gb\|AAQ98428.1\|, \|37682839\|gb\|AAQ98419.1\|, \|37682829\|gb\|AAQ98410.1\|, \|37682819\|gb\|AAQ98401.1\|, \|37682809\|gb\|AAQ98392.1\|, \|37682799\|gb\|AAQ98383.1\|, \|37682789\|gb\|AAQ98374.1\|, \|37682779\|gb\|AAQ98365.1\|, \|37682769\|gb\|AAQ98356.1\|, \|37682759\|gb\|AAQ98347.1\|, \|37682749\|gb\|AAQ98338.1\|, \|37682739\|gb\|AAQ98329.1\|, \|37682729\|gb\|AAQ98320.1\|, \|37682719\|gb\|AAQ98311.1\|, \|37682709\|gb\|AAQ98302.1\|, \|33331483\|gb\|AAQ10927.1\|, \|33331473\|gb\|AAQ10918.1\|, \|33331463\|gb\|AAQ10909.1\|, \|44194557\|gb\|AAS46887.1\|, \|44194555\|gb\|AAS46886.1\|, \|44194553\|gb\|AAS46885.1\|, \|44194551\|gb\|AAS46884.1\|, \|44194549\|gb\|AAS46883.1\|, \|44194547\|gb\|AAS46882.1\|, \|44194545\|gb\|AAS46881.1\|, \|4336345\|gb\|AAD17771.1\|, \|4336336\|gb\|AAD17762.1\|, \|22003835\|gb\|AAM88881.1\|, \|22003833\|gb\|AAM88880.1\|, \|22003831\|gb\|AAM88879.1\|, \|22003829\|gb\|AAM88878.1\|, \|22003827\|gb\|AAM88877.1\|, \|22003825\|gb\|AAM88876.1\|, \|22003823\|gb\|AAM88875.1\|, \|22003821\|gb\|AAM88874.1\|, \|22003819\|gb\|AAM88873.1\|, \|22003815\|gb\|AAM88872.1\|, \|22003813\|gb\|AAM88871.1\|, \|22003811\|gb\|AAM88870.1\|, \|37935587\|gb\|AAO65560.1\|, \|37909408\|gb\|AAO65569.1\|, \|37935987\|gb\|AAO47224.1\|, \|37935977\|gb\|AAO47215.1\|, \|37935967\|gb\|AAO47206.1\|, \|37935958\|gb\|AAO47198.1\|, \|37935948\|gb\|AAO47189.1\|, \|37935938\|gb\|AAO47180.1\|, \|37935928\|gb\|AAO47171.1\|, \|37935918\|gb\|AAO47162.1\|, \|37935907\|gb\|AAO47153.1\|, \|37935898\|gb\|AAO47145.1\|, \|37935887\|gb\|AAO47136.1\|, \|37935878\|gb\|AAO47128.1\|, \|37935868\|gb\|AAO47119.1\|, \|37935858\|gb\|AAO47110.1\|, \|37935848\|gb\|AAO47101.1\|, \|30269373\|gb\|AAP29651.1\|, \|37725246\|gb\|AAR02309.1\|, \|34811841\|gb\|AAO40784.1\|, \|32189806\|gb\|AAP75717.1\|, \|28933410\|gb\|AAO62624.1\|AF468970_9, \|23394933\|gb\|AAN31654.1\|, \|23394926\|gb\|AAN31648.1\|, \|33390887\|gb\|AAQ17106.1\|, \|32344854\|gb\|AAM82309.1\|, \|32344844\|gb\|AAM82300.1\|, \|33328328\|gb\|AAQ09617.1\|, \|33328206\|gb\|AAQ09554.1\|, \|33328196\|gb\|AAQ09545.1\|, \|30720414\|gb\|AAP33682.1\|, \|25807938\|gb\|AAN74525.1\|, \|25807928\|gb\|AAN74516.1\|, \|29119350\|gb\|AAO63263.1\|, \|29119337\|gb\|AAO63251.1\|, \|29119332\|gb\|AAO63247.1\|, \|29119323\|gb\|AAO63239.1\|, \|29119313\|gb\|AAO63230.1\|, \|29119304\|gb\|AAO63222.1\|, \|29119294\|gb\|AAO63213.1\|, \|29119284\|gb\|AAO63204.1\|, \|29119274\|gb\|AAO63195.1\|, \|29119262\|gb\|AAO63184.1\|, \|29293587\|gb\|AAO72220.1\|, \|29293585\|gb\|AAO72219.1\|, \|29293583\|gb\|AAO72218.1\|, \|29293581\|gb\|AAO72217.1\|, \|29293578\|gb\|AAO72216.1\|, \|29293576\|gb\|AAO72215.1\|, \|29293573\|gb\|AAO72214.1\|, \|29293571\|gb\|AAO72213.1\|, \|29293569\|gb\|AAO72212.1\|, \|29293567\|gb\|AAO72211.1\|, \|29293564\|gb\|AAO72210.1\|, \|29293562\|gb\|AAO72209.1\|, \|29293560\|gb\|AAO72208.1\|, \|29293558\|gb\|AAO72207.1\|, \|29293556\|gb\|AAO72206.1\|, \|29293554\|gb\|AAO72205.1\|, \|29293552\|gb\|AAO72204.1\|, \|29293550\|gb\|AAO72203.1\|, \|29293548\|gb\|AAO72202.1\|, \|29293546\|gb\|AAO72201.1\|, \|29293544\|gb\|AAO72200.1\|, \|29293542\|gb\|AAO72199.1\|, \|29293540\|gb\|AAO72198.1\|, \|29293538\|gb\|AAO72197.1\|, \|29293536\|gb\|AAO72196.1\|, \|29293532\|gb\|AAO72195.1\|, \|29293530\|gb\|AAO72194.1\|, \|29293528\|gb\|AAO72193.1\|, \|29293526\|gb\|AAO72192.1\|, \|29293524\|gb\|AAO72191.1\|, \|29293522\|gb\|AAO72190.1\|, \|29293519\|gb\|AAO72189.1\|, \|29293517\|gb\|AAO72188.1\|, \|29293511\|gb\|AAO72187.1\|, \|29293509\|gb\|AAO72186.1\|, \|29293507\|gb\|AAO72185.1\|, \|29293505\|gb\|AAO72184.1\|, \|29293503\|gb\|AAO72183.1\|, \|29293501\|gb\|AAO72182.1\|, \|29293499\|gb\|AAO72181.1\|, \|29293497\|gb\|AAO72180.1\|, \|29293495\|gb\|AAO72179.1\|, \|29293493\|gb\|AAO72178.1\|, \|29293491\|gb\|AAO72177.1\|, \|29293489\|gb\|AAO72176.1\|, \|29293487\|gb\|AAO72175.1\|, \|29293485\|gb\|AAO72174.1\|, \|29293483\|gb\|AAO72173.1\|, \|29293480\|gb\|AAO72172.1\|, \|29293478\|gb\|AAO72171.1\|, \|29293476\|gb\|AAO72170.1\|, \|29293474\|gb\|AAO72169.1\|, \|29293472\|gb\|AAO72168.1\|, \|29293470\|gb\|AAO72167.1\|, \|29293468\|gb\|AAO72166.1\|, \|29293466\|gb\|AAO72165.1\|, \|29293464\|gb\|AAO72164.1\|, \|29293460\|gb\|AAO72163.1\|, \|29293458\|gb\|AAO72162.1\|, \|26518645\|gb\|AAN83919.1\|, \|22074615\|gb\|AAL82562.1\|, \|22074598\|gb\|AAL82561.1\|, \|22074595\|gb\|AAL82560.1\|, \|22074593\|gb\|AAL82559.1\|, \|22074590\|gb\|AAL82558.1\|, \|22074586\|gb\|AAL82557.1\|, \|22074582\|gb\|AAL82556.1\|, \|22074577\|gb\|AAL82555.1\|, \|22074572\|gb\|AAL82554.1\|, \|22074565\|gb\|AAL82553.1\|, \|22074561\|gb\|AAL82552.1\|, \|22074557\|gb\|AAL82551.1\|, \|22074554\|gb\|AAL82550.1\|, \|22074550\|gb\|AAL82549.1\|, \|22074546\|gb\|AAL82548.1\|, \|22074542\|gb\|AAL82547.1\|, \|22074539\|gb\|AAL82546.1\|, \|22074535\|gb\|AAL82545.1\|, \|22074529\|gb\|AAL82544.1\|, \|22074520\|gb\|AAL82543.1\|, \|22074458\|gb\|AAL82542.1\|, \|22074454\|gb\|AAL82541.1\|, \|24754012\|gb\|AAN64130.1\|, \|24754002\|gb\|AAN64121.1\|, \|24753991\|gb\|AAN64112.1\|, \|24753980\|gb\|AAN64103.1\|, \|24753969\|gb\|AAN64094.1\|, \|24753958\|gb\|AAN64085.1\|, \|24181516\|gb\|AAN47135.1\|, \|24181506\|gb\|AAN47126.1\|, \|24181496\|gb\|AAN47117.1\|, \|24181486\|gb\|AAN47108.1\|, \|22596582\|gb\|AAN03336.1\|AF457090_9, \|22596572\|gb\|AAN03327.1\|AF457089_9, \|22596562\|gb\|AAN03318.1\|AF457088_9, \|22596552\|gb\|AAN03309.1\|AF457087_9, \|22596542\|gb\|AAN03300.1\|AF457086_9, \|22596532\|gb\|AAN03291.1\|AF457085_9, \|22596522\|gb\|AAN03282.1\|AF457084_9, \|22596512\|gb\|AAN03273.1\|AF457083_9, \|22596502\|gb\|AAN03264.1\|AF457082_9, \|22596492\|gb\|AAN03255.1\|AF457081_9, \|22596482\|gb\|AAN03246.1\|AF457080_9, \|22596472\|gb\|AAN03237.1\|AF457079_9, \|22596462\|gb\|AAN03228.1\|AF457078_9, \|22596452\|gb\|AAN03219.1\|AF457077_9, \|22596439\|gb\|AAN03208.1\|AF457075_9, \|22596427\|gb\|AAN03198.1\|AF457073_9, \|22596417\|gb\|AAN03189.1\|AF457072_9, \|22596406\|gb\|AAN03180.1\|AF457070_9, \|22596396\|gb\|AAN03171.1\|AF457069_9, \|22596386\|gb\|AAN03162.1\|AF457068_9, \|22596376\|gb\|AAN03153.1\|AF457067_9, \|22596366\|gb\|AAN03144.1\|AF457066_9, \|22596356\|gb\|AAN03135.1\|AF457065_9, \|22596346\|gb\|AAN03126.1\|AF457064_9, \|22596336\|gb\|AAN03117.1\|AF457063_9, \|22596326\|gb\|AAN03108.1\|AF457062_9, \|22596316\|gb\|AAN03099.1\|AF457061_9, \|22596306\|gb\|AAN03090.1\|AF457060_4, \|22596301\|gb\|AAN03086.1\|AF457059_9, |

| VPR proteins |
| --- |
| \|22596291\|gb\|AAN03077.1\|AF457058_9, \|22596280\|gb\|AAN03068.1\|AF457056_9, \|22596270\|gb\|AAN03059.1\|AF457055_9, \|22596260\|gb\|AAN03050.1\|AF457054_9, \|22596250\|gb\|AAN03041.1\|AF457053_9, \|22596240\|gb\|AAN03032.1\|AF457052_9, \|22596230\|gb\|AAN03023.1\|AF457051_9, \|20513087\|gb\|AAM21153.1\|, \|2286141\|gb\|AAB64287.1\|, \|2286132\|gb\|AAB64279.1\|, \|17902156\|gb\|AAL47819.1\|, \|17902145\|gb\|AAL47810.1\|, \|17902134\|gb\|AAL47801.1\|, \|17902123\|gb\|AAL47792.1\|, \|17902112\|gb\|AAL47703.1\|, \|17902101\|gb\|AAL47774.1\|, \|17864059\|gb\|AAL47052.1\|, \|17864049\|gb\|AAL47043.1\|, \|17864039\|gb\|AAL47034.1\|, \|22532300\|gb\|AAM97893.1\|AF492624_9, \|22532290\|gb\|AAM97884.1\|AF492623_9, \|22532148\|gb\|AAM97859.1\|AF460974_9, \|22532139\|gb\|AAM97851.1\|AF460972_9, \|22297048\|gb\|AAM94504.1\|, \|902807\|gb\|AAB60579.1\|, \|818223\|gb\|AAB47935.1\|, \|463064\|gb\|AAA99884.1\|, \|328908\|gb\|AAA75023.1\|, \|71726050\|gb\|AAZ39178.1\|, \|71726040\|gb\|AAZ39169.1\|, \|71726030\|gb\|AAZ39160.1\|, \|71726020\|gb\|AAZ39151.1\|, \|71726010\|gb\|AAZ39142.1\|, \|71726000\|gb\|AAZ39133.1\|, \|71725990\|gb\|AAZ39124.1\|, \|71725980\|gb\|AAZ39115.1\|, \|71725970\|gb\|AAZ39106.1\|, \|71725960\|gb\|AAZ39097.1\|, \|83026821\|gb\|ABB96456.1\|, \|83026813\|gb\|ABB96449.1\|, \|83026803\|gb\|ABB96440.1\|, \|83026793\|gb\|ABB96431.1\|, \|83026783\|gb\|ABB96422.1\|, \|62461844\|gb\|AAX83060.1\|, \|82571414\|gb\|ABB84171.1\|, \|82571404\|gb\|ABB84162.1\|, \|82571393\|gb\|ABB84152.1\|, \|82571385\|gb\|ABB84145.1\|, \|82571377\|gb\|ABB84138.1\|, \|82571367\|gb\|ABB84129.1\|, \|82571357\|gb\|ABB84120.1\|, \|82571347\|gb\|ABB84111.1\|, \|82571337\|gb\|ABB84102.1\|, \|82571327\|gb\|ABB84093.1\|, \|82571317\|gb\|ABB84084.1\|, \|82571307\|gb\|ABB84075.1\|, \|82571297\|gb\|ABB84066.1\|, \|82571287\|gb\|ABB84057.1\|, \|82571277\|gb\|ABB84048.1\|, \|82571267\|gb\|ABB84039.1\|, \|82571258\|gb\|ABB84031.1\|, \|82571248\|gb\|ABB84022.1\|, \|82571238\|gb\|ABB84013.1\|, \|82571228\|gb\|ABB84004.1\|, \|82571218\|gb\|ABB83995.1\|, \|82571209\|gb\|ABB83987.1\|, \|82571199\|gb\|ABB83978.1\|, \|55560594\|gb\|AAV53165.1\|, \|55560592\|gb\|AAV53164.1\|, \|55560590\|gb\|AAV53163.1\|, \|55560588\|gb\|AAV53162.1\|, \|55560586\|gb\|AAV53161.1\|, \|55560584\|gb\|AAV53160.1\|, \|55560582\|gb\|AAV53159.1\|, \|55560580\|gb\|AAV53158.1\|, \|55560578\|gb\|AAV53157.1\|, \|55560576\|gb\|AAV53156.1\|, \|55560574\|gb\|AAV53155.1\|, \|55560572\|gb\|AAV53154.1\|, \|55560570\|gb\|AAV53153.1\|, \|55560568\|gb\|AAV53152.1\|, \|55560566\|gb\|AAV53151.1\|, \|55560564\|gb\|AAV53150.1\|, \|55560562\|gb\|AAV53149.1\|, \|55560560\|gb\|AAV53148.1\|, \|55560558\|gb\|AAV53147.1\|, \|55560556\|gb\|AAV53146.1\|, \|55560554\|gb\|AAV53145.1\|, \|55560552\|gb\|AAV53144.1\|, \|55560550\|gb\|AAV53143.1\|, \|55560547\|gb\|AAV53142.1\|, \|55560545\|gb\|AAV53141.1\|, \|55560543\|gb\|AAV53140.1\|, \|55560541\|gb\|AAV53139.1\|, \|55560539\|gb\|AAV53138.1\|, \|55560537\|gb\|AAV53137.1\|, \|55560535\|gb\|AAV53136.1\|, \|55560533\|gb\|AAV53135.1\|, \|55560531\|gb\|AAV53134.1\|, \|55560529\|gb\|AAV53133.1\|, \|55560527\|gb\|AAV53132.1\|, \|55560525\|gb\|AAV53131.1\|, \|55560523\|gb\|AAV53130.1\|, \|55560521\|gb\|AAV53129.1\|, \|55560519\|gb\|AAV53128.1\|, \|55560517\|gb\|AAV53127.1\|, \|55560515\|gb\|AAV53126.1\|, \|55560513\|gb\|AAV53125.1\|, \|55560511\|gb\|AAV53124.1\|, \|55560509\|gb\|AAV53123.1\|, \|55560507\|gb\|AAV53122.1\|, \|55560505\|gb\|AAV53121.1\|, \|55560503\|gb\|AAV53120.1\|, \|55560501\|gb\|AAV53119.1\|, \|55560499\|gb\|AAV53118.1\|, \|55560497\|gb\|AAV53117.1\|, \|55560495\|gb\|AAV53116.1\|, \|55560493\|gb\|AAV53115.1\|, \|55560491\|gb\|AAV53114.1\|, \|55560489\|gb\|AAV53113.1\|, \|55560487\|gb\|AAV53112.1\|, \|55560485\|gb\|AAV53111.1\|, \|55560483\|gb\|AAV53110.1\|, \|55560481\|gb\|AAV53109.1\|, \|55560479\|gb\|AAV53108.1\|, \|55560477\|gb\|AAV53107.1\|, \|55560475\|gb\|AAV53106.1\|, \|55560473\|gb\|AAV53105.1\|, \|55560471\|gb\|AAV53104.1\|, \|55560469\|gb\|AAV53103.1\|, \|55560467\|gb\|AAV53102.1\|, \|55560465\|gb\|AAV53101.1\|, \|55560463\|gb\|AAV53100.1\|, \|55560461\|gb\|AAV53099.1\|, \|55560459\|gb\|AAV53098.1\|, \|55560457\|gb\|AAV53097.1\|, \|55560455\|gb\|AAV53096.1\|, \|55560453\|gb\|AAV53095.1\|, \|55560451\|gb\|AAV53094.1\|, \|55560449\|gb\|AAV53093.1\|, \|55560447\|gb\|AAV53092.1\|, \|55560445\|gb\|AAV53091.1\|, \|55560443\|gb\|AAV53090.1\|, \|55560441\|gb\|AAV53089.1\|, \|55560439\|gb\|AAV53088.1\|, \|55560437\|gb\|AAV53087.1\|, \|55560435\|gb\|AAV53086.1\|, \|55560433\|gb\|AAV53085.1\|, \|55560431\|gb\|AAV53084.1\|, \|55560429\|gb\|AAV53083.1\|, \|55560427\|gb\|AAV53082.1\|, \|55560424\|gb\|AAV53081.1\|, \|55560422\|gb\|AAV53080.1\|, \|55560420\|gb\|AAV53079.1\|, \|55560418\|gb\|AAV53078.1\|, \|55560416\|gb\|AAV53077.1\|, \|55560414\|gb\|AAV53076.1\|, \|55560412\|gb\|AAV53075.1\|, \|55560410\|gb\|AAV53074.1\|, \|55560408\|gb\|AAV53073.1\|, \|55560406\|gb\|AAV53072.1\|, \|55560403\|gb\|AAV53071.1\|, \|55560401\|gb\|AAV53070.1\|, \|55560399\|gb\|AAV53069.1\|, \|55560397\|gb\|AAV53068.1\|, \|55560395\|gb\|AAV53067.1\|, \|55560393\|gb\|AAV53066.1\|, \|55560391\|gb\|AAV53065.1\|, \|55560389\|gb\|AAV53064.1\|, \|55560387\|gb\|AAV53063.1\|, \|55560385\|gb\|AAV53062.1\|, \|55560383\|gb\|AAV53061.1\|, \|55560381\|gb\|AAV53060.1\|, \|55560379\|gb\|AAV53059.1\|, \|55560377\|gb\|AAV53058.1\|, \|55560375\|gb\|AAV53057.1\|, \|55560373\|gb\|AAV53056.1\|, \|55560371\|gb\|AAV53055.1\|, \|55560369\|gb\|AAV53054.1\|, \|55560366\|gb\|AAV53053.1\|, \|55560364\|gb\|AAV53052.1\|, \|55560362\|gb\|AAV53051.1\|, \|55560360\|gb\|AAV53050.1\|, \|55560358\|gb\|AAV53049.1\|, \|55560356\|gb\|AAV53048.1\|, \|55560354\|gb\|AAV53047.1\|, \|55560352\|gb\|AAV53046.1\|, \|55560350\|gb\|AAV53045.1\|, \|55560348\|gb\|AAV53044.1\|, \|55560346\|gb\|AAV53043.1\|, \|55560344\|gb\|AAV53042.1\|, \|55560342\|gb\|AAV53041.1\|, \|55560340\|gb\|AAV53040.1\|, \|55560338\|gb\|AAV53039.1\|, \|55560336\|gb\|AAV53038.1\|, \|55560334\|gb\|AAV53037.1\|, \|55560332\|gb\|AAV53036.1\|, \|55560330\|gb\|AAV53035.1\|, \|55560328\|gb\|AAV53034.1\|, \|55560326\|gb\|AAV53033.1\|, \|55560324\|gb\|AAV53032.1\|, \|55560322\|gb\|AAV53031.1\|, \|55560320\|gb\|AAV53030.1\|, \|55560318\|gb\|AAV53029.1\|, \|55560316\|gb\|AAV53028.1\|, \|55560314\|gb\|AAV53027.1\|, \|55560312\|gb\|AAV53026.1\|, \|55560310\|gb\|AAV53025.1\|, \|55560308\|gb\|AAV53024.1\|, \|55560306\|gb\|AAV53023.1\|, \|55560304\|gb\|AAV53022.1\|, \|55560302\|gb\|AAV53021.1\|, \|55560300\|gb\|AAV53020.1\|, \|55560298\|gb\|AAV53019.1\|, \|55560296\|gb\|AAV53018.1\|, \|55560294\|gb\|AAV53017.1\|, \|55560292\|gb\|AAV53016.1\|, \|55560290\|gb\|AAV53015.1\|, \|55560288\|gb\|AAV53014.1\|, \|55560286\|gb\|AAV53013.1\|, \|55560284\|gb\|AAV53012.1\|, \|55560282\|gb\|AAV53011.1\|, \|55560280\|gb\|AAV53010.1\|, \|55560278\|gb\|AAV53009.1\|, \|55560276\|gb\|AAV53008.1\|, \|55560274\|gb\|AAV53007.1\|, |

| VPR proteins |
|---|
| \|55560272\|gb\|AAV53006.1\|, \|55560270\|gb\|AAV53005.1\|, \|55560268\|gb\|AAV53004.1\|, \|55560266\|gb\|AAV53003.1\|, \|55560264\|gb\|AAV53002.1\|, \|55560262\|gb\|AAV53001.1\|, \|55560260\|gb\|AAV53000.1\|, \|55560258\|gb\|AAV52999.1\|, \|55560256\|gb\|AAV52998.1\|, \|55560254\|gb\|AAV52997.1\|, \|55560252\|gb\|AAV52996.1\|, \|55560250\|gb\|AAV52995.1\|, \|55560248\|gb\|AAV52994.1\|, \|55560246\|gb\|AAV52993.1\|, \|55560244\|gb\|AAV52992.1\|, \|55560242\|gb\|AAV52991.1\|, \|55560240\|gb\|AAV52990.1\|, \|55560238\|gb\|AAV52989.1\|, \|55560236\|gb\|AAV52988.1\|, \|55560234\|gb\|AAV52987.1\|, \|55560232\|gb\|AAV52986.1\|, \|55560230\|gb\|AAV52985.1\|, \|55560228\|gb\|AAV52984.1\|, \|55560226\|gb\|AAV52983.1\|, \|55560224\|gb\|AAV52982.1\|, \|55560222\|gb\|AAV52981.1\|, \|55560220\|gb\|AAV52980.1\|, \|55560218\|gb\|AAV52979.1\|, \|55560216\|gb\|AAV52978.1\|, \|55560214\|gb\|AAV52977.1\|, \|55560212\|gb\|AAV52976.1\|, \|55560210\|gb\|AAV52975.1\|, \|55560208\|gb\|AAV52974.1\|, \|55560206\|gb\|AAV52973.1\|, \|55560204\|gb\|AAV52972.1\|, \|55560202\|gb\|AAV52971.1\|, \|82322074\|sp\|Q50D69\|Q50D69__9HIV1, \|82322071\|sp\|Q50D60\|Q50D60__9HIV1, \|82322069\|sp\|Q50D55\|Q50D55__9HIV1, \|82321274\|sp\|Q4ZFQ7\|Q4ZFQ7__9HIV1, \|82321270\|sp\|Q79796\|Q79796__9HIV1, \|82321025\|sp\|Q52VK7\|Q52VK7__9HIV1, \|82319471\|sp\|Q9IW36\|Q9IW36__9HIV1, \|82319168\|sp\|Q9IH70\|Q9IH70__9HIV1mutant, \|82318844\|sp\|Q9DRR7\|Q9DRR7__9HIV1truncated, \|82313427\|sp\|Q8Q617\|Q8Q617__9HIV1, \|82311516\|sp\|Q7SPQ2\|Q7SPQ2__9HIV1, \|82311513\|sp\|Q7SPP7\|Q7SPP7__9HIV1, \|82310816\|sp\|Q6YA56\|Q6YA56__9HIV1, \|82310792\|sp\|Q6X6X9\|Q6X6X9__9HIV1, \|82310781\|sp\|Q6X6R0\|Q6X6R0__9HIV1, \|82310775\|sp\|Q6X6M5\|Q6X6M5__9HIV1, \|82310769\|sp\|Q6X6J2\|Q6X6J2__9HIV1, \|82310765\|sp\|Q6X6H5\|Q6X6H5__9HIV1, \|82310761\|sp\|Q6X4Q7\|Q6X4Q7__9HIV1, \|82310758\|sp\|Q6X4P9\|Q6X4P9__9HIV1, \|82310755\|sp\|Q6X4P1\|Q6X4P1__9HIV1, \|82310752\|sp\|Q6X4N3\|Q6X4N3__9HIV1, \|82310750\|sp\|Q6X4M5\|Q6X4M5__9HIV1, \|82309888\|sp\|Q6PR10\|Q6PR10__9HIV1, \|82309836\|sp\|Q5MH20\|Q5MH20__9HIV1, \|82309833\|sp\|Q5MH11\|Q5MH11__9HIV1, \|82309830\|sp\|Q5MH02\|Q5MH02__9HIV1, \|82309827\|sp\|Q5MGZ3\|Q5MGZ3__9HIV1, \|82309824\|sp\|Q5MGY4\|Q5MGY4__9HIV1, \|82309821\|sp\|Q5MGX5\|Q5MGX5__9HIV1, \|82309818\|sp\|Q5MGW6\|Q5MGW6__9HIV1, \|82309815\|sp\|Q5MGV8\|Q5MGV8__9HIV1, \|82309813\|sp\|Q5MGU4\|Q5MGU4__9HIV1, \|82309810\|sp\|Q5MGT6\|Q5MGT6__9HIV1, \|82309381\|sp\|Q5C9Y2\|Q5C9Y2__9HIV1, \|82309378\|sp\|Q5C9X3\|Q5C9X3__9HIV1, \|82308944\|sp\|O41886\|O41886__9HIV1, \|82308942\|sp\|O41881\|O41881__9HIV1, \|82308470\|sp\|Q9YYU9\|Q9YYU9__9HIV1, \|82308469\|sp\|Q9YYU8\|Q9YYU8__9HIV1, \|82308468\|sp\|Q9YYU7\|Q9YYU7__9HIV1, \|82308467\|sp\|Q9YYU6\|Q9YYU6__9HIV1, \|82308466\|sp\|Q9YYU5\|Q9YYU5__9HIV1, \|82308465\|sp\|Q9YYU4\|Q9YYU4__9HIV1, \|82308464\|sp\|Q9YYU3\|Q9YYU3__9HIV1, \|82308463\|sp\|Q9YYU2\|Q9YYU2__9HIV1, \|82308429\|sp\|Q9YX74\|Q9YX74__9HIV1, \|82308428\|sp\|Q9YX73\|Q9YX73__9HIV1, \|82308427\|sp\|Q9YX72\|Q9YX72__9HIV1, \|82308426\|sp\|Q9YX71\|Q9YX71__9HIV1, \|82308377\|sp\|Q9YVE8\|Q9YVE8__9HIV1, \|82308355\|sp\|Q9YV13\|Q9YV13__9HIV1, \|82308353\|sp\|Q9YV07\|Q9YV07__9HIV1, \|82308351\|sp\|Q9YUZ9\|Q9YUZ9__9HIV1, \|82308278\|sp\|Q9YPN8\|Q9YPN8__9HIV1, \|82308277\|sp\|Q9YPN7\|Q9YPN7__9HIV1, \|82308276\|sp\|Q9YPN6\|Q9YPN6__9HIV1, \|82308275\|sp\|Q9YPN5\|Q9YPN5__9HIV1, \|82308274\|sp\|Q9YPN4\|Q9YPN4__9HIV1, \|82308273\|sp\|Q9YPN3\|Q9YPN3__9HIV1, \|82308272\|sp\|Q9YPN2\|Q9YPN2__9HIV1, \|82308271\|sp\|Q9YPN1\|Q9YPN1__9HIV1, \|82308270\|sp\|Q9YPN0\|Q9YPN0__9HIV1, \|82308269\|sp\|Q9YPM9\|Q9YPM9__9HIV1, \|82308268\|sp\|Q9YPM8\|Q9YPM8__9HIV1, \|82308267\|sp\|Q9YPM7\|Q9YPM7__9HIV1, \|82308244\|sp\|Q9YP54\|Q9YP54__9HIV1, \|82308243\|sp\|Q9YP53\|Q9YP53__9HIV1, \|82308223\|sp\|Q9YNC0\|Q9YNC0__9HIV1, \|82308222\|sp\|Q9YNB9\|Q9YNB9__9HIV1, \|82308221\|sp\|Q9YNB8\|Q9YNB8__9HIV1, \|82308220\|sp\|Q9YNB7\|Q9YNB7__9HIV1, \|82308219\|sp\|Q9YNA3\|Q9YNA3__9HIV1, \|82307984\|sp\|Q9WSF2\|Q9WSF2__9HIV1, \|82307982\|sp\|Q9WSE3\|Q9WSE3__9HIV1, \|82307973\|sp\|Q9WS44\|Q9WS44__9HIV1, \|82307901\|sp\|Q9WQI1\|Q9WQI1__9HIV1, \|82307899\|sp\|Q9WQH3\|Q9WQH3__9HIV1, \|82307732\|sp\|Q9WM30\|Q9WM30__9HIV1, \|82307731\|sp\|Q9WM29\|Q9WM29__9HIV1, \|82307730\|sp\|Q9WM28\|Q9WM28__9HIV1, \|82307729\|sp\|Q9WM27\|Q9WM27__9HIV1, \|82307728\|sp\|Q9WM26\|Q9WM26__9HIV1, \|82307727\|sp\|Q9WM25\|Q9WM25__9HIV1, \|82307726\|sp\|Q9WM24\|Q9WM24__9HIV1, \|82307725\|sp\|Q9WM23\|Q9WM23__9HIV1, \|82307724\|sp\|Q9WM22\|Q9WM22__9HIV1, \|82307723\|sp\|Q9WM21\|Q9WM21__9HIV1, \|82307722\|sp\|Q9WM20\|Q9WM20__9HIV1, \|82307721\|sp\|Q9WM19\|Q9WM19__9HIV1, \|82307720\|sp\|Q9WM18\|Q9WM18__9HIV1, \|82307719\|sp\|Q9WM17\|Q9WM17__9HIV1, \|82307718\|sp\|Q9WM16\|Q9WM16__9HIV1, \|82307696\|sp\|Q9WLM7\|Q9WLM7__9HIV1, \|82307695\|sp\|Q9WLM6\|Q9WLM6__9HIV1, \|82307694\|sp\|Q9WLM5\|Q9WLM5__9HIV1, \|82307693\|sp\|Q9WLM4\|Q9WLM4__9HIV1, \|82307687\|sp\|Q9WLH2\|Q9WLH2__9HIV1, \|82307686\|sp\|Q9WLG9\|Q9WLG9__9HIV1, \|82307574\|sp\|Q9WK41\|Q9WK41__9HIV1, \|82307573\|sp\|Q9WK40\|Q9WK40__9HIV1, \|82307572\|sp\|Q9WK39\|Q9WK39__9HIV1, \|82307571\|sp\|Q9WK38\|Q9WK38__9HIV1, \|82307545\|sp\|Q9WJR3\|Q9WJR3__9HIV1, \|82307542\|sp\|Q9WIU1\|Q9WIU1__9HIV1, \|82307539\|sp\|Q9WIT1\|Q9WIT1__9HIV1, \|82307535\|sp\|Q9WIS2\|Q9WIS2__9HIV1, \|82307276\|sp\|Q9WC70\|Q9WC70__9HIV1, \|82307274\|sp\|Q9WC61\|Q9WC61__9HIV1, \|82307187\|sp\|Q9W9D3\|Q9W9D3__9HIV1, \|82307113\|sp\|Q9QSU1\|Q9QSU1__9HIV1, \|82307111\|sp\|Q9QST2\|Q9QST2__9HIV1, \|82307109\|sp\|Q9QSS3\|Q9QSS3__9HIV1, \|82307107\|sp\|Q9QSR5\|Q9QSR5__9HIV1, \|82307105\|sp\|Q9QSQ6\|Q9QSQ6__9HIV1, \|82306567\|sp\|Q9QNX6\|Q9QNX6__9HIV1, \|82306524\|sp\|Q9QML5\|Q9QML5__9HIV1, \|82306522\|sp\|Q9QMK7\|Q9QMK7__9HIV1, \|82306495\|sp\|Q9QM82\|Q9QM82__9HIV1, \|82305929\|sp\|Q9Q6Y5\|Q9Q6Y5__9HIV1, \|82305927\|sp\|Q9Q6W8\|Q9Q6W8__9HIV1, \|82305924\|sp\|Q9Q6V7\|Q9Q6V7__9HIV1, \|82305922\|sp\|Q9Q6U9\|Q9Q6U9__9HIV1, \|82305871\|sp\|Q9Q5H6\|Q9Q5H6__9HIV1, \|82305870\|sp\|Q9Q5H5\|Q9Q5H5__9HIV1, \|82305869\|sp\|Q9Q5H4\|Q9Q5H4__9HIV1, \|82305868\|sp\|Q9Q5H3\|Q9Q5H3__9HIV1, \|82305867\|sp\|Q9Q5H2\|Q9Q5H2__9HIV1, \|82305866\|sp\|Q9Q5H1\|Q9Q5H1__9HIV1, \|82305865\|sp\|Q9Q5H0\|Q9Q5H0__9HIV1truncated, |

-continued

| VPR proteins |
|---|
| |82305864|sp|Q9Q5G9|Q9Q5G9__9HIV1truncated, |82305863|sp|Q9Q5G8|Q9Q5G8__9HIV1, |82305862|sp|Q9Q5G7|Q9Q5G7__9HIV1, |82305861|sp|Q9Q5G6|Q9Q5G6__9HIV1, |82305860|sp|Q9Q5G5|Q9Q5G5__9HIV1, |82305859|sp|Q9Q5G4|Q9Q5G4__9HIV1, |82305858|sp|Q9Q5G3|Q9Q5G3__9HIV1, |82305857|sp|Q9Q5G2|Q9Q5G2__9HIV1, |82305856|sp|Q9Q5G1|Q9Q5G1__9HIV1, |82305855|sp|Q9Q5G0|Q9Q5G0__9HIV1, |82305854|sp|Q9Q5F9|Q9Q5F9__9HIV1, |82305853|sp|Q9Q5F8|Q9Q5F8__9HIV1, |82305852|sp|Q9Q5F7|Q9Q5F7__9HIV1, |82305851|sp|Q9Q5F6|Q9Q5F6__9HIV1truncated, |82305850|sp|Q9Q5F5|Q9Q5F5__9HIV1truncated, |82305849|sp|Q9Q5F4|Q9Q5F4__9HIV1truncated, |82305848|sp|Q9Q5F3|Q9Q5F3__9HIV1truncated, |82305847|sp|Q9Q5F2|Q9Q5F2__9HIV1, |82305846|sp|Q9Q5F1|Q9Q5F1__9HIV1, |82305845|sp|Q9Q5F0|Q9Q5F0__9HIV1, |82305844|sp|Q9Q5E9|Q9Q5E9__9HIV1, |82305843|sp|Q9Q5E8|Q9Q5E8__9HIV1, |82305842|sp|Q9Q5E7|Q9Q5E7__9HIV1, |82305841|sp|Q9Q5E6|Q9Q5E6__9HIV1, |82305840|sp|Q9Q5E5|Q9Q5E5__9HIV1, |82305839|sp|Q9Q5E4|Q9Q5E4__9HIV1, |82305838|sp|Q9Q5E3|Q9Q5E3__9HIV1, |82305837|sp|Q9Q5E2|Q9Q5E2__9HIV1, |82305836|sp|Q9Q5E1|Q9Q5E1__9HIV1, |82305835|sp|Q9Q5E0|Q9Q5E0__9HIV1, |82305834|sp|Q9Q5D9|Q9Q5D9__9HIV1, |82305833|sp|Q9Q5D8|Q9Q5D8__9HIV1, |82305832|sp|Q9Q5D7|Q9Q5D7__9HIV1, |82305831|sp|Q9Q5D6|Q9Q5D6__9HIV1, |82305830|sp|Q9Q5D5|Q9Q5D5__9HIV1, |82305829|sp|Q9Q5D4|Q9Q5D4__9HIV1truncated, |82305828|sp|Q9Q5D3|Q9Q5D3__9HIV1, |82305827|sp|Q9Q5D2|Q9Q5D2__9HIV1, |82305826|sp|Q9Q5D1|Q9Q5D1__9HIV1, |82305825|sp|Q9Q5D0|Q9Q5D0__9HIV1, |82305824|sp|Q9Q5C9|Q9Q5C9__9HIV1, |82305823|sp|Q9Q5C8|Q9Q5C8__9HIV1, |82305822|sp|Q9Q5C7|Q9Q5C7__9HIV1, |82305821|sp|Q9Q5C6|Q9Q5C6__9HIV1, |82305820|sp|Q9Q5C5|Q9Q5C5__9HIV1, |82305819|sp|Q9Q5C4|Q9Q5C4__9HIV1, |82305818|sp|Q9Q5C3|Q9Q5C3__9HIV1, |82305817|sp|Q9Q5C2|Q9Q5C2__9HIV1, |82305816|sp|Q9Q5C1|Q9Q5C1__9HIV1, |82305815|sp|Q9Q5C0|Q9Q5C0__9HIV1, |82305814|sp|Q9Q5B9|Q9Q5B9__9HIV1, |82305813|sp|Q9Q5B8|Q9Q5B8__9HIV1, |82305812|sp|Q9Q5B7|Q9Q5B7__9HIV1, |82305811|sp|Q9Q5B6|Q9Q5B6__9HIV1, |82305810|sp|Q9Q5B4|Q9Q5B4__9HIV1, |82305809|sp|Q9Q5B1|Q9Q5B1__9HIV1, |82305808|sp|Q9Q5B0|Q9Q5B0__9HIV1, |82305807|sp|Q9Q5A9|Q9Q5A9__9HIV1, |82305806|sp|Q9Q5A8|Q9Q5A8__9HIV1, |82305805|sp|Q9Q5A7|Q9Q5A7__9HIV1, |82305804|sp|Q9Q5A6|Q9Q5A6__9HIV1, |82305803|sp|Q9Q5A5|Q9Q5A5__9HIV1, |82305802|sp|Q9Q5A4|Q9Q5A4__9HIV1, |82305801|sp|Q9Q5A3|Q9Q5A3__9HIV1, |82305800|sp|Q9Q5A2|Q9Q5A2__9HIV1, |82305799|sp|Q9Q5A1|Q9Q5A1__9HIV1, |82305798|sp|Q9Q5A0|Q9Q5A0__9HIV1, |82305797|sp|Q9Q599|Q9Q599__9HIV1, |82305796|sp|Q9Q598|Q9Q598__9HIV1, |82305795|sp|Q9Q597|Q9Q597__9HIV1, |82305794|sp|Q9Q596|Q9Q596__9HIV1, |82305793|sp|Q9Q595|Q9Q595__9HIV1, |82305792|sp|Q9Q594|Q9Q594__9HIV1, |82305571|sp|Q9PX72|Q9PX72__9HIV1, |82305564|sp|Q9PX20|Q9PX20__9HIV1truncated, |82305563|sp|Q9PX11|Q9PX11__9HIV1truncated, |82305553|sp|Q9PWX8|Q9PWX8__9HIV1, |82305401|sp|Q9JAC0|Q9JAC0__9HIV1, |82305096|sp|Q9IW45|Q9IW45__9HIV1, |82305060|sp|Q9IV96|Q9IV96__9HIV1, |82305058|sp|Q9IV87|Q9IV87__9HIV1, |82305056|sp|Q9IV11|Q9IV11__9HIV1, |82304828|sp|Q9IH73|Q9IH73__9HIV1mutant, |82304827|sp|Q9IH72|Q9IH72__9HIV1, |82304826|sp|Q9IH71|Q9IH71__9HIV1, |82304825|sp|Q9IH68|Q9IH68__9HIV1, |82304824|sp|Q9IH67|Q9IH67__9HIV1, |82304823|sp|Q9IH66|Q9IH66__9HIV1, |82304822|sp|Q9IH65|Q9IH65__9HIV1, |82304821|sp|Q9IH64|Q9IH64__9HIV1, |82304701|sp|Q9ID97|Q9ID97__9HIV1, |82304699|sp|Q9ID88|Q9ID88__9HIV1, |82304154|sp|Q9E2H7|Q9E2H7__9HIV1, |82303646|sp|Q9DRX1|Q9DRX1__9HIV1, |82303645|sp|Q9DRX0|Q9DRX0__9HIV1, |82303644|sp|Q9DRW9|Q9DRW9__9HIV1, |82303643|sp|Q9DRW8|Q9DRW8__9HIV1, |82303642|sp|Q9DRW7|Q9DRW7__9HIV1, |82303641|sp|Q9DRW6|Q9DRW6__9HIV1, |82303640|sp|Q9DRW5|Q9DRW5__9HIV1, |82303639|sp|Q9DRW4|Q9DRW4__9HIV1, |82303638|sp|Q9DRW3|Q9DRW3__9HIV1, |82303637|sp|Q9DRW2|Q9DRW2__9HIV1, |82303636|sp|Q9DRW1|Q9DRW1__9HIV1, |82303635|sp|Q9DRW0|Q9DRW0__9HIV1, |82303634|sp|Q9DRV9|Q9DRV9__9HIV1, |82303633|sp|Q9DRV8|Q9DRV8__9HIV1, |82303632|sp|Q9DRV7|Q9DRV7__9HIV1, |82303631|sp|Q9DRV6|Q9DRV6__9HIV1, |82303630|sp|Q9DRV5|Q9DRV5__9HIV1, |82303629|sp|Q9DRV4|Q9DRV4__9HIV1, |82303628|sp|Q9DRV3|Q9DRV3__9HIV1, |82303627|sp|Q9DRV2|Q9DRV2__9HIV1, |82303626|sp|Q9DRV1|Q9DRV1__9HIV1, |82303625|sp|Q9DRV0|Q9DRV0__9HIV1, |82303624|sp|Q9DRU9|Q9DRU9__9HIV1, |82303623|sp|Q9DRU8|Q9DRU8__9HIV1, |82303622|sp|Q9DRU7|Q9DRU7__9HIV1, |82303621|sp|Q9DRU6|Q9DRU6__9HIV1, |82303620|sp|Q9DRU5|Q9DRU5__9HIV1, |82303619|sp|Q9DRU2|Q9DRU2__9HIV1, |82303618|sp|Q9DRU1|Q9DRU1__9HIV1truncated, |82303617|sp|Q9DRU0|Q9DRU0__9HIV1, |82303616|sp|Q9DRT9|Q9DRT9__9HIV1, |82303615|sp|Q9DRT8|Q9DRT8__9HIV1, |82303614|sp|Q9DRT7|Q9DRT7__9HIV1, |82303613|sp|Q9DRT6|Q9DRT6__9HIV1, |82303612|sp|Q9DRT5|Q9DRT5__9HIV1, |82303611|sp|Q9DRT4|Q9DRT4__9HIV1truncated, |82303610|sp|Q9DRT3|Q9DRT3__9HIV1, |82303609|sp|Q9DRT2|Q9DRT2__9HIV1truncated, |82303608|sp|Q9DRT1|Q9DRT1__9HIV1, |82303607|sp|Q9DRT0|Q9DRT0__9HIV1, |82303606|sp|Q9DRS9|Q9DRS9__9HIV1, |82303605|sp|Q9DRS8|Q9DRS8__9HIV1truncated, |82303604|sp|Q9DRS7|Q9DRS7__9HIV1truncated, |82303603|sp|Q9DRS6|Q9DRS6__9HIV1truncated, |82303602|sp|Q9DRS4|Q9DRS4__9HIV1, |82303601|sp|Q9DRS3|Q9DRS3__9HIV1, |82303600|sp|Q9DRS2|Q9DRS2__9HIV1, |82303599|sp|Q9DRS1|Q9DRS1__9HIV1, |82303598|sp|Q9DRR9|Q9DRR9__9HIV1, |82303597|sp|Q9DRR5|Q9DRR5__9HIV1truncated, |82303596|sp|Q9DRR4|Q9DRR4__9HIV1truncated, |82303595|sp|Q9DRR3|Q9DRR3__9HIV1truncated, |82303594|sp|Q9DRR2|Q9DRR2__9HIV1, |82303593|sp|Q9DRR1|Q9DRR1__9HIV1, |82303592|sp|Q9DRR0|Q9DRR0__9HIV1, |82303591|sp|Q9DRQ9|Q9DRQ9__9HIV1, |82303590|sp|Q9DRQ8|Q9DRQ8__9HIV1, |82303589|sp|Q9DRQ7|Q9DRQ7__9HIV1, |82303588|sp|Q9DRQ6|Q9DRQ6__9HIV1, |

| VPR proteins |
|---|
| |82303587|sp|Q9DRQ5|Q9DRQ5__9HIV1, |82303586|sp|Q9DRQ4|Q9DRQ4__9HIV1, |82303585|sp|Q9DRQ3|Q9DRQ3__9HIV1, |82303584|sp|Q9DRQ2|Q9DRQ2__9HIV1, |82303583|sp|Q9DRQ1|Q9DRQ1__9HIV1, |82303582|sp|Q9DRP9|Q9DRP9__9HIV1, |82303581|sp|Q9DRP8|Q9DRP8__9HIV1, |82303580|sp|Q9DRP7|Q9DRP7__9HIV1, |82303579|sp|Q9DRP6|Q9DRP6__9HIV1, |82303578|sp|Q9DRP5|Q9DRP5__9HIV1, |82303577|sp|Q9DRP4|Q9DRP4__9HIV1, |82303576|sp|Q9DRP3|Q9DRP3__9HIV1, |82303575|sp|Q9DRP1|Q9DRP1__9HIV1truncated, |82303574|sp|Q9DRP0|Q9DRP0__9HIV1, |82303573|sp|Q9DRN9|Q9DRN9__9HIV1truncated, |82303572|sp|Q9DRN8|Q9DRN8__9HIV1, |82303571|sp|Q9DRN7|Q9DRN7__9HIV1, |82303570|sp|Q9DRN6|Q9DRN6__9HIV1, |82303569|sp|Q9DRN5|Q9DRN5__9HIV1, |82303325|sp|Q9DQ25|Q9DQ25__9HIV1, |82303320|sp|Q9DQ16|Q9DQ16__9HIV1, |82303318|sp|Q9DQ09|Q9DQ09__9HIV1, |82303317|sp|Q9DQ02|Q9DQ02__9HIV1, |82303316|sp|Q9DPZ7|Q9DPZ7__9HIV1, |82303158|sp|Q9DHB8|Q9DHB8__9HIV1truncated, |82303154|sp|Q9DH15|Q9DH15__9HIV1, |82303152|sp|Q9DGX7|Q9DGX7__9HIV1, |82303150|sp|Q9DGU1|Q9DGU1__9HIV1, |82303145|sp|Q9DGR9|Q9DGR9__9HIV1, |82302372|sp|Q998H0|Q998H0__9HIV1, |82302363|sp|Q994R4|Q994R4__9HIV1, |82302361|sp|Q994Q5|Q994Q5__9HIV1, |82302359|sp|Q994P6|Q994P6__9HIV1, |82302357|sp|Q994N7|Q994N7__9HIV1, |82302355|sp|Q994M8|Q994M8__9HIV1, |82302352|sp|Q994L0|Q994L0__9HIV1, |82302350|sp|Q994K1|Q994K1__9HIV1, |82302348|sp|Q994J2|Q994J2__9HIV1, |82302346|sp|Q994I3|Q994I3__9HIV1, |82302344|sp|Q994H4|Q994H4__9HIV1, |82302342|sp|Q994G5|Q994G5__9HIV1, |82302340|sp|Q994F6|Q994F6__9HIV1, |82301451|sp|Q90VU7|Q90VU7__9HIV1, |82301355|sp|Q90VI1|Q90VI1__9HIV1, |82301353|sp|Q90VH8|Q90VH8__9HIV1, |82301351|sp|Q90VH5|Q90VH5__9HIV1, |82301348|sp|Q90VG9|Q90VG9__9HIV1, |82301345|sp|Q90VF9|Q90VF9__9HIV1, |82301343|sp|Q90VF6|Q90VF6__9HIV1, |82301338|sp|Q90VE8|Q90VE8__9HIV1, |82301336|sp|Q90VE5|Q90VE5__9HIV1, |82300720|sp|Q90QQ4|Q90QQ4__9HIV1, |82300718|sp|Q90QP6|Q90QP6__9HIV1, |82300716|sp|Q90QN9|Q90QN9__9HIV1, |82300715|sp|Q90QN4|Q90QN4__9HIV1, |82300714|sp|Q90QN1|Q90QN1__9HIV1, |82300713|sp|Q90QM6|Q90QM6__9HIV1, |82300712|sp|Q90QM5|Q90QM5__9HIV1, |82300708|sp|Q90QJ5|Q90QJ5__9HIV1, |82300630|sp|Q90M16|Q90M16__9HIV1, |82300629|sp|Q90M15|Q90M15__9HIV1, |82300557|sp|Q90DZ6|Q90DZ6__9HIV1, |82300515|sp|Q90DU0|Q90DU0__9HIV1, |82300509|sp|Q90D23|Q90D23__9HIV1, |82300507|sp|Q90D14|Q90D14__9HIV1, |82300505|sp|Q90D05|Q90D05__9HIV1, |82300503|sp|Q90CZ6|Q90CZ6__9HIV1, |82300501|sp|Q90CY7|Q90CY7__9HIV1, |82300499|sp|Q90CX8|Q90CX8__9HIV1, |82300497|sp|Q90CX0|Q90CX0__9HIV1, |82300495|sp|Q90CW1|Q90CW1__9HIV1, |82300493|sp|Q90CV2|Q90CV2__9HIV1, |82300491|sp|Q90CK5|Q90CK5__9HIV1, |82299666|sp|Q903T9|Q903T9__9HIV1truncated, |82299631|sp|Q902U1|Q902U1__9HIV1, |82299629|sp|Q902T2|Q902T2__9HIV1, |82299627|sp|Q902S3|Q902S3__9HIV1, |82299625|sp|Q902R4|Q902R4__9HIV1, |82299623|sp|Q902Q5|Q902Q5__9HIV1, |82299621|sp|Q902P6|Q902P6__9HIV1, |82299619|sp|Q902N7|Q902N7__9HIV1, |82299617|sp|Q902M3|Q902M3__9HIV1, |82299615|sp|Q902L3|Q902L3__9HIV1, |82299613|sp|Q902K4|Q902K4__9HIV1, |82299610|sp|Q902J2|Q902J2__9HIV1, |82299608|sp|Q902I3|Q902I3__9HIV1, |82299606|sp|Q902H4|Q902H4__9HIV1, |82299604|sp|Q902G5|Q902G5__9HIV1, |82299540|sp|Q901Y9|Q901Y9__9HIV1, |82299538|sp|Q901Y0|Q901Y0__9HIV1, |82299536|sp|Q901X1|Q901X1__9HIV1, |82299534|sp|Q901W2|Q901W2__9HIV1, |82299510|sp|Q900Z3|Q900Z3__9HIV1, |82299507|sp|Q900Y4|Q900Y4__9HIV1, |82299437|sp|Q900A5|Q900A5__9HIV1truncated, |82299181|sp|Q8USP6|Q8USP6__9HIV1, |82299180|sp|Q8USP5|Q8USP5__9HIV1, |82299179|sp|Q8USP4|Q8USP4__9HIV1, |82299178|sp|Q8USP3|Q8USP3__9HIV1, |82299177|sp|Q8USP2|Q8USP2__9HIV1, |82299176|sp|Q8USP1|Q8USP1__9HIV1, |82299175|sp|Q8USP0|Q8USP0__9HIV1, |82299174|sp|Q8USN9|Q8USN9__9HIV1, |82299173|sp|Q8USN8|Q8USN8__9HIV1, |82299172|sp|Q8USN7|Q8USN7__9HIV1, |82299171|sp|Q8USN6|Q8USN6__9HIV1, |82299170|sp|Q8USN5|Q8USN5__9HIV1, |82299169|sp|Q8USN4|Q8USN4__9HIV1, |82299168|sp|Q8USN3|Q8USN3__9HIV1, |82299167|sp|Q8USN2|Q8USN2__9HIV1, |82299166|sp|Q8USN1|Q8USN1__9HIV1, |82299165|sp|Q8USN0|Q8USN0__9HIV1, |82299164|sp|Q8USM9|Q8USM9__9HIV1, |82299163|sp|Q8USM8|Q8USM8__9HIV1, |82299162|sp|Q8USM7|Q8USM7__9HIV1, |82299161|sp|Q8USM6|Q8USM6__9HIV1, |82299160|sp|Q8USM5|Q8USM5__9HIV1, |82299159|sp|Q8USM3|Q8USM3__9HIV1, |82299158|sp|Q8USM1|Q8USM1__9HIV1, |82299157|sp|Q8USM0|Q8USM0__9HIV1truncated, |82299156|sp|Q8USL9|Q8USL9__9HIV1, |82299155|sp|Q8USL7|Q8USL7__9HIV1, |82299154|sp|Q8USL5|Q8USL5__9HIV1, |82299153|sp|Q8USL4|Q8USL4__9HIV1, |82299152|sp|Q8USL3|Q8USL3__9HIV1, |82299151|sp|Q8USL2|Q8USL2__9HIV1, |82299149|sp|Q8USL0|Q8USL0__9HIV1, |82299148|sp|Q8USK9|Q8USK9__9HIV1, |82299147|sp|Q8USK8|Q8USK8__9HIV1, |82299146|sp|Q8USK6|Q8USK6__9HIV1, |82299145|sp|Q8USK5|Q8USK5__9HIV1, |82299143|sp|Q8USK3|Q8USK3__9HIV1, |82299142|sp|Q8USK2|Q8USK2__9HIV1, |82299141|sp|Q8USJ9|Q8USJ9__9HIV1, |82299140|sp|Q8USJ8|Q8USJ8__9HIV1, |82299139|sp|Q8USJ7|Q8USJ7__9HIV1, |82299138|sp|Q8USJ6|Q8USJ6__9HIV1, |82299137|sp|Q8USJ5|Q8USJ5__9HIV1, |82299136|sp|Q8USJ4|Q8USJ4__9HIV1, |82299135|sp|Q8USJ3|Q8USJ3__9HIV1, |82299134|sp|Q8USJ1|Q8USJ1__9HIV1, |82299133|sp|Q8USJ0|Q8USJ0__9HIV1, |82299132|sp|Q8USI9|Q8USI9__9HIV1, |82299131|sp|Q8USI8|Q8USI8__9HIV1, |82299130|sp|Q8USI7|Q8USI7__9HIV1, |82299129|sp|Q8USI6|Q8USI6__9HIV1, |82299128|sp|Q8USI5|Q8USI5__9HIV1, |82299127|sp|Q8USI4|Q8USI4__9HIV1, |82299126|sp|Q8USI3|Q8USI3__9HIV1, |82299125|sp|Q8USI2|Q8USI2__9HIV1, |82299124|sp|Q8USI1|Q8USI1__9HIV1, |82299123|sp|Q8USI0|Q8USI0__9HIV1, |82299122|sp|Q8USH9|Q8USH9__9HIV1, |

-continued

| VPR proteins |
|---|
| |82299121|sp|Q8USH8|Q8USH8__9HIV1, |82299120|sp|Q8USH7|Q8USH7__9HIV1, |
| |82299119|sp|Q8USH6|Q8USH6__9HIV1, |82299118|sp|Q8USH5|Q8USH5__9HIV1, |
| |82299073|sp|Q8UPQ4|Q8UPQ4__9HIV1, |82299071|sp|Q8UPP6|Q8UPP6__9HIV1, |
| |82299069|sp|Q8UPN7|Q8UPN7__9HIV1, |82299067|sp|Q8UPM9|Q8UPM9__9HIV1, |
| |82299065|sp|Q8UPM0|Q8UPM0__9HIV1, |82299063|sp|Q8UPL1|Q8UPL1__9HIV1, |
| |82299057|sp|Q8UNL8|Q8UNL8__9HIV1, |82299055|sp|Q8UNK9|Q8UNK9__9HIV1, |
| |82299053|sp|Q8UNK0|Q8UNK0__9HIV1, |82298938|sp|Q8UMG9|Q8UMG9__9HIV1, |
| |82298936|sp|Q8UMG0|Q8UMG0__9HIV1, |82298932|sp|Q8UMD3|Q8UMD3__9HIV1, |
| |82298901|sp|Q8UM91|Q8UM91__9HIV1, |82298900|sp|Q8UM89|Q8UM89__9HIV1, |
| |82298898|sp|Q8UM86|Q8UM86__9HIV1, |82298897|sp|Q8UM85|Q8UM85__9HIV1, |
| |82298867|sp|Q8QFK8|Q8QFK8__9HIV1, |82298866|sp|Q8QFK6|Q8QFK6__9HIV1, |
| |82298821|sp|Q8QDF4|Q8QDF4__9HIV1, |82298620|sp|Q8Q7Y9|Q8Q7Y9__9HIV1, |
| |82298539|sp|Q8Q662|Q8Q662__9HIV1, |82298538|sp|Q8Q661|Q8Q661__9HIV1, |
| |82298537|sp|Q8Q660|Q8Q660__9HIV1, |82298536|sp|Q8Q659|Q8Q659__9HIV1, |
| |82298535|sp|Q8Q658|Q8Q658__9HIV1, |82298534|sp|Q8Q657|Q8Q657__9HIV1, |
| |82298533|sp|Q8Q656|Q8Q656__9HIV1, |82298532|sp|Q8Q655|Q8Q655__9HIV1, |
| |82298531|sp|Q8Q654|Q8Q654__9HIV1, |82298530|sp|Q8Q653|Q8Q653__9HIV1, |
| |82298529|sp|Q8Q652|Q8Q652__9HIV1, |82298528|sp|Q8Q651|Q8Q651__9HIV1, |
| |82298527|sp|Q8Q650|Q8Q650__9HIV1, |82298526|sp|Q8Q649|Q8Q649__9HIV1, |
| |82298525|sp|Q8Q648|Q8Q648__9HIV1, |82298524|sp|Q8Q647|Q8Q647__9HIV1, |
| |82298523|sp|Q8Q646|Q8Q646__9HIV1, |82298522|sp|Q8Q645|Q8Q645__9HIV1, |
| |82298521|sp|Q8Q644|Q8Q644__9HIV1, |82298520|sp|Q8Q643|Q8Q643__9HIV1, |
| |82298519|sp|Q8Q642|Q8Q642__9HIV1, |82298518|sp|Q8Q641|Q8Q641__9HIV1, |
| |82298517|sp|Q8Q640|Q8Q640__9HIV1, |82298516|sp|Q8Q639|Q8Q639__9HIV1, |
| |82298515|sp|Q8Q638|Q8Q638__9HIV1, |82298514|sp|Q8Q637|Q8Q637__9HIV1, |
| |82298513|sp|Q8Q636|Q8Q636__9HIV1, |82298512|sp|Q8Q635|Q8Q635__9HIV1, |
| |82298511|sp|Q8Q634|Q8Q634__9HIV1, |82298510|sp|Q8Q633|Q8Q633__9HIV1, |
| |82298509|sp|Q8Q632|Q8Q632__9HIV1, |82298508|sp|Q8Q631|Q8Q631__9HIV1, |
| |82298507|sp|Q8Q630|Q8Q630__9HIV1, |82298506|sp|Q8Q629|Q8Q629__9HIV1, |
| |82298505|sp|Q8Q628|Q8Q628__9HIV1, |82298504|sp|Q8Q627|Q8Q627__9HIV1, |
| |82298503|sp|Q8Q626|Q8Q626__9HIV1, |82298502|sp|Q8Q625|Q8Q625__9HIV1, |
| |82298501|sp|Q8Q623|Q8Q623__9HIV1, |82298500|sp|Q8Q622|Q8Q622__9HIV1, |
| |82298499|sp|Q8Q621|Q8Q621__9HIV1, |82298498|sp|Q8Q620|Q8Q620__9HIV1, |
| |82298497|sp|Q8Q619|Q8Q619__9HIV1, |82298496|sp|Q8Q618|Q8Q618__9HIV1, |
| |82298495|sp|Q8Q616|Q8Q616__9HIV1, |82298494|sp|Q8Q615|Q8Q615__9HIV1, |
| |82298493|sp|Q8Q614|Q8Q614__9HIV1, |82298492|sp|Q8Q613|Q8Q613__9HIV1, |
| |82298491|sp|Q8Q611|Q8Q611__9HIV1, |82298490|sp|Q8Q610|Q8Q610__9HIV1, |
| |82298489|sp|Q8Q609|Q8Q609__9HIV1, |82298488|sp|Q8Q608|Q8Q608__9HIV1, |
| |82298487|sp|Q8Q606|Q8Q606__9HIV1, |82298486|sp|Q8Q605|Q8Q605__9HIV1, |
| |82298485|sp|Q8Q604|Q8Q604__9HIV1, |82298484|sp|Q8Q603|Q8Q603__9HIV1, |
| |82298483|sp|Q8Q602|Q8Q602__9HIV1, |82298482|sp|Q8Q601|Q8Q601__9HIV1, |
| |82298481|sp|Q8Q600|Q8Q600__9HIV1, |82298480|sp|Q8Q5Z9|Q8Q5Z9__9HIV1, |
| |82298479|sp|Q8Q5Z8|Q8Q5Z8__9HIV1, |82298478|sp|Q8Q5Z7|Q8Q5Z7__9HIV1, |
| |82298477|sp|Q8Q5Z6|Q8Q5Z6__9HIV1, |82298476|sp|Q8Q5Z5|Q8Q5Z5__9HIV1, |
| |82298475|sp|Q8Q5Z4|Q8Q5Z4__9HIV1, |82298474|sp|Q8Q5Z3|Q8Q5Z3__9HIV1, |
| |82298473|sp|Q8Q5Z2|Q8Q5Z2__9HIV1, |82298472|sp|Q8Q5Z1|Q8Q5Z1__9HIV1, |
| |82298471|sp|Q8Q5Z0|Q8Q5Z0__9HIV1, |82298470|sp|Q8Q5Y9|Q8Q5Y9__9HIV1, |
| |82298469|sp|Q8Q5Y8|Q8Q5Y8__9HIV1, |82298468|sp|Q8Q5Y7|Q8Q5Y7__9HIV1, |
| |82298467|sp|Q8Q5Y5|Q8Q5Y5__9HIV1, |82298466|sp|Q8Q5Y4|Q8Q5Y4__9HIV1, |
| |82298465|sp|Q8Q5Y3|Q8Q5Y3__9HIV1, |82298464|sp|Q8Q5Y2|Q8Q5Y2__9HIV1, |
| |82298463|sp|Q8Q5Y1|Q8Q5Y1__9HIV1, |82298462|sp|Q8Q5Y0|Q8Q5Y0__9HIV1, |
| |82298461|sp|Q8Q5X9|Q8Q5X9__9HIV1, |82298460|sp|Q8Q5X8|Q8Q5X8__9HIV1, |
| |82298459|sp|Q8Q5X7|Q8Q5X7__9HIV1, |82298458|sp|Q8Q5X6|Q8Q5X6__9HIV1, |
| |82298457|sp|Q8Q5X5|Q8Q5X5__9HIV1, |82298456|sp|Q8Q5X4|Q8Q5X4__9HIV1, |
| |82298123|sp|Q8Q0Y3|Q8Q0Y3__9HIV1, |82298093|sp|Q8JEL6|Q8JEL6__9HIV1, |
| |82297857|sp|Q8JC70|Q8JC70__9HIV1, |82297855|sp|Q8JC61|Q8JC61__9HIV1, |
| |82297853|sp|Q8JC52|Q8JC52__9HIV1, |82297851|sp|Q8JC43|Q8JC43__9HIV1, |
| |82297849|sp|Q8JC34|Q8JC34__9HIV1, |82297847|sp|Q8JC25|Q8JC25__9HIV1, |
| |82297845|sp|Q8JC16|Q8JC16__9HIV1, |82297843|sp|Q8JC07|Q8JC07__9HIV1, |
| |82297841|sp|Q8JC03|Q8JC03__9HIV1, |82297839|sp|Q8JBZ4|Q8JBZ4__9HIV1, |
| |82297837|sp|Q8JBY5|Q8JBY5__9HIV1, |82297835|sp|Q8JBX6|Q8JBX6__9HIV1, |
| |82297833|sp|Q8JBW7|Q8JBW7__9HIV1, |82297831|sp|Q8JBV8|Q8JBV8__9HIV1, |
| |82297829|sp|Q8JBU9|Q8JBU9__9HIV1, |82297827|sp|Q8JBU0|Q8JBU0__9HIV1, |
| |82297825|sp|Q8JBT1|Q8JBT1__9HIV1, |82297823|sp|Q8JBS2|Q8JBS2__9HIV1, |
| |82297821|sp|Q8JBR3|Q8JBR3__9HIV1, |82297819|sp|Q8JBQ4|Q8JBQ4__9HIV1, |
| |82297817|sp|Q8JBP5|Q8JBP5__9HIV1, |82297814|sp|Q8JBN5|Q8JBN5__9HIV1, |
| |82297811|sp|Q8JBM4|Q8JBM4__9HIV1, |82297809|sp|Q8JBL5|Q8JBL5__9HIV1, |
| |82297807|sp|Q8JBK6|Q8JBK6__9HIV1, |82297805|sp|Q8JBJ7|Q8JBJ7__9HIV1, |
| |82297803|sp|Q8JBI8|Q8JBI8__9HIV1, |82297801|sp|Q8JBH9|Q8JBH9__9HIV1, |
| |82297799|sp|Q8JBH0|Q8JBH0__9HIV1, |82297797|sp|Q8JBG1|Q8JBG1__9HIV1, |
| |82297795|sp|Q8JBF2|Q8JBF2__9HIV1, |82297793|sp|Q8JBE3|Q8JBE3__9HIV1, |
| |82297791|sp|Q8JBD4|Q8JBD4__9HIV1, |82297789|sp|Q8JBC5|Q8JBC5__9HIV1, |
| |82297787|sp|Q8JBB6|Q8JBB6__9HIV1, |82297785|sp|Q8JBA7|Q8JBA7__9HIV1, |
| |82297782|sp|Q8JAX5|Q8JAX5__9HIV1, |82297780|sp|Q8JAW7|Q8JAW7__9HIV1, |
| |82297584|sp|Q8J9B7|Q8J9B7__9HIV1, |82297582|sp|Q8J9A8|Q8J9A8__9HIV1, |
| |82297363|sp|Q8J6B9|Q8J6B9__9HIV1, |82297362|sp|Q8J6B8|Q8J6B8__9HIV1, |
| |82297361|sp|Q8J6B7|Q8J6B7__9HIV1, |82297360|sp|Q8J6B6|Q8J6B6__9HIV1, |

-continued

| VPR proteins |
|---|
| |82297359|sp|Q8J6B5|Q8J6B5__9HIV1, |82297358|sp|Q8J6B4|Q8J6B4__9HIV1, |
| |82297357|sp|Q8J6B3|Q8J6B3__9HIV1, |82297356|sp|Q8J6B2|Q8J6B2__9HIV1, |
| |82297355|sp|Q8J6B1|Q8J6B1__9HIV1, |82297354|sp|Q8J6B0|Q8J6B0__9HIV1, |
| |82297353|sp|Q8J6A9|Q8J6A9__9HIV1, |82297352|sp|Q8J6A8|Q8J6A8__9HIV1, |
| |82297106|sp|Q8J580|Q8J580__9HIV1, |82297105|sp|Q8J579|Q8J579__9HIV1, |
| |82297104|sp|Q8J578|Q8J578__9HIV1, |82297103|sp|Q8J577|Q8J577__9HIV1, |
| |82297102|sp|Q8J576|Q8J576__9HIV1, |82297101|sp|Q8J575|Q8J575__9HIV1, |
| |82297100|sp|Q8J574|Q8J574__9HIV1, |82297099|sp|Q8J573|Q8J573__9HIV1, |
| |82297098|sp|Q8J572|Q8J572__9HIV1, |82297097|sp|Q8J571|Q8J571__9HIV1, |
| |82297096|sp|Q8J570|Q8J570__9HIV1, |82297095|sp|Q8J569|Q8J569__9HIV1, |
| |82297094|sp|Q8J568|Q8J568__9HIV1, |82297093|sp|Q8J567|Q8J567__9HIV1, |
| |82297092|sp|Q8J566|Q8J566__9HIV1, |82297091|sp|Q8J565|Q8J565__9HIV1, |
| |82297090|sp|Q8J564|Q8J564__9HIV1, |82297089|sp|Q8J563|Q8J563__9HIV1, |
| |82297088|sp|Q8J562|Q8J562__9HIV1, |82297087|sp|Q8J561|Q8J561__9HIV1, |
| |82297086|sp|Q8J560|Q8J560__9HIV1, |82297085|sp|Q8J559|Q8J559__9HIV1, |
| |82296965|sp|Q8J3U2|Q8J3U2__9HIV1, |82296964|sp|Q8J3M9|Q8J3M9__9HIV1, |
| |82296963|sp|Q8J3M8|Q8J3M8__9HIV1, |82296962|sp|Q8J3M7|Q8J3M7__9HIV1, |
| |82296961|sp|Q8J3M6|Q8J3M6__9HIV1, |82296960|sp|Q8J3M5|Q8J3M5__9HIV1, |
| |82296959|sp|Q8J3M4|Q8J3M4__9HIV1, |82296958|sp|Q8J3M3|Q8J3M3__9HIV1, |
| |82296957|sp|Q8J3M2|Q8J3M2__9HIV1, |82296956|sp|Q8J3M1|Q8J3M1__9HIV1, |
| |82296955|sp|Q8J3M0|Q8J3M0__9HIV1, |82296954|sp|Q8J3L9|Q8J3L9__9HIV1, |
| |82296953|sp|Q8J3L8|Q8J3L8__9HIV1, |82296952|sp|Q8J3L7|Q8J3L7__9HIV1, |
| |82296951|sp|Q8J3L6|Q8J3L6__9HIV1, |82296950|sp|Q8J3L5|Q8J3L5__9HIV1, |
| |82296949|sp|Q8J3L4|Q8J3L4__9HIV1, |82296948|sp|Q8J3L3|Q8J3L3__9HIV1, |
| |82296947|sp|Q8J3L2|Q8J3L2__9HIV1, |82296946|sp|Q8J3L1|Q8J3L1__9HIV1, |
| |82296945|sp|Q8J3L0|Q8J3L0__9HIV1, |82296944|sp|Q8J3K9|Q8J3K9__9HIV1, |
| |82296943|sp|Q8J3K8|Q8J3K8__9HIV1, |82296942|sp|Q8J3K7|Q8J3K7__9HIV1, |
| |82296829|sp|Q8J3I2|Q8J3I2__9HIV1, |82296828|sp|Q8J3I0|Q8J3I0__9HIV1, |
| |82296827|sp|Q8AUH8|Q8AUH8__9HIV1, |82296801|sp|Q8AU85|Q8AU85__9HIV1, |
| |82296799|sp|Q8AU76|Q8AU76__9HIV1, |82296797|sp|Q8AU67|Q8AU67__9HIV1, |
| |82296795|sp|Q8AU58|Q8AU58__9HIV1, |82296794|sp|Q8AU56|Q8AU56__9HIV1, |
| |82296793|sp|Q8AU55|Q8AU55__9HIV1, |82296792|sp|Q8AU54|Q8AU54__9HIV1, |
| |82296791|sp|Q8AU53|Q8AU53__9HIV1, |82296790|sp|Q8AU52|Q8AU52__9HIV1, |
| |82296789|sp|Q8AU51|Q8AU51__9HIV1, |82296788|sp|Q8AU50|Q8AU50__9HIV1, |
| |82296787|sp|Q8AU49|Q8AU49__9HIV1, |82296786|sp|Q8AU48|Q8AU48__9HIV1, |
| |82296785|sp|Q8AU47|Q8AU47__9HIV1, |82296784|sp|Q8AU46|Q8AU46__9HIV1, |
| |82296783|sp|Q8AU45|Q8AU45__9HIV1, |82296782|sp|Q8AU44|Q8AU44__9HIV1, |
| |82296781|sp|Q8AU43|Q8AU43__9HIV1, |82296780|sp|Q8AU42|Q8AU42__9HIV1, |
| |82296779|sp|Q8AU41|Q8AU41__9HIV1, |82296778|sp|Q8AU40|Q8AU40__9HIV1, |
| |82296777|sp|Q8AU39|Q8AU39__9HIV1, |82296776|sp|Q8AU38|Q8AU38__9HIV1, |
| |82296775|sp|Q8AU37|Q8AU37__9HIV1, |82296774|sp|Q8AU36|Q8AU36__9HIV1, |
| |82296773|sp|Q8AU35|Q8AU35__9HIV1, |82296772|sp|Q8AU34|Q8AU34__9HIV1, |
| |82296771|sp|Q8AU33|Q8AU33__9HIV1, |82296770|sp|Q8AU32|Q8AU32__9HIV1, |
| |82296769|sp|Q8AU31|Q8AU31__9HIV1, |82296768|sp|Q8AU30|Q8AU30__9HIV1, |
| |82296767|sp|Q8AU29|Q8AU29__9HIV1, |82296766|sp|Q8AU28|Q8AU28__9HIV1, |
| |82296765|sp|Q8AU27|Q8AU27__9HIV1, |82296764|sp|Q8AU26|Q8AU26__9HIV1, |
| |82296732|sp|Q8ATN7|Q8ATN7__9HIV1, |82296730|sp|Q8ATN1|Q8ATN1__9HIV1, |
| |82296655|sp|Q8AQV6|Q8AQV6__9HIV1, |82296653|sp|Q8AQU7|Q8AQU7__9HIV1, |
| |82296651|sp|Q8AQT8|Q8AQT8__9HIV1, |82296649|sp|Q8AQS9|Q8AQS9__9HIV1, |
| |82296647|sp|Q8AQS0|Q8AQS0__9HIV1, |82296646|sp|Q8AQR9|Q8AQR9__9HIV1, |
| |82296645|sp|Q8AQR8|Q8AQR8__9HIV1, |82296644|sp|Q8AQR7|Q8AQR7__9HIV1, |
| |82296643|sp|Q8AQR6|Q8AQR6__9HIV1, |82296642|sp|Q8AQR5|Q8AQR5__9HIV1, |
| |82296641|sp|Q8AQR4|Q8AQR4__9HIV1, |82296640|sp|Q8AQR3|Q8AQR3__9HIV1, |
| |82296639|sp|Q8AQR2|Q8AQR2__9HIV1, |82296638|sp|Q8AQR1|Q8AQR1__9HIV1, |
| |82296637|sp|Q8AQR0|Q8AQR0__9HIV1, |82296636|sp|Q8AQQ9|Q8AQQ9__9HIV1, |
| |82296635|sp|Q8AQQ8|Q8AQQ8__9HIV1, |82296634|sp|Q8AQQ7|Q8AQQ7__9HIV1, |
| |82296633|sp|Q8AQQ6|Q8AQQ6__9HIV1, |82296632|sp|Q8AQQ5|Q8AQQ5__9HIV1, |
| |82296631|sp|Q8AQQ4|Q8AQQ4__9HIV1, |82296630|sp|Q8AQQ3|Q8AQQ3__9HIV1, |
| |82296629|sp|Q8AQQ2|Q8AQQ2__9HIV1, |82296628|sp|Q8AQQ1|Q8AQQ1__9HIV1, |
| |82296627|sp|Q8AQQ0|Q8AQQ0__9HIV1, |82296626|sp|Q8AQP9|Q8AQP9__9HIV1, |
| |82296625|sp|Q8AQP8|Q8AQP8__9HIV1, |82296623|sp|Q8AQP6|Q8AQP6__9HIV1, |
| |82296622|sp|Q8AQP5|Q8AQP5__9HIV1, |82296621|sp|Q8AQP4|Q8AQP4__9HIV1, |
| |82296620|sp|Q8AQP3|Q8AQP3__9HIV1, |82296619|sp|Q8AQP2|Q8AQP2__9HIV1, |
| |82296618|sp|Q8AQP1|Q8AQP1__9HIV1, |82296617|sp|Q8AQP0|Q8AQP0__9HIV1, |
| |82296616|sp|Q8AQN9|Q8AQN9__9HIV1, |82296615|sp|Q8AQN8|Q8AQN8__9HIV1, |
| |82296613|sp|Q8AQN6|Q8AQN6__9HIV1, |82296612|sp|Q8AQN5|Q8AQN5__9HIV1, |
| |82296611|sp|Q8AQN4|Q8AQN4__9HIV1, |82296610|sp|Q8AQN3|Q8AQN3__9HIV1, |
| |82296609|sp|Q8AQN2|Q8AQN2__9HIV1, |82296608|sp|Q8AQN1|Q8AQN1__9HIV1, |
| |82296607|sp|Q8AQN0|Q8AQN0__9HIV1, |82296606|sp|Q8AQM9|Q8AQM9__9HIV1, |
| |82296605|sp|Q8AQM8|Q8AQM8__9HIV1, |82296604|sp|Q8AQM7|Q8AQM7__9HIV1, |
| |82296603|sp|Q8AQM6|Q8AQM6__9HIV1, |82296602|sp|Q8AQM5|Q8AQM5__9HIV1, |
| |82296601|sp|Q8AQM4|Q8AQM4__9HIV1, |82296600|sp|Q8AQM3|Q8AQM3__9HIV1, |
| |82296599|sp|Q8AQM2|Q8AQM2__9HIV1, |82296370|sp|Q8AMH4|Q8AMH4__9HIV1, |
| |82296369|sp|Q8AMH3|Q8AMH3__9HIV1, |82296368|sp|Q8AMH2|Q8AMH2__9HIV1, |
| |82296367|sp|Q8AMH1|Q8AMH1__9HIV1, |82296366|sp|Q8AMH0|Q8AMH0__9HIV1, |
| |82296365|sp|Q8AMG9|Q8AMG9__9HIV1, |82296364|sp|Q8AMG8|Q8AMG8__9HIV1, |
| |82296363|sp|Q8AMG7|Q8AMG7__9HIV1, |82296362|sp|Q8AMG6|Q8AMG6__9HIV1, |

| VPR proteins |
| --- |
| |82296361|sp|Q8AMG5|Q8AMG5__9HIV1, |82296360|sp|Q8AMG4|Q8AMG4__9HIV1, |82296359|sp|Q8AMG3|Q8AMG3__9HIV1, |82296358|sp|Q8AMG2|Q8AMG2__9HIV1, |82296357|sp|Q8AMG1|Q8AMG1__9HIV1, |82296356|sp|Q8AMG0|Q8AMG0__9HIV1, |82296355|sp|Q8AMF9|Q8AMF9__9HIV1, |82296354|sp|Q8AMF8|Q8AMF8__9HIV1, |82296353|sp|Q8AMF7|Q8AMF7__9HIV1, |82296352|sp|Q8AMF6|Q8AMF6__9HIV1, |82296351|sp|Q8AMF5|Q8AMF5__9HIV1, |82296350|sp|Q8AMF4|Q8AMF4__9HIV1, |82296349|sp|Q8AMF3|Q8AMF3__9HIV1, |82296348|sp|Q8AMF2|Q8AMF2__9HIV1, |82296347|sp|Q8AMF1|Q8AMF1__9HIV1, |82296346|sp|Q8AMF0|Q8AMF0__9HIV1, |82296345|sp|Q8AME9|Q8AME9__9HIV1, |82296344|sp|Q8AME8|Q8AME8__9HIV1, |82296343|sp|Q8AME7|Q8AME7__9HIV1, |82296342|sp|Q8AME6|Q8AME6__9HIV1, |82296341|sp|Q8AME5|Q8AME5__9HIV1, |82296340|sp|Q8AME4|Q8AME4__9HIV1, |82296339|sp|Q8AME3|Q8AME3__9HIV1, |82296338|sp|Q8AME2|Q8AME2__9HIV1, |82296337|sp|Q8AME1|Q8AME1__9HIV1, |82296336|sp|Q8AME0|Q8AME0__9HIV1, |82296335|sp|Q8AMD9|Q8AMD9__9HIV1, |82296334|sp|Q8AMD8|Q8AMD8__9HIV1, |82296241|sp|Q8AK08|Q8AK08__9HIV1, |82296239|sp|Q8AJZ9|Q8AJZ9__9HIV1, |82295651|sp|Q8AF20|Q8AF20__9HIV1, |82295605|sp|Q8AE73|Q8AE73__9HIV1, |82295602|sp|Q8AE65|Q8AE65__9HIV1, |82295599|sp|Q8AE57|Q8AE57__9HIV1, |82295596|sp|Q8AE49|Q8AE49__9HIV1, |82295593|sp|Q8AE41|Q8AE41__9HIV1, |82295590|sp|Q8AE33|Q8AE33__9HIV1, |82295587|sp|Q8AE25|Q8AE25__9HIV1, |82295584|sp|Q8AE16|Q8AE16__9HIV1, |82295581|sp|Q8AE08|Q8AE08__9HIV1, |82295578|sp|Q8AE00|Q8AE00__9HIV1, |82295575|sp|Q8ADZ2|Q8ADZ2__9HIV1, |82295572|sp|Q8ADY4|Q8ADY4__9HIV1, |82295569|sp|Q8ADX6|Q8ADX6__9HIV1, |82295566|sp|Q8ADW8|Q8ADW8__9HIV1, |82295563|sp|Q8ADW0|Q8ADW0__9HIV1, |82295560|sp|Q8ADV2|Q8ADV2__9HIV1, |82295557|sp|Q8ADU4|Q8ADU4__9HIV1, |82295554|sp|Q8ADT6|Q8ADT6__9HIV1, |82295551|sp|Q8ADS8|Q8ADS8__9HIV1, |82295548|sp|Q8ADS0|Q8ADS0__9HIV1, |82295545|sp|Q8ADR2|Q8ADR2__9HIV1, |82295542|sp|Q8ADQ4|Q8ADQ4__9HIV1, |82295539|sp|Q8ADP6|Q8ADP6__9HIV1, |82295536|sp|Q8ADN8|Q8ADN8__9HIV1, |82295533|sp|Q8ADN0|Q8ADN0__9HIV1truncated, |82295531|sp|Q8ADM2|Q8ADM2__9HIV1, |82295528|sp|Q8ADL4|Q8ADL4__9HIV1, |82295523|sp|Q8ADJ8|Q8ADJ8__9HIV1, |82295520|sp|Q8ADJ0|Q8ADJ0__9HIV1, |82295514|sp|Q8ADJ2|Q8ADJ2__9HIV1, |82295511|sp|Q8ADH4|Q8ADH4__9HIV1, |82295508|sp|Q8ADG6|Q8ADG6__9HIV1, |82295505|sp|Q8ADF8|Q8ADF8__9HIV1, |82295502|sp|Q8ADF0|Q8ADF0__9HIV1, |82295499|sp|Q8ADE2|Q8ADE2__9HIV1, |82295496|sp|Q8ADD4|Q8ADD4__9HIV1, |82295493|sp|Q8ADC6|Q8ADC6__9HIV1, |82295490|sp|Q8ADB8|Q8ADB8__9HIV1, |82295487|sp|Q8ADB0|Q8ADB0__9HIV1, |82295484|sp|Q8ADA2|Q8ADA2__9HIV1, |82295481|sp|Q8AD94|Q8AD94__9HIV1, |82295478|sp|Q8AD86|Q8AD86__9HIV1, |82295475|sp|Q8AD78|Q8AD78__9HIV1, |82295472|sp|Q8AD70|Q8AD70__9HIV1, |82295435|sp|Q8ACA6|Q8ACA6__9HIV1, |82295430|sp|Q8AC81|Q8AC81__9HIV1, |82295428|sp|Q8AC73|Q8AC73__9HIV1, |82295426|sp|Q8AC64|Q8AC64__9HIV1, |82295416|sp|Q8AC02|Q8AC02__9HIV1, |82293901|sp|Q8O156|Q8O156__9HIV1, |82293611|sp|Q7ZMI3|Q7ZMI3__9HIV1, |82293609|sp|Q7ZMH4|Q7ZMH4__9HIV1, |82293607|sp|Q7ZMG6|Q7ZMG6__9HIV1, |82293605|sp|Q7ZMF6|Q7ZMF6__9HIV1, |82293476|sp|Q7ZJJ0|Q7ZJJ0__9HIV1, |82293474|sp|Q7ZJG5|Q7ZJG5__9HIV1, |82293472|sp|Q7ZJF4|Q7ZJF4__9HIV1, |82293470|sp|Q7ZJE5|Q7ZJE5__9HIV1, |82293468|sp|Q7ZJD6|Q7ZJD6__9HIV1, |82293466|sp|Q7ZJC7|Q7ZJC7__9HIV1, |82293464|sp|Q7ZJB9|Q7ZJB9__9HIV1, |82293462|sp|Q7ZJB0|Q7ZJB0__9HIV1, |82293460|sp|Q7ZJA2|Q7ZJA2__9HIV1, |82293459|sp|Q7ZJ98|Q7ZJ98__9HIV1, |82293456|sp|Q7ZJ86|Q7ZJ86__9HIV1, |82293453|sp|Q7ZJ82|Q7ZJ82__9HIV1, |82293452|sp|Q7ZJ81|Q7ZJ81__9HIV1, |82293451|sp|Q7ZJ80|Q7ZJ80__9HIV1, |82293450|sp|Q7ZJ79|Q7ZJ79__9HIV1, |82293449|sp|Q7ZJ78|Q7ZJ78__9HIV1, |82293448|sp|Q7ZJ77|Q7ZJ77__9HIV1, |82293447|sp|Q7ZJ76|Q7ZJ76__9HIV1, |82293446|sp|Q7ZJ75|Q7ZJ75__9HIV1, |82293445|sp|Q7ZJ74|Q7ZJ74__9HIV1, |82293444|sp|Q7ZJ73|Q7ZJ73__9HIV1, |82293443|sp|Q7ZJ72|Q7ZJ72__9HIV1, |82293442|sp|Q7ZJ71|Q7ZJ71__9HIV1, |82293441|sp|Q7ZJ70|Q7ZJ70__9HIV1, |82293440|sp|Q7ZJ69|Q7ZJ69__9HIV1, |82293439|sp|Q7ZJ68|Q7ZJ68__9HIV1, |82293438|sp|Q7ZJ67|Q7ZJ67__9HIV1, |82293437|sp|Q7ZJ66|Q7ZJ66__9HIV1, |82293436|sp|Q7ZJ65|Q7ZJ65__9HIV1, |82293435|sp|Q7ZJ64|Q7ZJ64__9HIV1, |82293434|sp|Q7ZJ63|Q7ZJ63__9HIV1, |82293433|sp|Q7ZJ62|Q7ZJ62__9HIV1, |82293432|sp|Q7ZJ61|Q7ZJ61__9HIV1, |82293431|sp|Q7ZJ60|Q7ZJ60__9HIV1, |82293430|sp|Q7ZJ59|Q7ZJ59__9HIV1, |82293429|sp|Q7ZJ58|Q7ZJ58__9HIV1, |82293428|sp|Q7ZJ57|Q7ZJ57__9HIV1, |82293427|sp|Q7ZJ56|Q7ZJ56__9HIV1, |82293426|sp|Q7ZJ55|Q7ZJ55__9HIV1, |82293425|sp|Q7ZJ54|Q7ZJ54__9HIV1, |82293424|sp|Q7ZJ53|Q7ZJ53__9HIV1, |82293423|sp|Q7ZJ51|Q7ZJ51__9HIV1, |82293422|sp|Q7ZJ50|Q7ZJ50__9HIV1, |82293421|sp|Q7ZJ49|Q7ZJ49__9HIV1, |82293420|sp|Q7ZJ48|Q7ZJ48__9HIV1, |82293419|sp|Q7ZJ47|Q7ZJ47__9HIV1, |82293418|sp|Q7ZJ46|Q7ZJ46__9HIV1, |82293417|sp|Q7ZJ45|Q7ZJ45__9HIV1, |82293416|sp|Q7ZJ44|Q7ZJ44__9HIV1, |82293415|sp|Q7ZJ43|Q7ZJ43__9HIV1, |82293414|sp|Q7ZJ42|Q7ZJ42__9HIV1, |82293413|sp|Q7ZJ41|Q7ZJ41__9HIV1, |82293412|sp|Q7ZJ40|Q7ZJ40__9HIV1, |82293411|sp|Q7ZJ39|Q7ZJ39__9HIV1, |82293410|sp|Q7ZJ38|Q7ZJ38__9HIV1, |82293409|sp|Q7ZJ37|Q7ZJ37__9HIV1, |82293408|sp|Q7ZJ36|Q7ZJ36__9HIV1, |82293407|sp|Q7ZJ35|Q7ZJ35__9HIV1, |82293406|sp|Q7ZJ34|Q7ZJ34__9HIV1, |82293405|sp|Q7ZJ33|Q7ZJ33__9HIV1, |82293404|sp|Q7ZJ32|Q7ZJ32__9HIV1, |82293403|sp|Q7ZJ31|Q7ZJ31__9HIV1, |82293258|sp|Q7ZFG9|Q7ZFG9__9HIV1, |82293257|sp|Q7ZFG8|Q7ZFG8__9HIV1, |82293256|sp|Q7ZFG7|Q7ZFG7__9HIV1, |82293255|sp|Q7ZFG6|Q7ZFG6__9HIV1, |82293254|sp|Q7ZFG5|Q7ZFG5__9HIV1, |82293253|sp|Q7ZFG4|Q7ZFG4__9HIV1, |82293252|sp|Q7ZFG3|Q7ZFG3__9HIV1, |

| VPR proteins |
| --- |
| l82293251\|sp\|Q7ZFG2\|Q7ZFG2__9HIV1, l82293250\|sp\|Q7ZFG1\|Q7ZFG1__9HIV1, l82293249\|sp\|Q7ZFG0\|Q7ZFG0__9HIV1, l82293248\|sp\|Q7ZFF9\|Q7ZFF9__9HIV1, l82293247\|sp\|Q7ZFF8\|Q7ZFF8__9HIV1, l82293246\|sp\|Q7ZFF7\|Q7ZFF7__9HIV1, l82293245\|sp\|Q7ZFF6\|Q7ZFF6__9HIV1, l82293244\|sp\|Q7ZFF5\|Q7ZFF5__9HIV1, l82293243\|sp\|Q7ZFF4\|Q7ZFF4__9HIV1, l82293242\|sp\|Q7ZFF3\|Q7ZFF3__9HIV1, l82293241\|sp\|Q7ZFF2\|Q7ZFF2__9HIV1, l82293240\|sp\|Q7ZFF1\|Q7ZFF1__9HIV1, l82293239\|sp\|Q7ZFF0\|Q7ZFF0__9HIV1, l82293238\|sp\|Q7ZFE9\|Q7ZFE9__9HIV1, l82293237\|sp\|Q7ZFE8\|Q7ZFE8__9HIV1, l82293236\|sp\|Q7ZFE7\|Q7ZFE7__9HIV1, l82293235\|sp\|Q7ZFE6\|Q7ZFE6__9HIV1, l82293234\|sp\|Q7ZFE5\|Q7ZFE5__9HIV1, l82293233\|sp\|Q7ZFE4\|Q7ZFE4__9HIV1, l82293232\|sp\|Q7ZFE3\|Q7ZFE3__9HIV1, l82293231\|sp\|Q7ZFE2\|Q7ZFE2__9HIV1, l82293230\|sp\|Q7ZFE1\|Q7ZFE1__9HIV1, l82293229\|sp\|Q7ZFE0\|Q7ZFE0__9HIV1, l82293228\|sp\|Q7ZFD9\|Q7ZFD9__9HIV1, l82293227\|sp\|Q7ZFD8\|Q7ZFD8__9HIV1, l82293226\|sp\|Q7ZFD7\|Q7ZFD7__9HIV1, l82293225\|sp\|Q7ZFD6\|Q7ZFD6__9HIV1, l82293224\|sp\|Q7ZFD5\|Q7ZFD5__9HIV1, l82293223\|sp\|Q7ZFD4\|Q7ZFD4__9HIV1, l82293222\|sp\|Q7ZFD3\|Q7ZFD3__9HIV1, l82293221\|sp\|Q7ZFD2\|Q7ZFD2__9HIV1, l82293220\|sp\|Q7ZFD1\|Q7ZFD1__9HIV1, l82293219\|sp\|Q7ZFD0\|Q7ZFD0__9HIV1, l82293218\|sp\|Q7ZFC9\|Q7ZFC9__9HIV1, l82293217\|sp\|Q7ZFC8\|Q7ZFC8__9HIV1, l82293216\|sp\|Q7ZFC7\|Q7ZFC7__9HIV1, l82293215\|sp\|Q7ZFC6\|Q7ZFC6__9HIV1, l82293214\|sp\|Q7ZFC5\|Q7ZFC5__9HIV1, l82293213\|sp\|Q7ZFC4\|Q7ZFC4__9HIV1, l82293212\|sp\|Q7ZFC3\|Q7ZFC3__9HIV1, l82293211\|sp\|Q7ZFC2\|Q7ZFC2__9HIV1, l82293210\|sp\|Q7ZFC1\|Q7ZFC1__9HIV1, l82293209\|sp\|Q7ZFC0\|Q7ZFC0__9HIV1, l82293208\|sp\|Q7ZFB9\|Q7ZFB9__9HIV1, l82293207\|sp\|Q7ZFB8\|Q7ZFB8__9HIV1, l82293206\|sp\|Q7ZFB7\|Q7ZFB7__9HIV1, l82293161\|sp\|Q7ZC20\|Q7ZC20__9HIV1, l82293160\|sp\|Q7ZBX0\|Q7ZBX0__9HIV1, l82293159\|sp\|Q7ZBW9\|Q7ZBW9__9HIV1, l82293158\|sp\|Q7ZBW8\|Q7ZBW8__9HIV1, l82293157\|sp\|Q7ZBW7\|Q7ZBW7__9HIV1, l82293156\|sp\|Q7ZBW6\|Q7ZBW6__9HIV1, l82293155\|sp\|Q7ZBW5\|Q7ZBW5__9HIV1, l82293154\|sp\|Q7ZBW4\|Q7ZBW4__9HIV1, l82293153\|sp\|Q7ZBW3\|Q7ZBW3__9HIV1, l82293152\|sp\|Q7ZBW2\|Q7ZBW2__9HIV1, l82293151\|sp\|Q7ZBW1\|Q7ZBW1__9HIV1, l82293150\|sp\|Q7ZBW0\|Q7ZBW0__9HIV1, l82293149\|sp\|Q7ZBV9\|Q7ZBV9__9HIV1, l82293148\|sp\|Q7ZBV8\|Q7ZBV8__9HIV1, l82293147\|sp\|Q7ZBV7\|Q7ZBV7__9HIV1, l82293146\|sp\|Q7ZBV6\|Q7ZBV6__9HIV1, l82293145\|sp\|Q7ZBV5\|Q7ZBV5__9HIV1, l82293144\|sp\|Q7ZBV4\|Q7ZBV4__9HIV1, l82293143\|sp\|Q7ZBV3\|Q7ZBV3__9HIV1, l82293142\|sp\|Q7ZBV2\|Q7ZBV2__9HIV1, l82293141\|sp\|Q7ZBV1\|Q7ZBV1__9HIV1, l82293140\|sp\|Q7ZBV0\|Q7ZBV0__9HIV1, l82293139\|sp\|Q7ZBU9\|Q7ZBU9__9HIV1, l82293138\|sp\|Q7ZBU8\|Q7ZBU8__9HIV1, l82293137\|sp\|Q7ZBU7\|Q7ZBU7__9HIV1, l82293136\|sp\|Q7ZBU5\|Q7ZBU5__9HIV1, l82293135\|sp\|Q7ZBU4\|Q7ZBU4__9HIV1, l82293134\|sp\|Q7ZBU3\|Q7ZBU3__9HIV1, l82293133\|sp\|Q7ZBU2\|Q7ZBU2__9HIV1, l82293132\|sp\|Q7ZBU1\|Q7ZBU1__9HIV1, l82293131\|sp\|Q7ZBU0\|Q7ZBU0__9HIV1, l82293130\|sp\|Q7ZBT9\|Q7ZBT9__9HIV1, l82293129\|sp\|Q7ZBT8\|Q7ZBT8__9HIV1, l82293121\|sp\|Q7ZBG0\|Q7ZBG0__9HIV1, l82293096\|sp\|Q7ZAP6\|Q7ZAP6__9HIV1, l82293095\|sp\|Q7ZAP5\|Q7ZAP5__9HIV1, l82293094\|sp\|Q7ZAP4\|Q7ZAP4__9HIV1, l82292629\|sp\|Q7SV37\|Q7SV37__9HIV1, l82292626\|sp\|Q7SV30\|Q7SV30__9HIV1, l82292623\|sp\|Q7SV21\|Q7SV21__9HIV1, l82292620\|sp\|Q7SV12\|Q7SV12__9HIV1, l82292617\|sp\|Q7SV03\|Q7SV03__9HIV1, l82292614\|sp\|Q7SUZ4\|Q7SUZ4__9HIV1, l82292612\|sp\|Q7SUY7\|Q7SUY7__9HIV1, l82292609\|sp\|Q7SUX8\|Q7SUX8__9HIV1, l82292606\|sp\|Q7SUW9\|Q7SUW9__9HIV1, l82292218\|sp\|Q7SQM7\|Q7SQM7__9HIV1, l82292216\|sp\|Q7SQA6\|Q7SQA6__9HIV1, l82292214\|sp\|Q7SQA1\|Q7SQA1__9HIV1, l82292170\|sp\|Q7SQ47\|Q7SQ47__9HIV1, l82292168\|sp\|Q7SQ38\|Q7SQ38__9HIV1, l82292155\|sp\|Q7SPU2\|Q7SPU2__9HIV1, l82292152\|sp\|Q7SPT2\|Q7SPT2__9HIV1, l82291718\|sp\|Q7SKH2\|Q7SKH2__9HIV1, l82291716\|sp\|Q7SKG3\|Q7SKG3__9HIV1, l82291714\|sp\|Q7SKF4\|Q7SKF4__9HIV1, l82291401\|sp\|Q7SII6\|Q7SII6__9HIV1, l82291396\|sp\|Q7SIH6\|Q7SIH6__9HIV1, l82290717\|sp\|Q78244\|Q78244__9HIV1, l82290250\|sp\|Q77378\|Q77378__9HIV1, l82289495\|sp\|Q74825\|Q74825__9HIV1, l82289494\|sp\|Q74824\|Q74824__9HIV1, l82289493\|sp\|Q74823\|Q74823__9HIV1, l82289492\|sp\|Q74813\|Q74813__9HIV1, l82288905\|sp\|Q72994\|Q72994__9HIV1, l82288902\|sp\|Q72985\|Q72985__9HIV1, l82288635\|sp\|Q71VG3\|Q71VG3__9HIV1, l82288631\|sp\|Q71AY4\|Q71AY4__9HIV1, l82288629\|sp\|Q71AX5\|Q71AX5__9HIV1, l82288627\|sp\|Q71AW6\|Q71AW6__9HIV1, l82288536\|sp\|Q71820\|Q71820__9HIV1, l82288467\|sp\|Q70XD9\|Q70XD9__9HIV1, l82288464\|sp\|Q70XD2\|Q70XD2__9HIV1, l82288461\|sp\|Q70XC5\|Q70XC5__9HIV1, l82288062\|sp\|Q70154\|Q70154__9HIV1, l82288059\|sp\|Q70143\|Q70143__9HIV1, l82288008\|sp\|Q6Y940\|Q6Y940__9HIV1, l82288006\|sp\|Q6Y931\|Q6Y931__9HIV1, l82288004\|sp\|Q6Y922\|Q6Y922__9HIV1, l82288002\|sp\|Q6Y913\|Q6Y913__9HIV1, l82288000\|sp\|Q6Y904\|Q6Y904__9HIV1, l82287999\|sp\|Q6Y8Z5\|Q6Y8Z5__9HIV1, l82287997\|sp\|Q6Y8Y6\|Q6Y8Y6__9HIV1, l82287995\|sp\|Q6Y8X7\|Q6Y8X7__9HIV1, l82287993\|sp\|Q6Y8W8\|Q6Y8W8__9HIV1, l82287991\|sp\|Q6Y8V9\|Q6Y8V9__9HIV1, l82287989\|sp\|Q6Y8V0\|Q6Y8V0__9HIV1, l82287987\|sp\|Q6Y8U1\|Q6Y8U1__9HIV1, l82287985\|sp\|Q6Y8T3\|Q6Y8T3__9HIV1, l82287983\|sp\|Q6Y8S4\|Q6Y8S4__9HIV1, l82287980\|sp\|Q6Y8R5\|Q6Y8R5__9HIV1, l82287925\|sp\|Q6XKC4\|Q6XKC4__9HIV1, l82287923\|sp\|Q6XKB5\|Q6XKB5__9HIV1, l82287894\|sp\|Q6X6X0\|Q6X6X0__9HIV1, l82287892\|sp\|Q6X6W1\|Q6X6W1__9HIV1, l82287890\|sp\|Q6X6U4\|Q6X6U4__9HIV1, l82287888\|sp\|Q6X6T5\|Q6X6T5__9HIV1, l82287886\|sp\|Q6X6S6\|Q6X6S6__9HIV1, l82287884\|sp\|Q6X6R7\|Q6X6R7__9HIV1, l82287882\|sp\|Q6X6Q1\|Q6X6Q1__9HIV1, l82287880\|sp\|Q6X6P2\|Q6X6P2__9HIV1, l82287878\|sp\|Q6X6N3\|Q6X6N3__9HIV1, l82287876\|sp\|Q6X6L6\|Q6X6L6__9HIV1, l82287874\|sp\|Q6X6K7\|Q6X6K7__9HIV1, l82287872\|sp\|Q6X6J8\|Q6X6J8__9HIV1, l82287870\|sp\|Q6X6I3\|Q6X6I3__9HIV1, l82287868\|sp\|Q6X6G6\|Q6X6G6__9HIV1, l82287811\|sp\|Q6WS68\|Q6WS68__9HIV1, |

| VPR proteins |
| --- |
| \|82287557\|sp\|Q6V3U8\|Q6V3U8__9HIV1, \|82287554\|sp\|Q6V3T3\|Q6V3T3__9HIV1, \|82287553\|sp\|Q6V3S5\|Q6V3S5__9HIV1, \|82287373\|sp\|Q6URH2\|Q6URH2__9HIV1, \|82287372\|sp\|Q6URH1\|Q6URH1__9HIV1, \|82287371\|sp\|Q6URH0\|Q6URH0__9HIV1, \|82287370\|sp\|Q6URG9\|Q6URG9__9HIV1, \|82287369\|sp\|Q6URG8\|Q6URG8__9HIV1, \|82287368\|sp\|Q6URG7\|Q6URG7__9HIV1, \|82287367\|sp\|Q6URG6\|Q6URG6__9HIV1, \|82287366\|sp\|Q6URG5\|Q6URG5__9HIV1, \|82287365\|sp\|Q6URG4\|Q6URG4__9HIV1, \|82287364\|sp\|Q6URG3\|Q6URG3__9HIV1, \|82287363\|sp\|Q6URG2\|Q6URG2__9HIV1, \|82287362\|sp\|Q6URG1\|Q6URG1__9HIV1, \|82287361\|sp\|Q6URG0\|Q6URG0__9HIV1, \|82287360\|sp\|Q6URF9\|Q6URF9__9HIV1, \|82287359\|sp\|Q6URF8\|Q6URF8__9HIV1, \|82287357\|sp\|Q6URF6\|Q6URF6__9HIV1, \|82287356\|sp\|Q6URF5\|Q6URF5__9HIV1, \|82287354\|sp\|Q6URF3\|Q6URF3__9HIV1, \|82287353\|sp\|Q6URF2\|Q6URF2__9HIV1, \|82287352\|sp\|Q6URF1\|Q6URF1__9HIV1, \|82287351\|sp\|Q6URF0\|Q6URF0__9HIV1, \|82287350\|sp\|Q6URE9\|Q6URE9__9HIV1, \|82287349\|sp\|Q6URE8\|Q6URE8__9HIV1, \|82287348\|sp\|Q6URE7\|Q6URE7__9HIV1, \|82287347\|sp\|Q6URE5\|Q6URE5__9HIV1, \|82287346\|sp\|Q6URE4\|Q6URE4__9HIV1, \|82287345\|sp\|Q6URE3\|Q6URE3__9HIV1, \|82287344\|sp\|Q6URE2\|Q6URE2__9HIV1, \|82287343\|sp\|Q6URE1\|Q6URE1__9HIV1, \|82287342\|sp\|Q6URE0\|Q6URE0__9HIV1, \|82287341\|sp\|Q6URD9\|Q6URD9__9HIV1, \|82287340\|sp\|Q6URD8\|Q6URD8__9HIV1, \|82287339\|sp\|Q6URD7\|Q6URD7__9HIV1, \|82287338\|sp\|Q6URD6\|Q6URD6__9HIV1, \|82287337\|sp\|Q6URD5\|Q6URD5__9HIV1, \|82287336\|sp\|Q6URD4\|Q6URD4__9HIV1, \|82287335\|sp\|Q6URD3\|Q6URD3__9HIV1, \|82287334\|sp\|Q6URD2\|Q6URD2__9HIV1, \|82287333\|sp\|Q6URD1\|Q6URD1__9HIV1, \|82287332\|sp\|Q6URD0\|Q6URD0__9HIV1, \|82287331\|sp\|Q6URC8\|Q6URC8__9HIV1, \|82287330\|sp\|Q6URC7\|Q6URC7__9HIV1, \|82287241\|sp\|Q6UFQ4\|Q6UFQ4__9HIV1, \|82287239\|sp\|Q6UFP5\|Q6UFP5__9HIV1, \|82287237\|sp\|Q6UFN6\|Q6UFN6__9HIV1, \|82287234\|sp\|Q6UFL9\|Q6UFL9__9HIV1, \|82287233\|sp\|Q6UFL3\|Q6UFL3__9HIV1, \|82287231\|sp\|Q6UFK4\|Q6UFK4__9HIV1, \|82287229\|sp\|Q6UFJ5\|Q6UFJ5__9HIV1, \|82287227\|sp\|Q6UFI6\|Q6UFI6__9HIV1, \|82287225\|sp\|Q6UFH7\|Q6UFH7__9HIV1, \|82287223\|sp\|Q6UFG8\|Q6UFG8__9HIV1, \|82287221\|sp\|Q6UFF9\|Q6UFF9__9HIV1, \|82287219\|sp\|Q6UFF1\|Q6UFF1__9HIV1, \|82287217\|sp\|Q6UFE2\|Q6UFE2__9HIV1, \|82287215\|sp\|Q6UFD1\|Q6UFD1__9HIV1, \|82287213\|sp\|Q6UFC2\|Q6UFC2__9HIV1, \|82287211\|sp\|Q6UFB3\|Q6UFB3__9HIV1, \|82287209\|sp\|Q6UFA4\|Q6UFA4__9HIV1, \|82287207\|sp\|Q6UF95\|Q6UF95__9HIV1, \|82287205\|sp\|Q6UF86\|Q6UF86__9HIV1, \|82287202\|sp\|Q6UF69\|Q6UF69__9HIV1, \|82287199\|sp\|Q6UF55\|Q6UF55__9HIV1, \|82287197\|sp\|Q6UF46\|Q6UF46__9HIV1, \|82287195\|sp\|Q6UF37\|Q6UF37__9HIV1, \|82287193\|sp\|Q6UF28\|Q6UF28__9HIV1, \|82287191\|sp\|Q6UF19\|Q6UF19__9HIV1, \|82287189\|sp\|Q6UF10\|Q6UF10__9HIV1, \|82287187\|sp\|Q6UF04\|Q6UF04__9HIV1, \|82287185\|sp\|Q6UEZ5\|Q6UEZ5__9HIV1, \|82287183\|sp\|Q6UEY6\|Q6UEY6__9HIV1, \|82287181\|sp\|Q6UEX7\|Q6UEX7__9HIV1, \|82287179\|sp\|Q6UEW8\|Q6UEW8__9HIV1, \|82287177\|sp\|Q6UEV9\|Q6UEV9__9HIV1, \|82287175\|sp\|Q6UEV0\|Q6UEV0__9HIV1, \|82287173\|sp\|Q6UEU1\|Q6UEU1__9HIV1, \|82287171\|sp\|Q6UET2\|Q6UET2__9HIV1, \|82287169\|sp\|Q6UES4\|Q6UES4__9HIV1, \|82287167\|sp\|Q6UER5\|Q6UER5__9HIV1, \|82287165\|sp\|Q6UEQ6\|Q6UEQ6__9HIV1, \|82287163\|sp\|Q6UEP7\|Q6UEP7__9HIV1, \|82287161\|sp\|Q6UEN9\|Q6UEN9__9HIV1, \|82287159\|sp\|Q6UEN0\|Q6UEN0__9HIV1, \|82287157\|sp\|Q6UEM4\|Q6UEM4__9HIV1, \|82287155\|sp\|Q6UEL5\|Q6UEL5__9HIV1, \|82287153\|sp\|Q6UEK6\|Q6UEK6__9HIV1, \|82287151\|sp\|Q6UEJ7\|Q6UEJ7__9HIV1, \|82286728\|sp\|Q6SZV9\|Q6SZV9__9HIV1, \|82286727\|sp\|Q6SZV8\|Q6SZV8__9HIV1, \|82286726\|sp\|Q6SZV7\|Q6SZV7__9HIV1, \|82286725\|sp\|Q6SZV5\|Q6SZV5__9HIV1, \|82286724\|sp\|Q6SZV4\|Q6SZV4__9HIV1, \|82286723\|sp\|Q6SZV3\|Q6SZV3__9HIV1, \|82286722\|sp\|Q6SZV2\|Q6SZV2__9HIV1, \|82286721\|sp\|Q6SZV1\|Q6SZV1__9HIV1, \|82286720\|sp\|Q6SZV0\|Q6SZV0__9HIV1, \|82286719\|sp\|Q6SZU9\|Q6SZU9__9HIV1, \|82286718\|sp\|Q6SZU8\|Q6SZU8__9HIV1, \|82286717\|sp\|Q6SZU7\|Q6SZU7__9HIV1, \|82286716\|sp\|Q6SZU6\|Q6SZU6__9HIV1, \|82286476\|sp\|Q6S884\|Q6S884__9HIV1, \|82286474\|sp\|Q6S875\|Q6S875__9HIV1, \|82286472\|sp\|Q6S867\|Q6S867__9HIV1, \|82286470\|sp\|Q6S860\|Q6S860__9HIV1, \|82286468\|sp\|Q6S852\|Q6S852__9HIV1, \|82286466\|sp\|Q6S844\|Q6S844__9HIV1, \|82286464\|sp\|Q6S835\|Q6S835__9HIV1, \|82286462\|sp\|Q6S829\|Q6S829__9HIV1, \|82286460\|sp\|Q6S821\|Q6S821__9HIV1, \|82286459\|sp\|Q6S813\|Q6S813__9HIV1, \|82286457\|sp\|Q6S805\|Q6S805__9HIV1, \|82286455\|sp\|Q6S7Z6\|Q6S7Z6__9HIV1, \|82286453\|sp\|Q6S7Y9\|Q6S7Y9__9HIV1, \|82286451\|sp\|Q6S7Y0\|Q6S7Y0__9HIV1, \|82286449\|sp\|Q6S7X1\|Q6S7X1__9HIV1, \|82286447\|sp\|Q6S7W2\|Q6S7W2__9HIV1, \|82286445\|sp\|Q6S7V5\|Q6S7V5__9HIV1, \|82286443\|sp\|Q6S7U6\|Q6S7U6__9HIV1, \|82286441\|sp\|Q6S7T8\|Q6S7T8__9HIV1, \|82286439\|sp\|Q6S7S9\|Q6S7S9__9HIV1, \|82286437\|sp\|Q6S7S1\|Q6S7S1__9HIV1, \|82286006\|sp\|Q6RJG5\|Q6RJG5__9HIV1, \|82286004\|sp\|Q6RJF8\|Q6RJF8__9HIV1, \|82286000\|sp\|Q6RJD7\|Q6RJD7__9HIV1, \|82285999\|sp\|Q6RJD0\|Q6RJD0__9HIV1, \|82285998\|sp\|Q6RJC3\|Q6RJC3__9HIV1, \|82285996\|sp\|Q6RJA2\|Q6RJA2__9HIV1, \|82285995\|sp\|Q6RJ81\|Q6RJ81__9HIV1, \|82285994\|sp\|Q6RJ74\|Q6RJ74__9HIV1, \|82285993\|sp\|Q6RJ67\|Q6RJ67__9HIV1, \|82285992\|sp\|Q6RJ60\|Q6RJ60__9HIV1, \|82285991\|sp\|Q6RJ53\|Q6RJ53__9HIV1, \|82285990\|sp\|Q6RJ46\|Q6RJ46__9HIV1, \|82285989\|sp\|Q6RJ39\|Q6RJ39__9HIV1, \|82285987\|sp\|Q6RFP0\|Q6RFP0__9HIV1, \|82285703\|sp\|Q6QKX8\|Q6QKX8__9HIV1, \|82285701\|sp\|Q6QKW9\|Q6QKW9__9HIV1, \|82285279\|sp\|Q6Q459\|Q6Q459__9HIV1, \|82285277\|sp\|Q6Q450\|Q6Q450__9HIV1, \|82285273\|sp\|Q6Q434\|Q6Q434__9HIV1, \|82285214\|sp\|Q6Q2V6\|Q6Q2V6__9HIV1, \|82285212\|sp\|Q6Q2U7\|Q6Q2U7__9HIV1, \|82285057\|sp\|Q6PRC4\|Q6PRC4__9HIV1, \|82285056\|sp\|Q6PRC2\|Q6PRC2__9HIV1, \|82285055\|sp\|Q6PRC0\|Q6PRC0__9HIV1, \|82285054\|sp\|Q6PRB9\|Q6PRB9__9HIV1, \|82285053\|sp\|Q6PRB8\|Q6PRB8__9HIV1, \|82285052\|sp\|Q6PRB7\|Q6PRB7__9HIV1, \|82285051\|sp\|Q6PRB6\|Q6PRB6__9HIV1, \|82285050\|sp\|Q6PRB3\|Q6PRB3__9HIV1, \|82285049\|sp\|Q6PRB2\|Q6PRB2__9HIV1, |

| VPR proteins |
| --- |
| \|82285048\|sp\|Q6PRB1\|Q6PRB1__9HIV1, \|82285047\|sp\|Q6PRB0\|Q6PRB0__9HIV1, \|82285046\|sp\|Q6PRA9\|Q6PRA9__9HIV1, \|82285045\|sp\|Q6PRA8\|Q6PRA8__9HIV1, \|82285044\|sp\|Q6PRA6\|Q6PRA6__9HIV1, \|82285043\|sp\|Q6PRA4\|Q6PRA4__9HIV1, \|82285042\|sp\|Q6PRA3\|Q6PRA3__9HIV1, \|82285041\|sp\|Q6PRA1\|Q6PRA1__9HIV1, \|82285040\|sp\|Q6PRA0\|Q6PRA0__9HIV1, \|82285039\|sp\|Q6PR98\|Q6PR98__9HIV1, \|82285038\|sp\|Q6PR97\|Q6PR97__9HIV1, \|82285037\|sp\|Q6PR95\|Q6PR95__9HIV1, \|82285036\|sp\|Q6PR94\|Q6PR94__9HIV1, \|82285035\|sp\|Q6PR93\|Q6PR93__9HIV1, \|82285034\|sp\|Q6PR92\|Q6PR92__9HIV1, \|82285033\|sp\|Q6PR91\|Q6PR91__9HIV1, \|82285032\|sp\|Q6PR90\|Q6PR90__9HIV1, \|82285031\|sp\|Q6PR88\|Q6PR88__9HIV1, \|82285030\|sp\|Q6PR86\|Q6PR86__9HIV1, \|82285029\|sp\|Q6PR85\|Q6PR85__9HIV1, \|82285028\|sp\|Q6PR84\|Q6PR84__9HIV1, \|82285027\|sp\|Q6PR83\|Q6PR83__9HIV1, \|82285026\|sp\|Q6PR82\|Q6PR82__9HIV1, \|82285025\|sp\|Q6PR81\|Q6PR81__9HIV1, \|82285024\|sp\|Q6PR80\|Q6PR80__9HIV1, \|82285023\|sp\|Q6PR79\|Q6PR79__9HIV1, \|82285022\|sp\|Q6PR78\|Q6PR78__9HIV1, \|82285021\|sp\|Q6PR77\|Q6PR77__9HIV1, \|82285019\|sp\|Q6PR25\|Q6PR25__9HIV1, \|82285017\|sp\|Q6PR16\|Q6PR16__9HIV1, \|82285015\|sp\|Q6PR01\|Q6PR01__9HIV1, \|82285013\|sp\|Q6PQZ4\|Q6PQZ4__9HIV1, \|82284944\|sp\|Q6JP17\|Q6JP17__9HIV1, \|82284943\|sp\|Q6JP08\|Q6JP08__9HIV1, \|82284941\|sp\|Q6JNZ9\|Q6JNZ9__9HIV1, \|82284940\|sp\|Q6JNZ0\|Q6JNZ0__9HIV1, \|82284938\|sp\|Q6JNY1\|Q6JNY1__9HIV1, \|82284936\|sp\|Q6JNX2\|Q6JNX2__9HIV1, \|82284934\|sp\|Q6JNW3\|Q6JNW3__9HIV1, \|82284932\|sp\|Q6JNV4\|Q6JNV4__9HIV1, \|82284930\|sp\|Q6JNU5\|Q6JNU5__9HIV1, \|82284928\|sp\|Q6JNT6\|Q6JNT6__9HIV1, \|82284926\|sp\|Q6JNS7\|Q6JNS7__9HIV1, \|82284925\|sp\|Q6JNR8\|Q6JNR8__9HIV1, \|82284924\|sp\|Q6JNQ9\|Q6JNQ9__9HIV1, \|82284922\|sp\|Q6JNQ0\|Q6JNQ0__9HIV1, \|82284920\|sp\|Q6JNP1\|Q6JNP1__9HIV1, \|82284918\|sp\|Q6JNN2\|Q6JNN2__9HIV1, \|82284916\|sp\|Q6JNM3\|Q6JNM3__9HIV1, \|82284914\|sp\|Q6JNK9\|Q6JNK9__9HIV1, \|82284912\|sp\|Q6JNK0\|Q6JNK0__9HIV1, \|82284910\|sp\|Q6JNJ1\|Q6JNJ1__9HIV1, \|82284908\|sp\|Q6JNI2\|Q6JNI2__9HIV1, \|82284906\|sp\|Q6JNH5\|Q6JNH5__9HIV1, \|82284904\|sp\|Q6JNG6\|Q6JNG6__9HIV1, \|82284902\|sp\|Q6JNF7\|Q6JNF7__9HIV1, \|82284900\|sp\|Q6JNE8\|Q6JNE8__9HIV1, \|82284897\|sp\|Q6JND9\|Q6JND9__9HIV1, \|82284895\|sp\|Q6JND0\|Q6JND0__9HIV1, \|82284893\|sp\|Q6JNC1\|Q6JNC1__9HIV1, \|82284891\|sp\|Q6JNB2\|Q6JNB2__9HIV1, \|82284889\|sp\|Q6JNA3\|Q6JNA3__9HIV1, \|82284887\|sp\|Q6JN95\|Q6JN95__9HIV1, \|82284885\|sp\|Q6JN86\|Q6JN86__9HIV1, \|82284883\|sp\|Q6JN77\|Q6JN77__9HIV1, \|82284881\|sp\|Q6JN68\|Q6JN68__9HIV1, \|82284826\|sp\|Q6IYB8\|Q6IYB8__9HIV1, \|82284825\|sp\|Q6IYB7\|Q6IYB7__9HIV1, \|82284824\|sp\|Q6IYB6\|Q6IYB6__9HIV1, \|82284823\|sp\|Q6IYB5\|Q6IYB5__9HIV1, \|82284822\|sp\|Q6IYB4\|Q6IYB4__9HIV1, \|82284821\|sp\|Q6IYB3\|Q6IYB3__9HIV1, \|82284820\|sp\|Q6IYB2\|Q6IYB2__9HIV1, \|82284819\|sp\|Q6IYB1\|Q6IYB1__9HIV1, \|82284818\|sp\|Q6IYB0\|Q6IYB0__9HIV1, \|82284817\|sp\|Q6IYA9\|Q6IYA9__9HIV1, \|82284816\|sp\|Q6IYA8\|Q6IYA8__9HIV1, \|82284815\|sp\|Q6IYA7\|Q6IYA7__9HIV1, \|82284814\|sp\|Q6IYA6\|Q6IYA6__9HIV1, \|82284813\|sp\|Q6IYA5\|Q6IYA5__9HIV1, \|82284812\|sp\|Q6IYA4\|Q6IYA4__9HIV1, \|82284811\|sp\|Q6IYA3\|Q6IYA3__9HIV1, \|82284810\|sp\|Q6IYA2\|Q6IYA2__9HIV1, \|82284809\|sp\|Q6IYA1\|Q6IYA1__9HIV1, \|82284808\|sp\|Q6IYA0\|Q6IYA0__9HIV1, \|82284807\|sp\|Q6IY99\|Q6IY99__9HIV1, \|82284806\|sp\|Q6IY98\|Q6IY98__9HIV1, \|82284805\|sp\|Q6IY97\|Q6IY97__9HIV1, \|82284804\|sp\|Q6IY96\|Q6IY96__9HIV1, \|82284803\|sp\|Q6IY95\|Q6IY95__9HIV1, \|82284802\|sp\|Q6IY94\|Q6IY94__9HIV1, \|82284801\|sp\|Q6IY93\|Q6IY93__9HIV1, \|82284800\|sp\|Q6IY92\|Q6IY92__9HIV1, \|82284799\|sp\|Q6IY91\|Q6IY91__9HIV1, \|82284798\|sp\|Q6IY90\|Q6IY90__9HIV1, \|82284797\|sp\|Q6IY89\|Q6IY89__9HIV1, \|82284796\|sp\|Q6IY88\|Q6IY88__9HIV1, \|82284795\|sp\|Q6IY87\|Q6IY87__9HIV1, \|82284794\|sp\|Q6IY86\|Q6IY86__9HIV1, \|82284793\|sp\|Q6IY85\|Q6IY85__9HIV1, \|82284792\|sp\|Q6IY84\|Q6IY84__9HIV1, \|82284791\|sp\|Q6IY83\|Q6IY83__9HIV1, \|82284790\|sp\|Q6IY82\|Q6IY82__9HIV1, \|82284789\|sp\|Q6IY81\|Q6IY81__9HIV1, \|82284788\|sp\|Q6IY80\|Q6IY80__9HIV1, \|82284787\|sp\|Q6IY79\|Q6IY79__9HIV1, \|82284786\|sp\|Q6IY78\|Q6IY78__9HIV1, \|82284785\|sp\|Q6IY77\|Q6IY77__9HIV1, \|82284784\|sp\|Q6IY76\|Q6IY76__9HIV1, \|82284730\|sp\|Q6H1T5\|Q6H1T5__9HIV1, \|82284728\|sp\|Q6H1S6\|Q6H1S6__9HIV1, \|82284726\|sp\|Q6H1R7\|Q6H1R7__9HIV1, \|82284724\|sp\|Q6H1Q8\|Q6H1Q8__9HIV1, \|82284722\|sp\|Q6H1P9\|Q6H1P9__9HIV1, \|82284720\|sp\|Q6H1P0\|Q6H1P0__9HIV1, \|82284718\|sp\|Q6H1N1\|Q6H1N1__9HIV1, \|82284716\|sp\|Q6H1M2\|Q6H1M2__9HIV1, \|82284702\|sp\|Q6EG84\|Q6EG84__9HIV1, \|82284700\|sp\|Q6EG57\|Q6EG57__9HIV1, \|82284699\|sp\|Q6EG48\|Q6EG48__9HIV1, \|82284697\|sp\|Q6EG39\|Q6EG39__9HIV1, \|82284696\|sp\|Q6EG30\|Q6EG30__9HIV1, \|82284694\|sp\|Q6EG21\|Q6EG21__9HIV1, \|82284693\|sp\|Q6EG03\|Q6EG03__9HIV1, \|82284691\|sp\|Q6EFZ4\|Q6EFZ4__9HIV1, \|82284690\|sp\|Q6EFY5\|Q6EFY5__9HIV1, \|82284688\|sp\|Q6EFX6\|Q6EFX6__9HIV1, \|82284687\|sp\|Q6EFW7\|Q6EFW7__9HIV1, \|82284684\|sp\|Q6EFV8\|Q6EFV8__9HIV1, \|82284682\|sp\|Q6EFM9\|Q6EFM9__9HIV1, \|82284680\|sp\|Q6EFM0\|Q6EFM0__9HIV1, \|82284399\|sp\|Q6B4P0\|Q6B4P0__9HIV1, \|82284359\|sp\|Q69GS9\|Q69GS9__9HIV1, \|82284356\|sp\|Q69GS0\|Q69GS0__9HIV1, \|82284354\|sp\|Q69GR1\|Q69GR1__9HIV1, \|82284352\|sp\|Q69GQ2\|Q69GQ2__9HIV1, \|82284350\|sp\|Q69GP3\|Q69GP3__9HIV1, \|82284348\|sp\|Q69GN4\|Q69GN4__9HIV1, \|82284346\|sp\|Q69GM5\|Q69GM5__9HIV1, \|82283879\|sp\|Q673V6\|Q673V6__9HIV1, \|82283877\|sp\|Q673U3\|Q673U3__9HIV1, \|82283875\|sp\|Q672U2\|Q672U2__9HIV1, \|82283873\|sp\|Q672T4\|Q672T4__9HIV1, \|82283871\|sp\|Q672S7\|Q672S7__9HIV1, \|82283869\|sp\|Q672R9\|Q672R9__9HIV1, \|82283827\|sp\|Q66TT3\|Q66TT3__9HIV1, \|82283825\|sp\|Q66TS3\|Q66TS3__9HIV1, \|82283823\|sp\|Q66TR5\|Q66TR5__9HIV1, \|82283821\|sp\|Q66TQ5\|Q66TQ5__9HIV1, \|82283280\|sp\|Q5UEH3\|Q5UEH3__9HIV1, \|82283278\|sp\|Q5UEG4\|Q5UEG4__9HIV1, \|82283276\|sp\|Q5U9B8\|Q5U9B8__9HIV1, \|82283274\|sp\|Q5U9A9\|Q5U9A9__9HIV1, \|82283272\|sp\|Q5U9A1\|Q5U9A1__9HIV1, |

| VPR proteins |
| --- |
| I82283270\|sp\|Q5U992\|Q5U992_9HIV1, I82283268\|sp\|Q5U984\|Q5U984_9HIV1, I82283266\|sp\|Q5U977\|Q5U977_9HIV1, I82283264\|sp\|Q5U968\|Q5U968_9HIV1, I82283263\|sp\|Q5U967\|Q5U967_9HIV1, I82283261\|sp\|Q5U960\|Q5U960_9HIV1, I82283259\|sp\|Q5U944\|Q5U944_9HIV1, I82283257\|sp\|Q5U937\|Q5U937_9HIV1, I82283256\|sp\|Q5U8K4\|Q5U8K4_9HIV1, I82283254\|sp\|Q5U8J5\|Q5U8J5_9HIV1, I82283252\|sp\|Q5U8I6\|Q5U8I6_9HIV1, I82283250\|sp\|Q5U8H7\|Q5U8H7_9HIV1, I82283248\|sp\|Q5U8G8\|Q5U8G8_9HIV1, I82283246\|sp\|Q5U8F9\|Q5U8F9_9HIV1, I82283244\|sp\|Q5U8F0\|Q5U8F0_9HIV1, I82283241\|sp\|Q5U8D2\|Q5U8D2_9HIV1, I82283239\|sp\|Q5U8C3\|Q5U8C3_9HIV1, I82283237\|sp\|Q5U8B4\|Q5U8B4_9HIV1, I82283235\|sp\|Q5U8A5\|Q5U8A5_9HIV1, I82283233\|sp\|Q5U896\|Q5U896_9HIV1, I82283231\|sp\|Q5U887\|Q5U887_9HIV1, I82283229\|sp\|Q5U878\|Q5U878_9HIV1, I82283228\|sp\|Q5SFQ1\|Q5SFQ1_9HIV1, I82283206\|sp\|Q5S3G0\|Q5S3G0_9HIV1, I82283205\|sp\|Q5S3F9\|Q5S3F9_9HIV1, I82283204\|sp\|Q5S3F8\|Q5S3F8_9HIV1, I82283203\|sp\|Q5S3F7\|Q5S3F7_9HIV1, I82283202\|sp\|Q5S3F6\|Q5S3F6_9HIV1, I82283201\|sp\|Q5S3F5\|Q5S3F5_9HIV1, I82283200\|sp\|Q5S3F4\|Q5S3F4_9HIV1, I82283199\|sp\|Q5S3F3\|Q5S3F3_9HIV1, I82283198\|sp\|Q5S3F2\|Q5S3F2_9HIV1, I82283197\|sp\|Q5S3F1\|Q5S3F1_9HIV1, I82283196\|sp\|Q5S3E9\|Q5S3E9_9HIV1, I82283195\|sp\|Q5S3E8\|Q5S3E8_9HIV1, I82283194\|sp\|Q5S3E7\|Q5S3E7_9HIV1, I82283193\|sp\|Q5S3E6\|Q5S3E6_9HIV1, I82283192\|sp\|Q5S3E5\|Q5S3E5_9HIV1, I82283191\|sp\|Q5S3E4\|Q5S3E4_9HIV1, I82283190\|sp\|Q5S3E2\|Q5S3E2_9HIV1, I82283189\|sp\|Q5S3E1\|Q5S3EL_9HIV1, I82283188\|sp\|Q5S3E0\|Q5S3E0_9HIV1, I82283187\|sp\|Q5S3D9\|Q5S3D9_9HIV1, I82283186\|sp\|Q5S3D8\|Q5S3D8_9HIV1, I82283185\|sp\|Q5S3D7\|Q5S3D7_9HIV1, I82283184\|sp\|Q5S3D6\|Q5S3D6_9HIV1, I82283183\|sp\|Q5S3D4\|Q5S3D4_9HIV1, I82283182\|sp\|Q5S3D2\|Q5S3D2_9HIV1, I82283181\|sp\|Q5S3D1\|Q5S3D1_9HIV1, I82283180\|sp\|Q5S3D0\|Q5S3D0_9HIV1, I82283179\|sp\|Q5S3C8\|Q5S3C8_9HIV1, I82283178\|sp\|Q5S3C7\|Q5S3C7_9HIV1, I82283177\|sp\|Q5S3C6\|Q5S3C6_9HIV1, I82283176\|sp\|Q5S3C5\|Q5S3C5_9HIV1, I82283175\|sp\|Q5S3C3\|Q5S3C3_9HIV1, I82283174\|sp\|Q5S3C2\|Q5S3C2_9HIV1, I82283173\|sp\|Q5S3B9\|Q5S3B9_9HIV1, I82283172\|sp\|Q5S3B7\|Q5S3B7_9HIV1, I82283171\|sp\|Q5S3B2\|Q5S3B2_9HIV1, I82283170\|sp\|Q5S3B0\|Q5S3B0_9HIV1, I82283169\|sp\|Q5S3A9\|Q5S3A9_9HIV1, I82283168\|sp\|Q5S3A8\|Q5S3A8_9HIV1, I82283167\|sp\|Q5S3A7\|Q5S3A7_9HIV1, I82283166\|sp\|Q5S3A6\|Q5S3A6_9HIV1, I82283165\|sp\|Q5S3A5\|Q5S3A5_9HIV1, I82283164\|sp\|Q5S3A3\|Q5S3A3_9HIV1, I82283163\|sp\|Q5S3A2\|Q5S3A2_9HIV1, I82283162\|sp\|Q5S3A1\|Q5S3A1_9HIV1, I82283161\|sp\|Q5S3A0\|Q5S3A0_9HIV1, I82283160\|sp\|Q5S397\|Q5S397_9HIV1, I82283159\|sp\|Q5S396\|Q5S396_9HIV1, I82283158\|sp\|Q5S395\|Q5S395_9HIV1, I82283157\|sp\|Q5S394\|Q5S394_9HIV1, I82283156\|sp\|Q5S393\|Q5S393_9HIV1, I82283155\|sp\|Q5S392\|Q5S392_9HIV1, I82283154\|sp\|Q5S391\|Q5S391_9HIV1, I82283153\|sp\|Q5S389\|Q5S389_9HIV1, I82283152\|sp\|Q5S387\|Q5S387_9HIV1, I82283151\|sp\|Q5S385\|Q5S385_9HIV1, I82283150\|sp\|Q5S384\|Q5S384_9HIV1, I82283149\|sp\|Q5S383\|Q5S383_9HIV1, I82283148\|sp\|Q5S382\|Q5S382_9HIV1, I82283147\|sp\|Q5S380\|Q5S380_9HIV1, I82283146\|sp\|Q5S377\|Q5S377_9HIV1, I82283145\|sp\|Q5S374\|Q5S374_9HIV1, I82283144\|sp\|Q5S371\|Q5S371_9HIV1, I82283143\|sp\|Q5S370\|Q5S370_9HIV1, I82283142\|sp\|Q5S369\|Q5S369_9HIV1, I82283141\|sp\|Q5S367\|Q5S367_9HIV1, I82283140\|sp\|Q5S366\|Q5S366_9HIV1, I82283139\|sp\|Q5S365\|Q5S365_9HIV1, I82283138\|sp\|Q5S364\|Q5S364_9HIV1, I82283137\|sp\|Q5S363\|Q5S363_9HIV1, I82283136\|sp\|Q5S362\|Q5S362_9HIV1, I82283135\|sp\|Q5S360\|Q5S360_9HIV1, I82283134\|sp\|Q5S359\|Q5S359_9HIV1, I82283133\|sp\|Q5S358\|Q5S358_9HIV1, I82283132\|sp\|Q5S357\|Q5S357_9HIV1, I82283131\|sp\|Q5S356\|Q5S356_9HIV1, I82283130\|sp\|Q5S355\|Q5S355_9HIV1, I82283129\|sp\|Q5S354\|Q5S354_9HIV1, I82283128\|sp\|Q5S353\|Q5S353_9HIV1, I82283127\|sp\|Q5S352\|Q5S352_9HIV1, I82283126\|sp\|Q5S350\|Q5S350_9HIV1, I82283125\|sp\|Q5S349\|Q5S349_9HIV1, I82283124\|sp\|Q5S348\|Q5S348_9HIV1, I82283123\|sp\|Q5S346\|Q5S346_9HIV1, I82283122\|sp\|Q5S344\|Q5S344_9HIV1, I82283121\|sp\|Q5S342\|Q5S342_9HIV1, I82283120\|sp\|Q5S341\|Q5S341_9HIV1, I82283119\|sp\|Q5S338\|Q5S338_9HIV1, I82283118\|sp\|Q5S337\|Q5S337_9HIV1, I82283117\|sp\|Q5S336\|Q5S336_9HIV1, I82283116\|sp\|Q5S332\|Q5S332_9HIV1, I82283115\|sp\|Q5S331\|Q5S331_9HIV1, I82283114\|sp\|Q5S330\|Q5S330_9HIV1, I82283113\|sp\|Q5S329\|Q5S329_9HIV1, I82283112\|sp\|Q5S328\|Q5S328_9HIV1, I82283111\|sp\|Q5S325\|Q5S325_9HIV1, I82283110\|sp\|Q5S323\|Q5S323_9HIV1, I82283109\|sp\|Q5S322\|Q5S322_9HIV1, I82283108\|sp\|Q5S319\|Q5S319_9HIV1, I82283107\|sp\|Q5S314\|Q5S314_9HIV1, I82283106\|sp\|Q5S312\|Q5S312_9HIV1, I82283105\|sp\|Q5S308\|Q5S308_9HIV1, I82283104\|sp\|Q5S307\|Q5S307_9HIV1, I82283103\|sp\|Q5S306\|Q5S306_9HIV1, I82283102\|sp\|Q5S304\|Q5S304_9HIV1, I82283101\|sp\|Q5S303\|Q5S303_9HIV1, I82283100\|sp\|Q5S302\|Q5S302_9HIV1, I82283099\|sp\|Q5S300\|Q5S300_9HIV1, I82283098\|sp\|Q5S2Z9\|Q5S2Z9_9HIV1, I82283097\|sp\|Q5S2Z8\|Q5S2Z8_9HIV1, I82283096\|sp\|Q5S2Z7\|Q5S2Z7_9HIV1, I82283095\|sp\|Q5S2Z6\|Q5S2Z6_9HIV1, I82283094\|sp\|Q5S2Z5\|Q5S2Z5_9HIV1, I82283093\|sp\|Q5S2Z4\|Q5S2Z4_9HIV1, I82283092\|sp\|Q5S2Z0\|Q5S2Z0_9HIV1, I82283091\|sp\|Q5S2Y8\|Q5S2Y8_9HIV1, I82283090\|sp\|Q5S2Y7\|Q5S2Y7_9HIV1, I82283089\|sp\|Q5S2Y6\|Q5S2Y6_9HIV1, I82283088\|sp\|Q5S2Y5\|Q5S2Y5_9HIV1, I82283087\|sp\|Q5S2Y4\|Q5S2Y4_9HIV1, I82283086\|sp\|Q5S2Y2\|Q5S2Y2_9HIV1, I82283085\|sp\|Q5S2Y1\|Q5S2Y1_9HIV1, I82283084\|sp\|Q5S2Y0\|Q5S2Y0_9HIV1, I82283083\|sp\|Q5S2X9\|Q5S2X9_9HIV1, I82283082\|sp\|Q5S2X8\|Q5S2X8_9HIV1, I82283081\|sp\|Q5S2X7\|Q5S2X7_9HIV1, I82283080\|sp\|Q5S2X6\|Q5S2X6_9HIV1, I82283079\|sp\|Q5S2X4\|Q5S2X4_9HIV1, I82283078\|sp\|Q5S2X1\|Q5S2X1_9HIV1, I82283077\|sp\|Q5S2X0\|Q5S2X0_9HIV1, I82283076\|sp\|Q5S2W9\|Q5S2W9_9HIV1, |

| VPR proteins |
| --- |
| I82283075\|sp\|Q5S2W8\|Q5S2W8__9HIV1, I82283074\|sp\|Q5S2W7\|Q5S2W7__9HIV1, I82283073\|sp\|Q5S2W6\|Q5S2W6__9HIV1, I82282925\|sp\|Q5QCV6\|Q5QCV6__9HIV1, I82282923\|sp\|Q5QCU7\|Q5QCU7__9HIV1, I82282921\|sp\|Q5QCT8\|Q5QCT8__9HIV1, I82282919\|sp\|Q5QCS9\|Q5QCS9__9HIV1, I82282917\|sp\|Q5QCS0\|Q5QCS0__9HIV1, I82282915\|sp\|Q5QCR1\|Q5QCR1__9HIV1, I82282913\|sp\|Q5PZV3\|Q5PZV3__9HIV1, I82282912\|sp\|Q5PYP9\|Q5PYP9__9HIV1, I82282909\|sp\|Q5PYM3\|Q5PYM3__9HIV1, I82282805\|sp\|Q5G7F0\|Q5G7F0__9HIV1, I82282803\|sp\|Q5G7E1\|Q5G7E1__9HIV1, I82282800\|sp\|Q5G7C4\|Q5G7C4__9HIV1, I82282798\|sp\|Q5G7B5\|Q5G7B5__9HIV1, I82282796\|sp\|Q5G7A6\|Q5G7A6__9HIV1, I82282762\|sp\|Q5G361\|Q5G361__9HIV1, I82282761\|sp\|Q5G360\|Q5G360__9HIV1, I82282760\|sp\|Q5G359\|Q5G359__9HIV1, I82282759\|sp\|Q5G358\|Q5G358__9HIV1, I82282758\|sp\|Q5G357\|Q5G357__9HIV1, I82282757\|sp\|Q5G356\|Q5G356__9HIV1, I82282756\|sp\|Q5G355\|Q5G355__9HIV1, I82282755\|sp\|Q5G354\|Q5G354__9HIV1, I82282754\|sp\|Q5G353\|Q5G353__9HIV1, I82282753\|sp\|Q5G352\|Q5G352__9HIV1, I82282752\|sp\|Q5G351\|Q5G351__9HIV1, I82282751\|sp\|Q5G350\|Q5G350__9HIV1, I82282750\|sp\|Q5G349\|Q5G349__9HIV1, I82282749\|sp\|Q5G348\|Q5G348__9HIV1, I82282748\|sp\|Q5G347\|Q5G347__9HIV1, I82282717\|sp\|Q5FY37\|Q5FY37__9HIV1, I82282714\|sp\|Q5FY28\|Q5FY28__9HIV1, I82282712\|sp\|Q5FY19\|Q5FY19__9HIV1, I82282710\|sp\|Q5FY10\|Q5FY10__9HIV1, I82282708\|sp\|Q5FY01\|Q5FY01__9HIV1, I82282706\|sp\|Q5FXZ2\|Q5FXZ2__9HIV1, I82282704\|sp\|Q5FXY3\|Q5FXY3__9HIV1, I82282702\|sp\|Q5FXX4\|Q5FXX4__9HIV1, I82282698\|sp\|Q5FXW5\|Q5FXW5__9HIV1, I82282696\|sp\|Q5FXV6\|Q5FXV6__9HIV1, I82282693\|sp\|Q5FXU7\|Q5FXU7__9HIV1, I82282690\|sp\|Q5FXT8\|Q5FXT8__9HIV1, I82282688\|sp\|Q5FXT0\|Q5FXT0__9HIV1, I82282686\|sp\|Q5FXS1\|Q5FXS1__9HIV1, I82282684\|sp\|Q5FXR2\|Q5FXR2__9HIV1, I82282682\|sp\|Q5FXQ5\|Q5FXQ5__9HIV1, I82282680\|sp\|Q5FXP6\|Q5FXP6__9HIV1, I82282678\|sp\|Q5FXN7\|Q5FXN7__9HIV1, I82282574\|sp\|Q5EEI9\|Q5EEI9__9HIV1, I82282572\|sp\|Q5EEI0\|Q5EEI0__9HIV1, I82282570\|sp\|Q5EEH1\|Q5EEH1__9HIV1, I82282568\|sp\|Q5EEG3\|Q5EEG3__9HIV1, I82282566\|sp\|Q5EEF4\|Q5EEF4__9HIV1, I82282564\|sp\|Q5EEE5\|Q5EEE5__9HIV1, I82282562\|sp\|Q5EED6\|Q5EED6__9HIV1, I82282560\|sp\|Q5EEC8\|Q5EEC8__9HIV1, I82282558\|sp\|Q5EEB9\|Q5EEB9__9HIV1, I82282556\|sp\|Q5EEB0\|Q5EEB0__9HIV1, I82282554\|sp\|Q5EEA1\|Q5EEA1__9HIV1, I82282552\|sp\|Q5EE94\|Q5EE94__9HIV1, I82282550\|sp\|Q5EE85\|Q5EE85__9HIV1, I82282548\|sp\|Q5EE77\|Q5EE77__9HIV1, I82282545\|sp\|Q5EE61\|Q5EE61__9HIV1, I82282543\|sp\|Q5EE53\|Q5EE53__9HIV1, I82282442\|sp\|Q5ECR6\|Q5ECR6__9HIV1, I82282441\|sp\|Q5ECR5\|Q5ECR5__9HIV1, I82282440\|sp\|Q5ECR4\|Q5ECR4__9HIV1, I82282439\|sp\|Q5ECR3\|Q5ECR3__9HIV1, I82282438\|sp\|Q5ECR2\|Q5ECR2__9HIV1, I82282437\|sp\|Q5ECR1\|Q5ECR1__9HIV1, I82282436\|sp\|Q5ECR0\|Q5ECR0__9HIV1, I82282435\|sp\|Q5ECQ9\|Q5ECQ9__9HIV1, I82282434\|sp\|Q5ECQ8\|Q5ECQ8__9HIV1, I82282433\|sp\|Q5ECQ7\|Q5ECQ7__9HIV1, I82282432\|sp\|Q5ECQ6\|Q5ECQ6__9HIV1, I82282431\|sp\|Q5ECQ5\|Q5ECQ5__9HIV1, I82282430\|sp\|Q5ECQ4\|Q5ECQ4__9HIV1, I82282429\|sp\|Q5ECQ3\|Q5ECQ3__9HIV1, I82282428\|sp\|Q5DJY4\|Q5DJY4__9HIV1, I82282427\|sp\|Q5DJY3\|Q5DJY3__9HIV1, I82282426\|sp\|Q5DJY0\|Q5DJY0__9HIV1, I82282425\|sp\|Q5DJX9\|Q5DJX9__9HIV1, I82282424\|sp\|Q5DJX8\|Q5DJX8__9HIV1, I82282423\|sp\|Q5DJX7\|Q5DJX7__9HIV1, I82282422\|sp\|Q5DJX6\|Q5DJX6__9HIV1, I82282421\|sp\|Q5DJX5\|Q5DJX5__9HIV1, I82282420\|sp\|Q5DJX4\|Q5DJX4__9HIV1, I82282419\|sp\|Q5DJX3\|Q5DJX3__9HIV1, I82282418\|sp\|Q5DJX2\|Q5DJX2__9HIV1, I82282417\|sp\|Q5DJX1\|Q5DJX1__9HIV1, I82282416\|sp\|Q5DJX0\|Q5DJX0__9HIV1, I82282415\|sp\|Q5DJW9\|Q5DJW9__9HIV1, I82282414\|sp\|Q5DJW8\|Q5DJW8__9HIV1, I82282413\|sp\|Q5DJW7\|Q5DJW7__9HIV1, I82282412\|sp\|Q5DJW6\|Q5DJW6__9HIV1, I82282411\|sp\|Q5DJW5\|Q5DJW5__9HIV1, I82282410\|sp\|Q5DJW4\|Q5DJW4__9HIV1, I82282409\|sp\|Q5DJW3\|Q5DJW3__9HIV1, I82282408\|sp\|Q5DJW2\|Q5DJW2__9HIV1, I82282407\|sp\|Q5DJW1\|Q5DJW1__9HIV1, I82282406\|sp\|Q5DJW0\|Q5DJW0__9HIV1, I82282405\|sp\|Q5DJV9\|Q5DJV9__9HIV1, I82282404\|sp\|Q5D577\|Q5D577__9HIV1, I82282403\|sp\|Q5D576\|Q5D576__9HIV1, I82282402\|sp\|Q5D575\|Q5D575__9HIV1, I82282401\|sp\|Q5D574\|Q5D574__9HIV1, I82282400\|sp\|Q5D573\|Q5D573__9HIV1, I82282399\|sp\|Q5D572\|Q5D572__9HIV1, I82282398\|sp\|Q5D571\|Q5D571__9HIV1, I82282397\|sp\|Q5D570\|Q5D570__9HIV1, I82282396\|sp\|Q5D565\|Q5D565__9HIV1, I82282395\|sp\|Q5D564\|Q5D564__9HIV1, I82282394\|sp\|Q5D563\|Q5D563__9HIV1, I82282393\|sp\|Q5D561\|Q5D561__9HIV1, I82282392\|sp\|Q5D560\|Q5D560__9HIV1, I82282391\|sp\|Q5D558\|Q5D558__9HIV1, I82282390\|sp\|Q5D557\|Q5D557__9HIV1, I82282389\|sp\|Q5D555\|Q5D555__9HIV1, I82282388\|sp\|Q5D553\|Q5D553__9HIV1, I82282387\|sp\|Q5D552\|Q5D552__9HIV1, I82282386\|sp\|Q5D551\|Q5D551__9HIV1, I82282385\|sp\|Q5D550\|Q5D550__9HIV1, I82282384\|sp\|Q5D548\|Q5D548__9HIV1, I82282383\|sp\|Q5D546\|Q5D546__9HIV1, I82282382\|sp\|Q5D545\|Q5D545__9HIV1, I82282381\|sp\|Q5D544\|Q5D544__9HIV1, I82282380\|sp\|Q5D543\|Q5D543__9HIV1, I82282379\|sp\|Q5D542\|Q5D542__9HIV1, I82282378\|sp\|Q5D540\|Q5D540__9HIV1, I82282377\|sp\|Q5D539\|Q5D539__9HIV1, I82282376\|sp\|Q5D538\|Q5D538__9HIV1, I82282375\|sp\|Q5D537\|Q5D537__9HIV1, I82282374\|sp\|Q5D536\|Q5D536__9HIV1, I82282373\|sp\|Q5D535\|Q5D535__9HIV1, I82282372\|sp\|Q5D534\|Q5D534__9HIV1, I82282371\|sp\|Q5D533\|Q5D533__9HIV1, I82282370\|sp\|Q5D532\|Q5D532__9HIV1, I82282369\|sp\|Q5D531\|Q5D531__9HIV1, I82282368\|sp\|Q5D530\|Q5D530__9HIV1, I82282367\|sp\|Q5D529\|Q5D529__9HIV1, I82282366\|sp\|Q5D528\|Q5D528__9HIV1, I82282365\|sp\|Q5D527\|Q5D527__9HIV1, I82282364\|sp\|Q5D526\|Q5D526__9HIV1, I82281946\|sp\|Q5MJ71\|Q5MJ71__9HIV1, I82281862\|sp\|Q5MC93\|Q5MC93__9HIV1, I82281861\|sp\|Q5MC92\|Q5MC92__9HIV1, I82281860\|sp\|Q5MC91\|Q5MC91__9HIV1, I82281859\|sp\|Q5MC90\|Q5MC90__9HIV1, I82281858\|sp\|Q5MC89\|Q5MC89__9HIV1, I82281856\|sp\|Q5MC88\|Q5MC88__9HIV1, I82281855\|sp\|Q5MC87\|Q5MC87__9HIV1, I82281854\|sp\|Q5MC86\|Q5MC86__9HIV1, |

VPR proteins

|82281853|sp|Q5MC85|Q5MC85__9HIV1, |82281852|sp|Q5MC84|Q5MC84__9HIV1,
|82281851|sp|Q5MC83|Q5MC83__9HIV1, |82281850|sp|Q5MC82|Q5MC82__9HIV1,
|82281849|sp|Q5MC81|Q5MC81__9HIV1, |82281848|sp|Q5MC80|Q5MC80__9HIV1,
|82281847|sp|Q5MC79|Q5MC79__9HIV1, |82281846|sp|Q5MC78|Q5MC78__9HIV1,
|82281844|sp|Q5MC77|Q5MC77__9HIV1, |82281843|sp|Q5MC76|Q5MC76__9HIV1,
|82281841|sp|Q5MC75|Q5MC75__9HIV1, |82281840|sp|Q5MC74|Q5MC74__9HIV1,
|82281839|sp|Q5MC73|Q5MC73__9HIV1, |82281838|sp|Q5MC72|Q5MC72__9HIV1,
|82281837|sp|Q5MC71|Q5MC71__9HIV1, |82281836|sp|Q5MC70|Q5MC70__9HIV1,
|82281835|sp|Q5MC69|Q5MC69__9HIV1, |82281834|sp|Q5MC68|Q5MC68__9HIV1,
|82281833|sp|Q5MC67|Q5MC67__9HIV1, |82281832|sp|Q5MC66|Q5MC66__9HIV1,
|82281831|sp|Q5MC65|Q5MC65__9HIV1, |82281829|sp|Q5MC64|Q5MC64__9HIV1,
|82281828|sp|Q5MC63|Q5MC63__9HIV1, |82281827|sp|Q5MC62|Q5MC62__9HIV1,
|82281826|sp|Q5MC61|Q5MC61__9HIV1, |82281825|sp|Q5MC60|Q5MC60__9HIV1,
|82281824|sp|Q5MC59|Q5MC59__9HIV1, |82281823|sp|Q5MC58|Q5MC58__9HIV1,
|82281822|sp|Q5MC57|Q5MC57__9HIV1, |82281821|sp|Q5MC56|Q5MC56__9HIV1,
|82281820|sp|Q5MC55|Q5MC55__9HIV1, |82281818|sp|Q5MC54|Q5MC54__9HIV1,
|82281817|sp|Q5MC53|Q5MC53__9HIV1, |82281816|sp|Q5MC52|Q5MC52__9HIV1,
|82281815|sp|Q5MC51|Q5MC51__9HIV1, |82281814|sp|Q5MC50|Q5MC50__9HIV1,
|82281813|sp|Q5MC49|Q5MC49__9HIV1, |82281812|sp|Q5MC48|Q5MC48__9HIV1,
|82281811|sp|Q5MC47|Q5MC47__9HIV1, |82281810|sp|Q5MC46|Q5MC46__9HIV1,
|82281809|sp|Q5MC45|Q5MC45__9HIV1, |82281807|sp|Q5MC44|Q5MC44__9HIV1,
|82281806|sp|Q5MC43|Q5MC43__9HIV1, |82281805|sp|Q5MC42|Q5MC42__9HIV1,
|82281804|sp|Q5MC40|Q5MC40__9HIV1, |82281803|sp|Q5MC39|Q5MC39__9HIV1,
|82281802|sp|Q5MC38|Q5MC38__9HIV1, |82281801|sp|Q5MC37|Q5MC37__9HIV1,
|82281800|sp|Q5MC36|Q5MC36__9HIV1, |82281799|sp|Q5MC35|Q5MC35__9HIV1,
|82281798|sp|Q5MC34|Q5MC34__9HIV1, |82281796|sp|Q5MC33|Q5MC33__9HIV1,
|82281795|sp|Q5MC32|Q5MC32__9HIV1, |82281794|sp|Q5MC31|Q5MC31__9HIV1,
|82281793|sp|Q5MC30|Q5MC30__9HIV1, |82281792|sp|Q5MC29|Q5MC29__9HIV1,
|82281791|sp|Q5MC28|Q5MC28__9HIV1, |82281790|sp|Q5MC27|Q5MC27__9HIV1,
|82281789|sp|Q5MC26|Q5MC26__9HIV1, |82281787|sp|Q5MC25|Q5MC25__9HIV1,
|82281786|sp|Q5MC24|Q5MC24__9HIV1, |82281785|sp|Q5MC23|Q5MC23__9HIV1,
|82281784|sp|Q5MC22|Q5MC22__9HIV1, |82281783|sp|Q5MC21|Q5MC21__9HIV1,
|82281782|sp|Q5MC20|Q5MC20__9HIV1, |82281781|sp|Q5MC19|Q5MC19__9HIV1,
|82281780|sp|Q5MC18|Q5MC18__9HIV1, |82281779|sp|Q5MC17|Q5MC17__9HIV1,
|82281778|sp|Q5MC16|Q5MC16__9HIV1, |82281776|sp|Q5MC15|Q5MC15__9HIV1,
|82281775|sp|Q5MC14|Q5MC14__9HIV1, |82281774|sp|Q5MC13|Q5MC13__9HIV1,
|82281773|sp|Q5MC12|Q5MC12__9HIV1, |82281772|sp|Q5MC11|Q5MC11__9HIV1,
|82281771|sp|Q5MC10|Q5MC10__9HIV1, |82281770|sp|Q5MC09|Q5MC09__9HIV1,
|82281769|sp|Q5MC08|Q5MC08__9HIV1, |82281768|sp|Q5MC07|Q5MC07__9HIV1,
|82281767|sp|Q5MC06|Q5MC06__9HIV1, |82281766|sp|Q5MC05|Q5MC05__9HIV1,
|82281764|sp|Q5MC04|Q5MC04__9HIV1, |82281763|sp|Q5MC03|Q5MC03__9HIV1,
|82281762|sp|Q5MC02|Q5MC02__9HIV1, |82281761|sp|Q5MC01|Q5MC01__9HIV1,
|82281760|sp|Q5MC00|Q5MC00__9HIV1, |82281759|sp|Q5MBZ9|Q5MBZ9__9HIV1,
|82281758|sp|Q5MBZ8|Q5MBZ8__9HIV1, |82281757|sp|Q5MBZ7|Q5MBZ7__9HIV1,
|82281756|sp|Q5MBZ6|Q5MBZ6__9HIV1, |82281755|sp|Q5MBZ5|Q5MBZ5__9HIV1,
|82281754|sp|Q5MBZ4|Q5MBZ4__9HIV1, |82281753|sp|Q5MBZ3|Q5MBZ3__9HIV1,
|82281752|sp|Q5MBZ2|Q5MBZ2__9HIV1, |82281751|sp|Q5MBZ1|Q5MBZ1__9HIV1,
|82281750|sp|Q5MBZ0|Q5MBZ0__9HIV1, |82281749|sp|Q5MBY9|Q5MBY9__9HIV1,
|82281748|sp|Q5MBY8|Q5MBY8__9HIV1, |82281747|sp|Q5MBY7|Q5MBY7__9HIV1,
|82281746|sp|Q5MBY6|Q5MBY6__9HIV1, |82281745|sp|Q5MBY5|Q5MBY5__9HIV1,
|82281744|sp|Q5MBY4|Q5MBY4__9HIV1, |82281742|sp|Q5MBY3|Q5MBY3__9HIV1,
|82281741|sp|Q5MBY2|Q5MBY2__9HIV1, |82281740|sp|Q5MBY1|Q5MBY1__9HIV1,
|82281739|sp|Q5MBY0|Q5MBY0__9HIV1, |82281738|sp|Q5MBX9|Q5MBX9__9HIV1,
|82281737|sp|Q5MBX8|Q5MBX8__9HIV1, |82281736|sp|Q5MBD7|Q5MBD7__9HIV1,
|82281735|sp|Q5MBD6|Q5MBD6__9HIV1, |82281734|sp|Q5MBD5|Q5MBD5__9HIV1,
|82281733|sp|Q5MBD4|Q5MBD4__9HIV1, |82281732|sp|Q5MBD3|Q5MBD3__9HIV1,
|82281731|sp|Q5MBD2|Q5MBD2__9HIV1, |82281730|sp|Q5MBD1|Q5MBD1__9HIV1,
|82281729|sp|Q5MBD0|Q5MBD0__9HIV1, |82281728|sp|Q5MBC9|Q5MBC9__9HIV1,
|82281727|sp|Q5MBC8|Q5MBC8__9HIV1, |82281726|sp|Q5MBC7|Q5MBC7__9HIV1,
|82281725|sp|Q5MBC6|Q5MBC6__9HIV1, |82281724|sp|Q5MBC5|Q5MBC5__9HIV1,
|82281722|sp|Q5MBC4|Q5MBC4__9HIV1, |82281721|sp|Q5MBC3|Q5MBC3__9HIV1,
|82281720|sp|Q5MBC2|Q5MBC2__9HIV1, |82281719|sp|Q5MBC1|Q5MBC1__9HIV1,
|82281718|sp|Q5MBC0|Q5MBC0__9HIV1, |82281717|sp|Q5MBB9|Q5MBB9__9HIV1,
|82281716|sp|Q5MBB8|Q5MBB8__9HIV1, |82281715|sp|Q5MBB7|Q5MBB7__9HIV1,
|82281714|sp|Q5MBB6|Q5MBB6__9HIV1, |82281713|sp|Q5MBB5|Q5MBB5__9HIV1,
|82281712|sp|Q5MBB4|Q5MBB4__9HIV1, |82281236|sp|P87925|P87925__9HIV1,
|82281203|sp|O93204|O93204__9HIV1, |82281180|sp|O93025|O93025__9HIV1,
|82281155|sp|O92887|O92887__9HIV1, |82281072|sp|O92593|O92593__9HIV1,
|82280765|sp|O91186|O91186__9HIV1, |82280764|sp|O91185|O91185__9HIV1,
|82280763|sp|O91184|O91184__9HIV1, |82280762|sp|O91183|O91183__9HIV1,
|82280740|sp|O91078|O91078__9HIV1, |82280739|sp|O91077|O91077__9HIV1,
|82280738|sp|O91076|O91076__9HIV1, |82280737|sp|O91075|O91075__9HIV1,
|82280736|sp|O91074|O91074__9HIV1, |82280735|sp|O91073|O91073__9HIV1,
|82280734|sp|O91072|O91072__9HIV1, |82280733|sp|O91071|O91071__9HIV1,
|82280732|sp|O91070|O91070__9HIV1, |82280731|sp|O91069|O91069__9HIV1,
|82280730|sp|O91068|O91068__9HIV1, |82280729|sp|O91067|O91067__9HIV1,
|82280728|sp|O91066|O91066__9HIV1, |82280727|sp|O91065|O91065__9HIV1,

| VPR proteins |
| --- |
| |82280726|sp|O91064|O91064__9HIV1, |82280725|sp|O91063|O91063__9HIV1,
|82280724|sp|O91062|O91062__9HIV1, |82280723|sp|O91061|O91061__9HIV1,
|82280722|sp|O91060|O91060__9HIV1, |82280721|sp|O91059|O91059__9HIV1,
|82280720|sp|O91058|O91058__9HIV1, |82280719|sp|O91057|O91057__9HIV1,
|82280718|sp|O91056|O91056__9HIV1, |82280717|sp|O91055|O91055__9HIV1,
|82280716|sp|O91054|O91054__9HIV1, |82280715|sp|O91053|O91053__9HIV1,
|82280714|sp|O91052|O91052__9HIV1, |82280713|sp|O91051|O91051__9HIV1,
|82280712|sp|O91050|O91050__9HIV1, |82280711|sp|O91049|O91049__9HIV1,
|82280710|sp|O91048|O91048__9HIV1, |82280709|sp|O91047|O91047__9HIV1,
|82280708|sp|O91046|O91046__9HIV1, |82280707|sp|O91045|O91045__9HIV1,
|82280706|sp|O91044|O91044__9HIV1, |82279882|sp|O71256|O71256__9HIV1,
|82279832|sp|O70680|O70680__9HIV1, |82279581|sp|O40522|O40522__9HIV1,
|82279580|sp|O40521|O40521__9HIV1, |82279579|sp|O40520|O40520__9HIV1,
|82279578|sp|O40519|O40519__9HIV1, |82279577|sp|O40518|O40518__9HIV1,
|82279576|sp|O40517|O40517__9HIV1, |82279575|sp|O40516|O40516__9HIV1,
|82279528|sp|O40367|O40367__9HIV1, |82279527|sp|O40365|O40365__9HIV1,
|82279526|sp|O40363|O40363__9HIV1, |82279525|sp|O40362|O40362__9HIV1,
|82279524|sp|O40361|O40361__9HIV1, |82279523|sp|O40359|O40359__9HIV1,
|82279522|sp|O40358|O40358__9HIV1, |82279479|sp|O40223|O40223__9HIV1,
|82279466|sp|O40178|O40178__9HIV1, |82279465|sp|O40177|O40177__9HIV1,
|78172857|gb|ABB29388.1|, |78172847|gb|ABB29379.1|, |78172837|gb|ABB29370.1|,
|78172825|gb|ABB29359.1|, |78172819|gb|ABB29354.1|, |63081185|gb|AAY30347.1|,
|55275264|gb|AAV49476.1|, |55275254|gb|AAV49467.1|, |55275244|gb|AAV49458.1|,
|55275234|gb|AAV49449.1|, |55275224|gb|AAV49440.1|, |55275214|gb|AAV49431.1|,
|55275204|gb|AAV49422.1|, |55275194|gb|AAV49413.1|, |55275184|gb|AAV49404.1|,
|55275174|gb|AAV49395.1|, |55275164|gb|AAV49386.1|, |55275154|gb|AAV49377.1|,
|55275144|gb|AAV49368.1|, |55275134|gb|AAV49359.1|, |55275124|gb|AAV49350.1|,
|73914001|gb|AAZ91961.1|, |73913983|gb|AAZ91945.1|, |73913973|gb|AAZ91936.1|,
|73913939|gb|AAZ91906.1|, |73913929|gb|AAZ91897.1|, |73913919|gb|AAZ91888.1|,
|73913910|gb|AAZ91880.1|, |73913900|gb|AAZ91871.1|, |73913890|gb|AAZ91862.1|,
|73913881|gb|AAZ91854.1|truncated, |73913871|gb|AAZ91845.1|,
|73913861|gb|AAZ91836.1|, |73913851|gb|AAZ91827.1|, |73913841|gb|AAZ91818.1|,
|73913831|gb|AAZ91809.1|, |73913821|gb|AAZ91800.1|, |73913811|gb|AAZ91791.1|,
|73913802|gb|AAZ91783.1|, |73913792|gb|AAZ91774.1|,
|73913782|gb|AAZ91765.1|truncated, |73913772|gb|AAZ91756.1|,
|73913762|gb|AAZ91747.1|, |46243172|gb|AAS83698.1|, |46243158|gb|AAS83685.1|,
|37681539|gb|AAQ97649.1|, |37681549|gb|AAQ97658.1|, |37677912|gb|AAQ97577.1|,
|37677902|gb|AAQ97568.1|, |37677892|gb|AAQ97559.1|, |37677882|gb|AAQ97550.1|,
|37677872|gb|AAQ97541.1|, |37677862|gb|AAQ97532.1|, |37677842|gb|AAQ97514.1|,
|37677832|gb|AAQ97505.1|, |37677822|gb|AAQ97496.1|, |37677811|gb|AAQ97486.1|,
|37677802|gb|AAQ97478.1|, |37677791|gb|AAQ97468.1|, |37677782|gb|AAQ97460.1|,
|37677772|gb|AAQ97451.1|, |37677762|gb|AAQ97442.1|, |62361775|gb|AAX81423.1|,
|71794631|emb|CAI28870.1|, |71794621|emb|CAI28861.1|, |71794611|emb|CAI28852.1|,
|71794602|emb|CAI28843.1|, |71794593|emb|CAI28834.1|, |71794583|emb|CAI28825.1|,
|57901115|gb|AAW57879.1|, |57901106|gb|AAW57871.1|, |57901096|gb|AAW57862.1|,
|57901077|gb|AAW57845.1|, |57901066|gb|AAW57835.1|, |58221045|gb|AAW68219.1|,
|58221035|gb|AAW68210.1|, |58221025|gb|AAW68201.1|, |58221015|gb|AAW68192.1|,
|58221007|gb|AAW68185.1|, |58220997|gb|AAW68176.1|, |58220987|gb|AAW68167.1|,
|58220978|gb|AAW68159.1|, |58220968|gb|AAW68150.1|, |58220958|gb|AAW68141.1|,
|58220948|gb|AAW68132.1|, |58220938|gb|AAW68123.1|, |58220928|gb|AAW68114.1|,
|58220918|gb|AAW68105.1|, |58220908|gb|AAW68096.1|, |58220898|gb|AAW68087.1|,
|58220888|gb|AAW68078.1|, |58220878|gb|AAW68069.1|, |58220868|gb|AAW68060.1|,
|38892790|gb|AAR27780.1|, |38892781|gb|AAR27772.1|, |38892771|gb|AAR27763.1|,
|38892762|gb|AAR27755.1|, |38892752|gb|AAR27746.1|, |38892744|gb|AAR27739.1|,
|38892734|gb|AAR27730.1|, |38892724|gb|AAR27721.1|, |38892714|gb|AAR27712.1|,
|38892706|gb|AAR27705.1|, |38892696|gb|AAR27696.1|, |38892687|gb|AAR27688.1|,
|38892678|gb|AAR27680.1|, |38892669|gb|AAR27672.1|, |38892662|gb|AAR27666.1|,
|38892651|gb|AAR27656.1|, |38892643|gb|AAR27649.1|, |38892634|gb|AAR27641.1|,
|38892626|gb|AAR27634.1|, |38892617|gb|AAR27626.1|, |38892607|gb|AAR27617.1|,
|55139356|gb|AAV41369.1|, |55139347|gb|AAV41361.1|, |55139336|gb|AAV41351.1|,
|55139326|gb|AAV41342.1|, |55139319|gb|AAV41336.1|, |55139315|gb|AAV41333.1|,
|55139306|gb|AAV41325.1|, |55139297|gb|AAV41317.1|, |55139286|gb|AAV41307.1|,
|55139277|gb|AAV41299.1|, |55139268|gb|AAV41291.1|, |55139260|gb|AAV41284.1|,
|68522161|gb|AAY98746.1|, |68522151|gb|AAY98737.1|, |68522142|gb|AAY98729.1|,
|68522132|gb|AAY98720.1|, |68522122|gb|AAY98711.1|, |68522112|gb|AAY98702.1|,
|68522102|gb|AAY98693.1|, |68522092|gb|AAY98684.1|, |68522082|gb|AAY98675.1|,
|68522072|gb|AAY98666.1|, |68522062|gb|AAY98657.1|, |68522052|gb|AAY98648.1|,
|68522042|gb|AAY98639.1|, |68522032|gb|AAY98630.1|, |68522022|gb|AAY98621.1|,
|68522012|gb|AAY98612.1|, |68522002|gb|AAY98603.1|, |68521992|gb|AAY98594.1|,
|68521982|gb|AAY98585.1|, |68521972|gb|AAY98576.1|, |68521962|gb|AAY98567.1|,
|68521952|gb|AAY98558.1|, |68521942|gb|AAY98549.1|, |67553119|gb|AAY68704.1|,
|67553109|gb|AAY68695.1|, |67553099|gb|AAY68686.1|, |67553089|gb|AAY68677.1|,
|67553079|gb|AAY68668.1|, |67553069|gb|AAY68659.1|, |67553059|gb|AAY68650.1|,
|67553049|gb|AAY68641.1|, |67553039|gb|AAY68632.1|, |67553029|gb|AAY68623.1|,
|67553004|gb|AAY68601.1|, |67552994|gb|AAY68592.1|, |67552984|gb|AAY68583.1|,
|66473535|gb|AAY46415.1|, |55416517|gb|AAV50222.1|, |55416515|gb|AAV50221.1|,
|55416513|gb|AAV50220.1|, |55416511|gb|AAV50219.1|, |55416509|gb|AAV50218.1|, |

-continued

| VPR proteins |
|---|
| \|55416507\|gb\|AAV50217.1\|, \|55416505\|gb\|AAV50216.1\|, \|55416503\|gb\|AAV50215.1\|, \|55416501\|gb\|AAV50214.1\|, \|55416499\|gb\|AAV50213.1\|, \|55416497\|gb\|AAV50212.1\|, \|55416495\|gb\|AAV50211.1\|, \|55416493\|gb\|AAV50210.1\|, \|55416491\|gb\|AAV50209.1\|, \|55416489\|gb\|AAV50208.1\|, \|55416487\|gb\|AAV50207.1\|, \|55416485\|gb\|AAV50206.1\|truncated, \|55416483\|gb\|AAV50205.1\|, \|55416481\|gb\|AAV50204.1\|, \|55416479\|gb\|AAV50203.1\|, \|55416477\|gb\|AAV50202.1\|, \|55416475\|gb\|AAV50201.1\|, \|55416473\|gb\|AAV50200.1\|, \|55416471\|gb\|AAV50199.1\|, \|55416469\|gb\|AAV50198.1\|truncated, \|55416467\|gb\|AAV50197.1\|, \|55416465\|gb\|AAV50196.1\|, \|55416463\|gb\|AAV50195.1\|, \|55416461\|gb\|AAV50194.1\|, \|55416459\|gb\|AAV50193.1\|, \|55416457\|gb\|AAV50192.1\|, \|55416455\|gb\|AAV50191.1\|, \|55416453\|gb\|AAV50190.1\|, \|55416451\|gb\|AAV50189.1\|, \|55416449\|gb\|AAV50188.1\|, \|55416447\|gb\|AAV50187.1\|, \|55416445\|gb\|AAV50186.1\|, \|55416443\|gb\|AAV50185.1\|, \|55416441\|gb\|AAV50184.1\|, \|55416439\|gb\|AAV50183.1\|, \|55416437\|gb\|AAV50182.1\|, \|55416435\|gb\|AAV50181.1\|, \|55416433\|gb\|AAV50180.1\|, \|55416431\|gb\|AAV50179.1\|, \|55416429\|gb\|AAV50178.1\|, \|55416427\|gb\|AAV50177.1\|, \|55416425\|gb\|AAV50176.1\|, \|55416423\|gb\|AAV50175.1\|, \|55416421\|gb\|AAV50174.1\|, \|55416419\|gb\|AAV50173.1\|, \|55416417\|gb\|AAV50172.1\|, \|63098438\|gb\|AAY32476.1\|, \|63098428\|gb\|AAY32467.1\|truncated, \|63098418\|gb\|AAY32458.1\|, \|63098408\|gb\|AAY32449.1\|, \|63098398\|gb\|AAY32440.1\|, \|63098388\|gb\|AAY32431.1\|, \|63098378\|gb\|AAY32422.1\|, \|63098369\|gb\|AAY32414.1\|, \|63098360\|gb\|AAY32406.1\|, \|63098351\|gb\|AAY32398.1\|, \|63098341\|gb\|AAY32389.1\|, \|63098331\|gb\|AAY32380.1\|truncated, \|63098321\|gb\|AAY32371.1\|, \|63098312\|gb\|AAY32363.1\|, \|63098303\|gb\|AAY32355.1\|, \|63098293\|gb\|AAY32346.1\|, \|56609344\|gb\|AAW03294.1\|, \|56609333\|gb\|AAW03285.1\|, \|56609317\|gb\|AAW03271.1\|, \|56609307\|gb\|AAW03262.1\|, \|56609297\|gb\|AAW03253.1\|, \|56609287\|gb\|AAW03244.1\|, \|56609277\|gb\|AAW03235.1\|, \|56609267\|gb\|AAW03226.1\|, \|56609257\|gb\|AAW03217.1\|, \|56609247\|gb\|AAW03208.1\|, \|3417244\|emb\|CAA76913.1\|, \|3417242\|emb\|CAA76912.1\|, \|3413755\|emb\|CAA76922.1\|, \|3413753\|emb\|CAA76921.1\|, \|3413751\|emb\|CAA76920.1\|, \|3413749\|emb\|CAA76919.1\|, \|3413747\|emb\|CAA76918.1\|, \|3413745\|emb\|CAA76917.1\|, \|3413743\|emb\|CAA76916.1\|, \|3413741\|emb\|CAA76915.1\|, \|3413739\|emb\|CAA76914.1\|, \|60200\|emb\|CAA77629.1\|, \|3163938\|emb\|CAA06954.1\|, \|37496504\|emb\|CAD48460.1\|, \|37496496\|emb\|CAD48453.1\|, \|37496488\|emb\|CAD48446.1\|, \|32399672\|emb\|CAD58651.1\|, \|32399664\|emb\|CAD58642.1\|, \|18074007\|emb\|CAC86572.1\|, \|18073417\|emb\|CAC88007.1\|, \|18073407\|emb\|CAC87998.1\|, \|15209258\|emb\|CAC51037.1\|, \|14041644\|emb\|CAC38428.1\|, \|14041634\|emb\|CAC38437.1\|, \|9368387\|emb\|CAB98176.1\|, \|9368377\|emb\|CAB98194.1\|, \|7657897\|emb\|CAB89151.1\|, \|7452917\|emb\|CAB86382.1\|, \|7452907\|emb\|CAB86373.1\|, \|7321152\|emb\|CAB82234.1\|, \|7321142\|emb\|CAB82225.1\|, \|5738574\|emb\|CAB53050.1\|, \|4539057\|emb\|CAB39746.1\|, \|4539042\|emb\|CAB39924.1\|, \|59895879\|gb\|AAX11319.1\|, \|59895877\|gb\|AAX11318.1\|, \|59895875\|gb\|AAX11317.1\|, \|59895873\|gb\|AAX11316.1\|, \|59895870\|gb\|AAX11315.1\|, \|59895868\|gb\|AAX11314.1\|, \|59895864\|gb\|AAX11313.1\|, \|59895860\|gb\|AAX11312.1\|, \|59895858\|gb\|AAX11311.1\|, \|59895856\|gb\|AAX11310.1\|, \|59895854\|gb\|AAX11309.1\|, \|59895852\|gb\|AAX11308.1\|, \|59895849\|gb\|AAX11307.1\|, \|59895847\|gb\|AAX11306.1\|, \|59895845\|gb\|AAX11305.1\|, \|59895843\|gb\|AAX11304.1\|, \|59895841\|gb\|AAX11303.1\|, \|59895838\|gb\|AAX11302.1\|, \|59895836\|gb\|AAX11301.1\|, \|59895834\|gb\|AAX11300.1\|, \|59895832\|gb\|AAX11299.1\|, \|59895829\|gb\|AAX11298.1\|, \|59895827\|gb\|AAX11297.1\|, \|59895825\|gb\|AAX11296.1\|, \|59895823\|gb\|AAX11295.1\|, \|59895821\|gb\|AAX11294.1\|, \|59895819\|gb\|AAX11293.1\|, \|59895817\|gb\|AAX11292.1\|, \|59895815\|gb\|AAX11291.1\|, \|59895813\|gb\|AAX11290.1\|, \|59895811\|gb\|AAX11289.1\|, \|59895807\|gb\|AAX11288.1\|, \|59895805\|gb\|AAX11287.1\|, \|59895803\|gb\|AAX11286.1\|, \|59895801\|gb\|AAX11285.1\|, \|59895799\|gb\|AAX11284.1\|, \|59895797\|gb\|AAX11283.1\|, \|59895795\|gb\|AAX11282.1\|, \|59895793\|gb\|AAX11281.1\|, \|59895791\|gb\|AAX11280.1\|, \|59895789\|gb\|AAX11279.1\|, \|59895787\|gb\|AAX11278.1\|, \|59895785\|gb\|AAX11277.1\|, \|59895783\|gb\|AAX11276.1\|, \|59895778\|gb\|AAX11275.1\|, \|59895776\|gb\|AAX11274.1\|, \|59895774\|gb\|AAX11273.1\|, \|59895772\|gb\|AAX11272.1\|, \|59895770\|gb\|AAX11271.1\|, \|59895768\|gb\|AAX11270.1\|, \|59895766\|gb\|AAX11269.1\|, \|59895764\|gb\|AAX11268.1\|, \|59003675\|gb\|AAW83670.1\|, \|59003665\|gb\|AAW83661.1\|, \|59003655\|gb\|AAW83652.1\|, \|truncated, \|59003645\|gb\|AAW83643.1\|, \|59003635\|gb\|AAW83634.1\|, \|59003625\|gb\|AAW83625.1\|, \|59003616\|gb\|AAW83617.1\|, \|59003606\|gb\|AAW83608.1\|, \|59003596\|gb\|AAW83599.1\|, \|59003586\|gb\|AAW83590.1\|, \|59003576\|gb\|AAW83581.1\|, \|59003566\|gb\|AAW83572.1\|, \|59003556\|gb\|AAW83563.1\|, \|59003546\|gb\|AAW83554.1\|, \|59003536\|gb\|AAW83545.1\|, \|59003526\|gb\|AAW83536.1\|, \|59003516\|gb\|AAW83527.1\|, \|45738228\|gb\|AAS75886.1\|, \|45738218\|gb\|AAS75877.1\|, \|57904558\|gb\|AAW58814.1\|, \|57904556\|gb\|AAW58813.1\|, \|57904554\|gb\|AAW58812.1\|, \|57904552\|gb\|AAW58811.1\|, \|57904548\|gb\|AAW58810.1\|, \|57904546\|gb\|AAW58809.1\|, \|57904544\|gb\|AAW58808.1\|, \|57904542\|gb\|AAW58807.1\|, \|57904540\|gb\|AAW58806.1\|, \|57904537\|gb\|AAW58805.1\|, \|57904535\|gb\|AAW58804.1\|, \|57904533\|gb\|AAW58803.1\|, \|57904531\|gb\|AAW58802.1\|, \|57904529\|gb\|AAW58801.1\|, \|57904527\|gb\|AAW58800.1\|, \|57338570\|gb\|AAW49364.1\|, \|57338561\|gb\|AAW49356.1\|, \|57338554\|gb\|AAW49350.1\|, \|57338547\|gb\|AAW49344.1\|, \|56609039\|gb\|AAW03150.1\|, \|56609037\|gb\|AAW03149.1\|, \|56609035\|gb\|AAW03148.1\|, \|56609033\|gb\|AAW03147.1\|, \|56609031\|gb\|AAW03146.1\|, \|56609029\|gb\|AAW03145.1\|, \|56609026\|gb\|AAW03144.1\|, \|56609024\|gb\|AAW03143.1\|, \|56609022\|gb\|AAW03142.1\|, \|56609020\|gb\|AAW03141.1\|, \|56609018\|gb\|AAW03140.1\|, \|56609016\|gb\|AAW03139.1\|, \|56609014\|gb\|AAW03138.1\|, \|56609012\|gb\|AAW03137.1\|, \|56609010\|gb\|AAW03136.1\|, \|56609008\|gb\|AAW03135.1\|, \|56609006\|gb\|AAW03134.1\|, \|56609004\|gb\|AAW03133.1\|, \|56609002\|gb\|AAW03132.1\|, \|56609000\|gb\|AAW03131.1\|, \|56608998\|gb\|AAW03130.1\|, \|56608996\|gb\|AAW03129.1\|, \|56608994\|gb\|AAW03128.1\|, \|56608992\|gb\|AAW03127.1\|, \|56608990\|gb\|AAW03126.1\|, \|56608988\|gb\|AAW03125.1\|, \|56608986\|gb\|AAW03124.1\|, |

| VPR proteins |
|---|
| \|56608984\|gb\|AAW03123.1\|, \|56608982\|gb\|AAW03122.1\|, \|56608980\|gb\|AAW03121.1\|, \|56608978\|gb\|AAW03120.1\|, \|56608976\|gb\|AAW03119.1\|, \|56608974\|gb\|AAW03118.1\|, \|56608972\|gb\|AAW03117.1\|, \|56608970\|gb\|AAW03116.1\|, \|56608968\|gb\|AAW03115.1\|, \|56608966\|gb\|AAW03114.1\|, \|56608964\|gb\|AAW03113.1\|, \|56608962\|gb\|AAW03112.1\|, \|56608960\|gb\|AAW03111.1\|, \|56608958\|gb\|AAW03110.1\|, \|56608956\|gb\|AAW03109.1\|, \|56608954\|gb\|AAW03108.1\|, \|56608952\|gb\|AAW03107.1\|, \|56608950\|gb\|AAW03106.1\|, \|56608948\|gb\|AAW03105.1\|, \|56608946\|gb\|AAW03104.1\|, \|56608944\|gb\|AAW03103.1\|, \|56608942\|gb\|AAW03102.1\|, \|56608940\|gb\|AAW03101.1\|, \|56608938\|gb\|AAW03100.1\|, \|56608936\|gb\|AAW03099.1\|, \|56608934\|gb\|AAW03098.1\|, \|56608932\|gb\|AAW03097.1\|, \|56608930\|gb\|AAW03096.1\|, \|56608928\|gb\|AAW03095.1\|, \|56608926\|gb\|AAW03094.1\|, \|56608924\|gb\|AAW03093.1\|, \|56608922\|gb\|AAW03092.1\|, \|56608920\|gb\|AAW03091.1\|, \|56608918\|gb\|AAW03090.1\|, \|56608916\|gb\|AAW03089.1\|, \|56608914\|gb\|AAW03088.1\|, \|56608912\|gb\|AAW03087.1\|, \|56608910\|gb\|AAW03086.1\|, \|56608908\|gb\|AAW03085.1\|, \|56608906\|gb\|AAW03084.1\|, \|56608904\|gb\|AAW03083.1\|, \|56608902\|gb\|AAW03082.1\|, \|56608900\|gb\|AAW03081.1\|, \|56608898\|gb\|AAW03080.1\|, \|56608896\|gb\|AAW03079.1\|, \|56608894\|gb\|AAW03078.1\|, \|56608892\|gb\|AAW03077.1\|, \|56608890\|gb\|AAW03076.1\|, \|56608888\|gb\|AAW03075.1\|, \|56608886\|gb\|AAW03074.1\|, \|56608884\|gb\|AAW03073.1\|, \|56608882\|gb\|AAW03072.1\|, \|56608880\|gb\|AAW03071.1\|, \|56608878\|gb\|AAW03070.1\|, \|56608876\|gb\|AAW03069.1\|, \|56608874\|gb\|AAW03068.1\|, \|56608872\|gb\|AAW03067.1\|, \|56608870\|gb\|AAW03066.1\|, \|56608868\|gb\|AAW03065.1\|, \|56608866\|gb\|AAW03064.1\|, \|56608864\|gb\|AAW03063.1\|, \|56608862\|gb\|AAW03062.1\|, \|56608860\|gb\|AAW03061.1\|, \|56608858\|gb\|AAW03060.1\|, \|56608856\|gb\|AAW03059.1\|, \|56608854\|gb\|AAW03058.1\|, \|56608852\|gb\|AAW03057.1\|, \|56608850\|gb\|AAW03056.1\|, \|56608848\|gb\|AAW03055.1\|, \|56608846\|gb\|AAW03054.1\|, \|56608844\|gb\|AAW03053.1\|, \|56608842\|gb\|AAW03052.1\|, \|56608840\|gb\|AAW03051.1\|, \|56608838\|gb\|AAW03050.1\|, \|56608836\|gb\|AAW03049.1\|, \|56608834\|gb\|AAW03048.1\|, \|56608832\|gb\|AAW03047.1\|, \|56608830\|gb\|AAW03046.1\|, \|56608828\|gb\|AAW03045.1\|, \|56608826\|gb\|AAW03044.1\|, \|56608824\|gb\|AAW03043.1\|, \|56608822\|gb\|AAW03042.1\|, \|56608820\|gb\|AAW03041.1\|, \|56608818\|gb\|AAW03040.1\|, \|56608816\|gb\|AAW03039.1\|, \|56608814\|gb\|AAW03038.1\|, \|56608812\|gb\|AAW03037.1\|, \|56608810\|gb\|AAW03036.1\|, \|56608808\|gb\|AAW03035.1\|, \|55925143\|gb\|AAV67947.1\|, \|55925135\|gb\|AAV67940.1\|, \|55925127\|gb\|AAV67933.1\|, \|55925119\|gb\|AAV67926.1\|, \|51572130\|gb\|AAU06777.1\|, \|51572120\|gb\|AAU06768.1\|, \|51572111\|gb\|AAU06760.1\|, \|51572102\|gb\|AAU06752.1\|, \|47060062\|gb\|AAT09648.1\|, \|49472956\|gb\|AAT66298.1\|, \|49472947\|gb\|AAT66290.1\|, \|49472939\|gb\|AAT66283.1\|, \|49472930\|gb\|AAT66275.1\|, \|37682607\|gb\|AAQ98287.1\|, \|37682597\|gb\|AAQ98278.1\|, \|37682587\|gb\|AAQ98269.1\|, \|37682577\|gb\|AAQ98260.1\|, \|37682568\|gb\|AAQ98252.1\|, \|37682558\|gb\|AAQ98243.1\|, \|37682548\|gb\|AAQ98234.1\|, \|37682538\|gb\|AAQ98225.1\|, \|37682528\|gb\|AAQ98216.1\|, \|37682518\|gb\|AAQ98207.1\|, \|37682508\|gb\|AAQ98198.1\|, \|37682498\|gb\|AAQ98189.1\|, \|37682489\|gb\|AAQ98181.1\|, \|37682479\|gb\|AAQ98172.1\|, \|37682469\|gb\|AAQ98163.1\|, \|37682459\|gb\|AAQ98154.1\|, \|37682449\|gb\|AAQ98145.1\|truncated, \|37682439\|gb\|AAQ98136.1\|, \|37682429\|gb\|AAQ98127.1\|, \|37682418\|gb\|AAQ98117.1\|, \|46486670\|gb\|AAS98773.1\|, \|46486662\|gb\|AAS98766.1\|, \|46486652\|gb\|AAS98757.1\|, \|46486644\|gb\|AAS98750.1\|, \|46486633\|gb\|AAS98740.1\|, \|46254446\|gb\|AAS86196.1\|, \|46254422\|gb\|AAS86180.1\|, \|46254412\|gb\|AAS86171.1\|, \|38679165\|gb\|AAR26417.1\|, \|38679155\|gb\|AAR26408.1\|, \|38679139\|gb\|AAR26394.1\|, \|19072112\|dbj\|BAB85759.1\|, \|32261289\|gb\|AAP74188.1\|, \|32261278\|gb\|AAP74178.1\|, \|32261267\|gb\|AAP74168.1\|, \|32351110\|gb\|AAP76518.1\|, \|31980444\|dbj\|BAC77763.1\|, \|31980434\|dbj\|BAC77754.1\|, \|31980424\|dbj\|BAC77745.1\|, \|31980414\|dbj\|BAC77736.1\|, \|31559698\|dbj\|BAC77519.1\|, \|31559688\|dbj\|BAC77510.1\|, \|31559678\|dbj\|BAC77501.1\|, \|31559670\|dbj\|BAC77494.1\|, \|31559660\|dbj\|BAC77485.1\|, \|31559650\|dbj\|BAC77476.1\|, \|31559640\|dbj\|BAC77467.1\|, \|31559630\|dbj\|BAC77458.1\|, \|31559622\|dbj\|BAC77451.1\|, \|4539079\|emb\|CAB39754.1\|, \|52000760\|sp\|Q9QPN3\|NEF__HV1LA, \|128023\|sp\|P03406\|NEF_HV1BR, \|128022\|sp\|P03407\|NEF_HV1A2, \|6093480\|sp\|P04601\|NEF__HV1H2, \|548343\|sp\|P35959\|NEF_HV1Y2, \|3024191\|sp\|Q70627\|NEF__HV1LW, \|128018\|sp\|P04324\|NEF_HV1I2, \|52001459\|sp\|P05854\|NEF__HV1H3, \|128027\|sp\|P19546\|NEF_HV1S1, \|128026\|sp\|P19545\|NEF__HV1S3, \|52001461\|sp\|P05857\|NEF_HV1SC, \|52001460\|sp\|P05856\|NEF__HV1MN, \|128041\|sp\|P04602\|NEF_HV1Z6, \|128038\|sp\|P24741\|NEF__HV1U4, \|128036\|sp\|P05858\|NEF_HV1RH, \|128035\|sp\|P03405\|NEF__HV1PV, \|128034\|sp\|P20886\|NEF_HV1OY, \|128033\|sp\|P04603\|NEF__HV1MA, \|128031\|sp\|P18801\|NEF_HV1ND, \|128029\|sp\|P12479\|NEF__HV1BN, \|128028\|sp\|P05859\|NEF_HV1ZH, \|128025\|sp\|P04604\|NEF__HV1EL, \|128024\|sp\|P20867\|NEF_HV1JR, \|128021\|sp\|P0S8SS\|NEF__HV1B8, \|128017\|sp\|P03404\|NEF_HV1B1, \|18766391\|gb\|AAL78997.1\|AF465242__9, \|10436129\|gb\|AAG16809.1\|, \|10436110\|gb\|AAG16792.1\|, \|1688158\|gb\|AAB36918.1\|, \|1688156\|gb\|AAB36917.1\|, \|1688154\|gb\|AAB36916.1\|, \|1688152\|gb\|AAB36915.1\|, \|1688150\|gb\|AAB36914.1\|, \|1688148\|gb\|AAB36913.1\|, \|1688146\|gb\|AAB36912.1\|, \|1688144\|gb\|AAB36911.1\|, \|1688142\|gb\|AAB36910.1\|, \|1688140\|gb\|AAB36909.1\|, \|1688138\|gb\|AAB36908.1\|, \|1688136\|gb\|AAB36907.1\|, \|1688134\|gb\|AAB36906.1\|, \|1688132\|gb\|AAB36905.1\|, \|1688130\|gb\|AAB36904.1\|, \|1688128\|gb\|AAB36903.1\|, \|1688126\|gb\|AAB36902.1\|, \|1688124\|gb\|AAB36901.1\|, \|1688122\|gb\|AAB36900.1\|, \|1688120\|gb\|AAB36899.1\|, \|1688118\|gb\|AAB36898.1\|, \|221482\|dbj\|BAA00999.1\|, \|1899130\|gb\|AAC57010.1\|, \|82278513\|sp\|O11408\|O11408__9PLVG, \|77272\|pir\|\|S03245, \|77270\|pir\|\|S03246, \|77269\|pir\|\|S03247, \|326684\|gb\|AAA44330.1\|, \|18426920\|gb\|AAL69558.1\|, \|328560\|gb\|AAB59874.1\|, \|4262345\|gb\|AAD14581.1\|, \|82298824\|sp\|Q8QDN3\|Q8QDN3__9PLVG, \|9629924\|ref\|NP_046131.1\|, \|2895574\|gb\|AAD12143.1\|, |

| VPR proteins |
| --- |
| \|2828046\|gb\|AAB99967.1\|, \|18699188\|gb\|AAL78448.1\|AF413987__3, \|58700475\|gb\|AAW80949.1\|, \|58700473\|gb\|AAW80948.1\|, \|58700471\|gb\|AAW80947.1\|, \|58700469\|gb\|AAW80946.1\|, \|58700467\|gb\|AAW80945.1\|, \|58700465\|gb\|AAW80944.1\|, \|58700463\|gb\|AAW80943.1\|, \|58700461\|gb\|AAW80942.1\|, \|328639\|gb\|AAA45064.1\|, \|328424\|gb\|AAA44993.1\|, \|392792\|gb\|AAA03700.1\|HIV-1 consensus, \|82294586\|sp\|Q85737\|Q85737__9HIV1 HIV-1 consensus, \|18699252\|gb\|AAL78493.1\|AF414006__5, \|1732492\|gb\|AAB38839.1\|, \|1732483\|gb\|AAB38831.1\|, \|33358354\|gb\|AAQ16648.1\|, \|33358352\|gb\|AAQ16647.1\|, \|33358350\|gb\|AAQ16646.1\|, \|33358348\|gb\|AAQ16645.1\|, \|33358346\|gb\|AAQ16644.1\|, \|33358344\|gb\|AAQ16643.1\|, \|33358342\|gb\|AAQ16642.1\|, \|33358340\|gb\|AAQ16641.1\|, \|33358338\|gb\|AAQ16640.1\|, \|33358336\|gb\|AAQ16639.1\|, \|33358334\|gb\|AAQ16638.1\|, \|33358331\|gb\|AAQ16637.1\|, \|33358329\|gb\|AAQ16636.1\|, \|37725255\|gb\|AAR02317.1\|, \|37725235\|gb\|AAR02299.1\|, \|37725225\|gb\|AAR02290.1\|, \|37725215\|gb\|AAR02281.1\|, \|37725205\|gb\|AAR02272.1\|, \|37725193\|gb\|AAR02261.1\|, \|27227859\|dbj\|BAC45032.1\|, \|27227849\|dbj\|BAC45023.1\|, \|23954644\|gb\|AAN40113.1 truncated, \|23954624\|gb\|AAN40103.1 \|truncated, \|1794250\|gb\|AAC56429.1\|, \|1794248\|gb\|AAC56428.1\|, \|1794246\|gb\|AAC56427.1\|, \|1794244\|gb\|AAC56426.1\|, \|1794242\|gb\|AAC56425.1\|, \|1794240\|gb\|AAC56424.1\|, \|1794238\|gb\|AAC56423.1\|, \|1794236\|gb\|AAC56422.1\|, \|1794234\|gb\|AAC56421.1\|, \|1794232\|gb\|AAC56420.1\|, \|1794230\|gb\|AAC56419.1\|, \|1794228\|gb\|AAC56418.1\|, \|1794225\|gb\|AAC56417.1\|, \|328448\|gb\|AAA83398.1\|, \|328038\|gb\|AAA44858.1\|, \|82304199\|sp\|Q9E526\|Q9E526__9HIV1, \|82295433\|sp\|Q8AC97\|Q8AC97__9HIV1, \|82295432\|sp\|Q8AC89\|Q8AC89__9HIV1, \|82287838\|sp\|Q6WWX7\|Q6WWX7__9HIV1, \|82287837\|sp\|Q6WWX6\|Q6WWX6__9HIV1, \|82287836\|sp\|Q6WWX5\|Q6WWX5__9HIV1, \|82287835\|sp\|Q6WWX4\|Q6WWX4__9HIV1, \|82287834\|sp\|Q6WWX3\|Q6WWX3__9HIV1, \|82287833\|sp\|Q6WWX2\|Q6WWX2__9HIV1, \|82287832\|sp\|Q6WWX1\|Q6WWX1__9HIV1, \|82287831\|sp\|Q6WWX0\|Q6WWX0__9HIV1, \|82287830\|sp\|Q6WWW9\|Q6WWW9__9HIV1, \|82287829\|sp\|Q6WWW8\|Q6WWW8__9HIV1, \|82287828\|sp\|Q6WWW7\|Q6WWW7__9HIV1, \|82287827\|sp\|Q6WWW6\|Q6WWW6__9HIV1, \|82287826\|sp\|Q6WWW5\|Q6WWW5__9HIV1, \|82281651\|sp\|P90287\|P90287__9HIV1, \|82281644\|sp\|P90278\|P90278__9HIV1, \|82281643\|sp\|P90277\|P90277__9HIV1, \|82281642\|sp\|P90276\|P90276__9HIV1, \|82281641\|sp\|P90275\|P90275__9HIV1, \|82281640\|sp\|P90274\|P90274__9HIV1, \|82281638\|sp\|P90273\|P90273__9HIV1, \|82281637\|sp\|P90272\|P90272__9HIV1, \|82281636\|sp\|P90271\|P90271__9HIV1, \|82281635\|sp\|P90270\|P90270__9HIV1, \|82281634\|sp\|P90269\|P90269__9HIV1, \|82281633\|sp\|P90268\|P90268__9HIV1, \|82281632\|sp\|P90267\|P90267__9HIV1, \|82281631\|sp\|P90266\|P90266__9HIV1, \|82281285\|sp\|P88528\|P88528__9HIV1, \|82281284\|sp\|P88526\|P88526__9HIV1, \|82281283\|sp\|P88524\|P88524__9HIV1, \|82281268\|sp\|P88425\|P88425__9HIV1, \|82281267\|sp\|P88424\|P88424__9HIV1, \|82281266\|sp\|P88423\|P88423__9HIV1, \|82281265\|sp\|P88422\|P88422__9HIV1, \|82281264\|sp\|P88421\|P88421__9HIV1, \|82281263\|sp\|P88420\|P88420__9HIV1, \|82281262\|sp\|P88419\|P88419__9HIV1, \|82281261\|sp\|P88418\|P88418__9HIV1, \|82281260\|sp\|P88417\|P88417__9HIV1, \|82281259\|sp\|P88416\|P88416__9HIV1, \|82281258\|sp\|P88415\|P88415__9HIV1, \|82281257\|sp\|P88414\|P88414__9HIV1, \|82281256\|sp\|P88413\|P88413__9HIV1, \|82281255\|sp\|P88412\|P88412__9HIV1, \|82281254\|sp\|P88411\|P88411__9HIV1, \|82281253\|sp\|P88410\|P88410__9HIV1, \|82281252\|sp\|P88409\|P88409__9HIV1, \|82281251\|sp\|P88408\|P88408__9HIV1, \|82281250\|sp\|P88407\|P88407__9HIV1, \|82281249\|sp\|P88406\|P88406__9HIV1, \|82281248\|sp\|P88405\|P88405__9HIV1, \|82281247\|sp\|P88204\|P88204__9HIV1, \|82281243\|sp\|P88156\|P88156__9HIV1, \|82278599\|sp\|O11910\|O11910__9HIV1, \|82278598\|sp\|O11909\|O11909__9HIV1, \|82278597\|sp\|O11908\|O11908__9HIV1, \|82278596\|sp\|O11907\|O11907__9HIV1, \|82278595\|sp\|O11906\|O11906__9HIV1, \|4205077\|gb\|AAD10948.1\|, \|4205068\|gb\|AAD10940.1\|, \|4205059\|gb\|AAD10932.1\|, \|4205050\|gb\|AAD10924.1\|, \|4205041\|gb\|AAD10916.1\|, \|4205032\|gb\|AAD10908.1\|, \|4205023\|gb\|AAD10900.1\|, \|4205014\|gb\|AAD10892.1\|, \|4205005\|gb\|AAD10884.1\|, \|4204996\|gb\|AAD10876.1\|, \|328667\|gb\|AAB59883.1\|, \|326425\|gb\|AAB59752.1\|, \|329397\|gb\|AAB53951.1\|, \|329404\|gb\|AAA45381.1\|, \|328574\|gb\|AAA45058.1\|, \|328458\|gb\|AAA45001.1\|, \|328414\|gb\|AAA44984.1\|, \|328163\|gb\|AAA44874.1\|, \|326431\|gb\|AAA44222.1\|, \|82320738\|sp\|Q52S68\|Q52S68__9HIV1, \|82320734\|sp\|Q52S57\|Q52S57__9HIV1, \|82320731\|sp\|Q52S48\|Q52S48__9HIV1, \|82320728\|sp\|Q52S38\|Q52S38__9HIV1, \|82320725\|sp\|Q52S27\|Q52S27__9HIV1, \|82308345\|sp\|Q9YTC4\|Q9YTC4__9HIV1, \|82308242\|sp\|Q9YP51\|Q9YP51__9HIV1, \|82308241\|sp\|Q9YP47\|Q9YP47__9HIV1, \|82308240\|sp\|Q9YP45\|Q9YP45__9HIV1, \|82308239\|sp\|Q9YP38\|Q9YP38__9HIV1, \|82308238\|sp\|Q9YP30\|Q9YP30__9HIV1, \|82308236\|sp\|Q9YP24\|Q9YP24__9HIV1, \|82308047\|sp\|Q9YJ66\|Q9YJ66__9HIV1, \|82307554\|sp\|Q9WJU7\|Q9WJU7__9HIV1, \|82307552\|sp\|Q9WJU3\|Q9WJU3__9HIV1, \|82304713\|sp\|Q9IDV1\|Q9IDV1__9HIV1, \|82299117\|sp\|Q8USH4\|Q8USH4__9HIV1, \|82296624\|sp\|Q8AQP7\|Q8AQP7__9HIV1truncated, \|82296614\|sp\|Q8AQN7\|Q8AQN7__9HIV1truncated, \|82291331\|sp\|Q79789\|Q79789__9HIV1, \|82290362\|sp\|Q77695\|Q77695__9HIV1, \|82287922\|sp\|Q6XDS8\|Q6XDS8__9HIV1, \|82287920\|sp\|Q6XDS4\|Q6XDS4__9HIV1, \|82282601\|sp\|Q5EFT8\|Q5EFT8__9HIV1, \|82282600\|sp\|Q5EFT7\|Q5EFT7__9HIV1, \|82282599\|sp\|Q5EFT6\|Q5EFT6__9HIV1, \|82282598\|sp\|Q5EFT5\|Q5EFT5__9HIV1, \|82282597\|sp\|Q5EFT4\|Q5EFT4__9HIV1, \|82282596\|sp\|Q5EFT3\|Q5EFT3__9HIV1, \|82282595\|sp\|Q5EFT2\|Q5EFT2__9HIV1, \|82282594\|sp\|Q5EFT1\|Q5EFT1__9HIV1, \|62548206\|gb\|AAX86757.1\|, \|62548196\|gb\|AAX86748.1\|, \|62548186\|gb\|AAX86739.1\|, \|62548176\|gb\|AAX86730.1\|, \|62548166\|gb\|AAX86721.1\|, \|8920160\|emb\|CAB96346.1\|, \|34330007\|gb\|AA065893.1\|, \|34330001\|gb\|AA065888.1\|, \|82291091\|sp\|Q79149\|Q79149__9HIV1 |

The preferred HIV strains referred to in the present invention, for example against which the present polypeptides should be immunogenic, are those containing these specific proteins. The above accession numbers specify explicitly the identity of the strain in addition to the specific protein sequence.

The percent homology of a first polypeptide sequence to a second polypeptide sequence, as referred to in the context of the present invention, is defined as the number of amino acid residues in the second sequence that match in both position (either absolute or relative) and identity to those in the first sequence, divided by the total number of amino acid residues in the second polypeptide (both first and second polypeptides must have the same number of amino acid residues) and multiplied by 100. Although not a common occurrence, not all HIV protein sequences are identical in length for all know strains. There are cases of proteins which are one or two amino acids longer or shorter than the general pool. The skilled person can readily identify these proteins. For this reason, the above definition extends to absolute position for proteins of the same length and relative position for proteins of differing lengths. This does not, however, affect the definition of the reactive position as defined regarding location (e.g. from amino acid 7 to 37) given above. In the present invention, it is preferred that the polypeptide homology to the defined sequences is 75% or more, 85% or more, 95% or more or 100% (or substantially 100%).

The epitopes within the sequences defined above are not especially limited, provided that they contain 7 amino acid residues or more. Preferably the epitopes are of a length that is appropriate for CTL epitopes in a particular vertebrate species, such as in a human, having a specific MHC. Typically the epitopes contain 8, 9, 10, or 11 amino acid residues, but may contain more if desired. Generally an appropriate epitope is one which is a CTL epitope in a vertebrate such as a human.

Typically, the polypeptide comprises between 7 and 100 amino acids, and preferably from 8-50 amino acids. The size should not be so great that useful epitopes suffer from competition with non-protective epitopes in the immune system (for this reason full proteins are not included), nor should the size be so small that only a very narrow range of protection is offered. More preferred ranges are from 8-45 amino acids, 15-45 amino acids and 20-45 amino acids and 15-35 amino acids. The most preferred length is from 25-45 amino acid residues. It is particularly preferred that the polypeptide consists substantially of a sequence selected from the sequences at the positions defined above in the specific list of proteins set out above.

In addition to the polypeptides described above, which should not be larger than 100 amino acid residues in length, the invention also provides multi-epitope immunogenic polypeptides comprising two or more polypeptides of the present invention. These multi-epitope polypeptides are not limited in size. Thus, they extend not only to the polypeptides having from 7-100 amino acid residues as outlined above, but also to larger polypeptides, provided that these larger polypeptides comprise two or more units, each unit consisting of a polypeptide of the invention. Thus, a polypeptide having 100 repeating units of a 7-mer according to the present invention is encompassed by the present invention, as is a polypeptide having, say 52 units of one 8-mer epitope, and 23 units of a second 10-mer epitope. Polypeptides of this type will not suffer from the competition problems associated with similar length polypeptides that comprise only one or two epitopes. For the avoidance of doubt, the multi-epitope polypeptide may comprise multiple copies of the same epitope, or single copies of a plurality of different epitopes, or multiple copies of 2 or more epitopes.

Also provided by the invention is a polypeptide composition comprising two or more different polypeptides as defined above. Thus, the polypeptide composition may comprise any number of polypeptides of the present invention together in the same mixture or formulation. The presence of a plurality of polypeptides together is useful since each may elicit its own immune response, widening the protective effect of the composition. It is particularly preferred that the composition contains all of the sequences of SEQ ID 1-4 either each in a separate peptide or several in a smaller number of peptides (e.g. 3 combined in one larger peptide and the other three 3 in another larger peptide, etc.).

The invention also provides a polypeptide construct, which construct comprises a polypeptide as defined above and a carrier. The construct may be formed by combining two or more epitopes and/or a polypeptide as defined above with the carrier. The carrier may be a molecule, such as an adjuvant and/or an excipient. Combining in this context means either mixing together, or attaching together (e.g. via a covalent linkage).

The present invention further provides a polypeptide as defined above for use in medicine. Also provided is a medicament or vaccine composition against an immunodeficiency virus, such as HIV, comprising a polypeptide as defined above, and one or more appropriate excipients and/or adjuvants (if the carrier part of the construct is itself an excipient or adjuvant, then a further excipient or adjuvant may not be needed). The excipient or adjuvant is not especially limited, and any excipients or adjuvants commonly used in medicaments and vaccines may be employed. The medicament or vaccine composition may be produced according to any known method appropriately adapted to the present invention, such as by mixing a polypeptide of the invention with an appropriate excipient or adjuvant.

A method of producing a polypeptide as defined above is also provided by the invention. The method is not especially limited, and typically comprises joining two or more epitopes to form the polypeptide. The polypeptide may, however, be synthesised by direct chemical synthesis (e.g. incorporating one amino acid at a time until the full polypeptide is formed) or by recombinant methods. Such general methods are well known to the skilled person and may be adapted to the present invention as desired. In some instances, the polypeptide of the present invention may comprise additional amino acid sequences at one or both termini to help in synthesis of the polypeptide. These additional sequences are preferably from 1-5 amino acids in length. Typically 3 amino acids are involved. For example, one may include a cysteine (C) or a Gly-Cys (G-C) chain at the N or C terminus in order to allow for chemical coupling to other protein components.

The invention still further provides use of a polypeptide or composition as defined above, in the manufacture of a medicament or vaccine, effective in the treatment or prevention of an immunodeficiency virus, such as HIV. Also provided is a method of treating or preventing an immunodeficiency virus such as HIV, which method comprises administering a polypeptide, a composition, a medicament or a vaccine as defined above to a vertebrate. The method of administration is not especially limited, and may comprise sub-cutaneous, intramuscular, intra-venous, intra-dermal, trans-dermal, or intra-nasal administration, or may be administered orally (e.g. in the form of a pill or a liquid preparation), or may be in the form of a suppository, if desired. The form of such administration preparations is not especially limited, and known forms may be employed with appropriate modifications that will be apparent to the skilled person. The dosage is not especially limited and may range from 1 ng to 100 g of the polypeptide per individual, depending upon the size, weight and species of the individual involved.

The invention may be applied to any vertebrate, since the immune systems of vertebrates operate in a related manner. Typically, the vertebrate referred to in the present context is a mammal. It is especially preferred that the vertebrate is a human. Examples of human MHCs (HLAs) that may be employed with the present invention include the following:

HLA-A
A*010101, A*010102, A*010103, A*0102, A*0103, A*0104N, A*0106, A*0107, A*0108, A*0109, A*0110, A*02010101, A*02010102L, A*020102, A*020103, A*020104, A*020105, A*020106, A*020107, A*020108, A*020109, A*020110, A*020111, A*0202, A*020301, A*020302, A*0204, A*0205, A*020601, A*020602, A*020603, A*0207, A*0208, A*0209, A*0210, A*0211, A*0212, A*0213, A*0214, A*0215N, A*0216, A*021701, A*021702, A*0218, A*0219, A*022001, A*022002, A*0221, A*0222, A*0224, A*0225, A*0226, A*0227, A*0228, A*0229, A*0230, A*0231, A*0232N, A*0233, A*0234, A*023501, A*023502, A*0236, A*0237, A*0238, A*0239, A*0240, A*0241, A*0242, A*0243N, A*0244, A*0245, A*0246, A*0247, A*0248, A*0249, A*0250, A*0251, A*0252, A*0253N, A*0254, A*0255, A*0256, A*0257, A*0258, A*0259, A*0260, A*0261, A*0262, A*0263, A*0264, A*0265, A*0266, A*0267, A*0268, A*0269, A*0270, A*0271, A*0272, A*0273, A*03010101, A*03010102N, A*03010103, A*030102, A*030103, A*0302, A*0303N, A*0304, A*0305, A*0306, A*0307, A*0308, A*0309, A*0310, A*0311N, A*0312, A*0313, A*0314, A*110101, A*110102, A*1102, A*1103, A*1104, A*1105, A*1106, A*1107, A*1108, A*1109, A*1110, A*1111, A*1112, A*1113, A*1114, A*1115, A*1116, A*1117, A*1118, A*1119, A*2301, A*2302, A*2303, A*2304, A*2305, A*2306, A*2307N, A*2308N, A*2309, A*2310, A*2311N, A*2312, A*24020101, A*24020102L, A*240202, A*240203, A*240204, A*240205, A*240206, A*240301, A*240302, A*2404, A*2405, A*2406, A*2407, A*2408, A*2409N, A*2410, A*2411N, A*2413, A*2414, A*2415, A*2417, A*2418, A*2419, A*2420, A*2421, A*2422, A*2423, A*2424, A*2425, A*2426, A*2427, A*2428, A*2429, A*2430, A*2431, A*2432, A*2433, A*2434, A*2435, A*2436N, A*2437, A*2438, A*2439, A*2440N, A*2441, A*2442, A*2443, A*2444, A*2445N, A*2446, A*250101, A*250102, A*2502, A*2503, A*2504, A*2601, A*2602, A*2603, A*2604, A*2605, A*2606, A*260701, A*260702, A*2608, A*2609, A*2610, A*2611N, A*2612, A*2613, A*2614, A*2615, A*2616, A*2617, A*2618, A*2619, A*2620, A*2621, A*2622, A*2623, A*29010101, A*29010102N, A*290201, A*290202, A*290203, A*2903, A*2904, A*2905, A*2906, A*2907, A*2908N, A*2909, A*2910, A*2911, A*300101, A*300102, A*300201, A*300202, A*3003, A*3004, A*3006, A*3007, A*3008, A*3009, A*3010, A*3011, A*3012, A*310102, A*3102, A*3103, A*3104, A*3105, A*3106, A*3107, A*3108, A*3109, A*3110, A*3201, A*3202, A*3203, A*3204, A*3205, A*3206, A*3207, A*3208, A*3301, A*330301, A*330302, A*3304, A*3305, A*3306, A*3307, A*3401, A*3402, A*3403, A*3404, A*3405, A*3406, A*3601, A*3602, A*3603, A*3604, A*4301, A*6601, A*6602, A*6603, A*6604, A*680101, A*680102, A*680103, A*6802, A*680301, A*680302, A*6804, A*6805, A*6806, A*6807, A*6808, A*6809, A*6810, A*6811N, A*6812, A*6813, A*6814, A*6815, A*6816, A*6817, A*6818N, A*6819, A*6820, A*6821, A*6822, A*6823, A*6824, A*6825, A*6826, A*6827, A*6901, A*7401, A*7402, A*7403, A*7404, A*7405, A*7406, A*7407, A*7408, A*7409, A*7410, A*8001.

HLA-B
B*070201, B*070202, B*070203, B*070204, B*0703, B*0704, B*0705, B*0706, B*0707, B*0708, B*0709, B*0710, B*0711, B*0712, B*0713, B*0714, B*0715, B*0716, B*0717, B*0718, B*0719, B*0720, B*0721, B*0722, B*0723, B*0724, B*0725, B*0726, B*0727, B*0728, B*0729, B*0730, B*0731, B*0732, B*0733, B*0734, B*0735, B*0736, B*0737, B*0738, B*0801, B*0802, B*0803, B*0804, B*0805, B*0806, B*0807, B*0808N, B*0809, B*0810, B*0811, B*0812, B*0813, B*0814, B*0815, B*0816, B*0817, B*0818, B*0819N, B*0820, B*0821, B*0822, B*1301, B*1302, B*1303, B*1304, B*1306, B*1307N, B*1308, B*1309, B*1310, B*1311, B*1312, B*1313, B*1401, B*1402, B*1403, B*1404, B*1405, B*140601, B*140602, B*15010101, B*15010102N, B*150102, B*150103, B*150104, B*150105, B*1502, B*1503, B*1504, B*1505, B*1506, B*1507, B*1508, B*1509, B*1510, B*151101, B*151102, B*1512, B*1513, B*1514, B*1515, B*1516, B*15170101, B*15170102, B*1518, B*1519, B*1520, B*1521, B*1523, B*1524, B*1525, B*1526N, B*1527, B*1528, B*1529, B*1530, B*1531, B*1532, B*1533, B*1534, B*1535, B*1536, B*1537, B*1538, B*1539, B*1540, B*1542, B*1543, B*1544, B*1545, B*1546, B*1547, B*1548, B*1549, B*1550, B*1551, B*1552, B*1553, B*1554, B*1555, B*1556, B*1557, B*1558, B*1560, B*1561, B*1562, B*1563, B*1564, B*1565, B*1566, B*1567, B*1568, B*1569, B*1570, B*1571, B*1572, B*1573, B*1574, B*1575, B*1576, B*1577, B*1578, B*1579N, B*1580, B*1581, B*1582, B*1583, B*1584, B*1585, B*1586, B*1587, B*1588, B*1589, B*1590, B*1591, B*1592, B*1593, B*1594N, B*180101, B*180102, B*1802, B*1803, B*1804, B*1805, B*1806, B*1807, B*1808, B*1809, B*1810, B*1811, B*1812, B*1813, B*1814, B*1815, B*1817N, B*1818, B*1819, B*1820, B*2701, B*2702, B*2703, B*2704, B*270502, B*270503, B*270504, B*270505, B*270506, B*270507, B*2706, B*2707, B*2708, B*2709, B*2710, B*2711, B*2712, B*2713, B*2714, B*2715, B*2716, B*2717, B*2718, B*2719, B*2720, B*2721, B*2723, B*2724, B*2725, B*2726, B*350101, B*350102, B*3502, B*3503, B*3504, B*3505, B*3506, B*3507, B*3508, B*350901, B*350902, B*3510, B*3511, B*3512, B*3513, B*351401, B*351402, B*3515, B*3516, B*3517, B*3518, B*3519, B*3520, B*3521, B*3522, B*3523, B*3524, B*3525, B*3526, B*3527, B*3528, B*3529, B*3530, B*3531, B*3532, B*3533, B*3534, B*3535, B*3536, B*3537, B*3538, B*3539, B*3540N, B*3541, B*3542, B*3543, B*3544, B*3545, B*3546, B*3547, B*3548, B*3549, B*3550, B*3551, B*3552, B*3553N, B*3701, B*3702, B*3703N, B*3704, B*3705, B*3706, B*3707, B*3801, B*380201, B*380202, B*3803, B*3804, B*3805, B*3806, B*3807, B*3808, B*3809, B*3810, B*390101, B*390103, B*390104, B*390201, B*390202, B*3903, B*3904, B*3905, B*390601, B*390602, B*3907, B*3908, B*3909, B*3910, B*3911, B*3912, B*3913, B*3914, B*3915, B*3916, B*3917, B*3918, B*3919, B*3920, B*3922, B*3923, B*3924, B*3925N, B*3926, B*3927, B*3928, B*3929, B*3930, B*3931, B*3932, B*400101, B*400102, B*400103, B*400104, B*400105, B*400201, B*400202, B*4003, B*4004, B*4005, B*40060101, B*40060102, B*4007, B*4008, B*4009, B*4010, B*4011, B*4012, B*4013, B*401401, B*401402, B*401403, B*4015,

B*4016, B*4018, B*4019, B*4020, B*4021, B*4022N, B*4023, B*4024, B*4025, B*4026, B*4027, B*4028, B*4029, B*4030, B*4031, B*4032, B*4033, B*4034, B*4035, B*4036, B*4037, B*4038, B*4039, B*4040, B*4042, B*4043, B*4044, B*4045, B*4046, B*4047, B*4048, B*4049, B*4050, B*4051, B*4052, B*4053, B*4054, B*4055, B*4056, B*4057, B*4101, B*4102, B*4103, B*4104, B*4105, B*4106, B*4201, B*4202, B*4204, B*420501, B*420502, B*4206, B*44020101, B*44020102S, B*440202, B*440203, B*440301, B*440302, B*4404, B*4405, B*4406, B*4407, B*4408, B*4409, B*4410, B*4411, B*4412, B*4413, B*4414, B*4415, B*4416, B*4417, B*4418, B*4419N, B*4420, B*4421, B*4422, B*4423N, B*4424, B*4425, B*4426, B*4427, B*4428, B*4429, B*4430, B*4431, B*4432, B*4433, B*4434, B*4435, B*4436, B*4437, B*4438, B*4439, B*4440, B*4501, B*4502, B*4503, B*4504, B*4505, B*4506, B*4507, B*4601, B*4602, B*4603, B*4604, B*47010101, B*47010102, B*4702, B*4703, B*4704, B*4705, B*4801, B*4802, B*4803, B*4804, B*4805, B*4806, B*4807, B*4808, B*4809, B*4810, B*4901, B*4902, B*4903, B*5001, B*5002, B*5004, B*510101, B*510102, B*510103, B*510104, B*510105, B*510201, B*510202, B*5103, B*5104, B*5105, B*5106, B*5107, B*5108, B*5109, B*5110, B*5111N, B*5112, B*511301, B*511302, B*5114, B*5115, B*5116, B*5117, B*5118, B*5119, B*5120, B*5121, B*5122, B*5123, B*5124, B*5126, B*5127N, B*5128, B*5129, B*5130, B*5131, B*5132, B*5133, B*5134, B*5135, B*5136, B*520101, B*520102, B*520103, B*520104, B*5202, B*5203, B*5204, B*5205, B*5206, B*530101, B*530102, B*5302, B*5303, B*5304, B*5305, B*5306, B*5307, B*5308, B*5309, B*5401, B*5402, B*5501, B*5502, B*5503, B*5504, B*5505, B*5507, B*5508, B*5509, B*5510, B*5511, B*5512, B*5513, B*5514, B*5515, B*5516, B*5601, B*5602, B*5603, B*5604, B*560501, B*560502, B*5606, B*5607, B*5608, B*5609, B*5610, B*5611, B*5612, B*5613, B*5614, B*570101, B*570102, B*5702, B*570301, B*570302, B*5704, B*5705, B*5706, B*5707, B*5708, B*5709, B*5801, B*5802, B*5804, B*5805, B*5806, B*5807, B*5808, B*5809, B*5810N, B*5901, B*670101, B*670102, B*6702, B*7301, B*7801, B*780201, B*780202, B*7803, B*7804, B*7805, B*8101, B*8102, B*8201, B*8202, B*8301.
HLA-C
Cw*010201, Cw*010202, Cw*0103, Cw*0104, Cw*0105, Cw*0106, Cw*0107, Cw*0108, Cw*0109, Cw*0110, Cw*020201, Cw*020202, Cw*020203, Cw*020204, Cw*020205, Cw*0203, Cw*0204, Cw*0205, Cw*0206, Cw*0207, Cw*0208, Cw*0209, Cw*030201, Cw*030202, Cw*030301, Cw*030302, Cw*030303, Cw*030304, Cw*030401, Cw*030402, Cw*030403, Cw*0305, Cw*0306, Cw*0307, Cw*0308, Cw*0309, Cw*0310, Cw*0311, Cw*0312, Cw*0313, Cw*0314, Cw*0315, Cw*0316, Cw*0317, Cw*0318, Cw*04010101, Cw*04010102, Cw*040102, Cw*0403, Cw*040401, Cw*040402, Cw*0405, Cw*0406, Cw*0407, Cw*0408, Cw*0409N, Cw*0410, Cw*0411, Cw*0412, Cw*0413, Cw*0414, Cw*0415, Cw*050101, Cw*050102, Cw*0502, Cw*0503, Cw*0504, Cw*0505, Cw*0506, Cw*0507N, Cw*0508, Cw*0509, Cw*0510, Cw*0602, Cw*0603, Cw*0604, Cw*0605, Cw*0606, Cw*0607, Cw*0608, Cw*0609, Cw*0610, Cw*0611, Cw*070101, Cw*070102, Cw*070103, Cw*07020101, Cw*07020102, Cw*07020103, Cw*0703, Cw*070401, Cw*070402, Cw*0705, Cw*0706, Cw*0707, Cw*0708, Cw*0709, Cw*0710, Cw*0711, Cw*0712, Cw*0713, Cw*0714, Cw*0715, Cw*0716, Cw*0717, Cw*0718, Cw*0719, Cw*0720, Cw*0721, Cw*0722, Cw*0723, Cw*0724, Cw*0725, Cw*0726, Cw*0727, Cw*0728, Cw*0729, Cw*080101, Cw*080102, Cw*0802, Cw*0803, Cw*0804, Cw*0805, Cw*0806, Cw*0807, Cw*0808, Cw*0809, Cw*0810, Cw*0811, Cw*0812, Cw*120201, Cw*120202, Cw*120203, Cw*120301, Cw*120302, Cw*120303, Cw*120401, Cw*120402, Cw*1205, Cw*1206, Cw*1207, Cw*1208, Cw*1209, Cw*1210, Cw*1211, Cw*1212, Cw*1213, Cw*1214, Cw*1215, Cw*140201, Cw*140202, Cw*140203, Cw*1403, Cw*1404, Cw*1405, Cw*150201, Cw*150202, Cw*1503, Cw*1504, Cw*150501, Cw*150502, Cw*150503, Cw*150504, Cw*1506, Cw*1507, Cw*1508, Cw*1509, Cw*1510, Cw*1511, Cw*1512, Cw*1601, Cw*1602, Cw*160401, Cw*1606, Cw*1701, Cw*1702, Cw*1703, Cw*1801, Cw*1802.
HLA-E
E*0101, E*010301, E*010302, E*010303, E*0104.
HLA-F
F*010101, F*010102.
HLA-G
G*010101, G*010102, G*010103, G*010104, G*010105, G*010106, G*010107, G*010108, G*0102, G*0103, G*010401, G*010402, G*010403, G*0105N, G*0106.
HLA-DRA
DRA*0101, DRA*010201, DRA*010202.
HLA-DRB1
DRB1*010101, DRB1*010102, DRB1*010103, DRB1*010201, DRB1*010202, DRB1*010203, DRB1*010204, DRB1*0103, DRB1*0104, DRB1*0105, DRB1*0106, DRB1*0107, DRB1*0108, DRB1*0109, DRB1*0110, DRB1*0111, DRB1*030101, DRB1*030102, DRB1*030201, DRB1*030202, DRB1*0303, DRB1*0304, DRB1*030501, DRB1*030502, DRB1*0306, DRB1*0307, DRB1*0308, DRB1*0309, DRB1*0310, DRB1*0311, DRB1*0312, DRB1*0313, DRB1*0314, DRB1*0315, DRB1*0316, DRB1*0317, DRB1*0318, DRB1*0319, DRB1*0320, DRB1*0321, DRB1*0322, DRB1*0323, DRB1*0324, DRB1*0325, DRB1*0326, DRB1*0327, DRB1*0328, DRB1*040101, DRB1*040102, DRB1*0402, DRB1*040301, DRB1*040302, DRB1*0404, DRB1*040501, DRB1*040502, DRB1*040503, DRB1*040504, DRB1*0406, DRB1*040701, DRB1*040702, DRB1*040703, DRB1*0408, DRB1*0409, DRB1*0410, DRB1*0411, DRB1*0412, DRB1*0413, DRB1*0414, DRB1*0415, DRB1*0416, DRB1*0417, DRB1*0418, DRB1*0419, DRB1*0420, DRB1*0421, DRB1*0422, DRB1*0423, DRB1*0424, DRB1*0425, DRB1*0426, DRB1*0427, DRB1*0428, DRB1*0429, DRB1*0430, DRB1*0431, DRB1*0432, DRB1*0433, DRB1*0434, DRB1*0435, DRB1*0436, DRB1*0437, DRB1*0438, DRB1*0439, DRB1*0440, DRB1*0441, DRB1*0442, DRB1*0443, DRB1*0444, DRB1*0445, DRB1*0446, DRB1*0447, DRB1*0448, DRB1*0449, DRB1*0450, DRB1*070101, DRB1*070102, DRB1*0703, DRB1*0704, DRB1*0705, DRB1*0706, DRB1*0707, DRB1*0708, DRB1*080101, DRB1*080102, DRB1*080201, DRB1*080202, DRB1*080203, DRB1*080302, DRB1*080401, DRB1*080402, DRB1*080403, DRB1*080404, DRB1*0805, DRB1*0806, DRB1*0807, DRB1*0808, DRB1*0809, DRB1*0810, DRB1*0811, DRB1*0812, DRB1*0813, DRB1*0814, DRB1*0815, DRB1*0816, DRB1*0817, DRB1*0818, DRB1*0819, DRB1*0820, DRB1*0821, DRB1*0822, DRB1*0823, DRB1*0824, DRB1*0825, DRB1*0826, DRB1*0827, DRB1*0828, DRB1*0829, DRB1*090102, DRB1*090103, DRB1*0902, DRB1*0903, DRB1*100101,

DRB1*100102, DRB1*110101, DRB1*110102, DRB1*110103, DRB1*110104, DRB1*110105, DRB1*1102, DRB1*1103, DRB1*110401, DRB1*110402, DRB1*1105, DRB1*110601, DRB1*110602, DRB1*1107, DRB1*110801, DRB1*110802, DRB1*1109, DRB1*1110, DRB1*1111, DRB1*111201, DRB1*111202, DRB1*1113, DRB1*1114, DRB1*1115, DRB1*1116, DRB1*1117, DRB1*1118, DRB1*1119, DRB1*1120, DRB1*1121, DRB1*1122, DRB1*1123, DRB1*1124, DRB1*1125, DRB1*1126, DRB1*112701, DRB1*112702, DRB1*1128, DRB1*1129, DRB1*1130, DRB1*1131, DRB1*1132, DRB1*1133, DRB1*1134, DRB1*1135, DRB1*1136, DRB1*1137, DRB1*1138, DRB1*1139, DRB1*1140, DRB1*1141, DRB1*1142, DRB1*1143, DRB1*1144, DRB1*1145, DRB1*1146, DRB1*1147, DRB1*1148, DRB1*1149, DRB1*1150, DRB1*1151, DRB1*1152, DRB1*1153, DRB1*1154, DRB1*120101, DRB1*120102, DRB1*120201, DRB1*120202, DRB1*120302, DRB1*1204, DRB1*1205, DRB1*1206, DRB1*1207, DRB1*1208, DRB1*1209, DRB1*1210, DRB1*130101, DRB1*130102, DRB1*130103, DRB1*130201, DRB1*130202, DRB1*130301, DRB1*130302, DRB1*1304, DRB1*1305, DRB1*1306, DRB1*130701, DRB1*130702, DRB1*1308, DRB1*1309, DRB1*1310, DRB1*1311, DRB1*1312, DRB1*1313, DRB1*131401, DRB1*131402, DRB1*1315, DRB1*1316, DRB1*1317, DRB1*1318, DRB1*1319, DRB1*1320, DRB1*1321, DRB1*1322, DRB1*1323, DRB1*1324, DRB1*1325, DRB1*1326, DRB1*1327, DRB1*1328, DRB1*1329, DRB1*1330, DRB1*1331, DRB1*1332, DRB1*1333, DRB1*1334, DRB1*1335, DRB1*1336, DRB1*1337, DRB1*1338, DRB1*1339, DRB1*1340, DRB1*1341, DRB1*1342, DRB1*1343, DRB1*1344, DRB1*1345, DRB1*1346, DRB1*1347, DRB1*1348, DRB1*1349, DRB1*1350, DRB1*1351, DRB1*1352, DRB1*1353, DRB1*1354, DRB1*1355, DRB1*1356, DRB1*1357, DRB1*1358, DRB1*1359, DRB1*1360, DRB1*1361, DRB1*1362, DRB1*1363, DRB1*1364, DRB1*1365, DRB1*140101, DRB1*140102, DRB1*1402, DRB1*140301, DRB1*140302, DRB1*1404, DRB1*140501, DRB1*140502, DRB1*1406, DRB1*140701, DRB1*140702, DRB1*1408, DRB1*1409, DRB1*1410, DRB1*1411, DRB1*1412, DRB1*1413, DRB1*1414, DRB1*1415, DRB1*1416, DRB1*1417, DRB1*1418, DRB1*1419, DRB1*1420, DRB1*1421, DRB1*1422, DRB1*1423, DRB1*1424, DRB1*1425, DRB1*1426, DRB1*1427, DRB1*1428, DRB1*1429, DRB1*1430, DRB1*1431, DRB1*1432, DRB1*1433, DRB1*1434, DRB1*1435, DRB1*1436, DRB1*1437, DRB1*1438, DRB1*1439, DRB1*1440, DRB1*1441, DRB1*1442, DRB1*1443, DRB1*1444, DRB1*1445, DRB1*1446, DRB1*1447, DRB1*1448, DRB1*150101, DRB1*150102, DRB1*150103, DRB1*150104, DRB1*150105, DRB1*150201, DRB1*150202, DRB1*150203, DRB1*1503, DRB1*1504, DRB1*1505, DRB1*1506, DRB1*1507, DRB1*1508, DRB1*1509, DRB1*1510, DRB1*1511, DRB1*1512, DRB1*1513, DRB1*1514, DRB1*1515, DRB1*1516, DRB1*160101, DRB1*160102, DRB1*160201, DRB1*160202, DRB1*1603, DRB1*1604, DRB1*160501, DRB1*160502, DRB1*1607, DRB1*1608.

HLA-DRB2-9

DRB2*0101, DRB3*010101, DRB3*01010201, DRB3*01010202, DRB3*010103, DRB3*010104, DRB3*0102, DRB3*0103, DRB3*0104, DRB3*0105, DRB3*0106, DRB3*0107, DRB3*0108, DRB3*0109, DRB3*0110, DRB3*0111, DRB3*0201, DRB3*020201, DRB3*020202, DRB3*020203, DRB3*020204, DRB3*0203, DRB3*0204, DRB3*0205, DRB3*0206, DRB3*0207, DRB3*0208, DRB3*0209, DRB3*0210, DRB3*0211, DRB3*0212, DRB3*0213, DRB3*0214, DRB3*0215, DRB3*0216, DRB3*0217, DRB3*0218, DRB3*0219, DRB3*030101, DRB3*030102, DRB3*0302, DRB3*0303, DRB4*01010101, DRB4*0102, DRB4*01030101, DRB4*01030102N, DRB4*010302, DRB4*010303, DRB4*010304, DRB4*0104, DRB4*0105, DRB4*0106, DRB4*0107, DRB4*0201N, DRB4*0301N, DRB5*010101, DRB5*010102, DRB5*0102, DRB5*0103, DRB5*0104, DRB5*0105, DRB5*0106, DRB5*0107, DRB5*0108N, DRB5*0109, DRB5*0110N, DRB5*0111, DRB5*0112, DRB5*0113, DRB5*0202, DRB5*0203, DRB5*0204, DRB5*0205, DRB6*0101, DRB6*0201, DRB6*0202, DRB7*010101, DRB7*010102, DRB8*0101, DRB9*0101.

HLA-DQA1

DQA1*010101, DQA1*010102, DQA1*010201, DQA1*010202, DQA1*0103, DQA1*010401, DQA1*010402, DQA1*0105, DQA1*0106, DQA1*0107, DQA1*0201, DQA1*030101, DQA1*0302, DQA1*0303, DQA1*040101, DQA1*040102, DQA1*0402, DQA1*0403N, DQA1*0404, DQA1*050101, DQA1*050102, DQA1*0502, DQA1*0503, DQA1*0504, DQA1*0505, DQA1*060101, DQA1*060102, DQA1*0602.

HLA-DQB1

DQB1*020101, DQB1*020102, DQB1*0202, DQB1*0203, DQB1*030101, DQB1*030102, DQB1*030201, DQB1*030202, DQB1*030302, DQB1*030303, DQB1*0304, DQB1*030501, DQB1*030502, DQB1*030503, DQB1*0306, DQB1*0307, DQB1*0308, DQB1*0309, DQB1*0310, DQB1*0311, DQB1*0312, DQB1*0313, DQB1*0401, DQB1*0402, DQB1*050101, DQB1*050102, DQB1*050201, DQB1*050202, DQB1*050301, DQB1*050302, DQB1*0504, DQB1*060101, DQB1*060102, DQB1*060103, DQB1*0602, DQB1*0603, DQB1*060401, DQB1*060402, DQB1*060501, DQB1*060502, DQB1*0606, DQB1*0607, DQB1*0608, DQB1*0609, DQB1*0610, DQB1*061101, DQB1*061102, DQB1*0612, DQB1*0613, DQB1*0614, DQB1*0615, DQB1*0616, DQB1*0617, DQB1*0618, DQB1*0619, DQB1*0620, DQB1*0621, DQB1*0622, DQB1*0623.

HLA-DPA1

DPA1*010301, DPA1*010302, DPA1*010303, DPA1*0104, DPA1*0105, DPA1*0106, DPA1*0107, DPA1*0108, DPA1*020101, DPA1*020102, DPA1*020103, DPA1*020104, DPA1*020105, DPA1*020106, DPA1*020201, DPA1*020202, DPA1*020203, DPA1*0203, DPA1*0301, DPA1*0302, DPA1*0303, DPA1*0401.

HLA-DPB1

DPB1*010101, DPB1*010102, DPB1*010103, DPB1*0102, DPB1*020102, DPB1*020103, DPB1*020104, DPB1*020105, DPB1*020106, DPB1*0202, DPB1*0203, DPB1*030101, DPB1*030102, DPB1*0302, DPB1*040101, DPB1*040102, DPB1*0402, DPB1*0501, DPB1*0601, DPB1*0801, DPB1*0901, DPB1*1001, DPB1*110101, DPB1*110102, DPB1*1301, DPB1*1401, DPB1*1501, DPB1*1601, DPB1*1701, DPB1*1801, DPB1*1901, DPB1*200101, DPB1*200102, DPB1*2101, DPB1*2201, DPB1*2301, DPB1*2401, DPB1*2501, DPB1*260101, DPB1*260102, DPB1*2701, DPB1*2801, DPB1*2901, DPB1*3001, DPB1*3101, DPB1*3201, DPB1*3301, DPB1*3401, DPB1*3501,

DPB1*3601, DPB1*3701, DPB1*3801, DPB1*3901, DPB1*4001, DPB1*4101, DPB1*4401, DPB1*4501, DPB1*4601, DPB1*4701, DPB1*4801, DPB1*4901, DPB1*5001, DPB1*5101, DPB1*5201, DPB1*5301, DPB1*5401, DPB1*5501, DPB1*5601, DPB1*5701, DPB1*5801, DPB1*5901, DPB1*6001, DPB1*6101N, DPB1*6201, DPB1*6301, DPB1*6401N, DPB1*6501, DPB1*6601, DPB1*6701, DPB1*6801, DPB1*6901, DPB1*7001, DPB1*7101, DPB1*7201, DPB1*7301, DPB1*7401, DPB1*7501, DPB1*7601, DPB1*7701, DPB1*7801, DPB1*7901, DPB1*8001, DPB1*8101, DPB1*8201, DPB1*8301, DPB1*8401, DPB1*8501, DPB1*8601, DPB1*8701, DPB1*8801, DPB1*8901, DPB1*9001, DPB1*9101, DPB1*9201, DPB1*9301, DPB1*9401, DPB1*9501, DPB1*9601, DPB1*9701, DPB1*9801, DPB1*9901.

HLA-DMA

DMA*0101, DMA*0102, DMA*0103, DMA*0104.

HLA-DMB

DMB*0101, DMB*0102, DMB*0103, DMB*0104, DMB*0105, DMB*0106.

HLA-DOA

DOA*01010101, DOA*01010201, DOA*01010202, DOA*01010203, DOA*010103, DOA*01010401, DOA*01010402, DOA*010105.

HLA-DOB

DOB*01010101, DOB*01010102, DOB*010102, DOB*010201, DOB*010202, DOB*0103, DOB*01040101, DOB*01040102.

The invention is not limited to such HLA molecules, and can be adapted to newly discovered such molecules, if desired, simply by establishing the reactivity of substances such as peptides with the molecules. This can be readily achieved using known techniques that are standard in the field. Particularly preferred HLA alleles for use with the present invention include the following:

HLA Class I

| HLA | HLA BA | HLA Cw |
|---|---|---|
| A*6802 | B*5801 | Cw*1701 |
| A*6801 | B*5701 | Cw*1601 |
| A*6601 | B*5501 | Cw*1502 |
| A*3303 | B*5201 | Cw*1402 |
| A*3301 | B*5101 | Cw*1203 |
| A*3201 | B*5001 | Cw*0802 |
| A*310102 | B*4901 | Cw*0801 |
| A*3002 | B*4501 | Cw*0704 |
| A*3001 | B*4403 | Cw*0703 |
| A*2902 | B*4402 | Cw*0702 |
| A*2608 | B*4101 | Cw*0701 |
| A*2601 | B*4002 | Cw*0602 |
| A*2501 | B*4001 | Cw*0501 |
| A*2402 | B*3901 | Cw*0401 |
| A*2301 | B*3801 | Cw*0304 |
| A*1101 | B*3701 | Cw*0303 |
| A*0302 | B*3503 | Cw*0202 |
| A*0301 | B*3501 | Cw*0102 |
| A*0205 | B*2705 | |
| A*0201 | B*1801 | |
| A*0101 | B*1501 | |
| | B*1402 | |
| | B*1401 | |
| | B*1302 | |
| | B*0801 | |
| | B*0705 | |
| | B*0702 | |

HLA Class II

| HLA DPB | HLA DQA | HLA DQB | HLA DRB |
|---|---|---|---|
| DPB1*1701 | DQA1*0505 | DQB1*0604 | DRB1*1601 |
| DPB1*1301 | DQA1*0501 | DQB1*0603 | DRB1*1501 |
| DPB1*1001 | DQA1*0401 | DQB1*0602 | DRB1*1401 |
| DPB1*0601 | DQA1*0303 | DQB1*0503 | DRB1*1302 |
| DPB1*0501 | DQA1*0302 | DQB1*0502 | DRB1*1301 |
| DPB1*0402 | DQA1*0301 | DQB1*0501 | DRB1*1201 |
| DPB1*0401 | DQA1*0201 | DQB1*0402 | DRB1*1104 |
| DPB1*0301 | DQA1*0104 | DQB1*0303 | DRB1*1101 |
| DPB1*0201 | DQA1*0103 | DQB1*0302 | DRB1*0801 |
| DPB1*0101 | DQA1*0102 | DQB1*0301 | DRB1*0701 |
| | DQA1*0101 | DQB1*0202 | DRB1*0404 |
| | | DQB1*0201 | DRB1*0401 |
| | | | DRB1*0301 |
| | | | DRB1*0103 |
| | | | DRB1*0102 |
| | | | DRB1*0101 |

The most preferred alleles according to the invention are the following:
HLA-A*0201, HLA-A*0206, HLA-A*0301, HLA-A*1101, HLA-A*2402, HLA-A*3401, HLA-B*0702, HLA-B*0801, HLA-B*1301, HLA-B*27, HLA-B*4002, HLA-B*5101, HLA-Cw*03, HLA-cW*07
HLA-DRB1*0301, HLA-DRB1*0401, HLA-DRB1*0701, HLA-DRB1*1501, HLA-DRB1*1104, HLA-DRB1*1101, HLA-DRB4*0101
HLA-DQA*101, HLA-DQA1*02, HLA-DQA1*05
HLA-DQB1*03, HLA-DQB1*04, HLA-DQB1*05, HLA-DQB1*06
HLA-DPA1*01, HLA-DPA1*02
HLA-DPB1*02, HLA-DPB1*04

The invention will now be described by way of example only, with reference to the following specific embodiments.

EXAMPLES

Experiment 1

Reactivity Against HIV Antigens

The purpose of the study is to assess reactivity of the above described HIV polypeptides and their ability to induce a specific Th1-type cytokine response against naturally processed and presented HIV proteins in the context of human HLA (HLA A*0201).

As background to the experiments, it is useful to understand that Th1 and Th2 responses are defined by the pattern of cytokines produced by the T helper cells involved in them. That, however, does not mean that the remaining lymphocytes (T and B cells) involved in those specific responses do not also produce cytokines that help drive the characteristic pattern of response in which they are involved. In this way, a Th1-like response is characterised by the production of IFN-γ and IL-2, leading to the stimulation of a CD8+ CTL response and an associated (in mice) IgG2a antibody response. The IFN-γ response can be produced both by the CD4+ T helper 1 cells as well as by the CD8+ T cells that also form part of it. In this case the IFN-γ component of the response produced by the CD8+ T cells was investigated. That was because the experiment was primarily investigating CD8+ T cell epitopes and it was desirable to prove that the response seen was caused by those cells. Since CD8+ T cells react to epitopes only on MHC class I molecules, human cells that share with the transgenic mouse only one MHC class I molecule (i.e. HLA-A*0201) were used. A Th2-like response is characterised by the production of IL-4 and IL-10, leading to the stimulation of an IgGE, IgG1 and (in mice) IgG2b antibody response. Both responses are antagonistic with IFN-γ and IL-10 down-regulating the production of each other. All the experiments described below were carried out in duplicate.

Materials and Methods
Peptides and Recombinant Proteins

All the polypeptides used in this study (i.e. P1: VPR aa 51 to 80 (SEQ ID 1); P2: VIF: aa 142 to 181 (SEQ ID 2); P3: REV aa 69 to 95 (SEQ ID 3); P4: NEF: aa 81 to 123 (SEQ ID 4); and NRP: a control non-relevant polypeptide were synthesised by Fmoc chemistry and re-suspended in 10% DMSO in PBS.

HIV-1 recombinant proteins VIF (ref: EVA659), REV (His-tag fusion; ref: ARP663.2) and NEF (ref: EVA650) were obtained from the Repository of HIV reagents (NIBSC, UK). Protein preparations were mixed in equimolar quantities in PBS at 1 mg/ml and stored at −80° C. until use.

Cell Lines

The T1 and JURKAT cell lines are human lymphoblastoid lines derived from HLA-A*0201 bearing and non-bearing individuals respectively. T1 was maintained in IMDM medium (Invitrogen) whilst JURKAT was maintained in RPMI-1640 medium (Sigma) containing 10 mM HEPES and 1 mM sodium pyruvate. Both media were supplemented with 50 IU/50 mg/ml of penicillin/streptomycin (Sigma) and, as complete medium, 10% FCS. Cell cultures were maintained at 37° C. in a humidified atmosphere of 5° % $CO_2$.

Primary splenocytes were maintained in IMDM medium (Invitrogen) supplemented with 0.02 mM R-mercaptoethanol (Sigma), 50 IU/50 mg/ml of penicillin/streptomycin (Sigma) and 10% FCS (Sigma) at 37° C. in a humidified atmosphere of 5% $CO_2$.

Preparation of Target Cells for Cytokine Analysis

Cell cultures in exponential phase were harvested by centrifugation (250 g, 5 min) and resuspended at a density of $10^6$ cells/ml in serum-free medium. Aliquots of the cell suspensions were transfected with a range of polypeptide antigens at a concentration of 5 μg per $10^6$ cells using Lipofectin (Invitrogen) according to the manufacturer's instructions and incubated in complete medium for 8-10 hours before Mytomicin C (MMC) treatment.

For MMC treatment, cells were harvested by centrifugation (250 g, 5 min) and resuspended in serum-free IMDM medium containing 50 μg/ml of Mitomycin C (Sigma). After 45 min incubation at 37° C., the cell suspensions were washed four times in serum-free IMDM medium (250 g, 5 min) and finally resuspended in complete IMDM medium.

Immunisations

Seven to ten week old C57BL/6-Tg(HLA-A2.1)|Enge/J mice (HLA-A*0201 transgenic on a C57/BL6 background, Jackson Labs) were immunised intradermally with a 100 μl dose (delivered in 5 sites at 20 μl/site) per mouse of the antigen preparation. In the test group, each dose of the antigen preparation contained 40 nmol of an equimolar mixture of all four peptides (HIV-v) (10 nmol each) and 0.5 nmol Cholera Toxin Subunit B (>99% pure, BioMol) and was prepared in Lipofectin (Invitrogen) according to the manufacturer's instructions. In the control group, each dose of the antigen preparation contained 40 nmol of the non-relevant polypeptide and 0.5 nmol Cholera Toxin Subunit B (>99% pure, BioMol) and was prepared in Lipofectin (Invitrogen) according to the manufacturer's instructions.

On day 14 post-immunisation, all animals received a booster immunisation using the same doses and route of delivery as used originally. Finally, on day 21 or 22, all animals were culled and their spleens collected.

The immunisation protocol can be represented schematically as follows:

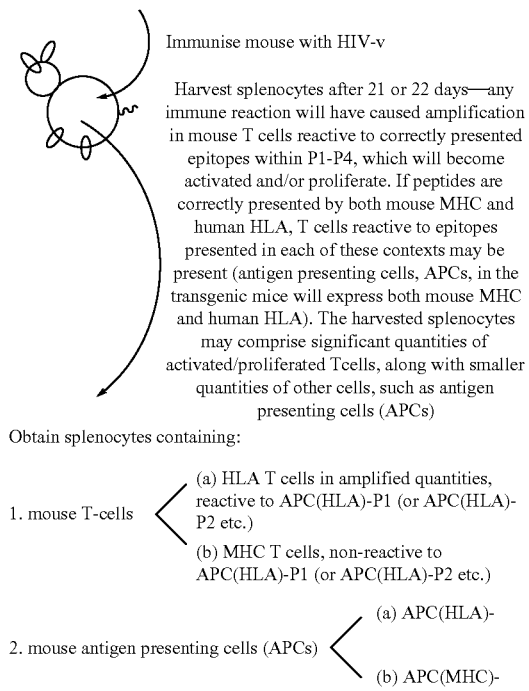

Scheme 1—inoculation

HIV-v = combination of P1 P2 P3 & P4

Immunise mouse with HIV-v

Harvest splenocytes after 21 or 22 days—any immune reaction will have caused amplification in mouse T cells reactive to correctly presented epitopes within P1-P4, which will become activated and/or proliferate. If peptides are correctly presented by both mouse MHC and human HLA, T cells reactive to epitopes presented in each of these contexts may be present (antigen presenting cells, APCs, in the transgenic mice will express both mouse MHC and human HLA). The harvested splenocytes may comprise significant quantities of activated/proliferated Tcells, along with smaller quantities of other cells, such as antigen presenting cells (APCs)

Obtain splenocytes containing:

1. mouse T-cells
   (a) HLA T cells in amplified quantities, reactive to APC(HLA)-P1 (or APC(HLA)-P2 etc.)
   (b) MHC T cells, non-reactive to APC(HLA)-P1 (or APC(HLA)-P2 etc.)

2. mouse antigen presenting cells (APCs)
   (a) APC(HLA)-
   (b) APC(MHC)-

The invention may be applied to any vertebrate, since the immune systems of vertebrates operate in a related manner. Typically, the vertebrate referred to in the present context is a mammal. It is especially preferred that the vertebrate is a human. Examples of human MHCs (HLAs) that may be employed with the present invention include the following:

Cytokine ELISA

Mouse spleens belonging to the same experimental group were pooled, gently pressed through cell strainers and red blood cells removed by treatment with red cell lysis buffer (nine parts 0.16 M $NH_4Cl$ and one part of 0.17 M Tris, pH 7.2). Splenocyte suspensions from each experimental group were plated in 24-well plates at a density of $4 \times 10^6$ cells/well containing a range of polypeptide antigens (5 μg/ml) or, alternatively, MMC treated cell lines (splenocyte to cell (S:C) ratio 10:1) transfected with polypeptide antigens as described above.

After 4 days incubation at 37° C., the supernatant was collected and analysed for IFN-γ and IL-4 by a sandwich cytokine ELISA according to the manufacturer's protocol (Pharmingen). The lower detection limits for the assay were 9.77 pg/ml for IL-4 and 39.06 pg/ml for IFN-γ.

After 4 days incubation at 37° C., the supernatant was collected and analysed for IFN-γ and IL-4 by a sandwich cytokine ELISA according to the manufacturer's protocol (Pharmingen). The lower detection limits for the assay were 9.77 pg/ml for IL-4 and 39.06 pg/ml for IFN-γ.

Results
Reactivity of Peptide 1

Each of the polypeptides described in this patent application (including P1, P2, P3 and P4 tested in this Example) contains several CD8+ T cell epitopes of which several are specific for HLA-A*0201. Upon internal processing of the polypeptide by the antigen presenting cells (APCs) of a HLA- A*0201 bearing recipient, these CD8+ T cell specific epitopes are presented in the surface of the APC where they proceed to activate naive CD8+ T cells and induce a Th1-like immune response specific to the peptide being tested, in this case P1, P2, P3 and P4.

To confirm this, HLA-A*0201 bearing (T1) and non-bearing (JURKAT) human cell lines were intracellularly loaded with P1 by means of a lipid vehicle (Lipofectin, INVITROGEN). Splenocytes from animals immunised with the HIV polypeptide preparation (HIV-v) were found to produce increased levels of IFN-γ compared to splenocytes from NRP immunised animals when co-cultured with MMC treated HLA-A*0201 bearing human cells (T1) transfected with P1, but not when co-cultured with non-HLA-A*0201 bearing human cells (JURKAT) treated in the same way (see FIG. 1, the data for which is presented in Table 1 below).

TABLE 1

| Δ IFN-γ to Lys (pg/ml) | NRP | HIV-v |
| --- | --- | --- |
| Con A | 2345.3 ± 45.9 | 2711.1 ± 44.5 |
| HIV Peptide 1 (sol) | 46.2 ± 4.0 | 46.7 ± 7.1 |
| T1-HIV pep 1 (pro) | 52.8 ± 7.3 | 1413.5 ± 43.4 |
| Ju-HIV pep 5 (pro) | <39 | 53.3 ± 2.7 |

Note:
"Lys" means the negative control background upon which all values are calculated.
"Sol" means soluble peptide presented to the primary splenocyte population.
"Pro" means that the peptide is being presented complexed with the cells HLA molecules following internal processing and loading of the resulting epitopes on to the MHC molecules.
Values represent average ± standard error of the Δ IFN-γ to Lys (pg/ml).

The experiment can be represented schematically as follows:

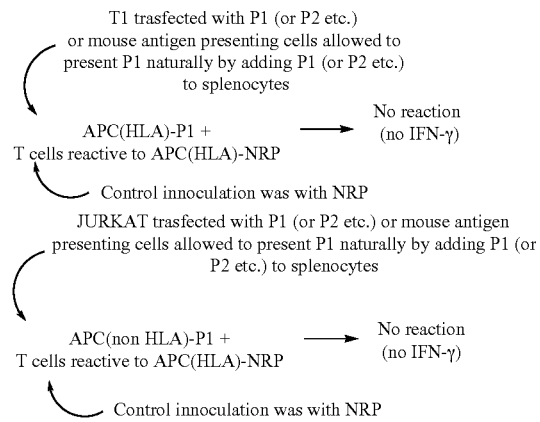

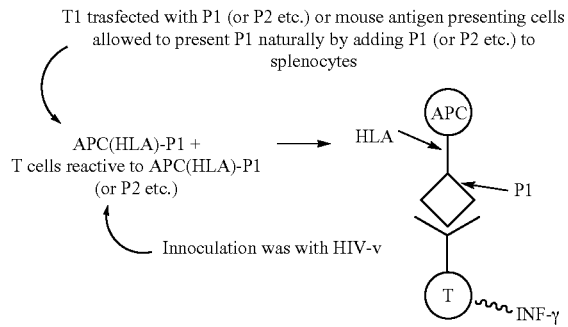

As the transgenic mice used in these experiments do not bear any other human HLA and the ability of its CD8+ T cells to specifically recognise P1-derived epitopes in the context of other human HLAs which they have never encountered is low, these results clearly show that the observed IFN-γ response is specifically caused by CD8+ T cells recognising P1-derived epitopes in association with HLA-A*0201 molecules.

It is also important to note that no IL-4 response can be detected against the P1 transfected cells in either HIV-v or NRP immunised animals (data not shown). Since IL-4 production is antagonistic to Th1 responses and hence to the creation of antigen specific CD8+ T cell responses, the lack of IL-4 production in either group clearly shows that immunisation with HIV-v induces a specific Th1-like response to the P1 component of the preparation.

Interestingly, no differential in IFN-γ production can be observed in the HIV-v compared to the NRP immunised groups when P1 is simply added to the culture (in the absence of T1 or JURKAT cells). This situation, however, can be explained on the basis that P1 contains primarily epitopes that are reactive in the context of human and not mouse HLAs. The transgenic mice used in these experiments contain a full complement of mouse MHC molecules in addition to the HLA-A*0201 molecules. Therefore, the primary splenocyte cultures here considered contain different T cell populations (CD8+ and CD4+) capable of responding to antigen presented in the context of both, the human and mouse MHC molecules present in the mouse APC population also found in these cultures. Only a small fraction of the P1 antigen captured and processed by these APCs would be expected to be available to the P1-specific CD8+ T lymphocytes in the required HLA-A*0201 context. As the level of an immune response in vitro is primarily determined by the availability of antigen, the P1-specific CD8+ T lymphocytes detected when human cells were used as stimulators would simply be unable to respond due to the lack of sufficient antigen presented to them in the appropriate HLA-A*0201 context.

Reactivity of Peptide 2

Figure 2:
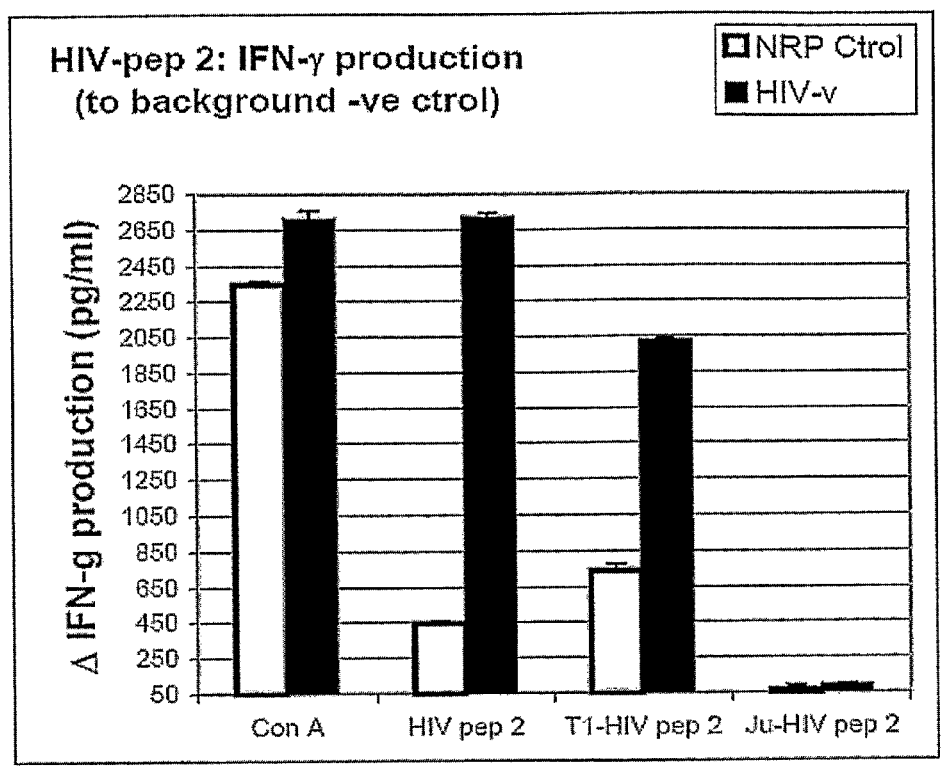

Splenocytes from animals immunised with the HIV polypeptide preparation (HIV-v) have been found to produce increased levels of IFN-γ compared to splenocytes from NRP immunised animals when co-cultured with MMC treated HLA-A*0201 bearing human cells (T1) transfected with P2, but not when co-cultured with non-HLA-A*0201 bearing human cells (JURKAT) treated in the same way (see FIG. 2, the data for which is set out in Table 2 below).

TABLE 2

| Δ IFN-γ to Lys (pg/ml) | NRP | HIV-v |
| --- | --- | --- |
| Con A | 2345.3 ± 45.9 | 2711.1 ± 44.5 |
| HIV Peptide 2 (sol) | 446.7 ± 10.6 | 2721.3 ± 22.7 |

TABLE 2-continued

| Δ IFN-γ to Lys (pg/ml) | NRP | HIV-v |
| --- | --- | --- |
| T1-HIV pep 2 (pro) | 737.4 ± 39.7 | 2027.8 ± 22.2 |
| Ju-HIV pep 2 (pro) | 62.1 ± 30.6 | 95.6 ± 2.3 |

Note:
"Lys" means the negative control background upon which all values are calculated.
"sol" means soluble peptide presented to the primary splenocyte population.
"pro" means that the peptide is being presented complexed with the cells HLA molecules following internal processing and loading of the resulting epitopes on to the MHC molecules.
Values represent average ± standard error of the Δ IFN-γ to Lys (pg/ml).

As was the case for P1, these results clearly show that the observed IFN-γ response is specifically caused by CD8+ T cells recognising P2-derived epitopes in association with HLA-A*0201 molecules.

It is also important to note that no IL-4 response can be detected against the P2 transfected cells in either HIV-v or NRP immunised animals (data not shown). Since IL-4 production is antagonistic to Th1 responses and hence to the creation of antigen specific CD8+ T cell responses, the lack of IL-4 production in either group clearly shows that immunisation with HIV-v induces a specific Th1-like response to the P2 component of the preparation.

In contrast to P1, increased IFN-γ production can be observed in the HIV-v compared to the NRP immunised groups when P2 is simply added to the splenocyte culture. This situation clearly shows that P2 harbours not only strong HLA-A*0201 epitopes but also mouse (H2-D) epitopes. It is important, however, to point out that the IFN-γ response measured in this case may not be uniquely associated to Class I MHC molecules. Dendritic cells have been shown (Peachman K K, Rao M, Alving C R, Palmer D R, Sun W, Rothwell S W, "Human dendritic cells and macrophages exhibit different intracellular processing pathways for soluble and liposome-encapsulated antigens." Immunobiology. 2005; 210(5):321-33.) to be able in vitro to process into the MHC Class II pathway soluble antigen captured from the medium. As a result the increased IFN-γ response observed in this case can be originated by either or both P2-specific CD8+ and CD4+ T cells.

Reactivity of Peptide 3

Similarly to P2, increased IFN-γ production can be observed in the HIV-v compared to the NRP immunised groups when P3 is simply added to the splenocyte culture. The causes for this have been explained previously and hence shall not be developed further here.

Figure 3:
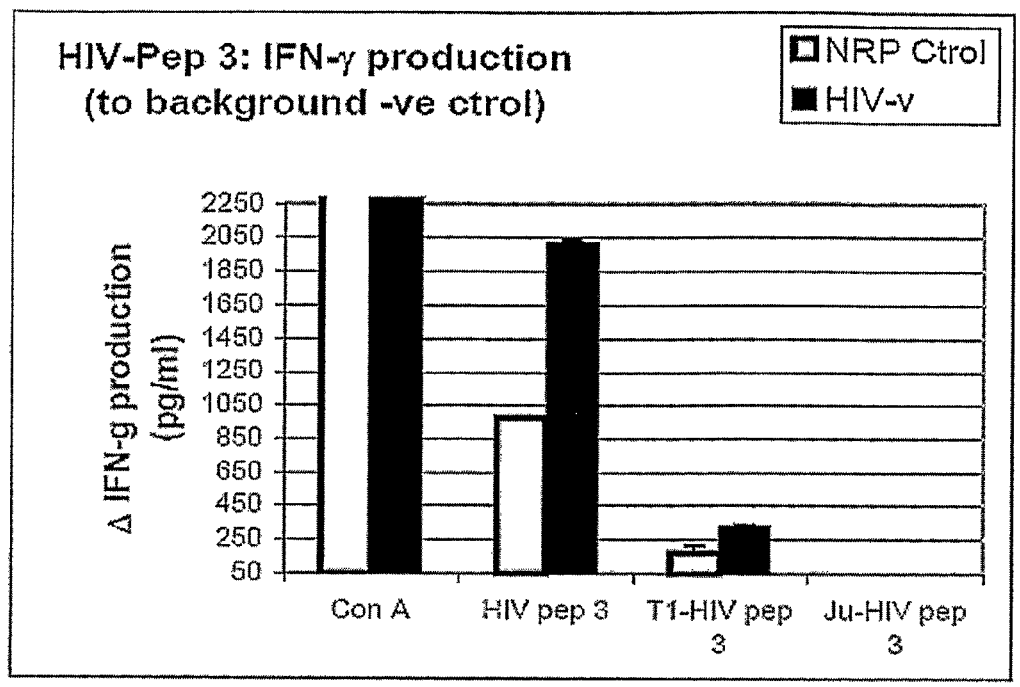

Regarding the HLA-A*0201 specific component of the response, again as was the case for P1 and P2, increased production of IFN-γ is observed in animals immunised with HIV-v compared to those receiving NRP, but to a lesser extent than in P1 (see FIG. 3, the data for which is set out in Table 3 below). This observation is explained in similar terms to those provided for P1.

TABLE 3

| Δ IFN-γ to Lys (pg/ml) | NRP | HIV-v |
| --- | --- | --- |
| Con A | 2345.3 ± 45.9 | 2711.1 ± 44.5 |
| HIV Peptide 3 (sol) | 976.3 ± 10.5 | 2027.5 ± 8.0 |

TABLE 3-continued

| Δ IFN-γ to Lys (pg/ml) | NRP | HIV-v |
| --- | --- | --- |
| T1-HIV pep 3 (pro) | 172.2 ± 40.2 | 329.3 ± 10.5 |
| Ju-HIV pep 3 (pro) | <39 | <39 |

Note:
"Lys" means the negative control background upon which all values are calculated.
"Sol" means soluble peptide presented to the primary splenocyte population.
"Pro" means that the peptide is being presented complexed with the cells HLA molecules following internal processing and loading of the resulting epitopes on to the MHC molecules.
Values represent average ± standard error of the Δ IFN-γ to Lys (pg/ml).

The primary splenocyte cultures from the transgenic animals used here contain different T cell populations (CD8+ and CD4+) capable of responding to antigen presented in the context of both the human and mouse MHC molecules present in the mouse APC population also found in these cultures. Following vaccination, P3-derived epitopes of both Class I and Class II could have been presented to CD8+ and CD4+ T cells. As the number of molecules in the mouse APCs only represent a small fraction of the total number of MHC molecules present (i.e. all the H2-D molecules plus the HLA-A*0201 molecules), only a fraction of the total P3 antigen delivered would be available to CD8+ T cells with a specificity for HLA-A*0201. In vivo as in vitro, the intensity of the T cell response is primarily dependent on the availability of antigen. Therefore, in a situation where there would be intense competition amongst MHC molecules for the P3 epitopes, it follows that those molecules representing a small fraction of the population would be responsible only for a small fraction of the total IFN-γ response.

Reactivity of Peptide 4

Figure 4:
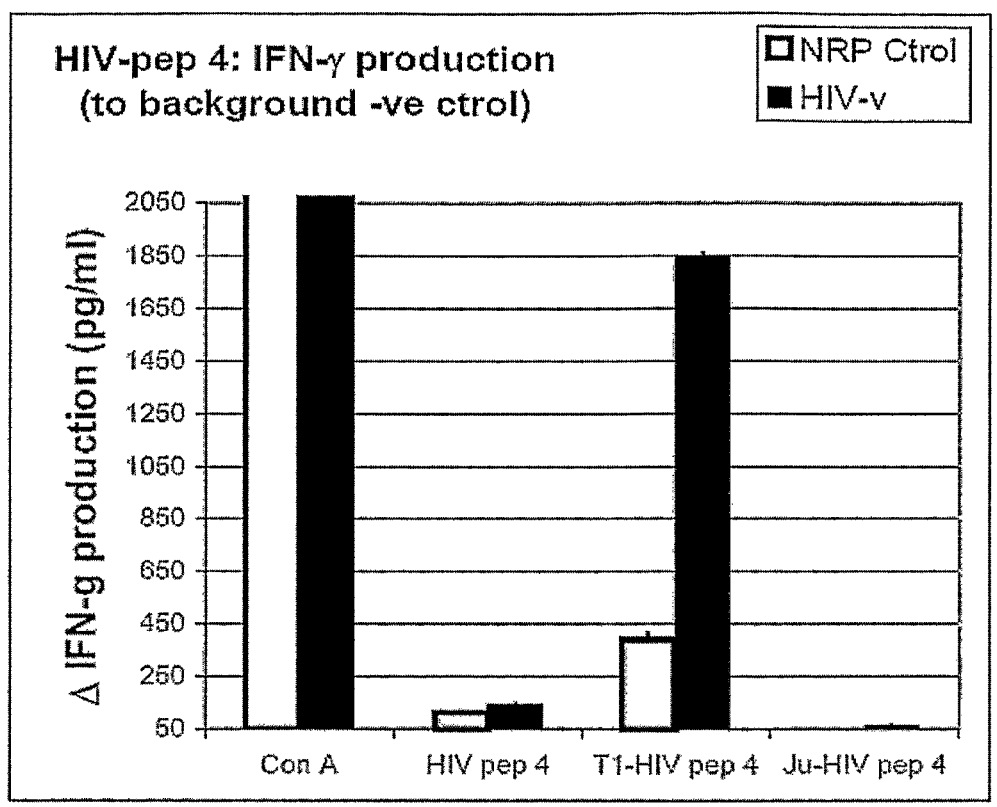

Similarly to P1, increased IFN-γ production can be observed in the HIV-v compared to the NRP immunised groups when P4 is simply added to the splenocyte culture as well as when it is presented via transfected human cells lines (see FIG. 4, the data for which is set out in Table 4 below). As the causes for these observations have already been explained for the case of P1 they shall not be developed further here and one shall refer to that earlier section.

TABLE 4

| Δ IFN-γ to Lys (pg/ml) | NRP | HIV-v |
| --- | --- | --- |
| Con A | 2345.3 ± 45.9 | 2711.1 ± 44.5 |
| HIV Peptide 4 (sol) | 112.2 ± 2.0 | 141.6 ± 7.0 |
| T1-HIV pep 4 (pro) | 391.9 ± 25.7 | 1843.8 ± 15.5 |
| Ju-HIV pep 4 (pro) | <39 | 62.5 ± 5.8 |

Note:
"Lys" means the negative control background upon which all values are calculated.
"Sol" means soluble peptide presented to the primary splenocyte population.
"Pro" means that the peptide is being presented complexed with the cells HLA molecules following internal processing and loading of the resulting epitopes on to the MHC molecules.
Values represent average ± standard error of the Δ IFN-γ to Lys (pg/ml).

Reactivity to HIV Recombinant Proteins

So far the experiments here described have clearly shown that immunisation with HIV-v induces a CD8+ T cell specific IFN-γ response against each of its constituent components. However, it is useful to establish whether HIV-v vaccinated mice are capable of recognising, and hence inducing a specific immune response to, epitopes created upon the capture and processing of the complete HIV proteins from which some of them are derived. Due to the safety constraints of using live HIV virus on human cells it was decided to study the IFN-γ response in HIV-v and NRP vaccinated mouse using the same approach used for P1, P2, P3 and P4, but in this case using as stimulating antigens an equimolar mixture of VIF, REV and NEF.

Figure 5:
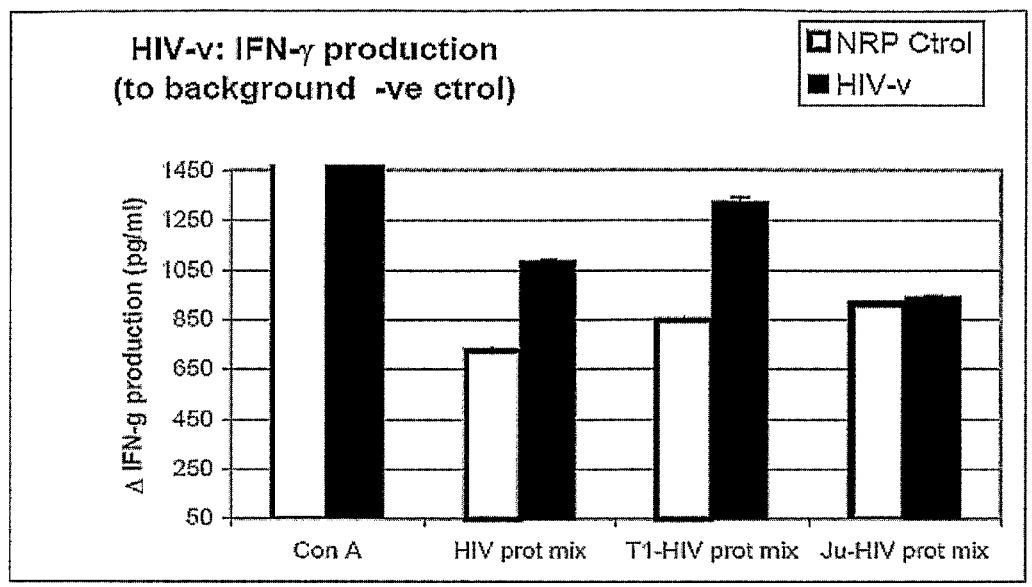

Again, HIV-v vaccination animals gave rise to a specific increase in IFN-γ production compared to NRP vaccination independently of whether the equimolar antigen preparation was simply added to the culture or presented to the activated CD8+ T cells via transfected human cells (see FIG. 5, the data for which is set out in Table 5 below). Interestingly, the background production of IFN-γ in all cases was greater than observed previously, probably reflecting the ability of the equimolar protein preparation to induce a non-specific IFN-γ response in the primary splenocyte cultures or changes in the transfected human cells that render them more susceptible to induce non-specific IFN-γ production in the splenocytes with which they were co-cultured. This observation, however, does not detract from the clear fact that vaccination with HIV-v leads to the specific recognition of HIV HLA-A*0201 epitope naturally processed and presented from complete HIV proteins.

TABLE 5

| Δ IFN-γ to Lys (pg/ml) | NRP | HIV-v |
| --- | --- | --- |
| Con A | 2345.3 ± 45.9 | 2711.1 ± 44.5 |
| HIV rProt mix (sol) | 724.6 ± 14.3 | 1086.6 ± 2.5 |
| T1-HIV rProt mix (pro) | 848.0 ± 8.5 | 1324.5 ± 14.4 |
| Ju-HIV rProt mix (pro) | 911.6 ± 10.5 | 940.9 ± 17.9 |

Note:
"Lys" means the negative control background upon which all values are calculated.
"Sol" means soluble peptide presented to the primary splenocyte population.
"Pro" means that the peptide is being presented complexed with the cells HLA molecules following internal processing and loading of the resulting epitopes on to the MHC molecules.
Values represent average ± standard error of the Δ IFN-γ to Lys (pg/ml).

Experiment 2

HIV-v Immunisation Induces an Antigen Specific Response Against Human Cells Infected with Field Isolates of HIV The purpose of this study is to assess whether immunisation with the identified HIV conserved T cell polyepitope peptides (HIV-v) induces and antigen specific response against human cells infected with HIV field isolates.

Materials and Methods
Peptides, Virus and Cell Line

The candidate vaccine (HIV-v) used in this study is composed of several polypeptides (i.e. P1: VPR aa 51 to 80 (SEQ ID 1); P2: VIF: aa 142 to 181 (SEQ ID 2); P3: REV aa 69 to 95 (SEQ ID 3); P4: NEF: aa 81 to 123 (SEQ ID 4)) which were all synthesised by Fmoc chemistry and resuspended in DMSO in PBS (the concentration of DMSO in the final preparation was less than 10%). Lysozyme (Sigma) denatured by boiling was used as the control non relevant preparation (NRP-v).

The infectious HIV-1 strains were sourced from NIBSC and represented Ugandan isolates of HIV-1 D clade (UG21-R5) and A clade (UG-29-X4). CEM is a CD4+ Lymphoblastoid T cell line susceptible to infection by the above named HIV isolates. This cell line was maintained in RPMI-1640 medium (Sigma) supplemented with 50 IU/50 mg/ml of penicillin/streptomycin (Sigma) and, as complete medium, 10% FCS. Cell cultures were maintained at 37° C. in a humidified atmosphere of 5% $CO_2$.

Primary splenocytes were maintained in IMDM medium (Invitrogen) supplemented with 0.02 mM β-mercaptoethanol (Sigma), 50 IU/50 mg/ml of penicillin/streptomycin (Sigma) and 10% FCS (Sigma) at 37° C. in a humidified atmosphere of 5% $CO_2$.

Immunisations

On day 1, seven to ten week old C57BL/6-Tg(HLA-A2.1) lEnge/J mice (HLA-A*0201 transgenic on a C57/BL6 background, Jackson Labs) were immunised subcutaneously at the base of the tail with a 200 μl dose of the antigen preparation emulsified in IFA (Sigma). In the test group (n=4), each dose of the antigen preparation contained 40 nmol of an equimolar mixture of all four peptides (10 nmol each) whilst in the control group (n=4), each dose of the antigen preparation contained 40 nmol of the non-relevant polypeptide.

On day 15 all animals received a booster immunisation using the same doses and route of delivery as used originally.

On Day 21 all animals were culled and their spleens harvested.

Intracellular Cytokine Staining

Mouse spleens belonging to the same experimental group were pooled, gently pressed through cell strainers and red blood cells removed by treatment with red cell lysis buffer (nine parts 0.16 M $NH_4Cl$ and one part of 0.17 M Tris, pH 7.2). Splenocyte suspensions from each experimental group were plated in 96 well plates (falcon, BD discovery labware) at a density of $2\times10^5$ cells/well containing either Ionomycin (0.78 μg/ml) and PMA (0.05 μg/ml), Concanavalin A at 5 μg/ml or $2\times10^4$ HIV-infected and non-infected UV irradiated CEM cells (splenocyte to cell (S:C) ratio 10:1).

After 3 hours incubation at 37° C. with 5% $CO_2$, Brefeldin A was added to all wells at 10 μg/ml final concentration. Plates were then incubated for a further 3 hours plates at 37° C. and then transferred plates to a +4° C. refrigerator for overnight storage. After centrifugation (200 g, 5 min), the supernatant was removed from the wells and the cells counterstained anti-CD3-FITC antibody for 15-20 minutes at room temperature in the dark. Cells were then washed with PBS by centrifugation (200 g, 5 min), fixed for 20 min at room temperature (fixation reagent A, Caltag) and washed again. After permeabilising the cells for 20 min (permeabilisation reagent B, Caltag) at room temperature, cells were washed and anti-IFNγ-PE and anti-IL4-APC antibodies added. After 30 min incubation, cells were washed twice and resuspended in 40% (w/v) formaldehyde in PBS before being analysed in a flow cytometer.

Results

The purpose of this study was to assess the ability of the HIV-v preparation to induce antigen specific immunity in HLA*A-0201 transgenic mice against HLA compatible HIV infected human cells.

Figure 6:
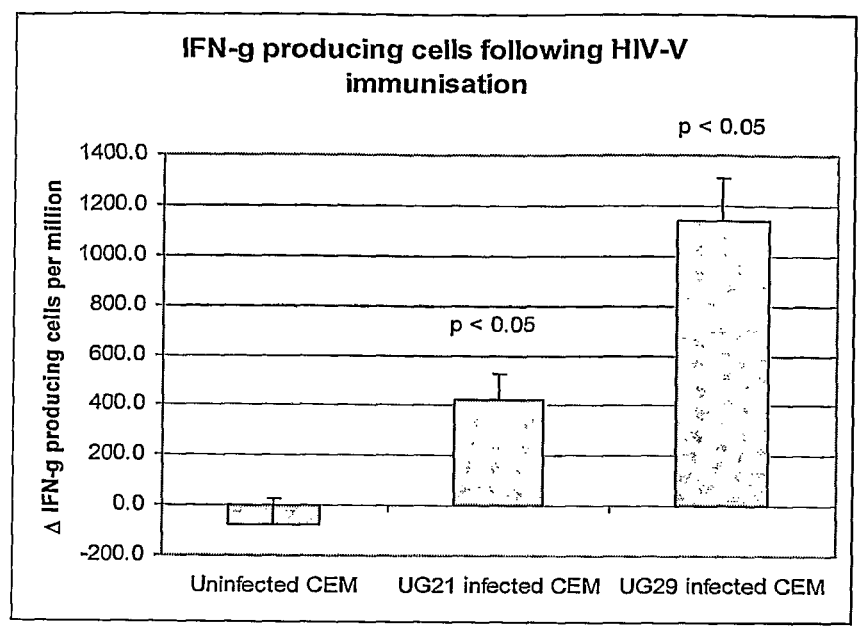

As shown in FIG. 6, splenocytes from animals immunised with HIV-v produced higher levels of IFN-γ when co-cultured against human cells infected with either D clade (UG21-R5) or A lade (UG-29-X4) HIV-1 virus isolates than splenocytes from animals immunised with a non-relevant polypeptide. No IL-4 response against the target cells was observed in any of experimental groups (data not shown).

The results of this study indicate that vaccination with the HIV-v peptide preparation induces a pathogen specific Th1 type T cell response against different clades of circulating HIV virus.

The invention claimed is:

1. An immunogenic composition to elicit an immune response against HIV disease, the composition comprising four isolated polypeptides, wherein the four isolated polypeptides are SEQ ID NO: 1, SEQ ID NO: 2, SEQ ID NO: 3, and SEQ ID NO: 4 and wherein each of the four isolated polypeptides elicits an immune response in vertebrates against at least one epitope of a HIV protein comprising SEQ ID NO: 1, SEQ ID NO: 2, SEQ ID NO: 3, or SEQ ID NO: 4.

2. The immunogenic composition according to claim 1, wherein the composition is immunogenic in a vertebrate expressing a major histocompatibility complex (MHC) allele.

3. The immunogenic composition according to claim 2, wherein the vertebrate is a human.

4. The immunogenic composition according to claim 1, which is immunogenic to an HIV strain.

5. The immunogenic composition according to claim 1, which is immunogenic to a plurality of HIV strains.

6. The immunogenic composition according to claim 1, wherein each of the four isolated polypeptides comprises a cytotoxic T lymphocyte (CTL), CD8+ T cell and/or CD4+ T cell epitope.

7. The immunogenic composition according to claim 6, wherein the epitope has 8, 9 10 or 11 amino acids or more.

8. The immunogenic composition according to claim 1, wherein each of the four isolated polypeptides is in a dose of 1 ng to 1 g.

9. The immunogenic composition according to claim 1, further comprising a carrier.

10. The immunogenic composition of claim 9, wherein the carrier comprises an adjuvant and/or an excipient.

11. The immunogenic composition according to claim 1, wherein the composition is administered subcutaneously, intramuscular, intra-venous, intra-dermal, intra-nasal or orally.

12. The immunogenic composition according to claim 1, wherein the composition is in the form of a pill or a liquid preparation.

13. An immunogenic composition to elicit an immune response against HIV disease, the composition comprising an isolated immunogenic multi-epitope polypeptide including two or more polypeptide units, each polypeptide unit having no more than 50 amino acids, wherein one of the two or more polypeptide units comprises SEQ ID NO: 2 and another of the two or more polypeptide units comprises SEQ ID NO: 1, SEQ ID NO: 3, or SEQ ID NO: 4.

14. The immunogenic composition according to claim 13, wherein the isolated multi-epitope polypeptide is immunogenic in a vertebrate expressing a major histocompatibility complex (MHC) allele.

15. The immunogenic composition according to claim 14, wherein the vertebrate is a human.

16. The immunogenic composition according to claim 13, which is immunogenic to an HIV strain.

17. The immunogenic composition according to claim 13, which is immunogenic to a plurality of HIV strains.

18. The immunogenic composition according to claim 13, wherein the two or more polypeptide units comprises multiple copies of the same epitope, a single copy of a plurality of different epitopes, or multiple copies of two or more epitopes.

19. The immunogenic composition according to claim 13, wherein the two or more polypeptide units comprises a cytotoxic T lymphocyte (CTL), CD8+ T cell and/or CD4+ T cell epitope.

20. The immunogenic composition according to claim 13, wherein the two or more polypeptide units comprises an epitope of 8, 9, 10 or 11 amino acids or more.

21. The immunogenic composition according to claim 13, wherein the isolated multi-epitope polypeptide is in a dose of 1 ng to 1 g.

22. The immunogenic composition according to claim 13, further comprising a carrier.

23. The immunogenic composition of claim 22, wherein the carrier comprises an adjuvant and/or an excipient.

24. The immunogenic composition according to claim 13, wherein the composition is administered subcutaneously, intramuscular, intra-venous, intra-dermal, intra-nasal or orally.

25. The immunogenic composition according to claim 13, wherein the composition is in the form of a pill or a liquid preparation.

* * * * *

SEQUENCE LISTING

<160> NUMBER OF SEQ ID NOS: 8

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Synthetic
      HIV consensus sequence

<400> SEQUENCE: 1

Gly Asp Thr Trp Ala Gly Val Glu Ala Ile Ile Arg Ile Leu Gln Gln
1               5                   10                  15

Leu Leu Phe Ile His Phe Arg Ile Gly Cys Gln His Ser Arg
            20                  25                  30

<210> SEQ ID NO 2
<211> LENGTH: 40
<212> TYPE: PRT
<213> ORGANISM: Artificial Sequence
<220> FEATURE:
<223> OTHER INFORMATION: Description of Artificial Sequence: Synthetic
      HIV consensus sequence

<400> SEQUENCE: 2

Lys Val Gly Ser Leu Gln Tyr Leu Ala Leu Thr Ala Leu Ile Thr Pro
1               5                   10                  15

Lys Lys Ile Lys Pro Pro Leu Pro Ser Val Lys Lys Leu Thr Glu Asp
            20                  25                  30

Arg Trp Asn Lys Pro Gln Lys Thr
            35                  40

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Synthetic
      HIV consensus sequence

<400> SEQUENCE: 3

Glu Pro Val Pro Leu Gln Leu Pro Pro Leu Glu Arg Leu Thr Leu Asp
1               5                   10                  15

Cys Ser Glu Asp Cys Gly Thr Ser Gly Thr Gln
            20                  25

<210> SEQ ID NO 4
<211> LENGTH: 43
<212> TYPE: PRT
<213> ORGANISM: Artificial Sequence
<220> FEATURE:
<223> OTHER INFORMATION: Description of Artificial Sequence: Synthetic
      HIV consensus sequence

<400> SEQUENCE: 4

Tyr Lys Gly Ala Leu Asp Leu Ser His Phe Leu Lys Glu Lys Gly Gly
1               5                   10                  15

Leu Glu Gly Leu Ile Tyr Ser Gln Lys Arg Gln Asp Ile Leu Asp Leu
            20                  25                  30

Trp Val Tyr His Thr Gln Gly Tyr Phe Pro Asp
            35                  40

<210> SEQ ID NO 5
<211> LENGTH: 96

<212> TYPE: PRT
<213> ORGANISM: Artificial Sequence
<220> FEATURE:
<223> OTHER INFORMATION: Description of Artificial Sequence: Synthetic
      VPR HIV consensus sequence

<400> SEQUENCE: 5

Met Glu Gln Ala Pro Glu Asp Gln Gly Pro Gln Arg Glu Pro Tyr Asn
1               5                   10                  15

Glu Trp Thr Leu Glu Leu Leu Glu Glu Leu Lys Asn Glu Ala Val Arg
            20                  25                  30

His Phe Pro Arg Pro Trp Leu His Gly Leu Gly Gln His Ile Tyr Glu
        35                  40                  45

Thr Tyr Gly Asp Thr Trp Ala Gly Val Glu Ala Ile Ile Arg Ile Leu
    50                  55                  60

Gln Gln Leu Leu Phe Ile His Phe Arg Ile Gly Cys Gln His Ser Arg
65                  70                  75                  80

Ile Gly Ile Ile Arg Gln Arg Arg Ala Arg Asn Gly Ala Ser Arg Ser
                85                  90                  95

<210> SEQ ID NO 6
<211> LENGTH: 193
<212> TYPE: PRT
<213> ORGANISM: Artificial Sequence
<220> FEATURE:
<223> OTHER INFORMATION: Description of Artificial Sequence: Synthetic
      VIF HIV consensus sequence

<400> SEQUENCE: 6

Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Ile Ser
            20                  25                  30

Lys Lys Ala Lys Gly Trp Phe Tyr Arg His His Tyr Glu Ser Thr His
        35                  40                  45

Pro Arg Ile Ser Ser Glu Val His Ile Pro Leu Gly Asp Asp Ala Lys
    50                  55                  60

Leu Val Ile Thr Thr Tyr Trp Gly Leu His Thr Gly Glu Arg Asp Trp
65                  70                  75                  80

His Leu Gly Gln Gly Val Ser Ile Glu Trp Arg Lys Lys Arg Tyr Ser
                85                  90                  95

Thr Gln Val Asp Pro Asp Leu Ala Asp Gln Leu Ile His Leu Tyr Tyr
            100                 105                 110

Phe Asp Cys Phe Ser Glu Ser Ala Ile Arg Lys Ala Ile Leu Gly His
        115                 120                 125

Ile Val Ser Pro Arg Cys Glu Tyr Gln Ala Gly His Asn Lys Val Gly
    130                 135                 140

Ser Leu Gln Tyr Leu Ala Leu Thr Ala Leu Ile Thr Pro Lys Lys Ile
145                 150                 155                 160

Lys Pro Pro Leu Pro Ser Val Lys Lys Leu Thr Glu Asp Arg Trp Asn
                165                 170                 175

Lys Pro Gln Lys Thr Lys Gly His Arg Gly Ser His Thr Met Asn Gly
            180                 185                 190

His

<210> SEQ ID NO 7
<211> LENGTH: 123
<212> TYPE: PRT

```
<213> ORGANISM: Artificial Sequence
<220> FEATURE:
<223> OTHER INFORMATION: Description of Artificial Sequence: Synthetic
      REV HIV consensus sequence

<400> SEQUENCE: 7

Met Ala Gly Arg Ser Gly Asp Ser Asp Glu Glu Leu Leu Lys Ala Val
1               5                   10                  15

Arg Ile Ile Lys Ile Leu Tyr Gln Ser Asn Pro Tyr Pro Ser Pro Glu
                20                  25                  30

Gly Thr Arg Gln Ala Arg Arg Asn Arg Arg Arg Arg Trp Arg Ala Arg
                35                  40                  45

Gln Arg Gln Ile Arg Ser Ile Ser Glu Arg Ile Leu Ser Thr Cys Leu
    50                  55                  60

Gly Arg Pro Ala Glu Pro Val Pro Leu Gln Leu Pro Pro Leu Glu Arg
65                  70                  75                  80

Leu Thr Leu Asp Cys Ser Glu Asp Cys Gly Thr Ser Gly Thr Gln Gln
                85                  90                  95

Ser Gln Gly Thr Glu Gly Val Gly Ser Pro Gln Ile Leu Val Glu
                100                 105                 110

Ser Pro Thr Val Leu Glu Ser Gly Thr Lys Glu
                115                 120

<210> SEQ ID NO 8
<211> LENGTH: 206
<212> TYPE: PRT
<213> ORGANISM: Artificial Sequence
<220> FEATURE:
<223> OTHER INFORMATION: Description of Artificial Sequence: Synthetic
      NEF HIV consensus sequence

<400> SEQUENCE: 8

Met Gly Gly Lys Trp Ser Lys Ser Ser Val Val Gly Trp Pro Ala Val
1               5                   10                  15

Arg Glu Arg Met Arg Arg Ala Glu Pro Ala Ala Glu Gly Val Gly Ala
                20                  25                  30

Val Ser Arg Asp Leu Glu Lys His Gly Ala Ile Thr Ser Ser Asn Thr
                35                  40                  45

Ala Ala Asn Asn Ala Asp Cys Ala Trp Leu Glu Ala Gln Glu Glu Glu
    50                  55                  60

Glu Val Gly Phe Pro Val Arg Pro Gln Val Pro Leu Arg Pro Met Thr
65                  70                  75                  80

Tyr Lys Gly Ala Leu Asp Leu Ser His Phe Leu Lys Glu Lys Gly Gly
                85                  90                  95

Leu Glu Gly Leu Ile Tyr Ser Gln Lys Arg Gln Asp Ile Leu Asp Leu
                100                 105                 110

Trp Val Tyr His Thr Gln Gly Tyr Phe Pro Asp Trp Gln Asn Tyr Thr
                115                 120                 125

Pro Gly Pro Gly Ile Arg Tyr Pro Leu Thr Phe Gly Trp Cys Phe Lys
    130                 135                 140

Leu Val Pro Val Glu Pro Glu Lys Val Glu Glu Ala Asn Glu Gly Glu
145                 150                 155                 160

Asn Asn Cys Leu Leu His Pro Met Ser Gln His Gly Met Glu Asp Pro
                165                 170                 175

Glu Arg Glu Val Leu Val Trp Lys Phe Asp Ser Arg Leu Ala Phe His
                180                 185                 190
```

```
His Met Ala Arg Glu Leu His Pro Glu Tyr Tyr Lys Asp Cys
        195                 200                 205
```